(12) United States Patent
Moquist

(10) Patent No.: US 11,944,689 B2
(45) Date of Patent: Apr. 2, 2024

(54) DRUG CONJUGATES WITH SELF-STABILIZING LINKERS HAVING IMPROVED PHYSIOCHEMICAL PROPERTIES

(71) Applicant: Seagen Inc., Bothell, WA (US)

(72) Inventor: Philip Moquist, Seattle, WA (US)

(73) Assignee: Seagen Inc., Bothell, WA (US)

( * ) Notice: Subject to any disclaimer, the term of this patent is extended or adjusted under 35 U.S.C. 154(b) by 976 days.

(21) Appl. No.: 16/324,198

(22) PCT Filed: Aug. 9, 2017

(86) PCT No.: PCT/US2017/046157
§ 371 (c)(1),
(2) Date: Feb. 8, 2019

(87) PCT Pub. No.: WO2018/031690
PCT Pub. Date: Feb. 15, 2018

(65) Prior Publication Data
US 2019/0167806 A1 Jun. 6, 2019

Related U.S. Application Data

(60) Provisional application No. 62/372,455, filed on Aug. 9, 2016.

(51) Int. Cl.
| | |
|---|---|
| A61K 47/68 | (2017.01) |
| A61K 31/40 | (2006.01) |
| A61K 39/00 | (2006.01) |
| A61K 47/54 | (2017.01) |
| A61K 47/60 | (2017.01) |
| A61K 47/65 | (2017.01) |
| A61P 35/00 | (2006.01) |
| C07D 403/04 | (2006.01) |
| C07K 16/28 | (2006.01) |

(52) U.S. Cl.
CPC .......... *A61K 47/6851* (2017.08); *A61K 31/40* (2013.01); *A61K 47/545* (2017.08); *A61K 47/549* (2017.08); *A61K 47/60* (2017.08); *A61K 47/65* (2017.08); *A61K 47/6803* (2017.08); *A61K 47/6867* (2017.08); *A61K 47/6873* (2017.08); *A61K 47/6889* (2017.08); *A61P 35/00* (2018.01); *C07D 403/04* (2013.01); *C07K 16/2803* (2013.01); *C07K 16/2878* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 4,880,935 A | 11/1989 | Thorpe | |
| 5,091,542 A | 2/1992 | Ahlem et al. | |
| 5,122,368 A | 6/1992 | Greenfield | |
| 5,225,539 A | 7/1993 | Winter | |
| 5,523,360 A | 6/1996 | Jelenic et al. | |
| 5,585,089 A | 12/1996 | Queen | |
| 5,622,929 A | 4/1997 | Willner | |
| 5,824,805 A | 10/1998 | King | |
| 5,973,166 A | 10/1999 | Mizori et al. | |
| 6,130,237 A | 10/2000 | Denny et al. | |
| 6,214,345 B1 | 4/2001 | Firestone et al. | |
| 7,091,186 B2 | 8/2006 | Senter | |
| 7,498,298 B2 | 3/2009 | Doronina et al. | |
| 7,553,816 B2 | 6/2009 | Senter | |
| 7,659,241 B2 | 2/2010 | Senter et al. | |
| 7,754,681 B2 | 7/2010 | Feng | |
| 7,968,687 B2 | 6/2011 | McDonagh et al. | |
| 7,989,434 B2 | 8/2011 | Feng | |
| 8,142,784 B2 | 3/2012 | Ebens, Jr. et al. | |
| 8,163,888 B2 | 4/2012 | Steeves et al. | |
| 8,257,706 B2 | 9/2012 | Mcdonagh | |
| 8,343,928 B2 | 1/2013 | Doronina et al. | |
| 9,504,756 B2 * | 11/2016 | Lyon .................. | C07D 207/36 |
| 11,103,593 B2 | 8/2021 | Lyon et al. | |
| 11,116,847 B2 | 9/2021 | Kolakowski et al. | |
| 11,510,959 B2 | 11/2022 | Doronina | |
| 2003/0083263 A1 | 5/2003 | Doronina et al. | |

(Continued)

FOREIGN PATENT DOCUMENTS

| | | |
|---|---|---|
| AU | 2003263964 | 8/2010 |
| AU | 2004316290 | 2/2012 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Strop et al., Chemistry and Biology 20: 161-167 (Year: 2013).*
Marei et al., Cancer Cell International 22: 255 (Year: 2022).*
Alley et al (Current Opinion in Chemical Biology, 2010, 14:529-537.
Chari et al, Angew Chem Int Ed, 2014, vol. 53, pp. 3796-3827.
Christie et al., "Stabilization of cysteine-linked antibody drug conjugates with N-aryl maleimides," J. Control. Release, 2015, 220:660-670.

(Continued)

*Primary Examiner* — Phuong Huynh
(74) *Attorney, Agent, or Firm* — MORRISON & FOERSTER LLP

(57) ABSTRACT

Compounds and compositions are disclosed in which a Drug Unit is linked to a targeting Ligand Unit through a self-stabilizing Linker Unit from which a drug compound or active drug moiety is released at the targeted site of action. Methods for treating diseases characterized by the targeted abnormal cells, such as cancer or an autoimmune disease using the compounds and compositions of the invention are also disclosed.

23 Claims, 2 Drawing Sheets

(56) References Cited

U.S. PATENT DOCUMENTS

| | | |
|---|---|---|
| 2004/0138107 A1 | 7/2004 | Fardis |
| 2004/0167287 A1 | 8/2004 | Kozlowski et al. |
| 2005/0009751 A1 | 1/2005 | Senter et al. |
| 2005/0238649 A1 | 10/2005 | Doronina et al. |
| 2006/0193865 A1 | 8/2006 | Govindan |
| 2006/0229253 A1 | 10/2006 | Doronina |
| 2006/0292616 A1 | 12/2006 | Neely et al. |
| 2009/0012241 A1 | 1/2009 | Kozlowski et al. |
| 2009/0018086 A1 | 1/2009 | Doronina et al. |
| 2009/0111756 A1 | 4/2009 | Doronina et al. |
| 2009/0274713 A1 | 11/2009 | Chari |
| 2010/0104589 A1 | 4/2010 | Govindan et al. |
| 2011/0020343 A1 | 1/2011 | Senter et al. |
| 2011/0256157 A1 | 10/2011 | Howard |
| 2013/0259860 A1 | 10/2013 | Smith |
| 2013/0309223 A1 | 11/2013 | Sutherland |
| 2013/0309256 A1* | 11/2013 | Lyon ............ C07K 7/02 424/179.1 |
| 2015/0320879 A1 | 11/2015 | Lyon et al. |
| 2016/0303254 A1 | 10/2016 | Kolakowski et al. |
| 2016/0310612 A1 | 10/2016 | Lyon |
| 2018/0154011 A1 | 6/2018 | Lyon et al. |
| 2019/0167806 A1 | 6/2019 | Moquist |
| 2020/0197524 A1 | 6/2020 | Neumann et al. |
| 2021/0283210 A1 | 9/2021 | Doronina et al. |
| 2021/0300867 A1 | 9/2021 | Lyon et al. |
| 2021/0361776 A1 | 11/2021 | Biechele et al. |
| 2022/0175947 A1 | 6/2022 | Waight et al. |

FOREIGN PATENT DOCUMENTS

| | | |
|---|---|---|
| AU | 2006269422 | 12/2012 |
| AU | 2010201459 | 12/2012 |
| AU | 2006269940 | 11/2013 |
| CA | 2494105 | 2/2004 |
| CA | 2802205 | 2/2004 |
| CA | 2543888 | 9/2005 |
| CA | 2614436 | 1/2007 |
| CA | 2616005 | 1/2007 |
| CN | 1938046 A | 3/2007 |
| CN | 102448494 | 5/2012 |
| CN | 104220458 A | 12/2014 |
| CN | 104244718 A | 12/2014 |
| EP | 0012023 A1 | 6/1980 |
| EP | 0171496 A2 | 2/1986 |
| EP | 0173494 A2 | 3/1986 |
| EP | 0184187 A2 | 6/1986 |
| EP | 0446071 A2 | 9/1991 |
| EP | 2850094 | 3/2015 |
| JP | 1994H06228091 A | 8/1994 |
| JP | 2009531325 A | 9/2009 |
| JP | 6423340 | 11/2018 |
| RU | 2448117 | 4/2012 |
| WO | 198601533 A1 | 3/1986 |
| WO | 198702671 A1 | 5/1987 |
| WO | 199734631 A1 | 9/1997 |
| WO | WO02/088172 A2 | 11/2002 |
| WO | WO2004/010957 A2 | 2/2004 |
| WO | WO2005/112919 A2 | 12/2005 |
| WO | 2007008603 A1 | 1/2007 |
| WO | WO2007/038658 A2 | 4/2007 |
| WO | 2007085930 A1 | 8/2007 |
| WO | WO2009/002993 A1 | 12/2008 |
| WO | WO 2010/063124 | 6/2010 |
| WO | WO2010/091150 A1 | 8/2010 |
| WO | 2011023883 A1 | 3/2011 |
| WO | WO2011/023883 A1 | 3/2011 |
| WO | WO2012/054748 A2 | 4/2012 |
| WO | WO2012/112708 A1 | 8/2012 |
| WO | 2013123152 A2 | 8/2013 |
| WO | WO2013/173337 A2 | 11/2013 |
| WO | WO2014/151030 A1 | 9/2014 |
| WO | 2013123152 A3 | 11/2014 |
| WO | WO2015/057699 A2 | 4/2015 |
| WO | 2015095755 A1 | 6/2015 |
| WO | 2016040684 A1 | 3/2016 |
| WO | WO 2018/031690 | 2/2018 |

OTHER PUBLICATIONS

Irani et al, Molecular Immunology, 2015, vol. 67, pp. 171-182.
Pelegrin et al, Trends in Microbiology, 2015, vol. 23, pp. 653-665.
Turk et al., "Cysteine cathepsins: From structure, function and regulation to new frontiers," Biochimica et Biophysica Acta, 2012, 1824:66-68.
Turner et al, International Journal for Parasitology, 2005, vol. 35, pp. 981-990.
Alouane, A. et al. (Jun. 22, 2015, e-pub. Jun. 5, 2015). "Self-Immolative Spacers: Kinetic Aspects, Structure—Property 15 Relationships, And Applications," Angew. Chem. Int. Ed. 54(26):7492-7509. (Abstract Only).
Amsberry, K.L. et al. (1990) "The Lactonizatin of 2'-Hydroxyhydrocinnamic Acid Amides: A Potential Prodrug For Amines," J. Org. Chem. 55(23):5867-5877.
Balasubramanian, R. et al. (May 1, 2008, e-pub. Mar. 20, 2008). "Tubulysin Analogs Incorporating Desmethyl and Dimethyl Tubuphenylalanine Derivatives," Bioorg. Med. Chem. Lett. 18(9):2996-2999.
Beidler, C.B. et al. (Dec. 1, 1988). "Cloning and High Level Expression Of A Chimeric Antibody With Specificity For Human Carcinoembryonic Antigen," J. Immunol. 141(11):4053-4060.
Berter, M. et al. (May 20, 1988). "*Escherichia coli* Secretion of an Active Chimeric Antibody Fragment," Science 240:1041-1043.
Blencowe, C.A. et al. (2011). "Self-immolative Linkers in Polymeric Delivery Systems," Polymer Chem 2:773-790.
Burkhart, J.L. et al. (2011). "Syntheses and Evaluation of Simplified Pretubulysin Analogues," Eur. J. Org. Chem. 2011(16):3050-3059.
Chari, R.V.J. et al. (Jan. 1, 1992). "Immunoconjugates Containing Noveal Maytansinoids: Promising Anticancer Drugs," Cancer Res. 52:127-131.
Dubowchik, G.M. et al. (Aug. 1999). "Receptor-Mediated and Enzyme-Dependent Targeting of Cytotoxic Anticancer Drugs," Pharm. Therapeutics 83(2):67-123.
Friestad. G.K. et al. (2016, e-pub. Feb. 17, 2016). "Stereoselective Access to Tubuphenylalanine and Tubuvaline: Improved Mn-Mediated Radical Additions and Assembly of a Tubulysin Tetrapeptide Analog," The Journal of Antobiotics 69:294-298.
Gaertner, H.F. et al. (Mar. 11, 1994). "Chemo-Enzymic Backbone Engineering of Proteins," J. Biol. Chem. 269(10):7224-7230.
Greenwald, R.B. et al. (1999, e-pub. Aug. 13, 1999). "Drug Delivery Systems Employing 1,4- Or 1,6-Elimination: Poly(Ethylene Glycol) Prodrugs Of Amine-Containing Compounds," J. Med. Chem. 42:3657-3667.
Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th Ed. Public Health Service, National Institutes of Health, Bethesda MD., Table of Contents, 21 pages.
Kabat, E.A. et al. (Sep. 1980). "Origins of Antibody Complementarity and Specificity—Hypervariable Regions and the Minigene Hypothesis," J Immunology 125(3):961-969.
Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451.
Kozbor, D. et al. (1983). "The Production of Monoclonal Antibodies From Human Lymphocytes," Immunology Today 4(3):72-79.
Liu, A.Y. et al. (May 1987). "Chimeric Mouse-Human IgG1 Antibody That Can Mediate Lysis of Cancer Cells," Proc. Natl. Acad. Sci. USA 84:3439-3443.

(56) References Cited

OTHER PUBLICATIONS

Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.
Morrison, S.L. (Sep. 1985). "Transfectomas Provide Novel Chimeric Antibodies," Science 229(4719):1202-1207.
Murray, B.C. et al. (May 2015). "Chemistry and Biology of Tubulysins: Antimitotic Tetrapeptides With Activity Against Drug Resistant Cancers," Nat. Prod. Rep.32(5):654-662.
Neville, D.M. et al. (Sep. 5, 1989). "Enhancement of Immunotoxin Efficacy by Acid-cleavable Crosslinking Agents Utilizing Diphtheria Toxin and Toxin Mutants," The Journal of Biological Chemistry 264(25):14653-14661.
Nicolaou, K.C. et al. (Feb. 1, 2016). "Total Synthesis and Biological Evaluation of Natural and Designed Tubulysins," J. Am. Chem. Soc. 138:1698-1708.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.
Oi, V.T. et al. (1986). "Chimeric Antibodies," Bio Techniques 4(3):214-219.
Olsson, L. et al. (1983), "Human-Human Monoclonal Antibody-Producing Hybridomas: Technical Aspects," Meth Enzymol. 92:3-16.
Pando, O. et al. (Apr. 29, 2011). "The Multicomponent Approach To Natural Product Mimics: Tubugis, N-substituted Anticancer Peptides With Picomolar Activity," J. Am. Chem. Soc. 133:7692-7695.
Park, Y. et al. (Nov. 1, 2015, e-pub. Oct. 9, 2015). "Synthesis of Stereochemically Diverse Cyclic Analogs of Tubulysins," Bioorg. Med. Chem. 23(21):6827-6483.
Patterson et al. (Jun. 20, 2008, e-pub. May 15, 2008). "Expedient Synthesis of N-Methyl Tubulysin Analogues with High Cytotoxicity," J. Org. Chem. 73(12):4362-4369.
Raghavan, B. et al. (Mar. 27, 2008, e-pub. Mar. 4, 2008). "Cytotoxic Simplified Tubulysin Analogues," J. Med. Chem. 51(6):1530-1533.
Rath, S. et al. (2012). "Anti-angiogenic Effects of the Tubulysin Precursor Pretubulysin and of Simplified Pretubulysin Derivatives," Br. J. Pharmacol. 167:1048-1061.
Rose, K. et al. (May-Jun. 1991). "Preparation Of Well-Defined Protein Conjugates Using Enzyme-Assisted Reverse Proteolysis," Bioconjugate Chem. 2(3):154-159.
Sanderson, R.J. et al. (Jan. 15, 2005). "In vivo Drug-Linker Stability of an Anti-CD30 Dipeptide-Linked Auristatin Immunoconjugate," Clin. Cancer Res. 11:843-852.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwartz, A. et al. (1990). "Enzymatic C-Terminal Biotinylation Of Proteins," Methods Enzymol. 184:160-162.
Shankar, S.P. et al. (2013). "Synthesis And Structure-Activity Relationship Studies Of Novel Tubulysin U Analogs—Effect On Cytotoxicity Of Structural Variations In The Tubuvaline Fragment," Org. Biomol. Chem. 11:2273-2287.
Shankar, S.P. et al. (Nov. 6, 2013, e-pub. Sep. 11, 2013). "Synthesis and Cytotoxicity Evaluation of Diastereoisomers and N-Terminal Analogues of Tubulysin-U," Tetrahedron Letters 54(45):6137-6141.
Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.
Shibue, T. et al. (Jan. 1, 2011, e-pub. Oct. 30, 2010). "Synthesis and Biological Evaluation of Tubulysin D Analogs Related to Stereoisomers of Tubuvaline," Bioorg. Med. Chem. Lett. 21:431-434.
Skehan, P. et al. (Jul. 4, 1990). "New Colorimetric Cytotoxicity Assay for Anticancer-Drug Screening," J. Nat'l Cancer Inst. 82(13):1107-1112.
Stahl, P.H. et al. (2002). Handbook of Pharmaceutical Salts: Properties, Selection and Use Weinheim/Zurich, Wiley-VCH/VHCA, Abstract Only.
Storm, D.R. et al. (Aug. 9, 1972). "Effect of Small Changes in Orientation on Reaction Rate," Journal of the American Chemical Society 94(16):5815-5825.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Teng, N.N.H. et al. (Dec. 1983). "Construction and Testing of Mouse-Human Heteromyelomas For Human Monoclonal Antibody Production," Proc. Natl. Acad. Sci. USA. 80:7308-7312.
Thorpe, P.E. et al. (Nov. 15, 1987). "New Coupling Agents for the Synthesis of Immunotoxins Containing a Hindered Disulfide Bond with Improved Stability in Vivo," Cancer Research 47:5924-5931.
Verhoeyan, M. et al. (Mar. 25, 1988). "Reshaping Human Antibodies: Grafting an Antilysozyme Activity," Science 239:1534-1536.
Wang, Z. et al. (Aug. 2007). "Structure-Activity and High-Content Imaging Analysis of Novel Tubulysins," Chem. Biol. Drug Des. 70(2):75-86.
Wawrzynczak, E.J. et al. (1987). "Chapter 3—Methods for Preparing Immunotoxins: Effect of the Linkage on Activity and Stability," in Immunoconjugates: Antibody Conjugates in Radioimagery and Therapy of Cancer pp. 28-55.
Wood, C.R. et al. (Apr. 4, 1985). "The Synthesis and in vivo Assembly of Functional Antibodies In Yeast," Nature 314(6010):446-449.
Xiangming, X. et al. (Oct. 2013). "Recent Advances In The Synthesis of Tubulysins," Mini-Rev. Med. Chem. 13(11):1572-1578.
Yang, X. et al. (2013, e-pub. Apr. 9, 2013). "Design, Synthesis, and Biological Activities of Triazole Tubulysin V Analogue," Tet. Lett. 54:2986-2988.
[No Author Listed], "Definitive Rules for Nomenclature of Organic Chemistry",Journal of the American Chemical Society, Nov. 1960, 82(21):5545-5574.
Collard et al., "Vinblastine-C4 alkyl maleoyl and amino acid maleoyl derivatives. II. Experimental antitumor activity against leukemias and human tumor xenografts," Anticancer Research, May 1989, 9(3):625-630.
Ducry et al., "Antibody-Drug Conjugates: Linking cytotoxic payloads to monoclonal antibodies", Bioconjugate Chemistry,2010, 21:5-13.
EP Extended European Supplementary Search Report in Appln. No. 17840229.3, dated Mar. 12, 2020, 6 pages.
Fridkin et al., "Peptide Synthesis" Ann. Rev. Biochem., 1974, 43:419-443.
Han et al., "Recent development of peptide coupling agents in organic synthesis", Tet., 2004, 60: 2447-2476.
Laguzza et al., "New antitumor monoclonal antibody-vinca conjugates LY203725 and related compounds: Design, preparation, and representative in vivo activity," J. Med Chem., 1989, 32(3):548-55.
Roa et al., "Vinblastine-C4 alkyl maleoyl and amino acid maleoyl derivatives: III. Experimental antitumor activities of lactosaminated serum albumin conjugates," Anticancer Research, 1989, 9(4):973-979.
Zentz et al., "Synthesis and Antimicrobial Activities of N-Substituted Imides", Il Farmaco, 2002, 57:421-426.
Abstract of Hayashi et al., Peptide Science, vol. 43 (2006), 2 pages).
Agarwal, Paresh et al., "A Pictet-Spengler ligation for protein chemical modification," Proc. Nat'l. Acad. Sci. (USA) 110(1): 46-51 (Jan. 2, 2013).
Ajaj, Khalid Abu et al., "Development of protein-binding bifunctional linkers for a new generation of dual-acting prodrugs" Bioconjugate Chem. 20: 390-396 (Jan. 20, 2009).
Alley et al., "Contribution of linker stability to the activities of anticancer immunoconjugates" Bioconjugate Chem. 19:759-765 (2008).
Author Unknown, "Pubchem CID 10495592" Created Oct. 25, 2006, Date Accessed Oct. 2, 2017, 9 pages.
Badescu, George et al., "A new reagent for stable thia-specific conjugation" Bioconjugate Chem. 25: 460-469 (2014).
Baldwin, Aaron D. et al., "Tunable degradation of maleimide-thiol adducts in reducing environments" Bioconjugate Chem. 22(10): 1946-1953 (Oct. 19, 2011).

(56) References Cited

OTHER PUBLICATIONS

Borah, H. N. et al., "Microwave-induced One-pot Synthesis of N-carboxyalkyl Maleimides and Phthalimides," J. Chem. Research (S), pp. 272-273, (1998).
Carey, Francis A. et al., Advanced Organic Chemistry, Part B: Reactions and Synthesis, "Section 1:10. Alkylation of Carbon by Conjugate Addition" pp. 24-28 (1977).
Extended European Search Report corresponding to EP13791383.6 dated May 26, 2016, 11 pages.
International Preliminary Report on Patentability (Chapter I) dated Apr. 28, 2015 corresponding to PCT/US2013/040951, 13 pages.
International Preliminary Report on Patentability (Chapter I) dated Feb. 21, 2019 corresponding to PCT/US2017/046157, 5 pages.
International Search Report corresponding to PCT/US2013/040951 dated Oct. 25, 2013, 16 pages.
International Search Report corresponding to PCT/US2017/046157 dated Oct. 24, 2017, 11 pages.
Kalia, Jeet et al., "Advances in bioconjugation" Curr. Org. Chem. 14(2): 138-147 (Jan. 2010).
Kalia, Jeet et al., "Catalysis of imido group hydrolysis in a maleimide conjugate" Bioorg. Med. Chem. Lett. 17: 6286-6289 (2007).
Knight, P., "Hydrolysis of p-N,N'-Phenylenebismaleimide and its adducts with cysteine" Biochem. J. 179: 191-197 (1979).
Lyon, Robert P. et al., "Self-hydrolyzing maleimides improve the stability and pharmacological properties of antibody-drug conjugates" Nature Biotechnology Letters Advance Online Publication (2014), 7 pages.
Lyon, Robert P. et al., "Self-Stabilizing ADCs: conjugates prepared with maleimido drug-linkers that catalyze their own thiosuccinimide ring hydrolysis," Abstract No. 4333, American Associate for Cancer Research (Apr. 2013, Washington DC), 1 page.
Ondrus, V. et al., "On the use of water as a solvent—simple and short one-step synthesis of maleimides" Arkivoc pp. 60-67 (2001).
Page, Brigitte et al., "A new fluorometric assay for cytotoxicity measurements in vitro" Intl. J. Oncology 3: 473-476 (1993).
Rao, Kandukuri S.P.B. et al., "Vinblastine-C4Alkyl Maleoyl and Amino Acid Maleoyl Derivatives: I. Chemistry and Physicochemical Data," Anticancer Research 9: 619-624 (Apr. 27, 1989).
Rodrigues, Maria L. et al., "Synthesis and 13-lactamase-mediated activation of a cephalosporin-taxol prodrug" Chemistry Biology 2(4): 223-227 (1995).
Ryan et al., "Tunable reagents for multi-functional bioconjugation: reversible or permanent chemical modification of proteins and peptides by control of maleimide hydrolysis" Chem. Commun. 47, 5452-5454 (2011).
Shen, B.-Q. et al., "Conjugation site modulates the in vivo stability and therapeutic activity of antibody drug conjugates" Nature Biotechnology 30(2): 184-191 (Feb. 2012).
Smith et al., "Protein modification, bioconjugation, and disulfide bridging using bromomaleimides" J. Am. Chem. Soc. 132(6) 1960-1965 (2010).
Walker, M.A., "The Mitsunobu Reaction: A Novel Method for the Synthesis of Bifunctional Maleimide Linkers" Tetrahedron Letters 35(5): 665-668 (1994).
Written Opinion, Intellectual Property Office of Singapore, dated Aug. 14, 2015 corresponding to Singapore Patent Application No. 11201406252W (11 pages).
Neri, D. et al. (2006)."Efforts Toward the Total Synthesis of Tubulysins: New Hopes for a More Effective Targeted Drug Delivery to Tumors," ChemMedChem, 1:175-180.
Non-Final Office Action, dated Apr. 5, 2023, for U.S. Appl. No. 17/111,982, filed Dec. 4, 2020, 16 pages.

* cited by examiner

DRUG CONJUGATES WITH SELF-STABILIZING LINKERS HAVING IMPROVED PHYSIOCHEMICAL PROPERTIES

CROSS-REFERENCE TO RELATED APPLICATION

This application is a U.S. national stage filing under 35 USC § 371 of International Application No. PCT/US2017/046157, filed Aug. 9, 2017, which claims the benefit of U.S. provisional application Ser. No. 62/372,455, filed on Aug. 9, 2016, which is incorporated by reference herein in its entirety.

BACKGROUND OF THE INVENTION

This invention relates to Ligand-Drug Conjugates for targeted delivery of biologically active compounds or derivatives thereof at or within abnormal cells associated with a given disease state or to the vicinity of such cells. The targeting moiety of such a Conjugate, referred herein as its Ligand Unit (L), selectively exposes abnormal cells, in contrast to normal cells that are distant from the abnormal cells, to the biologically active compound or its derivative so as to exert a therapeutic effect. That selective exposure is accomplished by directing the compound or its derivative to the desired site of action as a result of selective binding of the Ligand Unit to the abnormal cells or to other targeted sites in the vicinity of these cells. As a result, exposure of the distant normal cells to the biologically active compound or its derivative is reduced, thus reducing undesired side effects, while reducing the contribution of the targeted abnormal cells to the disease state.

In general, the design of an Ligand Drug Conjugate (LDC) involves consideration of a variety of factors including the requirement that in order for a biologically active compound or derivative thereof to become a Drug Unit of a LDC that compound or a precursor thereof requires a suitable site for attachment to a linker, referred herein as a Linker Unit (LU), which joins the Drug Unit to the Ligand Unit in the form of a drug linker moiety and is capable of releasing the Drug Unit as the biologically active compound or derivative thereof at the targeted site. The Linker Unit of a LDC is one important feature for improving the delivery of a biologically active compound or its derivative to, or within the vicinity of, abnormal cells in a therapeutically effective amount so that the targeted compound is better tolerated than if the compound had been administered in unconjugated form. An electrophilic maleimide moiety in a Linker Unit of a Drug Linker compound, which can be used in the preparation of a LDC, has proven to be very useful due to its high degree of specificity for reacting with thiol functional groups (eqn. 1) of a targeting agent. For example, a cysteine residue that is native to or introduced into an antibody and is solvent accessible typically exhibits very fast kinetics for conjugate addition (Michael addition) of its thiol functional group to the maleimide moiety. That addition occurs under sufficiently mild conditions consistent with the sensitivity of antibodies and other peptide-based targeting agents towards denaturation and/or degradation. A Conjugate in which an antibody is the targeting agent that becomes an antibody Ligand Unit by that or any other manner is known as an Antibody Drug Conjugate (ADC).

In equations 1 and 2, L is a Ligand Unit, LU' is the remainder of the Linker Unit and D is a Drug Unit incorporating the biologically active compound or its derivative. When that compound has a tertiary amine as the site of conjugation, the Drug Unit from that compound is quaternized as represented by $D^+$ replacing D in those equations.

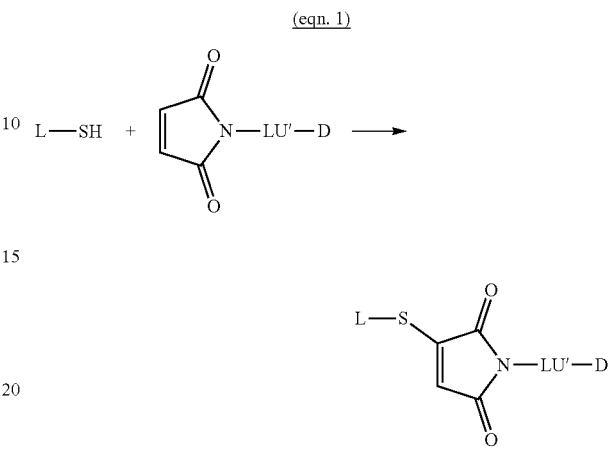

(eqn. 1)

As has been noted by investigators in the bioconjugate field, the thio-substituted product of the reaction between the electrophilic maleimide moiety and a sulfur atom of a free thiol functional group of an antibody is subject to slow elimination, thus reversing the above reaction. When this type of reversible reaction occurs in a purified preparation of an ADC, or other LDC prepared in similar manner, the reaction may be undetectable because the maleimide and thiol functional groups, which are regenerated through the elimination process, can simply react again, thus reforming, to some extent, the intact Conjugate. However, when other thiol functional groups are present, the net effect can be the transfer of a maleimide-containing drug linker moiety that is so liberated from the LDC onto any other available moiety have a reactive thiol functional group. As a result, that drug linker moiety is permanently lost, resulting in reduced effectiveness of the LDC and possible off-target effects due untethering of its Drug Unit. That unconjugation by retro-Michael addition has been documented to occur in plasma in which the drug linker moiety of an ADC transfers to cysteine 34 of serum albumin (Alley et al., *Bioconjugate Chem.* 2008, 19, 759-765). That unconjugation has also been reported when an ADC is incubated in the presence of excess cysteine or glutathione (Shen et al., *Nature Biotech.,* 30(2): 184-9, 2012).

A prior solution to the problem of premature loss of a drug linker moiety from a Ligand Drug Conjugate due to retro-Michael addition is described in WO 2013/17337 2013/173337. That solution employs an acyclic basic substituent as a component of the Linker Unit, henceforth referred to as an acyclic Basic Unit (aBU). In one such solution, the acyclic Basic Unit is placed on a carbon atom of an alkylene moiety attached to imide nitrogen of a maleimide moiety in a Drug Linker compound so that once conjugate addition by a thiol functional group of a targeting agent to the maleimide moiety occurs to provide a Ligand Drug Conjugate, the resultant thio-substituted succinimide ring system undergoes sufficiently rapid hydrolysis to a ring-opened form(s). Without being bound by theory, it is believed the rapid hydrolysis of the thio-substituted succinimide moiety precludes or reduces drug linker loss through retro-Michael addition, which would cause the Drug Unit of the Conjugate to be deconjugated, in comparison to a corresponding Ligand Drug Conjugate not having the acyclic Basic Unit. Without being bound by theory, those ring-opened forms, referred to as succinic acid amides (e.g., eqn. 2), are believed to be resistant to retro-Michael addition due to their increased conformational flexibility. As a result of that latent resistance, Linker Units in Ligand Drug Conjugate compounds having that characteristic of rapid hydrolysis are referred to as self-stabilizing, while Linker Units in Ligand Drug Conjugates compounds that have hydrolyzed to the ring opened forms are referred to as self-stabilized.

(eqn. 2)

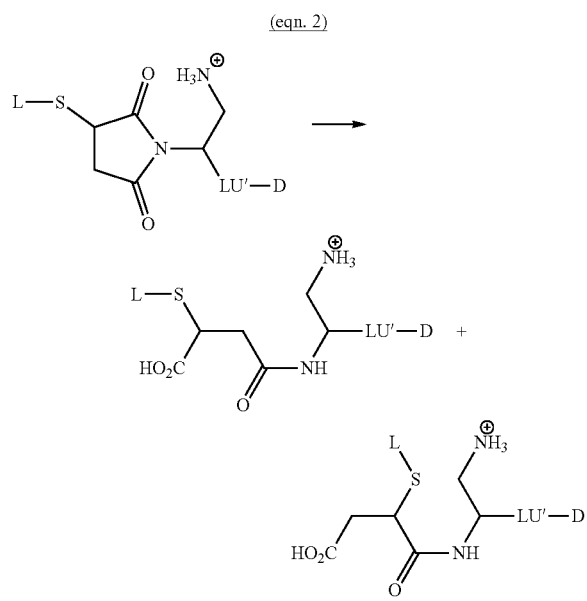

It has been unexpectedly found that the stereochemistry of the carbon to which an acyclic Basic Unit is attached in some instances can have a deleterious influence on release kinetics of the conjugated biologically active compound or derivative thereof. It has also been unexpectedly found that loss of stereochemical integrity at the site of attachment of an acyclic Basic Unit in a Drug Linker compound can occur prior and/or subsequent to its conjugation to a Linker Unit. Aside from any negative effect that it may have on conditional release of the biologically active compound or derivative thereof at the desired site of action from a Ligand Drug Conjugate prepared from that Drug Linker compound, loss of stereochemical control presents problems for manufacturing attributable to heterogeneity in the resulting drug linker moieties of the Ligand Drug Conjugate. The present invention provides, inter alia, solutions to both of those previously unknown problems with self-stabilizing Linker Units.

SUMMARY OF THE INVENTION

Principle embodiments of the invention are Ligand Drug Conjugate (LDC) compositions that are represented by Formula 1 and/or Formula 2.

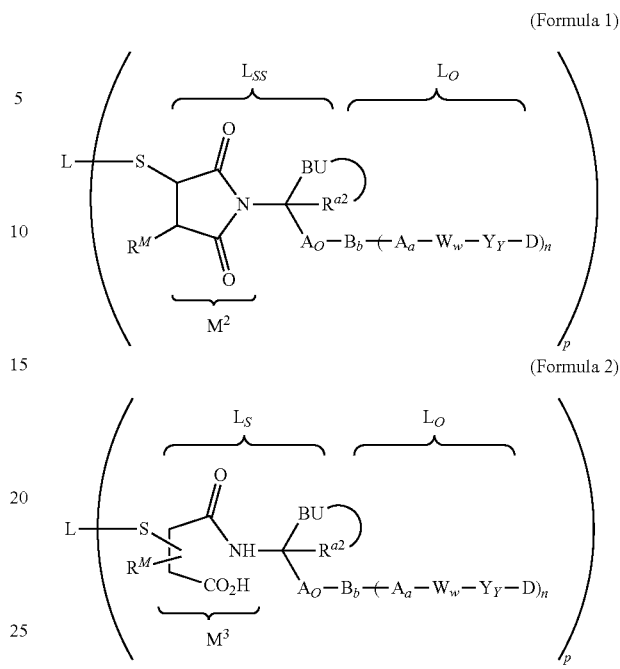

or pharmaceutically acceptable salt(s) thereof, wherein L is a Ligand Unit, S is a sulfur atom of the Ligand Unit, which in Formula 2 is bonded to the carbon α or β to the shown carboxylic acid functional group of its succinic acid amide ($M^3$) moiety; $R^M$ is hydrogen or an optionally substituted $C_1$-$C_6$ alkyl, which in Formula 2 is bonded to the saturated carbon adjacent to the carbon substituted by L-S—, subscripts a and b independently are 0 or 1, indicating the absence or presence, respectively, of A or B; subscript n is 1, 2, 3 or 4; A is a first optional Stretcher; $A_O$ is a second optional Stretcher Unit; B is a Branching Unit, when subscript b is 1 and subscript n is 2, 3 or 4, or B is absent, so that subscript b is 0, when subscript n is 1; wherein each of A, $A_O$ and B is an independently selected single unit or is optionally comprised or consists of two, three or four independently selected subunits; subscript w is 0 or 1, indicating the absence or presence, respectively, of W; subscript y is 0, 1 or 2, indicating the absence or presence of one or two of Y, respectively, wherein Y is a Spacer Unit, or an optionally substituted heteroatom or functional group, independently selected when subscript y is 2 so that $Y_y$ is —Y—Y'—, wherein Y' is a second optionally substituted heteroatom or functional group, or a second independently selected Spacer Unit; and W is a Peptide Cleavable Unit or a Glucuronide Unit of formula —Y(W')— when subscript w is 1, wherein W' represents a carbohydrate moiety with glycosidic bonding to Y through a optionally substituted heteroatom, provided Y bonded to W' is required to be a first self-immolative Spacer Unit; subscript y is 0, 1 or 2, provided subscript y is 1 and Y is a self-immolative Spacer Unit bonded to D and W when D is a quaternized Drug Unit ($D^+$) and W is a Peptide Cleavable Unit, and provided subscript y is 1 or 2, when W is a Glucuronide Unit, in which instance subscript y is inclusive of the required self-immolative Spacer Unit, provided that subscript y is 1 and Y is a self-immolative Spacer Unit bonded to D when D is a quaternized Drug Unit ($D^+$);

BU is a Basic Unit and $R^{a2}$ is an optionally substituted $C_1$-$C_{12}$ alkyl group that together with the carbon atom to which both are attached, as represented by the solid curved line, define a cyclic Basic Unit having an optionally substituted spiro $C_3$-$C_{20}$ heterocyclo containing a basic skeletal secondary or tertiary nitrogen atom, an optionally substituted spiro $C_3$-$C_{20}$ carbocyclo with exocyclic substitution by an optionally substituted basic nitrogen of a secondary or tertiary amine, or an optionally substituted spiro $C_3$-$C_{20}$ carbocyclo having exocyclic substitution by an optionally substituted $C_1$-$C_{12}$ aminoalkyl in which the optionally substituted nitrogen atom of the amino moiety of the aminoalkyl is that of a basic primary, secondary or tertiary amine, wherein the optionally substituted basic nitrogen atom of the exocyclic amine or aminoalkyl along with its optionally substituted alkyl moiety is attributable to BU; and wherein the basic skeletal secondary amine nitrogen, or the basic nitrogen of the exocyclic primary or secondary amine or aminoalkyl, is optionally protonated or suitably protected by a nitrogen protecting group, and wherein the basic skeletal tertiary amine nitrogen or the basic nitrogen of the exocyclic tertiary amine or aminoalkyl is optionally protonated, or BU is a Basic Unit and $R^{a2}$ is an optionally substituted $C_1$-$C_{12}$ alkyl formally cyclized to the basic nitrogen atom of an acyclic Basic Unit of corresponding structure to that of Formula 1 and/or Formula 2 in which the solid curved lined between BU and $R^2$ is absent, or to a carbon atom of an optionally substituted $C_1$-$C_{12}$ alkylene bearing that basic nitrogen atom, both of which comprise the acyclic Basic Unit, thus forming an optionally substituted spiro $C_3$-$C_{20}$ heterocyclo incorporating the basic nitrogen as a skeletal heteroatom, or an optionally substituted $C_3$-$C_{20}$ carbocyclo substituted directly by the basic nitrogen atom, or substituted indirectly by the basic nitrogen atom through an optionally substituted $C_1$-$C_{12}$ alkylene remaining from said formal cyclization and whose structure is dependent on the site of cyclization, so in either instance a cyclic Basic Unit (cBU) is defined, as indicated by the solid curved line; and wherein the basic amine nitrogen is optionally protonated or suitably protected by a nitrogen protecting group, dependent on the degree of substitution of the basic nitrogen upon formal cyclization; and D is a Drug Unit or a quaternized Drug Unit represented as $D^+$ so that $D^+$ replaces D in Formula 1 and Formula 2; subscript p is an average drug linker moiety loading when subscript n is other than 1 or an average drug loading when subscript n is 1, wherein subscript p in either instance is a number ranging from 1 to 24; wherein when subscript w is 1, which indicates the presence of a Cleavable Unit, enzymatic or non-enzymatic cleavage of that Unit initiates release of a biologically active compound or derivative thereof from a Ligand Drug Conjugate compound of the composition, or when subscript w is 0, which indicates the absence of a Cleavable Unit, enzymatic or non-enzymatic cleavage of the bond between the indicated $L_{SS}$ and $L_O$ moieties in Formula 1 or the bond between the indicated $L_S$ and $L_O$ moieties in Formula 2, when $L_O$ is present, wherein $L_{SS}$ is a self-stabilizing linker, $L_S$ is a self-stabilized linker and $L_O$ is an optional secondary linker, or the bond between $L_{SS}$ or $L_S$ and D, when $L_O$ is absent, initiates release of D or $D^+$ as a biologically active compound or derivative thereof from a Ligand Drug Conjugate compound of the composition, wherein the Ligand Drug Conjugate compound corresponds in structure to that of Formula 1 or Formula 2 in which p is replaced by p', wherein p' is an integer ranging from 1 to 24.

In some aspects, $A_O$ is present and is comprised or consists of a Hydrolysis Enhancing [HE] Unit and W is a Peptide Cleavable Unit and subscript y is 0, 1 or 2, or W is a Glucuronide Unit of structure —Y(W')—, so that subscript y is 1 or 2 in Formula 1, Formula 2, wherein Y is a self-immolative Spacer Unit and W' is a carbohydrate moiety (Su) with attachment to Y by glycosidic bonding through an optionally substituted heteroatom (E') wherein $D/D^+$ is attached directly to Y when subscript y is 1 or D is attached indirectly to Y through bonding to a second Spacer Unit designated Y' when subscript y is 2.

In some of those aspects in which subscript y is 2, Y and Y' are both self-immolative Spacer Units, which undergo self-immolation upon enzymatic processing of the Peptide Cleavable Unit or Glucuronide Unit as, for example, when one self-immolative Spacer Unit (Y) is capable of 1,4- or 1,6-elimination and the other self-immolative Spacer Unit (Y') is a methylene carbamate unit or a carbamate functional group capable of $CO_2$ elimination as described herein.

In other aspects, only one Y of $Y_y$ undergoes self-immolation upon conditional enzymatic processing of the Peptide or Glucuronide Unit to release D, when subscript y is 1, or to release Y'-D, when subscript y is 2, as a biologically active compound or derivative thereof, which sometimes are referred to as a drug compound or active drug moiety, respectively. In some of those aspects Y' of —Y'-D also can undergo self-immolation to release D as a biologically active compound or derivative thereof. In still other aspects, W is a Cleavable Unit that is not reliant upon enzymatic cleavage for release of the biologically active compound or derivative thereof and in some instances is acted upon non-enzymatically for that release.

In preferred aspects, the functionality of BU in acyclic form to effect self-stabilization of a corresponding Ligand Drug Conjugate composition by conversion of Formula 1 to Formula 2 in which the curved dashed line is not present is substantially retained by cBU in a majority of compounds in the LDC composition of Formula 1 in which the curved dashed line is present.

In other preferred aspects, the targeting moiety of the Ligand Drug Conjugate is that of an antibody, sometimes referred to as an antibody Ligand Unit, thereby defining an Antibody Drug Conjugate (ADC) composition, and the targeted moiety recognized by its antibody Ligand Unit is an cell-surface antigen of targeted abnormal cells or normal cells peculiar to and in the vicinity of the abnormal cells, wherein the antigen so bound from said recognition in some aspects is capable of cellular internalization of a Conjugate compound of the ADC composition, wherein the antigen is preferentially present on the abnormal cells or nearby normal cells in comparison to normal cells distant from the abnormal cells.

In any one of those preferred aspects, the released biologically active compound or derivative thereof exerts a therapeutic effect due to its biological activity at the desired site of action.

Other principle embodiments of the invention provide for compounds having the structure of Formula I:

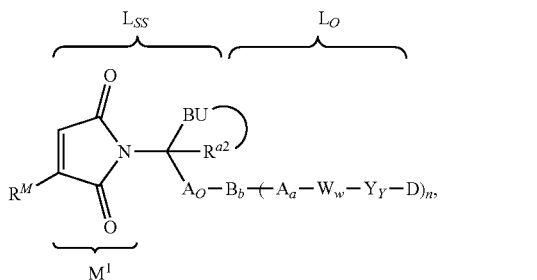

(Formula I)

wherein $L_{SS}$, as indicated, is a self-stabilizing primary linker, $L_O$, as indicated, is an optional secondary linker and wherein the variable groups of Formula I are as defined for Formula 1.

In any one of the above aspects in which BU is cyclized to $R^{a2}$ though its basic amine nitrogen so that a cyclized Basic Unit (cBU) having a skeletal secondary nitrogen atom is defined, the secondary amine functional group from cyclization to that heteroatom may be suitably protected or may be in protonated form. In any one of the above aspects when BU is cyclized to $R^{a2}$ though its basic nitrogen atom so that a cBU having a tertiary amine functional group is defined, that amine functional group may be in protonated form.

In any one of the above aspects in which an acyclic Basic Unit (aBU) is formally cyclized to $R^{a2}$ through its optionally substituted $C_1$-$C_{12}$ alkyl moiety, that alkylene moiety is incorporated in whole or in part into an optionally substituted spiro $C_3$-$C_{20}$ carbocyclo having substitution by a basic amine functional group attributable to aBU through its basic nitrogen atom, directly or indirectly through any intervening optionally substituted acyclic alkylene moiety remaining from said incorporation, wherein the basic amine nitrogen atom is that of a primary, secondary, or tertiary amine functional group, thus defining a cyclic Basic Unit (cBU) in which the degree of substitution of the basic amine nitrogen of that functional group prior to said formal cyclization is retained, wherein that basic amine functional group may be in protected or protonated form, dependent on the degree of substitution of its basic nitrogen atom.

In other aspects, the invention provides for Ligand Drug Conjugate compositions prepared from contacting a Formula I compound with a targeting agent having a reactive thiol functional group under suitable conditions to effect condensation of a sulfur atom of that functional group with its maleimide moiety so as to provide a composition represented by the structure of Formula 1, which converts in whole or at least in part to Formula 2.

DETAILED DESCRIPTION OF THE INVENTION

Definitions

Figure 1:
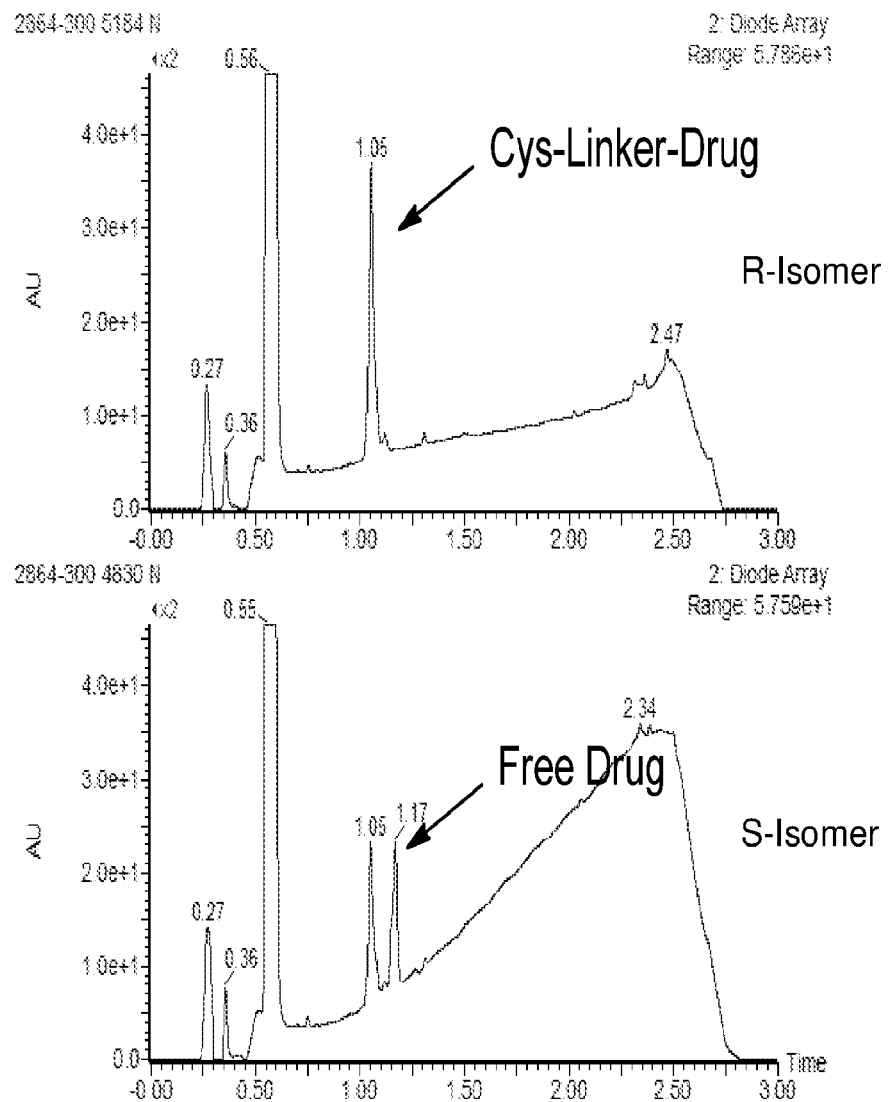
FIG. 1. Differential in vitro kinetics for Auristatin T Drug Unit release from Cysteine Drug Conjugates acting as surrogate Ligand Drug Conjugates of Formula 2, wherein release is initiated by exposure to the protease Cathepsin B, and wherein the Conjugates have a glu-dpr-Peptide Cleavable Unit, which is cleavable by the protease, and self-stabilized Linker Units comprised of an acyclic Basic Unit and succinic acid amide ($M^3$) moieties, the latter of which result from prior hydrolysis of the succinimide ($M^2$) moieties of their Formula 1 precursors, wherein the Conjugates differ in the stereochemical configuration of the carbon to which the acyclic Basic Unit is attached.

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions or methods that consist of or consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, use of the term "including", as well as other forms such as "include", "includes," and "included", is not limiting. Finally, the term "consisting essentially of" admits for the inclusion of unrecited elements that have no discernable material effect on the functionality of the disclosed compositions, devices, articles of manufacture or methods for its intended purpose and is further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques and pharmacology are employed.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values may vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values, typically by 10% to 0.5%, more typically by 5% to 1%, while still describing the particular property.

With respect to subscript p, which denotes the average number of drug linker moieties in a Ligand Drug Conjugate composition as further defined herein, the term "about" reflects the accepted uncertainty in the art for determining that value from a distribution of Ligand Drug Conjugate compounds within that composition as determined by standard methods of size exclusion or HIC chromatography or HPLC-MS.

"Essentially retains", "essentially retaining" and like terms as used herein refers to a property, characteristic, function or activity of a compound, composition or moiety thereof that has not detectably changed or is within experimental error of determination of that same activity, characteristic or property of a compound, composition or moiety of related structure.

"Substantially retains", "substantially retaining" and like terms as used herein refers to a measured value of a physical property or characteristic of a compound, composition or moiety thereof that is statistically different of the determination of that same physical property of another compound, composition or moiety of related structure, but which such difference does not translate to a statistically significant or meaningful difference in biological activity or pharmacological property in a suitable biological test system for evaluating that activity or property so that the biological activity or property is deemed to be essentially retained. Thus the phrase "substantially retains" is made in reference to the effect that a physical property or characteristic of a compound or composition has on a physiochemical or pharmacological property or biological activity that is explicitly associated with that physical property or characteristic. In some aspects, Linker Units in a majority of compounds in a Ligand Drug Conjugate composition having a cyclic Basic Unit substantially retains the property of self-stabilization in a suitable test system within a majority of compounds in a Ligand Drug Conjugate composition having a corresponding acyclic Basic Unit by exhibiting hydrolysis kinetics for conversion of the succinimide moiety of the Linker Units of the Conjugate compounds to corresponding succinic acid amide(s), for which said hydrolysis provides for self-stabilized Linker Units, by exhibiting a rate of hydrolysis that effectively competes with drug linker loss through retro-Michael addition.

"Negligibly" or "negligible" as used herein is an amount of an impurity below the level of quantification by HPLC analysis and if present represents from about 0.5% to about 0.1 w/w % or less of the composition that it contaminates. Depending on context those terms may also mean that no statistically significant difference is observed between measured values or outcomes or within experimental error of the instrumentation used to obtain those values. Negligible differences in values of a parameter determined experimentally do not imply that an impurity characterized by that parameter is present in negligible amount.

"Predominately containing", "predominately having" and like terms as used herein refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

The term "electron-withdrawing group" as the term is used herein refers to a functional group or electronegative atom that draws electron density away from an atom to which it is bonded either inductively and/or through resonance, whichever is more dominant (i.e. a functional group or atom may be electron donating through resonance but may overall be electron withdrawing inductively), and tends to stabilize anions or electron rich moieties. The electron withdrawing effect is typically transmitted inductively, albeit in attenuated form, to other atoms attached to the bonded atom that has been made electron deficient by the electron withdrawing group (EWG) thus reducing the electron density of a more remote reactive center.

Exemplary electron withdrawing groups include, but are not limited to —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^{op}$)$_2$, —NO, —NH$_2$, —N(R')(R$^{op}$), —N(R$^{op}$)$_3$$^+$, and salts thereof, wherein X is —F, —Br, —Cl, or —I, and R$^{op}$ is, at each occurrence, independently selected from a group described herein for optional substituents and in some aspects are independently selected from the group consisting of C$_1$-C$_6$ alkyl and phenyl, and wherein R' is hydrogen or R$^{op}$ selected from a group as described elsewhere for optional substituents and in some aspects is a C$_1$-C$_{12}$ alkyl or C$_1$-C$_6$ alkyl. Exemplary EWGs can also include aryl groups (e.g., phenyl) depending on substitution and certain heteroaryl groups (e.g., pyridine). Thus, the term "electron withdrawing groups" also includes aryls or heteroaryls that are further substituted with electron withdrawing groups. In some aspects an electron withdrawing group is selected from the group consisting of —C(=O), —CN, —NO$_2$, —CX$_3$, and —X, wherein X is halogen. Depending on its substituents, an optionally substituted alkyl moiety may also be an electron withdrawing group. In some aspects, an electron withdrawing group is a substituent of a Glucuronide Unit that increases the glycosidase cleavage rate of that Unit in a Drug Linker compound or Ligand Drug Conjugate when measured in a suitable in vitro enzyme assay in comparison to a corresponding Drug Linker compound or Conjugate in which the EWG is not present as a Glucuronide Unit substituent.

"Electron donating group" as the term is used herein refers to a functional group or electropositive atom that increases electron density of an atom to which it is bonded either inductively and/or through resonance, whichever is more dominant (i.e., a functional group or atom may be electron withdrawing inductively but may overall be electron donating through resonance), and tends to stabilize cations or electron poor systems. The electron donating effect is typically transmitted through resonance to other atoms attached to the bonded atom that has been made electron rich by the electron donating group (EDG) thus increasing the electron density of a more remote reactive center. Exemplary electron donating groups include, but are not limited to, —OH, —OR', —NH$_2$, —NHR' and N(R')$_2$, wherein each R' is an independently selected C$_1$-C$_{12}$ alkyl, typically C$_1$-C$_6$ alkyl. Depending on its substituents, an aryl, heteroaryl or unsaturated alkyl moiety may also be an electron donating group. In some aspects, an electron donating group is a substituent of PAB or PAB-type self-immolative Spacer Unit that accelerates its fragmentation on activation through stabilization of the quinone methide byproduct.

"Compound" as the term is used herein, refers to and encompasses the chemical compound itself, either named or represented by structure, and salt form(s) thereof, whether explicitly stated or not, unless context makes clear that such salt forms are to be excluded. Compound salts include zwitterionic salt forms and acid addition and base addition salt forms having organic counterions or inorganic counterions and salt forms involving two or more counterions, which may be the same or different. In some aspects, the salt form is a pharmaceutically acceptable salt form of the compound. The term "compound" further encompasses solvate forms of the compound, in which solvent is noncovalently associated with the compound or is reversibly associated covalently with the compound, as when a carbonyl group of the compound is hydrated to form a gem-diol. Solvate forms include those of the compound itself and its salt form(s) and are inclusive of hemisolvates, monosolvates, disolvates, including hydrates; and when a compound can be associated with two or more solvent molecules, the two or more solvent molecules may be the same or different. In some instances, a compound of the invention will include an explicit reference to one or more of the above forms, e.g., salts and solvates, which typically does not imply solid state forms of the compound; however, this reference is for emphasis only, and is not to be construed as excluding any other of the forms as identified above. Furthermore, when explicit reference to a salt and/or solvate form of a compound or a Ligand Drug Conjugate composition is not made, that omission is not to be construed as excluding the salt and/or solvate form(s) of the compound or Conjugate unless context make clear that such salt and/or solvate forms are to be excluded.

"Moiety" as used herein means a specified segment, fragment or functional group of a molecule or compound. Chemical moieties are sometimes indicated as chemical entities that are embedded in or appended to (i.e., a substituent or variable group) a molecule, compound or chemical formula.

For any substituent group or moiety described herein by a given range of carbon atoms, the designated range means that any individual number of carbon atoms is described. Thus, reference to, e.g., "optionally substituted $C_1$-$C_4$ alkyl", "optionally substituted alkenyl $C_2$-$C_6$ alkenyl specifically means that a 1, 2, 3 or 4 carbon alkyl moiety, optionally substituted, as defined herein is present, or a 2, 3, 4, 5 or 6 carbon alkenyl, or a 3, 4, 5, 6, 7 or 8 carbon alkenyl moiety, optionally substituted, as defined herein is present. All such numerical designations are expressly intended to disclose all of the individual carbon atom groups; and thus "optionally substituted $C_1$-$C_4$ alkyl" includes, methyl, ethyl, 3 carbon alkyls, and 4 carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents of that base moiety. For esters, carbonates, carbamates and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are referred to as carbocyclyls as defined herein.

When referring to an alkyl moiety or group as an alkyl substituent, that alkyl substituent to a Markush structure or another organic moiety with which it is associated is methyl or that chain of contiguous carbon atoms covalently attached to the structure or moiety through a $sp^3$ carbon of the alkyl substituent. An alkyl substituent, as used herein, therefore contains at least one saturated moiety and may also be optionally substituted with cycloalkyl or aromatic or heteroaromatic moieties or groups or by an alkenyl or alkynyl moiety resulting in an unsaturated alkyl. Thus, an optionally substituted alkyl substituent may additionally contain one, two, three or more independently selected double bonds and/or triple bonds or may be substituted by alkenyl or alkynyl moieties or some combination thereof to define an unsaturated alkyl substituent and may be substituted by other moieties that include appropriate optional substituents as described herein. The number of carbon atoms in a saturated or unsaturated alkyl moiety or group can vary and typically is 1-50, 1-30 or 1-20, and more typically is 1-8 or 1-6.

A saturated alkyl moiety contains saturated, acyclic carbon atoms (i.e., acyclic $sp^3$ carbons) and no $sp^2$ or sp carbon atoms, but may be substituted with an optional substituent as described herein, provided that such substitution is not through an $sp^3$, $sp^2$ or sp carbon atom of the optional substituent as that would affect the identity of the base alkyl moiety so substituted. Unless otherwise indicated or implied by context, the term "alkyl" will indicate a saturated, non-cyclic hydrocarbon radical, wherein the hydrocarbon radical has the indicated number of covalently linked saturated carbon atoms so that terms such as "$C_1$-$C_6$ alkyl" or "C1-C6 alkyl" means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms. Typically a saturated alkyl is a $C_1$-$C_6$ or $C_1$-$C_4$ alkyl moiety with the latter sometimes referred to as lower alkyl and in some aspects will refer to a saturated $C_1$-$C_8$ alkyl moiety having from 1 to 8 contiguous acyclic $sp^3$ carbon atoms when the number of carbon atoms is not indicated.

When an alkyl substituent, moiety or group is specified, species include those derived from removing a hydrogen atom from a parent alkane (i.e., an alkyl moiety is monovalent) and may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as used herein, by itself of as part of another term, unless otherwise stated or implied by context, refers to a saturated, branched, cyclic or straight chain hydrocarbon diradical, substituted or unsubstituted, wherein one or more of the carbon atoms is unsaturated (i.e., is comprised of one or more sp$^3$ carbons), of the stated number of carbon atoms, typically 1-10 carbon atoms, and having two radical centers (i.e., is divalent) derived by the removal of two hydrogen atoms from the same or two different saturated (i.e., sp$^3$) carbon atoms of a parent alkane. Alkylene moieties further include alkyl radicals as described herein in which a hydrogen atom has been removed from another of its saturated carbons or from the radical carbon of an alkyl radical to form a diradical. Typically, alkylene moieties include, but are not limited to, divalent moieties derived from removing a hydrogen atom from a saturated carbon atom of a parent alkyl moiety and are exemplified by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon typically containing only sp$^3$ carbons (i.e., is fully saturated notwithstanding the radical carbon atoms).

"Carbocyclyl" as used herein, by itself of as part of another term, unless otherwise stated or implied by context, refers to a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more sp$^3$ carbons). Thus, a carbocyclyl is a cyclic arrangement of saturated carbons but may also contain unsaturated carbon atom(s) and therefore its carbocyclic ring may be saturated or partially unsaturated or may be fused with an aromatic moiety, wherein the points of fusion to the cycloalkyl and aromatic rings are to adjacent unsaturated carbons of the carbocyclyl moiety and adjacent aromatic carbons of the aromatic moiety.

Unless otherwise specified, a carbocyclyl can be substituted (i.e. optionally substituted) with moieties described for alkyl, alkenyl, alkynyl, aryl, arylalkyl, alkylaryl and the like or can be substituted with another cycloalkyl moiety. Cycloalkyl moieties, groups or substituents include cyclopropyl, cyclopentyl, cyclohexyl, adamantly or other cyclic moieties that have only carbon atoms in their cyclic ring systems.

When carbocyclyl is used as a Markush group (i.e., a substituent) the carbocyclyl is attached to a Markush formula or another organic moiety with which it is associated through a carbon that is involved in the carbocyclic ring system of the carbocyclyl moiety provided that carbon is not an aromatic carbon. When an unsaturated carbon of an alkene moiety comprising the carbocyclyl substituent is attached to a Markush formula with which it is associated that carbocyclyl is sometimes referred to as a cycloalkenyl substituent. The number of carbon atoms in a carbocyclyl substituent is defined by the total number of skeletal atoms of its carbocyclic ring system. That number can vary and typically ranges from 3 to 50, 1-30 or 1-20, and more typically 3-8 or 3-6 unless otherwise specified, e.g., C$_3$-C$_8$ carbocyclyl means an carbocyclyl substituent, moiety or group containing 3, 4, 5, 6, 7 or 8 carbocyclic carbon atoms and C$_3$-C$_6$ carbocyclyl means an carbocyclyl substituent, moiety or group containing 3, 4, 5 or 6 carbocyclic carbon atoms. A carbocyclyl may be derived by the removal of one hydrogen atom from a ring atom of a parent cycloalkane or cycloalkene. Representative C$_3$-C$_8$ carbocyclyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3 or 4 carbon atoms, typically 2 or 3.

"Carbocyclo," by itself or as part of another term, unless otherwise stated or implied by context, refers to a carbocyclyl as defined above wherein another hydrogen atom of it cycloalkyl ring is replaced with a bond (i.e., it is divalent) and typically is a C$_3$-C$_{10}$ carbocycle, C$_3$-C$_8$ carbocyclo or C$_3$-C$_6$ carbocyclo, more typically a C$_3$, C$_5$ or C$_6$ carbocyclo. In some aspects, the replaced second hydrogen is that of the monovalent carbon atom of the parent cycloalkyl thus forming a spiro carbon atom, which in some instances may interrupt an alkyl moiety with that carbocyclic carbon atom. In such instances, the spiro carbon atom is attributed to the carbon atom count of the interrupted alkyl moiety and the carbocyclo ring system with the carbocyclo indicated as being incorporated into the alkyl moiety.

"Alkenyl" as the terms are used herein, by itself or as part of another term, unless otherwise stated or implied by context, refers to an organic moiety, substituent or group that comprises one or more double bond functional groups (e.g., a —CH=CH— moiety) or 1, 2, 3, 4, 5 or 6 or more, typically 1, 2 or 3 of such functional groups and can be substituted (i.e., optionally substituted) with an aryl moiety or group such as phenyl, or linked normal, secondary, tertiary or cyclic carbon atom(s), i.e., linear, branched, cyclic or any combination thereof unless the alkenyl substituent, moiety or group is a vinyl moiety (e.g., a —CH=CH$_2$ moiety). An alkenyl moiety, group or substituent having multiple double bonds may have the double bonds arranged contiguously (i.e., a 1,3 butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

When an alkenyl moiety, group or substituent is specified, species include, by way of example and not limitation, any of the optionally substituted alkyl or carbocyclyl, groups moieties or substituents described herein that has an one or more endo double bonds and monovalent moieties derived from removal of a hydrogen atom from a sp$^2$ carbon of a parent alkene compound. Such monovalent moieties typically include vinyl (—CH=CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, and other linear, cyclic and branched chained, all carbon-containing moieties containing at least one double bond functional group. When alkenyl is used as a Markush group (i.e., is a substituent) the alkenyl moiety is attached to a Markush formula or another organic moiety with which it is associated through a double-bonded carbon (i.e., a sp$^2$ carbon) of an alkene functional group of the alkene moiety. The number of carbon atoms in an alkenyl substituent is defined by the number of $sp^2$ carbon atoms of the alkene functional group that defines it as an alkenyl substituent and the total number of contiguous non-aromatic carbon atoms appended to each of these $sp^2$ carbons not including any carbon atom of the larger moiety or Markush structure for which the alkenyl moiety is a variable group. That number can vary and unless otherwise specified ranges from 1 to 50, e.g., typically 1 to 30 or 1 to 20, more typically 1 to 8 or 1 to 6, when the double bond functional group is doubly bonded to a Markush structure (e.g. =CH$_2$), or can vary and unless otherwise specified ranges from 2 to 50, typically 2 to 30 or 2 to 20, more typically 2 to 8 or 2 to 6, when the double bond functional group is singly bonded to the Markush structure (e.g., —CH=CH$_2$). For example, $C_2$-$C_8$ alkenyl or C2-C8 alkenyl means an alkenyl moiety containing 2, 3, 4, 5, 6, 7 or 8 carbon atoms in which at least two are $sp^2$ carbons in conjugation with each other and $C_2$-$C_6$ alkenyl or C2-C6 alkenyl means an alkenyl moiety containing 2, 3, 4, 5 or 6 carbon atoms in which at least two are $sp^2$ carbons that are in conjugation with each other. Typically, an alkenyl substituent is a $C_2$-$C_6$ or $C_2$-$C_4$ alkenyl moiety having only two $sp^2$ carbons that are in conjugation with each other.

"Alkenylene" as used herein, by itself of as part of another term, unless otherwise stated or implied by context, refers to a an organic moiety, substituent or group that comprises one or more double bond moieties, as previously described for alkenyl, of the stated number of carbon atoms, typically 1 to 10 carbon atoms when a double bond functional group of the alkenylene is doubly bonded to a larger organic moiety or 2 to 10 carbon atoms when a double bond functional group of the alkenylene is singly bonded to a larger organic moiety and has two radical centers derived by the removal of two hydrogen atoms from the same or two different $sp^2$ carbon atoms of an alkene functional group in a parent alkene. Alkenylene moieties also include alkenyl radicals as described herein in which a hydrogen atom has been removed from the same or different $sp^2$ carbon atom of a double bond functional group of an alkenyl radical to form a diradical, or from a $sp^2$ carbon from a different double bonded moiety to provide another radical carbon. Typically, alkenylene moieties include diradicals having the structure of —C=C— or —C=C—X$^1$—C=C— wherein X$^1$ is absent or is an alkylene as defined herein. The number of carbon atoms in an alkenylene moiety is defined by the number of $sp^2$ carbon atoms of its alkene functional group(s) that defines it as an alkenylene moiety and the total number of contiguous non-aromatic carbon atoms appended to each of its $sp^2$ carbons not including any carbon atoms of the larger moiety or Markush structure in which the alkenyl moiety is a present as a variable group. That number can vary and unless otherwise specified ranges from 2 to 50, typically 2-30 or 2-20, more typically 2 to 8 or 2-6. For example, $C_2$-$C_8$ alkenylene or C2-C8 alkenylene means an alkenylene moiety containing 2, 3, 4, 5, 6, 7 or 8 carbon atoms in which at least two are $sp^2$ carbons in conjugation with each other and $C_2$-$C_6$ alkenylene or C2-C6 alkenylene means an alkenyl moiety containing 2, 3, 4, 5 or 6 carbon atoms in which at least two are $sp^2$ carbons that are in conjugation with each other. Typically, an alkenylene substituent is a $C_2$-$C_6$ or $C_2$-$C_4$ alkenylene having only two $sp^2$ carbons that are in conjugation with each other.

"Aryl" as the terms are used herein, by itself or as part of another term, unless otherwise stated or implied by context, refers to an organic moiety, substituent or group defined by an aromatic ring system or a fused ring system with no ring heteroatoms comprising 1, 2, 3 or 4 to 6 aromatic rings, typically 1 to 3 aromatic rings, wherein the rings are composed of only carbon atoms that participate in a cyclically conjugated system of 4n+2 electrons (Hückel rule), typically 6, 10 or 14 electrons some of which may additionally participate in exocyclic conjugation with a heteroatom (cross-conjugated, e.g., quinone). Aryl substituents, moieties or groups are typically formed by six, eight, ten or more aromatic carbon atoms. Aryl substituents, moieties or groups are optionally substituted. Exemplary aryls include $C_6$-$C_{10}$ aryls such as phenyl and naphthalenyl and phenanthryl. As aromaticity in a neutral aryl moiety requires an even number or electrons it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group. Depending on the structure, an aryl group can be a monoradical (i.e., monovalent) or a diradical (i.e., an arylene group as described herein, which is divalent).

"Arylene," or "heteroarylene" as used herein, by itself or as part of another term, unless otherwise stated or implied by context, is an aromatic diradical moiety that forms two covalent bonds (i.e., it is divalent) within a larger moiety, which can be in the ortho, meta, or para configurations or an. Arylene and heteroarylenes include divalent species by removal of a hydrogen atom from a parent aryl moiety or group as defined herein. Heteroarylene further those in which heteroatom(s) replaces one or more but not all of the aromatic carbon atoms of a parent arylene. Exemplary arylenes include, but are not limited to, phenyl-1,2-ene, phenyl-1,3-ene, and phenyl-1,4-ene as shown in the following structures:

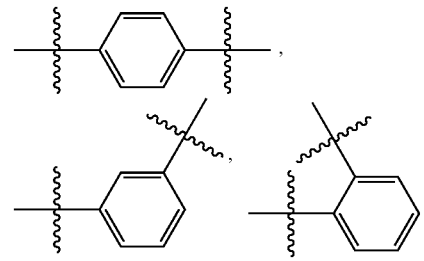

"Arylalkyl" or "heteroarylalkyl as the terms are used herein, by itself or as part of another term, refers to an aryl or heteroaryl moiety bonded to an alkyl moiety, i.e., (aryl)-alkyl-, where alkyl and aryl groups are as described above, e.g., $C_6H_5$—CH$_2$—, $C_6H_5$—CH(CH$_3$)CH$_2$— or $C_6H_5$—CH$_2$—CH(CH$_2$CH$_2$CH$_3$)—. When (hetero)arylalkyl is used as a Markush group (i.e., a substituent) the alkyl moiety of the (hetero)arylalkyl is attached to a Markush formula with which it is associated through a $sp^3$ carbon of its alkyl moiety.

"Alkylaryl" or "alkylheteroaryl" as the terms are used herein, by itself or as part of another term, unless otherwise stated or implied by context, refers to an alkyl moiety bonded to an aryl or heteroaryl moiety, i.e., -(hetero)aryl-alkyl, where (hetero)aryl and alkyl groups are as described above, e.g., —C$_6$H$_4$—CH$_3$ or —C$_6$H$_4$—CH$_2$CH(CH$_3$). When alkyl(hetero)aryl is used as a Markush group (i.e., a substituent) the (hetero)aryl moiety of the alkyl(hetero)aryl is attached to a Markush formula with which it is associated through a $sp^2$ carbon of its aryl or heteroaryl moiety.

"Heterocyclyl" as the terms is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms, optionally substituted where permitted, including N/NH, O, S, Se, B, Si, P, wherein two or more heteroatoms may be adjacent to each other or separated by one or more carbon atoms within the same ring system, typically by 1 to 3 atoms. Those heteroatoms typically include N, O or S and further include optionally substituted NH. A heterocyclyl typically contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of O, S and N/NH, with the proviso that any one ring does not contain two adjacent O or S atoms. Exemplary heterocyclyls and heteroaryls, which are defined below and together with heterocyclyls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., a substituent) a saturated or unsaturated heterocycle ring system of the heterocyclyl is attached to a Markush formula or larger moiety with which it is associated through a carbon or a heteroatom of that heterocycle ring, where such attachment does not result in an unstable or disallowed formal oxidation state of that carbon or heteroatom. A heterocyclyl in that context is a monovalent moiety in which the heterocyclic ring system defining it as a heterocyclyl is non-aromatic, but may be fused with a carbocyclic, aryl or heteroaryl ring and includes phenyl- (i.e., benzo) fused heterocycloalkyl moieties.

Typically, a heterocyclyl is a carbocyclyl wherein 1, 2 or 3 carbons of its cycloalkyl ring is replaced along with its attached hydrogens with a heteroatom selected from the group consisting of nitrogen (N/NH, optionally substituted), oxygen, and sulfur and is a $C_3$-$C_{24}$ heterocycloalkyl, more typically a $C_3$-$C_{12}$ or $C_5$-$C_{12}$ heterocycloalkyl in which the subscript indicates the total number of skeletal atoms (inclusive of its carbon atoms and heteroatoms) of the heterocyclic ring system of the heterocyclyl. Non-limiting heterocyclyls may contain 0 to 2 N atoms, 0 to 2 O atoms or 0 to 1 S atoms or some combination thereof provided at least one of said heteroatoms is present in the cyclic ring system which may be substituted with one or two oxo (=O) moieties, as in pyrrolidin-2-one. More typically, heterocycloalkyls include pyrrolidinyl, piperidinyl, morpholinyl and piperazinyl.

"Heteroaryl" as the term is used herein, by itself or as part of another term, unless otherwise stated or implied by context, refers to an aryl moiety, group or substituent as defined herein in which one or more but not all of the aromatic carbons of an aromatic ring of the aryl is replaced by a heteroatom. A heteroaryl typically contains a total one to four heteroatoms in the ring(s) of the heteroaryl ring system, provided that not all of the skeletal atoms of any one ring system in the heteroaryl are heteroatoms, optionally substituted where permitted, and have 0 to 3 N atoms, 1 to 3 N atoms or 0 to 3 N atoms, typically 0 to 1 O atoms and/or 0 to 1 S atoms, provided that at least one heteroatom is present. A heteroaryl may be monocyclic, bicyclic or polycyclic. Monocyclic heteroaryls include $C_5$-$C_{24}$ heteroaryls, typically $C_5$-$C_{12}$ or $C_5$-$C_6$ heteroaryls, in which the subscript indicates the total number of skeletal atoms (inclusive of its carbon atoms and heteroatoms) of the aromatic ring system(s) of the heteroaryl. In some aspects a heteroaryl is an aryl moiety wherein one 1, 2 or 3 of the carbon atoms of the aromatic ring(s) and their attached hydrogen atoms of a parent aryl moiety are replaced by a heteroatom, optionally substituted where permitted, including N/NH, O and S, provided that not all of the skeletal atoms of any one aromatic ring system in the aryl moiety are replaced by heteroatoms and more typically are replaced by oxygen (—O—), sulfur (—S—) nitrogen (=N—) or —NR— wherein R is —H, a protecting group or $C_1$-$C_{20}$ alkyl, $C_6$-$C_{24}$ aryl or is nitrogen substituted with another organic moiety in a manner which retains the cyclic conjugated system, wherein the nitrogen, sulfur or oxygen heteroatom participates in the conjugated system either through pi-bonding with an adjacent atom in the ring system or through a lone pair of electrons on the heteroatom. In other aspects, a heteroaryl is a heterocyclyl as defined herein that is aromatized.

Typically, a heteroaryl is monocyclic which in some aspects has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s). $C_5$-heteroaryls are monovalent moieties derived from removing a hydrogen atom from an aromatic carbon or an electron from an aromatic heteroatom, where permitted, from a parent heterocycle compound including pyrrole, furan, thiophene, oxazole, isoxazole, thiazole, isothiazole, imidazole, pyrazole, triazole and tetrazole. $C_6$ heteroaryls, which are 6-membered, are exemplified by monovalent moieties derived from removing a hydrogen atom from an aromatic carbon or an electron from an aromatic heteroatom, where permitted, from a parent heterocycle compounds including pyridine, pyridazine, pyrimidine, and a triazine.

A "5-membered nitrogen heteroaryl" as the terms are used herein, by itself or as part of another term, unless otherwise stated or implied by context, refers to a monovalent 5-membered heteroaromatic moiety containing at least one nitrogen atom in its aromatic ring system and is typically a monocyclic heteroaryl or is fused to an aryl or another heteroaryl ring system, wherein the 5-membered heteroaromatic moiety may contain one or more other independently selected heteroatoms such as N/NH, O or S. Exemplary 5-membered heteroaryls include thiazole, imidazole, oxazole, and triazole and is typically thiazole or oxazole, more typically thiazole.

"Heterocyclo", as the term is used herein, by itself or as part of another term, unless otherwise stated or implied by context, refers to a heterocyclyl moiety, group or substituent as defined above wherein a hydrogen atom from its monovalent carbon atom, if present, a hydrogen atom of a different skeletal carbon atom, or an electron from a skeletal nitrogen atom, where permitted and if present, is removed or an electron from a nitrogen ring atom that is not already monovalent, if present, is removed and is replaced with a bond (i.e., it is divalent). In some aspects, the replaced second hydrogen is that of the monovalent carbon atom of the parent heterocyclyl thus forming a spiro carbon atom, which in some instances may interrupt an alkyl moeity with that carbocyclic carbon atom. In such instances, the spiro carbon atom is attributed to the carbon atom count of the interrupted alkyl moiety and the heterocyclic ring system with the heterocyclo indicated as being incorporated into the alkyl moeity.

"Heteroarylene", as the term is used herein, by itself or as part of another term, unless otherwise stated or implied by context refers to heteroaryl moiety, group or substituent as defined above wherein a hydrogen atom or an electron, where permitted, from a different aromatic carbon atom or an electron from an aromatic nitrogen ring atom if present is replaced with a bond (i.e., it is divalent). A "5-membered nitrogen heteroarylene is divalent and is similarly related in structure to a 5-membered nitrogen heteroaryl as described above.

"Heteroalkyl," as used herein by itself or in combination with another term, unless otherwise stated or implied by context, refers to an optionally substituted straight or branched chain hydrocarbon, fully saturated or containing from 1 to 3 degrees of unsaturation, consisting of 1 to 20 carbon atom and from 1 to 10, preferably 1 to 5, heteroatoms selected from the group consisting of O, N, Si and S (typically O, N, and S), and wherein each nitrogen and sulfur atom is optionally oxidized to an N-oxide or a sulfoxide, respectively, or wherein one of the nitrogen atoms is optionally quaternized. The heteroatom(s) O, N, S and/or Si may be placed at any interior position of the heteroalkyl group or at the position at which the alkyl group is attached to the remainder of the molecule with which it is associated. Non-limiting examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. In some aspects, a heteroalkyl is fully saturated. A heteroalkyl is typically denoted by the number of its contiguous heteroatoms and non-aromatic carbon atoms unless indicated otherwise or by context. Thus, —$CH_2$—$CH_2$—O—$CH_3$ and —$CH_2$—$CH_2$—S(O)—$CH_3$ are both $C_4$-heteroalkyls and —$CH_2$—CH=N—O—$CH_3$, and —CH=CH—N($CH_3$)—$CH_3$ are both $C_5$ heteroalkyl.

"Heteroalkylene" as used herein by itself or in combination with another term, unless otherwise stated or implied by context, means a divalent group derived from heteroalkyl (as discussed above), by removal of a hydrogen atom or an electron form a parent heteroalkyl and are exemplified by —$CH_2$—$CH_2$—S—$CH_2$—$CH_2$— and —$CH_2$—S—$CH_2$—$CH_2$—NH—$CH_2$—. For a heteroalkylene, heteroatoms may be interior to or may occupy either or both of the chain termini. When a heteroalkylene is a component of a Linker Unit both orientations of that component within the Linker Unit is permitted unless indicated or implied by context.

"Aminoalkyl" as used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two alkyl moieties, respectively, as described above, which in some aspects together with the nitrogen to which both moieties are attached define a $C_3$-$C_8$ heterocyclyl containing the basic nitrogen as a skeletal atom, typically a $C_3$-$C_6$ heterocyclyl. When aminoalkyl is used as a Markush group (i.e., a substituent) the alkylene moiety of the aminoalkyl is attached to a Markush formula with which it is associated through a sp$^3$ carbon of that moiety (i.e., the other radical terminus of the aforementioned alkylene). In some aspects, an aminoalkyl when part of a self-stabilizing Linker Unit ($L_{SS}$) or self-stabilized Linker Unit ($L_S$) is an exemplary acyclic Basic Unit. An aminoalkyl is typically denoted by the number of contiguous carbon atoms of its alkylene moiety. Thus, a $C_1$ aminoalkyl includes —$CH_2NH_2$, —$CH_2NHCH_3$ and —$CH_2N(CH_3)_2$ and a $C_2$ amino alkyl includes —$CH_2CH_2NH_2$, —$CH_2CH_2NHCH_3$ and —$CH_2CH_2N(CH_3)_2$.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects an alkene function group replaces two contiguous sp3 carbon atoms of an alkyl substituent, provided that the radical carbon of the alkyl moiety is not replaced, so that the optionally substituted alkyl is an unsaturated alkyl substituent.

Optional substituent replacing hydrogen(s) in any one of the foregoing substituents, moieties or groups is independently selected from the group consisting of aryl, heteroaryl, hydroxyl, alkoxy, aryloxy, cyano, halogen, nitro, fluoroalkoxy, and amino, including mono-, di- and tri-substituted amino groups, and the protected derivatives thereof, or is selected from the group consisting of —X, —OR', —SR', —$NH_2$, —N(R')(R$^{op}$), —N(R$^{op}$)$_3$, =NR', —CX$_3$, —CN, —NO$_2$, —NR'C(=O)H, —NR'C(=O)R$^{op}$, —NR'C(=O)R$^{op}$, —C(=O)R', —C(=O)NH$_2$, —C(=O)N(R')R$^{op}$, —S(=O)$_2$R$^{op}$, —S(=O)$_2$NH$_2$, —S(=O)$_2$N(R')R$^{op}$, —S(=O)$_2$NH$_2$, —S(=O)$_2$N(R')R$^{op}$, —S(=O)$_2$OR', —S(=O)R$^{op}$, —OP(=O)(OR')(OR$^{op}$), —OP(OH)$_3$, —P(=O)(OR')(OR$^{op}$), —PO$_3$H$_2$, —C(=O)R', —C(=S)R$^{op}$, —CO$_2$R', —C(=S)OR$^{op}$, —C(=O)SR', —C(=S)SR', —C(=S)NH$_2$, —C(=S)N(R')(R$^{op}$)$_2$, —C(=NR')NH$_2$, —C(=NR')N(R')R$^{op}$, and salts thereof, wherein each X is independently selected from the group consisting of a halogen: —F, —Cl, —Br, and —I; and wherein each R$^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl (including $C_5$-$C_{24}$ heteroaryl), a protecting group, and a prodrug moiety or two of R$^{op}$ together with the heteroatom to which they are attached defines a heterocyclyl; and R' is hydrogen or R$^{op}$, wherein R$^{op}$ is selected from the group consisting of $C_1$-$C_{20}$ alkyl, $C_6$-$C_{24}$ aryl, $C_3$-$C_{24}$ heterocyclyl (including $C_5$-$C_{24}$ heteroaryl), and a protecting group.

Typically, optional substituents are selected from the group consisting of —X, —OH, —OR$^{op}$, —SH, —SR$^{op}$, —NH$_2$, —NH(R$^{op}$), —NR'(R$^{op}$)$_2$, —N(R$^{op}$)$_3$, =NH, =NR$^{op}$, —CX$_3$, —CN, —NO$_2$, —NR'C(=O)H, NR'C(=O)R$^{op}$, —CO$_2$H, —C(=O)H, —C(=O)R$^{op}$, —C(=O)NH$_2$, —C(=O)NR'R$^{op}$, —S(=O)$_2$R$^{op}$, —S(=O)$_2$NH$_2$, —S(=O)$_2$N(R')R$^{op}$, —S(=O)$_2$NH$_2$, —S(=O)$_2$N(R') (R$^{op}$), —S(=O)$_2$OR', —S(=O)R$^{op}$, —C(=S)R$^{op}$, —C(=S)NH$_2$, —C(=S)N(R')RP, —C(=NR')N(R$^{op}$)$_2$, and salts thereof, wherein each X is independently selected from the group consisting of —F and —Cl, R$^{op}$ is typically selected from the group consisting of C$_1$-C$_6$ alkyl, C$_6$-C$_{10}$ aryl, C$_3$-C$_{10}$ heterocyclyl (including C$_5$-C$_{10}$ heteroaryl), and a protecting group; and R' independently is hydrogen, C$_1$-C$_6$ alkyl, C$_6$-C$_{10}$ aryl, C$_3$-C$_{10}$ heterocyclyl (including C$_5$-C$_{10}$ heteroaryl), and a protecting group, independently selected from R$^{op}$. More typically, substituents are selected from the group consisting of —X, —R$^{op}$, —OH, —OR$^{op}$, —NH$_2$, —NH(R$^{op}$), —N(R$^{op}$)$_2$, —N(R$^{op}$)$_3$, —CX$_3$, —NO$_2$, —NHC(=O)H, —NHC(=O)R$^{op}$, —C(=O)NH$_2$, —C(=O)NHR$^{op}$, —C(=O)N(R$^{op}$)$_2$, —CO$_2$H, —CO$_2$R$^{op}$, —C(=O)H, —C(=O)R$^{op}$, —C(=O)NH$_2$, —C(=O)NH(R$^{op}$), —C(=O)N(R$^{op}$)$_2$, —C(=NR')NH$_2$, —C(=NR')NH(R$^{op}$), —C(=NR')N(R$^{op}$)$_2$, a protecting group and salts thereof, wherein each X is —F, R$^{op}$ is independently selected from the group consisting of C$_1$-C$_6$ alkyl, C$_6$-C$_{10}$ aryl, C$_5$-C$_{10}$ heteroaryl and a protecting group; and R' is selected from the group consisting of hydrogen, C$_1$-C$_6$ alkyl and a protecting group, independently selected from R$^{op}$.

In some aspects, an alkyl substituent is selected from the group consisting —NH$_2$, —NH(R$^{op}$), —N(R$^{op}$)$_2$, —N(R$^{op}$)$_3$, —C(=NR')NH$_2$, —C(=NR')NH(RP), and —C(=NR')N(RP)$_2$, wherein R' and R$^{op}$ is as defined for any one of the R' or R$^{op}$ groups above. In some of those aspects the R' and/or R$^{op}$ substituents provide for a Basic Unit (BU) (i.e., the basic functional group of BU) as when R$^{op}$ is independently selected from the group consisting of hydrogen and C$_1$-C$_6$ alkyl. Alkylene, carbocyclyl, carbocyclo, arylene, heteroalkyl, heteroalkylene, heterocyclyl, heterocyclo, heteroaryl, and heteroarylene groups as described above may also be similarly substituted.

"Optionally substituted heteroatom" as used herein, unless otherwise stated or implied by context, refers to a heteroatom within a functional group or other organic moiety in which the heteroatom is not further substitution and/or refers to —NH— within a functional group or other organic in which the hydrogen is retained or is replaced by a substituent that suitably retains the localization of the lone pair electrons on the nitrogen atom. Therefore, such substituents include optionally substituted alkyl, arylalkyl, and heteroarylalkyl, and may further include optionally substituted alkenyl, alkynyl, aryl, alkylaryl, and arylheteroalkyl, as those terms are defined herein, but whose inclusion is dependent on the amount of delocalization of the nitrogen lone pair electrons into these substituents, and in some aspects excludes carbonyl-containing substituents in which the carbonyl functional group of that substituent is bonded to the nitrogen atom. In some aspects, when variable group J' of a PAB or PAB-type moiety, as described by the embodiments of the invention, is optionally substituted —NH—, the nitrogen atom so substituted suitably retains the localization of its nitrogen lone pair electrons when cleavage of the Linker Unit to release J' allows for self-immolation of the PAB or PAB-type moiety. In other aspects, when variable group E' of a glycosidic bond been W' and Y of a Glucuronide Unit, as described by the embodiments of the invention, is an optionally substituted —NH— moiety, the nitrogen atom so substituted suitably retains the localization of its nitrogen lone pair electrons when its participation in the glycosidic bond between Y and W provides for a recognition site for a glycosidase that effectively competes with spontaneous hydrolysis of that bond.

Typically, an optional substituent replacing carbon in an acyclic carbon chain that provides for a heteroalkyl or heteroalkylene is selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O.

"O-linked moiety", "O-linked substituent" and like terms as used herein, unless otherwise stated or implied by context, refers to a group or substituent that is attached to a moiety directly through an oxygen atom of the group or substituent. An O-linked group may be monovalent including groups such as —OH, acetoxy (i.e., —OC(=O)CH$_3$), acyloxy (i.e., —OC(=O)R$^b$, wherein R$^b$ is —H, optionally substituted C$_1$-C$_{20}$ alkyl, optionally substituted C$_3$-C$_{20}$ cycloalkyl, optionally substituted C$_3$-C$_{20}$ alkenyl, optionally substituted C$_2$-C$_{20}$ alkynyl, optionally substituted C$_6$-C$_{24}$ aryl, optionally substituted C$_5$-C$_{24}$ heteroaryl or optionally substituted C$_3$-C$_{24}$ heterocycle, and further include monovalent groups such as C$_1$-C$_{20}$ alkyloxy also referred to as C$_1$-C$_{20}$ aliphatic ether, optionally substituted, wherein the alkyl moiety is saturated or unsaturated, and other ethers including C$_6$-C$_{24}$ aryloxy (Aryl-O—), phenoxy (Ph-O—), C$_5$-C$_{20}$ heteroaryloxy (Heteroaryl-O—), optionally substituted, and silyloxy of formula R$_3$SiO—, wherein each R independently is C$_1$-C$_{20}$ alkyl or C$_6$-C$_{24}$ aryl, optionally substituted), and —OR$^{PR}$, wherein R$^{PR}$ is a protecting group as previously defined, or an O-linked group may be divalent, i.e., =O or —X—(CH$_2$)$_n$—Y—, wherein X and Y independently are S and O and subscript n is 2 to 3, to form a spiro ring system with the carbon to which X and Y are attached.

Typically, a O-linked substituent is a monovalent moiety selected from the group consisting of —OH, —OC(=O)CH$_3$), —OC(=O)R$^b$, C$_1$-C$_6$ saturated alkyl ether and C$_3$-C$_6$ unsaturated ether, wherein R$^a$ is C$_1$-C$_6$ saturated alkyl or C$_3$-C$_6$ unsaturated alkyl or C$_2$-C$_6$ alkenyl, or is selected from that group excluding —OH. Other exemplary O-linked substituent are provided by definitions for carbamate, ether and carbonate as disclosed herein in which the monovalent oxygen atom of the carbamate, ether and carbonate functional group is bonded to the Markush structure or larger organic moiety with which it is associated.

"Halogen" as used herein, unless otherwise stated or implied by context, refers to fluorine, chlorine, bromine or iodine and is typically —F or —Cl.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid interfering with the nucleophilicity of organometallic reagents or other highly basic reagents, where hydroxyl is typically protected as an ether, including alkyl or heterocycloalkyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$—, wherein least one of R$^{PR}$ is a nitrogen atom protecting group or both R$^{PR}$ together define a protecting group.

A protecting group is a suitable protecting when it is capable of preventing or substantially avoiding unwanted side-reactions or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. In some aspects a suitable protecting group is typically a protecting group used in peptide coupling reactions. For example, a suitable protecting group for nitrogen is an acid-labile carbamate protecting group such as t-butyloxycarbonyl (BOC).

"Ester" as used herein, unless otherwise stated or implied by context, refers to a substituent, moiety or group that contains a —C(=O)—O— structure (i.e., ester functional group) wherein the carbon atom of the structure is not directly connected to another heteroatom and is directly connected to —H or another carbon atom of an organic moiety, and the monovalent oxygen atom is attached to the same organic moiety to provide a lactone or to some other organic moiety. Typically, esters comprise or consist of organic moieties containing 1 to 50 carbon atoms, typically 1 to 20 carbon atoms or more typically 1 to 8 carbon atoms and 0 to 10 independently selected heteroatoms (e.g., O, S, N, P, Si, but usually O, S and N), typically 0 to 2 where the organic moieties are bonded through the —C(=O)—O— structure (i.e., through the ester functional group). When an ester is a substituent or variable group of a Markush structure that substituent is bonded to the structure with which it is associated through the monovalent oxygen atom of the ester functional group. In those instances the organic moiety attached to the carbonyl carbon of the ester functional group comprises any one of the organic groups described herein, e.g., $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, $C_3$-$C_{24}$ heterocyclyls or substituted derivatives of any of these, e.g., comprising 1, 2, 3, 4 or more substituents, where each substituent as defined herein for optional substituent is independently chosen. Exemplary esters include, by way of example and not limitation, acetate, propionate, isopropionate, isobutyrate, butyrate, valerate, isovalerate, caproate, isocaproate, hexanoate, heptanoate, octanoate, phenylacetate esters or benzoate esters or have the structure of —OC(=O)R$^b$ wherein R$^b$ is as defined for acyloxy O-linked substituent and is typically selected from the group consisting of methyl, ethyl, propyl, isopropyl, 3-methyl-prop-1-yl, 3,3-dimethyl-prop-1-yl and vinyl. Ester substituents as disclosed herein are exemplary monovalent O-linked substituents.

"Ether" as used herein, unless otherwise stated or implied by context, refers to an organic moiety, group or substituent that comprises 1, 2, 3, 4 or more —O— (i.e., oxy) moieties that are not bonded to carbonyl moiety(ies), usually 1 or 2, wherein no two —O-moieties are immediately adjacent (i.e., directly attached) to each other. Typically, an ether structure is comprised or consists of the formula —O-organic moiety wherein organic moiety is as described for an organic moiety bonded to an ester functional group. More typically, an ether moiety, group or substituent has the formula of —O-organic moiety wherein the organic moiety is as described herein for an optionally substituted alkyl group. When ether is used as a Markush group (i.e., an ether substituent) the oxygen of the ether functional group is attached to a Markush formula with which it is associated. When ether is a used as substituent in a Markush group it is sometimes designated as an "alkoxy" group, which is an exemplary O-linked substituent. $C_1$-$C_{20}$ alkoxy includes $C_1$-$C_4$ ether substituents such as, by way of example and not limitation, methoxy, ethoxy, propoxy, isopropoxy, butoxy and allyloxy (i.e., —OCH$_2$CH=CH$_2$).

"Amide" or "carboxamide" as used herein, unless otherwise stated or implied by context, refers to an moiety that contains a R—C(=O)N(R$^c$)— or —C(=O)N(R$^c$)$_2$ structure (i.e., amide or carboxamide functional group, respectively) with no other heteroatom directly attached to the carbonyl carbon of the structure and where R$^c$, independently selected, is hydrogen, a protecting group or an organic moiety wherein the organic moiety is as described herein for an organic moiety bonded to an ester functional group and is typically an optionally substituted $C_1$-$C_{20}$ alkyl. Typically, hydrogen or an organic moiety, independently selected from R$^c$, is bonded to the carboxamide or amide functional group, wherein the organic moiety is also as described herein for an organic moiety bonded to an ester functional group. When bonded to an organic moiety the resulting structure is represented by organic moiety-C(=O)N(R$^c$)$_2$, or R$^c$—C(=O)N(R$^c$)-organic moiety. When an amide is recited as a variable for a Markush structure, the amide nitrogen is bonded to that structure. For carboxamide substituents the carbonyl carbon of the amide functional group is bonded to the Markush structure. Amides and carboxamides are typically prepared by condensing an acid halide, such an acid chloride, with a molecule containing a primary or secondary amine. Alternatively, amide coupling reactions well known in the art of peptide synthesis, which oftentimes proceed through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a —O—C(=O)—O— structure (i.e., carbonate functional group). Typically, carbonate groups as used here comprise or consist of an organic moiety, wherein the organic moiety is as described herein for an organic moiety bonded to an ester functional group, bonded through the —O—C(=O)—O— structure, e.g., organic moiety-O—C(=O)—O—. When carbonate is used as a Markush group (i.e., a substituent) one of the monovalent oxygen atoms of the carbonate functional group is attached to a Markush formula with which it is associated and the other is bonded to a carbon atom of an organic moiety as previously described for organic moiety bonded to an ester functional group. In such instances carbonate is an exemplary O-linked substituent.

"Carbamate" or "urethane" as used here means a substituent, moiety or group that contains a structure represented by —O—C(=O)N($R^c$)— (i.e., carbamate functional group) or —O—C(=O)N($R^c$)$_2$, —O—C(=O)NH(optionally substituted alkyl) or —O—C(=O)N(optionally substituted alkyl)$_2$ (i.e., exemplary carbamate substituents) wherein $R^c$ and optionally substituted alkyl are independently selected wherein $R^c$, independently selected, is hydrogen, a protecting group or an organic moiety, wherein the organic moiety is as described herein for an organic moiety bonded to an ester functional group and is typically an optionally substituted alkyl. Typically, carbamate groups as used herein comprise or consist of an organic moiety, independently selected from $R^c$, wherein the organic moiety is as described herein for an organic moiety bonded to an ester functional group, bonded through the —O—C(=O)—N($R^c$)— structure, wherein the resulting structure has the formula of organic moiety-O—C(=O)—N($R^c$)— or —O—C(=O)—N($R^c$)-organic moiety. When carbamate is used as a Markush group (i.e., a substituent), the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents. In some aspects a carbamate functional group interconnects a Drug Unit and a PAB or PAB-type self-immolative moiety of a self-immolative Spacer Unit and functions as a second self-immolative Spacer Unit by undergoing spontaneous decomposition to release $CO_2$ and D as a drug compound subsequent to self-immolation of the first Spacer Unit.

"Antibody" as used herein, unless otherwise stated or implied by context, refers to is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment has the requisite number of sites for covalent attachment to the requisite number of drug-linker moieties. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., (2001), "Immunol. Biology, 5th ed.", Garland Publishing, New York). An antibody can be of any type (e.g., IgG, IgE, IgM, IgD, and IgA), class (e.g., $IgG_1$, $IgG_2$, $IgG_3$, $IgG_4$, $IgA_1$ and $IgA_2$) or subclass. The antibody can be derived from any suitable species. In some embodiments, the antibody is of human or murine origin. An antibody can be, for example, human, humanized or chimeric. An antibody or antibody fragment thereof, is an exemplary targeting agent that is incorporated as a Ligand Unit into an LDC of the present invention and in these instances is sometimes referred to as an antibody Ligand Unit.

In some aspects an antibody selectively and specifically binds to an epitope on hyper-proliferating or hyper-stimulated mammalian cells (i.e., abnormal cells), wherein the epitope is preferentially displayed by or is more characteristic the abnormal cells in contrast to normal cells, or is preferentially displayed by or is more characteristic of normal cells in the vicinity of abnormal cells in contrast to normal cells not localized to the abnormal cells. In those aspects the mammalian cells are typically human cells.

"Monoclonal antibody" as used herein, unless otherwise stated or implied by context, refers to an antibody obtained from a population of substantially homogeneous antibodies, i.e., the individual antibodies comprising the population are identical except for possible naturally-occurring mutations that may be present in minor amounts or differences in glycosylation patterns. A monoclonal antibody (mAb) is highly specific, being directed against a single antigenic site. The modifier "monoclonal" indicates the character of the antibody as being obtained from a substantially homogeneous population of antibodies, and is not to be construed as requiring production of the antibody by any particular method.

"Antibody fragment" as used herein, unless otherwise stated or implied by context, refers to a portion of an intact antibody that is comprised of the antigen-binding site or variable region of the intact antibody and remains capable of binding to the cognate antigen of the intact antibody. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically binds to a target antigen (e.g., a cancer cell antigen, an immune cell antigen, a viral antigen or a microbial antigen).

"Cytotoxic activity" as used herein, unless otherwise stated or implied by context, refers to a cell-killing effect of a drug, Ligand-Drug Conjugate, or an intracellular metabolite of a Ligand Drug Conjugate. Cytotoxic activity may be expressed as an $IC_{50}$ value, which is the concentration (molar or mass) per unit volume at which half the cells survive.

"Cytostatic activity" as used herein, unless otherwise stated or implied by context, refers to an anti-proliferative effect of a drug, Ligand-Drug Conjugate, or an intracellular metabolite of a Ligand Drug Conjugate, that is not dependent on cell killing but whose effect is due to inhibition of cell division of hyper-proliferating cells, hyper-stimulated immune cells or other abnormal or unwanted cells.

"Specific binding" and "specifically binds" as the terms are used herein, unless otherwise stated or implied by context, refers to an antibody, a fragment thereof, or antibody Ligand Unit as the targeting moiety in an Ligand Drug Conjugate that is capable of binding, in a selective manner with its corresponding targeted antigen and not with a multitude of other antigens. Typically, the antibody or fragment thereof binds its targeted antigen with an affinity of at least about $1 \times 10^{-7}$ M, and preferably $10^{-8}$ M to $10^{-9}$ M, $10^{-10}$ M, $10^{-11}$ M, or $10^{-12}$ M and binds to that predetermined antigen with an affinity that is at least two-fold greater than its affinity for binding to a non-specific antigen (e.g., BSA, casein) other than for a closely-related antigen, wherein said affinities are substantially retained when incorporated into a Ligand Drug Conjugate as an antibody Ligand Unit.

"Ligand-Drug Conjugate" or "LDC" as the term is used herein, unless otherwise stated or implied by context, refers to a construct comprised of a Ligand Unit, which is from a targeting agent, and a Drug Unit (D), which incorporate a biologically active compound or derivative thereof and includes a quaternized Drug Unit ($D^+$) that incorporates the structure of a tertiary-amine containing drug, bonded to each other through a Linker Unit, wherein the targeting Ligand Unit of the LDC selectively binds to its cognate targeted moiety. In some instances, the term LDC is a plurality (i.e., composition) of individual LDC compounds differing primarily by the number of D (or $D^+$) units bonded to each Ligand Unit or the location on the Ligand Unit at which the D (or $D^+$) units are bound. In other instances the term LDC applies to an individual member of the composition.

"Targeting moiety", "targeting agent", or like terms as the terms are used herein, unless otherwise stated or implied by context, refers to a moiety incorporated as a Ligand Unit in a LDC that binds selectively to a targeted moiety typically present on, within, or in the vicinity of hyper-proliferating cells, hyper-stimulated immune cells or other abnormal or unwanted cells in comparison to other moieties present on, within, or in the vicinity of normal cells where these abnormal or unwanted cells are typically not present. Sometimes a targeted moiety is present on, within, or in the vicinity of abnormal in greater abundance in comparison to normal cells or the environment of normal cells where abnormal cells are typically not present. In some instances the targeting agent is an antibody that specifically binds to an accessible antigen characteristic of an abnormal cell or is an accessible antigen that is particular to the surrounding environment in which these cells are found. In other instances the targeting agent is a receptor ligand that specifically binds to an accessible receptor characteristic of, or in greater abundance on, abnormal cells or other unwanted cells, or to an accessible receptor that is particular to cells of the surrounding environment in which abnormal cells are found. Typically a targeting agent is an antibody as defined herein that binds selectively to a targeted moiety of an abnormal or unwanted mammalian cell, more typically a targeted moiety of an abnormal or unwanted a human cell.

"Target cells", "targeted cells", or like terms as used herein, unless otherwise stated or implied by context, are the intended cells (i.e., abnormal or other unwanted cells) to which an LDC is designed to interact in order to inhibit the proliferation or other unwanted activity of the intended cells. In some instances the targeted cells are hyper-proliferating cells or hyper-activated immune cells, which are exemplary abnormal cells. Typically those abnormal cells are mammalian cells and more typically are human cells. In other instances the targeted cells are within the vicinity of abnormal or unwanted cells so that action of the LDC on the nearby cells has an intended effect on the abnormal or unwanted cells. For example, the nearby cells may be epithelial cells that are characteristic of the abnormal vasculature of a tumor. Targeting of those vascular cells by an LDC will either have a cytotoxic or cytostatic effect on these cells, which inhibits nutrient delivery to the abnormal cells of the tumor to indirectly have a cytotoxic or cytostatic effect on the nearby abnormal cells, and/or that targeting will have a direct cytotoxic or cytostatic effect on the nearby abnormal cells by releasing a biologically active compound or derivative in the vicinity of these cells.

"Targeted moiety" as the term is used herein, unless otherwise stated or implied by context, is a moiety preferentially recognized by a targeting agent or Ligand unit of a Ligand-Drug Conjugate incorporating that targeting agent (i.e., is selectively bound by the Ligand Unit) and is present on, within or in the vicinity of targeted cells. Sometimes the targeted moiety is an antigen accessible to selective binding by an antibody, which is an exemplary targeting agent that is incorporated in a LDC as an antibody Ligand Unit. In those instances, such an antigen is a cell-surface protein present on abnormal cells or other unwanted cells, or is present on cells that are particular to the surrounding environment in which the abnormal or unwanted cells are found, such as vascular cells that are characteristic of the environment of hyper-proliferating cells in a tumor. More typically, the antigen is a cell-surface protein of an abnormal cell or other unwanted cell that is capable of internalization upon binding with a cognate targeting moiety, wherein that moiety is provided by the Ligand Unit of a Ligand Drug Conjugate. In other instances, the targeting moiety is that of a ligand for an extracellularly accessible cell membrane receptor that may be internalized upon binding of a cognate targeting moiety provided by the Ligand Unit of a Ligand Drug Conjugate incorporating that ligand, or is capable of passive or facilitative transport of the LDC targeting the cell-surface receptor. In some aspects, the targeted moiety is present on abnormal mammalian cells or on mammalian cells characteristic of the environment of such abnormal cells.

"Antigen" as the term is used herein, unless otherwise stated or implied by context, is a moiety that is capable of selective binding to an unconjugated antibody or a fragment thereof or to an ADC, which is comprised of an antibody Ligand Unit. In some aspects, the antigen is an extracellularly-accessible cell-surface protein, glycoprotein, or carbohydrate preferentially displayed by abnormal or other unwanted cells in comparison to normal cells. In some instances, the unwanted cells having the antigen are hyper-proliferating cells in a mammal. In other instances, the unwanted cells having the antigen are hyper-activated immune cells in a mammal. In other aspects, the specifically bound antigen is present in the particular environment of hyper-proliferating cells or hyper-activated immune cells in a mammal in contrast to the environment typically experienced by normal cells in the absence of such abnormal cells. In still other aspects, the cell-surface antigen is capable of internalization upon selective binding by a Conjugate compound of an ADC composition wherein the antigen is associated with cells that are particular to the environment in which hyper-proliferating or hyper-stimulated immune cells are found in the absence of such abnormal cells. An antigen is an exemplary targeted moiety of an LDC wherein its Ligand Unit is that of an antibody that preferentially recognizes that antigen through selective binding.

Antigens associated with hyper-proliferating cells that are cell-surface accessible to an ADC include by way of example and not limitation CD19, CD70, CD30, CD33, NTB-A, $\alpha v \beta 6$, and CD123.

"Antibody-drug conjugate" or "ADC" as the term is used herein, unless otherwise stated or implied by context, refers to an LDC wherein the targeting moiety of the Conjugate is an antibody, wherein the antibody is covalently associated with a Drug Unit D (or $D^+$), typically through an intervening Linker Unit. Oftentimes the term refers to a collection (i.e., population or plurality) of Conjugate compounds having the same antibody ligand Unit, Drug Unit, and Linker Unit, but having variable loading or a distribution of the linker-drug moieties for each antibody (as for example when the number of D (or $D^+$) any two ADCs in a plurality of such constructs is the same but the location of their sites of attachment to the targeting moiety differ). In those instances an ADC is described by the averaged drug linker or drug loading of the conjugate compounds of the ADC composition, depending on the presence or absence, respectively of branching within the Linker Units. An ADC obtained from the methods described herein have the general formula of Ab-$(L_R-L_O-D)_p$, or Ab-$(L_R-L_O-D^+)_p$ wherein Ab is an antibody Ligand Unit, subscript p is the average number of drug linker moieties of Drug Units connected to the antibody Ligand Unit and $L_R$-$L_O$ defines the Linker Unit, wherein $L_R$ is a primary linker ($L_R$) linker, which contains a succinimide ($M^2$) or succinic acid amide ($M^3$) moiety and an acyclic or cyclic Basic Unit, as these terms are described elsewhere, and is so named because that component is required to be present in a Linker Unit of an ADC, and wherein $L_O$ is an optional secondary linker that when present is susceptible to enzymatic (e.g., protease or glycosidase) or non-enzymatic (e.g., reductive or hydrolytic) cleavage to effect release of the Drug Unit as a biologically active compound or derivative thereof. In some instances that cleavage is enhanced in the environment of abnormal or occurs subsequent to intracellular internalization of an ADC compound on binding of it targeting antibody Ligand Unit to its cognate antigen. In the generalized ADC structures disclosed herein, D is a Drug Unit, which unless otherwise indicated or implied by context includes a quaternized Drug Unit ($D^+$), wherein $D^+$ incorporates a tertiary amine-containing biologically active compound or its derivative and in some aspects is obtained from quaternization of the tertiary amine functional group of that compound, wherein the Drug Unit is released subsequent to enzymatic or non-enzymatic action on $L_O$ as a tertiary amine-containing biologically active compound or derivative thereof.

The average number of antibody Ligand Units in an ADC composition (i.e., an averaged number in a population of antibody drug conjugate compounds within the composition that differ primarily by the number of conjugated Drug Units (D or $D^+$) is designated as p or when the linkers are branched, p is the average number of drug-linker moieties. In that context p is a number ranging from about 2 to about 20 and is typically about 2, about 4, or about 8. In other contexts p represents the number of Drug Units when the Linker Units are not branched, or drug linker moieties when the Linker Units are branched, that are covalently bonded to an antibody Ligand Unit of an antibody drug conjugate compound within a population of such compounds in a ADC composition differing primarily by the number and/or location of attached linker-drug moieties in each of the Conjugate compounds, and is designated as p'. In that context p' is an integer ranging from 1 to 20, typically 1 to 12, 1 to 10 or 1 to 8 and is more typically 2, 4 or 8.

The average number of Drugs Units or drug linker moieties per Ligand Unit in a preparation from a conjugation reaction may be characterized by conventional means such as mass spectroscopy, ELISA assay, HIC and/or HPLC. In some instances, separation, purification, and characterization of homogeneous Ligand-Drug Conjugates, where p is a certain value (i.e., p becomes p') from Ligand Drug Conjugate compounds with other drug loadings may be achieved by means such as reverse phase HPLC or electrophoresis.

"Ligand Unit" as the term is used herein, unless otherwise stated or implied by context, refers to a targeting moiety of a Ligand Drug Conjugate (LDC) that binds selectively to its cognate targeted moiety and incorporates the structure of a targeting agent. A Ligand Unit (L) includes without limitation those of receptor ligands, antibodies to cell-surface antigens, and transporter substrates. Sometimes, the receptor, antigen or transporter to be bound by a LDC compound is present in greater abundance on abnormal cells in contrast to normal cells. Other times the receptor, antigen or transporter to be bound by a LDC compound is present in greater abundance on normal cells that are in the vicinity of abnormal cells in contrast to normal cells that are distant from the site of the abnormal cells. Various aspects of Ligand Units, including antibody Ligand Units, are further described by embodiments of the invention.

"Linker Unit" as the term is used herein, unless otherwise stated or implied by context, refers to an organic moiety in a ligand drug conjugate (LDC) intervening between and covalently attached to a Drug Unit D (or $D^+$) and a Ligand Unit (L) as those terms are defined herein. A Linker Unit (LU) is comprised of a primary linker ($L_R$), which is a required component of that Unit, and an optional secondary linker ($L_O$), which in some instances is also present within a drug linker moiety of LDC or a Drug Linker compound. In some aspects, $L_R$ is comprised of succinimide ($M^2$) or a succinic acid amide ($M^3$) moiety and an acyclic or cyclic Basic Unit in a Linker Unit of a LDC, and in other aspects it is comprised of a maleimide ($M^1$) moiety and an acyclic or cyclic Basic Unit within a Linker Unit of a Drug Linker compound. As a Drug Linker compound as described herein is comprised of a maleimide ($M^1$) moiety, attachment of a targeting agent, which results in a Ligand Unit, occurs to such a Drug Linker compound through a reactive thiol functional group of the targeting agent by way of Michael addition of its thiol functional group to the maleimide ring system of $M^1$. When the targeting agent is an antibody, the reactive thiol in some aspects is provided by a cysteine thiol group of the antibody. As a result of that addition, a Linker Unit of an LDC contains a succinimide ($M^2$) moiety having a thio-substituted succinimide ring system. Subsequent hydrolysis of that ring system under controlled conditions due to the presence of the Basic Unit as part of a self-stabilizing linker ($L_{SS}$) (i.e., $L_R$ within an LDC is $L_{SS}$), results in a succinic acid-amide ($M^3$) moiety, which is a component of self-stabilized ($L_S$) moiety, as further described herein ($L_{SS}$ in an LDC is hydrolyzed so that $L_R$ as $L_{SS}$ is now $L_S$). That hydrolysis is controllable due to the Basic Unit (BU) being in appropriate proximity to the succinimide ring system.

As described herein, BU in cyclized form is typically connected to $M^1$ or $M^2$ of $L_{SS}$ or $M^3$ of $L_S$ through an optionally substituted $C_1$-$C_{12}$ alkylene moiety in which that moiety incorporates the cyclized Basic Unit and is bonded to the maleimide or succinimide nitrogen of $M^1$ or $M^2$, respectively, or the amide nitrogen of $M^3$. In some aspects the $C_1$-$C_{12}$ alkylene moiety incorporating the cyclic Basic Unit is covalently bonded to $L_O$ when that Linker Unit component is present and typically occurs through intermediacy of an ether, ester, carbonate, urea, disulfide, amide carbamate or other functional group, more typically through an ether, amide or carbamate functional group.

"Primary linker" as the term is used herein, unless otherwise stated or implied by context, refers to a required component of Linker Unit (LU), and for Ligand Drug Conjugates and Drug Linker compounds of the present invention are either a self-stabilizing linker ($L_{SS}$) or a self-stabilized linker ($L_S$), as further described herein. A $L_{SS}$ moiety in a Drug Conjugate compound or Ligand Drug Conjugate (LDC) is characterized by a maleimide ($M^1$) or succinimide ($M^2$) moiety, respectively, while a $L_S$ moiety in a LDC is characterized by a succinic acid amide ($M^3$) moiety. An $L_{SS}$ or $L_S$ moiety of the present invention is also characterized by a $C_1$-$C_{12}$ alkylene moiety bonded to the imide nitrogen of the maleimide or succinimide ring system of $M^1$ or $M^2$ or the amide nitrogen of $M^3$, wherein the alkylene moiety is substituted by an acyclic Basic Unit and may be further substituted by optional substituents or which incorporates a cyclic Basic Unit and is optionally substituted. Linker Drug compounds having $L_{SS}$ as a primary linker are typically represented in general as $L_{SS}$-$L_O$-D (or $L_{SS}$-$L_O$-$D^+$) while Ligand Drug Conjugates having $L_{SS}$ as a primary linker are typically represented in general as L-($L_{SS}$-$L_O$-D)$_p$ or L-($L_{SS}$-$L_O$-$D^+$)$_p$ in which the variable groups are as previously defined herein.

A maleimide ($M^1$) moiety of $L_{SS}$ in a Drug Linker Compound is capable of reacting with a thiol functional group of a targeting agent to form a thio-substituted succinimide moiety ($M^2$) in a $L_{SS}$ primary linker of a Ligand Drug Conjugate, wherein the thio-substituent is a Ligand Unit incorporating the structure of the targeting agent, wherein the Ligand Unit is bonded to $M^2$ through a sulfur atom from one of the targeting agent's thiol functional groups. As a result of that reaction, the targeting agent becomes covalently bonded to the primary linker ($L_R$) as a Ligand Unit. Subsequent hydrolysis of $M^2$ results in $L_S$ as the primary linker in which $M^2$ is a succinic acid amide moiety ($M^3$). That linker moiety may exist as a mixture of two regioisomers ($M^{3A}$ and $M^{3B}$), depending on the relative reactivity of the two carbonyls of the succinimide ring system to hydrolysis. A LDC having $L_S$ as a primary linker is typically represented in general as L-($L_S$-$L_O$-D)$_p$ or L-($L_S$-$L_O$-$D^+$)$_p$, wherein the variable groups are as previously described herein.

"Secondary linker" as used herein, unless otherwise stated or implied by context, refers to an organic moiety in a Linker Unit (LU), wherein the secondary linker ($L_O$) is an optional component of that Unit that interconnects a Drug Unit to a primary linker ($L_R$) in which $L_R$ is a self-stabilizing linker ($L_{SS}$) in a Drug Linker compound or within a Ligand Drug Conjugate (LDC) or in a self-stabilized linker ($L_S$) within a LDC upon hydrolysis of $L_{SS}$. Typically, $L_R$ is attached to $L_O$, when present, through a heteroatom or functional group shared between the two Linker Unit components. For some aspects of a LDC or Drug Linker compound, a secondary linker is present and covalently attached to $L_R$ and a Drug Unit (D), which may be quaternized so that D is represented by $D^+$, wherein covalent attachment of $D^+$ is to the benzylic position of a PAB or PAB-type self-immolating moiety of a self-immolative Spacer Unit. For some of those aspects, in addition to a self-immolative Spacer Unit (Y) having a PAB or PAB-type moiety, secondary linkers are comprised of a Peptide Cleavable Unit (W). In those aspects W, Y and D (or $D^+$) are arranged in linear configuration, as represented by —W—$Y_y$-D, wherein subscript y 1 or 2, or by —W—$Y_y$-$D^+$, wherein subscript y is 1, wherein Y bonded to W is the PAB or PAB-type self-immolative Spacer Unit. In other aspects involving a PAB or PAB-type moiety, W is Glucuronide Unit, in which the self-immolative Spacer Unit having the PAB or PAB-type self-immolative moiety is attached to a carbohydrate moiety (Su) through a glycoside cleavable bond in which the carbohydrate moiety and the glycosidic heteroatom (E') that attaches Su to Y is sometimes referred to as W' so that W', Y and D (or $D^+$) are arranged in an orthogonal configuration, as represented by —$Y_y$(W')-D, wherein subscript y is 1 or 2, or by $Y_y$(W')-$D^+$, wherein subscript y is 1, wherein Y bonded to W' is the self-immolative Spacer Unit.

In either of those aspects, a secondary linker is further comprised of a first optional Stretcher Unit (A) and/or a Branching Unit (B) when LU is attached to more than one Drug Unit. When present, a first optional Stretcher Unit (A), interconnects $L_{SS}$ or $L_S$ derived therefrom, with the remainder of the secondary linker, optionally through intermediacy of B, depending on its presence or absence, or interconnects $L_{SS}$ or $L_S$ with D (or $D^+$), optionally by way of $A_O$ as a component of $L_{SS}$ or $L_S$, depending on its presence or absence, through —W—$Y_y$— or —$Y_y$(W')— wherein Y of $Y_y$ covalently attached to W or W' is a self-immolative Spacer Unit having a PAB or PAB-type moiety.

In other aspects, a PAB or PAB-type self-immolative Spacer Unit is absent, as for example when D is directly attached to W, wherein W is a Peptide Cleavable Unit so that LU has the structure of -$A_a$-W—$Y_y$-D in which subscript y is 0 or subscript y is 1 and Y is an optionally substituted heteroatom or functional group in which the latter may be capable of self-immolation and thus would be considered a self-immolative Spacer Unit, or LU has the structure of $A_a$-W—$Y_y$-$D^+$ in which subscript y is 1, wherein Y covalently attached to W and $D^+$ is capable of self-immolation. In still other aspects in which W is a Peptide Cleavable Unit or a Glucuronide Unit (i.e., W is —Y(W')—) wherein Y is a PAB-type self-immolative Spacer Unit, a second Spacer Unit (Y') is absent or may be present, which for the latter in some instances may either be a functional group, which may be capable of self-immolation and thus considered as a self-immolative Spacer Unit, or a second self-immolative Spacer Unit having a PAB or PAB-type self-immolative moiety, so that LU, for example, has the structure -$A_a$-W—Y—Y'-D/$D^+$, or -$A_a$-Y(W')—Y'-D/$D^+$ in which W is a Peptide Cleavable Unit cleavable by a protease and W' is a carbohydrate moiety (Su) bonded to Y through a heteroatom (E') of a glycosidic bond cleavable by a glucosidase. Sometimes that second self-immolative Spacer Unit (Y') is other than a PAB or PAB-type self-immolative Spacer Unit such as a carbamate functional group or a methylene carbamate unit as described elsewhere, both of which are capable of self-immolation. In other aspects the second Spacer Unit (Y') does not undergo self-immolation so that a biologically active compound or its derivative of structure Y'-D is released, which can undergo further enzymatic or non-enzymatic processing to release D as the biologically active compound. In all of those aspects, LU in general is represented by -$A_a$-W—$Y_y$-D($D^+$) in which W is a Peptide Cleavable Unit and subscript y is 0, 1 or 2 or W is a Glucuronide Unit of formula —Y(W')— and subscript y is 1 or 2, wherein one Y of $Y_y$ is present in —Y(W')—.

In some aspects, $L_O$ within a LDC or Drug Linker compound is comprised of a self-immolative Spacer Unit that is covalently attached directly to a Drug Unit through a shared optionally substituted heteroatom or indirectly through a functional group acting as a second Spacer Unit, wherein that Spacer Unit may or may not also undergo self-immolation, such that cleavage of W as a Peptide Cleavable Unit or W' of a Glucuronide Unit under conditions more likely experienced within or in the vicinity of abnormal cells in comparison to normal cells distant from the abnormal cell or the environment of such cells which either case is attached to a first self-immolative Spacer Unit, results in fragmentation of the first self-immolating Spacer Unit, which is followed by fragmentation of the second Spacer Unit if that unit is also capable of self-immolation, with concomitant release of D as a biologically active compound or derivative thereof.

$L_O$ in other aspects of an LDC or Drug Linker compound is comprised of a second self-immolative Spacer Unit that is covalently attached to a first self-immolative Spacer Unit such that cleavage of W of a Peptide Cleavable Unit or W' of a Glucuronide Unit under conditions more likely experienced within abnormal cells distant from the abnormal cells results in sequential fragmentation of the first and second self-immolating Spacer Units resulting in release of D. Alternatively, that cleavage may be occur in the vicinity of those cells, in comparison to the environment of normal cells distant from the site of the abnormal cells. Typically, that fragmentation of the first self-immolative Spacer Unit occurs through a 1,6-elimination of its PAB or PAB-type moiety as described herein and is followed by fragmentation of a carbamate functional group or a methylene carbamate (MAC) unit, as described herein, wherein that functional group or MAC Unit serves as the second self-immolative Spacer Unit.

A secondary linker ($L_O$) when bonded to D (or $D^+$) in a Linker Unit attached to only one Drug Unit and with no second optional Stretcher Unit is typically represented by the structure of (1) or (2):

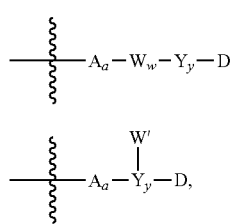

wherein the variable groups are as defined herein. In some aspects of the invention, $Y_y$ in structure (1) is comprised or consists of a PAB or PAB-type self-immolative Spacer Unit (Y) as described herein, wherein its PAB or PAB-type moiety is substituted with W and D (or $D^+$). In other aspects of the invention, $Y_y$ in structure (2) is comprised or consists of a PAB or PAB-type moiety self-immolating Spacer Unit as described herein wherein it PAB or PAB-type moiety is substituted with W' and D (or $D^+$), and in a Ligand Drug Conjugate or Drug Linker compound that moiety is further substituted with $L$-$L_{SS}$-$A_a$- or $L_{SS}$-$A_a$-, respectively.

Typically, secondary linkers with structure (1) in which subscripts a is 0 or 1, and subscripts y and w are each 1 and subscript y is 1 or 2 are represented by:

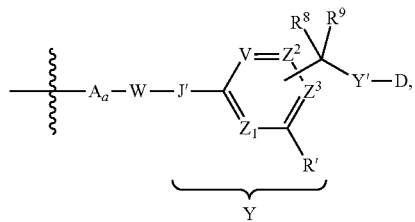

and secondary linkers with structure (2) in which subscripts a is 0 or 1 and subscript y is 1 or 2 are represented by:

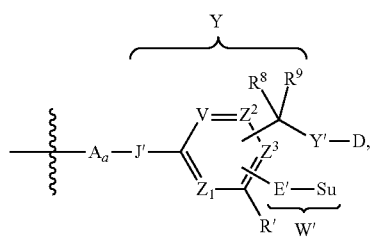

wherein Y' is an optionally substituted heteroatom or functional group shared between Y and D, or a second self-immolative moiety, as when the shared functional group is a carbamate or when Y' is a MAC Unit, or Y' is absent and D is a Drug Unit, which in some embodiments incorporate a tertiary amine-containing compound so that D is a quaternized Drug Unit ($D^+$), and wherein J', V, $Z^1$, $Z^2$, $Z^3$, R', $R^8$ and $R^9$ are as defined in embodiments for PAB or PAB-type self-immolative Spacer Units, and E' and Su are as defined in embodiments for Glucuronide Units of formula —Y(W')—, wherein the $A_a$-W-J'- and —$C(R^8)(R^9)$—Y'-D substituents on the central (hetero)arylene in a secondary linker of structure (1) are ortho or para to each other or the -E'-Su (i.e., W') and —$C(R^8)(R^9)$—Y'-D substituents on the central (hetero)arylene in secondary linker of structure (2) are ortho or para to each other.

"Maleimide moiety" as used herein, unless otherwise stated or implied by context, refers to is a component of a primary linker ($L_R$) when $L_R$ is self-stabilizing linker ($L_{SS}$). A maleimide moiety ($M^1$) is capable of participating in Michael addition (i.e., 1,4-conjugate addition) by a reactive thiol functional group of a targeting agent to provide a thio-substituted succinimide ($M^2$) moiety, wherein the thio substituent is a Ligand Unit that incorporates the structure of the targeting agent as described herein in an LDC. An $M^1$ moiety of a Drug Linker compound is attached to the remainder of the primary linker ($L_R$), through its imide nitrogen. Other than the imide nitrogen, an $M^1$ moiety is typically unsubstituted, but may be asymmetrically substituted at the cyclic double bond of its maleimide ring system. Such substitution can result in regiochemically preferred conjugate addition of a reactive thiol of a targeting agent to the less hindered or more electronically deficient double bond carbon (dependent on the more dominant contribution) of the maleimide ring system. Typically, that conjugate addition results in a succinimide ($M^2$) moiety, which is thio-substituted by a Ligand Unit though a sulfur atom from a thiol functional group of the targeting agent.

When present in a self-stabilizing linker ($L_{SS}$), controlled hydrolysis of the succinimide ring system of the thio-substituted succinimide ($M^2$) moiety can provide regio-chemical isomers of succinic acid-amide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be partially attributed to any substituent(s) that were present in the $M^1$ precursor.

"Succinimide moiety" as used herein, unless otherwise stated or implied by context, refers to a component of a self-stabilizing linker ($L_{SS}$), which in turn is a component of a Linker Unit of a Ligand Drug Conjugate and results from Michael addition of an thiol functional group of a targeting agent to the maleimide ring system of a maleimide moiety ($M^1$) in a Drug Linker compound. A succinimide ($M^2$) moiety is therefore comprised of a thio-substituted succinimide ring system that has its imide nitrogen substituted with the remainder of the primary linker through its optionally substituted $C_1$-$C_{12}$ alkylene moiety, wherein that moiety incorporates a cyclic Basic Unit or is substituted by an acyclic Basic Unit as described elsewhere, and is optionally substituted with substituent(s) that may have been present on the $M^1$ precursor.

"Succinic acid-amide moiety" as used herein, unless otherwise stated or implied by context, refers to component of a self-stabilized linker ($L_S$) of a Linker Unit within a Ligand Drug Conjugate and has the structure of a succinic amide hemi-acid having substitution of its amide nitrogen by another component of $L_S$ wherein that component is an optionally substituted $C_1$-$C_{12}$ alkylene moiety, which incorporates cyclic Basic Unit or is substituted by a acyclic Basic Unit, and having further substitution by L-S—, wherein L is Ligand Unit incorporating a targeting agent and S is a sulfur atom from that targeting agent. Thus a succinic acid-amide moiety has a free carboxylic acid functional group and an amide functional group whose nitrogen heteroatom is attached to the remainder of the primary linker, and is substituted by L-S— at the carbon that is alpha to the carboxylic acid or amide functional group. A succinic acid-amide ($M^3$) moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit. Without being bound by theory, it is believed the aforementioned hydrolysis, which results in a succinic acid-amide ($M^3$) moiety, provides a Linker Unit in a Ligand Drug Conjugate that is less likely to suffer premature loss from the Conjugate of its targeting Ligand Unit through elimination of the thio substituent.

Controlled hydrolysis in a self-stabilizing linker of the succinimide ring system of the thio-substituted succinimide ($M^2$) moiety can provide regiochemical isomers of succinic acid amide ($M^3$) moieties (individually referred to as $M^{3A}$ and $M^{3B}$) in variable amounts that are due to presumed differences in reactivity of the two carbonyl carbons of $M^2$ attributed to thio-substitution by the L-S-moiety and to any other substituent(s) that may have been present in the $M^1$ precursor to $M^2$.

"Self-stabilizing linker" as used herein, unless otherwise stated or implied by context, refers to a $M^2$-containing component in a primary linker of a Linker Unit in a Ligand Drug Conjugate (LDC) or is an $M^1$-containing component of a Linker Unit in a Drug Conjugate compound wherein that component is a precursor to a $M^2$-containing component of a self-stabilized linker ($L_S$) by conversion under controlled hydrolysis conditions, which is facilitated by its Basic Unit, such that an LDC initially comprised of a self-stabilizing linker ($L_{SS}$) becomes more resistant to premature loss of its Ligand Unit, by virtue of its Linker Unit (LU), which is now comprised of $L_S$. The $L_{SS}$ moiety, in addition to its $M^1$ or $M^2$ moiety, is comprised of $A_R$, which is a required Stretcher Unit, and optionally in combination with $A_O$ is typically comprised of an optionally substituted $C_1$-$C_{12}$ alkylene moiety that incorporates a cyclic Basic Unit or is substituted by an acyclic Basic Unit to which $M^1$ or $M^2$ and the remainder of LU are covalently attached, wherein that Basic Unit assists in the aforementioned controlled hydrolysis.

In the context of the present invention, $L_{SS}$ of a Drug Linker compound prior to its incorporation into an LDC as a drug linker moiety contains a maleimide ($M^1$) moiety (through which a targeting agent is to be attached) and $A_R$, which optionally in combination with $A_O$, is typically comprised of an optionally substituted $C_1$-$C_{12}$ alkylene moiety that incorporates a cyclic Basic Unit or is substituted by an acyclic Basic Unit as defined elsewhere. That alkylene moiety is attached to the imide nitrogen of the maleimide ring system of $M^1$ in a Drug Linker compound and to the remainder of the Linker Unit with the latter attachment optionally through $A_O$ of $L_{SS}$, which in some aspects consists or is comprised of an optionally substituted electron withdrawing heteroatom or functional group, referred herein as a Hydrolysis-Enhancing (HE) Unit, which in some aspects, in addition to BU, may enhance the hydrolysis rate of the $M^2$ moiety in the corresponding $L_{SS}$ of an LDC. After incorporation of the Drug Linker compound into a LDC, $L_{SS}$ now contains a maleimide ($M^2$) moiety that is thio-substituted by the Ligand Unit (i.e., Ligand Unit attachment occurs through Michael addition of a targeting agent's reactive thiol to the maleimide ring system of $M^1$).

In some aspects, a cyclized Basic unit (cBU) corresponds in structure to an acyclic Basic Unit through formal cyclisation to the basic nitrogen so that the cyclic Basic Unit is incorporated into $A_R$ as a spiro $C_4$-$C_{12}$ heterocyclo. In such constructs the spiro carbon is attached to the maleimide nitrogen of $M^1$, and hence to that nitrogen in $M^2$, and is further attached to the remainder of the Linker Unit optionally through $A_O$, which in some aspects is HE. In other aspects, a cyclized Basic unit (cBU), in which formal cyclization is to the optionally substituted $C_1$-$C_{12}$ alkylene moiety bearing the basic-amine of a corresponding acyclic Basic Unit, is incorporated into $A_R$, as an optionally substituted spiro $C_3$-$C_{12}$ carbocyclo in which its spiro carbon is bonded to $M^1/M^2$ imide nitrogen, wherein $A_R$ is also bonded to the remainder of the Linker Unit optionally through $A_O$, which is some aspects is HE. As a result of the latter cyclization the basic amine nitrogen is either directly attached to the spiro carbocyclo as a substituent or is indirectly attached through one or more intervening acyclic carbon atoms, optionally substituted, which are attributable to the alkylene moiety remaining from said formal cyclization of the corresponding acyclic Basic Unit, and is dependent on the site of cyclization to that alkylene moiety. In either of those aspects, BU assists in the hydrolysis of the succinimide moiety of $M^2$ to its corresponding ring-opened form(s) represented by $M^3$, which may be enhanced by HE When BU is a cyclic Basic Unit (cBU) undue loss of stereochemical integrity of the carbon atom that is bonded to the imide nitrogen (i.e., the α-carbon) in the $M^2$ precursor, which is now bonded to the amide nitrogen of the hydrolysis product $M^3$, prior to or during that conversion is prevented. That undue loss unexpectedly occurs in those Linker Units in which their Basic Units are in acyclic form (i.e., those comprised of aBU). That uncontrolled loss of stereochemical integrity has negative consequences, as further described herein, in manufacturing of Drug Linker compounds and may adversely impact drug release kinetics from Linker Drug Conjugates prepared from these compounds.

In some aspects, a $L_{SS}$ moiety in a Drug Linker compound or a Ligand Drug Conjugate, according to the present invention, can be represented by the general formula of $M^1$-$A_R$(cBU)-$A_O$- or -$M^2$-$A_R$(cBU)-$A_O$-, respectively, wherein $A_R$(cBU) is a required Stretcher Unit ($A_R$) incorporating a cyclic Basic Unit (cBU), $M^1$ and $M^2$ are maleimide and succinimide moieties, respectively, and $A_O$ is an second optional Stretcher Unit, which in some aspects consists or is comprised of HE, wherein HE is an optional Hydrolysis-enhancing Unit.

Exemplary $L_{SS}$ structures are those of general Formula 1A, wherein these structures are present in exemplary Ligand Drug Conjugates compounds, represented by:

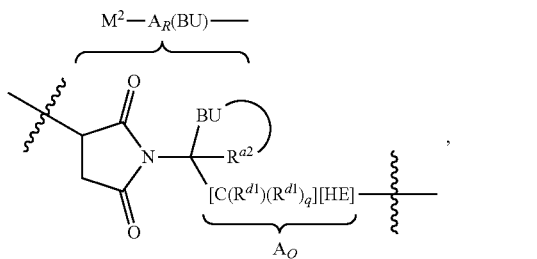

(Formula 1A)

wherein the $[C(R^{d1})R^{d1})]_q$—[HE] moiety is $A_O$ in Formula 1 in which $A_O$ is present, wherein HE is an optional hydrolysis Enhancing Unit, subscript q is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; BU is a Basic Unit and $R^2$ is an optionally substituted $C_1$-$C_{12}$ alkyl that together with the carbon atom to which they are attached, as represented by the solid curved line, define a cyclic Basic Unit as an optionally substituted spiro $C_4$-$C_{12}$ heterocyclo having a skeletal secondary or tertiary basic nitrogen atom, or as an optionally substituted spiro $C_3$-$C_{12}$ carbocyclo, wherein $R^{a2}$ is in incorporated in whole or in part into the spiro carbocyclo, wherein the spiro carbocyclo is substituted directly, or indirectly through any intervening carbons of $R^2$ remaining from said incorporation, such that the cyclic Basic Unit is capable of increasing the rate of hydrolysis of the shown succinimide moiety to provide succinic acid amide moieties at a suitable pH in comparison to the corresponding Conjugate in which $R^2$ is hydrogen and the dotted curved line is absent, or BU is a Basic Unit and $R^{a2}$ is an optionally substituted $C_1$-$C_{12}$ alkylene cyclized to a basic nitrogen atom of BU, as indicated by the curved dashed line so that a cyclic Basic Unit (cBU) is defined, wherein the functionality of BU in acyclic form that effects self-stabilization by conversion of Formula 1 to Formula 2 in which the curved dashed line is not present is substantially retained by cBU in a majority of compounds in the LDC composition that have Formula 1 in which the curved dashed line is present.

Other exemplary $L_{SS}$ structures are those of general Formula IB, which are present in Drug Linker compounds typically used intermediates in the preparation of LDC compositions represented by Formula I:

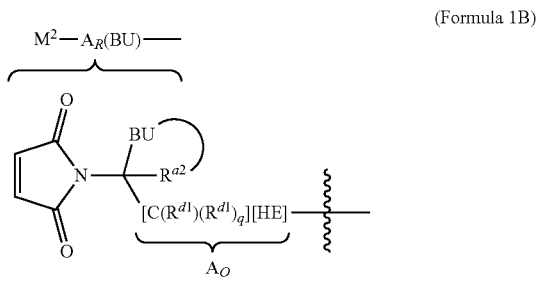

(Formula 1B)

wherein BU is as defined for the structure of Formula 1A and the other variable groups are as defined for Formula 1A and in the embodiments for this and other exemplary $L_{SS}$ structures. When a Drug Linker compound having Formula IB is used in the preparation of a LDC Formula IB is converted t Formula IA "Self-stabilized linker" is an organic moiety derived from an $M^2$-containing moiety of a self-stabilizing linker ($L_{SS}$) in an LDC that has undergone hydrolysis under controlled conditions so as to provide a corresponding $M^3$-moiety of an self-stabilized linker ($L_S$) wherein that LU component is less likely to reverse the condensation reaction of a targeting moiety with a $M^1$-containing moiety that provided the original $M^2$-containing $L_{SS}$ moiety. In addition to the $M^3$ moiety, a self-stabilized linker ($L_S$) is comprised of $A_R$ incorporating a cyclic Basic Unit or substituted by an acyclic Basic Unit wherein $A_R$ is covalently attached $M^3$ and the remainder of the Linker Unit in which $L_S$ is a component. The $M^3$ moiety is obtained from conversion of a succinimide moiety ($M^2$) of $L_{SS}$ in a Ligand Drug Conjugate, wherein the $M^2$ moiety has a thio-substituted succinimide ring system resulting from Michael addition of a sulfhydryl group of a targeting moiety to the maleimide ring system of $M^1$ of a LSS moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen, which corresponds to the imide nitrogen in the $M^2$-containing $L_{SS}$ precursor. Typically, that basic functional group is an amino group whose reactivity for base-catalyzed hydrolysis is controlled by pH.

Thus, a self-stabilized linker ($L_S$) typically has the structure of an $M^3$ moiety covalently bond $A_R$ incorporating a cyclic Basic Unit or substituted by an acyclic Basic Unit, wherein $A_R$ in turn is covalently bonded to the secondary linker $L_O$. $L_S$ with its $M^3$, $A_R$, $A_O$ and BU components and $L_O$ arranged in the manner so indicated is represented by the formula of $M^3$-$A_R$(BU)-$A_O$-$L_O$- or $M^3$-$A_R$(BU)-$A_O$-$L_{O^-}$, wherein BU represents either type of Basic Unit (cyclic or acyclic).

Exemplary structures of $L_{SS}$ and $L_S$ moieties with $M^2$ or $M^3$, and $A_R$(BU), $A_O$ and $L_O$ arranged in the manner indicated above in which BU is acyclic is shown by way of example but not limitation by:

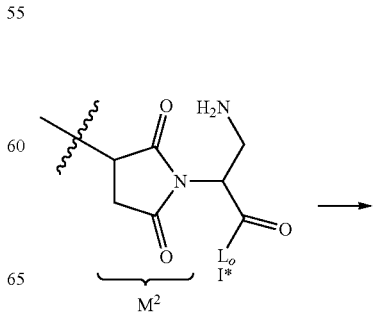

-continued

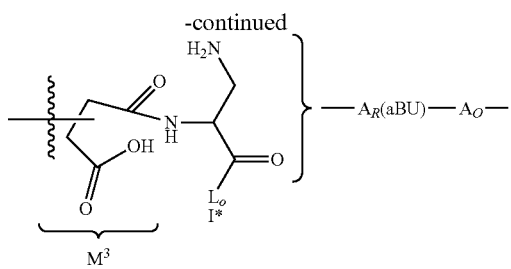

wherein the indicated $CH(CH_2NH_2)C(=O)$ moiety is $A_R(aBU)$-$A_O$-, in which $A_R$ is covalently bonded to the imide or amide nitrogen of $M^2$ or $M^3$, respectively, and is substituted by the acyclic Basic Unit (aBU), —$CH_2NH_2$, and wherein $A_O$ is [HE], which is bonded to $L_O$, wherein [HE] is —C(=O)—. Those exemplary structures contain a succinimide ($M^2$) moiety or a succinic acid-amide ($M^3$) moiety from succinimide ring hydrolysis of $M^2$ in the conversion of $L_{SS}$ to $L_S$.

Exemplary structures of $L_{SS}$ and $L_S$ moieties with $M^2$ or $M^3$, and $A_R(BU)$ and $A_O$ components bonded to $L_O$ in the manner indicated above in which BU is incorporated into $A_R$ as a cyclic Basic Unit (cBU) is shown by way of example but not limitation by:

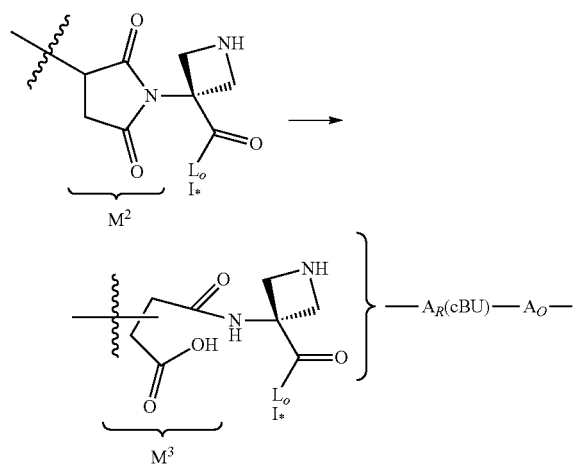

In the above $A_R(cBU)$-$A_O$ moieties, the heterocyclo cBU structure corresponds to the aminoalkyl of aBU in the $A_R(aBU)$ moiety in which the basic nitrogen of aBU has been formally cyclized back through $R^{a2}$ to the carbon alpha to the succinimide nitrogen of $M^2$ to which aBU is attached. The wavy line in each of the above $L_{SS}$ and $L_S$ moieties indicates the site of covalent attachment of a sulfur atom of a Ligand Unit derived from a thiol functional group of a targeting agent upon Michael addition of that thiol group to the maleimide ring system of an $M^1$ moiety in a corresponding Drug Linker compound. The asterisk in each of the above structures indicate the site of covalent attachment of a Drug Unit to the -$L_{SS}$-$L_O$- and $L_S$-$L_O$- structures of $M^2/M^3$-$A_R(BU)$-$A_O$-$L_O$- in which BU is cyclic or acyclic. Since the succinimide ring system of $M^2$ is asymmetrically substituted due to its thio substituent, regiochemical isomers of succinic acid-amide ($M^3$) moieties as defined herein differing in position relative to the liberated carboxylic acid group may result on $M^2$ hydrolysis. In the above structures, the carbonyl functional group attached to $L_O$ exemplifies a hydrolysis enhancer [HE] as defined herein in which [HE] is the indicated $A_O$ component of $L_{SS}$ or $L_S$ that is covalently attached to -$A_R(BU)$ and $L_O$.

The -$M^3$-$A_R(aBU)$- and -$M^3$-$A_R(cBU)$- moieties represent exemplary structures of self-stabilized linker ($L_S$) moieties, since these structures are less likely to eliminate the thio substituent of the Ligand Unit, and thus cause loss of that targeting moiety, in comparison to the corresponding $L_{SS}$ moieties of formula $M^2$-$A_R(aBU)$ and $M^2$-$A_R(cBU)$. Without being bound by theory, it is believed the increased stability results from the greater conformational flexibility in $M^3$ in comparison to $M^2$, which no longer constrains the thio substituent in a conformation favorable for E2 elimination.

"Basic Unit" as used herein, unless otherwise stated or implied by context, refers to an organic moiety within a self-stabilizing linker ($L_{SS}$) moiety, as described herein, which is carried forward into a corresponding $L_S$ moiety by BU participating in base catalyzed hydrolysis of the succinimide ring system within a $M^2$ moiety comprising $L_{SS}$ (i.e., catalyzes water addition of a water molecule to one of the succinimide carbonyl-nitrogen bonds). The base-catalyzed hydrolysis is typically initiated under controlled conditions tolerable by the targeting Ligand Unit attached to $L_{SS}$. In one aspect, the basic functional group of an acyclic basic unit (aBU) and its relative position in $L_{SS}$ with respect to its $M^2$ component is selected for its ability to hydrogen bond to a carbonyl group of $M^2$, which effectively increases its electrophilicity and hence its susceptibility to water attack. In another aspect, those selections are made so that a water molecule, whose nucleophilicity is increased by hydrogen bonding to the basic functional group of BU, is directed to an $M^2$ carbonyl group. In a third aspect, those selections are made so the basic nitrogen on protonation increases the electrophilicity of the succinimide carbonyls by inductive electron withdrawing. In a final aspect, some combination of those mechanisms contributes to catalysis for hydrolysis of $L_{SS}$ to $L_S$.

Typically, an acyclic Basic Unit (aBU), acting through any of the above mechanistic aspects, is comprised of 1 carbon atom or 2 to 6 contiguous carbon atoms, more typically of 1 carbon atom or 2 or 3 contiguous carbon atoms, that connect its basic amino functional group to the remainder of the $L_{SS}$ moiety to which it is attached. In order for that basic amine be in the required proximity to assist in the hydrolysis of a succinimide ($M^2$) moiety to its corresponding ring-opened succinic acid amide ($M^3$) moiety, the amine-bearing carbon chain of aBU is typically attached to $A_R$ of $L_{SS}$ at the alpha carbon of that moiety relative to the point of attachment of $A_R$ to the succinimide nitrogen of $M^2$ (and hence to the maleimide nitrogen of its corresponding $M^1$-$A_R$ structure). Typically, that alpha carbon in an acyclic Basic Unit has the (S) stereochemical configuration or the configuration corresponding to that of the alpha carbon of L-amino acids.

Typically, a cyclic Basic Unit (cBU) incorporates the structure of an acyclic BU by formally cyclizing aBU to an optionally substituted $C_1$-$C_{12}$ alkyl ($R^{a2}$) bonded to the same alpha carbon as aBU, thus forming a spirocyclic ring system so that cBU is incorporated into the structure of $A_R$ rather than being a substituent of $A_R$ as when BU is acyclic. In some aspects, the formal cyclization is to the basic amine nitrogen of aBU thus providing cBU as an optionally substituted symmetrical or asymmetrical spiro $C_4$-$C_{12}$ heterocyclo, depending on the relative carbon chain lengths in the two alpha carbon substituents, in which the basic nitrogen is now a basic skeletal heteroatom. In order for that cyclization to substantially retain the basic properties of the aBU nitrogen in cBU, the aBU nitrogen should be a primary or secondary amine and not a tertiary amine since that would result in a quaternized skeletal nitrogen in the cBU heterocyclo. In other aspects, the formal cyclization is to optionally substituted $C_1$-$C_{12}$ alkylene moiety of aBU, which intervenes between the alpha carbon of $A_R$ and the basic functional group of BU. That formal cyclization to $R^{a2}$, which is also bonded to the alpha carbon, results is an optionally substituted $C_3$-$C_{12}$ spiro carbocyclo to which the basic functional group is now a substituent and which may have one or more intervening carbons between it and carboxcylic ring system depending on the site of formal cyclization of $R^2$ to the $C_1$-$C_{12}$ alkylene of aBU. The basic amine of cBU resulting from that formal cyclization can be a primary, secondary or tertiary amine as the degree of substitution of the basic nitrogen atom is not increased upon the formal cyclization in contrast to a formal cyclization of $R^2$ to the basic nitrogen atom of aBU.

In either aspect of formal cyclization of aBU to cBU, in order to substantially retain the ability of the basic nitrogen to assist in hydrolysis of $M^2$ to $M^3$ in conversion of $L_{SS}$ to $L_S$, the resulting cBU structure in these primary linkers will typically have its basic nitrogen located so that no more than three, and typically one or two, intervening carbon atoms are between the basic nitrogen heteroatom and the spiro alpha carbon of the $A_R$ component. Cyclic Basic Units incorporated into $A_R$ and the $L_{SS}$ and $L_S$ moieties having those as components are further described by the embodiments of the invention.

"Hydrolysis Enhancer Unit" as used herein, unless otherwise stated or implied by context, refers to is electron withdrawing group or moiety that is an optional substituent of an $L_{SS}$ moiety and its hydrolysis product $L_S$. When present, a Hydrolysis Enhancer Unit (HE) is a second Stretcher Unit attached to $A_R$ of $L_{SS}$, wherein $A_R$ is bonded to the imide nitrogen of an $M^2$ moiety, which is another component of $L_{SS}$, so that its electron withdrawing effects can increase the electrophilicity of the succinimide carbonyl groups in that moiety for its conversion to a $M^3$ moiety of $L_S$. With $A_R$ incorporating or substituted by cBU or aBU moiety, respectively, the potential effect of HE on the carbonyl groups of $M^2$ for increasing the hydrolysis rate to $M^3$ by induction and the aforementioned effect(s) of either type of BU, are adjusted so that premature hydrolysis of $M^1$ does not occur to an appreciable extent during preparation of an Ligand Drug Conjugate from a Drug Linker compound having the structure of $M^1$-$A_R$(BU)—[HE]-. Instead, the combined effects of BU and [HE] to promote hydrolysis (i.e., conversion of an -$M^2$-$A_R$(BU)—[HE]- moiety of an LDC to its corresponding -$M^3$-$A_R$(BU)—[HE]- moiety) under controlled conditions (as when pH is purposely increased) that are tolerable by the targeting Ligand Unit of the Conjugate are such that an undue molar excess of Drug Linker compound to compensate for hydrolysis of its $M^1$ moiety is not required. Therefore, Michael addition of the reactive thiol of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that use of an acceptable molar excess of Drug Linker compound can compensate for any loss due to premature $M^1$ hydrolysis that does occur during the time course for completion of the Michael addition of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1$/$M^2$ carbonyl groups. Typically, the HE Unit is a carbonyl moiety (i.e., ketone or —C(=O)—) or other carbonyl-containing functional group located distal to the end of $A_R$ that is bonded to $M^2$, or $M^3$ derived therefrom, and that also provides covalent attachment of $L_{SS}$ or $L_S$ to the secondary linker ($L_O$). Carbonyl-containing functional groups other than ketone include esters, carbamates, carbonates and ureas. When HE is a carbonyl-containing functional group other than ketone the carbonyl moiety of that functional group is typically bonded to the remainder of $A_R$. In some aspects, the HE Unit may be sufficiently distant within $A_R$ from the imide nitrogen to which the remainder of $A_R$ is covalently bonded so that no discernable effect on hydrolytic sensitivity of the succinimide carbonyl-nitrogen bonds of an $M^2$-containing moiety is observable, but instead is driven primarily from BU.

"Stretcher Unit" as used herein, unless otherwise stated or implied by context, refers to an organic moiety in a primary or secondary linker of a Linker Unit that physically separates the targeting Ligand Unit from other intervening components of the Linker Unit that are distal to a particular Stretcher Unit. An $A_R$ Stretcher Unit is a required component in a $L_{SS}$ or $L_S$ primary linker since it provides the Basic Unit. The presence of a first optional Stretcher Unit (A) and/or second optional Stretcher Unit ($A_O$) may be required when there is insufficient steric relief from the Ligand Unit provided by an $L_{SS}$ primary linker that does not have one or both of those optional Stretcher Units to allow for efficient processing of a Linker Unit in a drug linker moiety of a Ligand Drug Conjugate for release of its Drug Unit as a biologically active compound or derivative thereof. Alternatively, or in addition to steric relief, those optional components may be included for synthetic ease in preparing a Drug Linker compound. A first or second optional Stretcher Unit (A or $A_O$) can be a single unit or can contain multiple subunits. Typically, A or $A_O$ is one distinct unit or has 2 to 4 additional distinct subunits. In some aspects A or $A_O$, or a subunit of either one of these Stretcher Units, has the formula of -$L^P$(PEG)-.

In some aspects, in addition to covalent attachment to $M^1$ of a Drug Linker compound or $M^2$/$M^3$ of a Ligand Drug Conjugate compound, $A_R$ is bonded to a secondary linker optionally through $A_O$ wherein $A_O$ as a component of $L_{SS}$/$L_S$ is a carbonyl-containing functional group, which can serve as a Hydrolysis Enhancing (HE) unit for improving the rate of conversion of $L_{SS}$ to $L_S$, which is catalyzed by cBU as incorporated into $A_R$ or by aBU as a substituent of $A_R$. In some of those aspects $A_R$ is bonded to a secondary linker ($L_O$) through a Branching Unit of $L_O$, if in Formula 1, Formula 2 or Formula I, subscript b is 1 and subscript n is 2 or more, or if in these formulae subscript n is 1 so that subscript b is 0, then $A_R$ is bonded to a secondary linker through an optional second Stretcher Unit ($A_O$) of $L_{SS}$ or $L_S$, or $A_R$ or $A_O$ is bonded to a secondary linker ($L_O$) through a first optional Stretcher Unit (A) of $L_O$, when subscript a is 1, or through W when subscript a is 0 and components W, Y and D/D⁺ are arranged linearly, wherein subscript w is 1 and W is a Peptide Cleavable Unit (i.e., arranged as —W—$Y_y$-D/D⁺, wherein subscript y is 0, 1 or 2), or $A_R$ or $A_O$ when subscript a is 0 or A, when subscript a is 1 is bonded to Y of $Y_y$, as is W', in formula —Y(W')— of a Glucuronide Unit, so that W, $Y_y$ and $D/D^+$ are arranged orthogonally (i.e., arranged as —$Y_y$(W')-$D/D^+$, wherein subscript y is 1 or 2). Finally $A_R$ or $A_O$ in Formula 1, Formula 2 or Formula I is bonded $Y_y$-$D/D^+$ when subscript a is 0 and subscript w is 0.

Some Linker Units in an LDC or Drug Linker compound contain the formula of -$L^P$(PEG)-$W_w$—$Y_y$—, in which subscript a is 1 and A, or a subunit thereof, in Formula 1, Formula 2 or Formula I is -$L^P$(PEG)-, and wherein subscript w is 1 and W is a Peptide Cleavable Unit, or contain the formula -$L^P$(PEG)-$Y_y$(W')— in which subscript a is 1 and A, or a subunit thereof, in Formula 1, Formula 2 or Formula I is -$L^P$(PEG)-, wherein —Y(W')— in $Y_y$(W')— is a Glucuronide Unit and subscript y is 1 or 2.

Typically, a first optional Stretcher Unit (A), has one carbon atom or two to six contiguous carbon atoms that connects A to $A_R$ or to a second optional Stretcher Unit ($A_O$), depending on the presence or absence of $A_O$, of the primary linker, when subscript b is 0 or to B when subscript b is 1, through one functional group and connects A to W, Y, or $D/D^+$, depending on the presence or absence W and/or Y and the configuration of A, W, and Y within the secondary linker through another functional group. In some aspects of Formula 1, Formula 2 or Formula I, subscript a is 0, so that no first Stretcher Unit is present, or subscript a is 1 wherein A is an α-amino acid, a β-amino acid or other amine-containing acid residue so that A is bonded $A_R$, $A_O$ or B, and to W, Y or $D/D^+$ through amide functional groups. In other aspects, A is bonded to $A_O$, when $A_O$ is present and consists or is comprised of a Hydrolysis Enhancing Unit (HE).

"Branching Unit" as used herein, unless otherwise stated or implied by context, refers to a tri-functional organic moiety that is an optional component of a Linker Unit (LU). A Branching Unit (B) is present when more than one Drug Unit (D or $D^+$), typically 2, 3 or 4, are attached to a Linker Unit (LU) of a drug linker moiety in a Ligand Drug Conjugate or Drug Linker compound. In a Ligand Drug Conjugate of Formula 1 or Formula 2 or a Drug Linker compound of Formula I, the presence of a Branching Unit is indicated when subscript b of $B_b$ is 1, which occurs when subscript n greater than 1 in any of these structural formulae. A Branching Unit is trifunctional in order to be incorporated into a secondary linker unit ($L_O$). In aspects where n is 1, a Branching Unit is not present, as indicated when subscript b is 0. Drug Linker or Ligand Drug Conjugates with a Branching Unit due to multiple $D/D^+$ units per LU have Linker Units containing formula —B-$A_a$-$W_w$—$Y_y$—, wherein subscripts a and w are independently 0 or 1 and subscript y is 0, 1 or 2, except that subscript y is 1 when D is a quaternized Drug Unit ($D^+$) and W is a Peptide Cleavable Unit, or have Linker Units containing formula —B-$A_a$-$Y_y$(W')—, wherein subscript a is 0 or 1 and subscript y is 1 or 2 except that subscript y is 1 when D is a quaternized Drug Unit ($D^+$), wherein —Y(W') within that formula is a Glucuronide Unit. As A can contain formula -$L^P$(PEG)-, in these instances Linker Units can contain formula -$L_P$(PEG)-$W_w$—$Y_y$— or -$L_P$(PEG)-$Y_y$(W')— when subscript b is 0.

In some aspects a natural or un-natural amino acid or other amine-containing acid compound having a functionalized side chain serves as a Branching unit. In some aspects B is a lysine, glutamic acid or aspartic acid moiety in the L- or D-configuration in which the epsilon-amino, gamma-carboxylic acid or beta-carboxylic acid functional group, respectively, interconnects B to the remainder of LU.

"Cleavable Unit" as used herein, unless otherwise stated or implied by context, refers to an organic moiety that provides for a reactive site within a Linker Unit wherein reactivity towards that site is greater within or surrounding abnormal cell such as hyper-proliferating cell or a hyper-stimulated immune cell in comparison to a normal cells that are not typically present at the site or are distant from the site of the abnormal cells such that action upon the reactive site of the Linker Unit results in preferential exposure of the abnormal cells to a biologically active compound or derivative thereof released from a Ligand Drug Conjugate (LDC) compound having that Linker Unit. The exposure from release of the biologically active compound or its derivative is initiated by enzymatic or non-enzymatic action on the Linker Unit having that Cleavable Unit. In some aspects of the invention, a Cleavable Unit or component thereof (W or W') contains a reactive site cleavable by an enzyme (i.e., W or W' provides for an enzyme substrate) whose activity or abundance is greater within or surrounding the hyper-proliferating, immune-stimulating or other abnormal cells compared to normal cells or the vicinity of normal cells that are distant from the site of the abnormal cells. In some of those aspects of the invention, the Cleavable Unit is a substrate for a protease, which in some aspects is a regulatory protease, or a hydrolase or glycosidase, wherein the protease, hydrolase or glycosidase is located intracellularly in targeted cells (i.e., the reactive site of the Cleavable Unit is a peptide bond or glycoside bond, respectively, cleavable by the protease, hydrolase or glycosidase). In those aspects, the peptide or glycoside bond of the Cleavable Unit is capable of selective cleavage by an intracellular regulatory protease, hydrolase or glycosidase in comparison to serum proteases, hydrolases, or glycosidases.

In other aspects, a Cleavable Unit is comprised of a reactive site cleavable by other mechanisms (i.e., non-enzymatic) more likely operable within or in the surrounding environment of abnormal cells targeted by a Ligand Unit of a Ligand Drug Conjugate in comparison to the environment of normal cells in which abnormal cells are typically not present or are distant from the site of the targeted cells. In some of those aspects, the reactive site is more likely operated upon enzymatically or non-enzymatically subsequent to cellular internalization of an LDC compound into a targeted abnormal cell.

Alternatively, W provides for a functional group that when incorporated into an Ligand Drug Conjugate composition is susceptible to the acidic environment of lysozymes upon preferential internalization of a compound of that composition into an abnormal cell, or is susceptible to the greater reductive environment in or around such cells in comparison to the environment of normal cells where abnormal cells are usually not present, such that release of $D/D^+$ from that Ligand Drug Conjugate compound as a biologically active compound or derivative thereof preferentially exposes the abnormal cell to that release compound in comparison to the normal cells Functional groups that provide for cleavable bonds include, by way of example and not limitation, include (a) sulfhydryl groups that form a disulfide bond, which are susceptible to the greater reductive conditions of abnormal cells in comparison to normal cells or excess glutathione produced under hypoxic conditions experienced by the abnormal cells, (b) aldehyde, ketone, or hydrazine groups that form a Schiff base or hydrazone functional groups, which are susceptible to the acidic conditions of lysozymes upon selective internalization of an LDC compound having a Linker Unit with that cleavable bond into an abnormal cell in comparison to internalization into normal cells, (c) carboxylic or amino groups that form an amide bond, as in peptide bonds, that are susceptible to enzymatic cleavage by proteases produced or excreted preferentially by abnormal cells in comparison to normal cells or by a regulatory protease within a targeted cell, and (d) amino or hydroxyl groups that form certain urea or carbamate groups or carboxylic or hydroxy groups that form ester or carbonate groups that are susceptible to enzymatic cleavage by hydrolases or esterases that are produced or excreted preferentially by abnormal cells in comparison to normal cells.

Still other functional groups that provide for cleavable bonds are found in sugars or carbohydrates having a glycosidic linkage that are substrates for glycosides which sometimes may be produced preferentially by abnormal cells in comparison to normal cells. Alternatively, the protease, hydrolase or glycosidase enzyme required for processing of the Linker Unit to release a biologically active compound or derivative thereof need not be produced preferentially by abnormal cells in comparison to normal cells provided the processing enzyme is not excreted by normal cells to an extent that would cause undesired side effects from premature release of the biologically active compound or derivative thereof. In other instances, the required protease, hydrolase or glycosidase enzyme may be excreted, but to avoid undesired premature release of drug, some aspects of the invention typically require the processing enzyme be excreted in the vicinity of abnormal cells and remain localized to that environment, whether produced by abnormal cells or nearby normal cells in response to the abnormal environment caused by the abnormal cells. In that respect W as a Peptide Cleavable Unit or W' of a Glucuronide Unit in which W has the formula of —Y(W')— is selected to be preferentially acted upon by a protease, hydrolase or glycosidase in or within the environment of abnormal cells in contrast to freely circulating enzymes. In those instances a LDC is less likely to release a biologically active compound or derivative thereof in the vicinity of normal cells nor would it be internalized to any appreciable extent into normal cells that do intracellularly produce but do not excrete the enzyme intended to act upon by the internalized Ligand Drug Conjugate compound since such cells are less likely to display a targeted moiety required for entry by that compound or have sufficient copy number of that targeted moiety.

In some aspects, W is a Peptide Cleavable Unit comprised of an amino acid or is comprised or consists of one or more sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative moiety of a self-immolative Spacer Unit Y wherein that moiety is a recognition sequence for that protease. In other aspects, W is a Glucuronide Unit of formula —Y(W')— wherein W' is a carbohydrate moiety (Su) attached to a self-immolative moiety of the Glucuronide's self-immolative Spacer Unit (Y) by a glycosidic bond through a optionally substituted heteroatom (E') that is cleavable by a glycosidase preferentially produced by abnormal cells, or is found in such cells to which an LDC compound having that Spacer Unit and carbohydrate moiety has selective entry due to the presence of the targeted moiety on the abnormal cells.

"Spacer Unit" as used herein, unless otherwise stated or implied by context, refers to a moiety in a secondary linker ($L_O$) within a Linker Unit of a Ligand Drug Conjugate or Drug Linker compound that is covalently bonded to $D/D^+$, or to another such moiety (Y') covalently bonded to D, and in some aspects the Spacer Unit (Y) is also covalently bonded to a first optional Stretcher Unit (A) if subscript b is 0 in Formula 1, Formula 2 or Formula I or to a Branching Unit (B) if subscript b is 1 in either one of these formulae or to a second optional Stretcher Unit ($A_O$), if A and B are absent (i.e., subscripts a and b are both 0), or to $A_R$ if none of these other Linker Unit components are present. In other aspects, Y is covalently bonded to W and to $D/D^+$ or another Spacer Unit (Y'). Each Y of $Y_y$ in Formula 1, Formula 2 or Formula I is independently selected from the group consisting of an optionally substituted heteroatom, an optionally substituted functional group, which may be capable of self-immolation, a non-self-immolative Spacer Unit and a self-immolative Spacer Unit. When W in any one of those formulae is a Peptide Cleavable Unit the Y bonded to W may be a self-immolative Spacer Unit and when W is a Glucuronide Unit of formula —Y(W'), then Y bonded to W' is required to be a self-immolative Spacer Unit in order for D or $D^+$ to be released subsequent to cleavage of the glycosidic bond in W'.

Typically, in one configuration W, $Y_y$, and D are arranged linearly with $D/D^+$ bonded to $Y_y$, wherein W is a Peptide Cleavable Unit and subscript y is 1 or 2, provided that subscript y is 1 when D is a quaternized Drug Unit ($D^+$) and the Spacer Unit Y bonded to $D^+$ is capable of self-immolation, so that protease action upon W initiates release $D/D^+$ which in the case of $D^+$ initiates its release as a tertiary amine-containing biologically active compound. When subscript y is 2 then protease cleavage of W releases —Y—Y'-D, which may be a biologically active in its own right, or Y in that released moiety is a self-immolative Spacer Unit so that Y'-D is subsequently released as a derivative of a biologically active compound to exert a therapeutic effect. Finally, both Spacer Units (Y and Y') are capable of self-immolation so that protease cleavage of W to release —Y—Y'-D is followed by sequential self-immolative events to release D as a biologically active compound.

Typically in another configuration in which a Ligand Drug Conjugate contains a Glucuronide Unit of formula —Y(W')— within a secondary linker ($L_O$), subscript y in Formula 1, Formula 2 or Formula I is 1 or 2 and W' of the Glucuronide Unit and D, $D^+$ or —Y'-D are covalently bonded Y, wherein Y is a self-immolative Spacer Unit or Y and Y' are each capable of self-immolation upon glycosidase action upon the Glucuronide Unit, and Y in turn is also bonded to A, B, $A_O$ or $L_R$, depending on the presence or absence of A, B and $A_O$, so that W' is orthogonal to the remainder of $L_O$. As before, when D is a quaternized Drug Unit ($D^+$), subscript y in Formula 1, Formula 2, or Formula I is 1 and when subscript y is 2 glycosidase action is followed by self-immolation of Y to release D or —Y'-D, which in the latter case when Y' is capable of self-immolation D is eventually released as a biologically active compound or D is released as a derivative of the biologically active compound in which a fragment of Y' is retained to exert a therapeutic effect. In either configuration, $Y_y$ may serve to separate the cleavage site of the Peptide Cleavable Unit or Glucuronide from $D/D^+$ to avoid steric interactions from that Unit that would interfere with cleavage of W/W' which could occur whenever that cleavage is preformed through enzymatic action.

Typically, a Spacer Unit bonded to $D/D^+$ is comprised or consists of a self-immolating moiety as defined herein wherein that moiety is covalently bonded to a Cleavage Unit so that enzymatic processing of the Cleavable Unit activates the self-immolative moiety for self-destruction thus initiating release of $D/D^+$ as a biologically active compound or derivative thereof. In some aspects, that self-immolative moiety of Y is bonded to W when W is a Peptide Cleavable Unit through an amide (or anilide) functional group with Y also covalently bonded to D through a shared heteroatom or functional group such as a carbamate, or Y is covalently bonded directly to the quaternary amine nitrogen of $D^+$ through its self-immolative moiety. In either instance, Y is bonded to $D/D^+$ such that spontaneous self-destruction of its self-immolative moiety initiated by enzymatic action on the amide or anilide functional group results in release of drug compound or active drug moiety which in the case of $D^+$ is a free tertiary amine-containing drug. In other aspects, the self-immolative moiety of Y is attached to W' of a Glucuronide Unit through a glycosidic bond so that cleavage of that bond initiates release $D/D^+$ as a drug compound or active drug moiety.

"Self-immolating moiety" as used herein refers to a bifunctional moiety within a Spacer Unit (Y) wherein the self-immolative moiety is covalently attached to D through a shared heteroatom or functional group, optionally substituted where permitted, or is directly attached to the quaternized nitrogen of $D^+$ and is also covalently attached to a peptide of W when W is a Peptide Cleavable Unit through another heteroatom (J'), optionally substituted where permitted, or to a glycosidic heteroatom (E') bonded to the carbohydrate moiety (Su) of W' when W is a Glucuronide Unit of formula —Y(W')— so that the self-immolative moiety incorporates these drug linker components into a normally stable tripartite molecule unless activated. On activation the covalent bond to the Peptide Cleavable Unit W or the glycosidic bond of W' in a Glucuronide Unit is cleaved, so that $D/D^+$ or —Y'-D, wherein Y' is a second Spacer Unit bonded to Y, spontaneously separates as a biologically active compound or derivative thereof from the tripartite molecule by self-destruction of its the self-immolative moiety. In some aspects that self-destruction occurs after cellular internalization of a LDC compound comprised of $D/D^+$ and a Linker Unit having a Spacer Unit that contains a self-immolating moiety bonded to Y-D, D or $D^+$.

An intervening organic moiety of a self-immolative Spacer Unit between Y'-D, D or $D^+$ and the optionally substituted the heteroatom J' bonded to W in which W is a Peptide Cleavable Unit or between Y'-D, D or $D^+$ and the optionally substituted heteroatom E' in W' of a Glucuronide Unit of formula —Y(W')— in some aspects is $C_6$-$C_{24}$ arylene-C($R^8$)($R^9$)—, $C_5$-$C_{24}$ heteroarylene- C($R^8$)($R^9$)—, $C_6$-$C_{24}$ arylene-C($R^8$)=C($R^9$)— or $C_5$-$C_{24}$ heteroarylene-C($R^8$)=C($R^9$)—, optionally substituted, wherein $R^8$ and $R^9$ are as described by the embodiments of the invention, and typically is $C_6$-$C_{10}$ arylene-$CH_2$— or $C_5$-$C_{10}$ heteroarylene-$CH_2$—, in which the (hetero)arylene is optionally substituted, wherein the intervening organic moiety is capable of undergoing fragmentation to form a imino-quinone methide or related structure by 1,4 or 1,6-elimination with concomitant release of D or Y'-D on cleavage of the protease cleavable bond between J' and W or on cleavage of the glycosidase cleavable bond of W'. In some aspects, a self-immolative moiety having the aforementioned intervening organic moiety is exemplified by and optionally substituted p-aminobenzyl alcohol (PAB) moiety, ortho or para-aminobenzylacetals, or other aromatic compounds that are electronically similar to the PAB group (i.e., PAB-type) such as 2-aminoimidazol-5-methanol derivatives (see, e.g., Hay et al., 1999, Bioorg. Med. Chem. Lett. 9:2237) or those in which the phenyl group of the p-aminobenzyl alcohol (PAB) moiety is replaced by other heteroarylenes.

In one aspect, an aromatic carbon of an arylene or heteroarylene group of a PAB or PAB-type self-immolative moiety that is incorporated into a Linker Unit is substituted with a functionalized electron-donating heteroatom attached to the cleavage site of W wherein the electron-donating capacity of that heteroatom so functionalized is attenuated (i.e., EDG ability is masked by incorporation of a self-immolative moiety of a Self-immolative Spacer Unit into a Linker Unit). The other substituent of the hetero(arylene) is a benzylic carbon that is attached to a second functional group, heteroatom or second Spacer Unit (Y') bonded to D or is bonded directly to $D^+$, wherein the benzylic carbon is attached to another aromatic carbon atom of the central arylene or heteroarylene, wherein the aromatic carbon bearing the attenuated electron-donating heteroatom is adjacent to (i.e., 1,2-relationship), or two additional positions removed (i.e., 1,4-relationship) from that benzylic carbon atom. The functionalized EDG heteroatom is chosen so that processing of the cleavage site of W restores the electron-donating capacity of the masked heteroatom thus triggering a 1,4- or 1,6-elimination to expel $D^+$, -D or —Y'-D as a biologically active compound or derivative thereof from the benzylic substituent, which in the case of $D^+$ is a tertiary amine-containing biologically active compound, or when Y'-D is released that compound may be capable of exerting a therapeutic effect as a derivative of a biologically active compound or subsequent self-immolation of Y' may be required to provide a biologically active compound in order to elicit a therapeutic effect. Exemplary self-immolative moieties and self-immolative Spacer Unit having those self-immolative moieties are exemplified by the embodiments of the invention.

"Methylene Carbamate Unit" as used herein, unless otherwise stated or implied by context, refers to an organic moiety capable of self-immolation and intervenes between a first self-immolative Spacer Unit and a Drug Unit within a Linker Unit of a Ligand Drug Conjugate or Drug linker compound and as such is an exemplary second Spacer Unit.

A Methylene Carbamate (MAC) Unit bonded to a Drug Unit is represented by formula III:

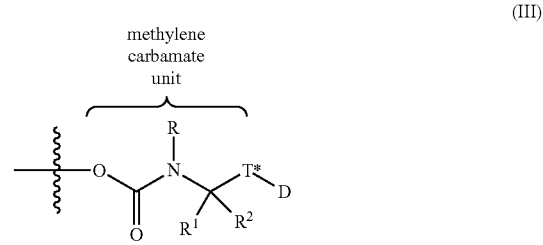

or a pharmaceutically acceptable salt thereof, wherein the wavy line indicates covalent attachment of the methylene carbamate unit to a first self-immolative Spacer Unit (Y); D is a Drug Unit having a functional group (e.g., hydroxyl, thiol, amide or amine functional group) that is incorporated into the methylene carbamate unit; T* is a heteroatom from said functional group, which includes oxygen, sulfur, or nitrogen (i.e, optionally substituted —NH—) that becomes incorporated into the methylene carbamate unit; and R, $R^1$ and $R^2$ are exemplified by the embodiments of the invention. Upon cleavage of a Linker Unit comprised of a MAC Unit, a first self-immolative Spacer Unit (Y) bonded to that MAC Unit as the second self-immolative Spacer Unit (Y') undergoes fragmentation to release —Y'-D of formula III. The MAC Unit then spontaneously decomposes to release D as a biologically active compound or derivative thereof, the presumed mechanism for which is indicated by the embodiments of the invention.

"Biologically active compound" as used herein, unless otherwise stated or implied by context, refers to a compound capable of exerting a therapeutic effect when delivered in unconjugated form, but which may exhibit intolerable side effects due to lack of targeting of the compound to the desired site of action for eliciting that therapeutic effect. In some aspects a biologically active compound has a suitable functional group for attachment to a Linker Unit to allow for its conjugation as a Drug Unit to a Ligand Unit thus providing a LDC Drug Conjugate capable of that targeting. In other aspects a biologically active compound is derivitized to allow for attachment to a Linker Unit, so that release of D/D$^+$ from a Ligand Drug Conjugate compound is in the form of a derivative of the biological compound. In other aspects a derivitized biologically active compound is selectively delivered to the desired site of action due to release of a Y'-D moiety from a Ligand Drug Conjugate compound, which exerts the desired therapeutic effect alone or in combination D, when D is subsequently released from —Y'-D as, for example, when Y' is a second self-immolative Spacer Unit. Non-limiting examples of biologically active compound suitable for practicing the invention include cytotoxic drugs, cytostatic drugs, immunosuppressive drugs and anti-inflammatory drugs.

"Cytotoxic drug" as used herein, unless otherwise stated or implied by context, refers to compound or a metabolite derived from an LDC that exerts an anti-survival effect on hyper-proliferating cells, hyper-activated immune cells or other abnormal cells. In some aspects the cytotoxic drug acts directly upon those cells or indirectly by acting upon the abnormal vasculature that supports the survival and/or growth of the hyper-proliferating or other abnormal or unwanted cells, or the cytotoxic drug acts within sites of infiltrating hyper-activated immune cells. Typically, the abnormal or unwanted cells acted upon by the cytotoxic drug are mammalian cells, more typically human cells. Cytotoxic activity of a cytotoxic drug may be expressed as an $IC_{50}$ value, which is the effective concentration, typically molar amount per unit volume, at which half the cancer cells in an in vitro cell model system survive exposure to the cytotoxic agent. Thus, an $IC_{50}$ value is model-dependent. Typically, a cytotoxic agent incorporated into an LDC will have an $IC_{50}$ value in an in vitro cell model comprised of hyper-proliferating cells of between 100 nM to 0.1 pM or more typically about 10 nM to 1 pM. A highly toxic cytotoxic drug typically has an $IC_{50}$ value in such models of about 100 pM or lower. Although multiple drug resistant inhibitors that reverse resistance to cytotoxic drugs are not cytotoxic in their own right they are sometimes included as cytotoxic drugs.

"Cytostatic drug" as used herein, unless otherwise stated or implied by context, refers to compound or a metabolite derived from an LDC that exerts an inhibitory effect on the growth and proliferation of hyper-proliferating cells, hyper-activated immune cells or other abnormal or unwanted cells. In some aspects the cytostatic drug acts directly upon those cells or indirectly by acting upon the abnormal vasculature that supports the survival and/or growth of the hyper-proliferating or other abnormal cells, or the cytotoxic drug acts within sites of infiltrating hyper-activated immune cells. Typically, the abnormal cells acted upon by the cytotoxic drug are mammalian cells, more typically human cells. Although multiple drug resistant inhibitors that reverse resistance to cytostatic drugs are not cytostatic in their own right they are sometimes included as cytostatic drugs.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sézary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocytic leukemia (AMoL). Other leukemias include hairy cell leukemia (HCL), T-cell lymphatic leukemia (T-PLL), large granular lymphocytic leukemia and adult T-cell leukemia.

"Quaternized drug unit" as used herein, unless otherwise stated or implied by context, refers to a tertiary amine-containing compound (D) having a cytotoxic, cytostatic, immunosuppressive or anti-inflammatory property, typically against mammalian cells, that has been incorporated into an Ligand Drug Conjugate or Drug Linker compound as its corresponding quaternary amine salt (D$^+$). In some aspects, a quaternized Drug Unit is obtained by condensing the tertiary amine nitrogen of the tertiary amine containing compound with a secondary linker $L_O$ precursor having a suitable leaving group. In some aspects the tertiary amine-containing compound is converted to its quaternized form upon its incorporation into a Drug Linker compound. In other aspects a tertiary amine-containing component of the compound is first quaternized with the remainder of the compound appended to complete the D$^+$ Unit. Therefore, structures such as L-$L_{SS}$-$L_O$-D$^+$, L-$L_S$-$L_O$-D$^+$ imply no particular method in which D$^+$ was formed in its corresponding Drug Linker compound and does not require that a reactant used in its formation be a tertiary-amine containing drug. Classes of tertiary-amine containing drugs released from an LDC having a quaternized Drug Unit of the present invention include without limitation certain tubulysin and auristatin compounds as described herein.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. Typically, hyper-proliferating cells are mammalian cells. In some aspects hyper-proliferating cells are hyper-stimulated immune cells as defined herein whose persistent state of cell division or activation occurs after the cessation of the stimulus that may have initially evoked the change in their cell division. In other aspects the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include but are not limited to those characterized as a precancer, hyperplasia, dysplasia, adenoma, sarcoma, blastoma, carcinoma, lymphoma, leukemia or papilloma. Precancers are usually defined as lesions that exhibit histological changes which are associated with an increased risk of cancer development and sometimes have some, but not all, of the molecular and phenotypic properties that characterize the cancer. Hormone associated or hormone sensitive precancers include, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells.

"Normal quiescent cells" as used herein, unless otherwise stated or implied by context, refer to are noncancerous cells in their resting $G_o$ state and have not been stimulated by stress or a mitogen or are immune cells that are normally inactive or have not been activated by pro-inflammatory cytokine exposure.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instance the stimulus that may have initially evoked the change in proliferation or stimulation is not attributable to an external insult but is internally derived as in an autoimmune disease. In some aspects a hyper-stimulated immune cells is a pro-inflammatory immune cell that has been hyper-activated through chronic pro-inflammatory cytokine exposure.

In some aspects of the invention a Ligand Drug Conjugate compound of an LDC composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and CD8$^+$ T cell activation.

"Glycosidase" as used herein, unless otherwise stated or implied by context, refers to a protein capable of enzymatic cleavage of a glycosidic bond. Typically, the glycosidic bond to be cleaved is present in a Glucuronide Unit as the Cleavable Unit of Ligand Drug Conjugate or Drug Linker compound. Sometimes the glycosidase acting upon a Ligand Drug Conjugate is present intracellularly in hyper-proliferating cells, hyper-activated immune cells or other abnormal cells to which the LDC has preferential access in comparison to normal cells, which is attributable to the targeting capability of its Ligand Unit. Sometimes the glycosidase is more specific to the abnormal or unwanted cells or is preferentially excreted by abnormal or unwanted cells in comparison to normal cells or is present in greater amount in the vicinity of abnormal cells in comparison to amounts of the glycosidase typically found in serum of an intended subject to whom the LDC is to be administered. Typically, the glycosidic bond within a Glucuronide Unit, which has the formula of —W'(Y)—, acted upon by a glycosidase connects the anomeric carbon of a carbohydrate moiety (Su) to a self-immolative Stretcher Unit (Y) through an optionally substituted heteroatom (E') so that W' is Su-E'-. In some aspects E', which forms the glycosidic bond to the carbohydrate moiety (Su), is a phenolic oxygen atom of a self-immolating moiety in a self-immolative Stretcher Unit Y such that glycosidic cleavage of that bond triggers 1,4- or 1,6-elimination of D or Y'-D as a biologically active compound or derivative thereof, or D$^+$ as a tertiary amine-containing drug in which that amine in quaternized form is bonded directly to the optionally substituted benzylic carbon of a PAB or PAB-type self-immolative moiety.

In some aspects, Drug Linker compounds or Ligand Drug Conjugates are represented by formula $L_{SS}$-B$_b$-(A$_a$-Y$_y$(W')-D/D$^+$)$_n$ or L-(L$_S$-B$_b$-(A$_a$-Y$_y$(W')-D/D$^+$)$_n$)$_p$, in which $L_{SS}$ is M$^1$-A$_R$(BU)-A$_O$- and L$_S$ is M$^2$-A$_R$(BU)-A$_O$ or M$^3$-A$_R$(BU)-A$_O$-, wherein A$_O$ is an second optionally Stretcher Unit, which in some aspects serves as Hydrolysis Enhancing (HE) Unit and A is a first optionally Stretcher Unit, wherein in some aspects A or a subunit thereof has the formula of -L$^P$(PEG)-, wherein -L$^P$ and PEG are as defined herein for parallel connector units and PEG Units, respectively; BU represents an acyclic or cyclic Basic Unit, and subscripts a and b are independently 0 or 1, and subscript n is 1, 2, 3 or 4, wherein B is a Branching Unit, and is present when subscript n is 2, 3 or 4 so that subscript b is 1 and wherein A is a first Stretcher Unit, when subscript a is 1, and subscript y is 1 or 2 unless D is a quaternized Drug Unit (D$^+$) in which case subscript y is 1.

In those aspects —Y(W')— typically is of the formula Su-O'—Y, wherein Su is a carbohydrate moiety, Y is a self-immolative Spacer Unit having a PAB or PAB-type self-immolative moiety with glycosidic bonding to Su, wherein O' represents the oxygen atom of the glycosidic bond cleavable by a glycosidase and D/D$^+$ is bonded directly to the self-immolative moiety of Y so that subscript y is 1, or D is bonded to that self-immolative moiety through Y' so that subscript y is 2, wherein Y' is a second Spacer Unit, which may or may not be capable of self-immolation, or an optionally substituted heteroatom or functional group the latter of which may also be capable of self-immolation upon release of Y'-D to provide D as a biologically active compound or derivative thereof, or Y' is a methylene carbamate unit, wherein Su-O'— is attached to the optionally substituted (hetero)arylene of the self-immolative moiety and D/D$^+$ or —Y'-D are attached to that (hetero)arylene through an optionally substituted benzylic carbon such that self-immolative release of D/D$^+$ or —Y'-D is initiated, thereby providing a biologically active compound or derivative thereof that in the case of D$^+$ is released as a tertiary amine-containing compound. Although such —Y(W')— moieties are referred to as Glucuronide Units Su of W' is not limited to a glucuronic acid residue.

Typically, Su-O'—SI— moieties (where —O'— represents the oxygen of the glycosidic bond and Su is a carbohydrate moiety) have structures described for self-immolating moieties in which E' bonded to the central (hetero)arylene moiety of a PAB or PAB-type moiety is an oxygen atom with that heteroatom bonded to the carbohydrate moiety (Su) through that moiety's anomeric carbon atom.

Such moieties attached to D include those of formula Su-O'—Y—Y'-D having the structure of:

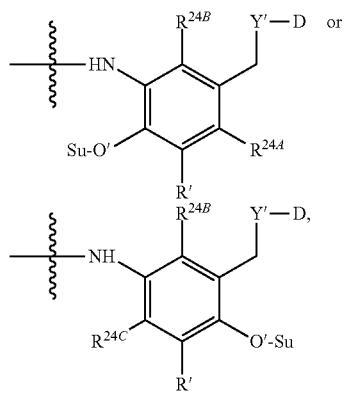

and such moieties attached to D$^+$ include those of formula Su-O'—Y-D$^+$ having the structure of:

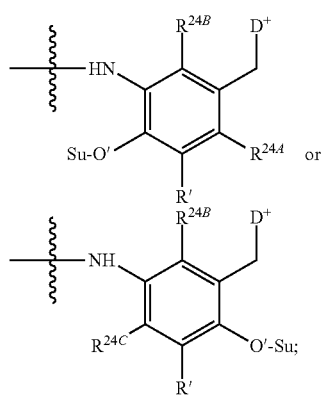

wherein Y' is absent, or is an optionally substituted heteroatom or functional group, which may be capable of self-immolation as when Y is a carbamate functional group or Y' is a second Spacer Unit, which may also be capable of self-immolation as when Y' is a methylene carbamate unit; $R^{24A}$, $R^{24B}$ and $R^{24C}$ are independently selected from the group consisting of hydrogen, $C_1$-$C_6$ alkyl, $C_1$-$C_6$ alkoxy, other EDGs, halogen, nitro and other EWGs or $R^{24}$ and R' if the left-hand structure of $R^{24C}$ and R' in the right-hand structure together with the aromatic carbons to which they are attached define an benzo-fused $C_5$-$C_6$ carbocycle, and are selected so that the electron donating ability of the phenolic —OH released from the glycosidic bond by enzymatic action of a glycosidase, the sensitivity to selective cleavage by the glycosidase, and the stability of the imino-quinone methide intermediate resulting from fragmentation by 1,4- or 1,6-elimination is balanced with the leaving ability of D/D$^+$ or —Y'D so that efficient release of a biologically active compound or derivative thereof occurs. The Su-O'—Y'— moieties in the above —Y$_y$(W')-D/D$^+$ structures are representative Glucuronide Units. When the glycosidic bond is to a glucuronic acid the glycosidase capable of enzymatic cleavage of that glycosidic bond is a glucuronidase. Further descriptions of Glucuronide Units are provided by the embodiments of the invention.

"Carbohydrate moiety" as used herein, unless otherwise stated or implied by context, refers to a monovalent radical of a monosaccharide having the empirical formula of $C_m(H_2O)_n$, wherein n is equal to m, containing an aldehyde moiety in its hemiacetal form or a derivative thereof in which a $CH_2OH$ moiety within that formula has been oxidized to a carboxylic acid (e.g., glucuronic acid from oxidation of the $CH_2OH$ group in glucose). Typically, a carbohydrate moiety (Su) is a monovalent radical of cyclic hexose, such as a pyranose, or a cyclic pentose, such as a furanose. Usually, the pyranose is a glucuronide or hexose in the β-D conformation. In some instances, the pyranose is a β-D-glucuronide moiety (i.e., β-D-glucuronic acid linked to the self-immolative moiety —SI— via a glycosidic bond that is cleavable by β-glucuronidase). Sometimes, the carbohydrate moiety is unsubstituted (e.g., is a naturally occurring cyclic hexose or cyclic pentose). Other times, the carbohydrate moiety can be a β-D-glucuronide derivative, e.g., glucuronic acid in which one or more, typically 1 or 2 of its hydroxyl moieties are independently replaced with moieties selected from the group consisting of halogen and $C_1$-$C_4$ alkoxy.

"Protease" as used herein, unless otherwise stated or implied by context, refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond.

When W is a Peptide Cleavable Unit bonded to a self-immolative Spacer Y when subscript y is 1 or 2, or to a Drug Unit when subscript y is 0 in Formula 1, Formula 2 or Formula I, through an amide or other carbonyl-nitrogen containing functional group cleavable by a protease that cleavage site is oftentimes limited to those recognized by proteases that are found in abnormal cells including hyper-proliferating cells and hyper-stimulated immune cells or within cells particular to the environment in which these abnormal cells are present. In those instances, the protease may or may not be preferentially present or found in greater abundance within cells targeted by a Ligand Drug Conjugate having that Peptide Cleavable Unit since it will have poorer access to cells that do not have the targeted moiety or have insufficient copy number of the targeted moiety to which its Ligand Unit is directed to have an adverse effect due to immunologically specific uptake of the Conjugate. Other times, the protease is preferentially excreted by abnormal cells or by cells in the environment in which those abnormal cells are found in comparison to normal cells or in comparison to typical environments in which those normal cells are found in the absence of abnormal cells. Thus, in those instances where the protease is excreted, the protease is typically required to be preferentially present or found in greater abundance in the vicinity of cells targeted by the Ligand Drug Conjugate in comparison to that of normal cells.

When incorporated into a Ligand Drug Conjugate composition, a peptide that comprises W and which is bonded to Y or D, dependent on the presence or absence of Y, through a carbon-nitrogen bond will present a recognition sequence to a protease that cleaves that bond resulting in fragmentation of the Linker Unit whereby release of a biologically active compound or derivative thereof from a compound of the composition occurs. Sometimes, the recognition sequence is selectively recognized by an intracellular protease present in abnormal cells to which the Ligand Drug Conjugate has preferred access in comparison to normal cells due to targeting of the abnormal cells by its Ligand Unit, or is preferentially produced by abnormal cells in comparison to normal cells, for the purpose of appropriately delivering a biologically active compound or derivative thereof to the desired site of action. Usually the peptide is resistant to circulating proteases in order to minimize premature release of the biologically active compound or its derivative and thus minimize unwanted systemic exposure to the released compound. In some aspects, the peptide will have one or more unnatural or non-classical amino acids in its sequence order to have that resistance. In that and other aspects, the amide bond that is specifically cleaved by a protease is produced by or present within an abnormal cell and is sometimes an anilide bond wherein the nitrogen of that anilide is a nascent electron-donating heteroatom (i.e., J') of an self-immolative moiety having one the previously defined structures for such moieties. Thus, protease action on such a peptide sequence in W results in release of a Drug Unit as a biologically active compound or derivative thereof from Linker Unit fragmentation occurring by 1,4- or 1,6-elimination through the central (hetero)arylene moiety of a PAB or PAB-type self-immolative Spacer Unit.

Regulatory proteases are typically located intracellularly and are required for the regulation of cellular activities, including cellular maintenance, proliferation or other intracellular activity, that sometimes becomes aberrant or dysregulated in abnormal cells. In some instances, when W is directed to a protease preferentially present intracellularly in comparison its extracellularly presence, that protease is typically a regulatory protease. In some instances, those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

In other instances, when W is directed to a protease that is preferentially distributed extracellularly in the vicinity of abnormal cells, such as hyper-proliferating or hyper-stimulated immune cells, in comparison to normal cells distant from the abnormal cells, that distribution is due to preferential excretion by the abnormal cells or by neighboring cells whose excretion of the protease is peculiar to the environment of hyper-proliferating or hyper-stimulated immune cells. In some of those instances the protease is a metalloprotease. Typically, those proteases are involved in tissue remodeling, which aids in the invasiveness of hyper-proliferating cells or undesired accumulation of hyper-activated immune cells, which often results in further recruitment of such cells.

"Tubulysin drug", "tubulysin compound" and like as used herein, unless otherwise stated or implied by context, refer to a peptide-based tubulin disrupting agent having cytotoxic, cytostatic or anti-inflammatory activity and is comprised of one natural or un-natural amino acid component and three other un-natural amino acid components wherein one of those components is characterized by a central 5-membered or 6-membered heteroarylene moiety or a 6-membered arylene (i.e., phenylene) moiety, optionally substituted, and another component at the N-terminus has a tertiary amine functional group for incorporation into a quaternized Drug Unit.

Tubulysin compounds include those have the structure of $D_G$ or $D_H$:

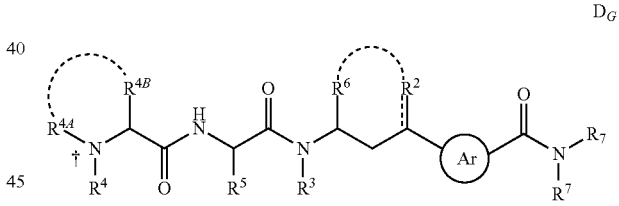

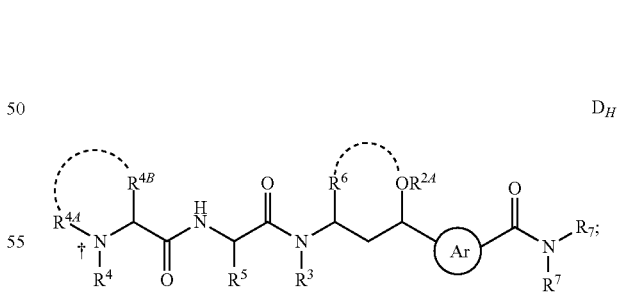

wherein the straight dashed line indicates an optional double bond, the curved dash lines indicate optional cyclization, the circled Ar indicates an arylene or heteroarylene that is 1,3-substituted within the tubulysin carbon skeleton, optionally substituted at the remaining positions, wherein the arylene or heteroarylene and other variable groups are as defined in the embodiments of the invention.

Naturally-occurring tubulysin compounds have the structure of $D_{G-6}$.

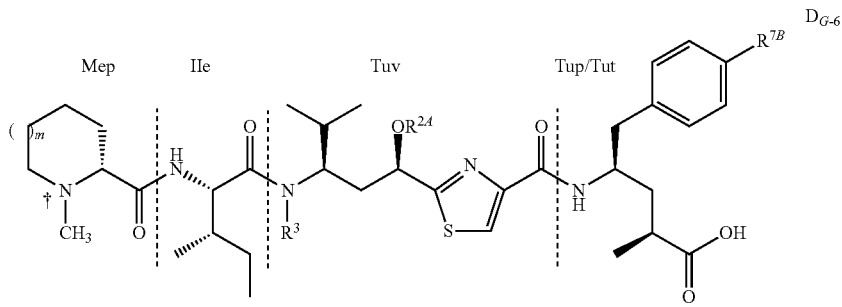

and are conveniently divided into four amino acid subunits, as indicated by the dashed vertical lines, named N-methyl-pipecolinic acid (Mep), isoleucine (Ile), tubuvaline (Tuv), and either tubuphenylalanine (Tup, when $R^{7A}$ is hydrogen) or tubutyrosine (Tut, when $R^{7A}$ is —OH). There are about a dozen naturally occurring tubulysins presently known named Tubulysin A-I, Tubulysin U, Tubulysin V and Tubulysin Z, whose structures are indicated by variable groups for structure $D_{G-6}$ defined in embodiments of tubulysin-based quaternized drug units.

Pretubulysins have the structure $D_G$ or $D_H$, wherein $R^3$ is —$CH_3$ and $R^2$ is hydrogen, and desmethyl tubulysins have the structure of $D_G$, $D_{G-1}$, $D_{G-6}$, $D_H$, $D_{H-1}$, or have other tubulysin structures given by the embodiments of tubulysin-based quaternized drug units, wherein $R^3$ is hydrogen, and wherein the other variable groups as described for tubulysin compounds described elsewhere. In some aspects pretubulysins and desmethyl tubulysins are optionally included in the definition of tubulysins. In other aspects pretubulysins and desmethyl tubulysins are included in the definition of tubulysins. In still other aspects, pretubulysins and desmethyl tubulysins are excluded from the definition of tubulysins.

In structures $D_G$, $D_{G-1}$, $D_{G-6}$, $D_H$, $D_{H-1}$, and other tubulysin structures described herein in embodiments of tubulysin-based quaternized Drug Units, the indicated (†) nitrogen is the site of quaternization when such structures are incorporated into an LDC or precursor thereof as a quaternized Drug Unit ($D^+$). When incorporated into a Ligand Drug Conjugate, Drug Linker compound or an Intermediate thereto that nitrogen is typically quaternized by covalent binding to a secondary linker ($L_O$) component. Typically, a quaternized Drug Unit ($D^+$) incorporates a tubulysin compound by covalent attachment of the tertiary amine moiety to the benzylic carbon of a PAB or PAB-type moiety of a self-immolative Spacer Unit in a secondary linker, thus forming a quaternized nitrogen atom. Structures of other exemplary tertiary amine-containing tubulysins and the manner of their incorporation into an LDC are provided in embodiments of quaternized tubulysin Conjugates.

Exemplary methods of preparing tubulysin drugs and structure-activity relationships are provided by Friestad et al. "Stereoselective access to tubuphenylalanine and tubuvaline: improved Mn-mediated radical additions and assembly of a tubulysin tetrapeptide analog" *J. Antibiotics* (Jpn) (2016) 2016: 1-5; Nicolaou et al. "Total synthesis and biological evaluation of natural and designed tubulysins" *J. Am. Chem. Soc.* (2016): 138: 1698-1708; Murray et al. "Chemistry and biology of tubulysins: antimitotic tetrapeptides with activity against drug resistant cancers" *Nat. Prod. Rep.* (2015) 32: 654-662: Park et al. "Synthesis of stereochemically diverse cyclic analogs of tubulysins" *Bioorg. Med. Chem.* (2015) 23: 6827-6483; Shankar et al. "Synthesis and structure-activity relationship studies of novel tubulysin U analogs-effect on cytotoxicity of structural variations in the tubuvaline fragment" *Org. Biomol. Chem.* (2013) 11: 2273-2287; Yang et al. "Design, synthesis, and biological activities of triazole tubulysin V analogue" *Tet. Lett.* (2013) 54: 2986-2988; Xiangming et al. "Recent advances in the synthesis of tubulysins" *Mini-Rev. Med. Chem.* (2013) 13: 1572-8; Rath et al. "Anti-angiogenic effects of the tubulysin precursor pretubulysin and of simplified pretubulysin derivatives" *Br. J. Pharmacol.* (2012) 167: 1048-1061; Pando et al. "The multicomponent approach to natural product mimics: Tubugis, N-substituted anticancer peptides with picomolar activity" *J. Am. Chem. Soc.* (2011) 133: 7692-7695; Shibue et al. "Synthesis and biological evaluation of tubulysin D analogs related to stereoisomers of tubuvaline" *Bioorg. Med. Chem. Lett.* (2011) 21: 431-434; Shankar et al. "Synthesis and cytotoxic evaluation of diastereomers and N-terminal analogs of Tubulysin-U" *Tet. Lett.* (2013) 54: 6137-6141; Burkhart et al. "Syntheses and evaluation of simplified pretubulysin analogues" *Eur. J. Org. Chem.* (2011) 2011: 3050-3059; Shankar et al. "Total synthesis and cytotoxicity evaluation of an oxazole analogue of Tubulysin U" *Synlett* (2011) 2011 (12): 1673-6; Patterson et al. "Expedient synthesis of N-methyl tubulysin analogs with high cytotoxicity" *J. Org. Chem.* (2008) 73: 4362-4369; Raghavan et al. "Cytotoxic simplified tubulysin analogues" *J. Med. Chem.* (2008) 51: 1530-3; Balasubramanian, R. et al. "Tubulysin analogs incorporating desmethyl and dimethyl tubuphenylalanine derivatives" *Bioorg. Med. Chem. Lett.* (2008) 18: 2996-9; Raghavan et al. "Cytotoxic simplified tubulysin analogues" *J. Med. Chem.* (2008) 51: 1530-3; and Wang et al. "Structure-activity and high-content imaging analysis of novel tubulysins" *Chem. Biol. Drug Des.* (2007) 70: 75-86. Structures of Tubulysin analogs in the above cited references are specifically incorporated herein and are encompassed by the definition of tubulysin drugs.

"Auristatin drug", "auristatin compound" and like terms as used herein, unless otherwise stated or implied by context, refer to a peptide-based tubulin disrupting agent having cytotoxic, cytostatic or anti-inflammatory activity that is comprised of a dolaproline and a dolaisoleucine residue or amino acid residues related thereto. Dolastatins, which are isolated from marine sources, are pentapeptides of related structure to auristatins and in some aspects are encompassed by the definition of auristatins. Non-limiting, representative dolastatins are Dolastatin 10 and Dolastatin 15, which have the following structures:

the auristatin is incorporated into a quaternized Drug Unit ($D^+$) through quaternization by the benzylic carbon of a PAB or PAB-type Spacer Unit so that subscript

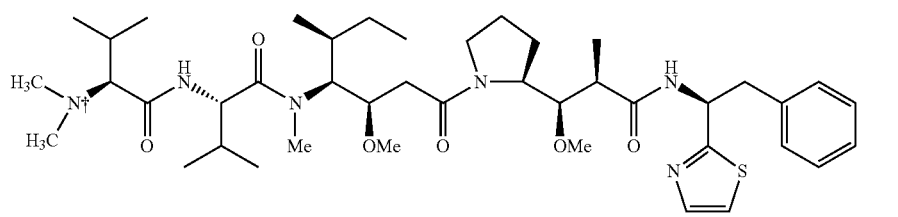

Dolastatin 10

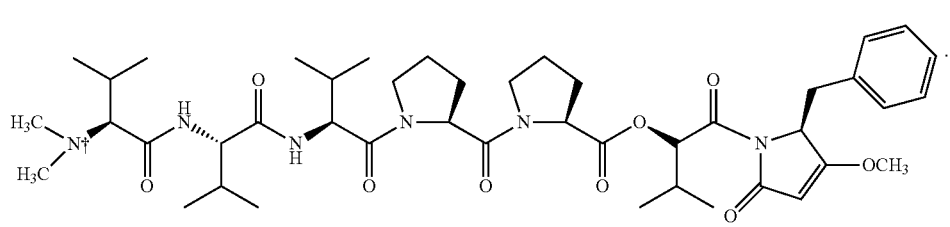

Dolastatin 15

Other exemplary dolastatins are those related to dolastatin 10 wherein the phenyl and thiazole substituents are replaced with independently selected $C_6$-$C_{24}$ aryl or $C_5$-$C_{24}$ heteroaryl moieties. Other exemplary dolastatins are related to dolastatin 15 wherein the C-terminal ester moiety is replaced by an amide wherein the amide nitrogen is substituted with a ($C_6$-$C_{24}$ aryl)-$C_1$-$C_{12}$ alkyl- or ($C_5$-$C_{24}$ heteroaryl)-$C_1$-$C_{12}$ alkyl-moiety. When incorporated into a Ligand Drug Conjugate or Drug Linker compound the indicated (†) tertiary amine nitrogen of the above and following auristatin compounds are quaternized.

Some exemplary auristatins have the structure of $D_E$ or $D_F$:

y in Formula 1, Formula 2 or Formula I is 1. Structures of other exemplary primary, secondary and tertiary amine-containing auristatins and the manner of their incorporation as D or $D^+$ into a Ligand Drug Conjugate or Drug Linker compound is provided in embodiments of auristatin-based Drug Units.

Other exemplary auristatins include, but are not limited to AE, AFP, AEB, AEVB, MMAF, and MMAE. The synthesis and structure of auristatins are described in U.S. Patent Application Publication Nos. 2003-0083263, 2005-0238649 2005-0009751, 2009-0111756, and 2011-0020343; Interna-

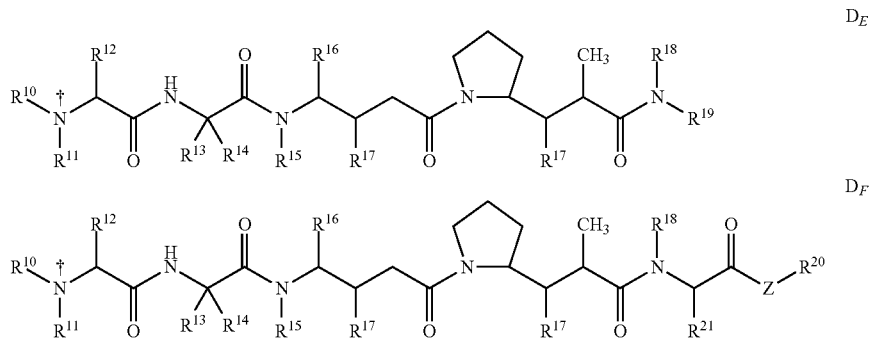

wherein Z is —O—, —S—, or —N($R^{19}$)—, and wherein $R^{10}$-$R^{21}$ are as defined in embodiments for auristatin Drug Units. When the indicated nitrogen (†) is that of a primary or secondary amine (i.e., one or both of $R^{10}$, $R^{11}$ are hydrogen), the auristatin is typically incorporated into a Drug Unit through a carbamate functional group comprised of that nitrogen atom. That carbamate functional group is an exemplary second Spacer Unit (Y') and is capable of undergoing self-immolation, which is turn is attached to a PAB or PAB-type Spacer Unit (Y) so that subscript y in Formula 1, Formula 2 or Formula I is 2. When the indicated nitrogen (†) is that of a tertiary amine (i.e., neither $R^{10}$ or $R^{11}$ is hydrogen), tional Patent Publication No. WO 04/010957, International Patent Publication No. WO 02/088172, and U.S. Pat. Nos. 7,659,241 and 8,343,928. Their structures and methods of their syntheses disclosed therein are specifically incorporated by reference herein.

"PBD compound" unless otherwise stated or implied by context, refers to a cytotoxic or cytostatic compound, or is a compound having anti-inflammatory activity, comprised of one or two independently selected benzodiazepine core structures, in which two of the core structure may be interconnected through a tether to form a PBD dimer. Exemplary benzodiazepine core structures typically found in such compounds are as follows:

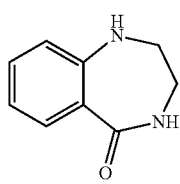

3,4-dihydro-1H-benzo[e][1,4]diazepin-5(2H)-one

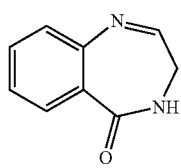

3H-benzo[e][1,4]diazepin-5(4H)-one

The benzodiazepine core structure can differ in the number, type and position of substituents on either ring of the benzodiazepine and in the degree of saturation of the diazepine ring system. They also may differ in the number of additional rings fused to its benzene and/or diazepine ring. Benzodiazepine core structures may additionally have its benzene or diazepine ring fused to one or more aromatic, or non-aromatic carbocyclic or heterocylic rings, typically one or two other aromatic or heteroaromatic rings. A benzodiazepine dimer is a compound that has been formed by joining two benzodiazepine core structures together via a tether attached to their respective benzodiazepine ring systems.

In one aspect, a PBD compound is comprised of one or two independently selected pyrrolobenzodiazepine core structures. Exemplary pyrrolobenzodiazepine core structures typically found in such compounds are as follows

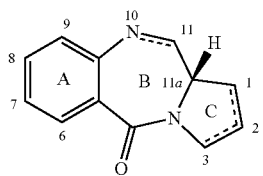

but can differ in the number, type and position of substituents, in both their aromatic A rings and pyrrolo C rings, and in the degree of saturation of the C ring. In the B-ring there is either an imine (N=C) or a carbinolamine (NH—CH(OH)), or a carbinolamine methyl ether (NH—CH(OMe)) functional group or other carbinolamine functional group in which another ether replaces methoxy at the $N^{10}$—$C^{11}$ positions, which are metabolic precursors to the imine functional group. Without being bound by theory, it is believed that the $N^{10}$—$C^{11}$ imine is the electrophilic center responsible for alkylating DNA. All of the known natural products based upon the pyrrolobenzodiazepine structure has the (S)-stereoconfiguration at the chiral $C^{11a}$ position, which provides them with a right-handed twist when viewed from the C ring towards the A ring. It is believed this configuration gives them the appropriate three-dimensional shape for isohelicity with the minor groove of B-form DNA, leading to a snug fit at the binding site. It is believed the ability of PBDs to form an adduct in the minor groove enables them to interfere with DNA processing, hence contributes to their use as antitumor agents, when targeted to cancer cells or their vicinity or to their anti-inflammatory effects through targeting of hyper-stimulated immune cells. The biological activity of those molecules can be potentiated by, for example, joining two PBD units together through C8/C' 8-hydroxyl substituent via a flexible alkylene or heteroalkylene linker to form a PBD dimer. The PBD dimers are thought to form sequence-selective DNA lesions, such as the palindromic 5'-Pu-GATC-Py-3' interstrand crosslink. Without being bound by theory, it is believed the ability to form interstrand crosslinks are thought to be mainly responsible for the biological activity of the PBD dimers.

PBD compounds as Drug Units are collectively referred to as PBD Drug Units Exemplary PBD Drug Units in which the incorporated PBD compound is a dimer have the structure of:

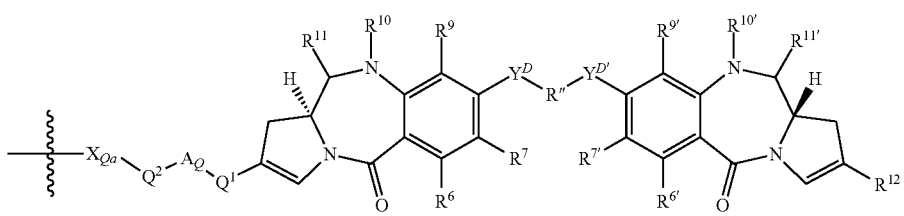

wherein the wavy line indicates covalent attachment of the PBD Drug Unit to a Linker Unit of a Ligand Drug Conjugate or Drug Linker compound and variable groups $X_{Qa}$, $Q^2$, $A_Q$, $Q^1$, $R^6$, $R^7$, $R^9$, $R^{10}$, $R^{11}$, $R^{6'}$, $R^{7'}$, $R^{9'}$, $R^{10'}$, $R^{11'}$ $Y^D$, $Y^{D'}$, and R" are as defined by the embodiments of the invention. In one aspect, the PBD Drug Unit has the structure of:

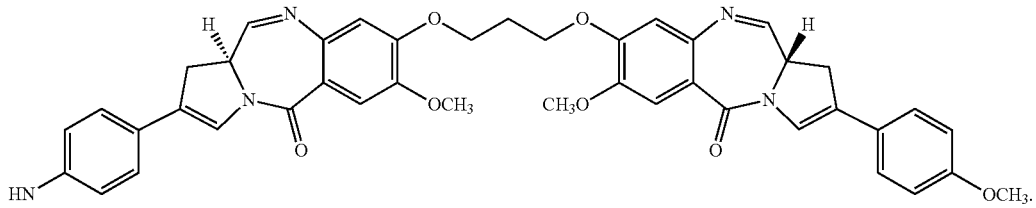

"Intracellularly cleaved", "intracellular cleavage" and like terms used herein refer to a metabolic process or reaction within a targeted cell occurring upon an Ligand Drug Conjugate or the like, whereby covalent attachment through its Linker Unit between the Drug Unit or quaternized Drug Unit and the Ligand Unit of the Conjugate is broken, resulting in release of drug compound, active drug moiety or other metabolite of the Conjugate within the targeted cell. The moieties from that cleavage are thus intracellular metabolites of the Ligand Drug Conjugate.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

The term "inhibit" or "inhibition of" unless otherwise stated or implied by context, means to reduce by a measurable amount, or to prevent entirely an undesired activity or outcome. In some aspects the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, a Ligand Drug Conjugate that targets an antigen that is not present or has low copy number on the abnormal cells of interest or is genetically engineered to not recognize any known antigen is used as a negative control.

The term "therapeutically effective amount" unless otherwise stated or implied by context, refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic or cytotoxic. For cancer therapy, efficacy can, for example, be measured by assessing the time to disease progression (TTP) determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-β, TNFα, INFγ and MCP-1, or numbers of classically activated macrophages.

In some aspects of the invention, the Ligand Drug Conjugate compound associates with an antigen on the surface of a target cell (i.e., an abnormal cell such as a hyper-proliferating cell or a hyper-stimulated immune cell), and the Conjugate compound is then taken up inside a target cell through receptor-mediated endocytosis. Once inside the cell, one or more Cleavage Units within a Linker Unit of the Conjugate are cleaved, resulting in release of D/D$^+$ as a biologically active compound or derivative thereof, which in the case of D$^+$ a tertiary amine-containing biologically active compound is released. The released compound is then free to migrate within the cytosol and induce cytotoxic or cytostatic activities, or in the case of hyper-stimulated immune cells may alternatively inhibit pro-inflammatory signal transduction. In another aspect of the invention, the Drug Unit (D) or quaternized Drug Unit (D$^+$) is released from a Ligand Drug Conjugate compound outside the targeted cell but within the vicinity of the targeted cell so that the released compound is able to subsequently penetrate the cell rather than being prematurely released at distal sites.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Treat", "treatment," and like terms, unless otherwise indicated by context, refer to therapeutic treatment or prophylactic measures to prevent relapse, wherein the object is to inhibit or slow down (lessen) an undesired physiological change or disorder, such as the development or spread of cancer or tissue damage from chronic inflammation. Typically, beneficial or desired clinical results of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term can also mean prolonging survival or quality of like of a subject as compared to expected survival or quality of life for a subject not receiving treatment. Those in need of treatment include those already having the condition or disorder as well as those prone to have the condition or disorder.

In the context of cancer or a disease state related to chronic inflammation, the term includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, inhibiting replication or stimulation of pro-inflammatory immune cells, inhibiting or decreasing the chronic inflammatory state of a dysregulated immune system or decreasing the frequency and/or intensity of flares experienced by subjects having an autoimmune condition or disease or ameliorating one or more symptoms associated with cancer or a hyper-immune stimulated disease or condition.

"Salt form" as used herein, unless otherwise indicated by context, refers to a charged compound in ionic association with a countercation(s) and/or counteranions so as to form an overall neutral species. Accordingly, salt forms include a protonated form of a compound in ionic association with a counteranion. Such a salt forms may result from interaction of a basic functional group and an acid functional group within the same compound or involve inclusion of a negatively charged molecule such as an acetate ion, a succinate ion or other counteranion. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound. Quaternary amine nitrogens including those of quaternized Drug Units are non-limiting examples of such permanently charged atoms. The counterion may be any charged organic or inorganic moiety that stabilizes an opposite charge on the parent compound. Furthermore, a compound in salt form may have more than one charged atoms in its structure. In instances where multiple charged atoms of the parent compound are part of the salt form, that salt from of the compound can have multiple counter ions. Hence, a salt form of a compound can have one or more charged atoms and/or one or more counterions.

A salt form of a compound not involving a quaternized nitrogen atom is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable $pK_a$, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basis amine functional group of a cyclic or acyclic Basic Unit.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Ziirich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

"Loading", "drug loading", "payload loading" or like terms as used herein, unless otherwise indicated by context, refer to the average number of payloads ("payload" and "drug" is used interchangeable herein with "biologically active compound or its derivative) in an population of Ligand Drug Conjugate compounds of a LDC composition. The drug loading of that composition, which can also include species lacking conjugated drug, is characterized by a distribution of attached $D/D^+$ Units or drug linker moieties per Ligand Unit. Other species may include those Conjugate compounds having the same number of $D/D^+$ Units or drug linker moieties per Ligand Unit but differ by the attachment sites of their respective drug linker moieties to the Linker Unit, but otherwise have substantially the structure with respect to the Ligand Unit, which allows for variations in glycosylation and mutational differences in peptide sequences. Drug loading may range from 1 to 24 Drug Units (D) or quaternized Drug Units ($D^+$) or drug linker moieties comprising D/D$^+$ per Ligand Unit and is sometimes referred to as the DAR, or drug to targeting moiety ratio, wherein the targeting moiety of a Ligand Drug Conjugate is its Ligand Unit. Ligand Drug Conjugate compositions described herein typically have DAR values ranging from 1 to 24, and in some aspects range from 1 to about 8, from about 2 to about 8, from about 2 to about 6, from about 2 to about 5 or from about 2 to about 4. Typically, DAR values are about 2, about 4, about 6 and about 8. The average number of conjugated drugs per Ligand Unit, or DAR value, of a Ligand Drug Conjugate composition may be characterized by conventional means such as UV/visible spectroscopy, mass spectrometry, ELISA assay, and HPLC. A quantitative DAR value may also be determined. In some instances, separation, purification, and characterization of homogeneous Ligand Drug Conjugate compounds having a particular DAR value may be achieved by methods using reverse phase HPLC or electrophoresis. DAR may be limited by the number of attachment sites on a targeting agent that is to be incorporated into a Ligand Drug Conjugate as its Ligand Unit.

For example, when the targeting agent is an antibody and the attachment site is a cysteine thiol functional group, the antibody may have only one or several that are sufficiently reactive towards the maleimide ring system of a M$^1$-A$_R$(BU)-containing moiety, such as a Drug Linker compound, so as to undergo Michael addition. Sometimes, the cysteine thiol functional group is from of a cysteine residue that participated in an interchain disulfide bond of an antibody. Other times, the cysteine thiol functional group is that of a cysteine residue that did not participate in an interchain disulfide bond, but was introduced through genetic engineering. Sometimes, less than the theoretical maximum of D/D$^+$ Units or drug linker moieties having these Units is conjugated to an antibody during a conjugation reaction.

I. Embodiments

Provided herein are Ligand Drug Conjugate (LDC) compositions and compounds, and their Drug Linker compound precursors and Intermediates thereof, wherein a LDC is capable of preferential delivery of a cytotoxic or cytostatic drug to hyperproliferating cells or hyper-activated immune cells or are capable of preferential delivery to the vicinity of such abnormal cells in comparison to normal cells or their environment in which these abnormal cells are typically not present and are thus useful for treating diseases and conditions characterized by these abnormal cells.

1.1 General:

A LDC has three major components: (1) a Ligand Unit, which incorporates a targeting agent that selectively binds to a targeted moiety present on, within or in the vicinity of abnormal cells or other unwanted cells in comparison to other moieties present on, within, or in the vicinity of normal cells where these abnormal or unwanted cells are typically not present, or the targeted moiety is present on, within, or in the vicinity of abnormal or other unwanted cells in greater abundance in comparison to normal cells or the environment of normal cells where abnormal or unwanted cells are typically not present, (2) a Drug Unit (D) incorporating the structure of a drug compound, which in the case of a tertiary amine-containing drug compound, D is a quaternized Drug Unit (D$^+$) due to attachment of the Linker Unit to the tertiary amine nitrogen, and (3) a Linker Unit, which interconnect D/D$^+$ and the Ligand Unit and is capable of conditionally releasing D/D$^+$ as a biologically active compound or derivative thereof, which in the case of D$^+$ is a tertiary amine-containing biologically active compound, wherein said release is preferably within or in the vicinity of abnormal cells or within or in the vicinity of targeted normal cells that are peculiar to the environment of the abnormal cells as opposed to normal cells distant from the site of the abnormal cells.

A biologically active compound or derivative thereof to be used in the present invention is one that primarily or selectively exerts its biological effect (e.g., cytotoxic, cytostatic effect) on mammalian cells as compared to prokaryotic cells. In some aspects, the targeted moiety, which is recognized by the targeting Ligand Unit, is an epitope of an extracellular displayed membrane protein and is preferentially found on abnormal or unwanted cells in comparison to normal cells. Specificity towards the abnormal (i.e., the targeted cells) results from the Ligand Unit (L) of the LDC. In some embodiments, the Ligand Unit is that of an antibody, which is an exemplary targeting agent, wherein the Ligand Unit substantially retains the antibody's ability to recognize the abnormal mammalian cells, and is sometimes referred to as an antibody Ligand Unit.

In some embodiments, it is preferred that the membrane protein targeted by the Ligand Unit have sufficient copy number and be internalized upon binding of a Ligand Drug Conjugate compound through its Ligand Unit in order to intracellularly deliver an effective amount of the biologically active compound or derivative thereof, which is preferably a cytotoxic, cytostatic, immune-suppressive or anti-inflammatory compound, to the abnormal cells.

A biologically active compound or its derivative for incorporation into a Drug Unit or quaternized Drug Unit may exhibit adverse peripheral effects when administered in unconjugated form. Due to selective delivery when in the form of D/D$^+$ in a LDC, such compounds, which include auristatins, tubulysin and PBD compounds, may now be administered. For that purpose the Linker Unit of an LDC is not merely a passive structure that serves as a bridge between a targeting Ligand Unit and D/D$^+$, but must be carefully engineered to have sufficient stability from the site of administration of the LDC until its delivery to the targeted site to prevent premature release of the drug Unit and then must efficiently release it as the free biologically active compound or derivative thereof. To accomplish that task, a targeting agent is typically reacted with a L$_{SS}$-containing moiety of a Drug Linker compound comprising the formula M$_1$-A$_R$(BU)-A$_O$- to form a L$_{SS}$-containing moiety comprising the formula of M$^2$-A$_R$(BU)-A$_O$- within a Ligand Drug Conjugate, which under controlled hydrolysis conditions is convertible to a L$_S$-containing moiety comprising the formula M$^3$-A$_R$(BU)-A$_O$-, wherein BU is a cyclic or acyclic Basic Unit, M$^1$, M$^2$ and M$^3$ are a maleimide, succinimide and succinic acid amide moiety, respectively, and A$_R$ is a required Stretcher Unit and A$_O$ is a second optional Stretcher Unit. The resulting Ligand Drug Conjugate is typically comprised of a targeting Ligand Unit, a Drug Unit or quaternized Drug Unit, and a intervening Linker Unit having L$_{SS}$ or L$_S$ as a primary linker (L$_R$), in which L$_R$ is bonded to the Ligand Unit and either directly to D/D$^+$ or through a secondary linker (L$_O$) so that one component of L$_O$ is attached to L$_R$ and the same or different component of L$_O$ is attached to D/D$^+$.

1.1 Primary Linker (L$_R$) with Basic Unit (BU):

A primary linker (L$_R$) is a component of a Linker Unit of a Ligand Drug Conjugate, a Drug Linker compound, or other Intermediate having a cyclic or acyclic Basic Unit, thus defining L$_R$ as a self-stabilizing linker (L$_{SS}$) or self-stabilized linker (L$_S$). In Ligand Drug Conjugate L$_R$ is attached to a Ligand Unit through a succinimide ($M^2$) moiety when $L_R$ is $L_{SS}$ or through a succinic acid amide ($M^3$) moiety when $L_R$ is $L_S$, in which the latter result from hydrolysis of the $M^2$ moiety mediated by its Basic Unit (BU), or $L_R$ is capable of that attachment through interaction of a reactive thiol functional group of a targeting agent with a maleimide ($M^1$) moiety of $L_{SS}$ as $L_R$ in a Drug Linker compound or other Intermediate.

1.1.1 Acyclic Basic Unit

In some embodiments, $L_R$- is a $L_{SS}$ moiety in a Drug Linker compound that has the formula $M^1$-$A_R$(BU)-$A_O$-, wherein BU is an acyclic Basic Unit (aBU). Exemplary $L_{SS}$ moieties of that formula in which $A_O$ is a Hydrolysis Enhancing (HE) Unit are represented by the substructure in Formula I of:

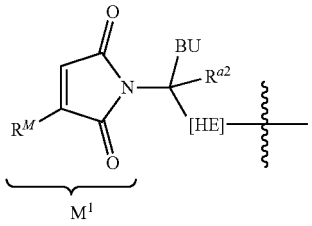

wherein the indicated $M^1$ moiety is a maleimide moiety, BU is aBU, the wavy line indicates covalent binding to -D, if $L_O$ is absent, or -$L_O$-D or -$L_O$-D* if $L_O$ is present, $R^M$ is hydrogen or optionally substituted $C_1$-$C_6$ alkyl, HE is an optional Hydrolysis Enhancer Unit, and $R^2$ is hydrogen or an optionally substituted $C_1$-$C_8$ alkyl. An acyclic Basic Unit is typically comprised of an optionally substituted $C_1$-$C_6$ alkylene in which one of its radical centers is bonded to the same carbon as $R^2$, wherein that carbon is in the alpha position relative to the imide nitrogen of the $M^1$ moiety, and the other radical center is bonded to a basic amine functional group of BU. To avoid premature hydrolysis of the maleimide ring system by base catalysis, the basic nitrogen of the basic amine functional group is typically protonated as a salt form, or the basic amine of the basic amine functional group is protected with an acid labile protecting group so that deprotection results in a protonated BU. For the former strategy to preclude premature hydrolysis, the basic amine of the basic functional group may be a primary, secondary or tertiary amine, while for the latter strategy, the basic amine of the basic functional group may be a primary or secondary amine.

On interaction with an reactive thiol functional group of a targeting agent, the $L_{SS}$ moiety of formula $M_1$-$A_R$(BU)— is converted to an L-$L_{SS}$- substructure of formula L-$M^2$-$A_R$(BU)-$A_O$- as exemplified by:

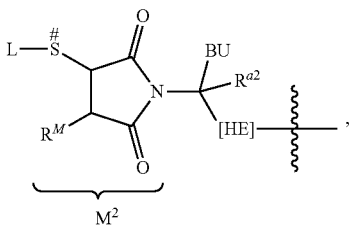

in Formula 1 in which subscript p is 1 and $A_O$ is HE, wherein the indicated $M^2$ moiety is a succinimide moiety, wherein that moiety is thio-substituted with L-S—, wherein L is a Ligand Unit and the indicated (#) sulfur atom is derived from a reactive thiol functional group of a targeting agent, BU is an acyclic Basic Unit (aBU), and the remaining variable groups are as defined for the corresponding $M^1$-$A_R$(BU)— substructure above in which BU is an acyclic Basic Unit, On controlled hydrolysis of the succinimide ring system mediated by aBU, the L-$L_{SS}$-moiety having the above L-$M^2$-$A_R$(BU)-$A_O$- substructure is converted to one having a $L_S$-containing moiety as exemplified by substructure(s):

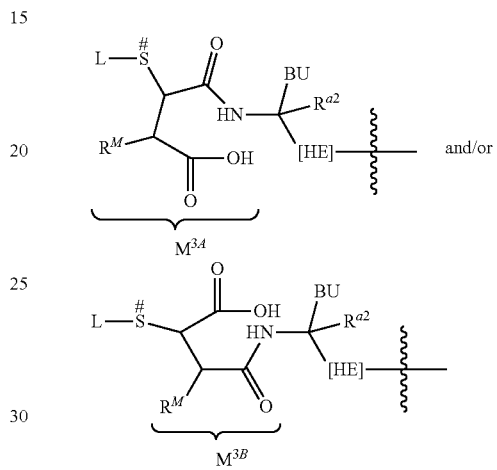

in Formula 2 in which subscript p is 1 and $A_O$ is HE, wherein Ligand Drug Conjugate compounds of that formula may be represented as having a single one of the above $L_S$-containing moieties or as having a mixture of both, collectively referred to as L-$M^3$-$A_R$(BU)-$A_O$-, wherein BU is aBU and the remaining variable groups are as previously defined for their $M^2$-containing precursor, wherein the indicated $M^{3A}$ and $M^{3B}$ moieties are succinic acid amide ($M^3$) moieties thio-substituted by L-S—, and wherein the contribution of the above L-$M^{3A}$-$A_R$(BU)-$A_O$- and L-$M^{3B}$-$A_R$(BU)-$A_O$- constituents to the Conjugate compound mixture is dependent on the relative reactivity of the two carbonyl carbons of the succinimide ring system of the succinic acid ($M^2$) moiety of the L-$M^2$-$A_R$(BU)-$A_O$-precursor to base catalyzed hydrolysis.

In preferred embodiments, $R^2$ in any one of the above $M^1$-$A_R$(BU)-$A_O$-, L-$M^2$-$A_R$(BU)-$A_O$- and L-$M^3$-$A_R$(BU)-$A_O$ substructures is —H, —$CH_3$, —$CH_2CH_3$, or —$CH_2CH_2CH_3$. In other preferred embodiments, [HE] as $A_O$ in any one of those structures is —C(=O)—. In any one of those embodiments, BU preferably has the formula of —[C($R^{a1}$)($R^{a1}$)]—[C($R^{a1}$)($R^{a1}$)]x-N($R^{a3}$)($R^{a3}$), wherein subscript x is 0, 1, 2 or 3, each $R^{a1}$ independently is hydrogen or $C_1$-$C_4$ alkyl, $C_6$-$C_{10}$ aryl, $C_5$-$C_{10}$ heteroaryl, ($C_6$-$C_{10}$ aryl)-$C_1$-$C_4$ alkyl-, or ($C_5$-$C_{10}$ heteroaryl)-$C_1$-$C_4$ alkyl-, optionally substituted, or two $R^{a1}$ together with the carbon(s) to which they are attached and any intervening carbons define an optionally substituted $C_3$-$C_6$ cycloalkyl; $R^{a3}$ independently are hydrogen, optionally substituted $C_1$-$C_6$ alkyl or a nitrogen protecting group, or together with the nitrogen atom to which they are attached define a $C_3$-$C_6$ heterocycloalkyl or both $R^3$ together define a nitrogen protecting group.

In more preferred embodiments an acyclic BU is of formula —$(CH_2)_x NH_2$, —$(CH_2)_x NHR^{a3}$, or —$(CH_2)_x N(R^3)_2$, wherein subscript x is an integer ranging from 1 to 4, with 1 or 2 particularly preferred; and R, at each instance, is independently hydrogen, —$CH_3$ or —$CH_2CH_3$, or both $R^3$ together with the nitrogen to which they are attached define an azetidinyl, pyrrolidinyl or piperidinyl heterocycloalkyl, in which a basic primary, secondary or tertiary amine so defined is optionally protonated or is in a pharmaceutically acceptable salt form.

In some of those more preferred embodiments $R^{a2}$ is hydrogen and in this and any of the above embodiments an acyclic BU having the structure of —$CH_2$—$NH_2$ or —$CH_2CH_2$—$NH_2$ is particularly preferred. A Ligand Drug Conjugate of Formula 2 wherein $R^{a2}$ is hydrogen and aBU is —$CH_2$—$NH_2$ may be used as a comparator to a corresponding Conjugate in which BU is a cyclic Basic Unit (cBU), the structure of which is incorporated into that of $A_R$ and is formally derived by cyclization of an acyclic BU to $R^{a2}$ in any one of the above $L_{SS}$ or $L_S$ structures, wherein $R^2$ is other than hydrogen, as described herein. In any one of those more preferred embodiments, $R^M$ is preferably hydrogen or $C_1$-$C_4$ alkyl, more preferably hydrogen.

1.1.2 Cyclic Basic Unit

As mentioned above, a $L_{SS}$ moiety or L-$L_{SS}$ or L-$L_S$-substructure having a cyclic Basic Unit (cBU) will, in some embodiments, correspond to any one of the above $M^1$-$A_R$(BU)-$A_O$, L-$M^2$-$A_R$(BU)-$A_O$ and L-$M^3$-$A_R$(BU)-$A_O$ formulae in which $R^2$ is an optionally substituted $C_1$-$C_6$ alkyl, as exemplified by substructures of:

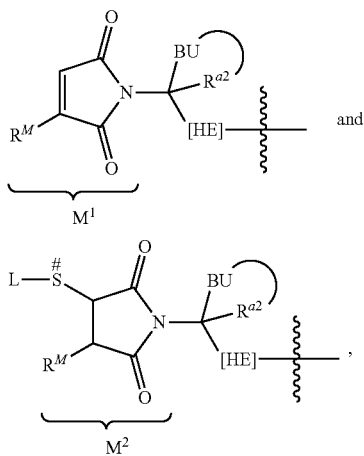

within Formula I and Formula 1 in which subscript p is 1, respectively, and as exemplified by substructure(s) of:

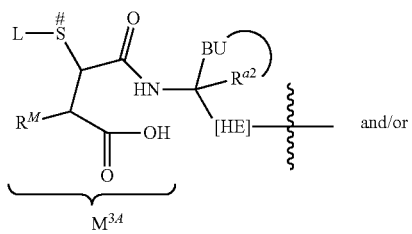

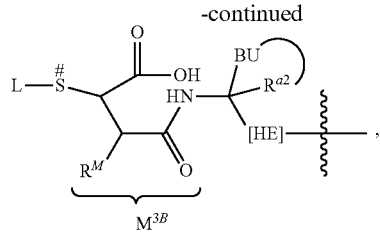

within Formula 2 in which subscript p is 1 in which BU is cyclized onto $R^{a2}$, as indicated by the solid curved line, and the remaining variable groups are as defined in the corresponding $L_{SS}$ and $L_S$ moieties in which BU is acyclic, so as to provide a cyclic Basic Unit.

Preferably the basic nitrogen of a cyclic BU is capable of increasing the rate of hydrolysis of the shown succinimide ($M^2$) moiety of Formula 1 to provide the shown succinic acid amide ($M^3$) moiety(ies) of Formula 2 at a suitable pH in comparison to a corresponding Conjugate in which $R^2$ is hydrogen and BU is absent.

Formally, in one group of embodiments a cyclic Basic Unit includes those derived from removing a hydrogen atom from a carbon atom in the $C_1$-$C_6$ alkylene chain of an acyclic Basic Unit to which its basic amine functional group is bonded and by removing a hydrogen atom from a carbon atom in the optionally substituted $C_1$-$C_6$ alkyl carbon chain of $R^{a2}$ to form another alkylene moiety and then combining the two alkylene moieties at their radical centers so as to form a corresponding spiro carbocyclo, which is at least substituted by the basic amine functional group, or at least substituted by an optionally substituted alkyl functionalized by the basic amine functional group of the acyclic Basic Unit so cyclized, and ii either instance is otherwise optionally substituted, wherein the carbon chain of the alkyl is attributed to that part of the BU alkylene moiety not participating in the carbocyclo ring system. Thus, a cyclic Basic Unit having a spiro carbocyclo that is directly substituted by the basic amine functional group results when the $R^{a2}$ alkyl is cyclized to the carbon atom of the acyclic BU alkylene carbon chain that is substituted by that basic amine functional group, whereas a spiro carbocyclo substituted by an optionally substituted alkyl that is functionalized by the basic amine functional group results from cyclization to a different carbon atom in that carbon chain.

$L_{SS}$ or $L_{SS}$-containing moieties in which BU is cyclic Basic Unit having a spiro carbocyclo directly substituted by a basic amine functional group or having a spiro carbocyclo substituted indirectly by a basic amine functional group through an intervening alkyl (e.g., a carbocyclo at least substituted by an aminoalkyl moiety) are exemplified by substructures of:

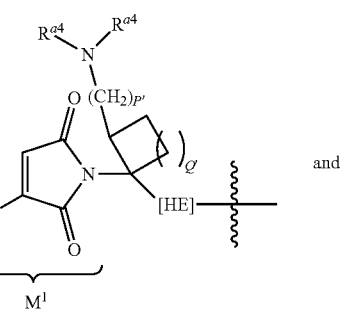

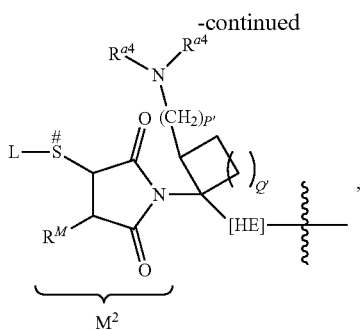

within Formula I and Formula 1 in which subscript p is 1, respectively, and exemplary $L_S$-containing moieties in which BU is a cyclic Basic Unit having a spiro cycloalkyl directly substituted by a basic amine functional group are exemplified by substructure(s) of:

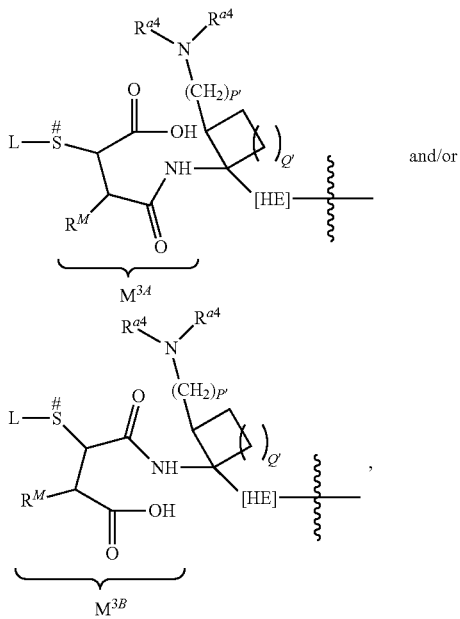

within Formula 2 in which subscript p is 1, wherein $R^M$ is hydrogen or optionally substituted $C_1$-$C_6$ alkyl; [HE] is an optional Hydrolysis Enhancer Unit; subscript P' is 0 or 1; subscript Q' is 0, or Q' ranges from 1 to 6; and each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein the basic nitrogen in either instance is optionally protonated, and the remaining variable groups are as previously defined for $L_{SS}$ and $L_S$ moieties having the corresponding acyclic Basic Units. In preferred embodiments, subscript P' is 0 and subscript Q is 1, 2 or 3. In other preferred embodiments, each $R^{a4}$ is independently selected from the group consisting of hydrogen, —$CH_3$, —$CH_2CH_3$ and the basic nitrogen to which they are attached is optionally protonated or is in a pharmaceutically acceptable salt form, or one $R^{a4}$ is hydrogen and the other $R^{a4}$ is a suitable nitrogen protecting group such as a suitable acid labile protecting group.

Formally, a cyclic Basic Unit in another group of embodiments includes those derived from removing a hydrogen atom from a basic nitrogen atom of a primary or secondary basic amine functional group of an acyclic Basic Unit and by removing a hydrogen atom from a carbon in the optionally substituted $C_1$-$C_{12}$ alkyl carbon chain of $R^{a2}$ to form an alkylene moiety and then combining the basic amino and alkylene moieties at their radical centers so as to form a corresponding spiro $C_4$-$C_{12}$ heterocyclo in which the radical nitrogen atom becomes a basic skeletal heteroatom of the heterocyclo, thereby resulting in a basic secondary or tertiary amine.

Preferably, the basic skeletal nitrogen atom of the spiro $C_4$-$C_{12}$ heterocyclo or the basic nitrogen atom directly or indirectly attached to the spiro $C_3$-$C_{12}$ carbocyclo is one or two carbon atoms removed from the imide nitrogen of $M^1/M^2$ and is thus preferably removed from the corresponding amide nitrogen of $M^3$ by the same number of carbon atoms subsequent to controlled hydrolysis of $M^2$.

$L_{SS}$ or $L_{SS}$-containing moieties in which BU is cyclic Basic Unit having a spiro heterocyclo in which the basic nitrogen atom of the basic amine functional group is a skeletal atom are exemplified by substructures within Formula I and Formula 1 in which subscript p is 1 of:

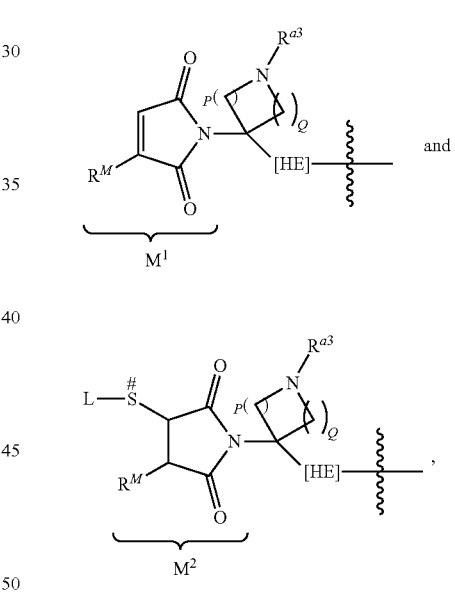

respectively, and $L_S$-containing moieties in which BU is cyclic Basic Unit having a spiro heterocyclo in which the basic nitrogen of the basic amine functional group is a skeletal atom are exemplified by substructures of:

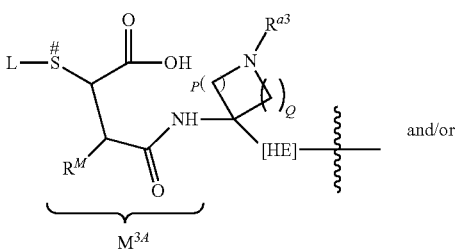

-continued

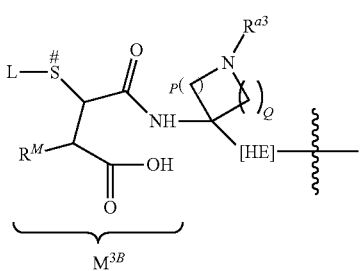

within Formula 2 in which subscript p is 1, wherein $R^M$ is hydrogen or optionally substituted $C_1$-$C_6$ alkyl; subscript P is 1 or 2; subscript Q ranges from 1 to 6; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkylene, and subscript n' ranges from 1 to 36, wherein the basic nitrogen bonded to $R^3$ is optionally protonated or is in a pharmaceutically acceptable salt form, or $R^{a3}$ is a nitrogen protecting group such as a suitable acid-labile protecting group, and the remaining variable groups are as previously defined for $L_{SS}$ and $L_S$ moieties having the corresponding acyclic Basic Units. In preferred embodiments subscript P is 1 and subscript Q is 1, 2 or 3 or subscript P is 2 and subscript Q is 1 or 2.

A suitable acid-labile protecting group for a basic amine nitrogen of a primary or secondary amine include —C(=O)O-t-Bu (BOC). In any one of the above structures in which BU is a cyclic basic Unit, [HE] is preferably —C(=O)—. In any one of those preferred embodiments, $R^M$ is preferably hydrogen or $C_1$-$C_4$ alkyl, more preferably hydrogen.

In more preferred embodiments $L_{SS}$ and $L_{SS}$-containing moieties having a cyclic Basic Unit are exemplified by substructures of:

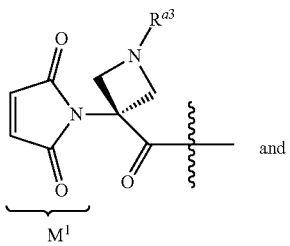

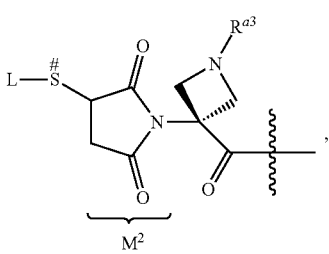

within Formula I and Formula 1 in which subscript p is 1, respectively, or by substructures:

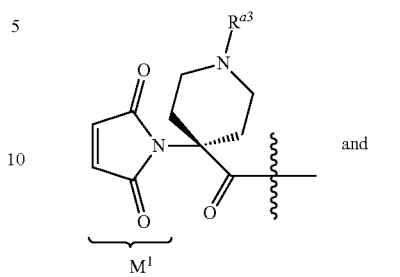

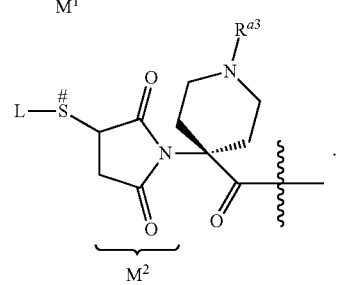

$L_S$-containing moieties derived from hydrolysis by the cyclic Basic Unit under controlled conditions of those $L_{SS}$-containing moieties are represented by substructure(s) of:

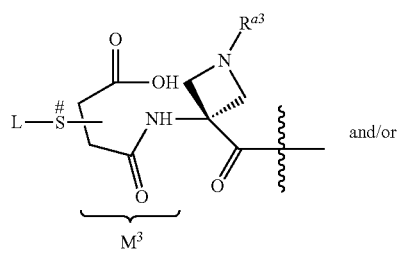

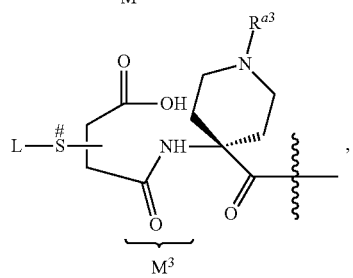

of Formula 2, in which subscript p is 1, wherein the thio substituent L-S— is bonded to the carbon alpha to the carboxylic acid functional group or the amide functional group of the succinic acid ($M^3$) amide moiety or is a mixture of the two regioisomers. In particularly preferred embodiments $R^{a3}$ is hydrogen, wherein the secondary amine so defined is optionally protonated or in a pharmaceutically acceptable salt form, or $R^{a3}$ is —C(=O)O-t-Bu (BOC).

1.2 Secondary Linkers ($L_O$):

Secondary linkers in a Linker Unit of Ligand Drug Conjugate or a Drug Linker compound or an Intermediate thereof, is an optional organic moiety situated between a primary linker ($L_R$) and a Drug Unit (D/D$^+$), when present, that is subject to enzymatic or non-enzymatic processing so as to release D/D$^+$ as a drug compound or active drug moiety. In some embodiments, a Cleavable Unit is present in $L_O$ to allow for that processing. In preferred embodiments when subscript w is 1 in Formula 1, Formula 2 or Formula I, W is a Peptide Cleavable Unit so that $L_O$ presents a cleavage site for enzymatic processing by a protease to initiate release of D/D$^+$. In some of those embodiments, Spacer Unit(s) intervene between W and the Drug Unit so that subscript y is 1 or 2, except when the Drug Unit is quaternized in which case -$L_O$-D$^+$ will be comprised of the structure —W—Y-D$^+$, so that subscript y in Formula 1, Formula 2 or Formula I is 1, wherein Y is a PAB or PAB-type self-immolative Spacer Unit. In other preferred embodiments when subscript w is 1 in Formula 1, Formula 2 or Formula I, W is a Glucuronide Unit of formula —Y(W')—, wherein W' is a carbohydrate moiety bonded to a self-immolative Spacer Unit (Y) through a glycosidic bond, wherein that bond allows for enzymatic processing of $L_O$ by a glycosidase to initiate release of D/D$^+$. In those embodiments having a quaternized Drug Unit, D$^+$ is released as a tertiary amine-containing compound.

In some embodiments W is a Peptide Cleavable Unit that provides a substrate for a protease present within or in the vicinity of hyper-proliferating cells, hyper-activated immune cells or other abnormal cells. Preferred are Peptide Cleavable Units that are not recognized or are poorly recognized by proteases excreted by normal cells distant from the site of the targeted abnormal cells. Other preferred Peptide Cleavable Units that are not recognized or are poorly recognized by proteases having systemic circulation so as to minimize non-targeted release of Drug Unit from its Ligand Drug Conjugate that would result in systemic exposure of a biologically active compound or derivative thereof that was conjugated as the Drug Unit. More preferred are those Peptide Cleavable Units that are recognized as substrates by proteases that are regulatory proteases or proteases found in lysosomes, the latter of which are cellular compartments to which a Ligand Drug Conjugate is sometimes delivered upon internalization of a membrane-surface receptor to which the Ligand Unit of a ligand Drug Conjugate compound has specifically bound. Regulatory and lysosomal proteases are exemplary intracellular proteases.

In one embodiment a Peptide Cleavable Unit (W) within a secondary linker is comprised or consists of a dipeptide moiety having the structure of:

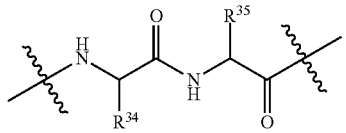

wherein the wavy lines indicate the sites of covalent attachment within a Linker Unit comprised of that secondary linker and $R^{34}$ is benzyl, methyl, isopropyl, isobutyl, sec-butyl, —CH(OH)CH$_3$ or
$R^{34}$ has the structure of

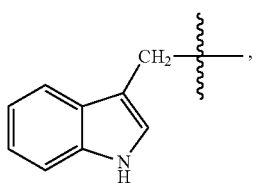 [SMILES: *Cc1c[nH]c2ccccc12]

wherein the wavy line indicates the site of covalent attachment to the dipeptide backbone, and $R^{35}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H, wherein the dipeptide moiety provides for a recognition site for a protease, preferably a regulatory or lysosomal protease.

In preferred embodiments the dipeptide is valine-alanine (val-ala). In another embodiment, W is comprised or consists of the dipeptide valine-citrulline (val-cit). In another embodiment W is comprised or consists of the dipeptide threonine-glutamic acid (thr-glu). In any one of those embodiments, the dipeptide moiety is covalently attached to a self-immolative moiety of a self-immolative Spacer Unit (Y) through an amide bond (i.e., a carbonyl-nitrogen bond). In some of those embodiments that amide bond is between the carbonyl carbon of the carboxylic acid functional group of alanine or citrulline and the nitrogen atom of an aryl or heteroaryl amino substituent of the central (hetero)arylene of a PAB or PAB-type self-immolative moiety of a self-immolative Spacer Unit (Y). In other preferred embodiments that amide bond is between the carbonyl carbon of the alpha carboxylic acid functional group of glutamate and the central (hetero)arylene nitrogen atom. Thus, in those embodiments a self-immolative moiety is comprised of an arylamine or heteroarylamine moiety to which the aforementioned carboxylic acid functional group of a dipeptide moiety is attached through an anilide bond with the amino nitrogen of that (hetero)arylamine moiety.

In another embodiment, a Cleavable Unit is a Glucuronide Unit of formula —Y(W')- within a secondary linker and is comprised of a glycoside-bonded carbohydrate moiety (W') having a recognition site for an glycosidase. In preferred embodiments the glycosidase is intracellularly located with cells targeted by a Ligand Drug Conjugate comprised of that Glucuronide Unit. In those embodiments W' is a carbohydrate moiety (Su) bonded to a glycosidic heteroatom (E') in which the bond between Su and E' is a glycosidic bond, wherein Su-E' provides a recognition site for cleavage of that bond. In those embodiments W' typically has the structure of

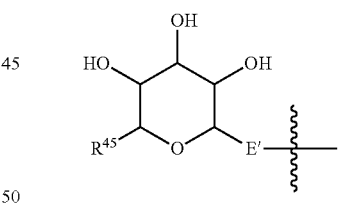

wherein $R^{45}$ is —CH$_2$OH or —CO$_2$H and E' is a heteroatom moiety such as —O—, —S— or optionally substituted-NH—, which is bonded to the carbohydrate moiety (Su) and to a self-immolative moiety of a self-immolative Spacer Unit Y (as indicated by the wavy line) wherein the bond to the carbohydrate moiety provides for a recognition site for a glycosidase. Preferably that site is recognized by a lysosome glycosidase. In some embodiments the glycosidase is a glucuronidase so that $R^{45}$ is —CO$_2$H.

In some preferred embodiments a secondary linker ($L_O$), in addition to a Peptide Cleavable Unit as W is also comprised of one or two Spacer Units (Y or Y—Y') and a first Stretcher Unit (A). In other preferred embodiments $L_O$, in addition to a Peptide Cleavable Unit as W, is also comprised of a first Stretcher Unit (A) but has no Spacer Units. In either of those embodiment A or a subunit thereof is -L$^P$(PEG)-. In other preferred embodiments, in addition to a Glucuronide Unit as the Cleavable Unit, $L_O$ is comprised of a first Stretcher Unit (A) and may be additionally comprised of an additional Spacer Unit (Y'). When W is a Peptide Cleavable Unit, A, W and Y are arranged in a linear relationship as represented within -$L_O$-D/D$^+$ structures of (1a). When W is a Glucuronide Unit, which has the formula —Y(W')—, A, W' and Y/Y' are arranged in an orthogonal relationship as represented within -$L_O$-D/D$^+$ structures of and (1b).

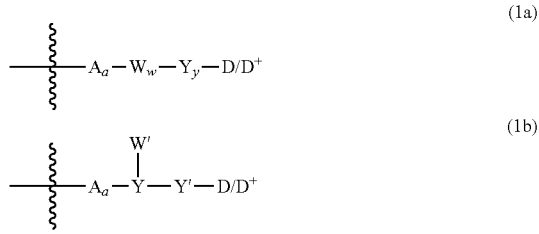

(1a)

(1b)

wherein the wavy line in either structure indicates the site of covalent bonding to $L_R$ in a Ligand Drug Conjugate or Drug Linker compound, subscript a is 0 or 1, subscript w is 1, subscript y is 0, 1 or 2 and Y' is an optional second Spacer Unit, which may or may not be self-immolative, provided that when the Drug Unit is a quaternized Drug Unit (D$^+$), subscript y is 1 in formula 1a and Y' is absent in formula 1b, wherein in both formulae Y is a self-immolative Spacer Unit. When a is 1, the wavy line before A indicates covalent bonding of that $L_O$ subunit to $L_{SS}$ or $L_S$ as $L_R$. When subscript a is 0 that wavy line indicates covalent binding to $L_{SS}$ or $L_S$ as $L_R$ by the Peptide Cleavable Unit in formula 1a, or by Y of the Glucuronide Unit of formula 1b.

In preferred embodiments subscript a is 1 in formula (1a) or (1b). In some of those embodiments -$A_O$ is present, which is covalently attached to A. Is some of those preferred embodiment A or a subunit thereof is -L$^P$(PEG)-. In other preferred embodiments of formula (1a), subscript y is 2 wherein the Spacer Unit attached to D (Y') is a methylene carbamate (MAC) unit, which is capable of self-immolation, and the Spacer Unit attached to Y' (Y) is also capable of self-immolation. In other preferred embodiments of formula (1a) when subscript y is 2 the Spacer Unit bonded to D is a carbamate functional group, which is capable of self-immolation and therefore is a second self-immolative Spacer Unit (Y') and the Spacer Unit bonded to Y' is also capable of self-immolation and therefore is a first self-immolative Spacer Unit. In other preferred embodiments -$L_O$-D has the structure of formula (1b) in which Y' is present, wherein Y' is a carbamate functional group or a methylene carbamate Unit, both of which are capable of self-immolation. In either one of those preferred embodiments of formula (1a) or formula (1b), the Spacer Unit (Y) bonded to W or W' is a self-immolative Spacer Unit comprised of a PAB or PAB-type self-immolative moiety.

In some embodiments in which subscript w is 1 in $L_O$ of formula (1a), subscript y is 0 so that D is directly attached to W. In those embodiments the W-D bond is cleavable by a protease to release D as a biologically active compound or derivative thereof. In other embodiments in which subscript w is 1 in $L_O$ of formula (1a), subscript y is 1 so that D is bonded to $L_O$ through Y, wherein Y bonded to D is a Spacer Unit that does not undergo self-immolation or is an optionally substituted heteroatom or functional group, which is some embodiments remains with D upon its release as a biologically active compound or derivative thereof. In those embodiments the W—Y bond is cleavable by a protease to release Y-D, which may be a biologically active compound in its own right or may undergo further enzymatic or non-enzymatic processing to release D as a biologically active compound or derivative thereof. In still other embodiments in which subscript w is 1 in $L_O$ of formula (1a), subscript y is 2 so that D is bonded to $L_O$ through Y and Y', wherein Y' bonded to D is a Spacer Unit that does not undergo self-immolation or is an optionally substituted heteroatom or functional group, which is some embodiments remains with D upon its release as a biologically active compound or derivative thereof. In those embodiments the W—Y bond is cleavable by a protease to release Y-'Y-D, which may be a biologically active compound in its own right or may undergo further enzymatic or non-enzymatic processing to release Y'-D or D as a biologically active compound or derivative thereof.

In some embodiments in which subscript w is 1 in $L_O$ of formula (1b), subscript y is 1 so that D is directly attached to Y. In those embodiments the W'—Y bond is cleavable by a glucosidase to release D as a biologically active compound or derivative thereof. In other embodiments in which subscript w is 1 in $L_O$ of formula (1b), subscript y is 2 so that D is bonded to $L_O$ through Y and Y', wherein Y' bonded to D is a Spacer Unit that does not undergo self-immolation or is an optionally substituted heteroatom or functional group, which is some embodiments remains with D upon its release as a biologically active compound or derivative thereof. In those embodiments the W'—Y bond is cleavable by a protease to release Y'-D, which may be a biologically active compound in its own right or may undergo further enzymatic or non-enzymatic processing to release D as a biologically active compound or derivative thereof.

Structures of some exemplary A/$A_O$, W and Y moieties in $L_O$ and their substituents are described in WO 2004/010957, WO 2007/038658, U.S. Pat. Nos. 6,214,345, 7,498,298, 7,968,687 and 8,163,888, and US Pat. Publ. Nos. 2009-0111756, 2009-0018086 and 2009-0274713 and these disclosures are specifically incorporated by reference herein.

In some embodiments A, or subunits thereof, has the structure of

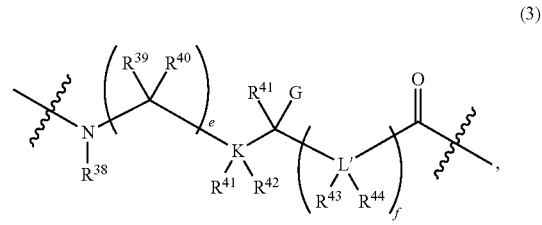

(3)

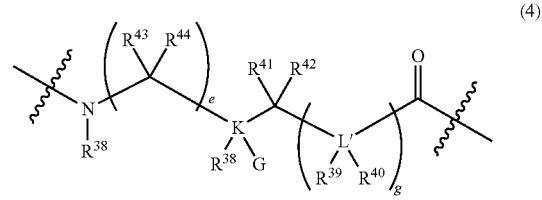

(4)

wherein the wavy lines indicated covalent attachment within the remainder of a Ligand Unit, and wherein for A the wavy line to the carbonyl moiety of either structure represents the point of covalent attachment to the amino terminus of a dipeptide moiety comprising W when Y is arranged linearly with respect to Y and D/D⁺ or to a self-immolating moiety of a self-immolative Spacer Unit described herein to which W' is bonded to Y and are arranged orthogonal with respect to D/D⁺, and wherein the wavy line to the amino moiety of either structures represents the site of covalent attachment to a carbonyl-containing functional group of another $L_O$ component or of $L_R$; and wherein K and L' independently are C, N, O or S, provided that when K or L' is O or S, $R^{41}$ and $R^{42}$ to K or $R^{43}$ and $R^{44}$ to L' are absent, and when K or L are N, one of $R^{41}$, $R^{42}$ to K or one of $R^{42}$, $R^{43}$ to L' are absent, and provided that no two adjacent L' are independently selected as N, O, or S;

wherein subscripts e and f are independently selected integers that range from 0 to 12, and subscript g is an integer ranging from 1 to 12:

wherein G is hydrogen, optionally substituted $C_1$-$C_6$ alkyl, —OH, —OR$^{PR}$, —CO$_2$H, CO$_2$R$^{PR}$, wherein R$^{PR}$ is a suitable protecting, —N(R$^{PR}$)(R$^{PR}$), wherein R$^{PR}$ are independently a protecting group or R$^{PR}$ together form a suitable protecting group, or —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-R independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^4$ together with L' to which they are attached when L' is C comprise a $C_3$-$C_6$ cycloalkyl, or $R^{40}$ and $R^{41}$, or $R^{40}$ and $R^{43}$, or $R^{41}$ and $R^{43}$ to together with the carbon or heteroatom to which they are attached and the atoms intervening between those carbon and/or heteroatoms comprise a 5- or 6-membered carbocyclo or heterocyclo, provided that when K is O or S, $R^{41}$ and $R^{42}$ are absent, when K is N, one of $R^{41}$, $R^{42}$ is absent, when L' is O or S, $R^{43}$ and $R^4$ are absent, and when L' is N, one of $R^{43}$, $R^{44}$ is absent.

In some embodiments $R^{38}$ of formula (3) or formula (4) is hydrogen. In other embodiments —K(R$^{41}$)(R$^{42}$) is —(CH$_2$)—. In other embodiments when subscript e is not 0, $R^{39}$ and $R^{40}$ are hydrogen in each occurrence. In other embodiments when subscript f is not 0, -L(R$^{43}$)(R$^{44}$)— is —CH$_2$— in each occurrence.

In preferred embodiments G is —CO$_2$H. In other preferred embodiments K and/or L are C. In other preferred embodiments subscript e or f is 0. In still other preferred embodiments subscripts e+f is an integer ranging from 1 to 4.

In some embodiments $A_O$, A, or a subunit thereof has the structure of —NH—$C_1$-$C_{10}$ alkylene-C(=O)—, —NH—$C_1$-$C_{10}$ alkylene-NH—C(=O)—$C_1$-$C_{10}$ alkylene-C(=O)—, —NH—$C_1$-$C_{10}$ alkylene-C(=O)—NH—$C_1$-$C_{10}$ alkylene (C=O)—, —NH—(CH$_2$CH$_2$O)$_s$—CH$_2$(C=O)—, —NH—(C$_3$-$C_8$ carbocyclo)(C=O)—, —NH—(C$_6$-$C_{10}$ arylene-)—C(=O)—, and —NH—(C$_3$-$C_8$ heterocyclo-)C(=O).

In other embodiments A, or a subunit thereof, has the structure of

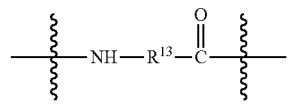

wherein $R^{13}$ is —$C_1$-$C_{10}$ alkylene-, —$C_3$-$C_8$ carbocyclo-, —$C_6$-$C_{10}$ arylene-, —$C_1$-$C_{30}$ heteroalkylene-, —$C_3$-$C_8$ heterocyclo-, —$C_1$-$C_{10}$ alkylene-$C_6$-$C_{10}$ arylene-, —$C_6$-$C_{10}$ arylene-$C_1$-$C_{10}$alkylene-, —$C_1$-$C_{10}$ alkylene-($C_3$-$C_8$carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, —($C_3$-$C_8$ heterocyclo)-$C_1$-$C_{10}$ alkylene-, —(CH$_2$CH$_2$O)$_{1-10}$(—CH$_2$)$_{1-3}$—, or —(CH$_2$CH$_2$NH)$_{1-10}$(—CH$_2$)$_{1-3}$—. In some embodiments, $R^{13}$ is —$C_1$-$C_{10}$ alkylene- or —$C_1$-$C_{30}$ heteroalkylene-. In some embodiments, $R^{13}$ is —$C_1$-$C_{10}$ alkylene-, —(CH$_2$CH$_2$O)$_{1-10}$—(CH$_2$)$_{1-3}$—, or —(CH$_2$CH$_2$NH)$_{1-10}$—(CH$_2$)$_{1-3}$—. In some embodiments, $R^{13}$ is —$C_1$-$C_{10}$ alkylene-polyethylene glycol, or -polyethyleneimine.

In more preferred embodiments A, or a subunit thereof, corresponds in structure to an alpha-amino acid-, a beta-amino acid moiety, or other amine-containing acid. Other embodiments of A as a single unit or having subunits $A_{1-4}$ of A are described in embodiments for Linker Units that have the formula of -$L_R$-$L_O$-.

In some embodiments, a self-immolative Spacer Unit is capable of undergoing a 1,4- or 1,6- elimination reaction subsequent to enzymatic processing of W/W' wherein W/W' is covalently bonded to a PAB or PAB-type self-immolative moiety of a self-immolative Spacer Unit Y. In some embodiments when W is a Peptide Cleavable Unit, —Y-D or —Y—Y'-D arranged linearly with respect to W in $L_O$ has the structure of:

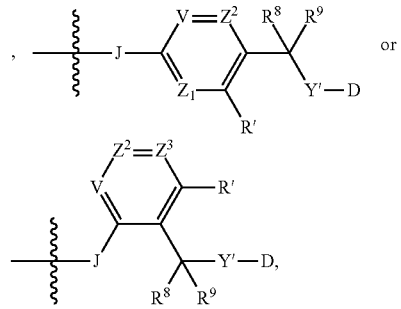

wherein Y' is absent or O, S, or optionally substituted —NH—, or Y' is a carbamate functional group or Y' is a methylene carbamate Unit; and V, $Z^1$, $Z^2$ and $Z^3$ independently are —C(R$^{24}$)= or —N=;

R$^{24}$ independently are hydrogen, halogen, —NO$_2$, —CN, —OR$^{25}$, —SR$^{26}$, —N(R$^{27}$)(R$^{28}$), optionally substituted $C_1$-$C_6$ alkyl, or —C(R$^{29}$)=C(R$^{30}$)—R$^{31}$, wherein R$^{25}$ is hydrogen, optionally substituted $C_1$-$C_6$ alkyl, optionally substituted $C_6$-$C_{10}$ aryl or optionally substituted $C_6$-$C_{10}$ heteroaryl, R$^{26}$ is optionally substituted $C_1$-$C_6$ alkyl, optionally substituted $C_6$-$C_{10}$ aryl or optionally substituted $C_5$-$C_{10}$ heteroaryl, R$^{27}$ and R$^{28}$ independently are hydrogen, optionally substituted $C_1$-$C_6$ alkyl, optionally substituted $C_6$-$C_{10}$ aryl or optionally substituted $C_5$-$C_{10}$ heteroaryl or both R$^{27}$ and R$^{28}$ together with the nitrogen to which they are attached define a 5- or 6-membered heterocyclyl, R$^{29}$ and R$^{30}$ independently are hydrogen, or optionally substituted $C_1$-$C_6$ alkyl, and $R^{31}$ is hydrogen, optionally substituted $C_1$-$C_6$ alkyl, optionally substituted $C_6$-$C_{10}$ aryl, optionally substituted $C_5$-$C_{10}$ heteroaryl, —C(=O)O$R^{32}$ or —C(=O)N$R^{32}$, wherein $R^{32}$ is hydrogen, optionally substituted $C_1$-$C_6$ alkyl, optionally substituted $C_6$-$C_{24}$ aryl, or optionally substituted $C_5$-$C_{24}$ heteroaryl, $R^8$ and $R^9$ independently are hydrogen, optionally substituted $C_1$-$C_6$ alkyl, or together with the benzylic carbon to which they are attached define an optionally substituted $C_3$-$C_6$ carbocyclo or one of $R^8$, $R^9$ is hydrogen or optionally substituted $C_1$-$C_6$ alkyl and the other is optionally substituted $C_5$-$C_{10}$ aryl or $C_5$-$C_{10}$ heteroaryl; and R' is hydrogen or is halogen, —NO$_2$, —CN or other electron withdrawing group or is —CH$_3$ or other an electron donating group; and J is —O—, S—, or optionally substituted NH, including -N($R^{33}$)—, wherein $R^{33}$ is as defined for $R^{32}$, and is preferably hydrogen or methyl, wherein the wavy line to J represents covalent bonding of that optionally substituted heteroatom to a functional group of W so as to inhibit the electron donating ability of J' sufficiently to stabilize the central (hetero)arylene of the self-immolative Spacer Unit and wherein enzymatic processing of W by a protease results in dis-inhibition of that ability (e.g., when J is bonded to the carbonyl moiety of a carbonyl-containing functional group of W). As a result of that processing release of the aforementioned benzylic substituent D/D$^+$ or —Y'-D is initiated to provide a biologically active compound or derivative thereof, which in the case of D$^+$ initiates release of a tertiary amine-containing biologically active compound.

In preferred embodiments no more than two of $R^{24}$ are other than hydrogen. In other preferred embodiments R' is hydrogen. In other preferred embodiments one or both of $R^8$ and $R^9$ are hydrogen or J' is —NH—. In still other preferred embodiments V, $Z^1$, $Z^2$ and $Z^3$ are each =CH—. In more preferred embodiments V, $Z^1$, $Z^2$ and $Z^3$ are each =CH— and R' is hydrogen or $R^8$ and $R^9$ are each hydrogen. In more preferred embodiments V, $Z^1$, $Z^2$ and $Z^3$ are each =CH—, R' is hydrogen or $R^8$ and $R^9$ are each hydrogen and J' is —NH—.

In other embodiments W is a Glucuronide Unit of formula —Y(W')—, wherein W' and Y are arranged orthogonally within $L_O$ of the Linker Unit with respect to —Y'-D or -D/D$^+$, wherein Y is self-immolative Spacer Unit Y having its self-immolative moiety bonded to a glycoside-bonded carbohydrate (Su) moiety through an optionally substituted heteroatom (E') so as to display a recognition site for a glycosidase. In those embodiments the orthogonal arrangement of Y and W' with respect to —Y'-D or -D/D$^+$ is represented by the structure of:

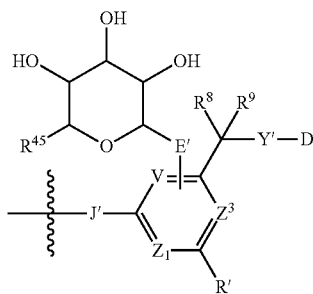

wherein Y' is absent or O, S, or optionally substituted —NH—, or Y' is a carbamate functional group or Y' is a methylene carbamate unit, both of which are capable of self-immolation; J' and E' are independently selected from the group consisting of —O—, S—, and optionally substituted NH, including —N($R^{33}$)—, wherein $R^{33}$ is as defined for $R^{32}$, preferably hydrogen or methyl;

V, $Z^1$ and $Z^3$ independently are =C($R^{24}$)= or =N=; $R^{24}$ independently are selected from the group consisting of hydrogen, halogen, —NO$_2$, —CN, —O$R^{25}$, —S$R^{26}$, —N($R^{27}$)($R^{28}$), —C($R^{29}$)=C($R^{30}$)—$R^{31}$, W' and optionally substituted $C_1$-$C_6$ alkyl;

provided that E' of W' is bonded to one of V, $Z^1$, $Z^3$, in which that variable group is defined as =C($R^{24}$)— (i.e., one of $R^{24}$ is W'— of formula Su-E'-) provided and the other V, $Z^1$, $Z^2$ is defined by =N— or =C($R^{24}$)— wherein $R^{24}$ is other than W'; and $R^{45}$ is —CH$_2$OH or —CO$_2$H; and wherein $R^{25}$ is hydrogen, optionally substituted $C_1$-$C_6$ alkyl, optionally substituted $C_6$-$C_{10}$ aryl or optionally substituted $C_5$-$C_{10}$ heteroaryl; $R^{26}$ is optionally substituted $C_1$-$C_6$ alkyl, optionally substituted $C_6$-$C_{10}$ aryl or optionally substituted $C_5$-$C_{10}$ heteroaryl, and $R^{27}$ and $R^{28}$ independently are hydrogen, optionally substituted $C_1$-$C_6$ alkyl, optionally substituted $C_6$-$C_{10}$ aryl or optionally substituted $C_5$-$C_{10}$ heteroaryl or both $R^{27}$ and $R^{28}$ together with the nitrogen to which they are attached define a 5- or 6-membered heterocyclyl, $R^{29}$ and $R^{30}$ independently are hydrogen, or optionally substituted $C_1$-$C_6$ alkyl, and $R^{31}$ is hydrogen, optionally substituted $C_1$-$C_6$ alkyl, optionally substituted $C_6$-$C_{10}$ aryl, optionally substituted $C_5$-$C_{10}$ heteroaryl, —CN, —C(=O)O$R^{32}$ or —C(=O)N$R^{32}$; wherein $R^{32}$ is hydrogen, optionally substituted $C_1$-$C_6$ alkyl, optionally substituted a $C_6$-$C_{10}$ aryl, or optionally substituted $C_6$-$C_{10}$ heteroaryl;

$R^8$ and $R^9$ independently are hydrogen or optionally substituted $C_1$-$C_6$ alkyl or together with the benzylic carbon to which both are attached define an optionally substituted $C_3$-$C_6$ carbocyclo or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; R' is hydrogen or is halogen, —NO$_2$, —CN or other electron withdrawing group, or is an electron donating group; $R^{45}$ is —CH$_2$OH or —CO$_2$H; E' is —O— or optionally substituted —NH—; J is —NH—; and Y' is an optional Spacer Unit, which is absent when D is a quaternized Drug Unit (D$^+$), or otherwise is an optionally substituted heteroatom, a carbamate functional group or a methylene carbamate unit; and wherein the wavy line to J' represents covalent bonding of J' to a functional group of A if subscript a is 1 or to $A_O$ if subscript a is 0 and $A_O$ is present (e.g., when J' is bonded to the carbonyl moiety of a carbonyl-containing functional group of A of $L_O$ or $A_O$ of $L_R$), or to $A_R$ if A and $A_O$ are both absent;

and wherein enzymatic processing of W'-E' by a glycosidase results in dis-inhibition of the ability of E' as an electron donating group to trigger 1,4- or 1,6-elimination of the benzylic substituent from the central (hetero) arylene of the PAB or PAB-type self-immolative Spacer Unit Y. As a result releases of that processing release of D/D$^+$ or —Y'-D as a biologically active compound or derivative thereof is initiated, which in the case of D$^+$ initiates release of a tertiary amine-containing biologically active compound.

In preferred embodiments, the orthogonal arrangement involving the self-immolative moiety of Y bonded to D/D⁺ directly or indirectly through Y', and W' is represented by the structure of:

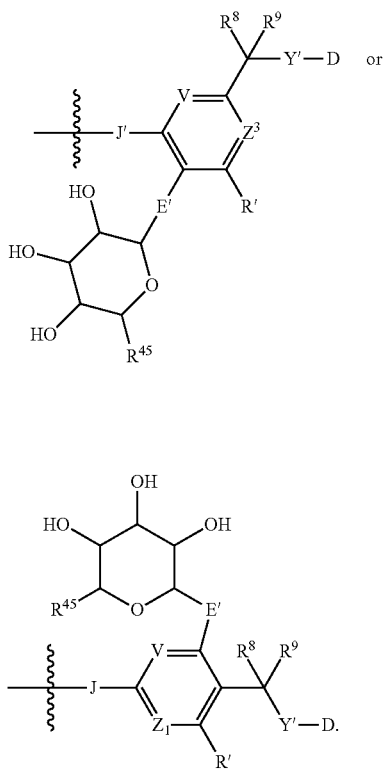

In more preferred embodiments of the above orthogonal arrangement -E'- is —O— or —NH—, wherein oxygen as the glycosidic bonded heteroatom is represented by O', and V or $Z^3$ is =C($R^{24}$), wherein $R^{24}$ is hydrogen or an electron withdrawing group. In other preferred embodiments $R^8$ and $R^9$ are hydrogen and V, $Z^1$ or $Z^2$ is =CH—. In other preferred embodiments -J- is —NH, V, $Z^1$ or $Z^2$ is =CH— and R' is hydrogen or an electron withdrawing group, preferably -$NO_2$.

In particularly preferred embodiments —$Y_y$(W')-D/D⁺, in which subscript y is 1 or 2, has the structure of:

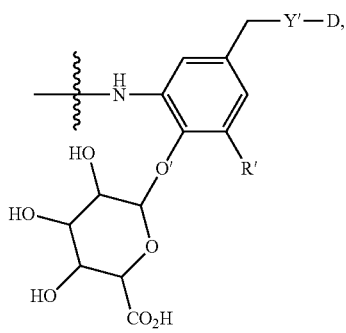

wherein R' is hydrogen or —$NO_2$ and Y' is a carbamate functional group or a methylene carbamate group or D is a quaternized Drug Unit (D⁺) so that Y' is absent.

1.3 $L_R$-$L_O$ as Linker Units

In one group of embodiments the Drug Unit (D/D⁺) in any of the —W—$Y_y$-D or —$Y_y$(W')-D structures disclosed herein represents a biologically active compound or derivative thereof in which a heteroatom or functional group of that compound is attached to the benzylic position of a PAB or PAB-type moiety in a self-immolative Spacer Unit, which in the case of D⁺ is the quaternized nitrogen of a tertiary amine (i.e., D⁺ is a quaternized tertiary amine-containing drug compound) in which case the quaternized nitrogen is attached to that benzylic position.

In some of those embodiments, -$L_{SS}$-$L_O$-D/D⁺ of a drug linker moiety within a Ligand Drug Conjugate compound and its hydrolysis product -$L_S$-$L_O$-D/D⁺, whose formation is catalyzed by a cyclic Basic Unit, has the structures of:

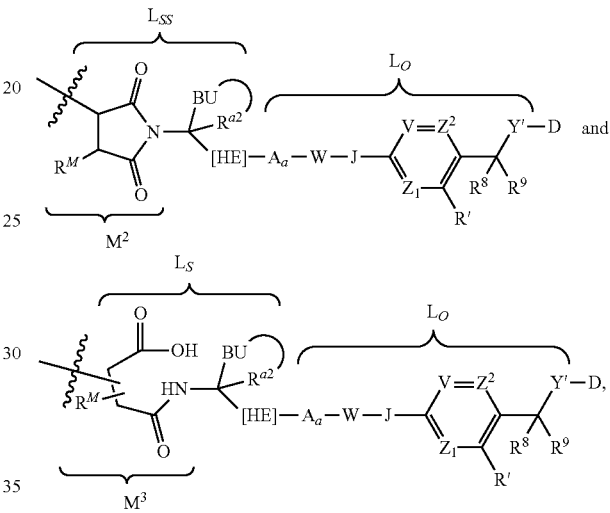

respectively, wherein [HE] is an optional Hydrolysis Enhancer Unit; $R^M$ is hydrogen or $C_1$-$C_4$ alkyl; V, $Z^1$ and $Z^2$ are independently =N— or =C($R^{24}$)—, wherein $R^{24}$, independently selected, is hydrogen, optionally substituted $C_1$-$C_6$ alkyl or an electron donating group; $R^8$ and $R^9$ independently are hydrogen or optionally substituted $C_1$-$C_6$ alkyl or together with the benzylic carbon to which they are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J is an optionally substituted heteroatom, such as —O— or optionally substituted —NH—, which includes —N($R^{33}$), wherein $R^{33}$ is hydrogen or optionally substituted $C_1$-$C_6$ alkyl; Y' is an optional second Spacer Unit, which can be an optionally substituted heteroatom or a functional group, in which the latter may also be capable of self-immolation as when Y' is —OC(=O)— covalently bonded to a heteroatom of D, or Y' is another self-immolative moiety such as a methylene carbamate unit, or Y' is absent when D is a quaternized Drug Unit (D⁺); and the wavy line indicates covalent bonding of a Ligand Unit, which for the $M^3$ moiety in $L_S$ is to the carbon atom that is adjacent to its acid or amide functional group with $R^M$ bonded to the carbon adjacent to the remaining functional group. In preferred embodiments, two of V, $Z^1$, $Z^2$ are =CH— and the other is =N— or =CH— or $R^8$ and $R^9$ are independently hydrogen or $C_1$-$C_4$ alkyl. In other preferred embodiments, J is —NH—. In more preferred embodiments V, $Z^1$, $Z^2$ are each =CH— and $R^8$ and $R^9$ are independently selected from the group consisting of hydrogen, —$CH_3$ and —$CH_2CH_3$; and J is —NH—. In those embodiments, the indicated $M^2$ and $M^3$ residues represent a succinimide moiety and a succinic acid amide moiety, respectively.

In other embodiments, a Drug Linker compound of formula $L_{SS}$-$L_O$-D/$D^+$ having $L_O$ of formula (1a) in which subscript y is 1 or 2 and having a cyclic Basic Unit is exemplified by the structure of:

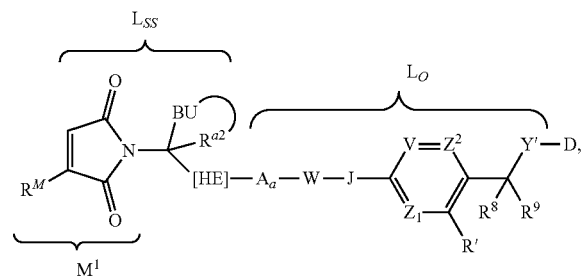

wherein the variable groups are as previously described for drug linker moieties in Ligand Drug Conjugates. In those embodiments the indicated $M^1$ residue represents a maleimide moiety.

In other group of embodiments $L_O$ in $L_{SS}$-$L_O$-D and its hydrolysis product -$L_S$-$L_O$-D have formula (1a) in which W is a Peptide Cleavable Unit and subscript y is 0 so that D is bonded directly to W or have formula (1a) in which in which W is a Peptide Cleavable Unit and subscript y is 1 wherein Y is an optionally substituted heteroatom or functional group. In those embodiments the W-D or W—Y bond is cleavable by a protease to release Y-D or D as a biologically active compound or derivative thereof. In those embodiments drug linker moieties of formula -$L_{SS}$-$L_O$-D and -$L_S$-$L_O$- in a Ligand Drug Conjugate compound in which subscript y is 0 or subscript y is 1, wherein Y is an optionally substituted heteroatom or functional group, have the structure of:

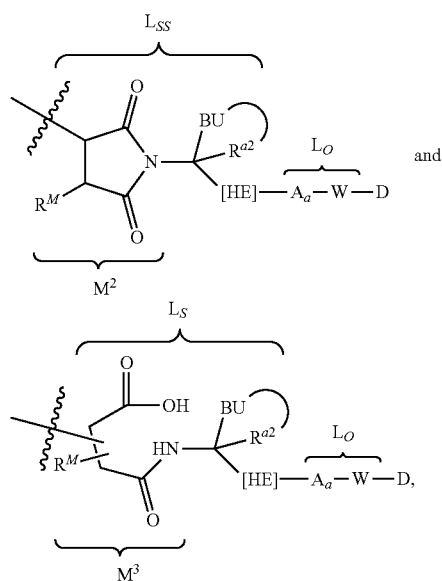

respectively, and corresponding Drug Linker Compounds have the structure of:

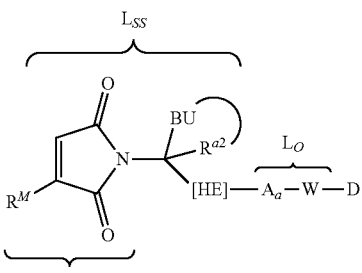

In preferred embodiments, -$L_{SS}$-$L_O$-D/$D^+$ and its hydrolysis product -$L_S$-$L_O$-D/$D^+$ in which $L_O$ is of formula (1a), wherein W is a Peptide Cleavable Unit and subscript y is 1 or 2 so that A, W and Y/Y' are in a linear configuration with respect to D/$D^+$, are represented by:

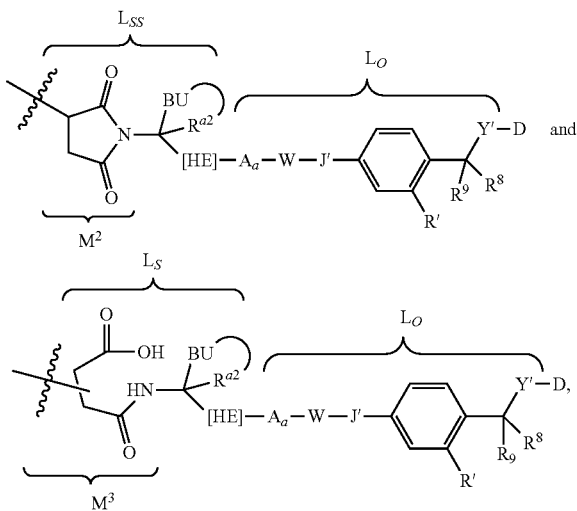

respectively, and corresponding Drug Linker compounds are represented by:

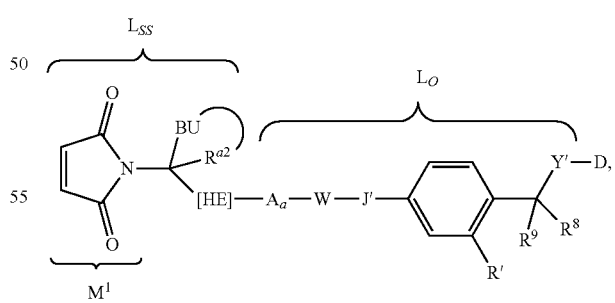

wherein the variable groups are as previously described for the above drug linker moieties in Peptide-cleavable Ligand Drug Conjugates and Drug Linker compounds.

In those drug linker moieties and Drug Linker compounds, preferably J' is —NH—. In other such embodiments, preferably V, $Z^1$ and $Z^2$ are each =CH—, or one of $R^8$, $R^9$ is hydrogen and the other is hydrogen, $C_1$-$C_4$ alkyl or optionally substituted phenyl. In still other such embodiments, preferably [HE] is —C(=O)—, R' is hydrogen or $R^8$ and $R^9$ are both hydrogen.

More preferred embodiments in which A, W and Y are in a linear configuration, a drug linker moiety of a Ligand Drug Conjugate of formula -$L_{SS}$-$L_O$-D/D⁺ and it hydrolysis product of formula -$L_{SS}$-$L_O$-D/D⁺ have the structures of:

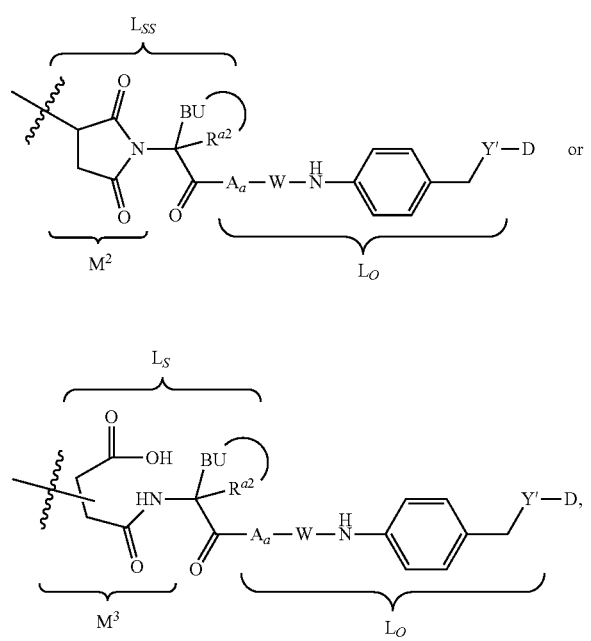

respectively, and corresponding Drug Linker compounds of formula $L_{SS}$-$L_O$-D/D⁺ have the structure of:

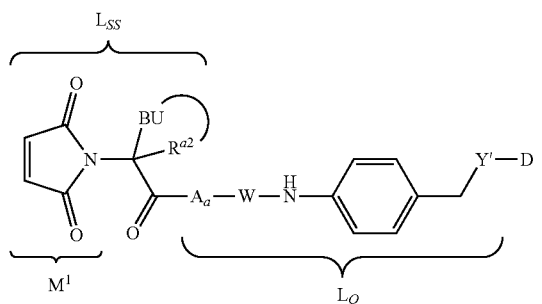

wherein W consists or is comprised of a dipeptide wherein the dipeptide subunit is at the distal end of W and the indicated bond is an amide bond specifically cleavable by an intracellular protease in comparison to freely circulating serum proteases and wherein the remaining variable groups are as previously defined for drug linker moieties in Ligand Drug Conjugates and for Drug Linker compounds.

In any one of the above embodiments where W is comprised of a dipeptide that dipeptide is recognized by an intracellular protease. Preferably that protease is a cathepsin protease in which preferred dipeptides recognized by the cathepsin protease have the structure of

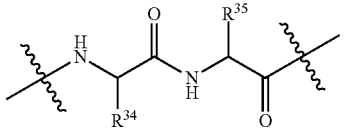

wherein $R^{34}$ is benzyl, methyl, isopropyl, isobutyl, sec-butyl, —CH(OH)CH₃ or has the structure of

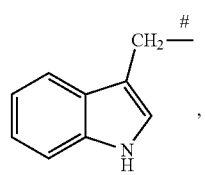

wherein the hash tag indicates the site of covalent attachment to the dipeptide backbone and $R^{35}$ is methyl, —(CH₂)₄—NH₂, —(CH₂)₃NH(C=O)NH₂, (CH₂)₃NH(C=NH)NH₂, or —(CH₂)₂CO₂H, wherein the wavy line at the dipeptide N-terminal indicates the site of covalent binding to A or $A_O$ or to $L_{SS}$ or $L_S$, depending on the presence or absence of A and $A_O$, and the wavy line at the dipeptide C-terminal indicates the site of covalent binding to J' or —NH—.

In other embodiments in which W is a Glucuronide Unit of formula —Y(W') so that $L_O$ is of formula 1b, which has A, W' and Y/Y' in an orthogonal configuration with respect to D/D⁺, -$L_{SS}$-$L_O$-D/D⁺ of a drug linker moiety within a Ligand Drug Conjugate compound and its hydrolysis product -$L_S$-$L_O$-D/D⁺, whose formation is catalyzed by a cyclic Basic Unit, have structures of:

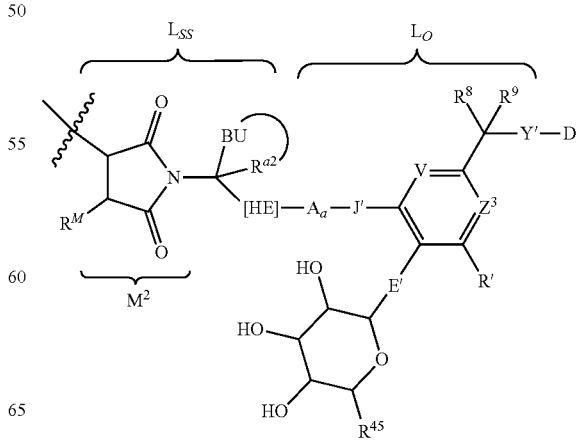

and

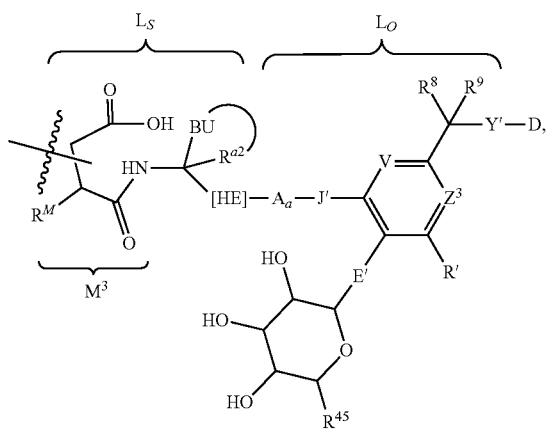

respectively, wherein [HE] is an optional Hydrolysis Enhancer Unit; $R^M$ is hydrogen or $C_1$-$C_4$ alkyl; V and $Z^3$ are independently =N— or =C($R^{24}$)—, wherein $R^{24}$, independently selected, is hydrogen, optionally substituted $C_1$-$C_6$ alkyl or an electron withdrawing group; $R^8$ and $R^9$ independently are hydrogen or optionally substituted $C_1$-$C_6$ alkyl or together with the benzylic carbon to which both are attached define an optionally substituted $C_3$-$C_6$ carbocyclo, or one of $R^8$, $R^9$ is hydrogen or optionally substituted $C_1$-$C_6$ alkyl and the other is optionally substituted $C_6$-$C_{10}$ aryl or optionally substituted $C_5$-$C_{10}$ heteroaryl; J' and E' are independently selected optionally substituted heteroatoms, such as —O— or optionally substituted —NH—, which includes —N($R^{33}$), wherein each $R^{33}$ is independently hydrogen or optionally substituted $C_1$-$C_6$ alkyl; Y' is an optional second Spacer Unit, which can be an optionally substituted heteroatom or a functional group, in which the latter may also be capable of self-immolation as when Y' is —OC(=O)-covalently bonded to a heteroatom of D, or Y' is another self-immolative moiety such as a methylene carbamate unit, or Y' is absent when D is a quaternized Drug Unit ($D^+$); $R^{45}$ is —CH$_2$OH or —CO$_2$H; and the wavy line indicates covalent bonding of a Ligand Unit, which for the $M^3$ moiety in $L_S$ is to the carbon atom that is alpha to the acid or amide functional group with $R^M$ bonded to the remaining beta carbon. In preferred embodiments, V and $Z^2$ are =CH— or $R^8$ and $R^9$ are independently hydrogen or $C_1$-$C_4$ alkyl. In other preferred embodiments, J' is —NH—. In more preferred embodiments, $R^8$ and $R^9$ are independently selected from the group consisting of hydrogen, —CH$_3$ and —CH$_2$CH$_3$; and J' is —NH—. In those embodiments the indicated $M^2$ and $M^3$ residues represent a succinimide moiety and a succinic acid amide moiety, respectively.

In other embodiments, a Drug Linker compound of formula $L_{SS}$-$L_O$-D/$D^+$ having a cyclic Basic Unit and a Glucuronide Unit is exemplified by the structure of:

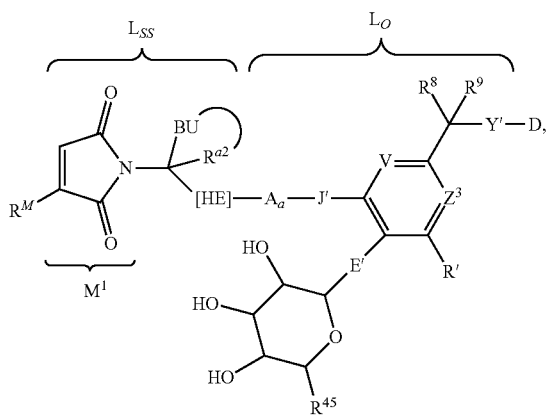

wherein the variable groups are as previously described for Glucuronide-based drug linker moieties in Ligand Drug Conjugates and Drug Linker compounds.

In preferred embodiments, -$L_{SS}$-$L_O$-D/$D^+$ and its hydrolysis product -$L_S$-$L_O$-D/$D^+$, in which W is a Glucuronide Unit of formula —Y(W')— have $L_O$ of formula (1b), so that A, W' and Y are in an orthogonal configuration with respect to D/$D^+$, are represented by:

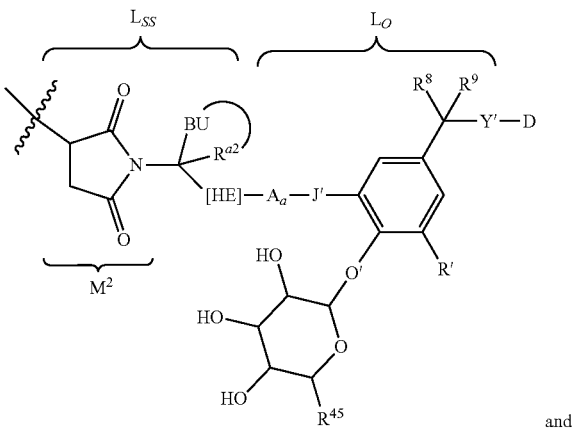

and

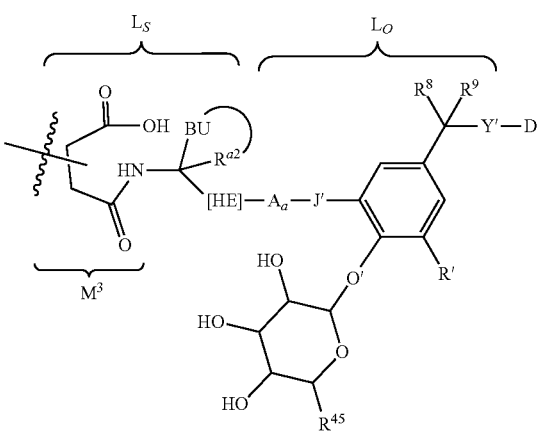

, respectively, and corresponding Drug Linker compounds are represented by:

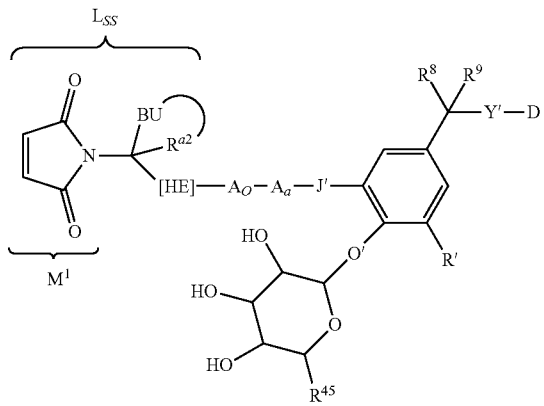

wherein O' represents a glycosidic-bonded oxygen, the bond to which is cleavable by a glycosidase. In those drug linker moieties and Drug Linker compounds, preferably one of $R^8$, $R^9$ is hydrogen and the other is hydrogen, $C_1$-$C_4$ alkyl or optionally substituted phenyl. In other such embodiments preferably J' is —O— or —N($R^{33}$), wherein $R^{33}$ is hydrogen or $C_1$-$C_4$ alkyl or R' is hydrogen or an electron withdrawing group. In more preferred embodiments J is —NH— and R' is hydrogen or —$NO_2$.

In more preferred embodiments where A, W' and Y are in an orthogonal configuration, a drug linker moiety of a Ligand Drug Conjugate compound of formula -$L_{SS}$-$L_O$-D/$D^+$ and it hydrolysis product of formula -$L_{SS}$-$L_O$-D/$D^+$ have the structures of:

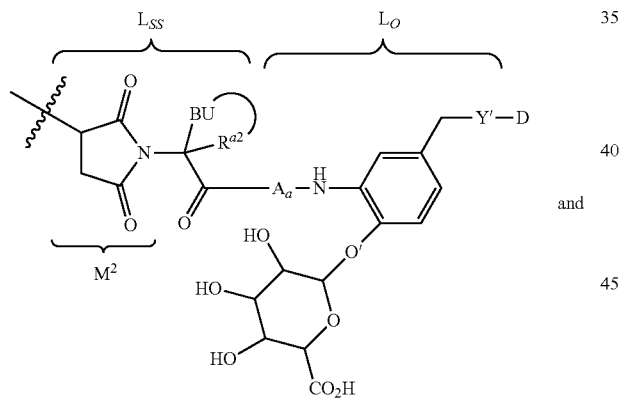

and

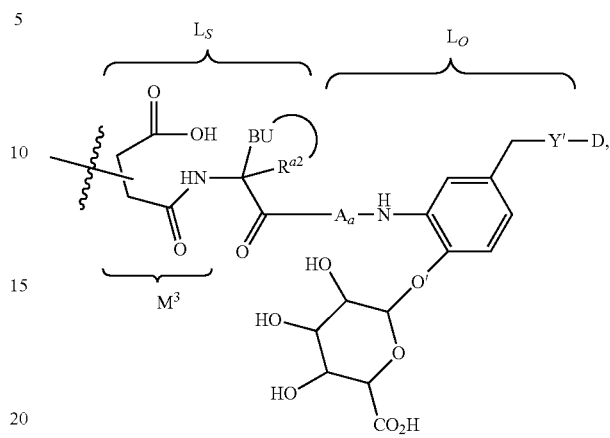

respectively, and corresponding Drug Linker compounds are represented by:

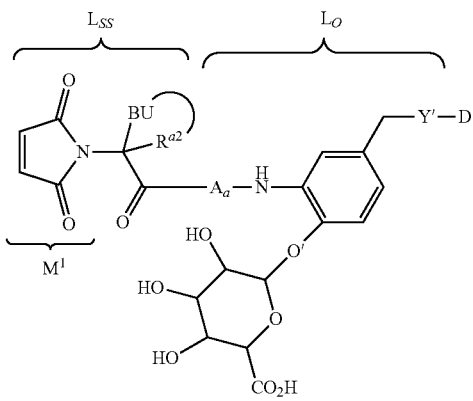

In any of the above embodiments the -$L_{SS}$ and -$L_S$ containing drug linker moieties of a Ligand Drug Conjugate compound having $L_O$ of formula 1a in which subscript y is 1 or 2 and having a carbocyclo cyclic Basic Unit with a Peptide Cleavable Unit preferably have the structure of:

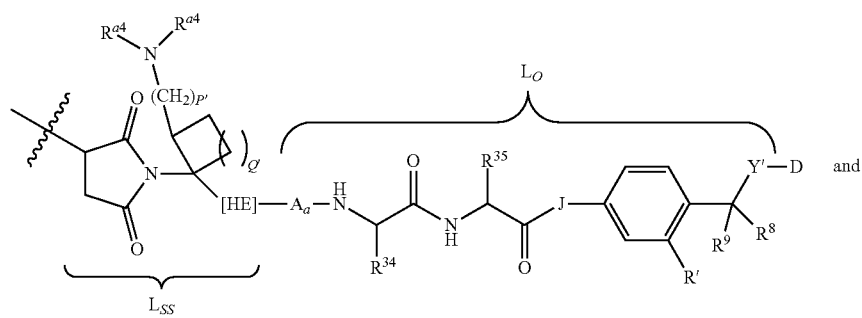

and

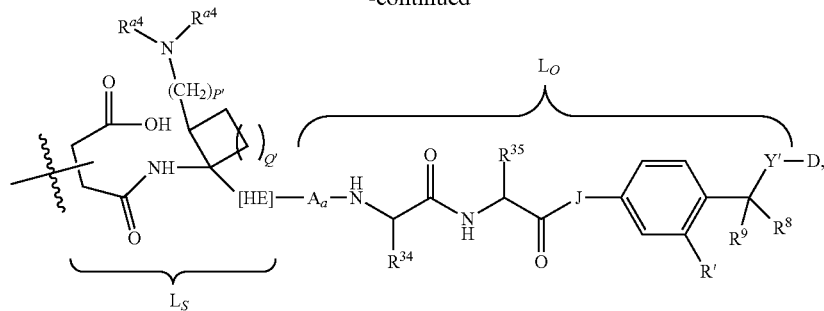

and corresponding Drug Linker compounds are represented by:

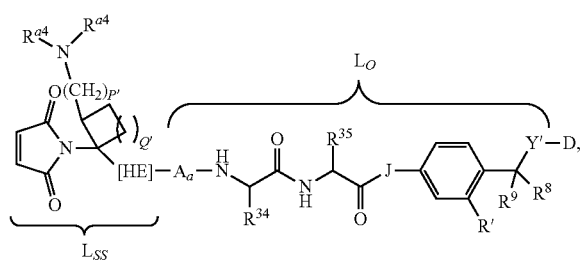

wherein $R^{a4}$ and subscripts P' and Q' are as previously defined for carbocyclo cyclic Basic Units, $R^{34}$ and $R^{35}$ are as previously defined for Peptide Cleavable Units and the remaining variable groups are as previously defined for drug linker moieties and Drug linker compounds comprised of these Peptide Cleavable Units.

In any of the above embodiments the -$L_{SS}$ and -$L_S$ containing drug linker moieties of a Ligand Drug Conjugate compound having $L_O$ of formula 1a in which W is a Peptide Cleavable Unit and subscript y is 0 or 1 and having a carbocyclo cyclic Basic Unit preferably have the structure of:

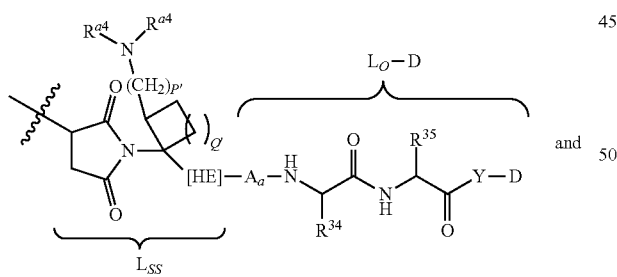

and

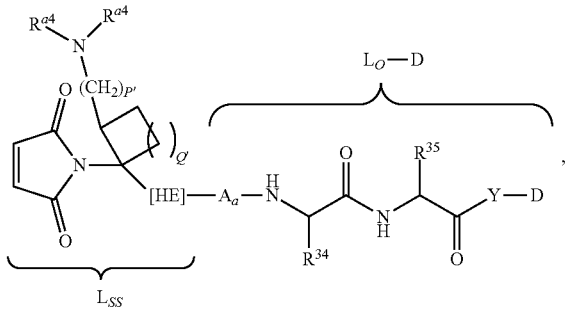

respectively, and corresponding Drug Linker compounds are represented by:

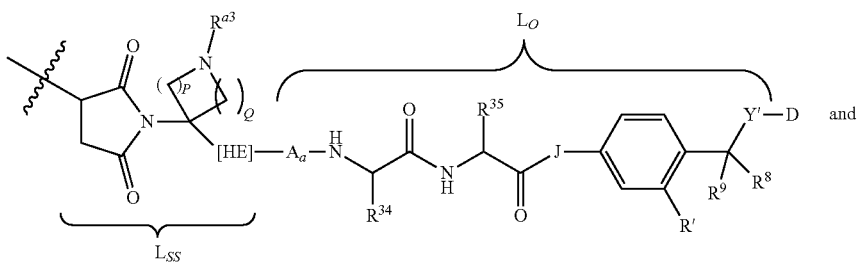

wherein Y is absent or is an optionally substituted heteroatom or an optionally substituted functional group not typically capable of self-immolation and protease cleavage of the W—Y bond within $L_O$ releases a biologically active compound or its derivative of formula D-H or D-Y—H.

In other preferred embodiments the -$L_{SS}$ and -$L_S$ containing drug linker moieties of a Ligand Drug Conjugate compound having $L_O$ of formula (1a) in which W is a Peptide Cleavable Unit and subscript y is 1 or 2 and having a heterocyclo cyclic Basic Unit are represented by:

-continued

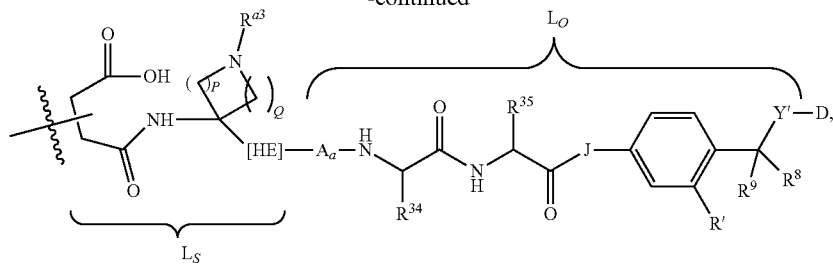

respectively, and corresponding Drug Linker compounds are represented by:

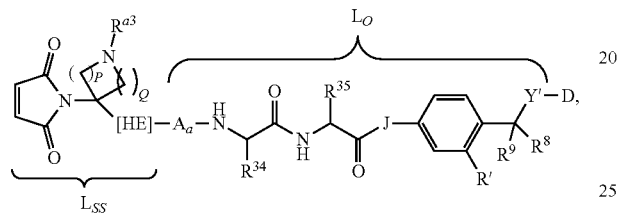

wherein $R^{a3}$ and subscripts P and Q are as previously defined for heterocyclo cyclic Basic Units, $R^{34}$ and $R^{35}$ are as previously defined for Peptide Cleavable Units and the remaining variable groups are as previously defined for drug linker moieties and Drug linker compounds comprised of these Peptide Cleavable Units.

In other preferred embodiments the -$L_{SS}$ and -$L_S$ containing drug linker moieties of a Ligand Drug Conjugate compound having $L_O$ of formula (1a) in which W is a Peptide Cleavable Unit and subscript y is 0 or 1, wherein Y, when present, is a optionally substituted heteroatom or functional group not typically capable of self-immolation, and having a heterocyclo cyclic Basic Unit are represented by:

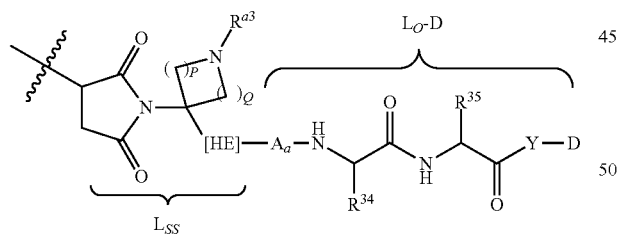

and

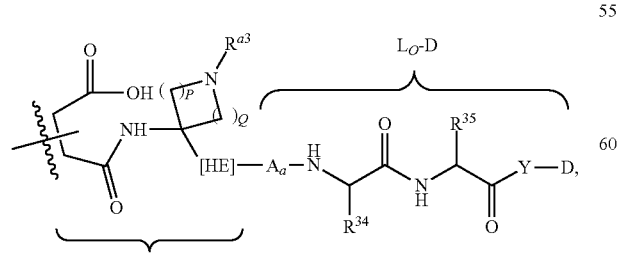

respectively, and corresponding Drug Linker compounds are represented by:

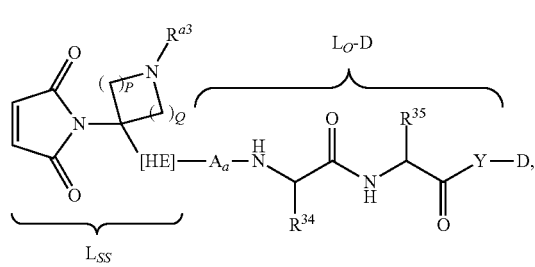

wherein protease cleavage of the W—Y bond within $L_O$ releases a biologically active compound or its derivative of formula D-H or D-Y—H.

In any of the above embodiments the -$L_{SS}$ and -$L_S$ containing drug linker moieties of a Ligand Drug Conjugate compound having a Glucuronide Unit in which $L_O$ is of formula (1b) and having a carbocyclo cyclic Basic Unit preferably have the structure of:

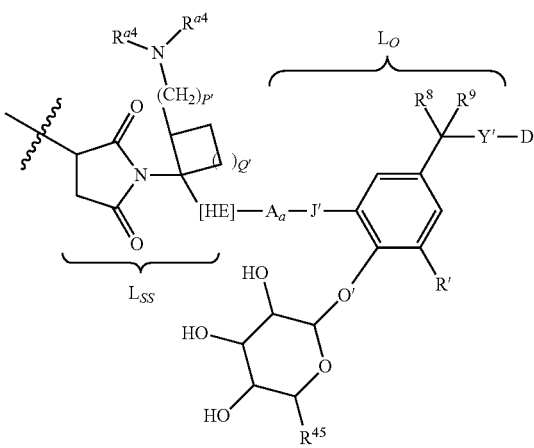

and

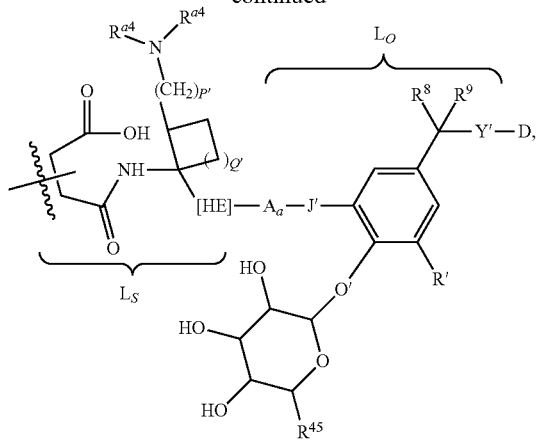

respectively, and corresponding Drug Linker compounds are represented by:

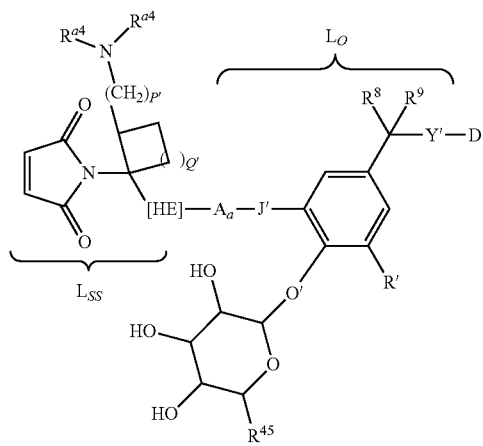

wherein O' represents a glycosidic-bonded oxygen, the bond to which is cleavable by a glycosidase.

In other preferred embodiments the $L_{SS}$- and $L_S$-containing drug linker moieties having a Glucuronide Unit in which $L_O$ is of formula 1b, and a heterocyclo cyclic Basic Unit within a Ligand Drug Conjugate compound have the structure of:

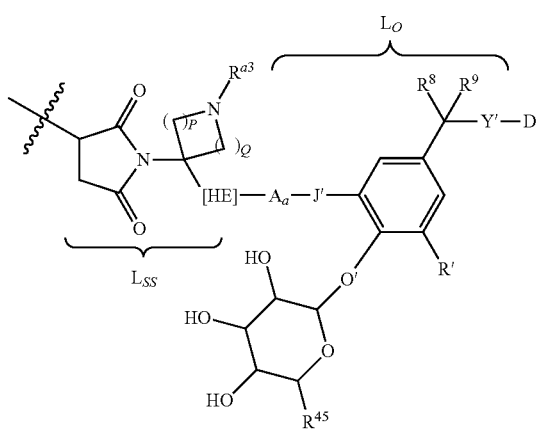

and

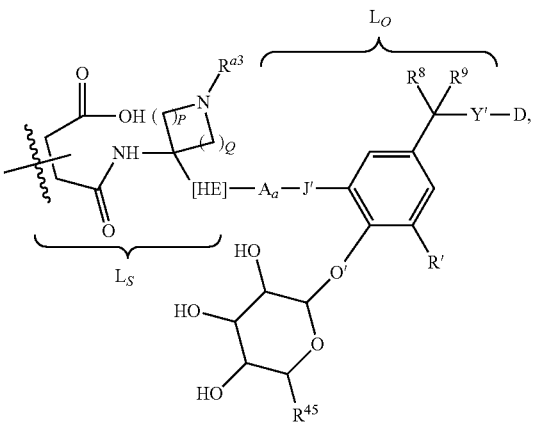

respectively, and corresponding Drug Linker compounds are represented by:

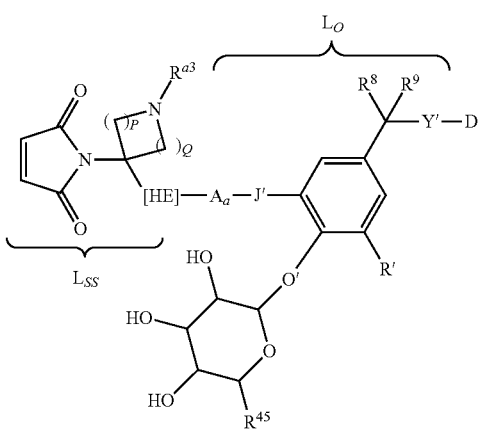

wherein O' represents a glycosidic-bonded oxygen, the bond to which is cleavable by a glycosidase.

In more preferred embodiments the -$L_{SS}$ containing drug linker moieties within a Ligand Drug Conjugate compound having $L_O$ of formula 1a, wherein W is a Peptide Cleavable Unit and subscript y is 1 or 2, and having a heterocyclo cyclic Basic Unit are represented by:

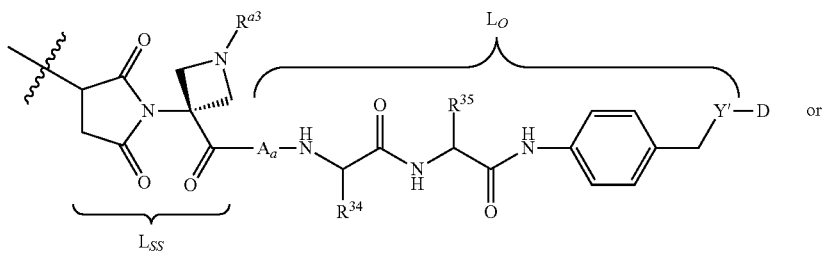
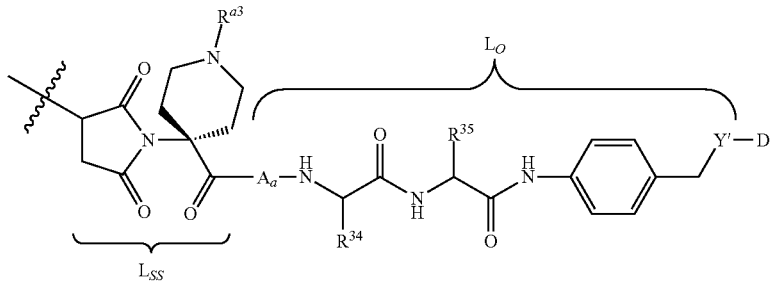
In more preferred embodiments $L_S$-containing drug linker moieties from controlled hydrolysis of the above drug linker moieties are represented by:
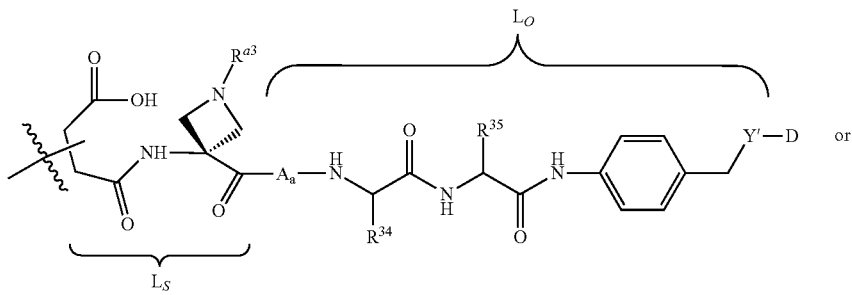
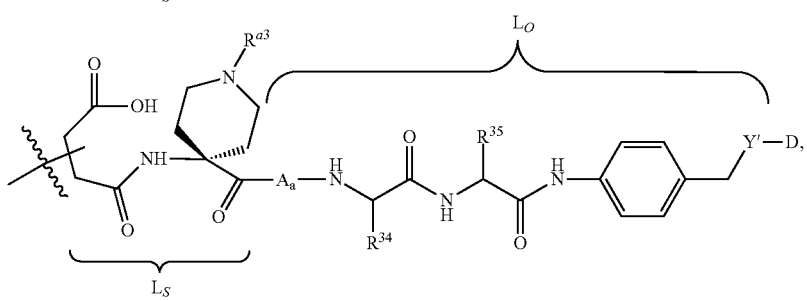
and corresponding Drug Linker compounds are represented by:
-continued
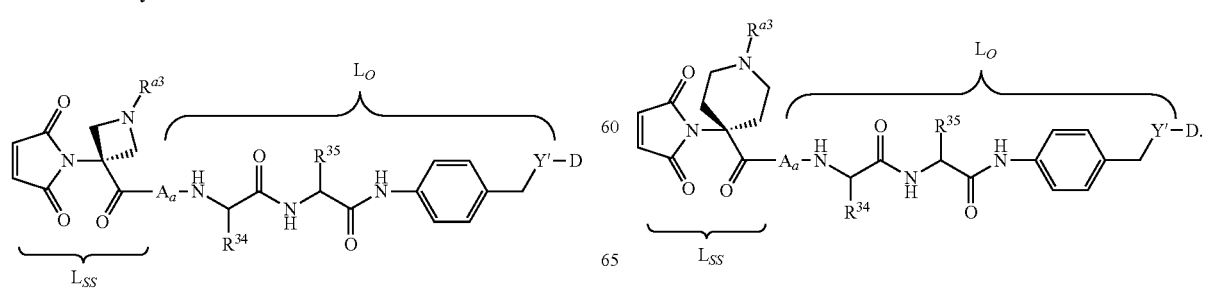

In other more preferred embodiments $L_{SS}$-containing drug linker moieties of a Ligand Drug Conjugate compound having $L_O$ of formula 1a in which W is a Peptide Cleavable Unit and subscript y is 0 or 1, wherein Y wherein Y is a optionally substituted heteroatom or optionally substituted functional group not typically capable of self-immolation, and having a heterocyclo cyclic Basic Unit are represented by:

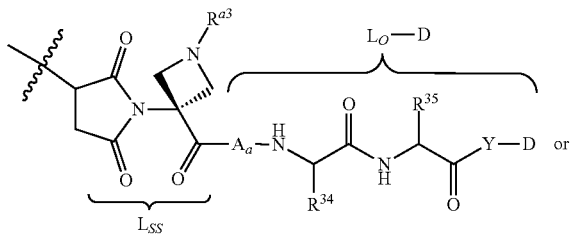

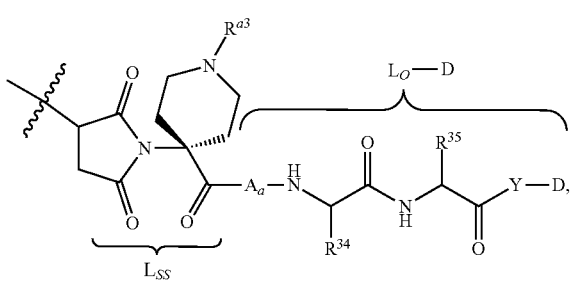

and $L_S$-containing drug linker moieties from controlled hydrolysis of the above drug linker moieties are represented by:

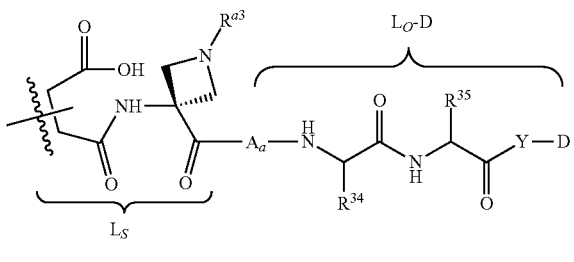

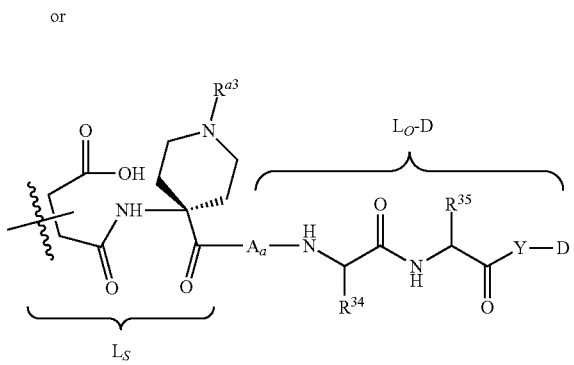

and corresponding Drug Linker compounds are represented by:

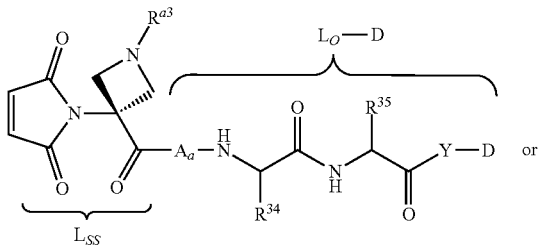

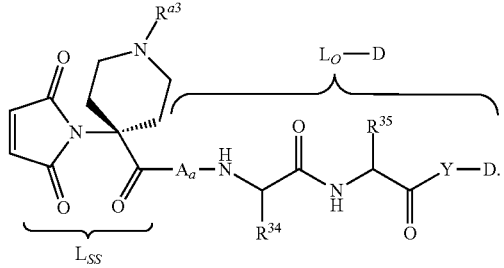

wherein protease cleavage of the W—Y within $L_O$ releases a biologically active compound or its derivative of formula D-H or D-Y—H.

In other more preferred embodiments the $-L_{SS}$ containing drug linker moieties having a Glucuronide Unit in which $L_O$ is of formula 1b and having a heterocyclo cyclic Basic Unit within a Ligand Drug Conjugate are represented by:

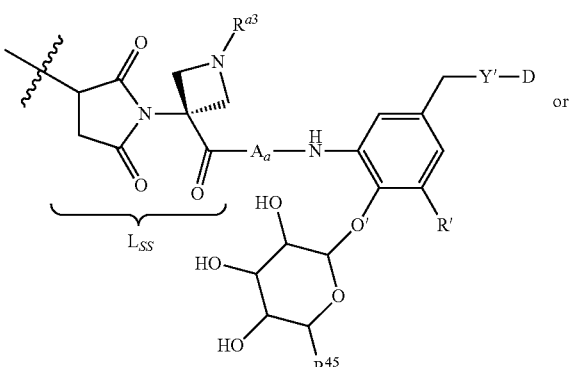

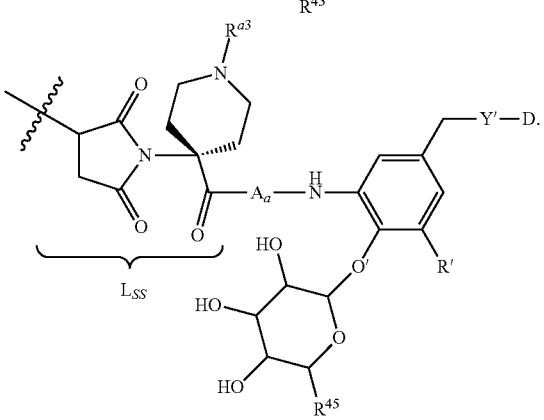

In more preferred embodiments the $L_S$-containing drug linker moieties having a Glucuronide Unit in which $L_O$ is of formula 1b and having heterocyclo cyclic Basic Unit within a Ligand Drug Conjugate compound have the structure of:

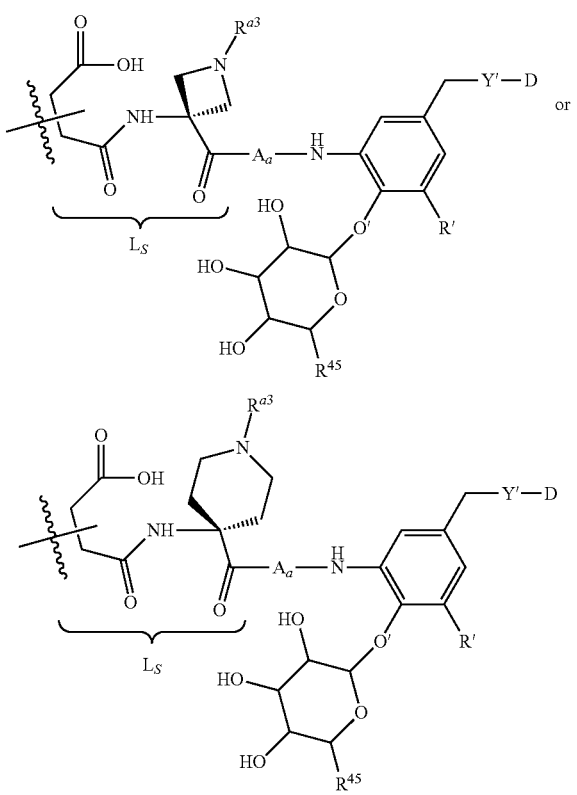

and corresponding Drug Linker compounds are represented by:

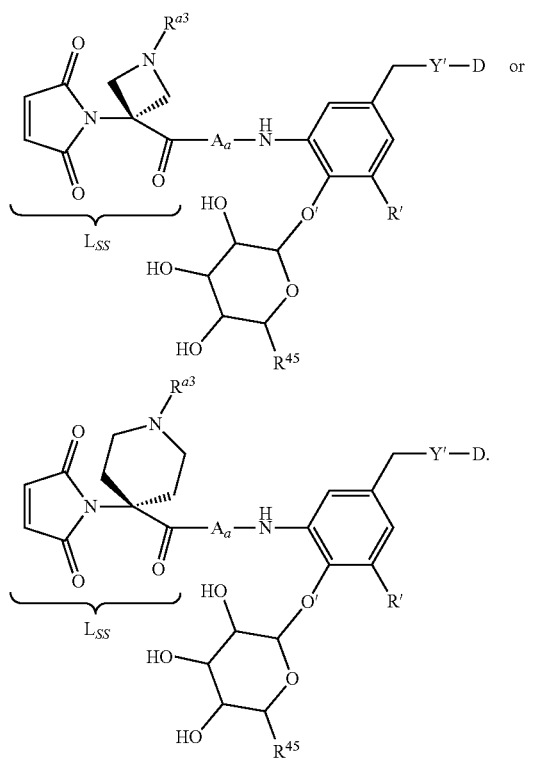

In the above preferred embodiments, the $L_{SS}$ and $L_S$ components within a drug linker moiety of a Ligand Drug Conjugate exemplify the general formula of $M^2$-$A_R$(cBU)-$A_O$- and $M^3$-$A_R$(cBU)-$A_O$-, respectively, in which [HE] as $A_O$ is —C(=O)—, wherein $M^2$ is succinimide moiety and $M^3$ is succinic acid amide moiety, and $L_{SS}$ of a Drug Linker compound exemplify the general formula of $M^1$-$A_R$(cBU)-$A_O$-, which is a precursor to representative $L_{SS}$ moieties of a Ligand Drug Conjugates comprised of a cyclic Basic Unit, wherein $M^1$ is a maleimide moiety and [HE] as $A_O$ is —C(=O)—.

In some of the above embodiments A, or a subunit thereof, when subscript a is 1 and is bonded to $A_O$ in any one of the above $L_R$-$L_o$-D/D$^+$ structures in which $L_R$ is either $L_{SS}$ or $L_S$, preferably has a structure corresponding to an independently selected amine-containing acid (e.g., an amino acid residue) wherein the carboxylic acid terminus of the amine-containing acid is bonded to W as an ester or amide, preferably as an amide, and its N-terminus is bonded to $L_{SS}$ of formulae $M^1$-$A_R$(cBU)-$A_O$- or $M^2$-$A_R$(cBU)-$A_O$- or $L_S$ of formula $M^3$-$A_R$(cBU)-$A_O$- through a carbonyl-containing functional group. In several of those embodiments $A_O$ is [HE] or is comprised of [HE], wherein HE is a carbonyl-containing functional group so that its carbonyl carbon is bonded to the N-terminus of W.

In other embodiments A, or a subunit thereof, has the formula of -$L^P$(PEG)-, wherein $L^P$ is a Parallel Connector Unit and PEG is a PEG Unit. In those embodiments, the PEG Unit contains a total of 2 to 36 ethyleneoxy monomer units and $L^P$ is comprised of an amine-containing acid residue, preferably an amino acid residue, covalently attached to W. In more preferred embodiments the covalent attachment of $L^P$ within the Linker Unit of a drug linker moiety of Ligand Drug Conjugate or of a Drug Linker compound is through amide functional groups. In other more preferred embodiments the PEG Unit contains a total of 4 to 24 contiguous ethyleneoxy monomer units.

In any one of the above -$L_{SS}$-$L_O$-D/D$^+$ and -$L_S$-$L_O$-D/D$^+$ Ligand Drug Conjugate sub-structures and the $L_{SS}$-$L_O$-D/D$^+$ Drug Linker compound structures having a carbocyclo or heterocyclo cyclic Basic Unit and a protease cleavable Peptide Cleavable Unit, preferably $R^{34}$ is methyl, isopropyl or —CH(OH)CH$_3$ and $R^{35}$ is methyl, —(CH$_2$)$_3$NH(C=O)NH$_2$ or —(CH$_2$)$_2$CO$_2$H. In any one of the above -$L_{SS}$-$L_O$-D/D$^+$ and -$L_S$-$L_O$-D/D$^+$ Ligand Drug Conjugate sub-structures and the $L_{SS}$-$L_O$-D/D$^+$ Drug Linker compound structures having a carbocyclo or heterocyclo cyclic Basic Unit and a glycosidase cleavable Glucuronide Unit preferably $R^{45}$ is —CO$_2$H. In any one of the above -$L_{SS}$-$L_O$-D/D$^+$ and -$L_S$-$L_O$-D/D$^+$ Ligand Drug Conjugate substructures and the $L_{SS}$-$L_O$-D/D$^+$ Drug Linker compound structures having a carbocyclo cyclic Basic Unit preferably subscript P' is 0 or 1 and subscript Q is 2 or 3. In other such embodiments preferably each $R^{a4}$ is independently selected from the group consisting of hydrogen and $C_1$-$C_4$ alkyl or both $R^{a4}$ together with the basic nitrogen atom to which they are attached define a pyrrolidine or piperidine heterocyclyl. In more preferred embodiments each $R^{a4}$ is hydrogen, methyl or ethyl with the basic nitrogen optionally protonated. In other more preferred embodiments, particularly for Drug Linker compounds, one $R^{a4}$ is hydrogen or $C_1$-$C_4$ alkyl and the other $R^{a4}$ is a suitable nitrogen protecting group including an acid-labile protecting group such as —C(=O)-t-Bu (BOC).

In preferred embodiments in which W', Y and D/D$^+$ are in an orthogonal configuration, a first Stretcher Unit (A) is present and has the structure previously defined for formula (3) or formula (4) or has the structure of formula (3a) or formula (4a):

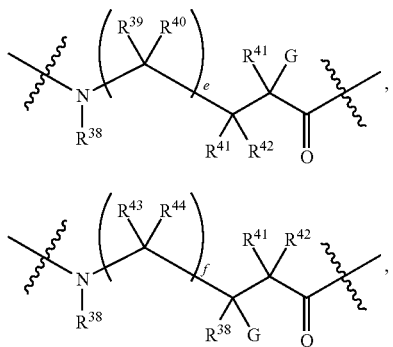

(3a)

(4a)

wherein subscript e or f is 0 or 1 and G and $R^{39}$-$R^{44}$ are as previously defined and the wavy line to the carbonyl moiety of any one of the formula (3), (3a), (4) and (4a) structures represents the point of attachment of A to J' preferably through an amide functional group and wherein the wavy line to the amino moiety of either one of these structures represents the point of attachment to a carbonyl-containing functional group of a second Stretcher Unit $A_O$ or to the carbonyl carbon of [HE] as $A_O$. In preferred embodiments of formula (3) or formula (4) L' is absent (i.e., subscript q is 0) and G is hydrogen, —$CO_2H$ or —$NH_2$ or the side chain of a naturally occurring amino acid such as aspartic acid, glutamic acid or lysine. In other preferred embodiments, L' and K are carbon and $R^{41}$, $R^{42}$, $R^{43}$ and $R^{44}$ in each occurrence is hydrogen. In other preferred embodiments $R^{38}$-$R^{44}$ in each occurrence is hydrogen. Other preferred embodiments have formula (3) wherein K is nitrogen and one of $R^{41}$, $R^{42}$ is absent and the other is hydrogen. Other preferred embodiments have formula (4) wherein subscript r is 1, K is nitrogen and one of $R^{41}$, $R^{42}$ is absent and the other is hydrogen. In other preferred embodiments subscripts p and q of structure (3) are both 0 or subscripts q and r of structure (4) are both 0. Other preferred embodiments have structure (3) wherein subscripts p and q are both 0 and K together with $R^{41}$ and $R^{42}$ is —C(=O)—. Other preferred embodiments have structure (4) wherein subscript q is 1 and L' together with $R^{43}$ and $R^{44}$ is —C(=O)—.

In preferred embodiments in which W, Y and D/D$^+$ are in a linear configuration, a first Stretcher Unit (A) is present having the same variable group preferences as described above for preferred embodiments in which W', Y and D/D$^+$ are in an orthogonal configuration. In such preferred embodiments, the wavy line to the carbonyl moiety of any one of the formula (3), (3a), (4) and (4a) structures represents the point of attachment of A to the N-terminus of the Peptide Cleavable Unit (W) and the wavy line to the amino moiety of either one of these structures represents the point of attachment to a carbonyl-containing functional group of a second Stretcher Unit $A_O$ or to the carbonyl carbon of [HE] as $A_O$.

In other preferred embodiments A and $A_O$ are both present A is selected from formula (3), (3a), (4) and (4a). In more preferred embodiments A is an alpha-amino, beta-amino or other amine-containing acid residue. In more preferred embodiment A is an alpha-amino, beta-amino or other amine-containing acid residue.

In any one of the above -$L_{SS}$-$L_O$-D/D$^+$ and -$L_S$-$L_O$-D/D$^+$ Ligand Drug Conjugate sub-structures and the $L_{SS}$-$L_O$-D/D$^+$ Drug Linker compound structures having a carbocyclo or heterocyclo cyclic Basic Unit in which A is present, particularly preferred amine-containing acids that correspond to A have the structure of $NH_2$—$X^1$—$CO_2H$ wherein $X^1$ is an optionally substituted $C_1$-$C_6$-alkylene.

Particularly preferred Ligand Drug Conjugates are represented by any one of the above -$L_{SS}$-$L_O$-D/D$^+$ and -$L_S$-$L_O$-D/D$^+$ Ligand Drug Conjugate sub-structures in which an antibody Ligand Unit is bonded to the $L_{SS}$ or $L_S$ moiety.

1.3.1 Ligand Unit

In some embodiments of the invention, a Ligand Unit is present. The Ligand Unit (L) is a targeting moiety of a Ligand Drug Conjugate that specifically binds to a targeted moiety. The Ligand Unit can specifically bind to a cell component (a Cell Binding Agent), which serves as the targeted moiety, or to other target molecules of interest. The Ligand Unit acts to target and present the Drug Unit of the Ligand Drug Conjugate to the particular target cell population with which the Ligand Unit interacts for selective release of D/D$^+$ as a biologically active compound or derivative thereof. Targeting agents that provide for Ligand Units include, but are not limited to, proteins, polypeptides and peptides. Exemplary Ligand Units include, but are not limited to, those provided by proteins, polypeptides and peptides such as antibodies, e.g., full-length antibodies and antigen binding fragments thereof, interferons, lymphokines, hormones, growth factors and colony-stimulating factors. Other suitable Ligand Units are those from vitamins, nutrient-transport molecules, or any other cell binding molecule or substance. In some embodiments a Ligand Unit is from non-antibody protein targeting agent. In other embodiments, a Ligand Unit is from protein targeting agent such as an antibody. Preferred targeting agents are larger molecular weight proteins, e.g., Cell Binding Agents having a molecular weight of at least about 80 Kd.

A targeting agent reacts with a $L_{SS}$ moiety of a Drug Linker compound to form a Ligand Unit covalently attached to drug-linker moiety wherein the drug-linker moiety has the formula -$L_{SS}$-D. The targeting agent has or is modified to have to have the appropriate number of attachment sites to accommodate the requisite number of drug-linker moieties, defined by subscript p, whether they be naturally occurring or non-naturally occurring (e.g., engineered). For example, in order for the value of subscript p to be from 6 to 14, a targeting agent has to be capable of forming a bond to 6 to 14 drug-linker moieties. The attachment sites can be naturally-occurring or engineered into the targeting agent. A targeting agent can form a bond to the $L_{SS}$ moiety of the Linker unit of a Drug Linker compound via a reactive or activatable heteroatom or a heteroatom-containing functional group of the targeting agent. Reactive or activatable heteroatoms or a heteroatom-containing functional groups that may be present on a targeting agent include sulfur (in one embodiment, from a thiol functional group of an targeting agent), C=O or (in one embodiment, from a carbonyl, carboxyl or hydroxyl group of a targeting agent) and nitrogen (in one embodiment, from a primary or secondary amino group of a targeting agent). Those heteroatoms can be present on the targeting agent in the targeting agent's natural state, for example a naturally-occurring antibody, or can be introduced into the targeting agent via chemical modification or biological engineering.

In one embodiment, a targeting agent has a thiol functional group and the Ligand Unit therefrom is attached to a drug linker moiety of a Ligand Drug Conjugate compound via the thiol functional group's sulfur atom.

In another embodiment, the targeting agent has lysine residues that can react with an activated ester, including but are not limited to, N-hydroxysuccinimide, pentafluorophenyl, and p-nitrophenyl esters), of $L_{SS}$ of the Linker Unit of a Drug Linker compound and thus results in an amide bond between the nitrogen atom from the Ligand Unit and the C=O functional group from the Linker Unit of the Drug Linker compound.

In yet another embodiment, the targeting agent has one or more lysine residues that can be chemically modified to introduce one or more thiol functional groups. The Ligand Unit from that targeting agent is attached to the Linker Unit via the introduced thiol functional group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the targeting agent can have one or more carbohydrate groups that can be chemically modified to have one or more thiol functional groups. The Ligand Unit from that targeting agent is attached to the Linker Unit via the introduced thiol functional group's sulfur atom, or the targeting agent can have one or more carbohydrate groups that can be oxidized to provide an aldehyde (—CHO) group (see, e.g., Laguzza, et al., 1989, *J. Med. Chem.* 32(3):548-55). The corresponding aldehyde can then react with a $L_{SS}$ moiety of a Drug Linker compound having nucleophillic nitrogen. Other reactive sites on $L_{SS}$ that can react with a carbonyl group on a targeting agent include, but are not limited to, hydrazine and hydroxylamine. Other protocols for the modification of proteins for the attachment of drug linker moieties are described in Coligan et al., *Current Protocols in Protein Science*, vol. 2, John Wiley & Sons (2002) (incorporated herein by reference).

In preferred embodiments, the reactive group of $L_{SS}$ of a Drug Linker compound is a maleimide ($M^1$) moiety and covalent attachment of L to $L_{SS}$ is accomplished through a thiol functional group of a targeting agent so that a thio-substituted succinimide ($M^2$) moiety is formed through Michael addition. The thiol functional group can be present on the targeting agent in the targeting agent's natural state, for example a naturally-occurring residue, or can be introduced into the targeting agent via chemical modification.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker moiety to undergo an elimination reaction and for the drug linker moiety to be transferred from the Ligand Unit of a bioconjugate to an alternative reactive thiol present in the milieu of the bioconjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are less susceptible to the elimination reaction (e.g., positions 239 according to the EU index as set forth in Kabat) in addition to other sites.

Thus, in more preferred embodiments, the targeting agent is an antibody and the thiol functional group is generated by reduction of an interchain disulfide. Accordingly, in some embodiments, the Linker Unit is conjugated to a cysteine residue of the reduced interchain disulfides of the Ligand Unit.

In yet another embodiment, the targeting agent is that of an antibody and the thiol functional group is chemically introduced into the antibody, for example by introduction of a cysteine residue. Accordingly, in some embodiments, the Linker Unit of a Ligand Drug Conjugate compound is conjugated to a drug linker moiety through an introduced cysteine residue.

When the conjugates comprise non-immunoreactive protein, polypeptide, or peptide ligands instead of an antibody, useful non-immunoreactive protein, polypeptide, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred targeting agents are antibodies, including intact antibodies. In fact, in any of the embodiments described herein, the Ligand Unit can be that of an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety). Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety). Such chimeric and humanized monoclonal antibodies can be produced by recombinant DNA techniques known in the art, for example using methods, each of which is specifically incorporated herein by reference, as described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., Science (1988) 240:1041-1043; Liu et al., Proc. Natl. Acad. Sci. (USA) (1987) 84:3439-3443; Liu et al., J. Immunol. (1987) 139: 3521-3526; Sun et al. Proc. Natl. Acad. Sci. (USA) (1987) 84:214-218; Nishimura et al. Cancer. Res. (1987) 47:999-1005; Wood et al., Nature (1985) 314:446-449; Shaw et al., J. Natl. Cancer Inst. (1988) 80:1553-1559; Morrison, Science (1985) 229:1202-1207; Oi et al. BioTechniques (1986) 4:214; U.S. Pat. No. 5,225,539; Jones et al., Nature 1986) (321:552-525; Verhoeyan et al., Science (1988) 239:1534; and Beidler et al., J. Immunol. (1988)141:4053-4060.

Completely human antibodies are particularly preferred and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some embodiments, the antibody will specifically bind CD19, CD20, CD30, CD33, CD70, alpha-v-beta-6, or Lewis Y antigen.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes). Exemplary attachment of the Linker Unit to the antibody Ligand Unit is via thioether linkages. The thioether linkages can be via interchain disulfide bonds, introduced cysteines resides, and combinations thereof.

1.3.2 Parallel Connector Unit

In some embodiments A or $A_O$ is a Parallel Connector Unit ($L^P$) having the structure of Formula A or Formula B:

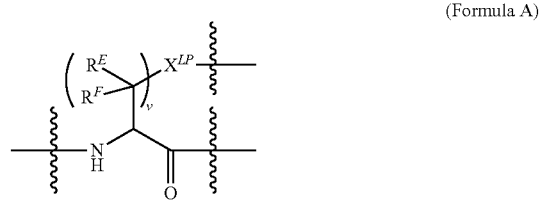

(Formula A)

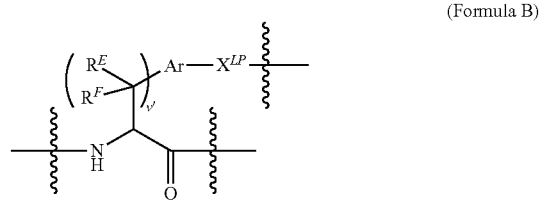

(Formula B)

wherein subscript v is an integer ranging from 1 to 4; subscript v' is an integer ranging from 0 to 4; $X^{LP}$ is provided by a natural or un-natural amino acid side chain or is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N (R$^{LP}$)—, and —N(R$^{LP}$)C(=NR$^{LP}$)N(R$^{LP}$)—, or heterocyclo wherein each R$^{LP}$ is independently selected from the group consisting of hydrogen and optionally substituted alkyl or two of R$^{LP}$ together along with their intervening atoms define a heterocycloalkyl and any remaining R$^{LP}$ are as previously defined; Ar is an arylene or heteroarylene, optionally substituted; each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons, defines a optionally substituted cycloalkyl with any remaining R$^E$ and R$^F$ substituents as previously defined; and wherein the wavy lines indicates covalent attachment of the Formula A or Formula B structure within a Ligand Drug Conjugate or Drug Linker compound structure.

In some embodiments -L$^P$(PEG)- has the structure of Formula A1 or A2:

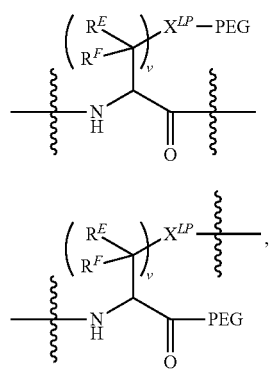

(Formula A1)

(Formula A2)

wherein the variable groups are as defined in Formula A.

In preferred embodiments, L$^P$ has the structure of Formula A1 wherein X$^{LP}$ is provided by a natural or un-natural amino acid side chain.

In preferred embodiments of Formula A, Formula A1, Formula A2 or Formula B, R$^E$ and R$^F$ are independently selected from the group consisting of —H, and —C$_1$-C$_4$ alkyl. In preferred embodiments of Formula A, Formula A1 or Formula A2, X$^{LP}$ is selected from the group consisting of —O—, —NH, —S— and —C(=O)—

In some embodiments, L$^P$ is selected from the group consisting of lysine, glutamic acid, aspartic acid, cysteine, penicillamine, serine or threonine in D- or L-stereochemical configuration.

In other embodiments, L$^P$ is selected from the group consisting of lysine, glutamic acid, aspartic acid, cysteine, or penicillamine in D- or L-stereochemical configuration.

In other embodiments, L$^P$ is a thiol containing amino acid residue in the D- or L-stereochemical configuration. The thiol containing amino acid is preferably cysteine, homocysteine, or penicillamine.

In other embodiments, L$^P$ is an aminoalkanedioic acid residue. Illustrative aminoalkanedioic acids include but are not limited to: N-alkylaminoalkanedioic acid, 2-aminohexanedioic acid, 2-aminoheptanedioic acid and 2-aminooctanedioic acid (H-Asu-OH).

In other embodiments, L$^P$ is a diaminoalkanoic acid residue. Illustrative of examples of diaminoalkanoic acids include but are not limited to: N-alkyl-diamino-alkanoic acids, N,N-dialkylamino-alkanoic acids, α,γ-diaminobutyric acid (H-Dab-OH), and α,β-diaminopropionic acid.

Exemplary lysine, cysteine or penicillamine amino acid residues for L$^P$ are shown below:

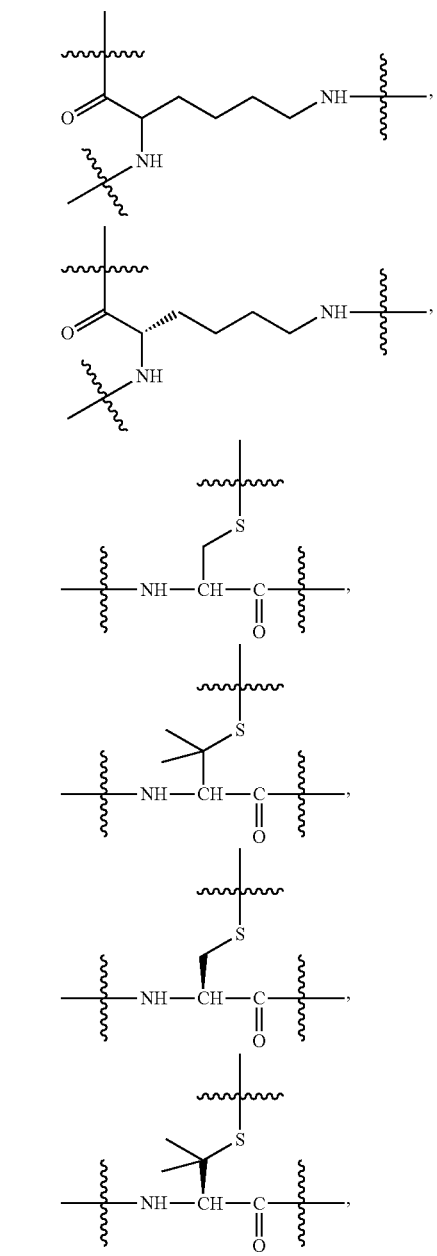

wherein the wavy lines indicate the points of covalent attachment to PEG and L' of L$^P$(PEG)- within a Linker Unit of a drug linker moiety or a Drug Linker compound.

Exemplary Ligand-Drug Conjugates having lysine as the L$^P$ unit are shown below wherein L, L$_S$, A, A$_O$, W, W', Y, Y', D, PEG, subscript y is 0, 1 or 2 and subscripts a and p are as described herein. (R)- and (S)-stereoisomers at the indicated (*) position are suitable for use herein.

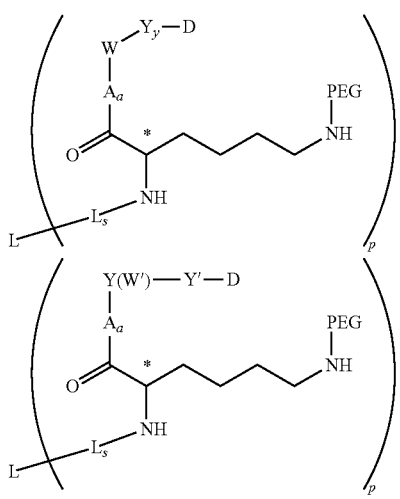

1.3.3 PEG Unit

The PEG Units as taught herein are designed to impart an suitable level of hydrophobicity masking of hydrophobic Drug Units(s) and other hydrophobic components of a drug-linker moiety within a Ligand Drug Conjugate. For that reason, the incorporation of PEG Unit as taught herein is particularly suitable for hydrophobic Drug Units that negatively impact the pharmacokinetics of the resultant Ligand Drug Conjugate as compared to the unconjugated targeting agent that is incorporated into its Ligand Unit. Those poorer pharmokinetics include greater plasma clearance, which can be attributed to the hydrophobicity of a hydrophobic drug incorporated into the Drug Unit the Ligand Drug Conjugate. Thus, Ligand Drug Conjugates having a hydrophobic Drug Unit that display significantly greater plasma clearance and correspondingly lower plasma exposure relative to the unconjugated targeting agent will benefit by a Linker Unit to which that hydrophobic Drug Unit is attached having a Stretcher Unit that is of formula -$L^P$(PEG)-. Ligand-Drug Conjugates whose Linker Units are comprised of such Stretcher Units will have those more favorable pharmokinetic properties due to the parallel orientation within a hydrophobic drug-linker moiety of a hydrophobic Drug Unit and a PEG Unit whereby the negative impact of hydrophobicity of the hydrophobic Drug Unit, which may be further aggravated by other hydrophobic components of the drug-linker moiety, on plasma clearance is sufficiently reduced or eliminated (i.e., hydrophobicity of a drug-linker moiety is masked).

The PEG Unit will be directly attached to the Ligand-Drug Conjugate (or Intermediate thereof) at the Parallel Connector Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit of the PEG Unit. The skilled artisan will understand that the PEG Unit in addition to comprising repeating polyethylene glycol subunits may also contain non-PEG material (e.g., to facilitate coupling of multiple PEG chains to each other or to facilitate coupling to the Parallel Connector Unit). Non-PEG material refers to the atoms in the PEG Unit that are not part of the repeating —$CH_2CH_2O$— subunits. In embodiments provided herein, the PEG Unit can comprise two monomeric PEG chains linked to each other via non-PEG elements.

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) *Methods Enzymol.* 184:160; Rose, et al. (1991) *Bioconjugate Chem.* 2:154; and Gaertner et al. (1994) *J. Biol. Chem.* 269:7224].

The addition of the PEG Unit may have two potential impacts upon the pharmacokinetics of the resulting Ligand-Drug Conjugate. The desired impact is the decrease in clearance (and consequent in increase in exposure) that arises from the reduction in non-specific interactions induced by the exposed hydrophobic elements of the drug-linker. The second impact is undesired impact and is the decrease in volume and rate of distribution that may arise from the increase in the molecular weight of the Ligand-Drug Conjugate. Increasing the number of PEG subunits increases the hydrodynamic radius of a conjugate, resulting in decreased diffusivity. In turn, decreased diffusivity may diminish the ability of the Ligand-Drug Conjugate to penetrate into a tumor (Schmidt and Wittrup, *Mol. Cancer Ther.* (2009) 8:2861-2871). Because of these two competing pharmacokinetic effects, it is desirable to use a PEG that is sufficiently large to decrease the LDC clearance thus increasing plasma exposure, but not so large as to greatly diminish its diffusivity, which may reduce the ability of the Ligand-Drug Conjugate to reach the intended target cell population.

In preferred embodiments, the PEG Unit is a derivitized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

Exemplary preferred linear PEG Units that can be used in any of the embodiments provided herein are as follows:

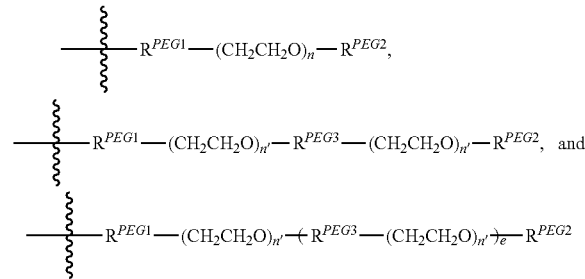

wherein the wavy line indicates site of attachment to the Parallel Connector Unit to $L^P$; $R^{PEG1}$ is a PEG Attachment Unit, $R^{PEG2}$ is a PEG Capping Unit; $R^{PEG3}$ is an PEG Coupling Unit (i.e., for coupling multiple PEG subunit chains together), subscript n is selected from 2 to 72 (preferably from 4 to 72, more preferably from 6 to 72, from 8 to 72, from 10 to 72, from 12 to 72 or from 6 to 24); subscript e is 2 to 5; and each subscript n' is independently selected from 1 to 72.

In more preferred embodiments, there are no more than 72 or 36 PEG subunits in a PEG Unit. In other more preferred embodiments, subscript n is 8 or about 8, 12 or about 12, or 24 or about 24.

The PEG Attachment Unit ($R^{PEG1}$) is part of a PEG Unit and acts to connect the PEG Unit to the Parallel Connector Unit ($L^P$) through a functional group of the PEG Unit. Functional groups for attachment of the PEG Unit to $L^P$ include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG Unit can be attached $L^P$, for example, via disulfide, thioether, hydrazone, oxime, peptide, ester, sulfonamide, carbamate, or amide bonds.

In exemplary embodiments, $R^{PEG1}$ is —C(O)—, —O—, —S—, —S(O)—, —NH—, —C(O)O—, —C(O)$C_1$-$C_{10}$alkyl, —C(O)$C_1$-$C_{10}$alkyl-O—, —C(O)$C_1$-$C_{10}$alkyl-$CO_2$—, —C(O)$C_1$-$C_{10}$alkyl-NH—, —C(O)$C_1$-$C_{10}$alkyl-S—, —C(O)$C_1$-$C_{10}$alkyl-C(O)—NH—, —C(O)$C_1$-$C_{10}$alkyl-NH—C(O)—, —$C_1$-$C_{10}$alkyl, —$C_1$-$C_{10}$alkyl-O—, —$C_1$-$C_{10}$alkyl-$CO_2$—, —$C_1$-$C_{10}$alkyl-NH—, —$C_1$-$C_{10}$alkyl-S—, —$C_1$-$C_{10}$alkyl-C(O)—NH—, —$C_1$-$C_{10}$alkyl-NH—C(O)—, —$CH_2CH_2SO_2$—$C_1$-$C_{10}$alkyl-, —$CH_2$C(O)—$C_1$-$C_{10}$ alkyl-, =N—(O or NH)—$C_1$-$C_{10}$alkyl-O—, =N—(O or NH)—$C_1$-$C_{10}$alkyl-NH—, =N—(O or NH)—$C_1$-$C_{10}$alkyl-$CO_2$—, =N—(O or NH)—$C_1$-$C_{10}$alkyl-S—,

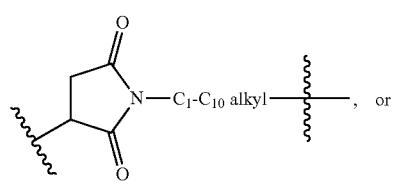

In preferred embodiments, $R^{PEG1}$ is —NH—, —C(=O)—, triazole-linked groups, or —S—, or maleimido- linked groups such as

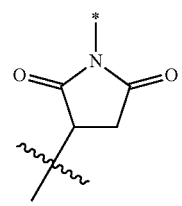 [SMILES: *C1CC(=O)N(*)C1=O]

wherein the wavy line indicates the site of attachment to $L^P$ and the asterisk indicates the site of attachment within the PEG Unit.

The PEG Capping Unit ($R^{PEG2}$) is part of the PEG Unit and acts to terminate a PEG Unit at its untethered end, which is distal to the tethered end of the PEG Unit.

In exemplary embodiments $R^{PEG2}$ is independently —$C_1$-$C_{10}$ alkyl, —$C_2$-$C_{10}$ alkyl-$CO_2$H, —$C_2$-$C_{10}$ alkyl-OH, —$C_2$-$C_{10}$ alkyl-$NH_2$, —$C_2$-$C_{10}$ alkyl-NH($C_1$-$C_3$ alkyl), or —$C_2$-$C_{10}$ alkyl-N($C_1$-$C_3$ alkyl)$_2$, wherein each $C_1$-$C_3$ alkyl is independently selected.

$R^{PEG3}$ is part of a PEG Unit when there two linear sequences of contiguous PEG subunits contained within the PEG Unit and acts to join these sequences together into a single linear chain. In exemplary embodiments $R^{PEG3}$ is —$C_1$-$C_{10}$ alkyl-C(O)—NH—, —$C_1$-$C_{10}$ alkyl-NH—C(O)—, —$C_2$-$C_{10}$ alkyl-NH—, —$C_2$-$C_{10}$ alkyl-O—, —$C_1$-$C_{10}$ alkyl-S—, or —$C_2$-$C_{10}$ alkyl-NH—.

Illustrative linear PEG Units that can be used in any of the embodiments provided herein are as follows:

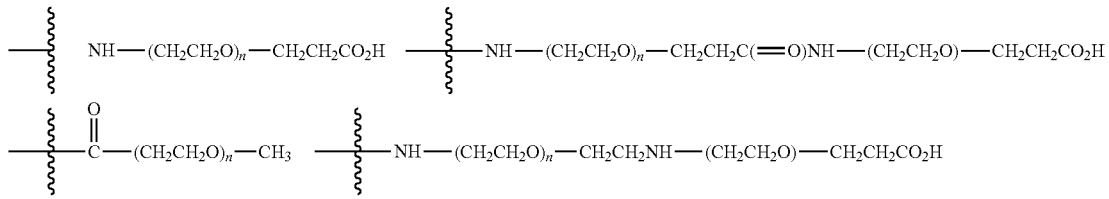

wherein the wavy line indicates site of covalent attachment to $L^P$, and each subscript n is independently selected from 4 to 72, 6 to 72, 8 to 72, 10 to 72, 12 to 72, 6 to 24, or 8 to 24. In some aspects, subscript n is about 8, about 12, or about 24.

It will be appreciated that when referring to PEG subunits, and depending on context, the number of subunits can represent an average number, e.g., when referring to a population of Ligand-Drug Conjugates or Intermediate Compounds (e.g., Drug Linker compounds), and/or when using polydisperse PEGs.

1.3.4 Cleavable Unit

A Cleavable Unit (W) is a component of a secondary linker within a drug linker moiety of a Ligand Drug Conjugate or is a component of a Linker Unit of a Drug Linker compound wherein W provides for a reactive site that when acted upon enzymatically or non-enzymatically results in breaking of a covalent bond within the secondary linker to initiate release of a drug compound or active drug moiety. In some embodiments, reactivity to that site is greater within or surrounding a hyper-proliferating cell or a hyper-stimulated immune cell (i.e., an abnormal cell) in comparison to a normal cell such that action upon that site results in preferential exposure to the abnormal cell of the released drug compound or active drug moiety. In some of those embodi-

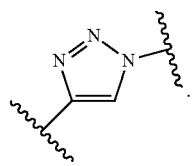

ments, a Cleavable Unit or component thereof (W or W') contains a reactive site cleavable by an enzyme (i.e., W or W' provides for an enzyme substrate) whose activity or abundance is greater within or surrounding the hyper-proliferating, immune-stimulating or other abnormal or unwanted cell compared to normal cells or the vicinity of normal cells that are distant from the site of the abnormal or unwanted cells. In other embodiments, a Cleavable Unit is comprised of a reactive site cleavable by other mechanisms (i.e., non-enzymatic) more likely operable in within or in the surrounding environment of abnormal cells targeted by a Ligand Unit of a Ligand Drug Conjugate in comparison to the environment of normal cells in which abnormal cells are typically not present or are distant from the site of the targeted cells. In some of those embodiments, the reactive site is more likely operated upon enzymatically or non-enzymatically subsequent to cellular internalization of a Ligand Drug Conjugate compound into a targeted abnormal cell. That internalization more likely occurs in those cells in comparison to normal cells due to greater presentation of the targeted moiety, which is recognized by the targeting moiety (i.e., the Ligand Unit) of the Ligand Drug Conjugate compound, on the cellular membrane of the targeted abnormal or unwanted cells. Therefore, the targeted cells will more likely be exposed intracellularly to drug compound or active drug moiety liberated from the Ligand Drug Conjugate compound on release of its Drug Unit. The Cleavable Unit can comprise one or multiple sites susceptible to cleavage under conditions of the targeted site or within the targeted cells, but typically has only one such site.

In some embodiments, the Cleavable Unit is a substrate for a protease, typically a regulatory protease, or a hydrolase or glycosidase, wherein the protease, hydrolase or glycosidase is located intracellularly in targeted cells (i.e., the reactive site of the Cleavable Unit is a peptide bond or glycoside bond, respectively, cleavable by the protease, hydrolase or glycosidase). In those aspects the peptide or glycoside bond of the Cleavable Unit is capable of selective cleavage by an intracellular regulatory protease, hydrolase or glycosidase in comparison to serum proteases, hydrolases, or glycosidases. Those intracellular regulatory proteases, hydrolases or glycosidases may be more specific to the targeted abnormal or other unwanted cells in comparison to normal cells distant from the site of the abnormal or unwanted cells. In other embodiments, a Cleavable Unit is a substrate for a protease, hydrolase or glycosidase excreted in greater amounts by the targeted abnormal or other unwanted cells in comparison to normal cells distant from the site of the abnormal or unwanted cells so that W or W' is capable of selective cleavage by the excreted protease, hydrolase or glycosidase. In still other aspects the Cleavable Unit is a substrate for a protease, hydrolase or glycosidase, present within or preferentially excreted by normal cells that are peculiar to the environment of the abnormal or unwanted cells in comparison to other normal cells in the periphery.

Alternatively, W provides for a functional group that when incorporated into an Ligand Drug Conjugate composition is susceptible to the acidic environment of lysozymes upon preferential internalization of a compound of that composition into an abnormal cell, or is susceptible to the greater reductive environment in or around such cells in comparison to the environment of normal cells where abnormal cells are usually not present, such that eventual release of $D/D^+$ from that Ligand Drug Conjugate compound as a drug compound or active drug moiety, which is initiated by action on the susceptible functional group, preferentially exposes the abnormal cell to that drug compound or moiety in comparison to the normal cells. In other embodiments, a Ligand Drug Conjugate compound is preferentially internalized into targeted normal cells that are peculiar to the environment of abnormal cells in comparison to normal cells in the periphery such that enzymatic or non-enzymatic action upon W or W' of the Conjugate compound will release a drug compound or active drug moiety thereby preferentially exposing the nearby abnormal cells to the drug compound or active drug moiety.

In some embodiments, a Cleavable Unit in a Drug Linker or Ligand Drug Conjugate compound is covalently attached to a Spacer Unit (Y) that is comprised or consists of a self-immolating moiety such that enzymatic action on the Cleavable Unit or component thereof (W or W') triggers self-destruction of that Unit within Y-D of —W—Y-D or —Y(W')-D, of that Drug Linker or Ligand Drug Conjugate compound to release D as a drug compound or active drug moiety, wherein W represents a Peptide Cleavable Unit and —Y(W')— is a Glucuronide Unit. In other aspects, a tertiary amine containing compound is incorporated into a Ligand Drug Conjugate composition as a quaternized Drug Unit ($D^+$) by covalent attachment to a self-immolative Spacer Unit (Y) as Y-$D^+$ of —W—Y-$D^+$ or —Y(W')-$D^+$ such that enzymatic action on W or W' releases the tertiary amine-containing drug compound. In some embodiments the Cleavable unit of a Drug Linker compound or a Ligand Drug Conjugate compound having a quaternized Drug Unit ($D^+$), provides for a cleavable bond (i.e., a reactive site) that upon action by an enzyme present within a hyper-proliferating cell or hyper-activated immune cells initiates release of $D^+$ as tertiary amine-containing drug.

Functional groups that provide for cleavable bonds include, by way of example and not limitation, (a) sulfhydryl groups that form a disulfide bond, which are susceptible to the greater reductive conditions of abnormal cells in comparison to normal cells or excess glutathione produced under hypoxic conditions experienced by the abnormal cells, (b) aldehyde, ketone, or hydrazine groups that form a Schiff base or hydrazone functional groups, which are susceptible to the acidic conditions of lysozymes upon selective internalization of an LDC compound having a Linker Unit with that cleavable bond into an abnormal cell in comparison to internalization into normal cells, (c) carboxylic or amino groups that form an amide bond, as in peptide bonds, that are susceptible to enzymatic cleavage by proteases produced or excreted preferentially by abnormal cells in comparison to normal cells or by a regulatory protease within a targeted cell (d) amino or hydroxyl groups that form certain urea or carbamate groups or carboxylic or hydroxy groups that form ester or carbonate groups that are susceptible to enzymatic cleavage by hydrolases or esterases that are produced or excreted preferentially by abnormal cells in comparison to normal cells.

Still other functional groups that provide for cleavable bonds are found in sugars or carbohydrates having a glycosidic linkage that are substrates for glycosides which sometimes may be produced preferentially by abnormal cells in comparison to normal cells. Alternatively, the protease, hydrolase or glycosidase enzyme required for processing of the Linker Unit to release a drug compound or active drug moeity need not be produced preferentially by abnormal cells in comparison to normal cells provided the processing enzyme is not excreted by normal cells to an extent that would cause undesired side effects from premature release of the drug compound or moeity. In other instances the required protease, hydrolase or glycosidase enzyme may be excreted, but to avoid undesired premature release of drug, it is preferred that the processing enzyme be excreted in the vicinity of abnormal cells and remain localized to that environment, whether produced by abnormal cells or nearby normal cells in response to the abnormal environment caused by the abnormal cells. In that respect W as a Peptide Cleavable Unit or W' of a Glucuronide Unit in which W is —Y(W')— is selected to be preferentially acted upon by a protease, hydrolase or glycosidase in or within the environment of abnormal cells in contrast to freely circulating enzymes. In those instances a Ligand Drug Conjugate compound is less likely to release its Drug Unit as a drug compound or active drug moiety in the vicinity of normal cells nor would it be internalized into normal cells that do intracellularly produce but do not excrete the enzyme intended for action upon the Ligand Drug Conjugate compound since such cells are less likely to display a targeted moiety required for entry by the Ligand Drug Conjugate compound.

In some embodiments, W is a Peptide Cleavable Unit comprised of an amino acid or is comprised or consists of one or more sequences of amino acids that provide a substrate for a protease present within abnormal cells or a protease localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative moiety of a self-immolative Y wherein that moiety is a recognition sequence for that protease. In other aspects, W is a Glucuronide Unit of formula —Y(W')—, wherein W' is a carbohydrate moiety (Su) having a glycosidic bond to a heteroatom (E') attached to a self-immolative moiety of the Glucuronide's self-immolative Spacer Unit (Y) wherein the glycosidic bond is cleavable by a glycosidase preferentially produced by abnormal cells, or is found in such cells to which an LDC having that Spacer Unit and carbohydrate moiety, has selective entry due to the presence of the targeted moiety on the abnormal cells.

1.3.4 Spacer Units

A secondary linker ($L_O$) when bonded to D (or $D^+$) in a Linker Unit attached to only one Drug Unit and with no second optional Stretcher Unit and having a PAB or PAB-related self-immolative Spacer Unit is typically represented by the structure of (1) or (2):

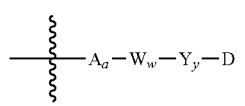
(1)

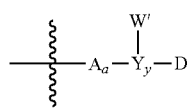
(2)

wherein subscript w is 1, subscript y is 1 or 2 and subscript a is 0 or 1, A is an optional first Stretcher Unit, W is a Peptide Cleavable Unit, W' is glycosidic-bonded carbohydrate, and wherein the peptide bond between W and Y is cleavable by a protease and the glycosidic bond between W' and Y is cleavable by a glycosidase. Exemplary PAB or PAB-related self-immolative moieties when present in a secondary linker bonded to -D or —Y'-D, in which subscript y is 1 or 2, respectively or bonded to -$D^+$, in which subscript y is 1, have a central arylene or heteroarylene substituted by a masked electron donating group (EDG) and a benzylic carbon directly bonded to $D^+$, or bonded to D through a shared heteroatom or functional group, or bonded to D indirectly through an intervening second Spacer Unit (Y'), wherein the masked EDG and benzylic carbon substituents are ortho or para to each other (i.e., 1,2 or 1,4 substitution pattern). In some of those embodiments the second Spacer Unit (Y') is capable of self-immolation or is absent.

Exemplary structures of self-immolative Spacer Units having a PAB or PAB-related self-immolative moiety in which the central (hetero)arylene has the requisite 1,2 or 1,4 substitution pattern that allows for 1,4- or 1,6-fragmentation to release $D/D^+$ or —Y'-D as a biologically active compound or derivative thereof or precursor thereto, as when Y' of released Y'-D is capable of self-immolation, are represented by:

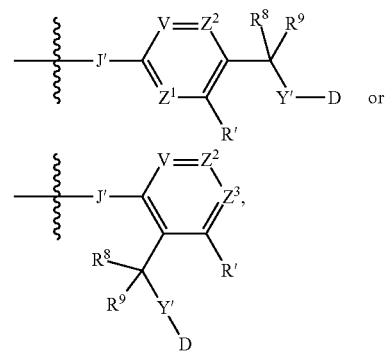

wherein the wavy line to J' indicates the point of covalent attachment to $L_R$ (i.e., $L_{SS}$ or $L_S$) or the remainder the secondary linker through J' or through a functional group comprising J', wherein J' is a heteroatom, optionally substituted where permitted (i.e., optionally substituted —NH—), Y' is a heteroatom, optionally substituted where permitted, a functional group, a second self-immolative moiety, such as a carbamate or a MAC Unit, or Y' is absent and D is a Drug Unit, which can incorporate a tertiary amine containing compound so that D is a quaternized Drug Unit ($D^+$) requiring Y' to be absent, and wherein V, $Z^1$, $Z^2$, $Z^3$ are independently =N or =C($R^{24}$)—, wherein each $R^{24}$ is independently selected from the group consisting of hydrogen and $C_1$-$C_{12}$ alkyl, $C_2$-$C_{12}$ alkenyl, $C_2$-$C_{12}$ alkynyl, $C_6$-$C_{20}$ aryl, ($C_6$-$C_{20}$ aryl)-$C_1$-$C_6$ alkyl-, $C_5$-$C_{20}$ heteroaryl and ($C_5$-$C_{20}$ heteroaryl)-$C_1$-$C_6$ alkyl-, optionally substituted, and halogen and an electron withdrawing group; R' is hydrogen or $C_1$-$C_{12}$ alkyl, $C_2$-$C_{12}$ alkenyl, $C_2$-$C_{12}$ alkynyl, $C_6$-$C_{20}$ aryl, ($C_6$-$C_{20}$ aryl)-$C_1$-$C_6$ alkyl-, $C_5$-$C_{20}$ heteroaryl, or $C_5$-$C_{20}$ heteroaryl)-$C_1$-$C_6$ alkyl- optionally substituted, or an electron donating group; and $R^8$ and $R^9$ are independently selected from the group consisting of hydrogen, $C_1$-$C_{12}$ alkyl, $C_2$-$C_{12}$ alkenyl, $C_2$-$C_{12}$ alkynyl, $C_6$-$C_{20}$ aryl and $C_5$-$C_{20}$ heteroaryl, optionally substituted, or both $R^8$ and $R^9$ together with the carbon atom to which they are attached define a $C_3$-$C_8$ carbocyclo. In preferred embodiments, one or more of V, $Z^1$, $Z^2$ or one or more of V, $Z^2$, $Z^3$ is =CH—. In other preferred embodiments R' is hydrogen or an electron donating group, including $C_1$-$C_6$ ethers such as —$OCH_3$ and —$OCH_2CH_3$, or one of $R^8$, $R^9$ is hydrogen and the other is hydrogen or $C_1$-$C_4$ alkyl. In more preferred embodiments two or more of V, $Z^1$ and $Z^2$ are =CH— or two or more of V, $Z^2$ and $Z^3$ are =CH—. In other more preferred embodiments $R^8$, $R^9$ and R' are each hydrogen.

In some embodiments, —W—$Y_y$-D, as shown in structure (1) in which subscript y is 2, and —W—$Y_y$-$D^+$, in which subscript y is 1; and wherein W is a protease cleavable Peptide Cleavable Unit, have structures of:

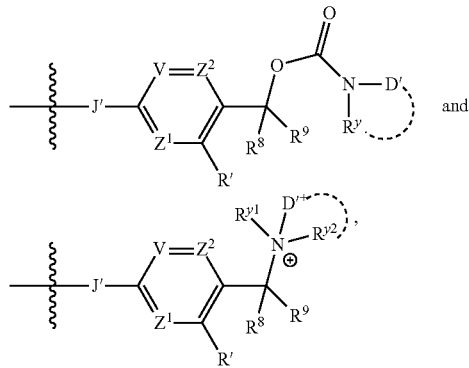

respectively, wherein —N($R^y$)D' and —N($R^{y1}$)($R^{y2}$)$D'^+$ moieties represent D and $D^+$, respectively, wherein D' and $D'^+$ are the remainder of D and $D^+$, and wherein the dotted line indicates optional cyclization of $R^Y$ or $R^{y2}$ to D' or $D'^+$, wherein $R^Y$ is hydrogen or $R^Y$ is optionally substituted $C_1$-$C_6$ alkyl in absence of cyclization to D' or optionally substituted $C_1$-$C_6$ alkylene when cyclized to D'; $R^{y1}$ is optionally substituted $C_1$-$C_6$ alkyl and $R^{y2}$ is optionally substituted $C_1$-$C_6$ alkyl in absence of cyclization to $D^+$ or $R^{y2}$ is optionally substituted $C_1$-$C_6$ alkylene when cyclized to $D^+$; -J'- is an optionally substituted heteroatom where permitted, including O, S and optionally substituted —NH—, wherein J' or a functional group comprised of J' is bonded to W as indicated by the adjacent wavy line, wherein cleavage of that bond initiates release of D as a primary or secondary amine-containing biologically active compound or initiates release of $D^+$ as a tertiary amine-containing biologically active compound from a compound of a Ligand Drug Conjugate composition and wherein the remaining variable groups are as defined above. Those variables are selected so that reactivity of J' when released from processing of Peptide Cleavable Unit W at the targeted site is balanced with the reactivity of Y'-D, D or the tertiary amine drug of $D^+$ eliminated from the PAB or PAB-type self-immolative moiety and the stability of the quinone-methide type intermediate resulting from that elimination.

In those embodiments, the intervening moiety between D and the benzylic carbon of the PAB or PAB-related self-immolative moiety of Spacer Unit Y represents Y' in —C($R^8$)($R^9$)—Y'-D so that a carbamate functional group is shared between Y and D. In such embodiments fragmentation of the Spacer Unit Y with expulsion of —Y'-D is followed by loss of $CO_2$ for release of D as biologically active compound or derivative thereof having a primary or secondary amine whose nitrogen atom was bonded to the secondary linker comprised of the PAB or PAB-related self-immolative moiety.

In some embodiments, a self-immolative Spacer Unit having a PAB or PAB-type moiety bound to —Y'-D or -$D^+$ has the structure of:

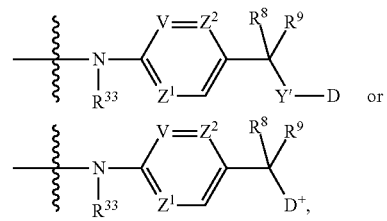

wherein the wavy line adjacent to the nitrogen atom indicates the point of covalent attachment to W, wherein that bond to W is cleavable by a protease, and $R^{33}$ is hydrogen or optionally substituted $C_1$-$C_6$ alkyl, preferably hydrogen or $C_1$-$C_4$ alkyl, more preferably hydrogen, —$CH_3$ or —$CH_2CH_3$. In more preferred embodiments V, $Z^1$ and $Z^2$ are each =CH— and $R^{33}$ is hydrogen.

Without being bound by theory, the sequential self-immolation of Y in which $R^{33}$ is —H and Y' is a carbamate functional group is illustrated for Ligand Drug Conjugates and Drug Linker compounds having a Peptide Cleavable Unit as:

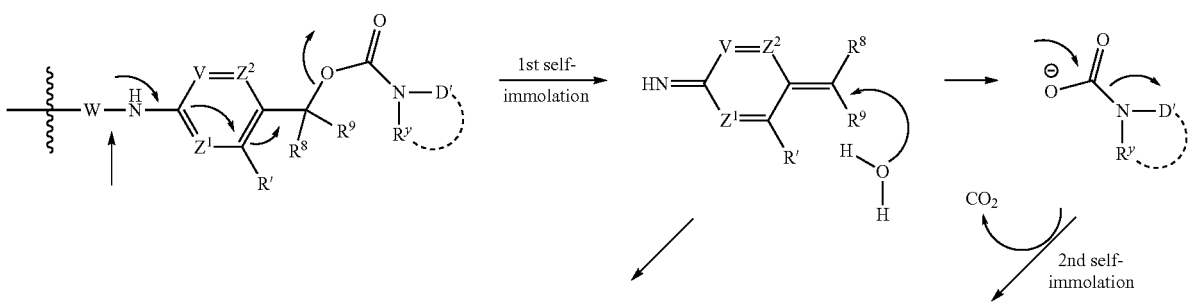

-continued

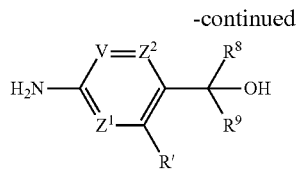

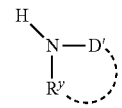

In some embodiments, —$Y_y$(W')-D, as shown in structure (2) in which subscript y is 2, or —$Y_y$(W')-$D^+$, in which subscript y is 1, and W is a Glucuronide Unit of formula —Y(W')— have structures of:

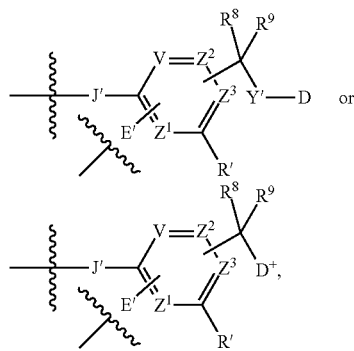

wherein J' is an optionally substituted heteroatom where permitted, including O, S and optionally substituted —NH—, and the wavy line to J' indicates the point of stable covalent bonding (i.e., not processed at the targeted site) to $L_R$ (i.e., $L_{SS}$ or $L_S$) or the remainder of the secondary linker through said heteroatom or a functional group comprised of that heteroatom; E', independently selected from J', is an electron donating moiety such as —O—, —S—, or —N($R^{33}$)—, wherein $R^{33}$ is as defined above, wherein the electron donating ability of E' is attenuated by its bonding to the carbohydrate moiety (Su) of W', wherein W' is -E'-Su, as indicated by the wavy line adjacent to E', wherein Su boned to E' provides for a cleavage site for a glycosidase, and E' and the benzylic carbon of the —C($R^8$)($R^9$)—Y'-D or —C($R^8$)($R^9$)-$D^+$ moiety are bonded to the central (hetero)arylene at positions defined by V, $Z^1$, $Z^2$ or $Z^3$, requiring at least two of V, $Z^1$, $Z^2$, $Z^3$ to be =C($R^{24}$)— in which one $R^{24}$ substituent is the —C($R^8$)($R^9$)—Y'-D or —C($R^8$)($R^9$)-$D^+$ moiety and the other is W', such that W' and the —C($R^8$)($R^9$)-$D^+$ moiety are in a 1,2 or 1,4 relationship so as to permit the 1,4- or 1,6-fragmentation on cleavage to release D or Y'-D, or a precursor thereto, biologically active compound or derivative thereof, or $D^+$ as a tertiary amine-containing biologically active compound; and the remaining variable groups are as previously defined for PAB or PAB-related self-immolative Spacer Units that are bonded to a Peptide Cleavable Unit. In preferred embodiments J' is —O—, —N($R^{33}$)— wherein $R^{33}$ is preferably hydrogen or $C_1$-$C_4$ alkyl. In other preferred embodiments one or both of the remaining V, $Z^1$, $Z^2$, $Z^3$ variable groups not bonded to W' and —C($R^8$)($R^9$)—Y'-D or —C($R^8$)($R^9$)-$D^+$ is =CH—. In still other preferred embodiments R' is hydrogen or an electron withdrawing group, including —CN, —$NO_2$ or halogen, or one of $R^8$, $R^9$ is hydrogen and the other is hydrogen or $C_1$-$C_4$ alkyl. In more preferred embodiments both remaining variable groups from V, $Z^1$, $Z^2$, $Z^3$ are =CH—. Without being bound by theory it is believed when R' is an electron withdrawing group in a Glucuronide Unit, that group makes the glycosidic bond of W' more susceptible to glycosidase cleavage thereby assisting in the release of D/$D^+$, from a Ligand Drug Conjugate compound reliant on that cleavage.

In some embodiments, for a secondary linker-D or -$D^+$ moiety of structure (2), a self-immolative Spacer Unit having a PAB or PAB-type moiety bound to Y'-D or $D^+$ has the structure of:

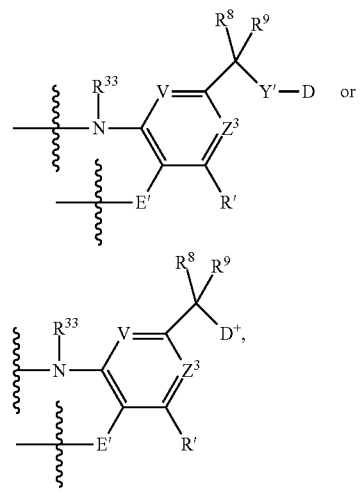

wherein the variable groups are as previously defined. In preferred embodiments both of V, $Z^3$ are =CH—. In other preferred embodiments $R^{33}$ is hydrogen. In still other more preferred embodiments, $R^8$ and $R^9$ are each hydrogen and R' is hydrogen or —$NO_2$.

The central (hetero)arylene of a self-immolative moiety may be further substituted to affect the kinetics of the 1,2- or 1,4-elimination in order to modulate the release of D/$D^+$, to improve the physiochemical properties of the Ligand Drug Conjugate (e.g., reduce hydrophobicity) into which it is incorporated and/or increase the sensitivity of the bond to protease or glycosidase cleavage. For example, to increase sensitivity to glycosidase cleavage R'
an be an electron withdrawing group such as chloro, fluoro, —CN or —$NO_2$, as when E' of W' is an oxygen atom of a glycosidic bond within a Glucuronide Unit that is cleavable by a glycosidase.

Exemplary and non-limiting examples of self-immolative structures, which can also be modified to accommodate a benzylic quaternary amine substituent when D is a quaternized Drug Unit, are provided by Alouane et al. Self-immolative spacers: Kinetic aspects, structure-property relationships, and applications" *Angew. Chem. Int. Ed.* (2015): 54: 7492-7509; Blencowe et al. "Self-immolative linkers in polymeric delivery systems" *Polym. Chem.* (2011) 2: 773-790; Greenwald et al. "Drug delivery systems employing 1,4- or 1,6-elimination: poly(ethylene glycol) prodrugs of amine-containing compounds" *J. Med. Chem.* (1999) 42: 3657-3667; and in U.S. Pat. Nos. 7,091,186; 7,754,681; 7,553,816; and 7,989,434, all of which are incorporated by reference herein in their entireties with the structures and variable groups provided therein specifically incorporated by reference.

In preferred embodiments Y' represents a carbamate functional group shared with D so that Y' is a second self-immolative Spacer Unit that spontaneously decomposes to $CO_2$ and D as a biologically active compound or derivative thereof, in the manner as shown above, and occurs subsequent to 1,6-fragmentation of the PAB or PAB-type moiety of the first self-immolative Spacer Unit. In other preferred embodiments Y' is a methylene carbamate unit having the structure when bonded to D of:

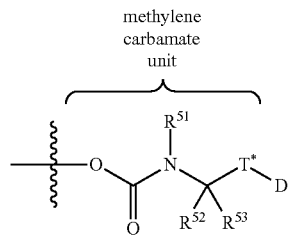

or a pharmaceutically acceptable salt thereof, wherein the wavy line indicates covalent attachment of the methylene carbamate unit to a first self-immolative Spacer Unit (Y); D is a Drug Unit of a biologically active compound or derivative thereof having a functional group (e.g., hydroxyl, thiol, amide or amine functional group) that has been incorporated into the methylene carbamate unit; T* is a heteroatom from said functional group (e.g., oxygen, sulfur, optionally substituted NH) that becomes incorporated into the methylene carbamate unit; $R^{51}$, $R^{52}$ and $R^{53}$ independently are hydrogen, optionally substituted $C_1$-$C_{12}$ alkyl, optionally substituted $C_6$-$C_{24}$ aryl, or optionally substituted C-linked $C_5$-$C_{24}$ heteroaryl, or $R^{51}$ and $R^{52}$ together with the nitrogen and carbon atoms to which they are attached define an optionally substituted $C_3$-$C_{20}$ heterocyclo and $R^{53}$ is hydrogen or optionally substituted $C_1$-$C_{12}$ alkyl.

Without being bound by theory, the sequential self-immolation of Y and Y' is illustrated as follows for Ligand Drug Conjugates and Drug Linker compounds having a Glucuronide Unit in which $R^{33}$ is —H and E' of W' is an oxygen atom (O') of a glycosidic bond:

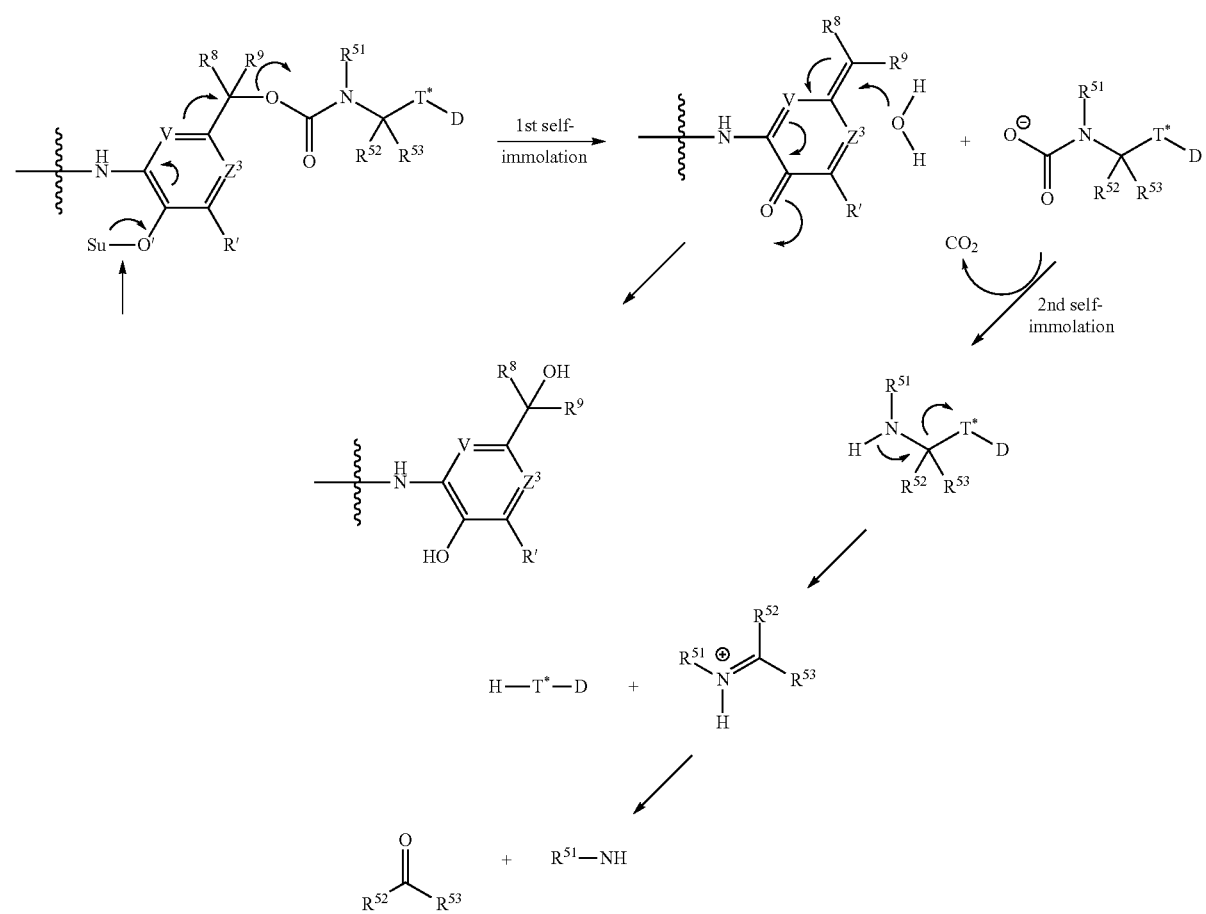

In preferred embodiments $R^{51}$, $R^{52}$ and $R^{53}$ independently are hydrogen, optionally substituted $C_1$-$C_6$ alkyl, optionally substituted $C_6$-$C_{10}$ aryl, or optionally substituted C-linked $C_5$-$C_{10}$ heteroaryl, or $R^{51}$ and $R^{52}$ together with the nitrogen and carbon atoms to which they are attached define an optionally substituted azetidinyl, pyrrolodinyl, piperidinyl, or homopiperidinyl moiety. In more preferred embodiments $R^{51}$, $R^{52}$ and $R^{53}$ are each hydrogen or $R^{51}$ and $R^{52}$ together with the nitrogen and carbon atoms to which they are attached define an optionally substituted pyrrolodinyl or piperidinyl moiety and $R^{53}$ is hydrogen.

Embodiments of Ligand Drug Conjugates of Formula 1 and/or Formula 2 having a Peptide Cleavable Unit and incorporating a MAC Unit as a second self-immolative moiety, are represented by the structure of Formula 3 and/or Formula 4:

Embodiments of Ligand Drug Conjugates of Formula 1 and/or Formula 2 and Drug Linker Compounds of Formula I having a Glucuronide Unit and incorporating a MAC Unit as a second self-immolative moiety have structures analogous to Formula 3, Formula 4, and Formula III in which —W—Y— in these formulae are replaced by —Y(W')—, wherein Y is a first self-immolative Spacer attached to W' through a glycosidic bond as described by embodiments for Glucuronide Units.

1.3.5 Quaternized Drug Units

In one group of embodiments, D in Formula 1, Formula 2 or Formula I is replaced by a quaternized Drug Unit designated as $D^+$, wherein subscript y is 1 when W is a Peptide Cleavable Unit or when W is a Glucuronide Unit,

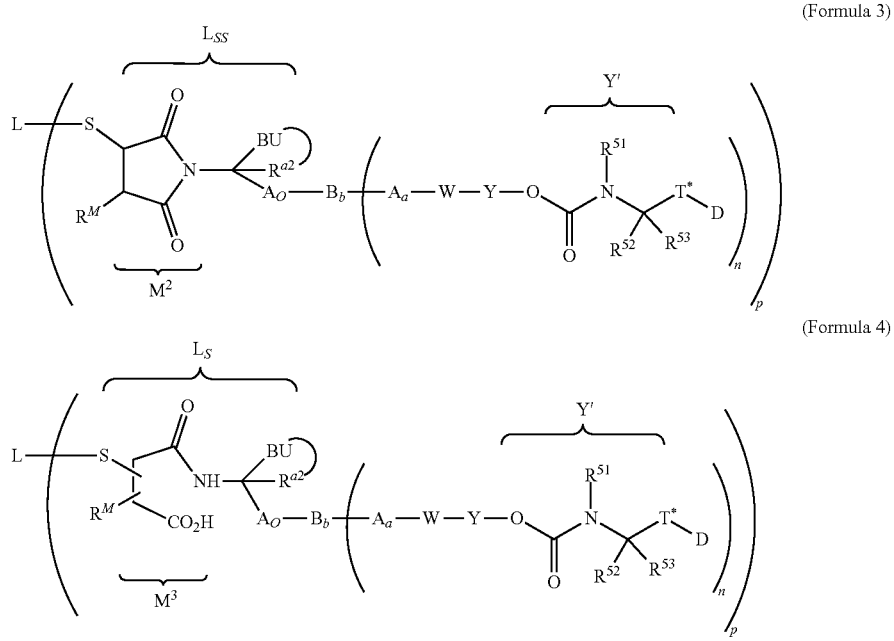

(Formula 3)

(Formula 4)

or a pharmaceutically acceptable salt thereof, and corresponding embodiments for Drug Linker Compounds are represented by Formula III,

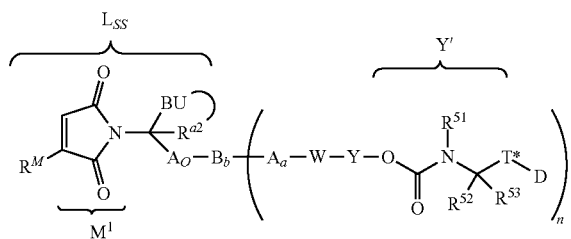

(Formula III)

or a pharmaceutically acceptable salt thereof,
wherein W is a Peptide Cleavable Unit and Y is a first self-immolative Spacer Unit and the indicated second self-immolative Spacer Unit is the MAC Unit so that subscript y is 2 in Formula 1 and Formula 2; and the remaining variable groups are as previously defined.

which has the formula of —Y(W')—. In preferred embodiments $D^+$ is of a tubulysin, which has a tertiary amine at its N-terminus, wherein the nitrogen atom of that tertiary amine is quaternized for incorporation into $D^+$.

In some embodiments, the quaternized tubulysin Drug Unit is that of a tubulysin represented by structures of Formula $D_G$ or $D_H$ wherein the indicated nitrogen (†) is the site of quaternization when such compounds are incorporated into an LDC or a Drug Linker compound as a quaternized drug unit ($D^+$):

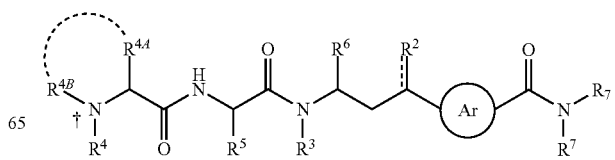

$D_G$

131
-continued

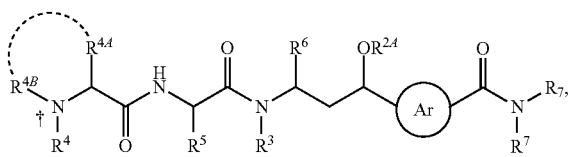

wherein the indicated nitrogen (1) is the site of quaternization when such a tubulysin compound is incorporated into an LDC or a Drug Linker compound as a quaternized drug unit (D+); the circle represents an 5-membered or 6-membered nitrogen-containing heteroaryl, wherein the indicated required substituents to that heteroaryl are in a 1,3- or meta-relationship to each other with optional substitution at the remaining positions; the curved dashed line represents optional cyclization; the straight dashed line to $R^2$ represents an optional double bond or optionally two instances of $R^2$ independently selected, or represents a divalent O-linked moiety; $R^{2A}$ is hydrogen, optionally substituted alkyl, saturated or unsaturated, or —C(=O)$R^B$, wherein $R^B$ is hydrogen, optionally substituted $C_1$-$C_{12}$ alkyl, saturated or unsaturated, optionally substituted $C_2$-$C_{12}$ alkenyl or optionally substituted $C_6$-$C_{24}$ aryl; $X^A$ is —O—, —S—, —N($R^{2C}$)—, —CH$_2$—, —C(=O)—, —(C=O)N($R^{2C}$)— or —O(C=O)N($R^{2C}$)—, wherein $R^{2C}$ is hydrogen or optionally substituted $C_1$-$C_{12}$ alkyl, or $R^2$ is an monovalent O-linked substituent, and the double bond to $R^2$ is absent, or $R^2$ is O and the double bond to $R^2$ is present; $R^3$ is hydrogen or optionally substituted $C_1$-$C_{12}$ alkyl; $R^4$, $R^{4A}$, $R^{4B}$, $R^5$ and $R^6$ are optionally substituted $C_1$-$C_{12}$ alkyl, independently selected, or $R^{4A}$ and $R^{4B}$, along with the atoms to which they are attached define an optionally substituted $C_3$-$C_8$ heterocycloalkyl, as indicated by the curved dashed line between $R^{4A}$ and $R^{4B}$ and $R^4$, $R^5$ and $R^6$ are as previously defined; one $R^7$ is hydrogen or optionally substituted $C_1$-$C_{12}$ alkyl and the other $R^7$ is optionally substituted ($C_6$-$C_{24}$ aryl)-$C_1$-$C_{12}$ alkyl-, or optionally substituted ($C_5$-$C_{24}$ heteroaryl)-$C_1$-$C_{12}$ alkyl-.

In preferred embodiments the quaternized drug is that of a tubulysin represented by the structure of Formula $D_G$ wherein one $R^7$ is hydrogen or optionally substituted $C_1$-$C_6$ alkyl, preferably hydrogen or $C_1$-$C_4$ alkyl, and the other $R^7$ is an independently selected optionally substituted $C_1$-$C_6$ alkyl, preferably $C_1$-$C_6$ alkyl substituted by —CO$_2$H or an ester prodrug thereof or optionally substituted phenyl; $R^{4A}$ and $R^{4B}$, along with the atoms to which they are attached define an optionally substituted $C_5$-$C_6$ heterocyclyl; and the other variable groups are as previously defined.

In some embodiments of Formula $D_G$, $R^2$ is $X^A$—$R^{2A}$, wherein $X^A$ is —O— and $R^{2A}$ is —C(=O)$R^c$, wherein $R^c$ is hydrogen, optionally substituted $C_1$-$C_6$ alkyl, saturated or unsaturated, preferably, methyl, ethyl, vinyl or a branched $C_1$-$C_6$ alkyl or $R^2$ is a monovalent O-linked substituent selected from the group consisting of esters.

In other embodiment of Formula $D_G$, $R^2$ is $X^A$—$R^{2A}$, wherein $X^A$ is —O—; and $R^{2A}$ is hydrogen or optionally substituted alkyl, saturated or unsaturated, or $R^2$ is a monovalent O-linked substituent selected from the group consisting of ethers.

In preferred embodiments, the quaternized Drug Unit is that of a tubulysin represented by the structure of Formula $D_G'$:

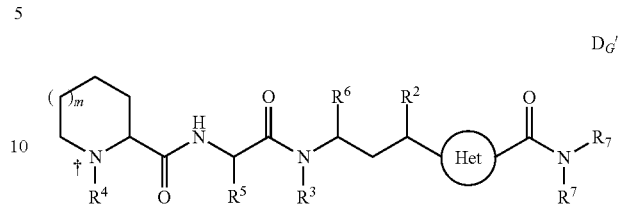

wherein subscript m is 0 or 1, one $R^7$ is hydrogen and the other $R^7$ is an optionally substituted ($C_6$-$C_{10}$ aryl)-$C_1$-$C_4$ alkyl-, wherein the alkyl moiety is substituted by —CO$_2$H or an ester thereof and the remaining variable groups are as defined for Formula $D_G$.

In other preferred embodiments —N($R^7$)($R^7$) of Formula $D_G$ is replaced by —N($R^7$)—CH($R^{10}$)(CH$_2$$R^{11}$) to define quaternized tubulysin Drug Unit of formula $D_H'$:

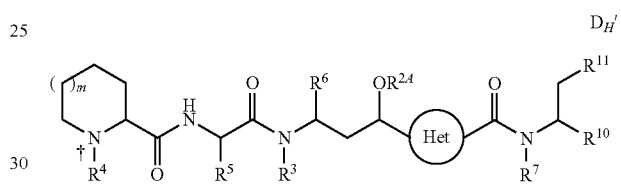

wherein $R^{10}$ is $C_1$-$C_6$ alkyl substituted with —CO$_2$H, or ester thereof, and $R^7$ is hydrogen or a $C_1$-$C_6$ alkyl independently selected from $R^{10}$, or $R^7$ and $R^{10}$ together with the atoms to which they are attached define a 5 or 6-membered heterocycle; and $R^{11}$ is a 5- or 6-membered heteroaryl or phenyl, optionally substituted, wherein the heteroaryl or phenyl is unsubstituted or is substituted with one or more, preferably 1 or 2, more preferably 1, substituent(s) independently selected from the group consisting of halogen, $C_1$-$C_4$ alkyl, —OH and —O—$C_1$-$C_6$ alkyl (i.e., $C_1$-$C_6$ ether), preferably —F, —CH$_3$, and —OCH$_3$; and the remaining variable groups are as defined for $D_H$.

In still other embodiments one $R^7$ in —N($R^7$)($R^7$) in Formula $D_G$ or Formula $D_H$ is hydrogen or $C_1$-$C_6$ alkyl, and the other $R^7$ is an independently selected $C_1$-$C_6$ alkyl optionally substituted by —CO$_2$H or an ester thereof, or by an optionally substituted phenyl.

In some embodiments of Formula $D_G$, $D_G'$ or $D_H$ one $R^7$ is hydrogen and the other $R^7$ is an optionally substituted arylalkyl having the structure of:

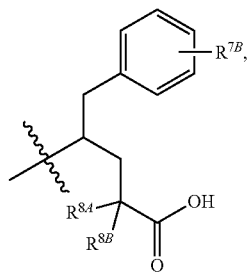

wherein $R^{7B}$ is absent (i.e., the aryl is unsubstituted) or $R^{7B}$ is an O-linked substituent, preferably —OH in the para position, and $R^{8A}$ and $R^{8B}$ are independently selected from the group consisting of hydrogen and $C_1$-$C_4$ alkyl, preferably one of $R^{8A}$ and $R^{8B}$ is hydrogen and the other is methyl or $R^{8A}$ and $R^{8B}$ together with the carbon atom to which both are attached define a $C_3$-$C_6$ carbocyclo, preferably a $C_3$ carbocyclo (i.e., spiro cyclopropyl); and wherein the wavy line indicates the point of attachment to the remainder of $D_G$ or $D_G'$.

In preferred embodiments of Formula $D_G$, $D_G'$ or $D_H$, one $R^7$ is hydrogen, and the other $R^7$ is an optionally substituted arylalkyl having the structure of

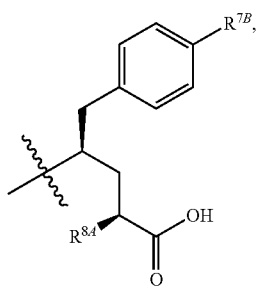

wherein $R^{7B}$ is —H or —OH; and wherein the wavy line indicates the point of attachment to the remainder of Formula $D_G$, $D_G'$ or $D_H$.

In other embodiments of Formula $D_G$, $D_G'$ or $D_H$, one $R^7$ is hydrogen or $C_1$-$C_4$ alkyl, preferably hydrogen or methyl, more preferably hydrogen, and the other $R^7$ is optionally substituted arylalkyl having the structure of one of:

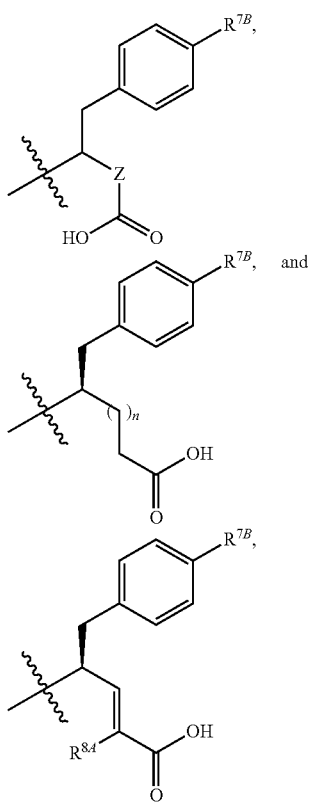

wherein Z is an optionally substituted $C_1$-$C_4$ alkylene or an optionally substituted $C_2$-$C_4$ alkenylene, $R^{7B}$ is hydrogen or an O-linked substituent, preferably hydrogen or —OH in the para position, $R^{8A}$ is hydrogen or $C_1$-$C_4$ alkyl, preferably methyl, and subscript n is 0, 1 or 2, preferably 0 or 1; and wherein the wavy line indicates the point of attachment to the remainder of Formula $D_G$, $D_G'$ or $D_H$.

In still other embodiments of Formula $D_G$, $D_G'$ or $D_H$-N$(R^7)(R^7)$ is —NH($C_1$-$C_6$ alkyl) wherein the $C_1$-$C_6$ alkyl is optionally substituted by —$CO_2H$ or an ester thereof, or by an optionally substituted phenyl, with —N($R^7$)($R^7$) is selected from the group consisting of —NH($CH_3$), —$CH_2CH_2$Ph, and —$CH_2$—$CO_2H$, —$CH_2CH_2CO_2H$ and —$CH_2CH_2CH_2CO_2H$ preferred.

In some embodiments of structure $D_H'$, $R^7$ and $R^{10}$ together with the atoms to which both are attached define an optionally substituted 5 or 6-membered heterocycle wherein —N($R^7$)—CH($R^{11}$)($CH_2R^{11}$) has the structure of:

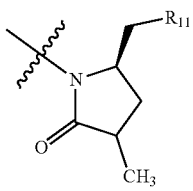

wherein the wavy line indicates the point of attachment to the remainder of $D_H'$.

Some preferred quaternized Drug Units are that of a tubulysin represented by Formula $D_{H-1}$, wherein the indicated nitrogen (†) is the site of quaternization when such a tubulysin compound is incorporated into an LDC or Drug Linker compound as a quaternized drug unit (D⁺):

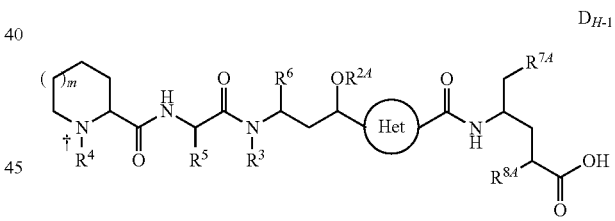

wherein the circle represents an 5-membered or 6-membered nitrogen-heteroaryl wherein the indicated required substituents to that heteroaryl are in a 1,3- or meta-relationship to each other with optional substitution at the remaining positions; $R^{24}$ is hydrogen or optionally substituted $C_1$-$C_6$ alkyl or $R^{24}$ along with the oxygen atom to which it is attached defines an O-linked substituent other than —OH; $R^3$ is hydrogen or optionally substituted $C_1$-$C_6$ alkyl; $R^4$, $R^{4A}$, $R^{4B}$, $R^5$ and $R^6$ are optionally substituted $C_1$-$C_6$ alkyl, independently selected; $R^{7A}$ is optionally substituted $C_6$-$C_{24}$ aryl, preferably optionally substituted $C_6$-$C_{10}$ aryl, or $R^{7A}$ is optionally substituted $C_5$-$C_{24}$ heteroaryl, preferably optionally substituted $C_5$-$C_{10}$ heteroaryl; $R^{8A}$ is hydrogen or optionally substituted alkyl and subscript m is 0 or 1.

In some preferred embodiments of Formula $D_G$, $D_G'$, $D_H'$, or $D_{H-1}$, $R^4$ is methyl or ethyl, $R^3$ is optionally substituted $C_1$-$C_4$ alkyl, preferably methyl or ethyl, and $R^5$ and $R^6$ are independently selected side chain residues of natural hydrophobic amino acids and the remaining variable groups are as defined for formula $D_H$.

In other preferred embodiments of Formula $D_{H-1}$, $R^{7A}$ is optionally substituted phenyl. In other preferred embodiment $R^{8A}$ is methyl in the (S)-configuration. In other preferred embodiments of $D_G$, $D_G{}'$, $D_H$, or $D_{H-1}$, $R^{2A}$ along with the oxygen atom to which it is attached defines an O-linked substituent other than —OH, more preferably an ester, ether or an O-linked carbamate. In more preferred embodiments the circle represents a 5-membered nitrogen-containing heteroarylene with a divalent oxazole or thiazole moiety particularly preferred. In other preferred embodiments $R^4$ is methyl or $R^{4A}$ and $R^{4B}$ are methyl. In other preferred embodiments $R^7$ is optionally substituted arylalkyl, wherein aryl is phenyl and $R^{7A}$ is optionally substituted phenyl. In other embodiments of Formula $D_G$, $D_G{}'$, $D_H$, $D_H{}'$ or $D_{H-1}$ the circle represents a 5-membered nitrogen heteroarylene, preferably represented by the structure

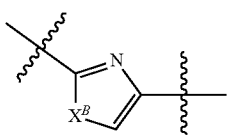

wherein $X^B$ is O, S, or N—$R^B$ wherein $R^B$ is hydrogen or lower alkyl. Preferably the quaternized drug is that of a tubulysin represented by structure Formula $D_G{}'$, $D_H$, $D_H{}'$ or $D_{H-1}$, wherein m is 1. More preferred are tubulysins represented by structure Formula $D_G$, $D_G{}'$, $D_H$, $D_H{}'$ or $D_{H-1}$, wherein m is 1 and the circle represents an optionally substituted divalent thiazole moiety.

Other quaternized Drug Units are that of a tubulysin represented by the structure of Formula $D_I$:

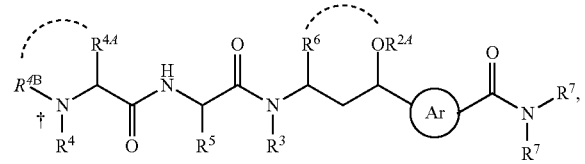

$D_I$ wherein the indicated nitrogen (†) is the site of quaternization when such a tubulysin compound is incorporated into an LDC or a Drug Linker compound as a quaternized drug unit ($D^+$), wherein $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the LDC structure.

In those embodiments the tubulysin compound preferably has the structure of Formula $D_{I-1}$:

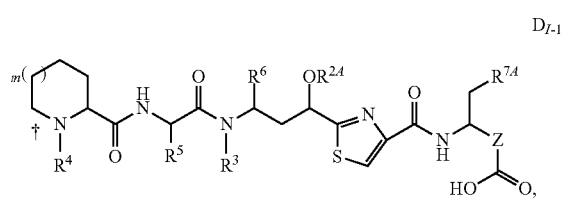

$D_{I-1}$ wherein subscript m is 0 or 1; Z is an optionally substituted alkylene or an optionally substituted alkenylene; $R^{7A}$ is optionally substituted aryl or optionally substituted heteroaryl; and the other variable groups are as previously defined for Formula $D_I$.

In preferred embodiments of Formula $D_I$ the tubulysin compound has the structure of Formula $D_{I-2}$:

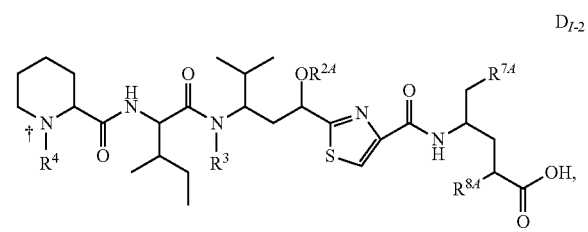

$D_{I-2}$ wherein $R^{7A}$ is optionally substituted phenyl; $R^{8A}$ is hydrogen or methyl; and the other variable groups are as previously defined for Formula $D_I$.

In other preferred embodiments of Formula $D_I$ the tubulysin compound has the structure of Formula $D_{I-3}$:

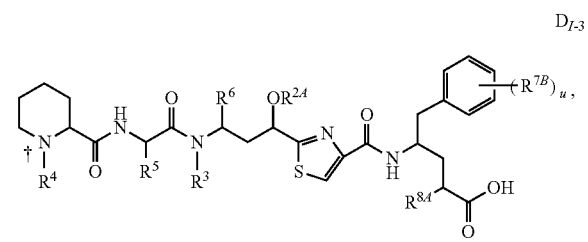

$D_{I-3}$ wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; $R^{8A}$ is hydrogen or optionally substituted alkyl; and the other variable groups are as previously defined for Formula $D_I$.

In more preferred embodiments of Formula $D_I$ the tubulysin compound has the structure of Formula $D_{I-4}$:

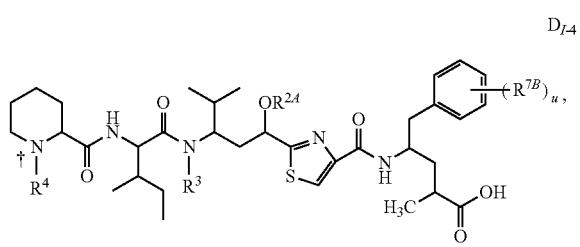

wherein the indicated nitrogen (†) is the site of quaternization when such a tubulysin compound is incorporated into an LDC or a Drug Linker compound as a quaternized drug unit (D⁺); $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

In other more preferred embodiments of Formula $D_I$ the tubulysin compound has the structure of Formula $D_{I-5}$:

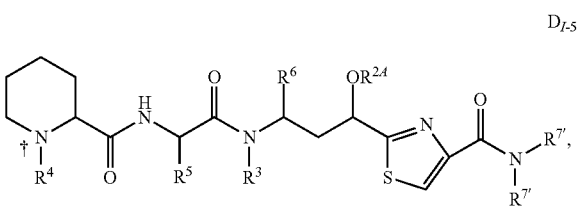

wherein the indicated nitrogen (†) is the site of quaternization when such a tubulysin compound is incorporated into an LDC or a Drug Linker compound as a quaternized drug unit (D⁺); $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are alkyl side chain residues of natural hydrophobic amino acids; and the —N(R$^{7'}$)(R$^{7'}$) moiety is —NH(C$_1$-C$_6$ alkyl) or —NH—N(C$_1$-C$_6$ alkyl)$_2$, wherein one and only one C$_1$-C$_6$ alkyl is optionally substituted by —CO$_2$H, or an ester thereof, or by an optionally substituted phenyl with the —N(R$^{7'}$)(R$^{7'}$) moiety preferably selected from the group consisting of —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

In any one of Formula $D_H$, $D_H'$, $D_{H-1}$, $D_I$, $D_{I-1}$, $D_{I-2}$, $D_{I-3}$, $D_{I-4}$ and $D_{I-5}$, preferably $R^{2A}$ is —CH$_2$CH$_3$, —CH$_2$—CH=CH$_2$ or —CH$_2$—C(CH$_3$)=CH$_2$.

In other more preferred embodiments of Formula $D_I$ the tubulysin compound has the structure of Formula $D_{I-6}$ or $D_{I-6}'$:

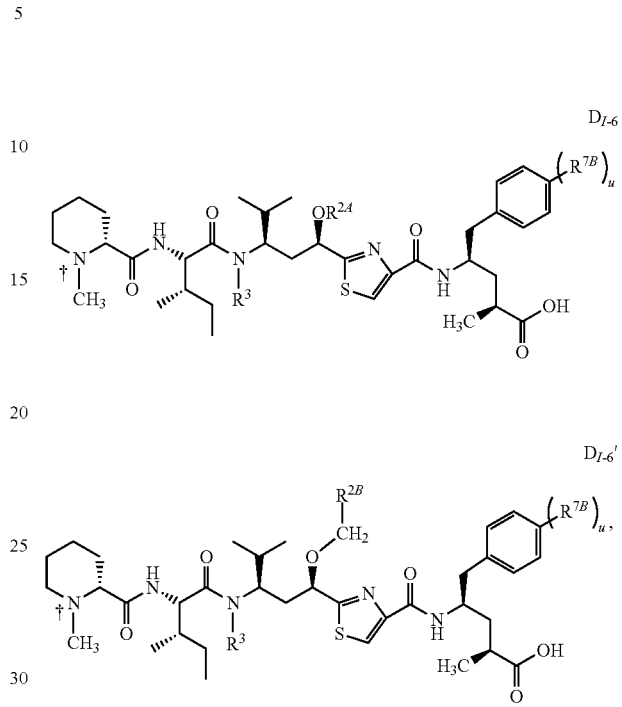

wherein the indicated nitrogen (†) is the site of quaternization when such a tubulysin compound is incorporated into an LDC or a Drug Linker compound as a quaternized drug unit (D⁺); subscript u is 0 or 1; $R^{2A}$ is —C(O)R$^{2B}$, —C(O)NHR$^{2D}$, or —CH$_2$C(O)R$^{2D}$; $R^{2B}$ is H, C$_1$-C$_6$ alkyl or C$_2$-C$_6$ alkenyl; $R^{2D}$ is —H, C$_1$-C$_4$ alkyl or C$_2$-C$_4$ alkyl; $R^3$ is methyl, ethyl or propyl; and $R^{7B}$, when present, is-OH.

In particularly preferred embodiments of Formula $D_I$ the tubulysin compound has the structure of Formula $D_{I-7}$:

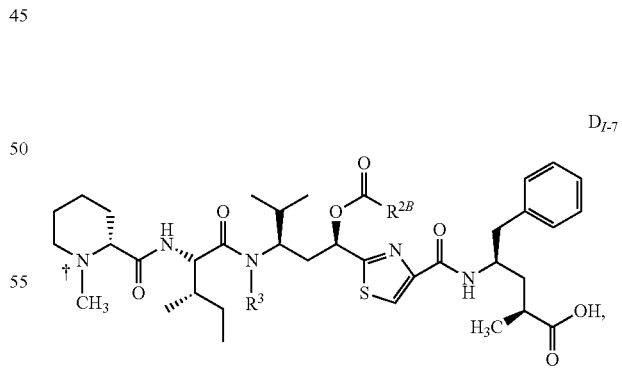

wherein the indicated nitrogen (†) is the site of quaternization when such a tubulysin compound is incorporated into an LDC or a Drug Linker compound as a quaternized drug unit (D⁺); $R^{2B}$ is methyl, ethyl, propyl, iso-propyl, 3-methyl-prop-1-yl, 3,3-dimethyl-prop-1-yl, or vinyl; and $R^3$ is methyl, ethyl or propyl, preferably methyl.

In other particularly preferred embodiments of Formula $D_I$ the tubulysin compound has the structure of Formula $D_{I-7}{}^t$:

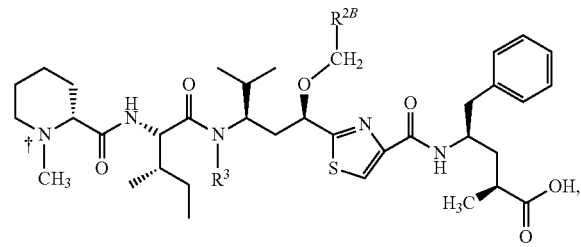

$D_{I-7}{}'$

-continued

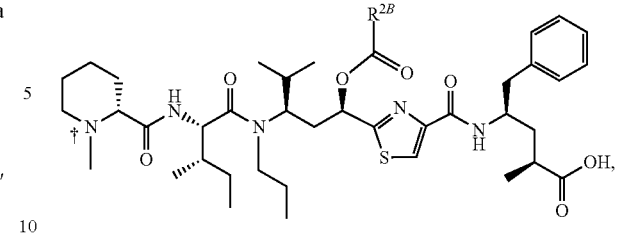

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$; and the indicated nitrogen (†) is the site of quaternization when such a tubulysin compound is incorporated into an LDC or a Drug Linker compound as a quaternized drug unit (D$^+$).

In other more particularly preferred embodiments of Formula $D_I$ the tubulysin compound has the structure of

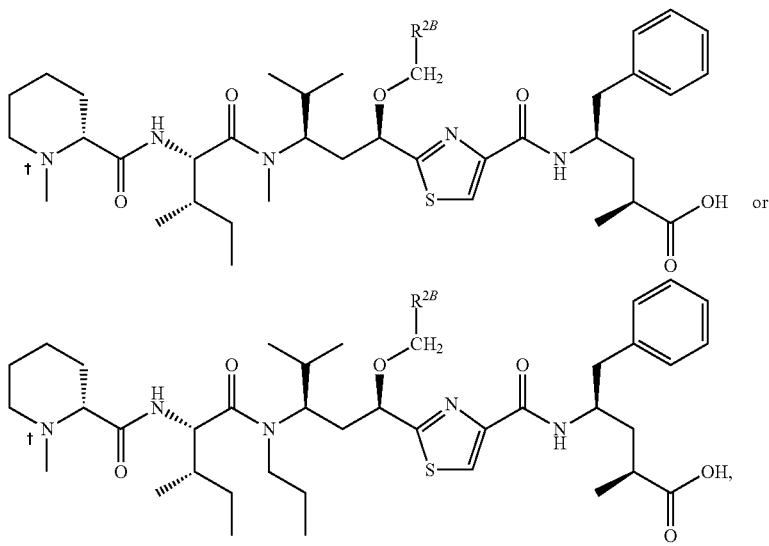

wherein the indicated nitrogen (†) is the site of quaternization when such a tubulysin compound is incorporated into an LDC or a Drug Linker compound as a quaternized drug unit (D$^+$); $R^{2B}$ is —H, methyl, ethyl, vinyl or —C(=CH$_2$)CH$_3$; and $R^3$ is methyl, ethyl or propyl, preferably methyl.

In more particularly preferred embodiments of Formula $D_I$ the tubulysin compound has the structure of wherein $R^{2B}$ is hydrogen, methyl or —OCH$_3$ (i.e., —OCH$_2$R$^{2B}$ is a methyl, ethyl, or methoxymethyl ether substituent), or —OCH$_2$R$^{2B}$ is —OCH$_2$CH=CH$_2$ or —OCH$_2$C(CH$_3$)=CH$_2$; and the indicated nitrogen (†) is the site of quaternization when such a tubulysin compound is incorporated into an LDC or a Drug Linker compound as a quaternized drug unit (D$^+$).

In especially preferred embodiments of Formula $D_I$ the tubulysin compound has the structure of one of:

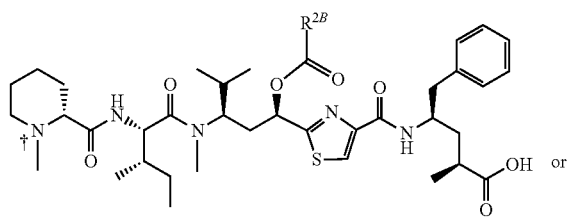 or

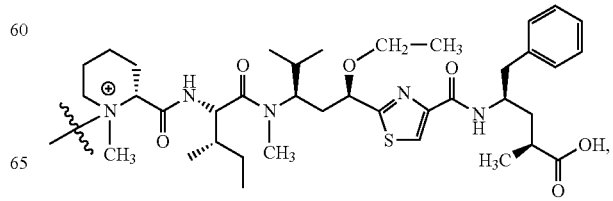

-continued

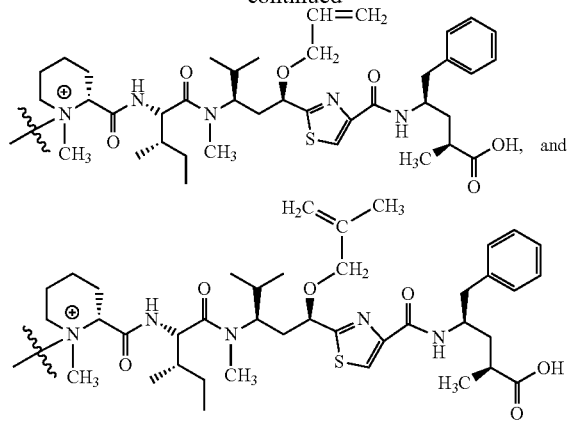

wherein the indicated nitrogen (†) is the site of quaternization when such a tubulysin compound is incorporated into an LDC or a Drug Linker compound as a quaternized drug unit (D⁺).

In other preferred embodiments of any one of Formula $D_{I-1}$, $D_{I-2}$, $D_{I-2}$, $D_{I-4}$, $D_{I-5}$, $D_{I-6}$, $D_{I-6}'$, $D_{I-7}$, and $D_{I-7}'$: the thiazole core heterocycle

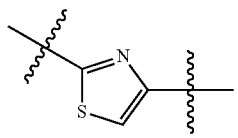 [SMILES: *c1csc(*)n1]

is replaced with

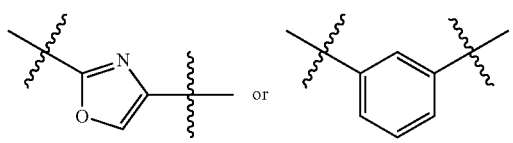

In some preferred embodiments of any one of Formula $D_H$, $D_{H'}$, $D_{H-1}$, $D_I$, $D_{I-1}$, $D_{I-2}$, $D_{I-3}$, $D_{I-4}$ and $D_{I-5}$, $R^3$ is methyl or is —CH$_2$OC(=O)R$^{3A}$, wherein R$^{3A}$ is optionally substituted alkyl. In other preferred embodiments of any one of those structures R$^3$ is —C(R$^{3A}$)(R$^{3A}$)C(=O)—X$^C$, wherein X$^C$ is —OR$^{3B}$ or —N(R$^{3C}$)(R$^{3C}$), wherein each R$^{3A}$, R$^{3B}$ and R$^{3C}$ independently is hydrogen, optionally substituted alkyl or optionally substituted cycloalkyl. Preferably R$^3$ is —C(R$^{3A}$)(R$^{3A}$)C(=O)—N(R$^{3C}$)(R$^{3C}$), with each R$^{3A}$ hydrogen, one R$^{3C}$ hydrogen and the other R$^{3C}$ n-butyl or isopropyl more preferred.

In other preferred embodiments the tubulysin incorporated as D⁺ in an LDC is a naturally occurring tubulysin including Tubulysin A, Tubulysin B, Tubulysin C, Tubulysin D, Tubulysin E, Tubulysin F, Tubulysin G, Tubulysin H, Tubulysin I, Tubulysin U, Tubulysin V, Tubulysin W, Tubulysin X or Tubulysin Z, whose structures are given by the following structure and variable group definitions wherein the indicated nitrogen (†) is the site of quaternization when such compounds are incorporated into an LDC as a quaternized drug unit (D⁺):

$D_{G-6}$

TABLE 1

| Some Naturally Occurring Tubulysins | | | |
|---|---|---|---|
| Tubulysin | R$^{7B}$ | R$^{2A}$ | R$^3$ |
| A | OH | C(=O)CH$_3$ | CH$_2$OC(=O)i-Bu |
| B | OH | C(=O)CH$_3$ | CH$_2$OC(=O)n-Pr |
| C | OH | C(=O)CH$_3$ | CH$_2$OC(=O)Et |
| D | H | C(=O)CH$_3$ | CH$_2$OC(=O)i-Bu |
| E | H | C(=O)CH$_3$ | CH$_2$OC(=O)n-Pr |
| F | H | C(=O)CH$_3$ | CH$_2$OC(=O)Et |
| G | OH | C(=O)CH$_3$ | CH$_2$OC(=O)CH=CH$_2$ |
| H | H | C(=O)CH$_3$ | CH$_2$OC(=O)Me |
| I | OH | C(=O)CH$_3$ | CH$_2$OC(=O)Me |
| U | H | C(=O)CH$_3$ | H |
| V | H | OH | H |
| Z | OH | OH | H |

In particularly preferred embodiments the quaternized tubulysin is that of Tubulysin M.

1.5 Treatment of Hyper-Proliferating Conditions

The Ligand-Drug Conjugates are useful for inhibiting the multiplication of a tumor cell or cancer cell, causing apoptosis in a tumor or cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cell-surface cancer-cell or a tumor-cell-associated antigen or receptor, and upon binding the Ligand-Drug Conjugate can be taken up (internalized) inside a tumor cell or cancer cell through antigen- or receptor-mediated endocytosis or other internalization mechanism. The antigen can be attached to a tumor cell or cancer cell or can be an extracellular matrix protein associated with the tumor cell or cancer cell. Once inside the cell, via a enzymatic or non-enzymatic cleavable mechanism, depending upon the components of the linker system, the drug is released within the cell. In an alternative embodiment, the Drug or Drug unit is cleaved from the Ligand-Drug Conjugate within the vicinity of the tumor cell or cancer cell, and the Drug or Drug unit subsequently penetrates the cell.

The Ligand-Drug Conjugates can provide conjugation-specific tumor or cancer drug targeting, thus reducing general toxicity of the drug.

In some embodiments, the Linker units stabilize the Ligand-Drug Conjugates in blood, yet are capable of liberating drug once inside the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, a ligand drug conjugate having a BR96 Ligand unit can be useful for treating antigen positive carcinomas including those of the lung, breast, colon, ovaries, and pancreas. Ligand-Drug Conjugates having an anti-CD30 or an anti-CD70 binding Ligand unit can be useful for treating hematologic malignancies.

Other particular types of cancers that can be treated with a ligand drug conjugates include, but are not limited to the following solid tumors, blood-borne cancers, acute and chronic leukemias, and lymphomas.

Solid tumors include but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Blood-borne cancers include but are not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, and multiple myeloma.

Acute and chronic leukemias include but are not limited to lymphoblastic, myelogenous, lymphocytic, and myelocytic leukemias.

Lymphomas include but are not limited to Hodgkin's disease, non-Hodgkin's Lymphoma, Multiple myeloma, Waldenström's macroglobulinemia, Heavy chain disease, and Polycythemia vera.

Cancers, including, but not limited to, a tumor, metastasis, or other diseases or disorders characterized by hyper-proliferating cells, can be treated or its progression inhibited by administration of an ADC composition.

In other embodiments, methods for treating cancer are provided, including administering to a patient in need thereof an effective amount of an LDC composition and a chemotherapeutic agent. In one embodiment the cancer to be treated with a chemotherapeutic in combination with an LDC has not been found to be refractory to the chemotherapeutic agent. In another embodiment, the cancer to be treated with a chemotherapeutic in combination with an ADC is refractory to the chemotherapeutic agent. The LDC compositions can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a ligand drug conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

1.6 Pharmaceutical Compositions

The present invention provides pharmaceutical compositions comprising an Ligand Drug Conjugate (LDC) composition described herein and a pharmaceutically acceptable carrier. The pharmaceutical compositions can be in any form that allows for an LDC to be administered to a patient for treatment of a disorder associated with expression of the antigen to which the antibody of the ADC binds. For example, the pharmaceutical compositions can be in the form of a liquid or a lyophilized solid. The preferred route of administration is parenteral. Parenteral administration includes subcutaneous injections, intravenous, intramuscular, and intrasternal injection or infusion techniques. In preferred embodiments, a pharmaceutical composition comprising an ADC is administered intravenously in the form of a liquid solution.

Pharmaceutical compositions can be formulated so as to allow a compound to be bioavailable upon administration of the composition to a patient. Such compositions can take the form of one or more dosage units, where for example, a lyophilized solid may provide a single dosage unit when reconstituted as a solution or suspension on addition of a suitable liquid carrier.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the pharmaceutical composition, the manner of administration, and the LDC composition employed.

The pharmaceutical composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, in some embodiments also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable pharmaceutical composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

A pharmaceutical composition of a LDC comprises an effective amount of an LDC composition such that a suitable dosage will be obtained for administration to a subject in need thereof. Typically, this amount is at least about 0.01% by weight of the pharmaceutical composition.

For intravenous administration, the pharmaceutical composition can comprise from about 0.01 to about 100 mg of an LDC composition per kg of the animal's body weight. In one aspect, the pharmaceutical composition can include from about 1 to about 100 mg of a ADC composition per kg of the animal's body weight. In another aspect, the amount administered will be in the range from about 0.1 to about 25 mg/kg of body weight of an ADC composition.

Generally, the dosage of an LDC composition administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, preferably 0.1 to 3.2 mg/kg, or more preferably 0.1 to 2.7 mg/kg of the subject's body weight over a treatment cycle.

An LDC can be administered by any convenient route, for example by infusion or bolus injection, by absorption through epithelial or mucocutaneous linings (e.g., oral mucosa, rectal and intestinal mucosa). Administration can be systemic or local. Various delivery systems are known, e.g., encapsulation in liposomes, microparticles, microcapsules, capsules, and can be used to administer a compound. In certain embodiments, more than one compounds or composition is administered to a patient.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

1.7 Numbered Embodiments

The following embodiments are provided to illustrate various aspects of the invention and are not intended to limit it in any way.

1. A Ligand Drug Conjugate (LDC) composition, wherein the composition is represented by the structures of Formula 1 and/or Formula 2:

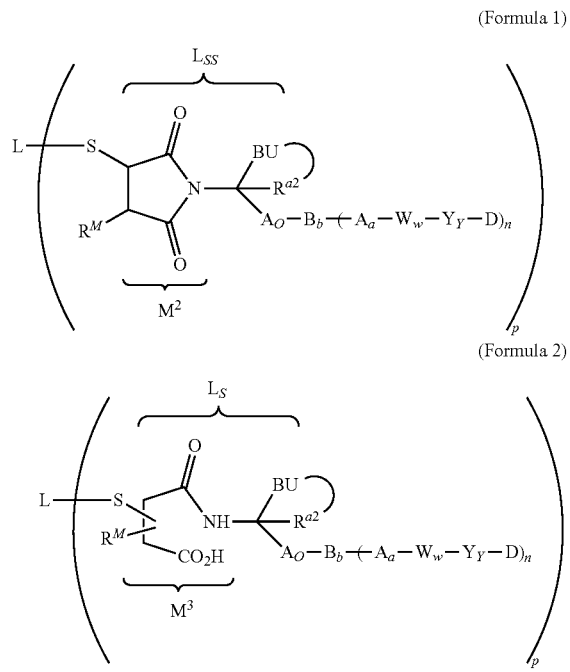

or a pharmaceutically acceptable salt thereof, wherein L is a Ligand Unit; S is a sulfur atom of the Ligand Unit, which in Formula 2 is bonded to the carbon atom α or β to the carboxylic acid functional group of the indicated succinic acid amide ($M^3$) moiety; $R^M$ is hydrogen or an optionally substituted $C_1$-$C_6$ alkyl, which in Formula 2 is bonded to the saturated carbon atom adjacent to the carbon substituted by L-S—; subscript w is 0 or 1; subscript n is 1, 2, 3 or 4; subscript a is 0 or 1; subscript b is 0 or 1, provided that subscript b is 1 when subscript n is 2, 3 or 4 and subscript b is 0 when subscript n is 1; A is a first optional Stretcher Unit; $A_O$ is a second optional Stretcher Unit; B is an optional Branching Unit; and wherein each of A, $A_O$ and B is an independently selected single unit or is optionally comprised or consists of two, three or four independently selected subunits;

Y is optionally present as an optionally substituted heteroatom, an optionally substituted functional group or a Spacer Unit, independently selected when subscript y is 2 so that $Y_y$ is —Y—Y'—, wherein Y and Y' are, respectively, a first and second optionally substituted heteroatom, optionally substituted functional group or Spacer Unit; subscript w is 0 or 1, wherein W is absent when subscript w is 0, or when subscript w is 1 then W is a Peptide Cleavable Unit, or W is a Glucuronide Unit of formula —Y(W')—, wherein W' represents a carbohydrate moiety with glycosidic bonding to Y through a optionally substituted heteroatom, provided that Y bonded to W' is a self-immolative Spacer Unit; subscript y is 0, 1 or 2, provided that subscript y is 1 or 2, when W is a Glucuronide Unit, in which instance subscript y is inclusive of the self-immolative Spacer Unit bonded to W', except that subscript y is 1 and Y of the Glucuronide Unit is bonded to D when D is a quaternized Drug Unit ($D^+$), and provided that subscript y is 1 and Y is a self-immolative Spacer Unit bonded to D and W when W is a Peptide Cleavable Unit and D is a quaternized Drug Unit ($D^+$);

BU is a Basic Unit and $R^{a2}$ is an optionally substituted $C_1$-$C_{12}$ alkyl group that together with the carbon atom to which both are attached, as represented by the solid curved line, define a cyclic Basic Unit having an optionally substituted spiro $C_3$-$C_{20}$ heterocyclo containing a skeletal basic nitrogen atom of a secondary or tertiary amine functional group, an optionally substituted spiro $C_3$-$C_{20}$ carbocyclo with exocyclic substitution by an optionally substituted basic nitrogen atom of a basic secondary or tertiary amine functional group, or an optionally substituted spiro $C_3$-$C_{20}$ carbocyclo having exocyclic substitution by an optionally substituted $C_1$-$C_{12}$ aminoalkyl in which the optionally substituted basic nitrogen atom of the amino moiety of the aminoalkyl is that of a primary, secondary or tertiary amine functional group, wherein the optionally substituted basic nitrogen atom of the exocyclic amine or aminoalkyl along with its optionally substituted alkyl moiety is attributable to BU, or BU is a Basic Unit and $R^{a2}$ is an optionally substituted $C_1$-$C_{12}$ alkyl formally cyclized to the basic nitrogen atom of an acyclic Basic Unit of corresponding structure to Formula 1 and/or Formula 2 in which the solid curved lined between BU and $R^{a2}$ is absent, or to a carbon atom of an optionally substituted $C_1$-$C_{12}$ alkylene bearing that basic nitrogen atom, both of which comprise the acyclic Basic Unit, thus forming an optionally substituted spiro $C_3$-$C_{20}$ heterocyclo, which incorporates the basic nitrogen atom as a skeletal heteroatom, or an optionally substituted spiro $C_3$-$C_{20}$ carbocyclo substituted directly by the basic nitrogen atom, or substituted indirectly by the basic nitrogen atom through an optionally substituted $C_1$-$C_{12}$ alkylene moiety remaining from said formal cyclization and whose structure is dependent on the site of cyclization, so in either instance a cyclic Basic Unit (cBU) is defined, as indicated by the solid curved line; and wherein the basic nitrogen atom of the cyclic Basic Unit is optionally suitably protected by a nitrogen protecting group, dependent on the degree of substitution of the basic nitrogen atom, or is optionally protonated;

subscript p ranges from 1 to 24; D is a Drug Unit, or D is a quaternized Drug Unit represented as $D^+$ so that $D^+$ replaces D in Formula 1 and Formula 2 provided that subscript w is 1; wherein if subscript w is 1, activation of the Glucuronide Unit by a glycosidase or activation of the Peptide Cleavable Unit by a protease within a compound of the Ligand Drug Conjugate composition initiates release of the Drug Unit or quaternized Drug Unit as a biologically active compound or derivative thereof from that Ligand Drug Conjugate compound, or if subscript w is 0, a biologically active compound or derivative thereof is released from a Ligand Drug Conjugate compound of the composition on enzymatic or non-enzymatic cleavage of a bond within a drug linker moiety of the Conjugate compound that attaches $Y_y$-D to the indicated $L_{SS}$ or $L_S$ structure of that drug linker moiety; and wherein the Ligand Drug Conjugate compound corresponds in structure to Formula 1 or Formula 2 in which p is replaced by p', wherein p' is an integer ranging from 1 to 24.

2. The Ligand Drug Conjugate (LDC) composition of embodiment 1, wherein the composition is represented by the structure of:

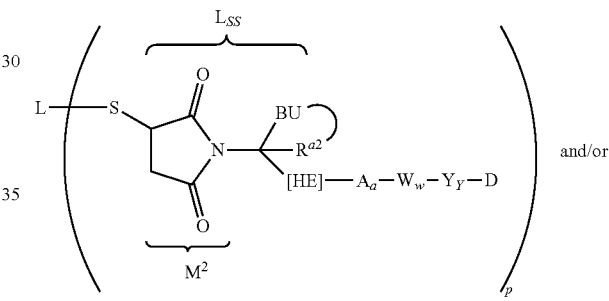

and/or

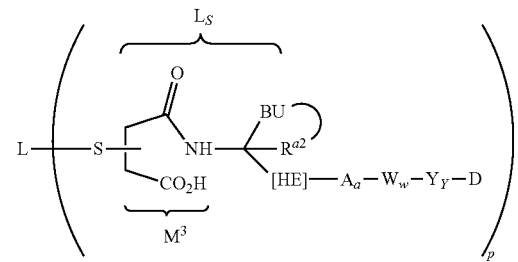

wherein [HE] as $A_O$ is an optional Hydrolysis Enhancing Unit; subscript w is 1; W is Peptide Cleavable Unit, or W is a Glucuronide Unit of formula —Y(W')— having the structure of:

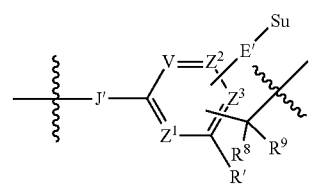

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit bonded to W'; J' is an independently selected heteroatom, optionally substituted; V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)-moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$—$C_6$ alkyl, or other electron donating group; and wherein glycosidase cleavage of the glycosidic bond within a compound of the Ligand Drug Conjugate composition initiates release of the Drug Unit or quaternized Drug Unit as a biologically active compound or derivative thereof from that Ligand Drug Conjugate compound; wherein the wavy line adjacent to J' indicates the point of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the point of covalent attachment of the Glucuronide Unit to Y' when subscript y is 2, or to D/$D^+$ when subscript y is 1.

3. The Ligand-Drug Conjugate composition of embodiment 2 wherein W is a Glucuronide Unit in which —W—$Y_y$-D and —W-$D^+$ have structures of:

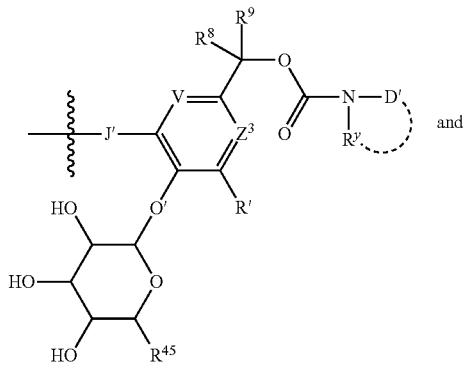

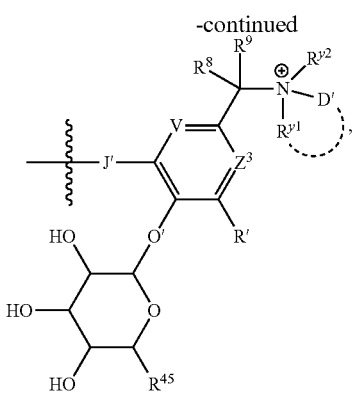

respectively, wherein the dotted curve line indicates optional cyclization of $R^Y$ or $R^{y1}$ to D'; $R^{45}$ is —$CH_2OH$ or —$CO_2H$; —N($R^Y$)D' and —$N^+$($R^{y1}$)($R^{y2}$)D' moieties, with or without cyclization, represent D and $D^+$, respectively, wherein D' is the remainder of D or $D^+$; wherein $R^Y$ is hydrogen or optionally substituted $C_1$-$C_6$ alkyl in absence of cyclization to D' or $R^Y$ is optionally substituted $C_1$-$C_6$ alkylene when cyclized to D'; $R^1$ is optionally substituted $C_1$-$C_6$ alkyl, in absence of its cyclization within $D^+$, or $R^{y1}$ is optionally substituted $C_1$-$C_6$ alkylene when cyclized within $D^+$; $R^{y2}$ is hydrogen or optionally substituted $C_1$-$C_6$ alkyl; and wherein —O'— as E' represents the oxygen heteroatom of an O-glycosidic bond cleavable by a glycosidase, wherein said cleavage within a compound of the Ligand Drug Conjugate composition initiates release of D as a primary or secondary amine-containing biologically active compound or derivative thereof, or initiates release of $D^+$ as a tertiary amine-containing biologically active compound or derivative thereof from that Ligand Drug Conjugate compound.

4. The Ligand-Drug Conjugate composition of embodiment 2 wherein W is a Peptide Cleavable Unit and —$Y_y$-D- and —$Y_y$-$D^+$ have structures of:

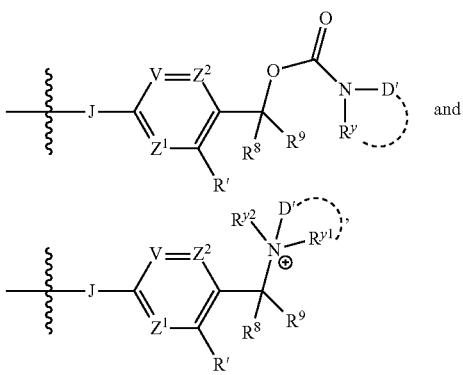

respectively,
wherein —N($R^Y$)D' and —$N^+$($R^{y1}$)($R^{y2}$)D' moieties represent D and $D^+$, respectively, wherein D' is the remainder of D or $D^+$, and wherein the dotted line indicates optional cyclization of $R^y$ or $R^{y1}$ to D'; wherein $R^y$ is hydrogen or $R^y$ is optionally substituted $C_1$-$C_6$ alkyl in absence of cyclization to D' or optionally substituted $C_1$-$C_6$ alkylene when cyclized to D'; $R^{y1}$ is optionally substituted $C_1$-$C_6$ alkyl in absence of cyclization to $D^+$ or $R^{y1}$ is optionally substituted $C_1$-$C_6$ alkylene when cyclized to $D^+$; $R^{y2}$ is optionally substituted $C_1$-$C_6$ alkyl; J is an optionally substituted heteroatom bonded to W as indicated by the wavy line, wherein cleavage of that bond within a compound of the Ligand Drug Conjugate composition initiates release of D as a primary or secondary amine-containing biologically active compound or derivative thereof or initiates release of $D^+$ as a tertiary amine-containing biologically active compound or derivative thereof from that Ligand Drug Conjugate compound.

5. The Ligand Drug Conjugate composition of embodiment 2, wherein the composition is represented by the structure of:

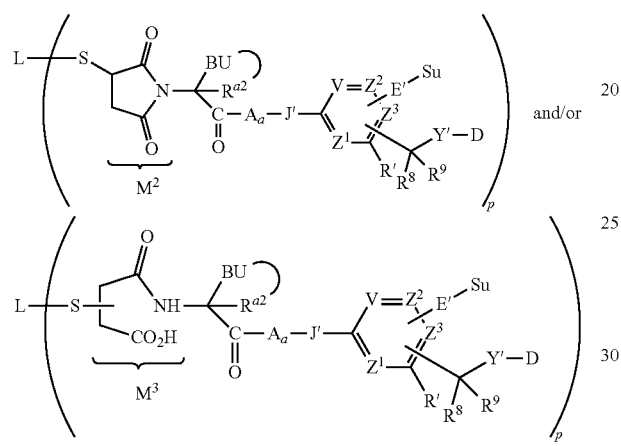

wherein Su is a carbohydrate moiety; E' represents an independently selected heteroatom, optionally substituted, of an glycosidic bond cleavable by a glycosidase; J' represents an independently selected heteroatom, optionally substituted; Y' is absent or Y' is —O—, —S—, —NH— or —O—C(=O)—, provided that Y' is absent when D is a quaternized Drug Unit ($D^+$); V, $Z^1$, $Z^2$ and $Z^3$ independently are =N— or =C($R^{24}$)—, wherein each $R^{24}$ is independently selected from the group consisting of hydrogen and $C_1$-$C_8$ alkyl, $C_2$-$C_8$ alkenyl and $C_2$-$C_8$ alkynyl, optionally substituted, halogen, an electron withdrawing group, an electron donating group, —O'-Su, —C($R^8$)($R^9$)—Y'-D and —C($R^8$)($R^9$)-$D^+$, provided that one and only one of —C($R^8$)($R^9$)—Y'-D and —C($R^8$)($R^9$)-$D^+$ moieties and one and only one —O'-Su moiety is present; wherein one of V, $Z^1$, $Z^2$ and $Z^3$ is =C($R^{24}$)—, in which $R^{24}$ is —C($R^8$)($R^9$)—Y'-D or —C($R^8$)($R^9$)-$D^+$ and another of V, $Z^1$, $Z^2$ and $Z^3$ is =C($R^{24}$)—, in which $R^{24}$ is —O'-Su, provided the —O'-Su and —C($R^8$)($R^9$)—Y'-D or —C($R^8$)($R^9$)-$D^+$ moieties are ortho or para to each other; $R^8$ and $R^9$ independently are hydrogen, $C_1$-$C_8$ alkyl, $C_2$-$C_8$ alkenyl and $C_2$-$C_8$ alkynyl, optionally substituted, or $C_5$-$C_{10}$ aryl or $C_5$-$C_{10}$ heteroaryl, optionally substituted or $R^8$ and $R^9$ together with the carbon atom to which both are attached define an optionally substituted spiro $C_5$-$C_6$ carbocyclo; and wherein glycosidase cleavage of the glycosidic bond within a compound of the Ligand Drug Conjugate composition initiates release of D/$D^+$ as a biologically active compound or derivative thereof from that Ligand Drug Conjugate compound.

6. The Ligand Drug Conjugate composition of embodiment 2, wherein the composition is represented by the structure of:

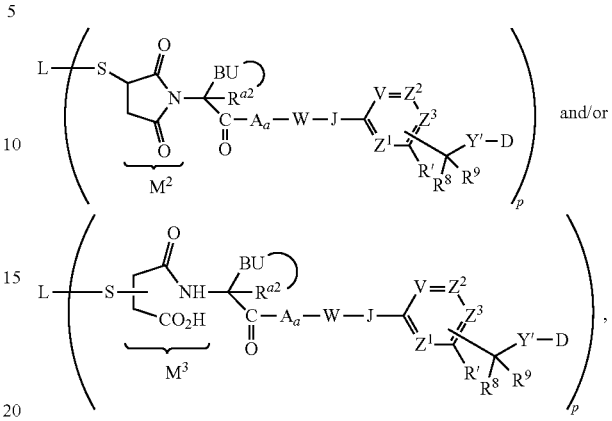

wherein J represents an independently selected heteroatom, optionally substituted; Y' is absent or Y' is —O—, —S—, —NH— or —O—C(=O)—, provided that —Y'— is absent when D is a quaternized Drug Unit ($D^+$); W is a Peptide Cleavable Unit; V, $Z^1$, $Z^2$ and $Z^3$ are independently =N— or =C($R^{24}$)—, wherein each $R^{24}$ is independently selected from the group consisting of hydrogen and $C_1$-$C_8$ alkyl, $C_2$-$C_8$ alkenyl and $C_2$-$C_8$ alkynyl, optionally substituted, halogen, an electron withdrawing group, an electron donating group, —C($R^8$)($R^9$)—Y'-D and —C($R^8$)($R^9$)-$D^+$, provided that one and only one of —C($R^8$)($R^9$)—Y'-D and —C($R^8$)($R^9$)-$D^+$ moieties is present, wherein one of V, $Z^1$, $Z^2$ and $Z^3$ is =C($R^{24}$)—, in which $R^{24}$ is —C($R^8$)($R^9$)—Y'-D or —C($R^8$)($R^9$)-$D^+$, provided the —C($R^8$)($R^9$)—Y'-D or —C($R^8$)($R^9$)-$D^+$ moiety is ortho or para to J'; $R^8$ and $R^9$ independently are hydrogen, $C_1$-$C_8$ alkyl, $C_2$-$C_8$ alkenyl and $C_2$-$C_8$ alkynyl, optionally substituted, or $C_5$-$C_{10}$ aryl or $C_5$-$C_{10}$ heteroaryl, optionally substituted, or $R^8$ and $R^9$ together with the carbon atom to which both are attached define an optionally substituted spiro $C_5$-$C_6$ carbocyclo; wherein protease action on W results in cleavage of the W-J bond within a compound of the Ligand Drug Conjugate composition so as to initiate release of D/$D^+$ as a biologically active compound or derivative thereof from that Ligand Drug Conjugate compound.

7. The Ligand-Drug Conjugate composition of embodiment 5, wherein the composition is represented by the structure of:

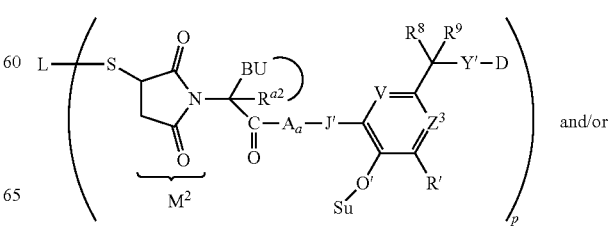

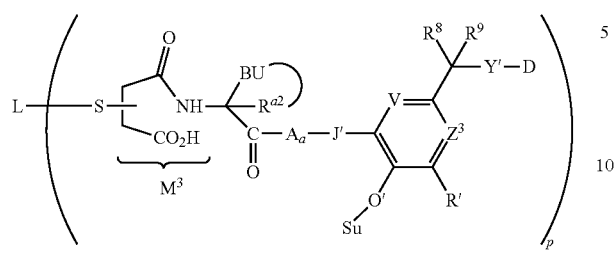

wherein —O'— represents the oxygen heteroatom of an O-glycosidic bond cleavable by a glycosidase.

8. The Ligand-Drug Conjugate composition of claim 6, wherein the composition is represented by the structure of:

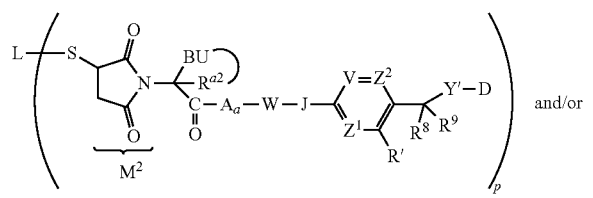

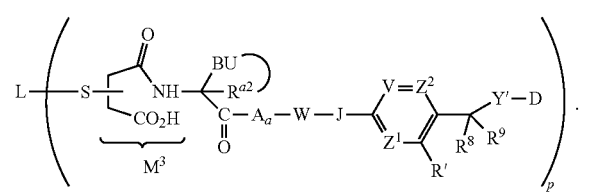

9. The Ligand-Drug Conjugate composition of claim 7, wherein the composition is represented by the structure of:

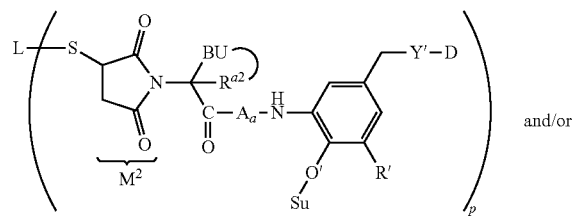

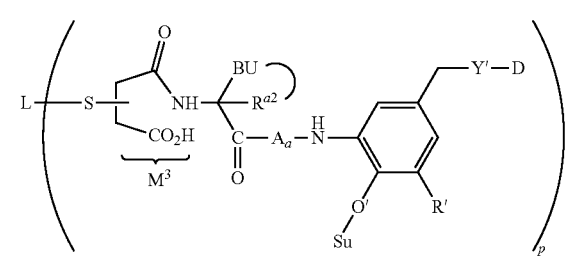

wherein R' is hydrogen or —NO$_2$.

10. The Ligand-Drug Conjugate composition of embodiment 8, wherein the composition is represented by the structure of:

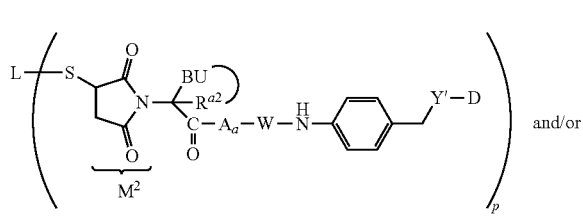

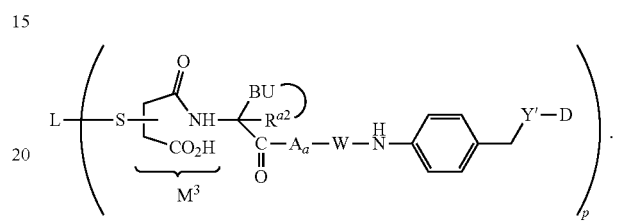

11. The Ligand-Drug Conjugate composition of any one of embodiments 1 to 10, wherein BU and R$^2$ together with the carbon atom to which both are attached, define an optionally substituted spiro C$_3$-C$_8$ heterocyclo having a skeletal secondary or tertiary basic nitrogen atom, wherein the skeletal basic nitrogen atom is attributable to BU.

12. The Ligand-Drug Conjugate composition of embodiment 9, wherein the composition is represented by the structure of:

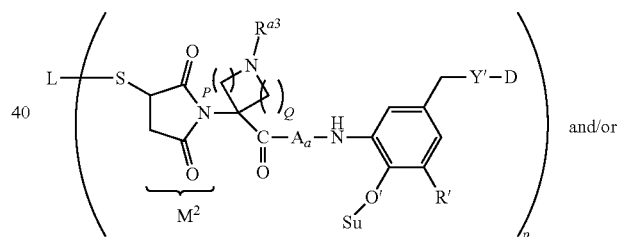

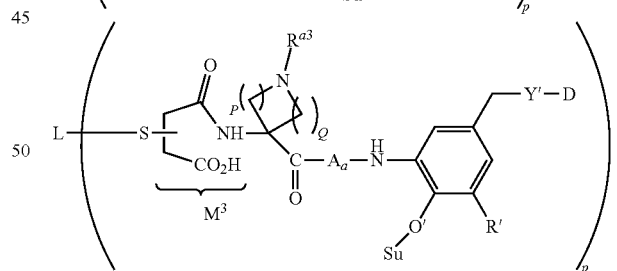

wherein subscript P is 1 or 2; subscript Q ranges from 1 to 6; and wherein R$^{a3}$ is —H, C$_1$-C$_6$ alkyl, —C$_1$-C$_4$ alkylene-(C$_6$-C$_{10}$ aryl), or —R$^{PEG1}$—O—(CH$_2$CH$_2$O)$_{n'}$—R$^{PEG2}$, wherein R$^{PEG1}$ is C$_1$-C$_4$ alkylene, R$^{PEG2}$ is —H or C$_1$-C$_4$ alkyl, and subscript n' ranges from 1 to 36, wherein the basic nitrogen bonded to R$^a$ is optionally protonated.

13. The Ligand-Drug Conjugate composition of embodiment 10, wherein the composition is represented by the structure of:

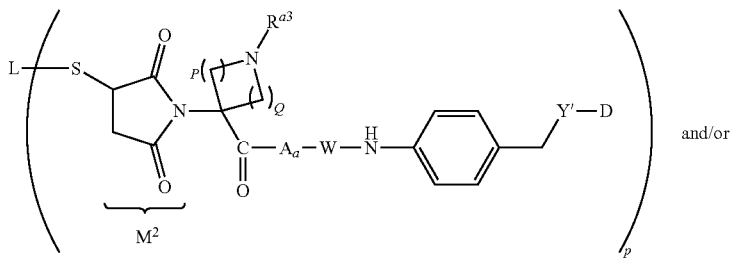

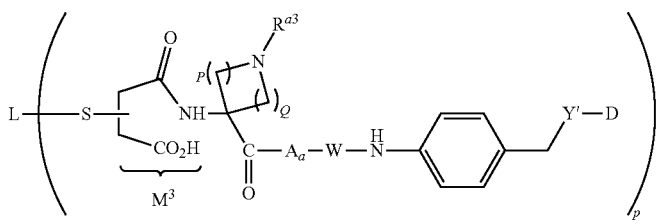

wherein subscript P is 1 or 2; subscript Q ranges from 1 to 6; and $R^{a3}$ is —H, $C_1$-$C_6$ alkyl, —$C_1$-$C_4$ alkylene-($C_6$-$C_{10}$ aryl) or —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen bonded to $R^{a3}$ is optionally protonated.

14. The Ligand-Drug Conjugate composition of embodiment 12 or 13, wherein subscript P is 1 and subscript Q is 1, 2 or 3 or subscript P is 2 and Q is 1 or 2.

15. The Ligand-Drug Conjugate composition of embodiment 14, wherein subscript P is 1, subscript Q is 1.

16. The Ligand-Drug Conjugate composition of any one of embodiments 1 to 10 wherein BU and $R^2$ together with the carbon atom to which both are attached define an optionally substituted spiro $C_3$-$C_8$ carbocyclo having exocyclic substitution by a primary, secondary or tertiary amine or by an optionally substituted $C_1$-$C_6$-aminoalkyl, wherein the basic nitrogen atom of the amine or aminoalkyl is attributable to BU and is optionally protonated.

17. The Ligand-Drug Conjugate composition of embodiment 16, wherein the composition is represented by the structure of:

-continued

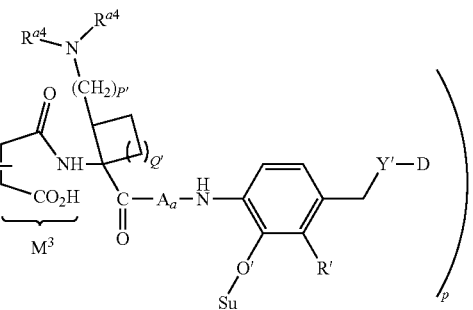

wherein subscript P' is 0 or 1; subscript Q' is 0, or Q' ranges from 1 to 6; each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein the basic nitrogen atom in either instance is optionally protonated.

18. The Ligand-Drug Conjugate composition of embodiment 16, wherein the composition is represented by the structure of:

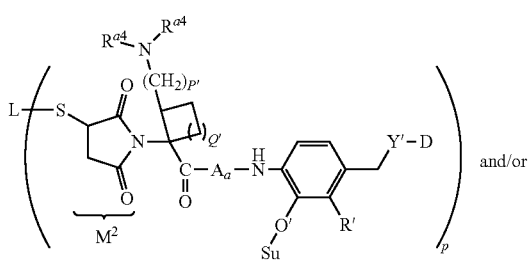

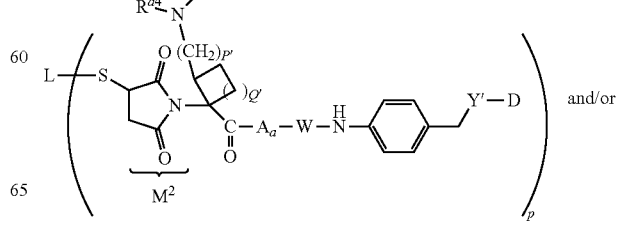

157

-continued

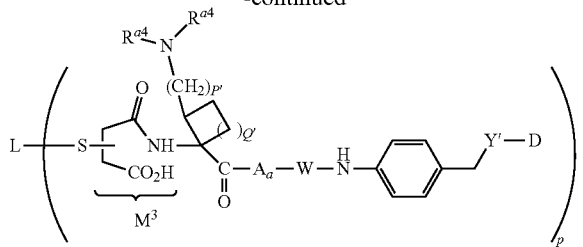

wherein subscript P' is 0 or 1; subscript Q' is 0, or Q' ranges from 1 to 6; each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein the basic nitrogen in either instance is optionally protonated.

19. The Ligand-Drug Conjugate composition of embodiment 7, 9, 12 or 17, wherein —O'-Su has the structure of:

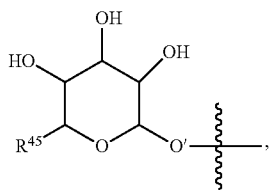

wherein the wavy line represents covalent bonding of O' to the remainder of the structure representing the Ligand-Drug Conjugate composition; and $R^{45}$ is —$CH_2OH$ or —$CO_2H$.

20. The Ligand-Drug Conjugate composition of embodiment 6, 8, 10, 13 or 18, wherein W is a Peptide Cleavable Unit comprised of a dipeptide wherein the C-terminus of the dipeptide is covalently bonded to J' wherein the dipeptide provides for a recognition site for a regulatory or lysosomal protease for cleavage by said protease of the W-J' bond within a compound of the Ligand Drug Conjugate composition so as to initiate release of D or $D^+$ as a biologically active compound or derivative thereof from that Ligand Drug Conjugate compound.

21. The Ligand-Drug Conjugate composition of embodiment 20 wherein the dipeptide of W has the structure of:

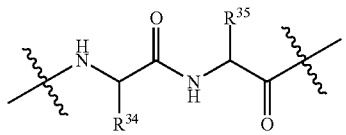

wherein $R^{34}$ is benzyl, methyl, isopropyl, isobutyl, sec-butyl, —$CH(OH)CH_3$ or has the structure of

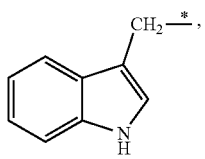

158 wherein the asterisk indicates the point of covalent attachment to the dipeptide backbone; and $R^{35}$ is methyl, —$(CH_2)_4$—$NH_2$, —$(CH_2)_3NH(C=O)NH_2$, —$(CH_2)_3NH(C=NH)NH_2$, or, —$(CH_2)_2CO_2H$; and wherein the wavy lines indicate the points of covalent attachment of the dipeptide into the structure representing the Ligand-Drug Conjugate composition.

22. The Ligand-Drug Conjugate composition of embodiment 20 wherein the dipeptide of W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, and -Trp-Cit-, wherein Cit is citrulline.

23. The Ligand-Drug Conjugate composition of any one of embodiments 5 to 22 wherein D is a quaternized Drug Unit ($D^+$), Y' is absent and subscript y is 1 wherein Y bonded to $D^+$ is a self-immolative Spacer Unit.

24. The Ligand-Drug Conjugate composition of embodiment 23, wherein the composition is represented by the structure of:

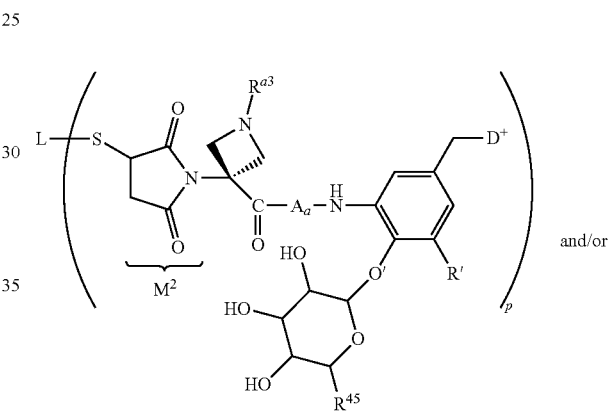

and/or

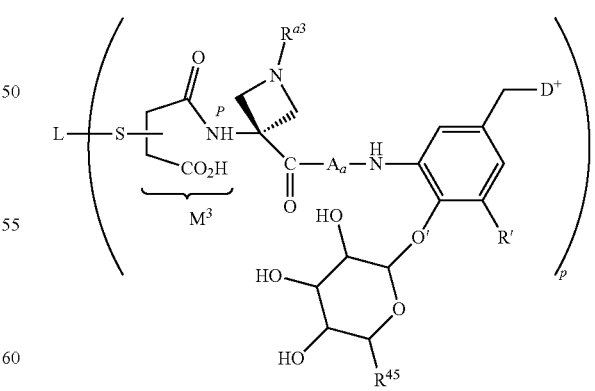

wherein $R^{a3}$ is —H, $C_1$-$C_6$ alkyl, —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated; R' is hydrogen or —NO$_2$; and $R^{45}$ is —CH$_2$OH or —CO$_2$H.

25. The Ligand-Drug Conjugate composition of embodiment 24, wherein the composition is represented by the structure of:

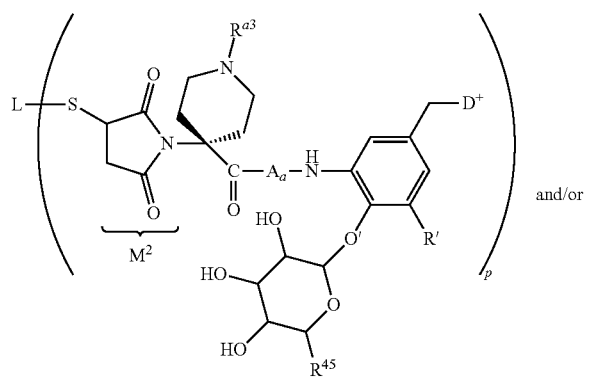

and/or

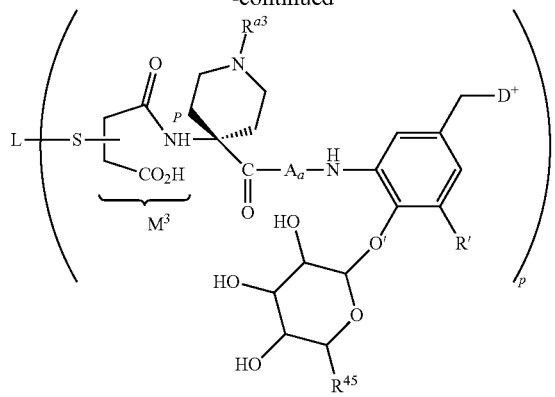

wherein $R^3$ is —H, optionally substituted $C_1$-$C_6$ alkyl, optionally substituted —$C_1$-$C_4$ alkylene-($C_6$-$C_{10}$ aryl) or —$R^{PEG1}$—O—(CH$_2$CH$_2$O)$_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated, or R' is hydrogen or —NO$_2$; and $R^{45}$ is —CH$_2$OH or —CO$_2$H.

26. The Ligand-Drug Conjugate composition of embodiment 23, wherein the composition is represented by the structure of:

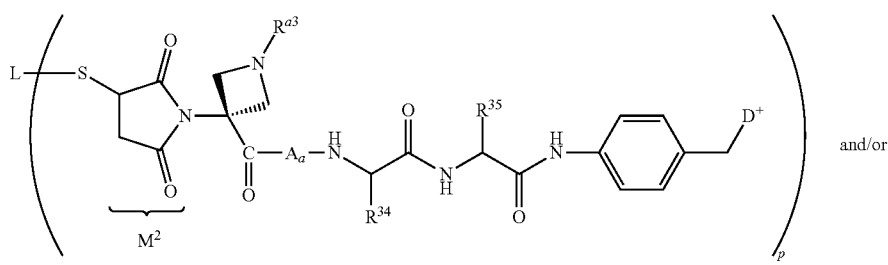

and/or

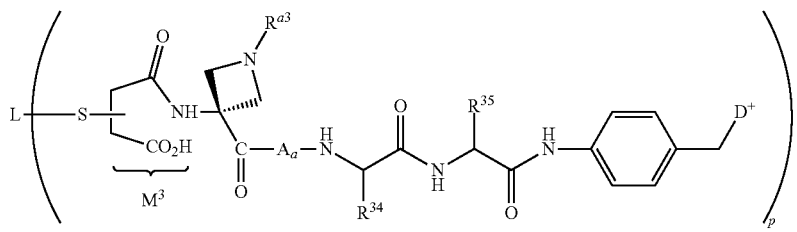

wherein $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—(CH$_2$CH$_2$O)$_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^3$ is optionally protonated.

27. The Ligand-Drug Conjugate composition of embodiment 23, wherein the composition is represented by the structure of:

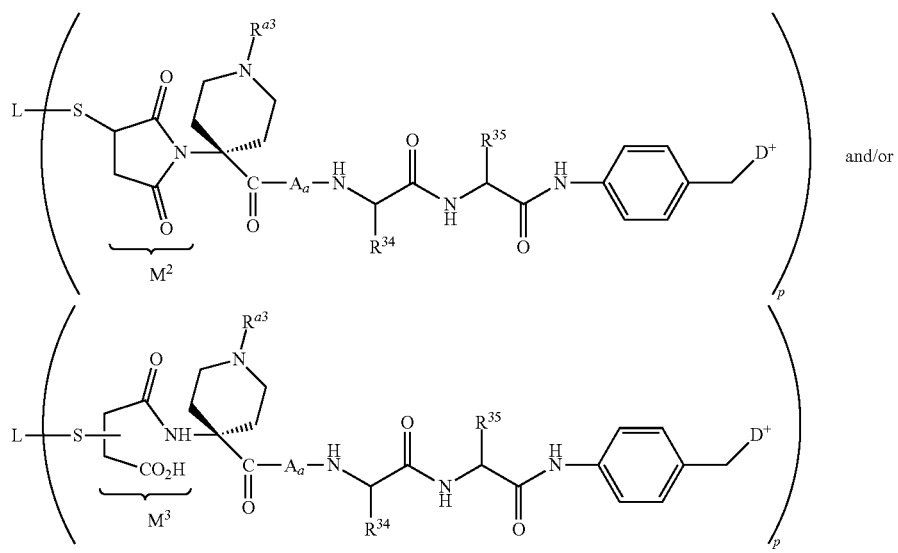

wherein $R^1$ is —H, optionally substituted $C_1$-$C_6$ alkyl, optionally substituted —$C_1$-$C_4$ alkylene-($C_6$-$C_{10}$ aryl) or —$R^{PEG1}$—O—$(CH_2CH_2O)_n$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^1$ is optionally protonated; $R^{34}$ is methyl or isopropyl; and $R^{35}$ is methyl, —$(CH_2)_4$—$NH_2$, —$(CH_2)_3NH(C=O)NH_2$, —$(CH_2)_3NH(C=NH)NH_2$, or —$(CH_2)_2CO_2H$.

28. The Ligand-Drug Conjugate composition of any one of embodiments 23 to 27 wherein the released tertiary amine-containing biologically active compound or derivative thereof is a tubulysin compound thereby defining $D^+$ as a quaternized tubulysin Drug Unit.

29. The Ligand-Drug Conjugate composition of any one of embodiments 1-28 wherein the quaternized Drug Unit -$D^+$ is a quaternized tubulysin Drug Unit having the structure of:

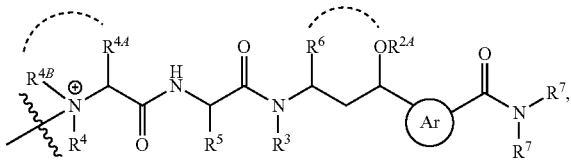

$R^{2A}$ is hydrogen or optionally substituted $C_1$-$C_{12}$ alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, thereby defining an oxygen-containing $C_5$-$C_6$-heterocyclo; the circled Ar moiety represents a 5-membered nitrogen-heteroarylene, wherein the indicated required substituents to that heteroarylene are in a 1,3-relationship with each other with optional substitution at the remaining positions; $R^3$ is hydrogen or optionally substituted $C_1$-$C_{12}$ alkyl; $R^4$, $R^5$ and $R^6$ are optionally substituted $C_1$-$C_{12}$ alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted $C_1$-$C_{12}$ alkyl and $R^{4B}$ is optionally substituted $C_1$-$C_{12}$ alkyl, or both together with the nitrogen to which they are attached, as indicated by the curved dotted line between $R^{4A}$ and $R^{4B}$, define a quaternized nitrogen-containing $C_3$-$C_8$ heterocyclyl, optionally substituted; one $R^7$ is hydrogen or optionally substituted $C_1$-$C_{12}$ alkyl and the other $R^7$ is optionally substituted ($C_6$-$C_{20}$ aryl)-$C_1$-$C_{12}$ alkyl- or ($C_5$-$C_{20}$ heteroaryl)-$C_1$-$C_{12}$ alkyl-; wherein the wavy line indicates the point of covalent attachment of $D^+$ to the remainder of the composition structure.

30. The Ligand-Drug Conjugate composition of embodiment 29 wherein $D^+$ has the structure of:

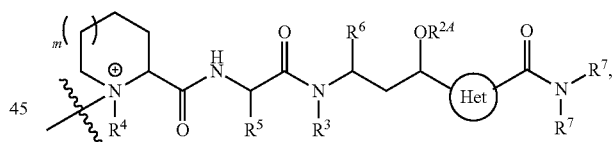

wherein subscript m is 0 or 1.

31. The Ligand-Drug Conjugate composition of embodiment 30 wherein the quaternized tubulysin Drug Unit -$D^+$ has the structure of:

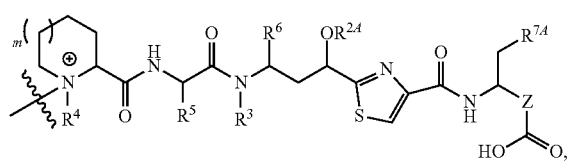

wherein
Z is an optionally substituted $C_1$-$C_6$ alkylene or an optionally substituted $C_2$-$C_6$ alkenylene; and $R^{7A}$ is optionally substituted $C_6$-$C_{10}$ aryl or optionally substituted $C_5$-$C_{10}$ heteroaryl.

32. The Ligand-Drug Conjugate composition of embodiment 31 wherein the quaternized tubulysin Drug Unit -$D^+$ has the structure of:

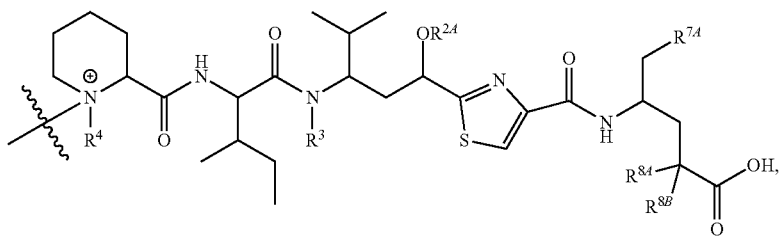

wherein $R^{7A}$ is optionally substituted phenyl and $R^{8A}$ and $R^{8B}$ are independently selected from the group consisting of hydrogen and optionally substituted $C_1$-$C_6$ alkyl, or $R^{8A}$ and $R^{8B}$ together with the carbon atom to which both are attached define an optionally substituted spiro $C_3$-$C_6$ carbocyclo.

33. The Ligand-Drug Conjugate composition of embodiment 32 wherein the quaternized tubulysin Drug Unit -D⁺ has the structure of:

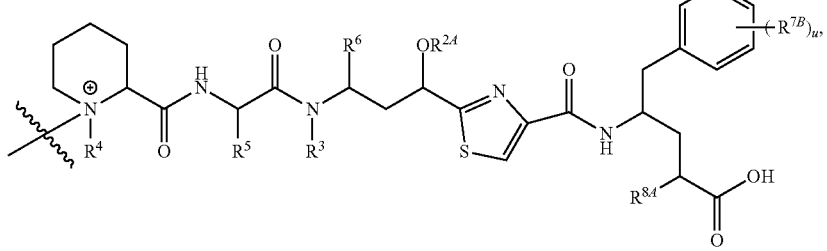

wherein $R^5$ and $R^6$ are independently selected alkyl side chain residues of natural hydrophobic amino acids; subscript u, indicating the number of $R^{7B}$ substituents, is 0, 1, 2 or 3; each $R^{7B}$, when present, is an independently selected O-linked substituent; and $R^{8A}$ is hydrogen or optionally substituted $C_1$-$C_4$ alkyl.

34. The Ligand-Drug Conjugate composition of embodiment 33 wherein the quaternized tubulysin Drug Unit -D⁺ has the structure of:

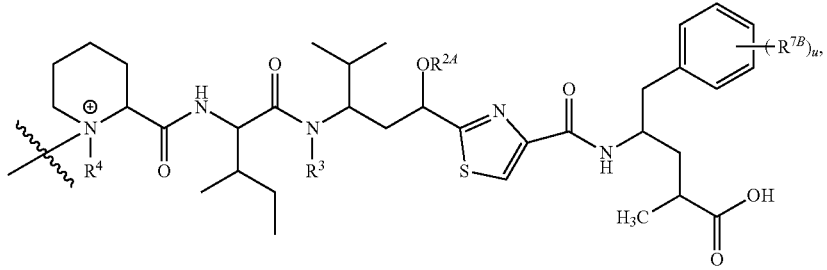

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is $C_1$-$C_6$ alkyl and R$^{3B}$ is H or $C_1$-$C_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —OCH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, $C_1$-$C_6$ alkyl and $C_2$-$C_6$ alkenyl; and each R$^{7B}$, when present, independently is —OH or —OCH$_3$.

35. The Ligand-Drug Conjugate composition of embodiment 29 wherein the quaternized tubulysin Drug Unit -D⁺ has the structure of:

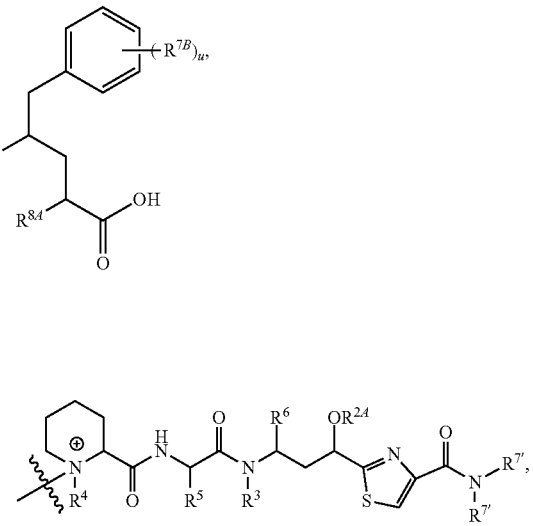

wherein $R^{2A}$ is hydrogen, an saturated $C_1$-$C_6$ alkyl, or an unsaturated $C_3$-$C_6$ alkyl, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are alkyl side chain residues of natural hydrophobic amino acids; and the —N(R$^{7'}$)(R$^{7'}$) moiety is —NH($C_1$-$C_6$ alkyl), wherein $C_1$-$C_6$ alkyl is unsubstituted or is substituted by one and only one —CO$_2$H, or an ester thereof, or by one and only one optionally substituted phenyl, and is otherwise optionally substituted, or the —N(R$^{7'}$)(R$^{7'}$) moiety is —N(C$_1$-C$_6$ alkyl)$_2$, wherein one and only one C$_1$-C$_6$ alkyl is substituted by one and only one —CO$_2$H, or an ester thereof, or by one and only one optionally substituted phenyl, and each C$_1$-C$_6$ alkyl is otherwise optionally substituted.

36. The Ligand-Drug Conjugate composition of embodiment 35 wherein the —N(R$^{7'}$)(R$^{7'}$) moiety is selected from the group consisting of —NH(CH$_3$), —NHCH$_2$CH$_2$Ph, —NHCH$_2$—CO$_2$H, —NHCH$_2$CH$_2$CO$_2$H and —NHCH$_2$CH$_2$CH$_2$CO$_2$H.

37. The Ligand-Drug Conjugate composition of any one of embodiments 29 to 36 wherein R$^{2A}$ is —CH$_2$CH$_3$.

38. The Ligand-Drug Conjugate composition of any one of embodiments 29 to 36 wherein R$^{2A}$ is —CH$_2$—CH=CH$_2$.

39. The Ligand-Drug Conjugate composition of embodiment 34 wherein —OR$^{2A}$ is —OCH$_2$CH$_3$, —OCH$_2$—CH=CH$_2$, —OCH$_2$C(CH$_3$)=CH$_2$, or —OC(O)R$^{2B}$, wherein —R$^{2B}$ is —CH$_3$; R$^3$ is —CH$_3$; and R$^{7B}$ is —OH or is absent; subscript u is 0 or 1, wherein R$^{7B}$ is —OH when subscript u is 1, and R$^{7B}$ is absent when subscript u is 0.

40. The Ligand-Drug Conjugate composition of embodiment 34 wherein the quaternized tubulysin Drug Unit -D$^+$ has the structure of:

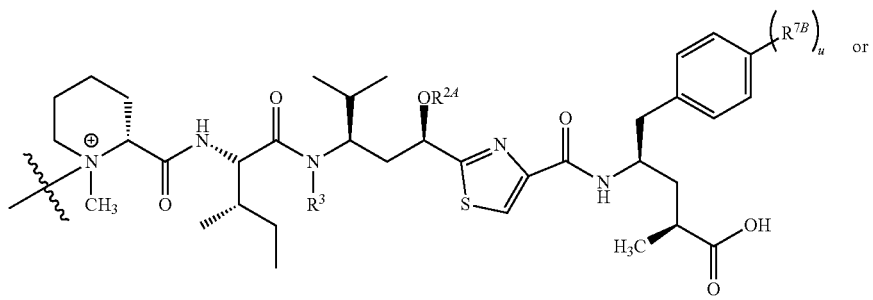

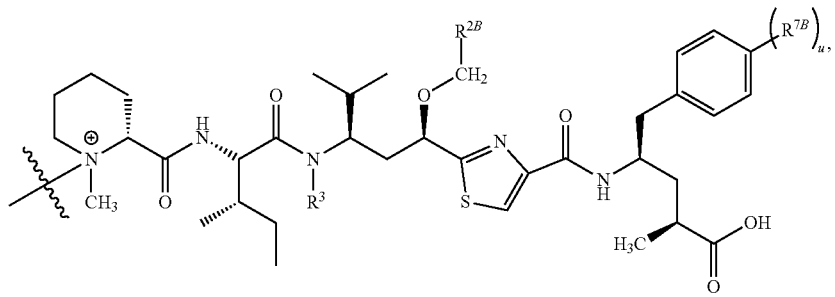

wherein R$^{2A}$ is —C(O)R$^{2B}$, —C(O)NHR$^{2D}$, or —CH$_2$C(O)R$^{2D}$; R$^{2B}$ is H, C$_1$-C$_6$ alkyl or C$_2$-C$_6$ alkenyl; R$^{2D}$ is —H, C$_1$-C$_4$ alkyl or C$_2$-C$_4$ alkenyl; R$^3$ is methyl, ethyl or propyl; R$^{7B}$ is —OH or is absent; and subscript u is 0 or 1, wherein R$^{7B}$ is —OH when subscript u is 1, and R$^{7B}$ is absent when subscript u is 0.

41. The Ligand-Drug Conjugate composition of embodiment 40 wherein the quaternized tubulysin Drug Unit -D$^+$ has the structure of:

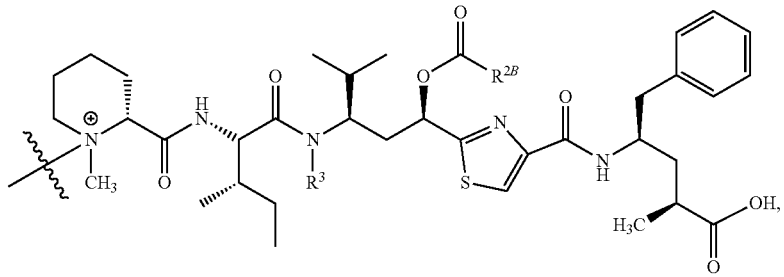

wherein $R^{2B}$ is a methyl, ethyl, propyl or a branched $C_3$-$C_6$ alkyl or is methyl, ethyl, propyl, iso-propyl, 3-methyl-prop-1-yl, 3,3-dimethyl-prop-1-yl, or vinyl.

42. The Ligand-Drug Conjugate composition of embodiment 41 wherein $R^{2B}$ is —$CH_3$ and $R^3$ is —$CH_3$.

43. The Ligand-Drug Conjugate composition of embodiment 40 wherein the quaternized tubulysin Drug Unit -$D^+$ has the structure of:

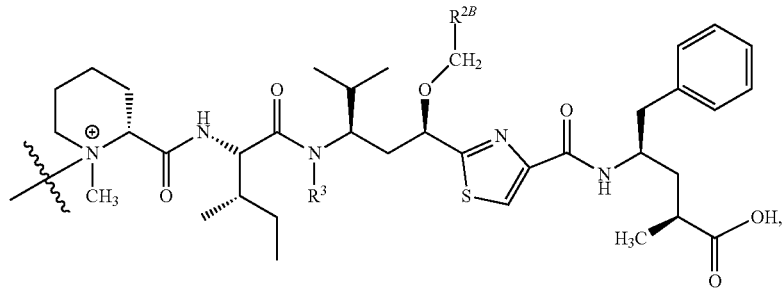

wherein $R^{2B}$ is —H, methyl, ethyl, vinyl or —C(=$CH_2$)$CH_3$.

44. The Ligand-Drug Conjugate composition of embodiment 43 wherein the quaternized tubulysin Drug Unit -$D^+$ has the structure of:

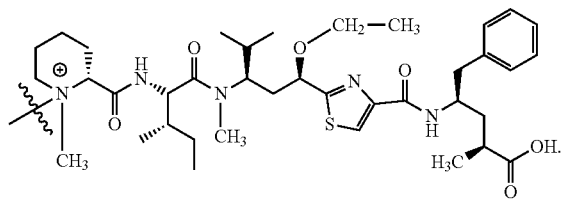

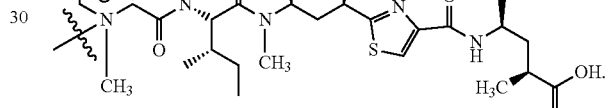

46. The Ligand-Drug Conjugate composition of embodiment 40 wherein the composition is represented by the structure of:

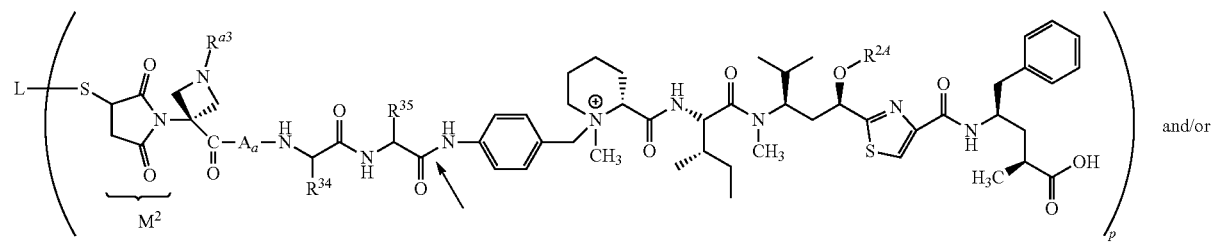

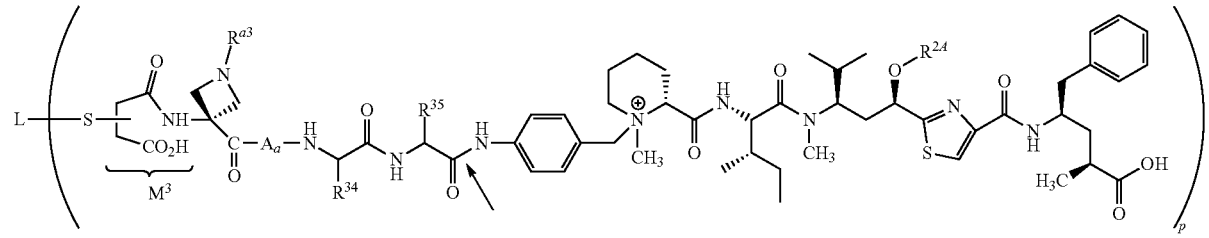

45. The Ligand-Drug Conjugate composition of embodiment 43 wherein the quaternized tubulysin Drug Unit -D has the structure of:

wherein subscript a is 1, so that A is present, wherein A is an α-amino acid or β-amino acid residue; R" is —H or $C_1$-$C_4$ alkyl; $R^{24}$ is —C(=O)$CH_3$, —$CH_2CH_3$, —CH$_2$CH=CH$_2$ or —CH$_2$C(=CH$_2$)CH$_3$; R$^{34}$ is isopropyl; R$^{35}$ is methyl or —(CH$_2$)$_3$NH(C=O)NH$_2$; and wherein the basic nitrogen atom bonded to R$^3$ is optionally protonated.

47. The Ligand-Drug Conjugate composition of embodiment 40 wherein the composition is represented by the structure of:

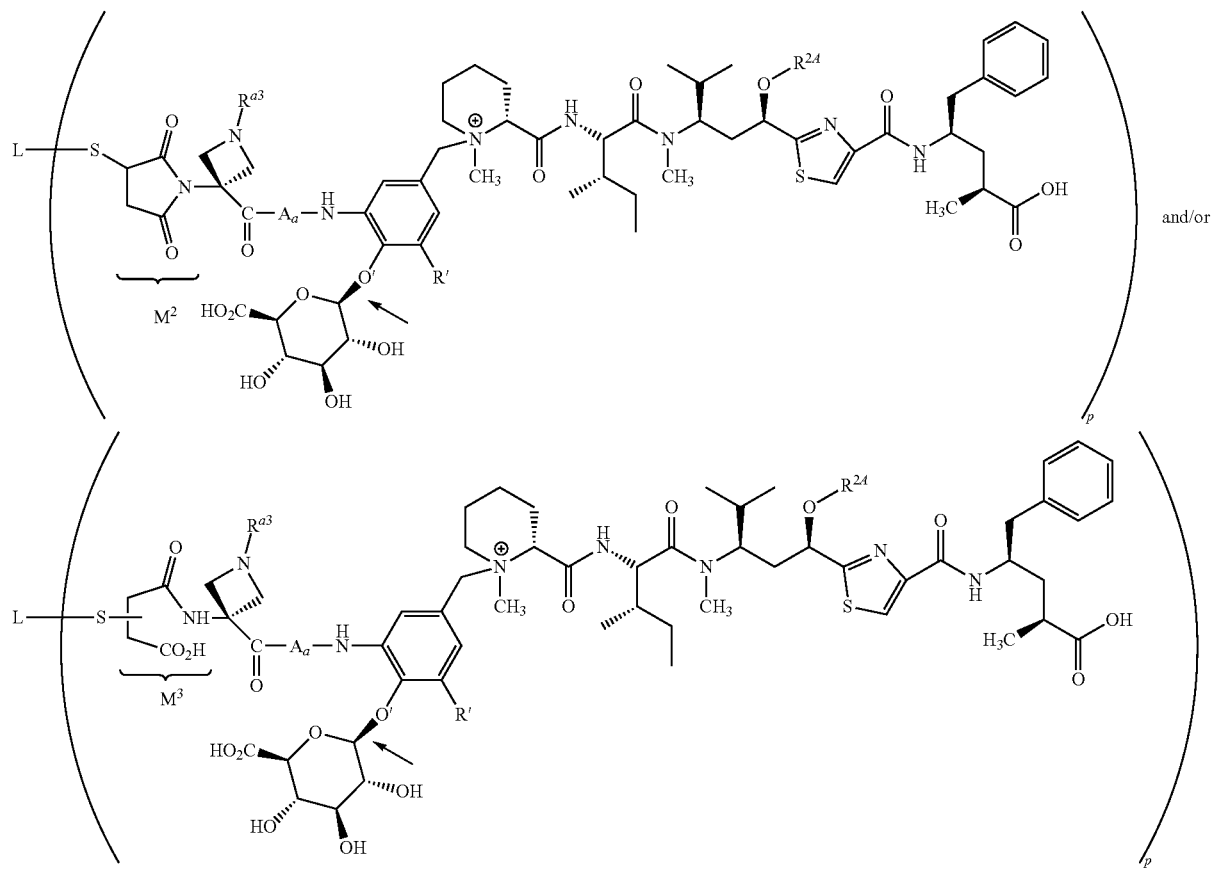

wherein subscript a is 1, so that A is present, wherein A is an α-amino acid or β-amino acid residue; R$^3$ is —H or C$_1$-C$_4$ alkyl; R$^{24}$ is —C(=O)CH$_3$, —CH$_2$CH$_3$, —CH$_2$CH=CH$_2$ or —CH$_2$C(=CH$_2$)CH$_3$; and wherein the basic nitrogen atom bonded to R$^3$ is optionally protonated.

48. The Ligand-Drug Conjugate composition of embodiment 12 wherein the composition is represented by the structure of:

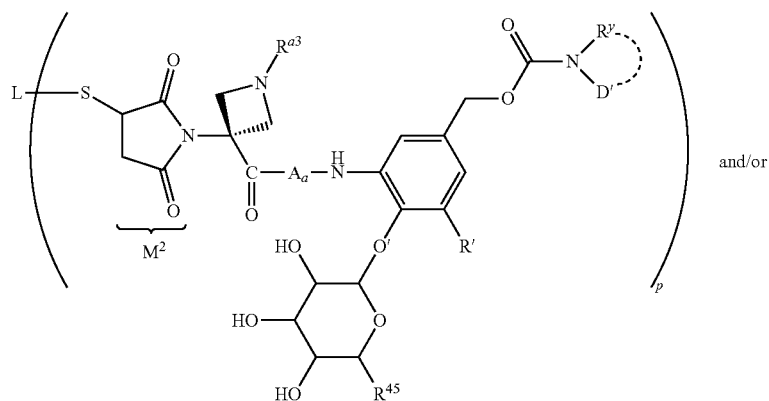

-continued

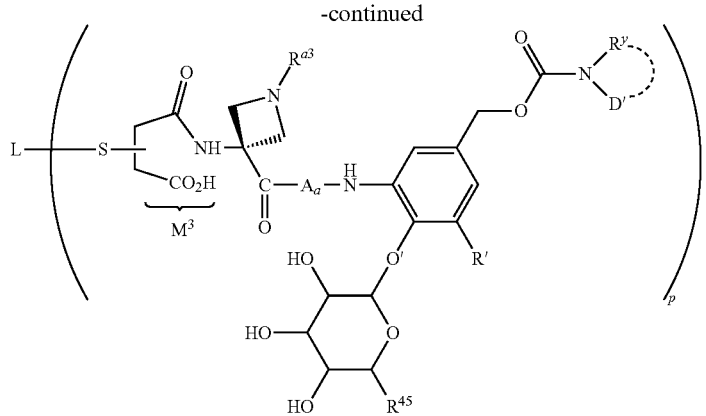

wherein $R^{a3}$ is —H, $C_1$-$C_6$ alkyl, —$C_1$-$C_4$ alkylene-($C_6$-$C_{10}$ aryl), or —$R^{PEG1}$—O—($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated; R' is hydrogen or —$NO_2$; $R^{45}$ is —$CH_2OH$ or —$CO_2H$; —N($R^y$)D' represents D, wherein D' is the remainder of D, and wherein the dotted line indicates optional cyclization of $R^y$ to D', wherein $R^y$ is hydrogen or optionally substituted $C_1$-$C_6$ alkyl in absence of cyclization to D' or $R^y$ is optionally substituted $C_1$-$C_6$ alkylene when cyclized to D'; wherein —O'— represents the oxygen heteroatom of an O-glycosidic bond cleavable by a glycosidase, wherein said cleavage within a compound of the Ligand Drug Conjugate composition initiates release of D as a primary or secondary amine-containing biologically active compound or derivative thereof from that Ligand Drug Conjugate compound.

49. The Ligand-Drug Conjugate composition of embodiment 12 wherein the composition is represented by the structure of:

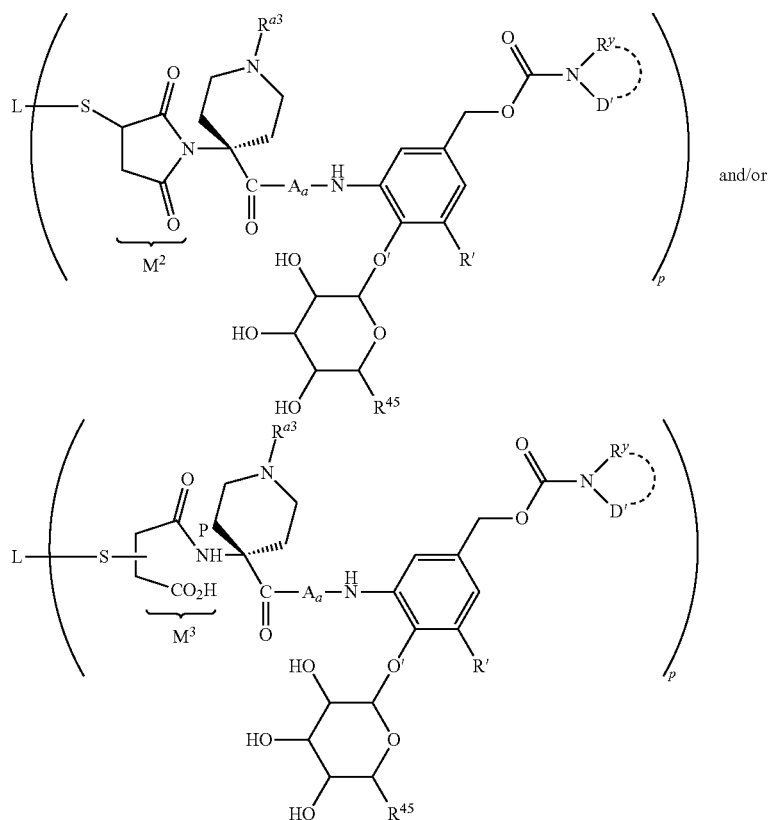

and/or wherein $R^{a3}$ is —H, $C_1$-$C_6$ alkyl, —$C_1$-$C_4$ alkylene-($C_6$-$C_{10}$ aryl), or —$R^{PEG1}$-O-($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated; R' is hydrogen or —$NO_2$; $R^{45}$ is —OH or —CO$_2$H; —N(R$^y$)D' represents D having covalent attachment to the remainder of the composition structure, wherein D' is the remainder of D, and wherein the dotted line indicates optional cyclization of R$^y$ to D', wherein R$^y$ is hydrogen or optionally substituted C$_1$-C$_6$ alkyl in absence of cyclization to D' or R$^y$ is optionally substituted C$_1$-C$_6$ alkylene when cyclized to D'; wherein —O'— represents the oxygen heteroatom of an O-glycosidic bond cleavable by a glycosidase, wherein said cleavage within a compound of the Ligand Drug Conjugate composition initiates release of D as a primary or secondary amine-containing biologically active compound or derivative thereof from that Ligand Drug Conjugate compound.

50. The Ligand-Drug Conjugate composition of embodiment 13, wherein the composition is represented by:

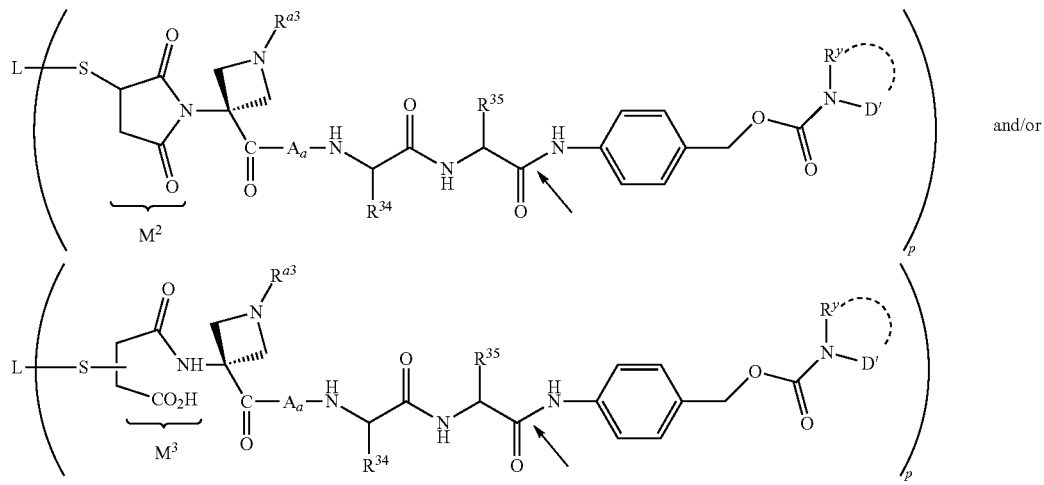

wherein R$^3$ is —H, C$_1$-C$_6$ alkyl, —C$_1$-C$_4$ alkylene-(C$_6$-C$_{10}$ aryl), or —R$^{PEG1}$—O—(CH$_2$CH$_2$O)$_{n'}$—R$^{PEG2}$, wherein R$^{PEG1}$ is C$_1$-C$_4$ alkylene, R$^{PEG2}$ is —H or C$_1$-C$_4$ alkyl, and subscript n' ranges from 1 to 36, wherein the basic nitrogen atom bonded to R$^{a3}$ is optionally protonated; R$^{34}$ is methyl or isopropyl; R$^{35}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H; —N(R$^y$)D' represents -D having covalent attachment to the remainder of the composition structure, wherein D' is the remainder of D, and wherein the dotted line indicates optional cyclization of R$^y$ to D', wherein R$^y$ is hydrogen or optionally substituted C$_1$-C$_6$ alkyl in absence of cyclization to D', or R$^y$ is optionally substituted C$_1$-C$_6$ alkylene when cyclized to D'; and wherein protease cleavage of the indicated bond within a compound of the Ligand Drug Conjugate composition initiates release of D as a primary or secondary amine-containing biologically active compound or derivative thereof from that Ligand Drug Conjugate compound.

51. The Ligand-Drug Conjugate composition of embodiment 13, wherein the composition is represented by:

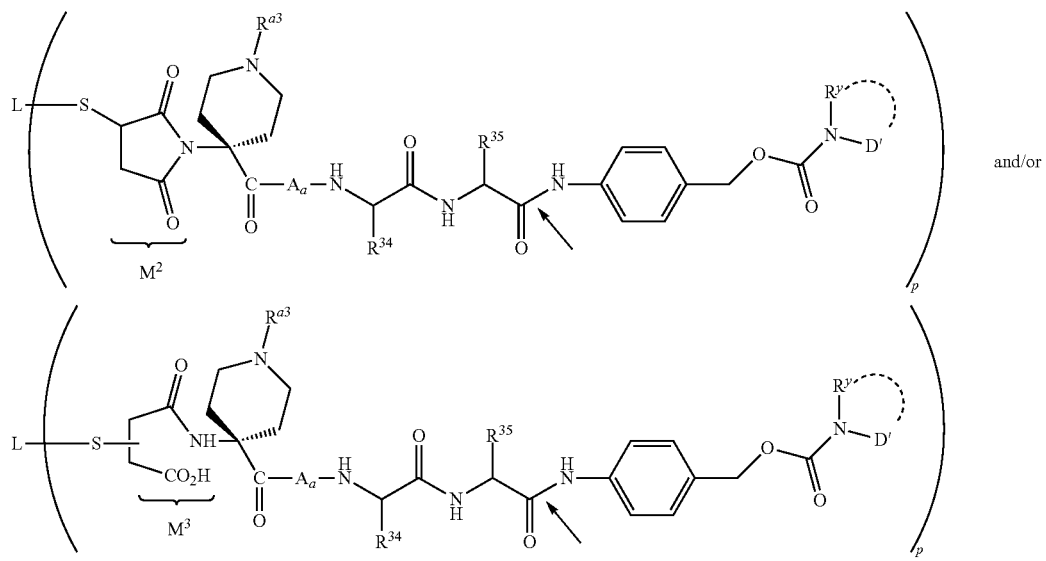

wherein $R^3$ is —H, $C_1$-$C_6$ alkyl, —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated; $R^{34}$ is methyl or isopropyl; $R^{35}$ is methyl, —$(CH_2)_4$—$NH_2$, —$(CH_2)_3NH(C=O)NH_2$, —$(CH_2)_3NH(C=NH)NH_2$, or, —$(CH_2)_2CO_2H$; —$N(R^y)D'$ represents -D having covalent attachment to the remainder of the composition structure, wherein D' is the remainder of D, and wherein the dotted line indicates optional cyclization of $R^y$ to D', wherein $R^y$ is hydrogen or optionally substituted $C_1$-$C_6$ alkyl in absence of cyclization to D', or $R^y$ is optionally substituted $C_1$-$C_6$ alkylene when cyclized to D'; and wherein protease cleavage of the indicated bond within a compound of the Ligand Drug Conjugate composition initiates release of D as a primary or secondary amine-containing biologically active compound or derivative thereof from that Ligand Drug Conjugate compound.

52. The Ligand-Drug Conjugate composition of any one of embodiments 24 to 27, wherein the released tertiary amine-containing biologically active compound or derivative thereof from $D^+$, or any one of claims 48-51, wherein the released primary or secondary amine-containing biologically active compound or derivative thereof from D is an auristatin drug compound thereby defining D as an auristatin Drug Unit or $D^+$ as a quaternized auristatin Drug Unit.

53. The Ligand-Drug Conjugate composition of embodiment 52, wherein the auristatin drug compound released from -D or -$D^+$ has the structure of:

compound is incorporated into the as -D and neither of $R^{10}$, $R^{11}$ is hydrogen when the auristatin drug compound is incorporated as -$D^+$:$R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl); $R^{13}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl and —$X^1$—($C_3$-$C_8$ heterocyclyl); $R^{14}$ is hydrogen or methyl, or $R^{13}$ and $R^{14}$ taken together with the carbon to which they are attached comprise a spiro $C_3$-$C_8$ carbocyclo; $R^{15}$ is hydrogen or $C_1$-$C_8$ alkyl; $R^{16}$ is hydrogen, $C_1$-$C_8$ alkyl, $C_3$-$C_8$ carbocyclyl, $C_6$-$C_{24}$ aryl, —$C_6$-$C_{24}$—$X^1$-aryl, —$X^1$—($C_3$-$C_8$ carbocyclyl), $C_3$-$C_8$ heterocyclyl and —$X^1$—($C_3$-$C_8$ heterocyclyl); $R^{17}$ independently are hydrogen, —OH, $C_1$-$C_8$ alkyl, $C_3$-$C_8$ carbocyclyl and O—($C_1$-$C_8$ alkyl); $R^{16}$ is hydrogen or optionally substituted $C_1$-$C_8$ alkyl; $R^{19}$ is —$C(R^{19A})_2$—$C(R^{19A})_2$—$C_6$-$C_{24}$ aryl, —$C(R^{19A})_2$—$C(R^{19A})_2$—($C_3$-$C_8$ heterocyclyl) or —$C(R^{19A})_2$—$C(R^{19A})_2$—($C_3$-$C_8$ carbocyclyl), wherein $C_6$-$C_{24}$ aryl and $C_3$-$C_8$ heterocyclyl are optionally substituted; $R^{19A}$ independently are hydrogen, optionally substituted $C_1$-$C_8$ alkyl, —OH or optionally substituted —O—$C_1$-$C_8$ alkyl; $R^{20}$ is hydrogen or $C_1$-$C_{20}$ alkyl, $C_6$-$C_{24}$ aryl or $C_3$-$C_8$ heterocyclyl, optionally substituted, or —$(R^{47}O)_m$—$R^{48}$, or —$(R^{47}O)_m$—$CH(R^{49})_2$; $R^{21}$ is —$C_1$-$C_8$ alkylene-($C_6$-$C_{24}$ aryl) or —$C_1$-$C_8$ alkylene-($C_5$-$C_{24}$ heteroaryl), optionally substituted, or $C_1$-$C_8$

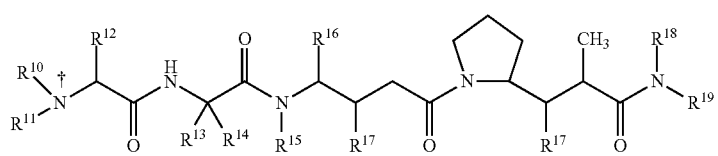

$D_E$

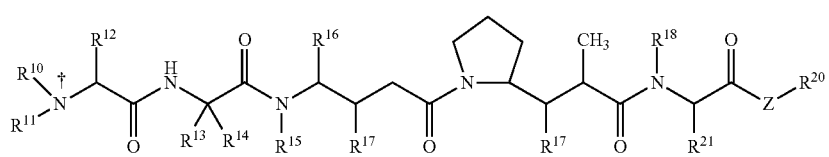

$D_F$ wherein the dagger indicates the site of covalent attachment of the nitrogen atom that provides a carbamate functional group, wherein —OC(=O)— of that functional group is Y', on incorporation of the auristatin drug compound as -D into a Ligand Drug Conjugate compound of the composition in which subscript y is 2, or results in a quaternary amine nitrogen on incorporation of the auristatin drug compound as -$D^+$ into a Ligand Drug Conjugate compound of the composition in which subscript y is 1;

$R^{10}$ and $R^{11}$ are independently selected from the group consisting of hydrogen and $C_1$-$C_8$ alkyl, provided that one of $R^{10}$, $R^{11}$ is hydrogen when the auristatin drug hydroxylalkyl, or optionally substituted $C_3$-$C_8$ heterocyclyl; Z is O, S, NH, or $NR^{46}$; $R^{46}$ is optionally substituted $C_1$-$C_8$ alkyl; subscript m is an integer ranging from 1-1000; $R^{47}$ is $C_2$-$C_8$ alkyl; $R^{48}$ is hydrogen or $C_1$-$C_8$ alkyl; $R^{49}$ independently are —COOH, —$(CH_2)_n$—$N(R^{50})_2$, —$(CH_2)_n$—$SO_3H$, or —$(CH_2)_n$—$SO_3$—$C_1$-$C_8$ alkyl; $R^{50}$ independently are $C_1$-$C_8$ alkyl, or —$(CH_2)_n$—COOH; subscript n is an integer ranging from 0 to 6; and $X^1$ is $C_1$-$C_{10}$ alkylene.

54. The Ligand-Drug Conjugate composition of embodiment 53, wherein the auristatin drug compound has the structure of Formula $D_{E-1}$, Formula $D_{E-2}$ or Formula $D_{F-1}$:

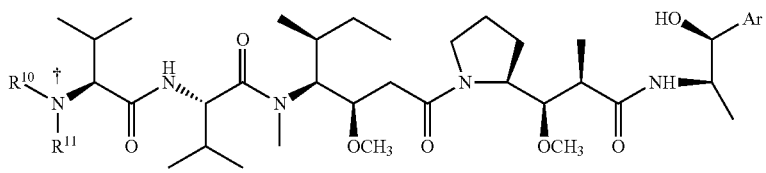
$D_{E-1}$

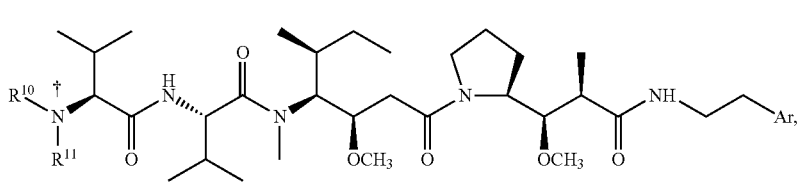
$D_{E-2}$

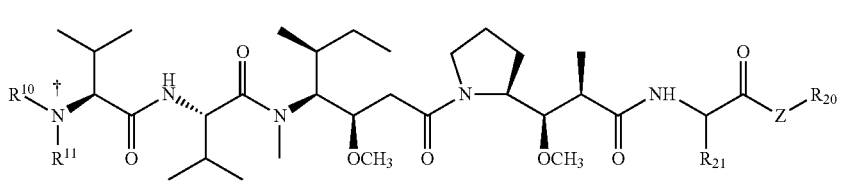
$D_{F-1}$ wherein Ar in Formula $D_{E-1}$ or Formula $D_{E-2}$ is $C_6$-$C_{10}$ aryl or $C_5$-$C_{10}$ heteroaryl, and in Formula $D_{F-1}$, Z is —O—, or —NH—; $R^{20}$ is hydrogen or $C_1$-$C_6$ alkyl, $C_6$-$C_{10}$ aryl or $C_5$-$C_{10}$ heteroaryl, optionally substituted; and $R^{21}$ is $C_1$-$C_6$ alkyl, —$C_1$-$C_6$ alkylene-($C_6$-$C_{10}$ aryl) or —$C_1$-$C_6$ alkylene-($C_5$-$C_{10}$ heteroaryl), optionally substituted.

55. The Ligand-Drug Conjugate composition of embodiment 54 wherein one of $R^{10}$ and $R^{11}$ is hydrogen or methyl and the other is methyl.

56. The Ligand-Drug Conjugate composition of embodiment 54 wherein in Formula $D_{E-1}$ or $D_{E-2}$, Ar is phenyl or 2-pyridyl.

57. The Ligand-Drug Conjugate composition of embodiment 54 wherein in Formula $D_{F-1}$, $R^{21}$ is $X^1$—S—$R^{21a}$ or $X^1$—Ar, wherein $X^1$ is $C_1$-$C_6$ alkylene, $R^{21a}$ is $C_1$-$C_4$ alkyl and Ar is phenyl or $C_5$-$C_6$ heteroaryl 58. The Ligand-Drug Conjugate composition of embodiment 54 wherein in Formula $D_{F-1}$, —Z— is —O— and $R^{20}$ is $C_1$-$C_4$ alkyl.

59. The Ligand-Drug Conjugate composition of embodiment 54 wherein in Formula $D_{F-1}$, Z is —NH— and $R^{20}$ is phenyl or $C_5$-$C_6$ heteroaryl.

60. The Ligand-Drug Conjugate composition of embodiment 53 wherein the auristatin drug compound has the structure of Formula $D_{F/E-3}$:

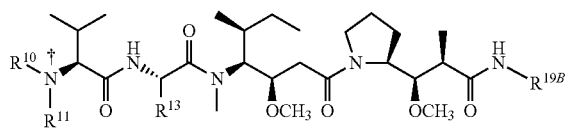
$D_{F/E-3}$ wherein one of $R^{10}$ and $R^{11}$ is hydrogen or methyl and the other is methyl; $R^{13}$ is isopropyl or —$CH_2$—CH $(CH_3)_2$; and $R^{19B}$ is —CH($CH_3$)—CH(OH)-Ph, —CH$(CO_2H)$—CH(OH)—$CH_3$, —CH($CO_2H$)—$CH_2$Ph, —CH($CH_2$Ph)-2-thiazolyl, —CH($CH_2$Ph)-2-pyridyl, —CH($CH_2$-p-$C_1$-Ph), —CH($CO_2$Me)-$CH_2$Ph, —CH$(CO_2Me)$-$CH_2CH_2SCH_3$, —CH($CH_2CH_2SCH_3$)C(=O)NH-quinol-3-yl, —CH($CH_2$Ph)C(=O)NH-p-$C_1$-Ph, or $R^{19B}$ has the structure of

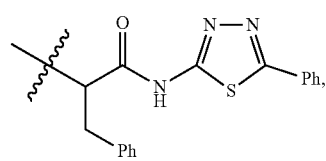 [SMILES: *C(Cc1ccccc1)C(=O)Nc1nnc(-c2ccccc2)s1]

wherein the wavy line indicates covalent attachment to the remainder of the auristatin compound.

61. The Ligand-Drug Conjugate composition of embodiment 53 wherein the released auristatin drug compound incorporated as an auristatin quaternized Drug Unit ($D^+$) is Auristatin E, Auristatin PE, Auristatin PHE, Auristatin PYE, Auristatin EFP, Auristatin EB and Auristatin EVB.

62. The Ligand-Drug Conjugate composition of embodiment 53 wherein the released auristatin drug compound incorporated into -D of a Ligand Drug Conjugate compound of the composition is monomethylauristatin E (MMAE) or monomethylauristatin F (MMAF), with covalent attachment of D through a carbamate functional group so that —OC(=O)— of that functional group is Y' wherein subscript y is 2.

63. The Ligand-Drug Conjugate composition of embodiment 53 wherein the composition is represented by the structure of:

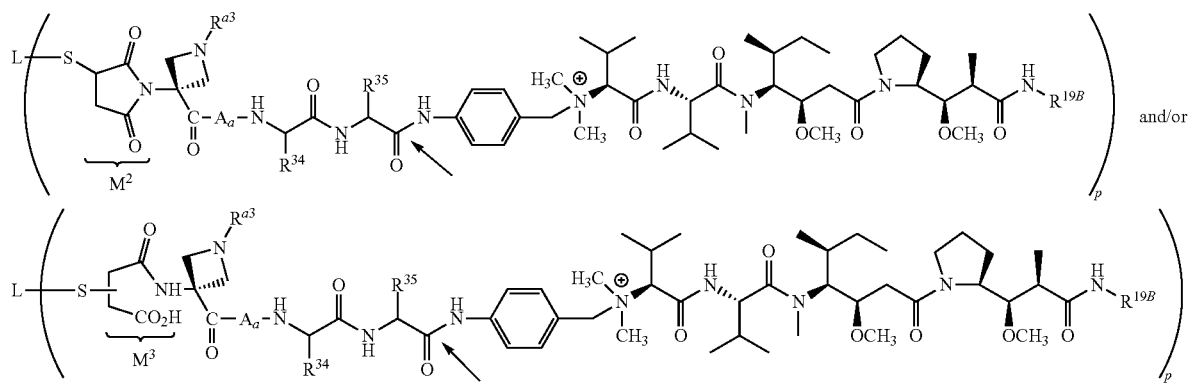

wherein subscript a is 1, so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen bonded to $R^{a3}$ is optionally protonated; $R^{19B}$ is —CH($CH_3$)—CH(OH)-Ph, —CH($CO_2H$)—CH(OH)—$CH_3$, or —CH($CO_2H$)—$CH_2$Ph; $R^{34}$ is isopropyl and $R^{35}$ is methyl or —$(CH_2)_3NH(C{=}O)NH_2$.

64. The Ligand-Drug Conjugate composition of embodiment 53 wherein the composition is represented by the structure of:

wherein subscript a is 1, so that A is present, wherein A is an α-amino acid or -amino acid residue; and $R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated.

65. The Ligand-Drug Conjugate composition of embodiment 53 wherein the composition is represented by the structure of:

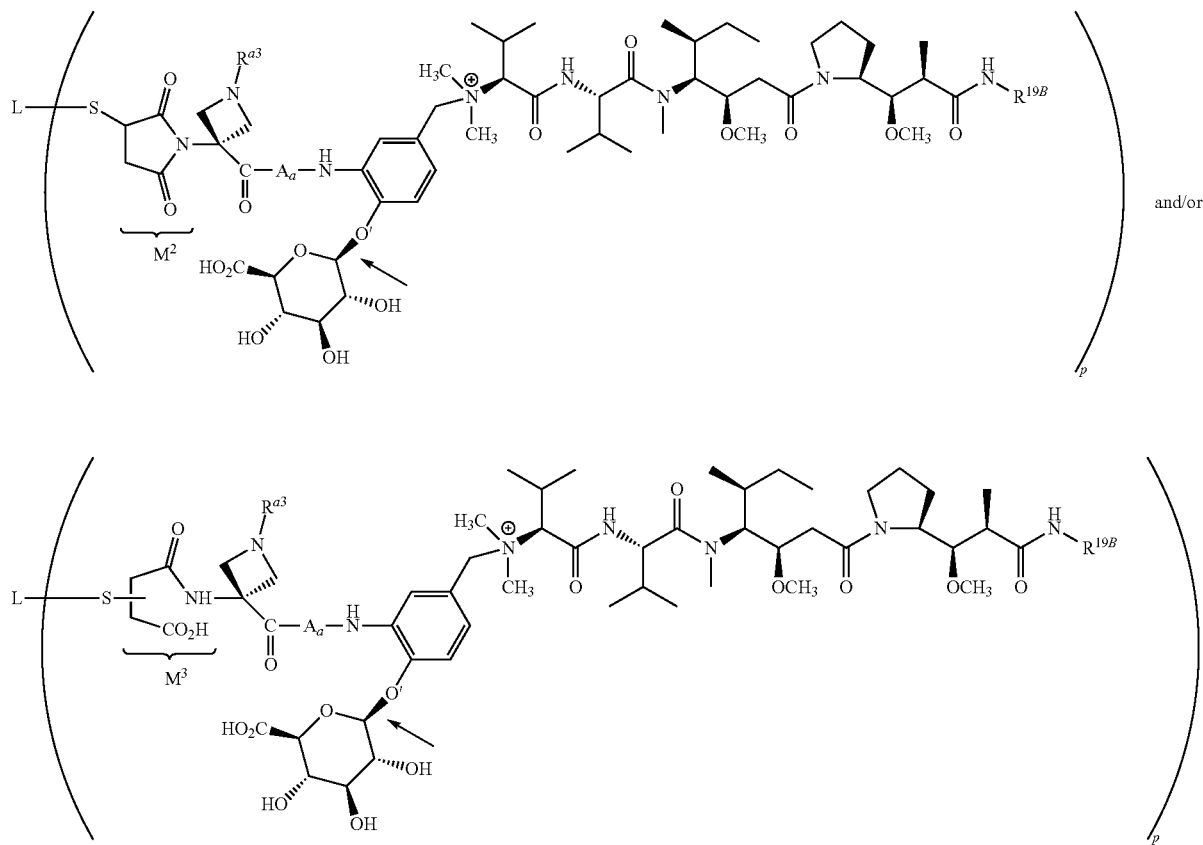

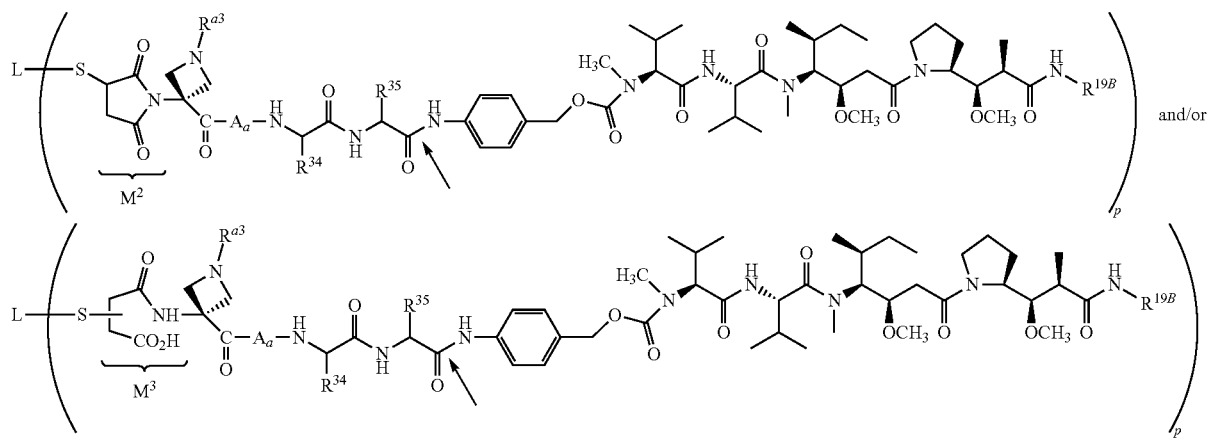

wherein subscript a is 1 so that A is present, wherein A is an α-amino acid or β-amino acid residue; $R^3$ is —H, optionally substituted $C_1$-$C_6$ alkyl, optionally substituted —$C_1$-$C_4$ alkylene-($C_6$-$C_{10}$ aryl), —$R^{PEG1}$—O—($CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^3$ is optionally protonated; $R^{19B}$ is —CH($CH_3$)—CH(OH)-Ph, —CH($CO_2H$)—CH(OH)—$CH_3$, or —CH($CO_2H$)—$CH_2$Ph; $R^{34}$ is isopropyl; and $R^{35}$ is methyl or —$(CH_2)_3$NH(C=O)$NH_2$.

66. The Ligand-Drug Conjugate composition of embodiment 53 wherein the composition is represented by the structure of:

wherein subscript a is 1, so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—($CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen bonded to $R^3$ is optionally protonated; and $R^{19B}$ is —CH($CH_3$)—CH(OH)-Ph, —CH($CO_2H$)—CH(OH)—$CH_3$, or —CH($CO_2H$)—$CH_2$Ph.

67. The Ligand-Drug Conjugate composition of embodiment 1, wherein subscript w is 1; subscript y is 1 or 2,

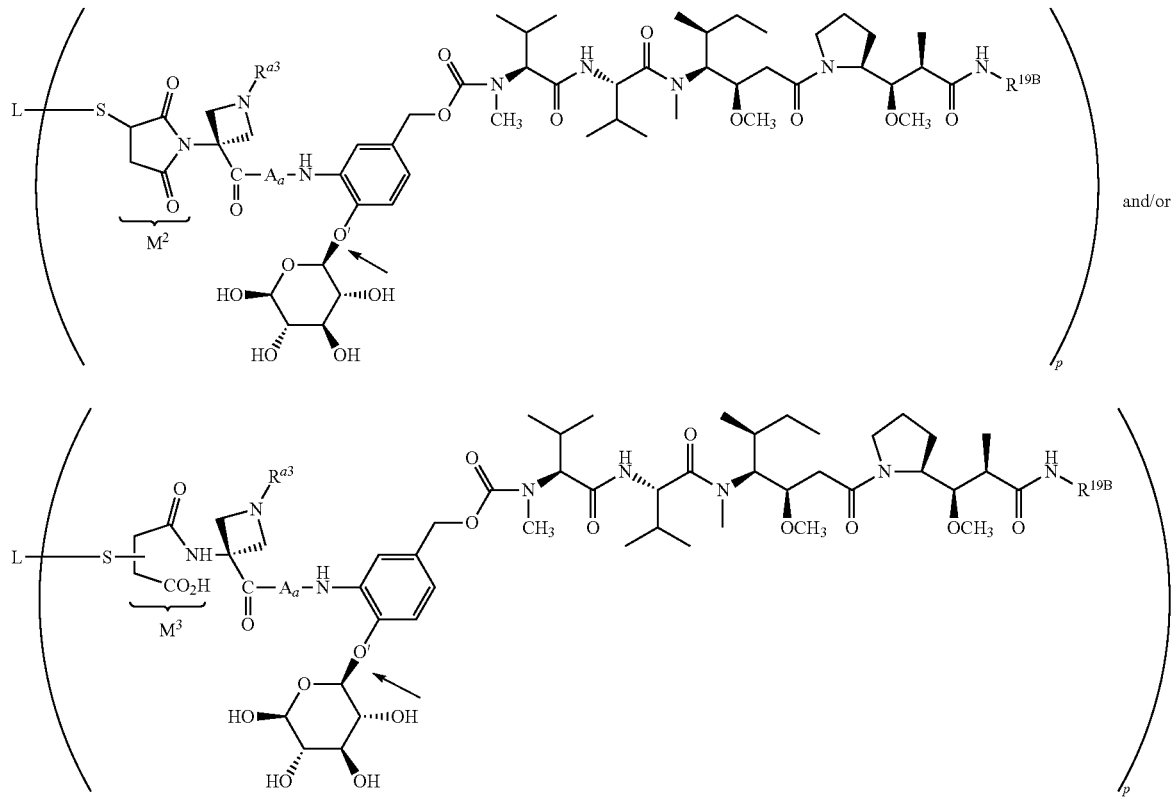

wherein Y attached to W is a self-immolative Spacer Unit; and D is that of a PBD dimer, thereby defining a PBD Drug Unit.

68. The Ligand-Drug Conjugate composition of claim 67 wherein the PBD Drug Unit has the structure of:

substituents independently selected from the group consisting of halo, nitro, cyano, —OR, $C_1$-$C_7$ alkyl, $C_3$-$C_7$ heterocyclyl, dimethyl-aminopropyloxy, piperazinyl and bis-oxy-$C_1$-$C_3$ alkylene, wherein R is as previously defined.

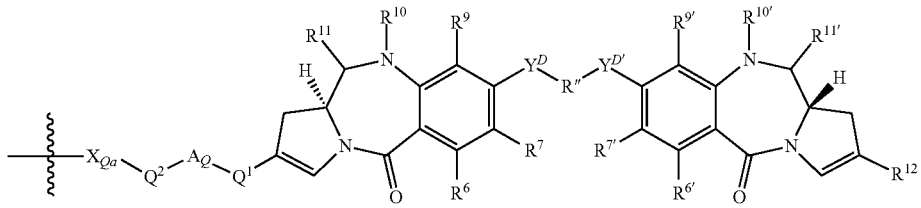

wherein the wavy line indicates the point of covalent attachment of the PBD Drug Unit to the remainder of composition structure; $A_Q$ is phenylene or $C_5$-$C_7$ heteroarylene, optionally substituted; $X_{Qa}$ is selected from the group consisting of —O—, —S—, —C(=O)O—, —C(=O)—, —NH(C=O)—, and —N($R^N$)—, wherein $R^N$ is selected from the group consisting of H, $C_1$-$C_4$ alkyl and $(C_2H_4O)_{n'}$—$CH_3$, wherein subscript n' ranges from 1 to 36, and either:

(i) $Q^1$ is a single bond, and $Q^2$ is selected from the group consisting of a single bond and —Z—$(CH_2)_n$—, wherein Z is selected from the group consisting of a single bond, O, S and NH, and subscript n ranges from 1 to 3, or (ii) $Q^1$ is —CH=CH—, and $Q^2$ is a single bond; and $R^{12}$ is $C_6$-$C_{10}$ aryl or $C_5$-$C_{10}$ heteroaryl; $R^6$ and $R^9$ are independently selected from the group consisting of H, R, OH, OR, SH, SR, $NH_2$, NHR, NRR', nitro and halo; $R^7$ is selected from the group consisting of H, R, OH, OR, SH, SR, $NH_2$, NHR, NRR', nitro and halo; R and R' are independently selected from the group consisting of optionally substituted $C_1$-$C_{12}$ alkyl, $C_3$-$C_{20}$ heterocyclyl, $C_6$-$C_{24}$ aryl and $C_5$-$C_{24}$ heteroaryl; and either: (a) $R^{10}$ is H, and $R^{11}$ is OH or $OR^A$, wherein $R^A$ is $C_1$-$C_4$ alkyl, (b) $R^{10}$ and $R^{11}$ form a nitrogen-carbon double bond between the nitrogen and carbon atoms to which they are attached, or (c) $R^{10}$ is H and $R^{11}$ is $SO_zM$, wherein subscript z is 2 or 3 and M is a monovalent cation; and R" is $C_3$-$C_{12}$ alkylene, the carbon chain of which is optionally interrupted by one, two or three heteroatoms selected from the group consisting of O, S and NH, and/or by an aromatic ring; $Y^D$ is selected from the group consisting of O, S and NH; $R^{6'}$, $R^{7'}$, $R^{9'}$, and $Y^{D'}$ are independently selected from the same groups as $R^6$, $R^7$, $R^9$, and $Y^D$, respectively, and $R^{10'}$ and $R^{11'}$ are selected independently from the same groups as $R^{10}$ and $R^{11}$, respectively, provided if $R^{11}$ and $R^{11'}$ are each $SO_zM$, each M is an independently selected monovalent cation or together represents a divalent cation; and wherein optional substitution is by one, two or three 69. The Ligand-Drug Conjugate composition of embodiment 68, wherein $R^7$ is selected from the group consisting of H, OH and OR.

70. The Ligand-Drug Conjugate composition of embodiment 69, wherein $R^7$ is $C_1$-$C_4$ alkyloxy.

71. The Ligand-Drug Conjugate composition of embodiment 68, 69 or 70, wherein $Y^D$ is O.

72. The Ligand-Drug Conjugate composition of any one of embodiments 68 to 71, wherein R" is $C_3$-$C_7$ alkylene.

73. The Ligand-Drug Conjugate composition of any one of embodiments 68 to 72, wherein $R^9$ is H.

74. The Ligand-Drug Conjugate composition of any one of embodiments 68 to 73, wherein $R^6$ is selected from the group consisting of H and halo.

75. The Ligand-Drug Conjugate composition of any one of embodiments 68 to 74, wherein $A_Q$ is phenyl.

76. The Ligand-Drug Conjugate composition of any one of embodiments 68 to 75, wherein $X_{QA}$ is selected from the group consisting of —O—, —S— and —NH—.

77. The Ligand-Drug Conjugate composition of any one of embodiments 68 to 76, wherein $Q^1$ is a single bond.

78. The Ligand-Drug Conjugate composition of any one of embodiments 68 to 76, wherein $Q^1$ is —CH=CH—.

79. The Ligand-Drug Conjugate composition of any one of embodiments 68 to 78, wherein $Q^2$ is a single bond.

80. The Ligand-Drug Conjugate composition of any one of embodiments 68 to 78, wherein $Q^2$ is —Z—$(CH_2)_n$—, Z is O or S and subscript n is 1 or 2.

81. The Ligand-Drug Conjugate composition of any one of embodiments 68 to 80, wherein $R^{12}$ is phenyl or $C_5$-$C_6$ heteroaryl, optionally substituted.

82. The Ligand-Drug Conjugate composition of embodiment 81, wherein $R^{12}$ is optionally substituted phenyl.

83. The Ligand-Drug Conjugate composition of embodiment 82, wherein $R^{12}$ is p-methoxyphenyl.

84. The Ligand-Drug Conjugate composition according to any one of embodiments 68 to 83, wherein $R^{10}$ and $R^{11}$ form a nitrogen-carbon double bond.

85. The Ligand-Drug Conjugate composition of any one of embodiments 68 to 84, wherein $R^{6'}$, $R^{7'}$, $R^{9'}$, $R^{1'}$, $R^{11'}$ and $Y^{D'}$ are the same as $R^6$, $R^7$, $R^9$, $R^{10}$, $R^{11}$ and $Y^D$ respectively.

86. The Ligand-Drug Conjugate composition of embodiment 68, wherein the composition is represented by the structure of:

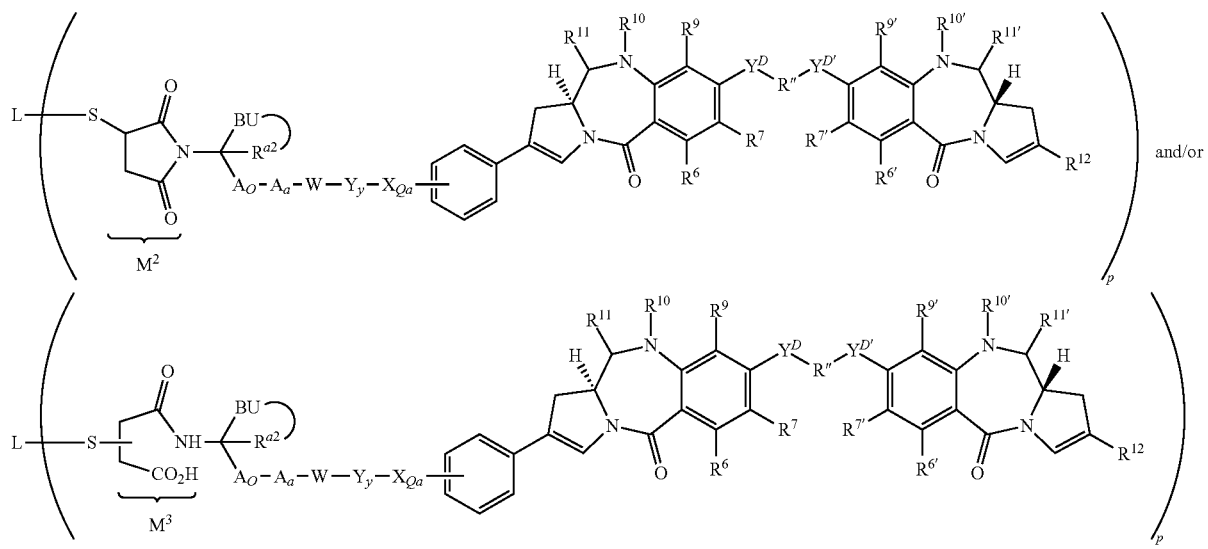

W is a Peptide Cleavable Unit; and subscript y is 1 or 2, wherein Y bonded to W is a self-immolative Spacer Unit, wherein the bond between W and that self-immolative Spacer Unit in a compound of the Ligand Drug Conjugate composition is cleavable by a protease to initiate release of the PBD Drug Unit as a PBD dimer from that Ligand Drug Conjugate compound, or subscript y is 0, wherein W is bonded to $X_{QA}$, wherein the bond between W and $X_{QA}$ in a compound of the Ligand Drug Conjugate composition is cleavable by a protease to initiate release of the PBD Drug Unit as a PBD dimer from that Ligand Drug Conjugate compound.

87. The Ligand-Drug Conjugate composition of embodiment 86 wherein the composition is represented by the structure of:

wherein subscript P is 1 or 2; subscript Q ranges from 1 to 6; and $X_{Qa}$ is —NH; $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—($CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated.

88. The Ligand-Drug Conjugate composition of embodiment 87, wherein subscript P is 1 and subscript Q is 1, 2 or 3 or subscript P is 2 and Q is 1 or 2.

89. The Ligand-Drug Conjugate composition of embodiment 88, wherein subscript P is 1, subscript Q is 1.

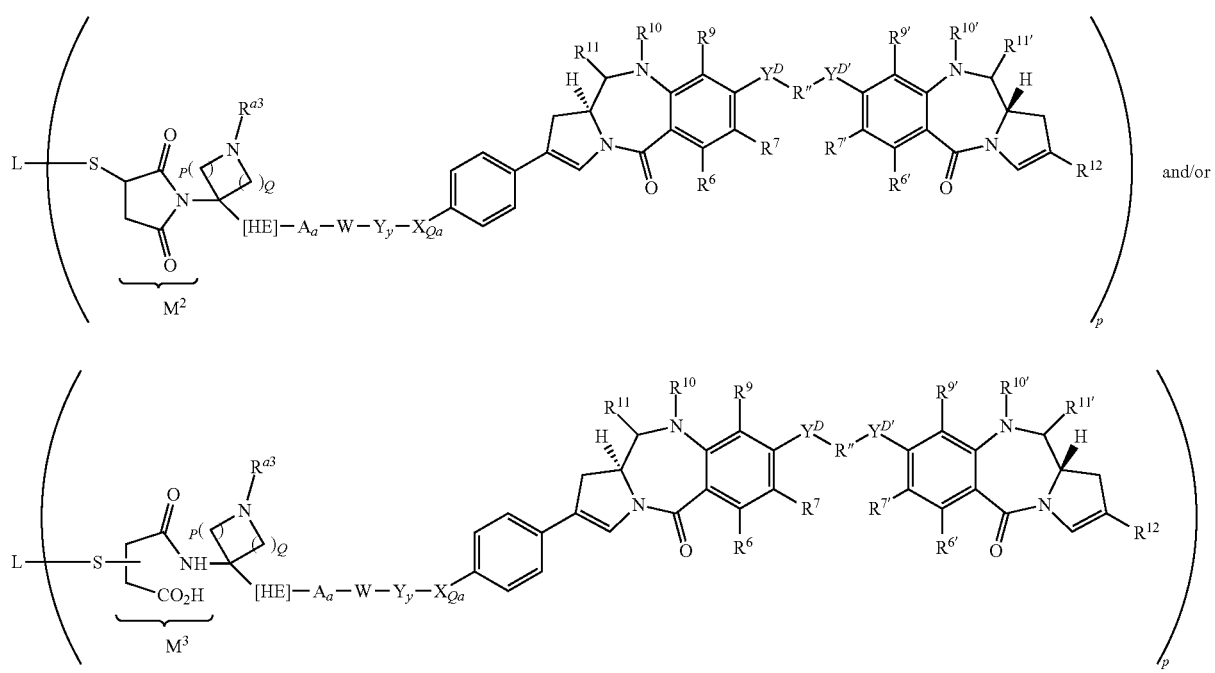

90. The Ligand-Drug Conjugate composition of embodiment 89, wherein the composition is represented by the structure of:

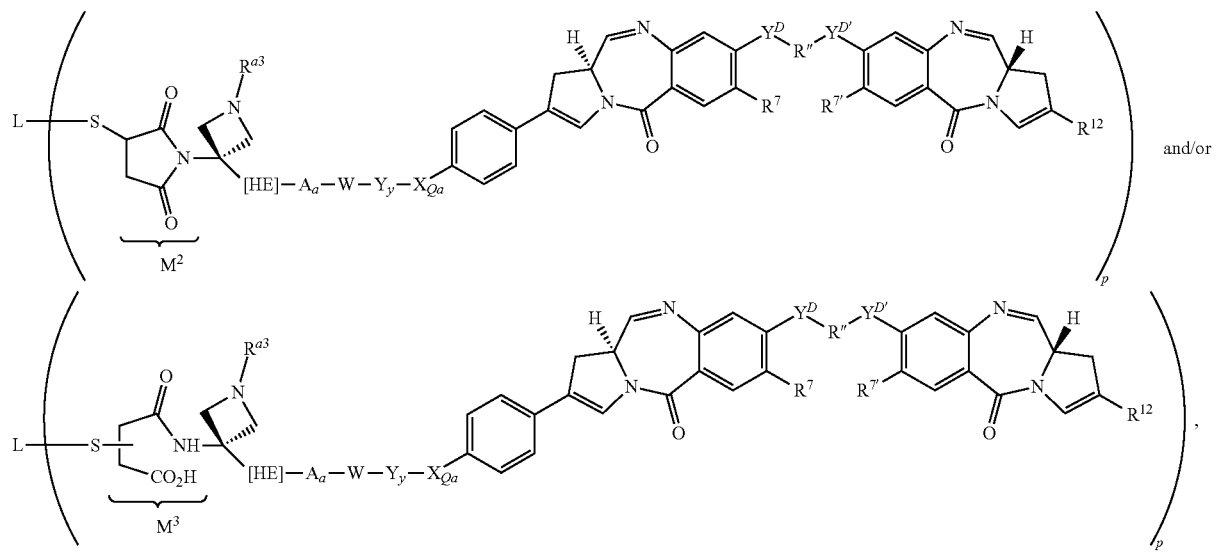

wherein $X_{Qa}$ is —NH—; $R^{a3}$ is —H, $C_1$-$C_4$ alkyl or —$R^{PEG1}$—O—$(CH_2CH_2O)_{n'}$—$R^{PEG2}$; $R^{PEG1}$ is —$CH_2$— or —$CH_2CH_2$—; $R^{PEG2}$ is —H, —$CH_3$ or —$CH_2CH_3$; subscript n' ranges from 1 to 36; and wherein the basic nitrogen atom bonded to $R^{a3}$ is optionally protonated.

91. The Ligand-Drug Conjugate composition of embodiment 89, wherein the composition is represented by the structure of:

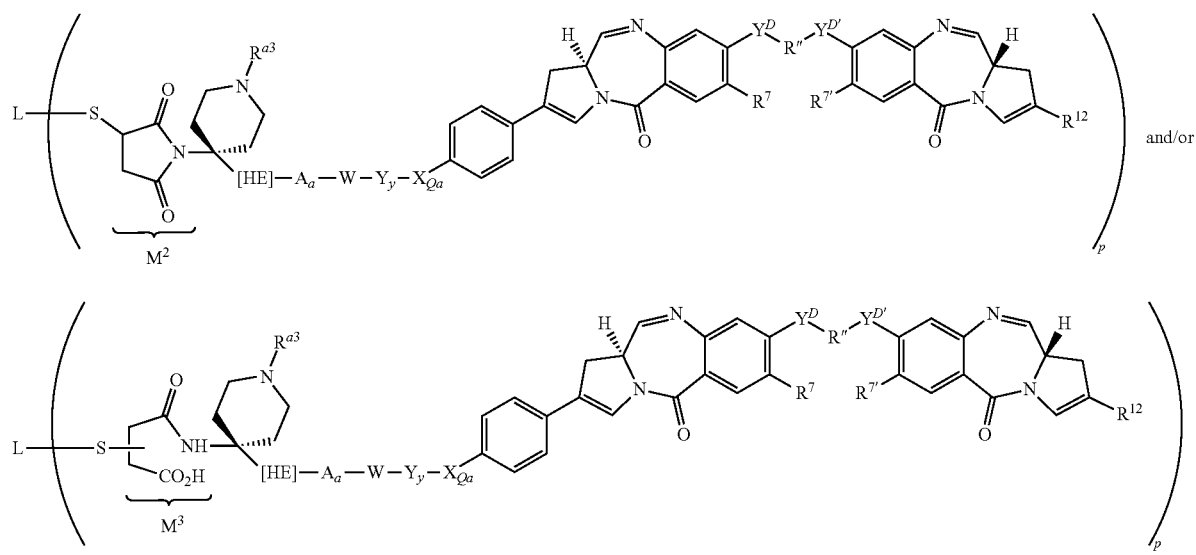

wherein $X_{Qa}$ is —NH—; $R^{a3}$ is —H, $C_1$-$C_4$ alkyl, or —$R^{PEG1}$—O—$(CH_2CH_2O)_{n'}$—$R^{PEG2}$; $R^{PEG1}$ is —$CH_2$— or —$CH_2CH_2$—; $R^{PEG2}$ is —H, —$CH_3$ or —$CH_2CH_3$; subscript n' ranges from 1 to 36; and wherein the basic nitrogen atom bonded to $R^{a3}$ is optionally protonated.

92. The Ligand-Drug Conjugate composition of any one of embodiments 86 to 91, wherein $Y^D$ and YD' are 0; $R^7$ is —OR and $R^{7'}$ is —OR', wherein R and R' are the same $C_1$-$C_6$ alkyl; and $R^{12}$ is optionally substituted phenyl.

93. The Ligand-Drug Conjugate composition of any one of embodiments 86 to 92, wherein R" is $C_3$-$C_8$ alkylene; $R^7$ and $R^{7'}$ are —$OCH_3$; subscript a is 0, so that A is absent, or subscript a is 1, so that A is present, wherein A is an amino acid residue, —NH—$R^{PEG1}$—O—$(CH_2CH_2O)_{n'}$—$R^{PEG3}$—C(=O)—, or other amine-containing acid moiety when HE is —C(=O), or A is $C_1$-$C_6$ alkylene-C(=O) or —$R^{PEG1}$—O—$(CH_2CH_2O)_{n'}$—$R^{PEG3}$—C(=O) when HE is absent; $R^{PEG1}$ and $R^{PEG3}$ are independently selected form the group consisting of —$CH_2$— and —$CH_2CH_2$—; $R^{PEG2}$ are independently selected form the group consisting of —H, —$CH_3$ and —CH$_2$CH$_3$; and subscript n' independently ranges from 1 to 36.

94. The Ligand-Drug Conjugate composition of embodiment 90, wherein the composition is represented by the structure of:

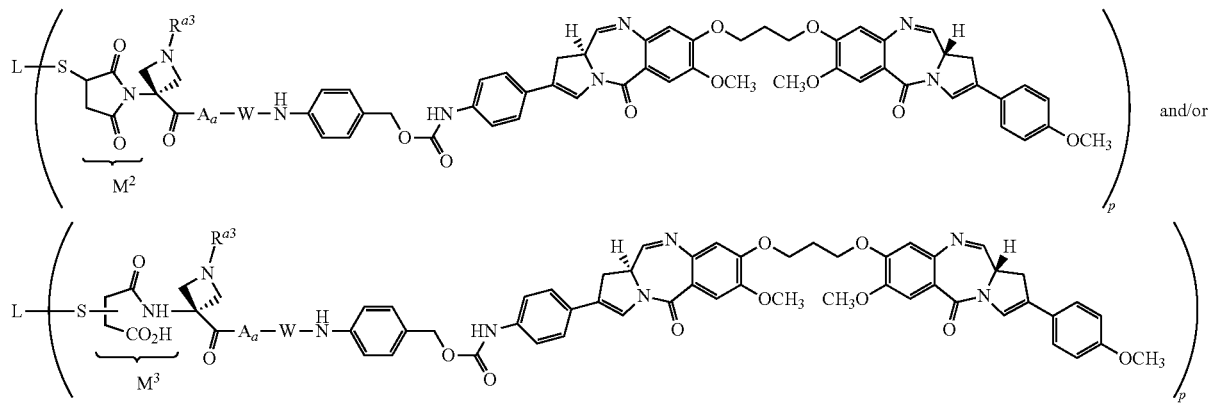

wherein A, if present, is an α-amino acid or a β-amino acid residue; and R$^{a3}$ is —H, wherein the basic nitrogen atom bonded to R$^{a3}$ is optionally protonated.

95. The Ligand-Drug Conjugate composition of embodiment 90, wherein the composition is represented by the structure of:

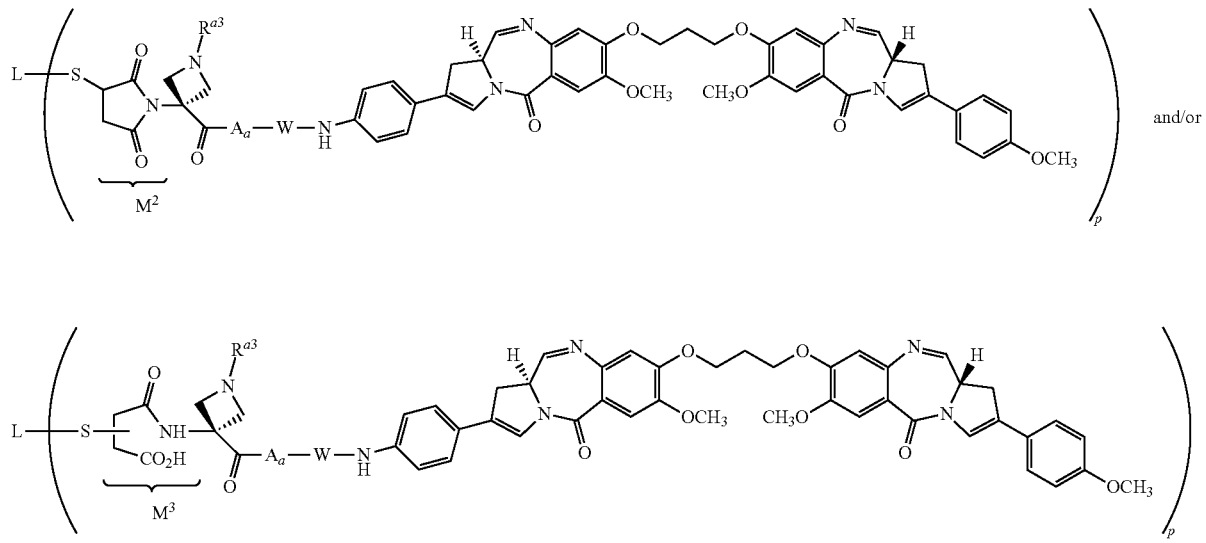

wherein A, if present, is an α-amino acid or β-amino acid residue; and R$^{a3}$ is —H, wherein the basic nitrogen atom bonded to R$^{a3}$ is optionally protonated.

96. The Ligand-Drug Conjugate composition of any one of embodiments 1 to 95, wherein if D/D$^+$, is that of a biologically active compound or derivative thereof, wherein that compound or its derivative is hydrophobic or has a S log P<0, then A or a subunit thereof is -L$^P$(PEG)-.

97. The Ligand-Drug Conjugate composition of embodiment 96 wherein -L$^P$- or a subunit thereof is a aminoalkane- dioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

98. The Ligand-Drug Conjugate composition of embodiment 96 wherein -L$^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

99. The Ligand-Drug Conjugate composition of embodiment 96 wherein L$_P$ or a subunit thereof is selected from the group consisting of lysine, glutamic acid, aspartic acid, cysteine, penicillamine, serine or threonine in its D- or L-stereochemical configuration.

100. The Ligand-Drug Conjugate composition of embodiment 96, wherein -L$^P$- or a subunit thereof has the structure of Formula L$^P$-1 or L$^P$-2:

(Formula L^P-1)

(Formula L^P-2)

wherein subscript v is an integer ranging from 1 to 4; subscript v' is an integer ranging from 0 to 4; $X^{LP}$ is provided by a natural or un-natural amino acid side chain or is selected from the group consisting of —O—, —$NR^{LP}$—, —S—, —S(=O)—, —S(=O)$_2$—, —C(=O)—, —C(=O)N($R^{LP}$)—, —N($R^{LP}$)C(=O)N($R^{LP}$)—, and —N($R^{LP}$)C(=N$R^{LP}$)N($R^{LP}$)—, or $C_3$-$C_8$ heterocyclo; wherein each $R^{LP}$ is independently selected from the group consisting of hydrogen and optionally substituted $C_1$-$C_6$ alkyl, or two of $R^{LP}$ together along with the carbons atoms to which they are attached and their intervening atoms define a $C_5$-$C_6$ heterocyclo and any remaining $R^{LP}$ are as previously defined; Ar is a $C_6$-$C_{10}$ arylene or a $C_5$-$C_{10}$ heteroarylene, optionally substituted; each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene or optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined; wherein one of the wavy lines indicate the point of covalent attachment of a PEG Unit and the other wavy lines indicates covalent attachment of Formula $L^P$-1 or Formula $L^P$-2 within the structure representing the Ligand Drug Conjugate composition.

101. The Ligand-Drug Conjugate composition of embodiment 96 wherein -$L^P$(PEG)- has the structure of Formula $L^P$-3 or Formula $L^P$-4:

(Formula L^P-3)

(Formula L^P-4)

102. The Ligand-Drug Conjugate composition of embodiment 100 or 101 wherein the side chain of —C($R^E$)($R^F$)—$X^{LP}$ is provided by a natural or un-natural amino acid side chain.

103. The Ligand-Drug Conjugate composition of embodiment 100 or 101 wherein $R^E$ and $R^F$ are independently selected from the group consisting of —H, and —$C_1$-$C_4$ alkyl.

104. The Ligand-Drug Conjugate composition of any one of embodiments 100 to 103 wherein $X^{LP}$ is selected from the group consisting of —O—, —NH, —S— and —C(=O)—.

105. The Ligand-Drug Conjugate composition of embodiment 101 wherein the composition is represented by the structure of Formula 1a or Formula 2a:

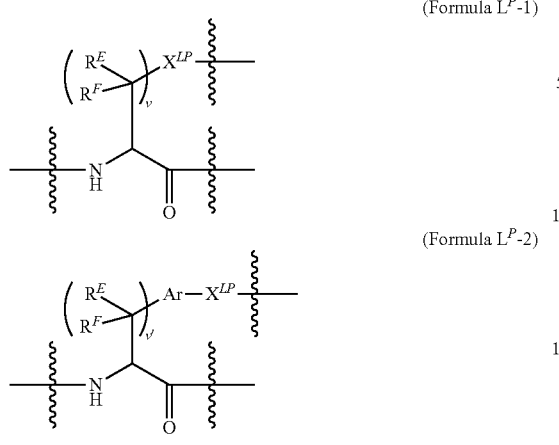

(Formula 1a)

and/or (Formula 2a)

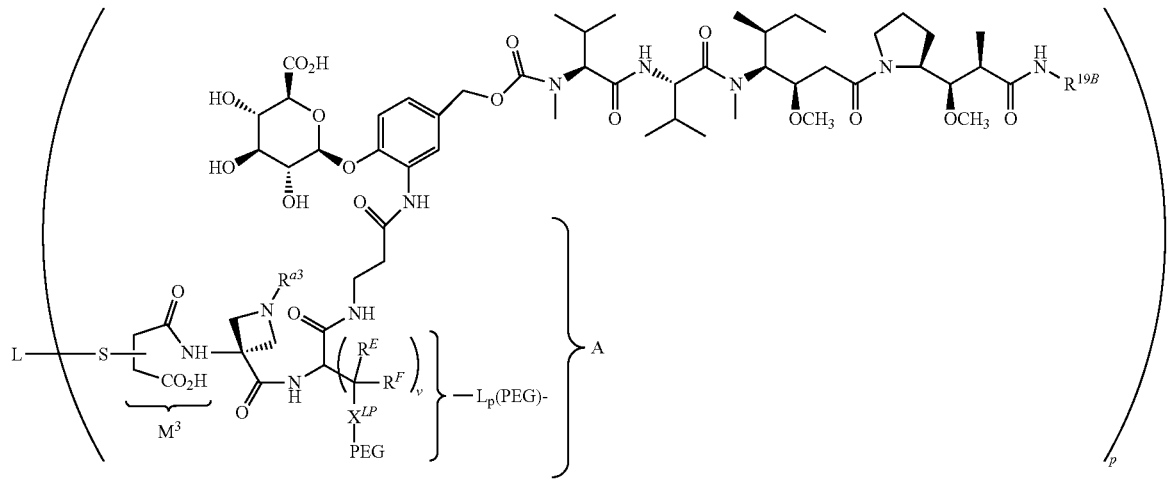

wherein $R^3$ is —H, optionally substituted $C_1$-$C_6$ alkyl or optionally substituted —$C_1$-$C_4$ alkylene-($C_6$-$C_{10}$ aryl), wherein the basic nitrogen atom bonded to $R^{a3}$ is optionally protonated; $R^{19B}$ is —CH(CH$_3$)—CH(OH)-Ph, —CH(CO$_2$H)—CH(OH)—CH$_3$, or —CH(CO$_2$H)—CH$_2$Ph; S is a sulfur atom of the Ligand Unit, wherein that sulfur atom in Formula 2a is bonded the carbon α or β to the carboxylic acid functional group of the indicated succinic acid amide ($M^3$) moiety.

106. The Ligand-Drug Conjugate composition of embodiment 101 wherein the composition is represented by the structure of Formula 1b or Formula 2b:

(Formula 1b)

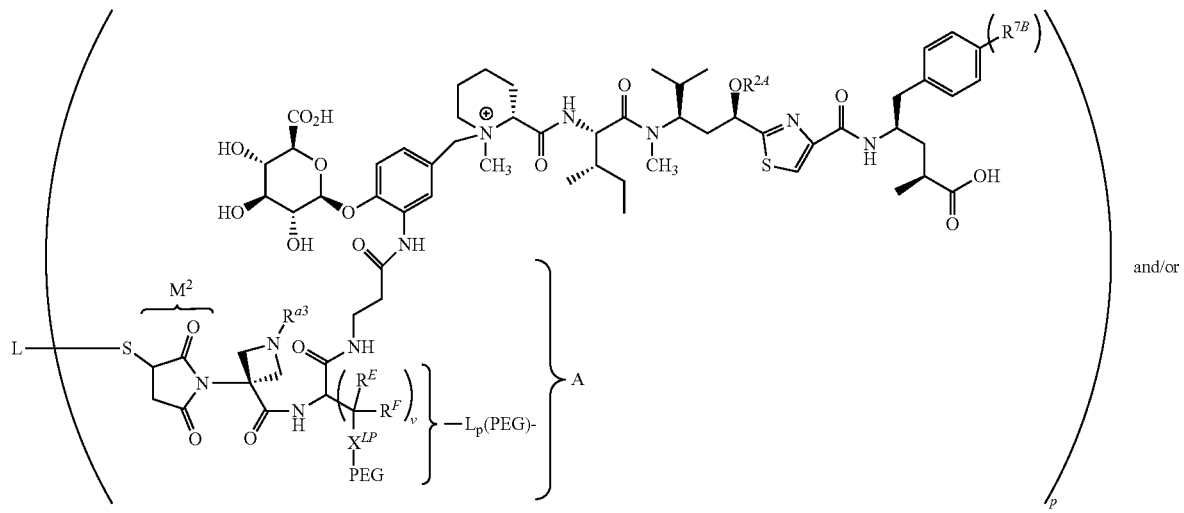

and/or

-continued (Formula 2b)

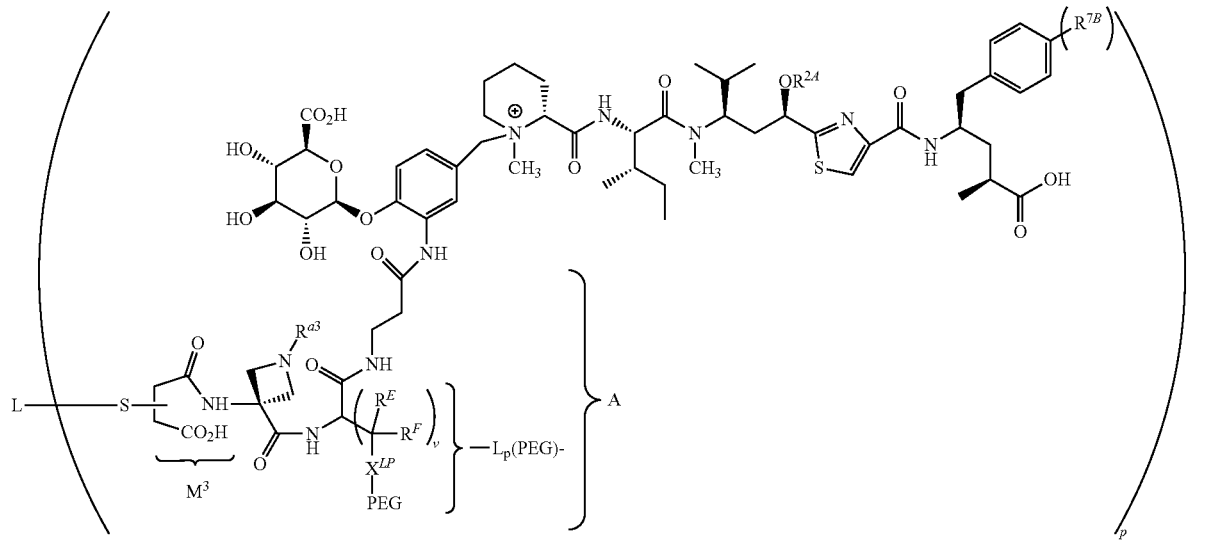

wherein $R^{2A}$ is —C(=O)CH$_3$, —CH$_2$CH$_3$, —CH$_2$CH=CH$_2$ or —CH$_2$C(=CH$_2$)CH$_3$; $R^{a3}$ is —H, optionally substituted C$_1$-C$_6$ alkyl or optionally substituted —C$_1$-C$_4$ alkylene-(C$_6$-C$_{10}$ aryl), wherein the basic nitrogen atom bonded to $R^{a3}$ is optionally protonated; subscript u is 0 or 1; and $R^{7B}$ is —OH when subscript u is 1 or is absent when subscript u is 0.

107. The Ligand-Drug Conjugate composition of any one of embodiments 96 to 106 wherein PEG has the structure selected from the group consisting of:

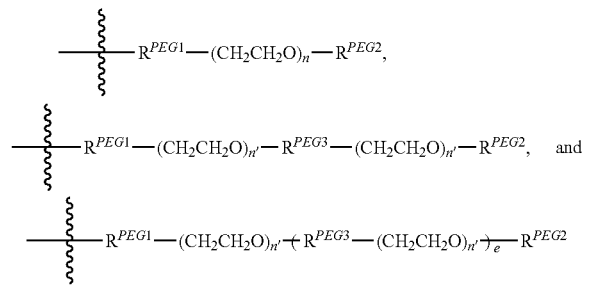

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

108. The Ligand-Drug Conjugate composition of any one of embodiments 101 to 106 wherein —$X^{LP}$—PEG has the structure of:

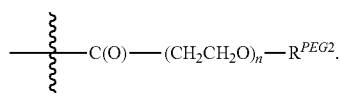

109. The Ligand-Drug Conjugate composition of embodiment 107 or 108 wherein subscript n is 12 and $R^{PEG2}$ is hydrogen or —CH$_3$.

110. The Ligand-Drug Conjugate composition of any one of embodiments 5 to 22 wherein —Y'-D has the structure of:

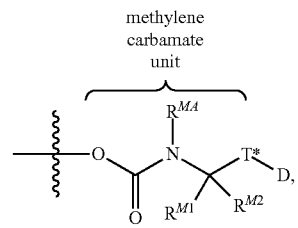

methylene carbamate unit wherein Y' is a methylene carbamate unit; the wavy line indicates the point of covalent attachment of the methylene carbamate unit to the remainder of the Ligand Drug Conjugate composition structure; D is a Drug Unit having an optionally substituted functional group incorporated into the methylene carbamate unit; T* is a heteroatom of said Drug Unit functional group; $R^{MA}$, $R^{M1}$ and $R^{M2}$ independently are hydrogen, optionally substituted C$_1$-C$_6$ alkyl, optionally substituted C$_6$-C$_{14}$ aryl, or optionally substituted C-linked C$_3$-C$_8$ heteroaryl, or $R^{MA}$ and $R^{M1}$ together with the nitrogen and carbon atoms to which both are attached define an azetidine, pyrrolidine, piperidine or homopiperidine heterocyclo, and $R^{M2}$ is hydrogen; wherein activation of the Glucuronide Unit or Peptide Cleavable Unit within a compound of the Ligand Drug Conjugate composition initiates releases of D from that compound as a biologically active compound or derivative thereof having a functional group comprised of -T*—H.

111. The Ligand-Drug Conjugate composition of embodiment 110 wherein the methylene carbamate unit covalently attached to D has the structure of:

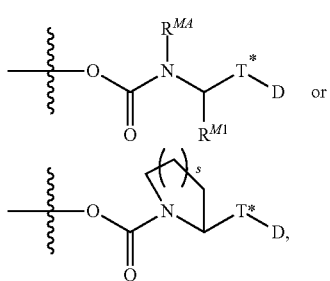

wherein subscript s is 0, 1 or 2.

112. The Ligand-Drug Conjugate composition of embodiment 111 wherein the methylene carbamate unit covalently attached to D has the structure of:

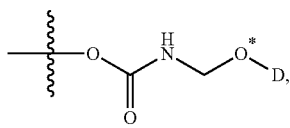

wherein activation of the Glucuronide Unit or Peptide Cleavable Unit within a compound of the Ligand Drug Conjugate composition initiates release of D from that compound as a biologically active compound or derivative thereof having a hydroxyl functional group whose oxygen atom corresponds to O*.

113. The Ligand-Drug Conjugate composition of any one of embodiments 1-104 wherein A or a subunit thereof has the structure of formula (3) or formula (4):

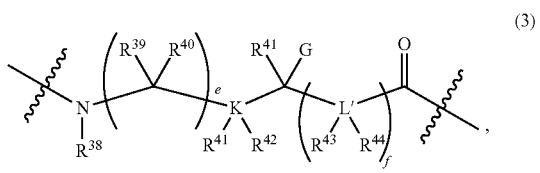

(3)

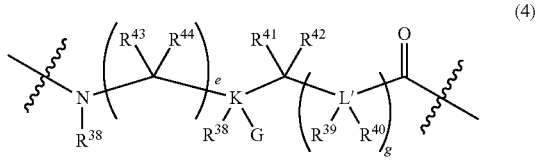

(4)

wherein the wavy lines indicated covalent attachment within the composition structure; wherein K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S; wherein subscripts e and f are independently selected integers that range from 0 to 12, and subscript g is an integer ranging from 1 to 12; wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, or G is —$N(R^{PR})(R^{PR})$, wherein $R^{PR}$ are independently a protecting group or $R^{PR}$ together form a suitable protecting group, or G is —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl;

$R^{39}$-$R^{44}$ are independently selected from the group consisting of hydrogen, optionally substituted $C_1$-$C_6$ alkyl, optionally substituted aryl, and optionally substituted heteroaryl, or $R^{39}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-R are as defined herein, or $R^{43}$, $R^{44}$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^4$ are absent, and when L' is N, one of $R^{43}$, $R^{44}$ is absent, or A or a subunit thereof is an alpha-amino, beta-amino or another amine-containing acid residue.

114. The Ligand-Drug Conjugate composition of embodiment 113 wherein formula (3) or formula (4) has the structure of formula (3a) or formula (4a):

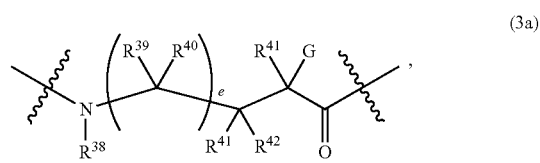

(3a)

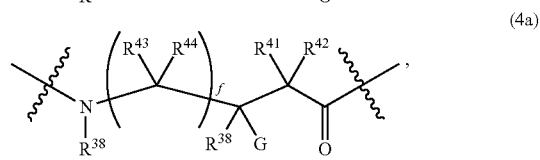

(4a)

wherein subscript e and f are independently 0 or 1.

115. The Ligand-Drug Conjugate composition of any one of embodiments 1 to 114 wherein the Ligand Unit is an antibody Ligand Unit, thereby defining an antibody drug conjugate (ADC), wherein the moiety targeted by the antibody Ligand Unit is an accessible cell-surface antigen of abnormal cells, wherein the targeted antigen is capable of cellular internalization of bound ADC and is present in greater copy number on the abnormal cells in comparison to normal cells distant from the site of the abnormal cells.

116. The Ligand-Drug Conjugate composition of embodiment 115 wherein the targeting agent is a cognate ligand of an accessible cell-surface receptor and the targeted moiety is that cell-surface receptor, wherein the targeted receptor on abnormal cells or other unwanted cells is capable of cellular internalization of bound LDC, and wherein the receptor is present in greater copy number on the abnormal cells in comparison to normal cells.

117. The Ligand-Drug Conjugate composition of embodiment 115 wherein the targeting agent is an antibody, thereby defining an antibody drug conjugate (ADC), wherein the targeted moiety of the antibody Ligand Unit is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

118. The Ligand Drug Conjugate composition of any one of embodiments 1 to 117 wherein subscript p is about 2, about 4, or about 8.

119. The Ligand Drug Conjugate composition of embodiment 118 wherein the Ligand Unit is that of an antibody or antigen-binding fragment thereof, thereby defining an antibody Ligand Unit, wherein the sulfur atom of the antibody Ligand Unit bonded to the succinic acid ($M^2$) moiety or succinic acid amide ($M^3$) moiety is that of a cysteine residue of the antibody or antigen-binding fragment thereof.

120. The Ligand Drug Conjugate composition of embodiment 119 wherein the cysteine residue is an introduced cysteine residue in the heavy chain or light chain of the antibody or antigen binding-fragment thereof.

121. A formulation comprising a Ligand Drug Conjugate composition of any one of embodiments 1-120 and one, two, three or more excipients.

122. The formulation of embodiment 121 wherein the formulation is a pharmaceutically acceptable formulation or a precursor thereof.

123. The formulation of embodiment 122 wherein the pharmaceutically acceptable formulation precursor is a solid suitable for reconstitution as a solution for intravenous injection to a subject.

124. The formulation of embodiment 122 wherein the pharmaceutically acceptable formulation is a liquid suitable for intravenous injection to a subject.

125. The formulation of embodiment 122, 123 or 124 wherein the Ligand Drug Conjugate composition is present in the formulation in an effective amount for treatment of a hyperproliferative disease or condition.

126. A method of treating a hyperproliferative disease or condition comprising the step of administering to a patient having said disease or condition an effective amount of a Ligand Drug Conjugate composition of any one of embodiments 1 to 120.

127. The method of embodiment 126 wherein the hyperproliferative disease or condition is a cancer.

128. The method of embodiment 127 wherein the cancer is a leukemia or lymphoma.

129. A method of inhibiting the multiplication of a tumor cell or cancer cell, or causing apoptosis in a tumor or cancer cell, by exposing said cell with an effective amount of a Ligand Drug Conjugate composition of any one of embodiments 1 to 120.

130. A Drug Linker compound, wherein the compound has the structure of:

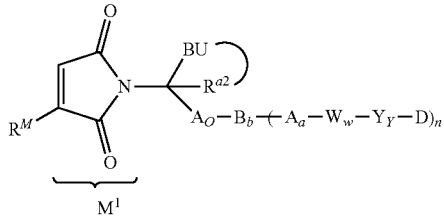

or a salt thereof, wherein $R^M$ is hydrogen or an optionally substituted $C_1$-$C_6$ alkyl; subscript w is 0 or 1; subscript n is 1, 2, 3 or 4; subscript a is 0 or 1; subscript b is 0 or 1, provided that subscript b is 1 when subscript n is 2, 3 or 4 and subscript b is 0 when subscript n is 1; A is a first optional Stretcher Unit; $A_O$ is a second optional Stretcher Unit; B is an optional Branching Unit; and wherein each of A, $A_O$ and B is an independently selected single unit or is optionally comprised or consists of two, three or four independently selected subunits; Y is optionally present as an optionally substituted heteroatom, an optionally substituted functional group or a Spacer Unit, independently selected when subscript y is 2 so that $Y_y$ is —Y—Y'—, wherein Y and Y' are respectively a first and second optionally substituted heteroatom, optionally substituted functional group or Spacer Unit;

subscript w is 0 or 1, wherein W is absent when subscript w is 0, or when subscript w is 1 then W is a Peptide Cleavable Unit, or W is a Glucuronide Unit of formula —Y(W')—, wherein W' represents a carbohydrate moiety with glycosidic bonding to Y through a optionally substituted heteroatom, provided that Y bonded to W' is a self-immolative Spacer Unit; subscript y is 0, 1 or 2, provided that subscript y is 1 or 2, when W is a Glucuronide Unit, in which instance subscript y is inclusive of the self-immolative Spacer Unit bonded to W', except that subscript y is 1 and Y of the Glucuronide Unit is bonded to D when D is a quaternized Drug Unit ($D^+$), and provided that subscript y is 1 and Y is a self-immolative Spacer Unit bonded to D and W when W is a Peptide Cleavable Unit and D is a quaternized Drug Unit ($D^+$); D is a Drug Unit, or D is a quaternized Drug Unit represented as $D^+$ so that $D^+$ replaces D in Formula 1 and Formula 2, provided that subscript w is 1;

BU is a Basic Unit and $R^{a2}$ is an optionally substituted $C_1$-$C_{12}$ alkyl group that together with the carbon atom to which both are attached, as represented by the solid curved line, define a cyclic Basic Unit having an optionally substituted spiro $C_3$-$C_{20}$ heterocyclo containing a skeletal basic nitrogen atom of a secondary or tertiary amine functional group, an optionally substituted spiro $C_3$-$C_{20}$ carbocyclo with exocyclic substitution by an optionally substituted basic nitrogen of a basic secondary or tertiary amine functional group, or an optionally substituted spiro $C_3$-$C_{20}$ carbocyclo having exocyclic substitution by an optionally substituted $C_1$-$C_{12}$ aminoalkyl in which the optionally substituted basic nitrogen atom of the amino moiety of the aminoalkyl is that of a primary, secondary or tertiary amine functional group, wherein the optionally substituted basic nitrogen atom of the exocyclic amine or aminoalkyl along with its optionally substituted alkyl moiety is attributable to BU, or BU is a Basic Unit and $R^{a2}$ is an optionally substituted $C_1$-$C_{12}$ alkyl formally cyclized to the basic nitrogen atom of an acyclic Basic Unit of corresponding structure to Formula 1 and/or Formula 2 in which the solid curved lined between BU and $R^2$ is absent, or to a carbon atom of an optionally substituted $C_1$-$C_{12}$ alkylene bearing that basic nitrogen atom, both of which comprise the acyclic Basic Unit, thus forming an optionally substituted spiro $C_3$-$C_{20}$ heterocyclo, which incorporates the basic nitrogen atom as a skeletal heteroatom, or an optionally substituted $C_3$-$C_{20}$ carbocyclo substituted directly by the basic nitrogen atom, or substituted indirectly by the basic nitrogen atom through an optionally substituted $C_1$-$C_{12}$ alkylene moiety remaining from said formal cyclization and whose structure is dependent on the site of cyclization, so in either instance a cyclic Basic Unit (cBU) is defined, as indicated by the solid curved line;

and wherein the basic nitrogen atom of the cyclic Basic Unit is optionally suitably protected by a nitrogen protecting group, dependent on the degree of substitution of the basic nitrogen atom, or is optionally protonated;

wherein if subscript w is 1, activation of the Glucuronide Unit by a glycosidase or activation of the Peptide Cleavable Unit by a protease initiates release of the Drug Unit or quaternized Drug Unit as a biologically active compound or derivative thereof from the Drug Linker compound or from a Ligand Drug Conjugate compound of a Ligand Drug Conjugate composition prepared from the Drug Linker compound, or if subscript w is 0, a biologically active compound or derivative thereof is released from the Drug Linker compound or from a Ligand Drug Conjugate compound of a Ligand Drug Conjugate composition prepared from the Drug Linker compound on enzymatic or non-enzymatic cleavage of a bond between $—Y_y$-D of and the remainder of the Drug Linker compound or Ligand Drug Conjugate compound.

131. The Drug Linker compound of embodiment 130, wherein the compound has the structure of:

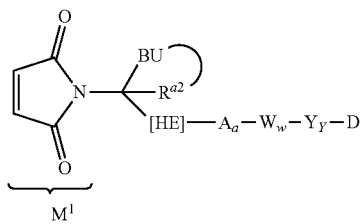

wherein [HE] as $A_O$ is an optional Hydrolysis Enhancing Unit; subscript w is 1; W is Peptide Cleavable Unit, or W is a Glucuronide unit of formula —Y(W')— having the structure of:

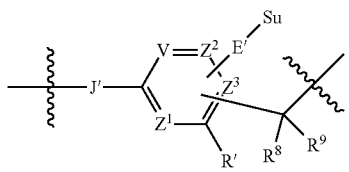

wherein Su is a carbohydrate moiety and -E'- represents an optionally substituted heteroatom of an glycosidic bond cleavable by a glycosidase so that Su-E' is W' and the remainder of the Glucuronide Unit structure is a self-immolative Spacer Unit; -J'- is an optionally substituted heteroatom; V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, halogen, an electron withdrawing group, an electron donating group, -E'-Su, and —C($R^8$)($R^9$)—, provided that one and only one —C($R^8$)($R^9$)— moiety and one and only one -E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is -E'-Su, provided the —C($R^8$)($R^9$)— and -E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; R' is hydrogen or —$NO_2$, or other electron withdrawing group or —$OC_1$—$C_6$ alkyl, or other electron donating group; and wherein glycosidase cleavage of the glycosidic bond initiates release of the Drug Unit or quaternized Drug Unit as a biologically active compound or derivative thereof from the Drug Linker compound or from a Ligand Drug Conjugate compound prepared from the Drug Linker compound; wherein the wavy line adjacent to J' indicates the point of attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the point of covalent attachment of the Glucuronide Unit to Y' when subscript y is 2, or to D/D$^+$ when subscript y is 1.

132. The Drug Linker compound of embodiment 131 wherein —W—$Y_y$-D and —W-D$^+$, in which W is a Glucuronide Unit, have structures of:

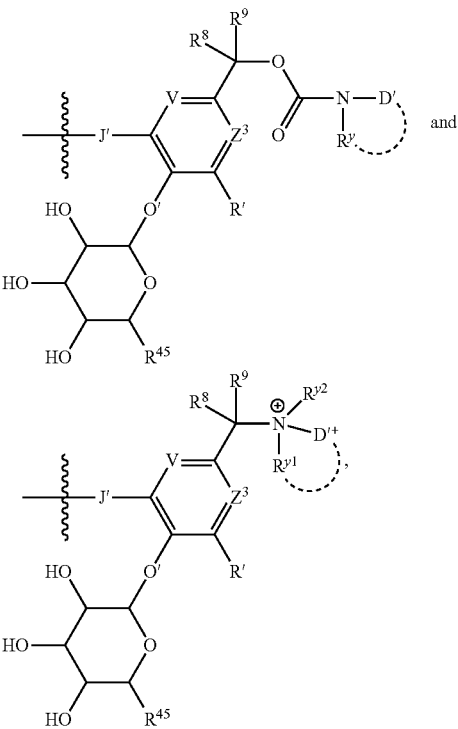

respectively, wherein the dotted curve line indicates optional cyclization of $R^y$ or $R^{y1}$ to D'; $R^{45}$ is —$CH_2OH$ or —$CO_2H$; —N($R^Y$)D' and —$N^+$($R^{y1}$)($R^{y2}$)D' moieties, with or without cyclization, represent D and D$^+$, respectively, wherein D' is the remainder of D or D$^+$; wherein $R^y$ is hydrogen or optionally substituted $C_1$-$C_6$ alkyl in absence of cyclization to D' or $R^y$ is optionally substituted $C_1$-$C_6$ alkylene when cyclized to D'; $R^{y1}$ is optionally substituted $C_1$-$C_6$ alkyl, in absence of its cyclization within D$^+$, or $R^1$ is optionally substituted $C_1$-$C_6$ alkylene when cyclized within D$^+$; $R^{y2}$ is hydrogen or optionally substituted $C_1$-$C_6$ alkyl; and wherein —O'— as E' represents the oxygen heteroatom of an O-glycosidic bond cleavable by a glycosidase, wherein said cleavage initiates release of D as a primary or secondary amine-containing a biologically active compound or derivative thereof or initiates release of $D^+$ as a tertiary amine-containing biologically active compound or derivative thereof from the Drug Linker compound or Ligand Drug Conjugate compound prepared from the Drug Linker compound.

133. The Drug Linker compound of claim 131 wherein W is a Peptide Cleavable Unit and —$Y_y$-D- and —$Y_y$-$D^+$ have structures of:

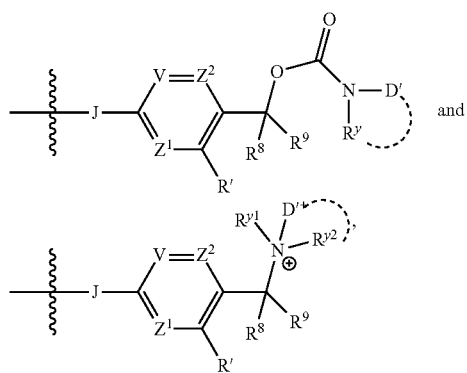

respectively, wherein —$N(R^y)D'$ and —$N(R^{y1})(R^{y2})D'^+$ moieties represent D and $D^+$, respectively, wherein D' and $D'^+$ are the remainder of D and $D^+$, and wherein the dotted line indicates optional cyclization of $R^y$ or $R^{y1}$ to D' or $D'^+$; wherein $R^y$ is hydrogen or $R^y$ is optionally substituted $C_1$-$C_6$ alkyl in absence of cyclization to D' or optionally substituted $C_1$-$C_6$ alkylene when cyclized to D'; $R^{y1}$ is optionally substituted $C_1$-$C_6$ alkyl and $R^{y2}$ is optionally substituted $C_1$-$C_6$ alkyl in absence of cyclization to $D^+$ or $R^{y2}$ is optionally substituted $C_1$-$C_6$ alkylene when cyclized to $D^+$; and -J- is an optionally substituted heteroatom bonded to W as indicated by the adjacent wavy line, wherein cleavage of that bond initiates release of D as a primary or secondary amine-containing a biologically active compound or derivative thereof or initiates release of $D^+$ as a tertiary amine-containing a biologically active compound or derivative thereof from the Drug Linker compound or from a Ligand Drug Conjugate compound prepared from the Drug Linker compound.

134. The Drug Linker compound of embodiment 131, wherein the compound has the structure of:

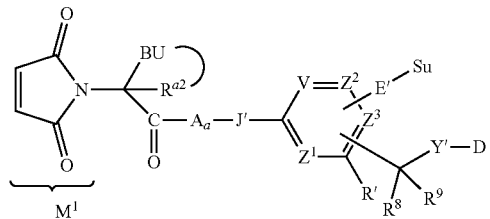

wherein Su is a carbohydrate moiety; -E'- represents an independently selected heteroatom, optionally substituted, of an glycosidic bond cleavable by a glycosidase; -J'- represents an independently selected heteroatom, optionally substituted; Y' is absent or Y' is —O—, —S—, —NH— or —O—C(=O)—, provided that Y' is absent when D is a quaternized Drug Unit ($D^+$); $R^8$ and $R^9$ independently are hydrogen, $C_1$-$C_8$ alkyl, $C_2$-$C_8$ alkenyl and $C_2$-$C_8$ alkynyl, optionally substituted, or $C_5$-$C_{10}$ aryl or $C_5$-$C_{10}$ heteroaryl, optionally substituted;

V, $Z^1$, $Z^2$ and $Z^3$ independently are =N— or =$C(R^{24})$—, wherein each $R^{24}$ is independently selected from the group consisting of hydrogen and $C_1$-$C_8$ alkyl, $C_2$-$C_8$ alkenyl and $C_2$-$C_8$ alkynyl, optionally substituted, halogen, an electron withdrawing group, an electron donating group, —O'-Su, —$C(R^8)(R^9)$—Y'-D and —$C(R^8)(R^9)$-$D^+$, provided that one and only one of —$C(R^8)(R^9)$—Y'-D and —$C(R^8)(R^9)$-$D^+$ moieties and one and only one —O'-Su moiety is present; wherein one of V, $Z^1$, $Z^2$ and $Z^3$ is =$C(R^{24})$—, in which $R^{24}$ is —$C(R^8)(R^9)$—Y'-D or —$C(R^8)(R^9)$-$D^+$ and another of V, $Z^1$, $Z^2$ and $Z^3$ is =$C(R^{24})$—, in which $R^{24}$ is —O'-Su, provided the —O'-Su and —$C(R^8)(R^9)$—Y'-D or —$C(R^8)(R^9)$-$D^+$ moieties are ortho or para to each other;

and wherein glycosidase cleavage of the glycosidic bond of the Drug Linker compound or a Ligand Drug Conjugate compound prepared from that Drug Linker compound initiates release of D/$D^+$ as a biologically active compound or derivative thereof from that Ligand Drug Conjugate compound.

135. The Drug Linker compound of embodiment 131, wherein the compound has the structure of:

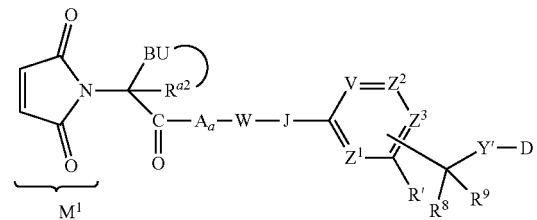

wherein J represents an independently selected heteroatom, optionally substituted; Y' is absent or Y' is -O—, —S—, —NH— or —O—C(=O)—, provided that Y' is absent when D is a quaternized Drug Unit ($D^+$); W is a Peptide Cleavable Unit; V, $Z^1$, $Z^2$ and $Z^3$ are independently =N— or =$C(R^{24})$—, wherein each $R^{24}$ is independently selected from the group consisting of hydrogen and $C_1$-$C_8$ alkyl, $C_2$-$C_8$ alkenyl and $C_2$-$C_8$ alkynyl, optionally substituted, halogen, an electron withdrawing group, an electron donating group, and —$C(R^8)(R^9)$—Y'-D, provided that one and only one —$C(R^8)(R^9)$—Y'-D moiety is present, wherein one of V, $Z^1$, $Z^2$ and $Z^3$ is =$C(R^{24})$—, in which $R^{24}$ is —$C(R^8)(R^9)$—Y'-D, provided the —$C(R^8)(R^9)$—Y'-D moiety is ortho or para to J'; $R^8$ and $R^9$ independently are hydrogen, $C_1$-$C_8$ alkyl, $C_2$-$C_8$ alkenyl and $C_2$-$C_8$ alkynyl, optionally substituted, or $C_5$-$C_{10}$ aryl or $C_5$-$C_{10}$ heteroaryl, optionally substituted; and wherein protease action on W results in cleavage of the W-J' bond within the Drug Linker compound or a Ligand Drug Conjugate compound prepared from that Drug Linker compound so as to initiate release of D/$D^+$ as a biologically active compound or derivative thereof from that Ligand Drug Conjugate compound.

136. The Drug Linker compound of embodiment 134, wherein the compound has the structure of:

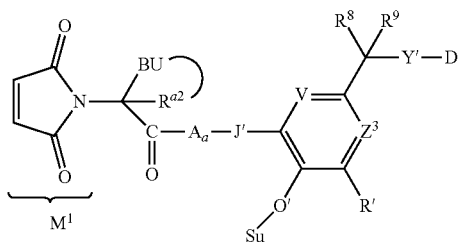

wherein —O'— represents the oxygen heteroatom of an O-glycosidic bond cleavable by a glycosidase.

137. The Drug Linker compound of embodiment 134, wherein the compound has the structure of:

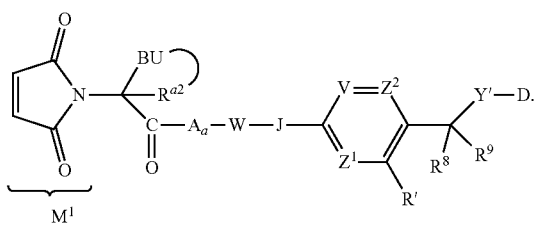

138. The Drug Linker compound of embodiment 136, wherein the compound has the structure of:

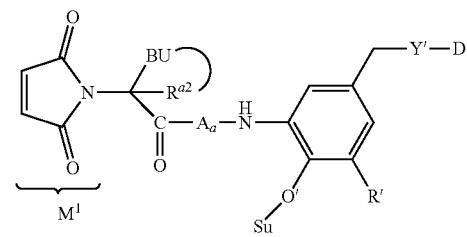

wherein R' is hydrogen or —$NO_2$.

139. The Drug Linker compound of embodiment 137, wherein the compound has the structure of:

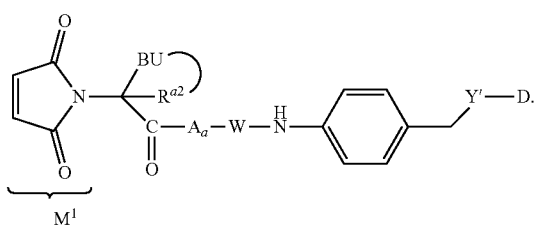

140. The Drug Linker compound of any one of claims 130 to 139, wherein BU and $R^{a2}$ together with the carbon atom to which both are attached, define an optionally substituted $C_3$-$C_8$ heterocyclo having a skeletal secondary or tertiary basic nitrogen atom, wherein the skeletal basic nitrogen atom is attributable to BU.

141. The Drug Linker compound of claim 138, wherein the compound has the structure of:

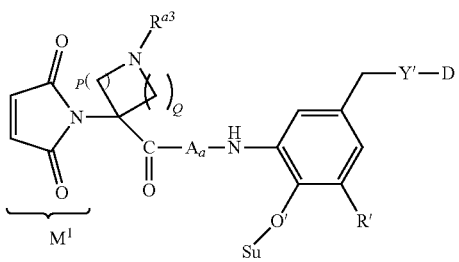

wherein subscript P is 1 or 2; subscript Q ranges from 1 to 6; and $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated, or $R^{a3}$ is a suitable nitrogen-protecting group.

142. The Drug Linker compound of embodiment 139, wherein the compound has the structure of:

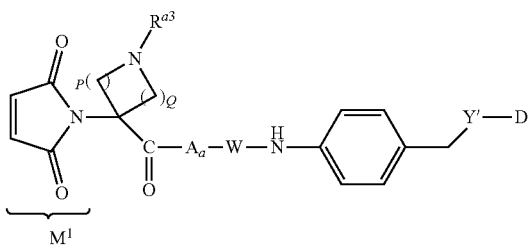

wherein subscript P is 1 or 2; subscript Q ranges from 1 to 6; and $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{n'}$—$R^{PEG2}$; and $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated, or $R^3$ is a suitable nitrogen-protecting group.

143. The Drug Linker compound of embodiment 141 or 142, wherein subscript P is 1 and subscript Q is 1, 2 or 3 or subscript P is 2 and Q is 1 or 2.

144. The Drug Linker compound of embodiment 143, wherein subscript P is 1, subscript Q is 1.

145. The Drug Linker compound of any one of embodiments 130 to 139, wherein BU and $R^2$ together with the carbon atom to which both are attached define an optionally substituted $C_3$-$C_8$ carbocyclo having exocyclic substitution by a primary, secondary or tertiary amine functional group or an optionally substituted $C_1$-$C_6$-aminoalkyl, wherein the basic nitrogen atom of the amine or aminoalkyl is attributable to BU is optionally protected by a suitable nitrogen protecting group, dependent on the degree of substitution of the basic nitrogen atom, or is optionally protonated.

146. The Drug Linker compound of embodiment 145, wherein the compound has the structure of:

207

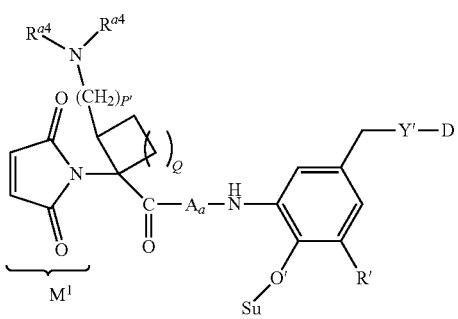

wherein subscript P' is 0 or 1; subscript Q' is 0, or Q' ranges from 1 to 6; each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein in either instance the basic nitrogen atom is optionally protonated, or one $R^{a4}$ is hydrogen or an optionally substituted $C_1$-$C_6$ alkyl and the other $R^{a4}$ is a suitable nitrogen-protecting group, or both $R^{a4}$ together form a suitable nitrogen-protecting group.

147. The Drug Linker compound of embodiment 145, wherein the compound has the structure of:

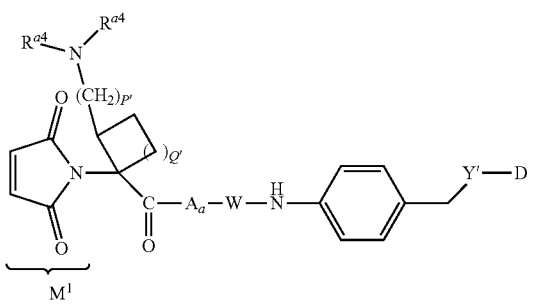

wherein subscript P' is 0 or 1; subscript Q' is 0, or Q' ranges from 1 to 6; each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein in either instance the basic nitrogen atom is optionally protonated, or one $R^{a4}$ is hydrogen or an optionally substituted $C_1$-$C_6$ alkyl and the other $R^{a4}$ is a suitable nitrogen-protecting group, or both $R^{a4}$ together form a suitable nitrogen-protecting group.

148. The Drug Linker compound of embodiment 131, 138, 141 or 146, wherein —O'-Su has the structure of:

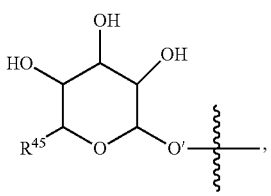

208 wherein the wavy line represents covalent bonding of O' to the remainder of the structure representing the Drug Linker compound; and $R^{45}$ is —$CH_2OH$ or —$CO_2H$.

149. The Drug Linker compound of embodiment 135, 137, 139, 142 or 147, wherein W is a Peptide Cleavable Unit comprised of a dipeptide wherein the C-terminus of the dipeptide is covalently bonded to J' wherein the dipeptide provides for a recognition site for a regulatory or lysosomal protease for cleavage of the W-J' bond by said protease thereby initiating release of D or $D^+$ as a biologically active compound or derivative thereof from the Drug Linker compound or from a Ligand Drug Conjugate compound prepared from the Drug Linker compound.

150. The Drug Linker compound of claim 149 wherein the dipeptide of W has the structure of:

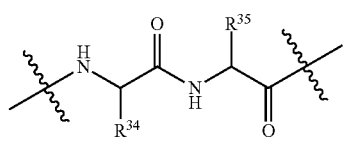

wherein $R^{34}$ is benzyl, methyl, isopropyl, isobutyl, sec-butyl, —CH(OH)$CH_3$ or has the structure of

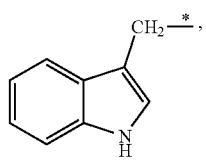

wherein the asterisk indicates the point of covalent attachment to the dipeptide backbone; and $R^{35}$ is methyl, —$(CH_2)_4$—$NH_2$, —$(CH_2)_3$NH(C=O)$NH_2$, —$(CH_2)_3$NH(C=NH)$NH_2$, or, —$(CH_2)_2CO_2H$; and wherein the wavy line indicates the points of covalent attachment of the dipeptide into the Drug Linker compound.

151. The Drug Linker compound of embodiment 149 wherein the dipeptide of W selected from the group consisting of -Phe-Lys-, —Val-Ala-, —Val-Lys-, -Ala-Lys-, —Val-Cit-, -Phe-Cit-, -Leu-Cit-, —Ile-Cit-, -Phe-Arg-, and -Trp-Cit-, wherein Cit is citrulline.

152. The Drug Linker compound of any one of embodiments 134 to 151 wherein D is a quaternized Drug Unit (-$D^+$), subscript y is 1 and Y' is absent, wherein said cleavage of the Peptide Cleavable Unit or Glucuronide Unit initiates release of $D^+$ as a tertiary amine-containing a biologically active compound or derivative thereof from the Drug Linker compound or from a Ligand Drug Conjugate compound prepared from the Drug Linker compound.

153. The Drug Linker compound of embodiment 152, wherein the compound has the structure of:

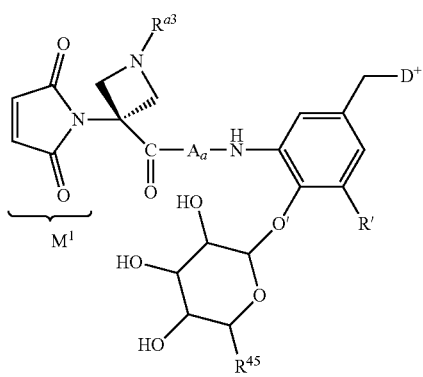

wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated, or $R^{a3}$ is a suitable nitrogen-protecting group; R' is hydrogen or —$NO_2$; and $R^{45}$ is —$CH_2OH$ or —$CO_2H$.

154. The Drug Linker compound of embodiment 153, wherein the compound has the structure of:

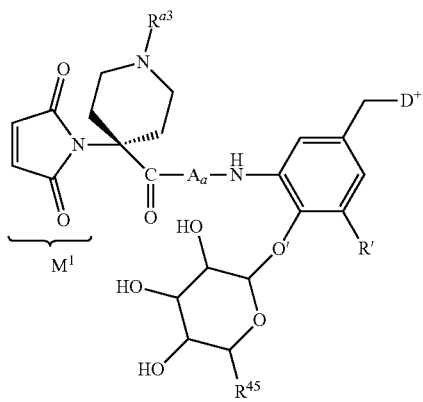

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated, or $R^3$ is a suitable nitrogen-protecting group; and R' is hydrogen or —$NO_2$; and $R^{45}$ is —$CH_2OH$ or —$CO_2H$.

155. The Drug Linker compound of embodiment 152, wherein the compound has the structure of:

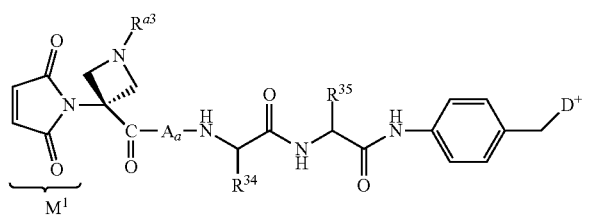

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated, or $R^3$ is a suitable nitrogen-protecting group.

156. The Drug Linker compound of embodiment 152, wherein the compound has the structure of:

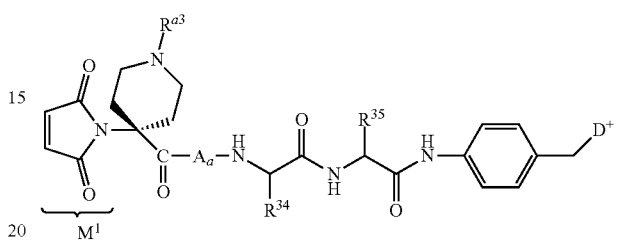

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O$)$_{n'}$—$R^{PEG2}$, wherein $R^{PEG1}$ is $C_1$-$C_4$ alkylene, $R^{PEG2}$ is —H or $C_1$-$C_4$ alkylene, and subscript n' ranges from 1 to 36, wherein the basic nitrogen bonded to $R^{a3}$ is optionally protonated, or $R^{a3}$ is a suitable nitrogen-protecting group; $R^{34}$ is methyl or isopropyl; and $R^{35}$ is methyl, —($CH_2$)$_4$—$NH_2$, —($CH_2$)$_3$NH(C=O)$NH_2$, —($CH_2$)$_3$NH(C=NH)$NH_2$, or, —($CH_2$)$_2$$CO_2H$.

157. The Drug Linker compound of any one of embodiments 152 to 156 wherein the released tertiary amine-containing biologically active compound or derivative thereof is a tubulysin compound thereby defining $D^+$ as a quaternized tubulysin Drug Unit.

158. The Drug Linker compound of any one of embodiments 130 to 157 wherein the quaternized Drug Unit -$D^+$ is a quaternized tubulysin Drug Unit having the structure of:

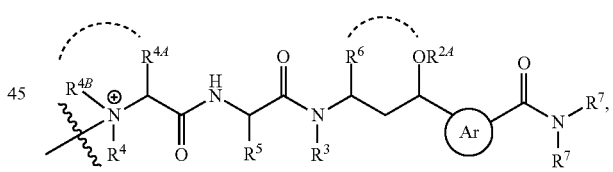

$R^{2A}$ is hydrogen or optionally substituted $C_1$-$C_{12}$ alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, thereby defining an oxygen-containing $C_5$-$C_6$-heterocyclo; the circled Ar moiety represents a 5-membered nitrogen-heteroarylene, wherein the indicated required substituents to that heteroarylene are in a 1,3-relationship with each other with optional substitution at the remaining positions; $R^3$ is hydrogen or optionally substituted $C_1$-$C_{12}$ alkyl; $R^4$, $R^5$ and $R^6$ are optionally substituted $C_1$-$C_{12}$ alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted $C_1$-$C_{12}$ alkyl and $R^{4B}$ is optionally substituted $C_1$-$C_{12}$ alkyl, or both together with the nitrogen to which they are attached, as indicated by the curved dotted line between $R^{4A}$ and $R^{4B}$, define a quaternized nitrogen-containing $C_3$-$C_8$ heterocyclyl, optionally substituted; one $R^7$ is hydrogen or optionally substituted $C_1$-$C_{12}$ alkyl and the other $R^7$ is optionally substituted ($C_6$-$C_{20}$ aryl)-$C_1$-$C_{12}$ alkyl- or ($C_5$-$C_{20}$ heteroaryl)-$C_1$-$C_{12}$ alkyl-; wherein the wavy line indicates the point of covalent attachment of $D^+$ to the remainder of the compound structure.

159. The Drug Linker compound of embodiment 158 wherein $D^+$ has the structure of:

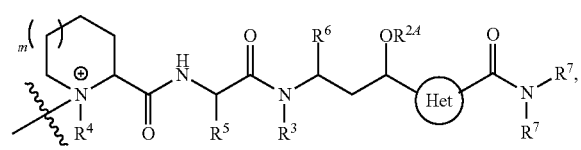

wherein subscript m is 0 or 1.

160. The Drug Linker compound of claim 159 wherein the quaternized tubulysin Drug Unit -$D^+$ has the structure of:

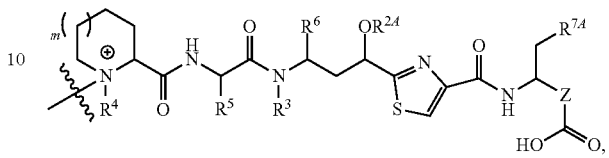

wherein Z is an optionally substituted $C_1$-$C_6$ alkylene or an optionally substituted $C_2$-$C_6$ alkenylene; and $R^{7A}$ is optionally substituted $C_6$-$C_{10}$ aryl or optionally substituted $C_5$-$C_{10}$ heteroaryl.

161. The Drug Linker compound of embodiment 160 wherein the quaternized tubulysin Drug Unit -$D^+$ has the structure of:

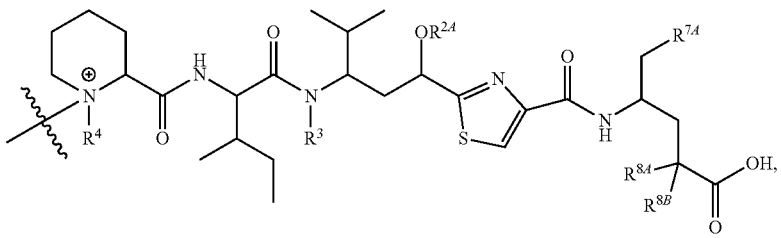

wherein $R^{7A}$ is optionally substituted phenyl and $R^{8A}$ and $R^{8B}$ are independently selected from the group consisting of hydrogen and optionally substituted $C_1$-$C_6$ alkyl or $R^{8A}$ and $R^{8B}$ together with the carbon atom to which both are attached define an optionally substituted spiro $C_3$-$C_6$ carbocyclo.

162. The Drug Linker compound of embodiment 161 wherein the quaternized tubulysin Drug Unit -$D^+$ has the structure of:

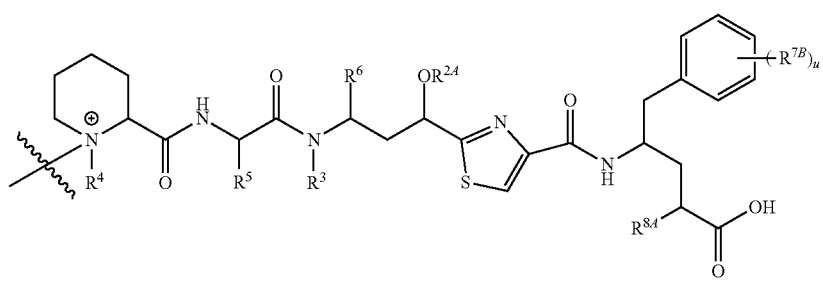

wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; and $R^4$ is hydrogen or optionally substituted $C_1$-$C_4$ alkyl.

163. The Drug Linker compound of embodiment 162 wherein the quaternized tubulysin Drug Unit -D⁺ has the structure of:

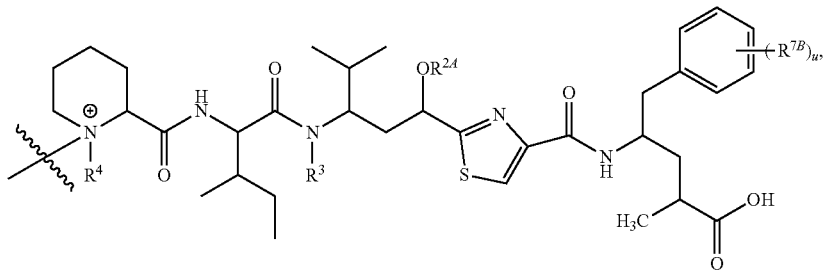

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —OCH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

164. The Drug Linker compound of embodiment 158 wherein the quaternized tubulysin Drug Unit -D⁺ has the structure of:

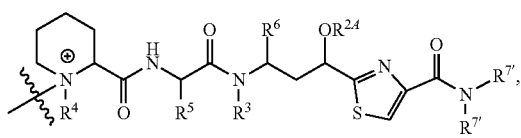

wherein $R^{2A}$ is hydrogen, an saturated C$_1$-C$_6$ alkyl, or an unsaturated C$_3$-C$_6$ alkyl, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are alkyl side chain residues of natural hydrophobic amino acids; and the —N(R$^{7'}$)(R$^{7'}$) moiety is —NH(C$_1$-C$_6$ alkyl), wherein C$_1$-C$_6$ alkyl is unsubstituted or is substituted by one and only one —CO$_2$H, or an ester thereof, or by one and only one optionally substituted phenyl, and is otherwise optionally substituted, or the —N(R$^{7'}$)(R$^{7'}$) moiety is —N(C$_1$-C$_6$ alkyl)$_2$, wherein one and only one C$_1$-C$_6$ alkyl is substituted by one and only one —CO$_2$H, or an ester thereof, or by one and only one optionally substituted phenyl, and each C$_1$-C$_6$ alkyl is otherwise optionally substituted, or each C$_1$-C$_6$ alkyl is unsubstituted.

165. The Drug Linker compound of embodiment 164 wherein the —N(R$^{7'}$)(R$^{7'}$) moiety is selected from the group consisting of —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

166. The Drug Linker compound of any one of embodiments 158 to 165 wherein R$^{2A}$ is —CH$_2$CH$_3$.

167. The Drug Linker compound of any one of embodiments 158 to 165 wherein R$^{2A}$ is —CH$_2$—CH=CH$_2$.

168. The Drug Linker compound of any one of embodiments 158 to 165 wherein —OR$^{2A}$ is —OCH$_2$CH$_3$, —OCH$_2$—CH=CH$_2$, —OCH$_2$C(CH$_3$)=CH$_2$, or —OC(O)R$^{2B}$, wherein —R$^{2B}$ is —CH$_3$; R$^3$ is —CH$_3$; and R$^{7B}$ is —OH or is absent; subscript u is 0 or 1, wherein R$^{7B}$ is —OH when subscript u is 1, and R$^{7B}$ is absent when subscript u is 0.

169. The Drug Linker compound of embodiment 163 wherein the quaternized tubulysin Drug Unit -D⁺ has the structure of:

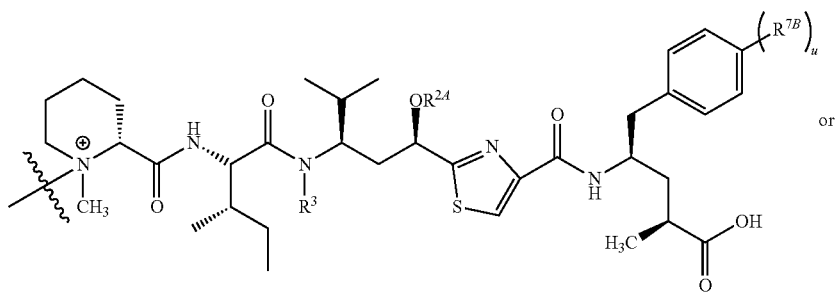

or

-continued

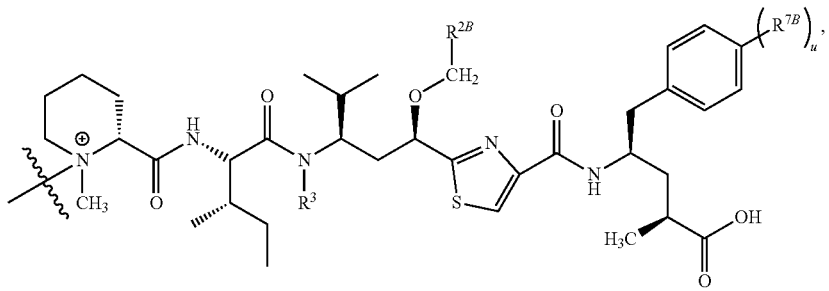

wherein $R^{2A}$ is —C(O)$R^{2B}$, —C(O)NH$R^{2D}$, or —CH$_2$C(O)$R^{2D}$; $R^{2B}$ is H, $C_1$-$C_6$ alkyl or $C_2$-$C_6$ alkenyl; $R^{2D}$ is —H, $C_1$-$C_4$ alkyl or $C_2$-$C_4$ alkenyl; $R^3$ is methyl, ethyl or propyl; $R^{7B}$ is —OH or is absent; subscript u is 0 or 1, wherein $R^{7B}$ is —OH when subscript u is 1, and $R^{7B}$ is absent when subscript u is 0.

170. The Drug Linker compound of embodiment 169 wherein the quaternized tubulysin Drug Unit -D⁺ has the structure of:

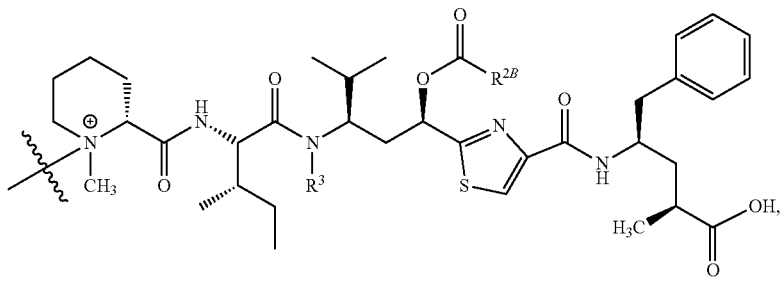

wherein $R^{2B}$ is a methyl, ethyl, propyl or a branched $C_3$-$C_6$ alkyl or is methyl, ethyl, propyl, iso-propyl, 3-methyl-prop-1-yl, 3,3-dimethyl-prop-1-yl, or vinyl.

171. The Drug Linker compound of embodiment 170 wherein $R^{2B}$ is —CH$_3$ and $R^3$ is —CH$_3$.

172. The Drug Linker compound of embodiment 169 wherein the quaternized tubulysin Drug Unit -D⁺ has the structure of:

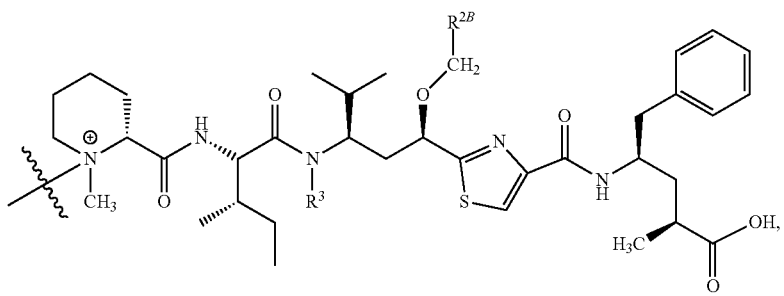

wherein $R^{2B}$ is —H, methyl, ethyl, vinyl or —C(=CH$_2$)CH$_3$.

173. The Drug Linker compound of embodiment 172 wherein the quaternized tubulysin Drug Unit -D⁺ has the structure of:

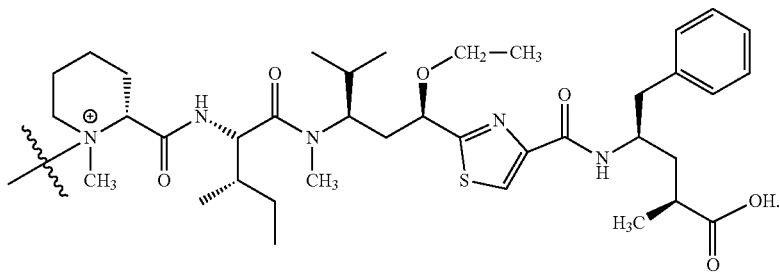

174. The Drug Linker compound of embodiment 172 wherein the quaternized tubulysin Drug Unit -D⁺ has the structure of:

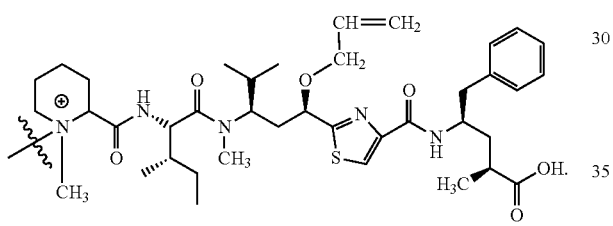

175. The Drug Linker compound of embodiment 169 wherein the compound has the structure of:

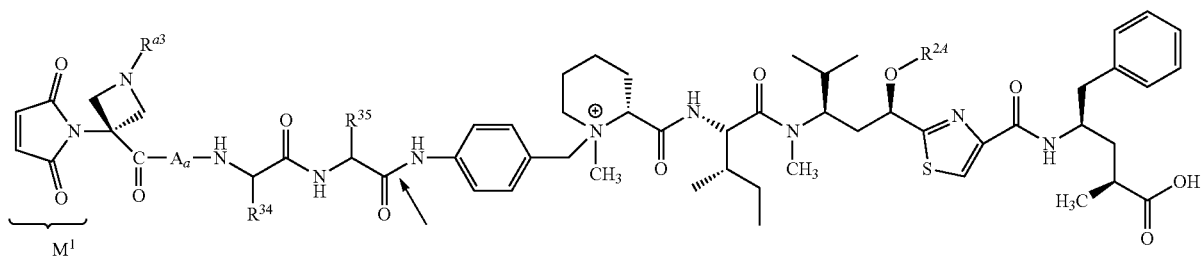

wherein subscript a is 1, so that A is present, wherein A is an α-amino acid or β-amino acid residue; $R^3$ is —H, $C_1$-$C_4$ alkyl, or —$R^{PEG1}$—O—$(CH_2CH_2O)_{n'}$—$R^{PEG2}$; $R^{PEG1}$ is —$CH_2$—, —$CH_2CH_2$—; $R^{PEG2}$ is —H or —$CH_3$ or —$CH_2CH_3$; subscript n' ranges from 1 to 36; and wherein the basic nitrogen bonded to $R^3$ is optionally protonated, or $R^{a3}$ is a suitable nitrogen-protecting group; $R^{24}$ is —C(=O)$CH_3$, —$CH_2CH_3$, —$CH_2CH=CH_2$ or —$CH_2C(=CH_2)CH_3$; and $R^{34}$ is isopropyl, and $R^{35}$ is methyl or —$(CH_2)_3NH(C=O)NH_2$.

176. The Drug Linker compound of embodiment 169 wherein compound has the structure of:

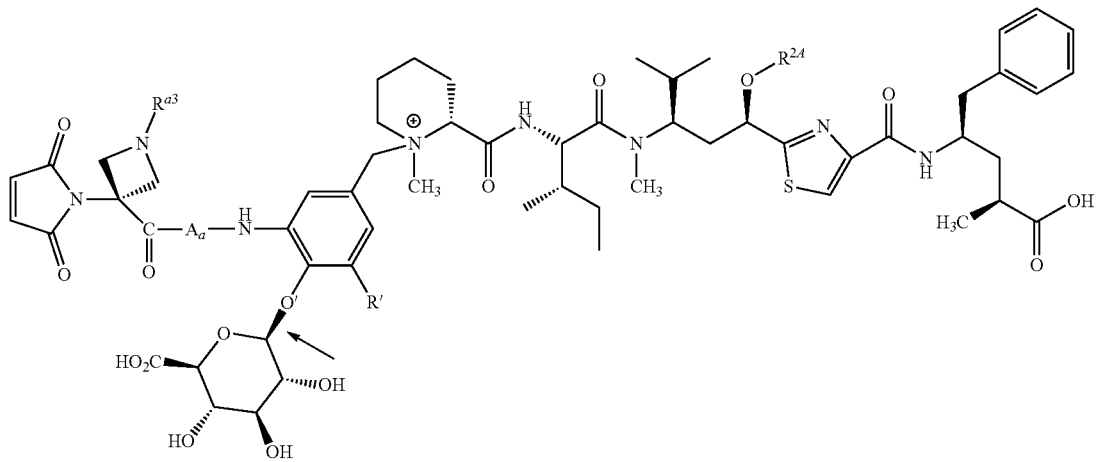

wherein subscript a is 1, so that A is present, wherein A is an α-amino acid or β-amino acid residue; $R^3$ is —H, $C_1$-$C_4$ alkyl, or —$R^{PEG1}$—O—$(CH_2CH_2O)_{n'}$—$R^{PEG2}$, wherein $R^{PEG1}$ is —$CH_2$— or —$CH_2CH_2$—; $R^{PEG2}$ is —H, —$CH_3$ or —$CH_2CH_3$; and subscript n' ranges from 1 to 36, wherein the basic nitrogen atom bonded to $R^{a3}$ is optionally protonated, or $R^{a3}$ is a suitable nitrogen-protecting group; and $R^{2A}$ is —C(=O)$CH_3$, —$CH_2CH_3$, —$CH_2CH$=$CH_2$ or —$CH_2C$(=$CH_2$)$CH_3$.

177. The Drug Linker compound of embodiment 132 wherein the compound has the structure of:

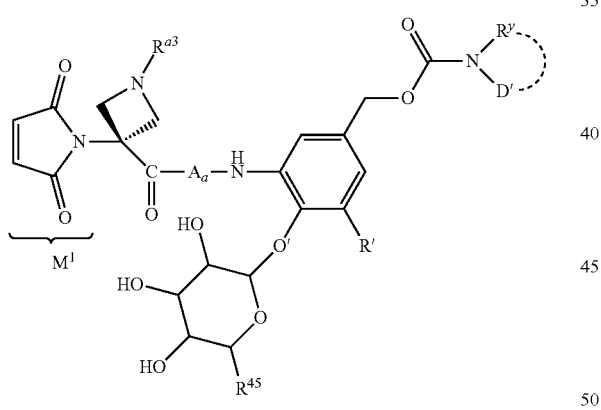

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated, or $R^3$ is a suitable nitrogen-protecting group; R' is hydrogen or —$NO_2$; $R^{45}$ is —$CH_2OH$ or —$CO_2H$; —N(R$^y$)D' represents D, wherein D' is the remainder of D, and wherein the dotted line indicates optional cyclization of R$^y$ to D', wherein R$^y$ is hydrogen or optionally substituted $C_1$-$C_6$ alkyl in absence of cyclization to D' or R$^y$ is optionally substituted $C_1$-$C_6$ alkylene when cyclized to D'; wherein —O'— represents the oxygen heteroatom of an O-glycosidic bond cleavable by a glycosidase, wherein said cleavage initiates release of D as a primary or secondary amine-containing a biologically active compound or derivative thereof from the Drug Linker compound or from a Ligand Drug Conjugate compound prepared from the Drug Linker compound.

178. The Drug Linker compound of embodiment 132 wherein the compound has the structure of:

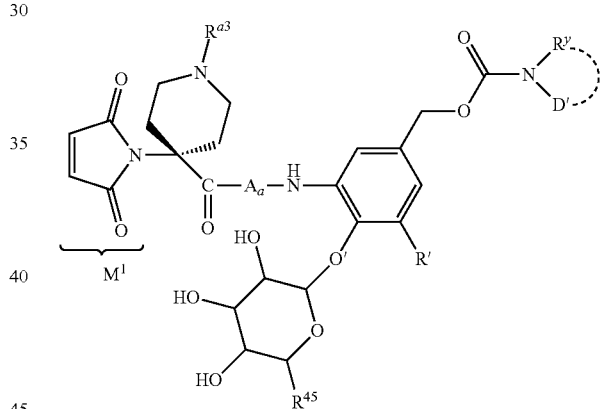

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^3$ is optionally protonated, or R" is a suitable nitrogen protecting group; R' is hydrogen or —$NO_2$; $R^{45}$ is —OH or —$CO_2H$; —N(R$^y$)D' represents D, wherein D' is the remainder of D, and wherein the dotted line indicates optional cyclization of R$^y$ to D', wherein R$^y$ is hydrogen or optionally substituted $C_1$-$C_6$ alkyl in absence of cyclization to D' or R$^y$ is optionally substituted $C_1$-$C_6$ alkylene when cyclized to D'; wherein —O'— represents the oxygen heteroatom of an O-glycosidic bond cleavable by a glycosidase, wherein said cleavage initiates release of D as a primary or secondary amine-containing a biologically active compound or derivative thereof from the Drug Linker compound or from a Ligand Drug Conjugate compound prepared from the Drug Linker compound.

179. The Drug Linker compound of embodiment 133, wherein the compound has the structure of:

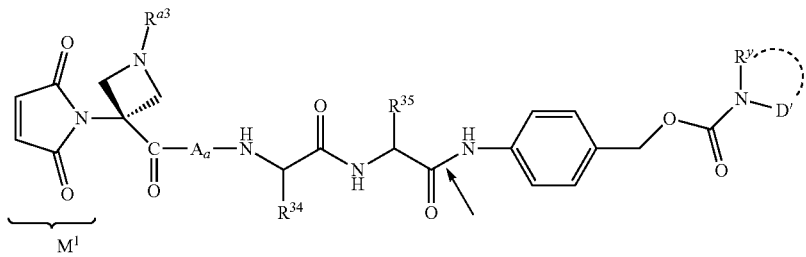

wherein $R^3$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2$)$_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen bonded to $R^{a3}$ is optionally protonated, or $R^{a3}$ is a suitable nitrogen-protecting group; $R^{34}$ is methyl or isopropyl; $R^{35}$ is methyl, —($CH_2$)$_4$—$NH_2$, —($CH_2$)$_3$NH(C=O)$NH_2$, —($CH_2$)$_3$NH(C=NH)$NH_2$, or, —($CH_2$)$_2$$CO_2$H; —N($R^y$)D' represents -D having covalent attachment to the remainder of the composition structure, wherein D' is the remainder of D, and wherein the dotted line indicates optional cyclization of $R^y$ to D', wherein $R^y$ is hydrogen or optionally substituted $C_1$-$C_6$ alkyl in absence of cyclization to D', or $R^y$ is optionally substituted $C_1$-$C_6$ alkylene when cyclized to D'; and wherein protease cleavage of the indicated bond initiates release of D as a primary or secondary amine-containing a biologically active compound or derivative thereof from the Drug Linker compound or from a Ligand Drug Conjugate compound prepared from the Drug Linker compound.

180. The Drug Linker compound of embodiment 133, wherein the compound has the structure of:

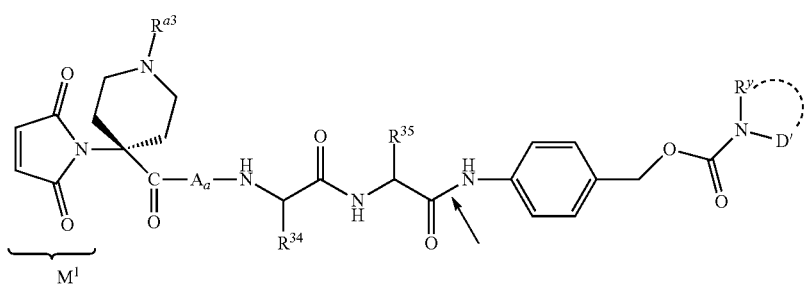

wherein $R^{a3}$ is —H, $C_1$-$C_6$ alkyl, —$C_1$-$C_4$ alkylene-($C_6$-$C_{10}$ aryl), or —$R^{PEG1}$—O—($CH_2CH_2O$)$_{n'}$—$R^{PEG2}$; $R^{PEG1}$ is $C_1$-$C_4$ alkylene; $R^{PEG2}$ is —H or $C_1$-$C_4$ alkylene; subscript n' ranges from 1 to 36; and wherein the basic nitrogen bonded to $R^{a3}$ is optionally protonated, or $R^{a3}$ is a suitable nitrogen-protecting group; $R^{34}$ is methyl or isopropyl; $R^{35}$ is methyl, —($CH_2$)$_4$—$NH_2$, —($CH_2$)$_3$NH(C=O)$NH_2$, —($CH_2$)$_3$NH(C=NH) $NH_2$, or, —($CH_2$)$_2$$CO_2$H; —N($R^y$)D' represents -D having covalent attachment to the remainder of the composition structure, wherein D' is the remainder of D, and wherein the dotted line indicates optional cyclization of $R^y$ to D', wherein $R^y$ is hydrogen or optionally substituted $C_1$-$C_6$ alkyl in absence of cyclization to D', or $R^y$ is optionally substituted $C_1$-$C_6$ alkylene when cyclized to D'; and wherein protease cleavage of the indicated bond initiates release of D as a primary or secondary amine-containing biologically active compound or derivative thereof from the Drug Linker compound or from a Ligand Drug Conjugate compound prepared from the Drug Linker compound.

181. The Drug Linker compound of any one of embodiments 153 to 156, wherein the released tertiary amine-containing drug compound from $D^+$, or any one of claims 177 to 180, wherein the released primary or secondary amine-containing biologically active compound or derivative thereof from D, is an auristatin drug compound thereby defining D as an auristatin Drug Unit or $D^+$ as a quaternized auristatin Drug Unit.

182. The Drug Linker compound of embodiment 181, wherein the auristatin drug compound released from -D or -$D^+$ has the structure of:

$D_E$

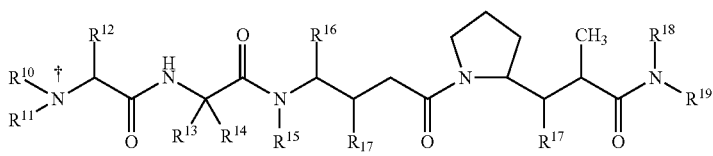

$D_F$

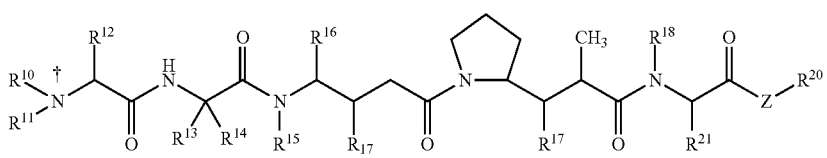

wherein the dagger indicates the site of covalent attachment of the nitrogen atom that provides a carbamate functional group, wherein —OC(=O)— of that functional group is Y', on incorporation of the auristatin drug compound as -D into the Drug Linker in which subscript y is 2, or results in a quaternary amine nitrogen on incorporation of the auristatin drug compound as -D$^+$ into the Drug Linker compound in which subscript y is 1;

$R^{10}$ and $R^{11}$ are independently selected from the group consisting of hydrogen and $C_1$-$C_8$ alkyl, provided that one of $R^{10}$, $R^{11}$ is hydrogen when the auristatin drug compound is incorporated into the as -D and neither of $R^{10}$, $R^{11}$ is hydrogen when the auristatin drug compound is incorporated as -D$^+$; $R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl); $R^{13}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl and —$X^1$—($C_3$-$C_8$ heterocyclyl); $R^{14}$ is hydrogen or methyl, or $R^{13}$ and $R^{14}$ taken together with the carbon to which they are attached comprise a spiro $C_3$-$C_8$ carbocyclo; $R^{15}$ is hydrogen or $C_1$-$C_8$ alkyl; $R^{16}$ is hydrogen, $C_1$-$C_8$ alkyl, $C_3$-$C_8$ carbocyclyl, $C_6$-$C_{24}$ aryl, —$C_6$-$C_{24}$—$X^1$-aryl, —$X^1$—($C_3$-$C_8$ carbocyclyl), $C_3$-$C_8$ heterocyclyl and —$X^1$—($C_3$-$C_8$ heterocyclyl);

$R^{17}$ independently are hydrogen, —OH, $C_1$-$C_8$ alkyl, $C_3$-$C_8$ carbocyclyl and O—($C_1$-$C_8$ alkyl); $R^{18}$ is hydrogen or optionally substituted $C_1$-$C_8$ alkyl; $R^{19}$ is —C($R^{19A}$)$_2$—C($R^{19A}$)$_2$— $C_6$-$C_{24}$ aryl, —C($R^{19A}$)$_2$—C($R^{19A}$)$_2$—($C_3$-$C_8$ heterocyclyl) or —C($R^{19A}$)$_2$—C($R^{19A}$)$_2$—($C_3$-$C_8$ carbocyclyl), wherein $C_6$-$C_{24}$ aryl and $C_3$-$C_8$ heterocyclyl are optionally substituted; $R^{19A}$ independently are hydrogen, optionally substituted $C_1$-$C_8$ alkyl, —OH or optionally substituted —O—$C_1$-$C_8$ alkyl; $R^{20}$ is hydrogen or $C_1$-$C_{20}$ alkyl, $C_6$-$C_{24}$ aryl or $C_3$-$C_8$ heterocyclyl, optionally substituted, or —($R^{47}$O)$_m$—$R^{48}$, or —($R^{47}$O)$_m$—CH($R^{49}$)$_2$; $R^{21}$ is —$C_1$-$C_8$ alkylene-($C_6$-$C_{24}$ aryl) or —$C_1$-$C_8$ alkylene-($C_5$-$C_{24}$ heteroaryl), optionally substituted, or $C_1$-$C_8$ hydroxylalkyl, or optionally substituted $C_3$-$C_8$ heterocyclyl; Z is O, S, NH, or NR$^{46}$; R$^{46}$ is optionally substituted $C_1$-$C_8$ alkyl; subscript m is an integer ranging from 1-1000; R$^{47}$ is $C_2$-$C_8$ alkyl; R$^{48}$ is hydrogen or $C_1$-$C_8$ alkyl; R$^{49}$ independently are —COOH, —(CH$_2$)$_n$—N(R$^{50}$)$_2$, —(CH$_2$)$_n$—SO$_3$H, or —(CH$_2$)$_n$—SO$_3$—$C_1$-$C_8$ alkyl; R$^{50}$ independently are $C_1$-$C_8$ alkyl, or —(CH$_2$)$_n$—COOH; subscript n is an integer ranging from 0 to 6; and $X^1$ is $C_1$-$C_{10}$ alkylene.

183. The Drug Linker compound of embodiment 182, wherein the auristatin drug compound has the structure of Formula $D_{E-1}$, Formula $D_{E-2}$ or Formula $D_{F-1}$:

$D_{E-1}$

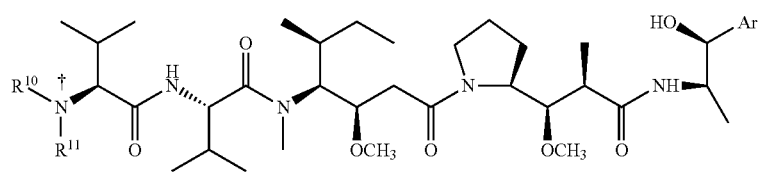

$D_{E-2}$

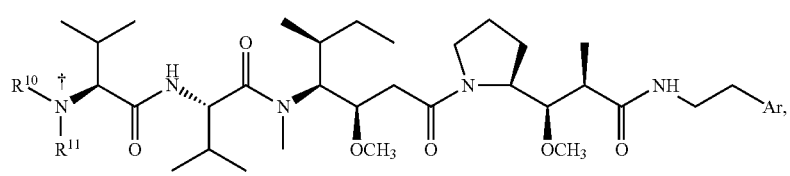

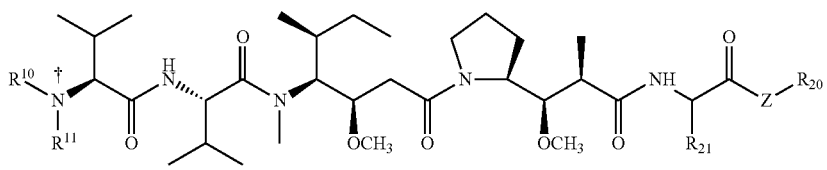

$D_{F-1}$ wherein Ar in Formula $D_{E-1}$ or Formula $D_{E-2}$ is optionally substituted $C_6$-$C_{10}$ aryl or optionally substituted $C_5$-$C_{10}$ heteroaryl, and in Formula $D_{F-1}$, Z is —O—, or —NH—; $R^{20}$ is hydrogen, $C_1$-$C_6$ alkyl, optionally substituted $C_6$-$C_{10}$ aryl or optionally substituted $C_5$-$C_{10}$ heteroaryl; and $R^{21}$ is optionally substituted $C_1$-$C_6$ alkyl, optionally substituted —$C_1$-$C_6$ alkylene-($C_6$-$C_{10}$ aryl) or optionally substituted —$C_1$-$C_6$ alkylene-($C_5$-$C_{10}$ heteroaryl).

184. The Drug Linker compound of embodiment 183 wherein one of $R^{10}$, $R^{11}$ is hydrogen or methyl and the other is methyl.

185. The Drug Linker compound of embodiment 183 wherein in Formula $D_{E-1}$ or $D_{E-2}$, Ar is optionally substituted phenyl or optionally substituted 2-pyridyl.

186. The Drug Linker compound of embodiment 183 wherein in Formula $D_{F-1}$, $R^{21}$ is $X^1$—S—$R^{21a}$ or $X^1$—Ar, wherein $X^1$ is $C_1$-$C_6$ alkylene, $R^{21a}$ is $C_1$-$C_4$ alkyl and Ar is optionally substituted phenyl or $C_5$-$C_{10}$ heteroaryl.

187. The Drug Linker compound of embodiment 183 wherein in Formula $D_{F-1}$, —Z— is —O— and $R^{20}$ is $C_1$-$C_4$ alkyl.

188. The Drug Linker compound of embodiment 183 wherein in Formula $D_{F-1}$, Z is —NH— and $R^{20}$ is optionally substituted phenyl or optionally substituted $C_5$-$C_{20}$ heteroaryl.

—CH(CH$_2$CH$_2$SCH$_3$)C(=O)NH-quinol-3-yl, —CH(CH$_2$Ph)C(=O)NH-p-C$_1$-Ph, or $R^{19B}$ has the structure of

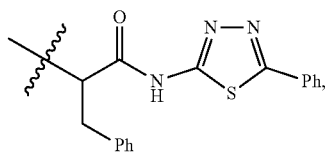 [SMILES: *C(Cc1ccccc1)C(=O)Nc1nnc(-c2ccccc2)s1]

wherein the wavy line indicates covalent attachment to the remainder of the auristatin compound.

190. The Drug Linker compound of embodiment 182 wherein the released auristatin drug compound incorporated as an auristatin quaternized Drug Unit (D$^+$) is Auristatin E, Auristatin PE, Auristatin PHE, Auristatin PYE, Auristatin EFP, Auristatin EB and Auristatin EVB.

191. The Drug Linker compound of embodiment 182 wherein the released auristatin drug compound incorporated into -D with covalent attachment through a carbamate functional group is monomethylauristatin E (MMAE) or monomethylauristatin F (MMAF).

192. The Drug Linker compound of embodiment 182 wherein the compound is represented by the structure of:

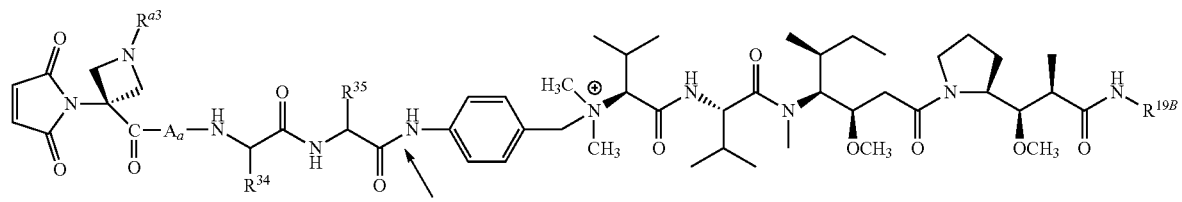

189. The Drug Linker compound of embodiment 182 wherein the auristatin drug compound has the structure of Formula $D_{F/E-3}$:

$D_{F/E-3}$

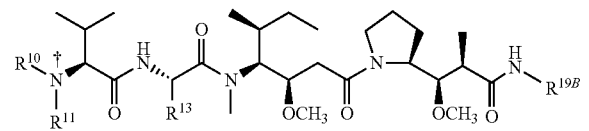

wherein one of $R^{10}$, $R^{11}$ is hydrogen or methyl and the other of $R^{10}$, $R^{11}$ is methyl; $R^{13}$ is isopropyl or —CH$_2$—CH(CH$_3$)$_2$; and $R^{19B}$ is —CH(CH$_3$)—CH(OH)-Ph, —CH(CO$_2$H)—CH(OH)—CH$_3$, —CH(CO$_2$H)—CH$_2$Ph, —CH(CH$_2$Ph)-2-thiazolyl, —CH(CH$_2$Ph)-2-pyridyl, —CH(CH$_2$-p-C$_1$-Ph), —CH(CO$_2$Me)-CH$_2$Ph, —CH(CO$_2$Me)-CH$_2$CH$_2$SCH$_3$, wherein subscript a is 1, so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—(CH$_2$CH$_2$O)$_{n'}$—$R^{PEG2}$; $R^{PEG1}$ is $C_1$-$C_4$ alkylene; $R^{PEG2}$ is —H or $C_1$-$C_4$ alkylene; subscript n' ranges from 1 to 36; and wherein the basic nitrogen atom bonded to $R^3$ is optionally protonated, or $R^3$ is a suitable nitrogen-protecting group; $R^{19B}$ is —CH(CH$_3$)—CH(OH)-Ph, —CH(CO$_2$H)—CH(OH)—CH$_3$, or —CH(CO$_2$H)—CH$_2$Ph; $R^{34}$ is isopropyl; and $R^{35}$ is methyl or —(CH$_2$)$_3$NH(C=O)NH$_2$.

193. The Drug Linker compound of embodiment 182 wherein the compound has the structure of:

227

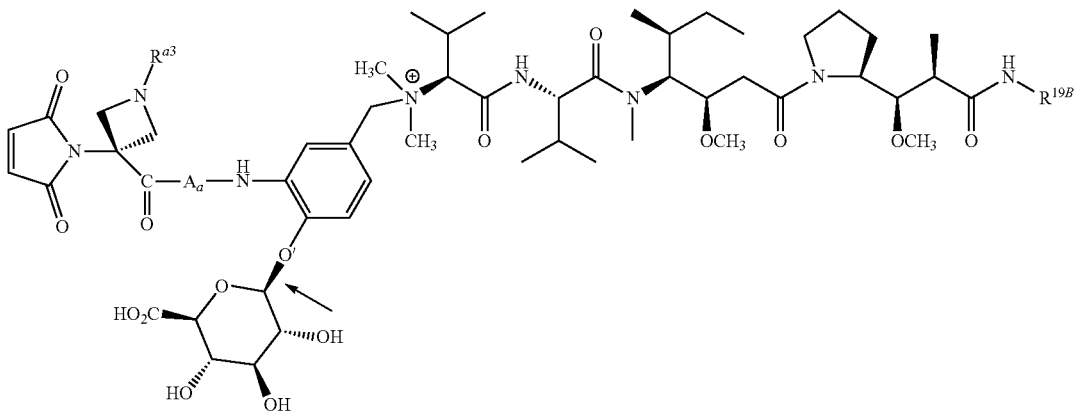

wherein subscript a is 1, so that A is present, wherein A is an α-amino acid or β-amino acid residue; and $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated, or $R^{a3}$ is a suitable nitrogen protecting group.

194. The Drug Linker compound of embodiment 182 wherein the compound has the structure of:

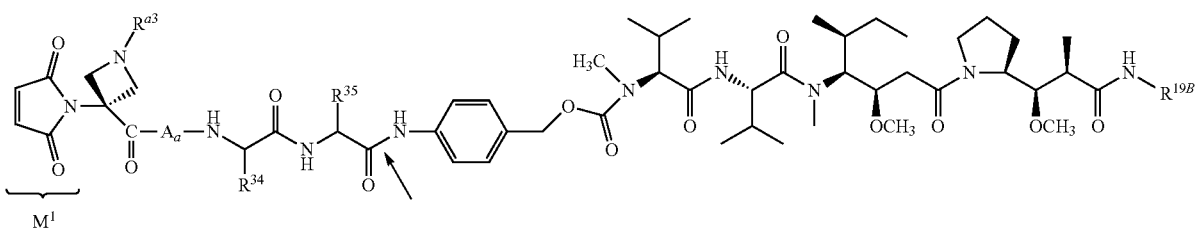

wherein subscript a is 1 and A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—$(CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^3$ is optionally protonated, or $R^{a3}$ is a suitable nitrogen-protecting group; $R^{19B}$ is —CH($CH_3$)—CH(OH)-Ph, —CH($CO_2H$)—CH(OH)—$CH_3$, or —CH($CO_2H$)—$CH_2$Ph; and $R^{34}$ is isopropyl and $R^{35}$ is methyl or —$(CH_2)_3NH(C=O)NH_2$.

195. The Drug Linker compound of embodiment 182 wherein the compound has the structure of:

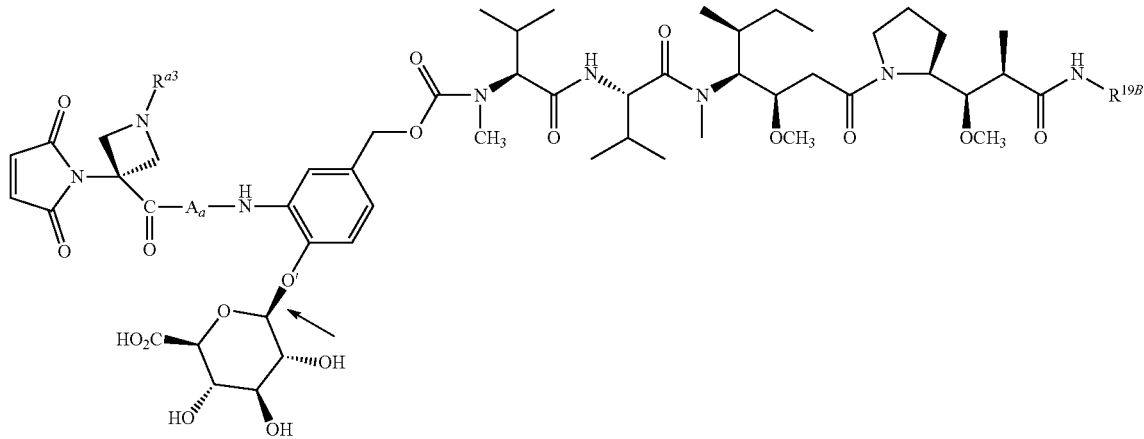

wherein subscript a is 1, so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—($CH_2CH_2O$)$_{n'}$—$R^{PEG2}$; $R^{PEG1}$ is $C_1$-$C_4$ alkylene; $R^{PEG2}$ is —H or $C_1$-$C_4$ alkyl; and subscript n' ranges from 1 to 36; and wherein the basic nitrogen bonded to $R^{a3}$ is optionally protonated, or $R^{a3}$ is a suitable nitrogen-protecting group; and $R^{19B}$ is —CH($CH_3$)—CH(OH)-Ph, —CH($CO_2H$)—CH(OH)—$CH_3$, or —CH($CO_2H$)—$CH_2$Ph.

196. The Drug Linker compound of embodiment 130, wherein subscript w is 1; subscript y is 1 or 2, wherein Y attached to W is a self-immolative Spacer Unit; and D is that of a PBD compound, thereby defining a PBD Drug Unit.

197. The Drug Linker compound of embodiment 196 wherein the PBD Drug Unit has the structure of:

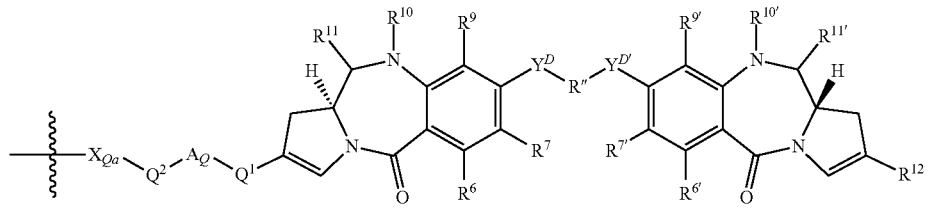

wherein the wavy line indicates covalent attachment of the PBD Drug Unit to the remainder of composition structure; $A_Q$ is a phenylene or $C_5$-$C_7$ heteroarylene, optionally substituted; $X_{Qa}$ is selected from the group consisting of —O—, —S—, —C(=O)O—, —C(=O)—, —NH(C=O)—, and —N($R^N$)—, wherein $R^N$ is selected from the group consisting of H, $C_1$-$C_4$ alkyl and ($C_2H_4O$)$_{n'}$—$CH_3$, wherein subscript n' ranges from 1 to 36, and either:
(i) $Q^1$ is a single bond, and $Q^2$ is selected from the group consisting of a single bond and —Z—($CH_2$)$_n$—, wherein Z is selected from the group consisting of a single bond, O, S and NH and subscript n ranges from 1 to 3, or (ii) $Q^1$ is —CH=CH—, and $Q^2$ is a single bond;
$R^{12}$ is $C_6$-$C_{10}$ aryl or $C_5$-$C_{10}$ heteroaryl; $R^6$ and $R^9$ are independently selected from the group consisting of H, R, OH, OR, SH, SR, $NH_2$, NHR, NRR', nitro and halo; $R^7$ is selected from the group consisting of H, R, OH, OR, SH, SR, $NH_2$, NHR, NRR', nitro and halo; R and R' are independently selected from the group consisting of optionally substituted $C_1$-$C_{12}$ alkyl, $C_3$-$C_{20}$ heterocyclyl, $C_6$-$C_{20}$ aryl and $C_5$-$C_{20}$ heteroaryl; and either:
(a) $R^{10}$ is H, and $R^{11}$ is OH or $OR^A$, wherein $R^A$ is $C_1$-$C_4$ alkyl, (b) $R^{10}$ and $R^{11}$ form a nitrogen-carbon double bond between the nitrogen and carbon atoms to which they are attached, or (c) $R^{10}$ is H and $R^{11}$ is $SO_zM$, where subscript z is 2 or 3 and M is a monovalent cation;
R" is $C_3$-$C_{12}$ alkylene, the carbon chain of which is optionally interrupted by one, two or three heteroatoms selected from the group consisting of O, S and NH, and/or by an aromatic ring; $Y^D$ is selected from the group consisting of O, S and NH; $R^{6'}$, $R^{7'}$, $R^{9'}$, and $YD'$ are independently selected from the same groups as $R^6$, $R^7$, $R^9$, and $Y^D$, respectively, and $R^{10'}$ and $R^{11'}$ are selected independently from the same groups as $R^{10}$ and $R^{11}$, respectively, provided if $R^{11}$ and $R^{11'}$ are each $SO_zM$, each M is an independently selected monovalent cation or together represents a divalent cation; and wherein optional substitution is by one, two or three substituents independently selected from the group consisting of halo, nitro, cyano, —OR, $C_1$-$C_7$ alkyl, $C_3$-$C_7$ heterocyclyl, dimethyl-aminopropyloxy, piperazinyl and bis-oxy-$C_1$-$C_3$ alkylene, wherein R is as previously defined.

198. The Drug Linker compound of embodiment 197, wherein $R^7$ is selected from the group consisting of H, OH and OR.

199. The Drug Linker compound of embodiment 198, wherein $R^7$ is $C_1$-$C_4$ alkyloxy.

200. The Drug Linker compound of embodiment 197, 198 or 199, wherein $Y^D$ is O.

201. The Drug Linker compound of any one of embodiments 197 to 200, wherein R" is $C_3$-$C_7$ alkylene.

202. The Drug Linker compound of any one of embodiments 197 to 201, wherein $R^9$ is H.

203. The Drug Linker compound of any one of embodiments 197 to 202, wherein $R^6$ is selected from the group consisting of H and halo.

204. The Drug Linker compound of any one of embodiments 197 to 203, wherein $A_Q$ is phenyl.

205. The Drug Linker compound of any one of embodiments 197 to 204, wherein $X_{QA}$ is selected from the group consisting of —O—, —S— and —NH—.

206. The Drug Linker compound of any one of embodiments 197 to 205, wherein $Q^1$ is a single bond.

207. The Drug Linker compound of any one of embodiments 197 to 205, wherein $Q^1$ is —CH=CH—.

208. The Drug Linker compound of any one of embodiment 197 to 207, wherein $Q^2$ is a single bond.

209. The Drug Linker compound of any one of embodiments 197 to 207, wherein $Q^2$ is —Z—($CH_2$)$_n$—, Z is O or S and subscript n is 1 or 2.

210. The Drug Linker compound of any one of embodiments 197 to 209, wherein $R^{12}$ is phenyl or $C_5$-$C_6$ heteroaryl, optionally substituted.

211. The Drug Linker compound of embodiment 210, wherein $R^{12}$ is optionally substituted phenyl.

212. The Drug Linker compound of embodiment 211, wherein $R^{12}$ is p-methoxyphenyl.

213. The Drug Linker compound according to any one of embodiments 197 to 212, wherein $R^{10}$ and R" form a nitrogen-carbon double bond.

214. The Drug Linker compound of any one of embodiments 197 to 213, wherein $R^{6'}$, $R^{7'}$, $R^{9'}$, $R^{1'}$, $R^{1'}$ and $Y^{D'}$ are the same as $R^6$, $R^7$, $R^9$, $R^{10}$, $R^{11}$ and $Y^D$, respectively.

215. The Drug Linker compound of embodiment 197, wherein the compound is represented by the structure of:

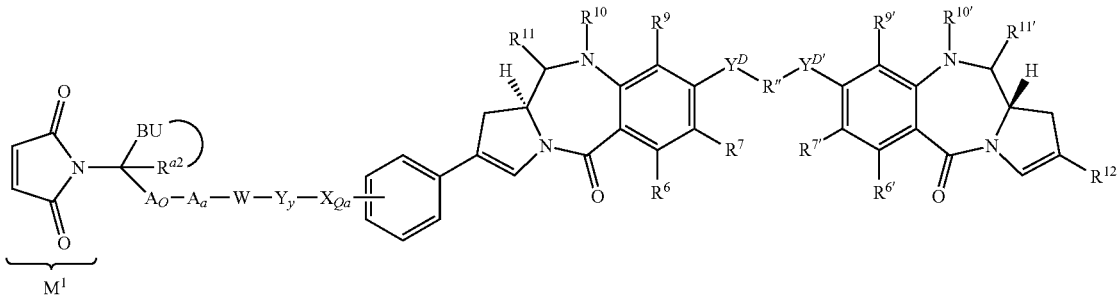

wherein W is a Peptide Cleavable Unit; and subscript y is 1 or 2, wherein Y bonded to W is a self-immolative Spacer Unit, wherein the bond between W and that self-immolative Spacer Unit in the Drug Linker compound or a Ligand Drug Conjugate compound prepared from the Drug Linker compound is cleavable by a protease to initiate release of the PBD Drug Unit as a PBD dimer from that Drug Linker compound or Ligand Drug Conjugate compound, or subscript y is 0, so that W is bonded to XQA, wherein the bond between W and XQA in the Drug Linker compound or a Ligand Drug Conjugate compound prepared from the Drug Linker compound is cleavable by a protease to initiate release of the PBD Drug Unit as a PBD dimer from that Drug Linker compound or Ligand Drug Conjugate compound.

216. The Drug Linker compound of embodiment 215 wherein the compound has the structure of:

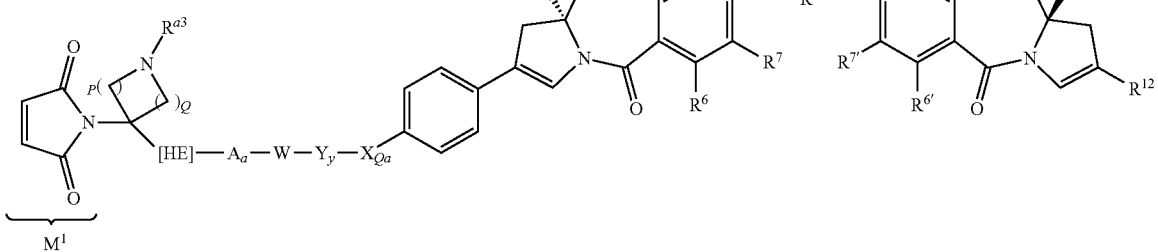

wherein subscript P is 1 or 2; subscript Q ranges from 1 to 6; $X_{Qa}$ is —NH—; and $R^{a3}$ is —H, optionally substituted $C_1$-$C_6$ alkyl, optionally substituted —$C_1$-$C_4$ alkylene-($C_6$—$C_{10}$ aryl) or —$R^{PEG1}$—O—$(CH_2CH_2O)_{n'}$—$R^{PEG2}$, wherein $R^{PEG1}$ is $C_1$-$C_4$ alkylene; $R^{PEG2}$ is —H or $C_1$-$C_4$ alkyl; and subscript n' ranges from 1 to 36; and wherein the basic nitrogen atom bonded to $R^{a3}$ is optionally protonated, or $R^{a3}$ is a suitable nitrogen-protecting group.

217. The Drug Linker compound of embodiment 216, wherein subscript P is 1 and subscript Q is 1, 2 or 3 or subscript P is 2 and Q is 1 or 2.

218. The Drug Linker compound of embodiment 217, wherein subscript P is 1, subscript Q is 1.

219. The Drug Linker compound of embodiment 218, wherein the compound has the structure of:

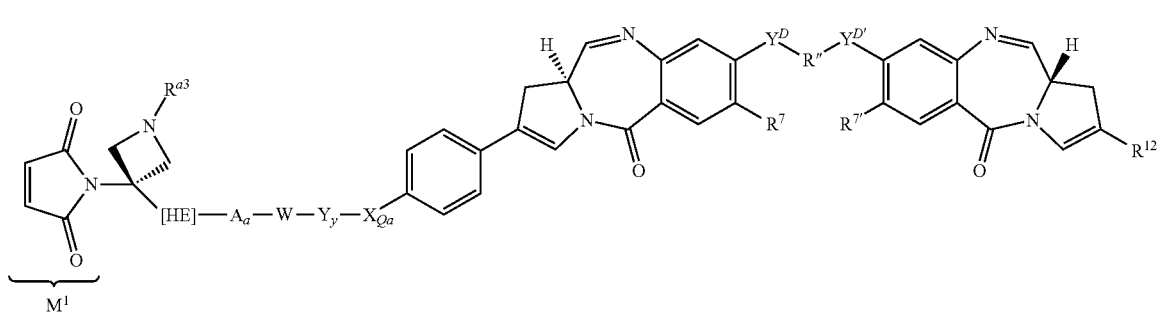

wherein $X_{Qa}$ is —NH—; $R^{a3}$ is —H, $C_1$-$C_4$ alkyl or —$R^{PEG1}$—O—$(CH_2CH_2O)_{n'}$—$R^{PEG2}$; $R^{PEG1}$ is —$CH_2$— or —$CH_2CH_2$—; $R^{PEG2}$ is —H, $CH_3$ or —$CH_2CH_3$; subscript n' ranges from 1 to 36; and wherein the basic nitrogen atom bonded to $R^3$ is optionally protonated, or $R^3$ is a suitable nitrogen-protecting group.

220. The Drug Linker compound of embodiment 218, wherein the compound has the structure of:

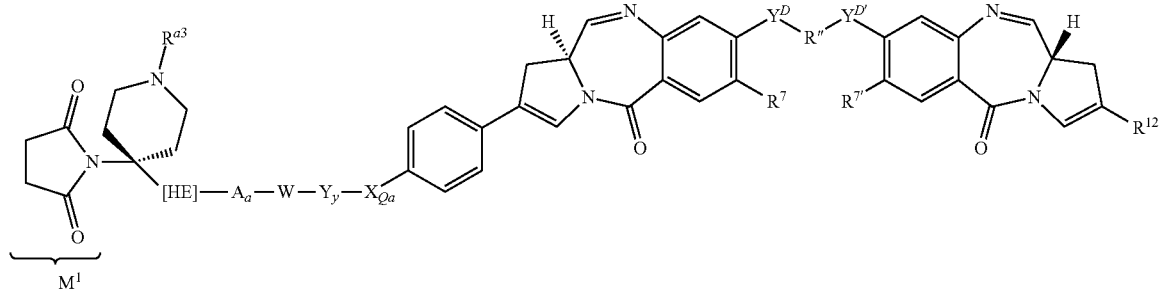

wherein $X_{Qa}$ is —NH—; $R^{a3}$ is —H, $C_1$-$C_4$ alkyl, or —$R^{PEG1}$—O—$(CH_2CH_2O)$.—$R^{PEG2}$, wherein $R^{PEG1}$ is —$CH_2$— or —$CH_2CH_2$—; $R^{PEG2}$ is —H, $CH_3$ or —$CH_2CH_3$; and subscript n' ranges from 1 to 36; and wherein the basic nitrogen bonded to $R^{a3}$ is optionally protonated, or $R^{a3}$ is a suitable nitrogen protecting group.

221. The Drug Linker compound of any one of embodiments 197 to 220, wherein $Y^D$ and YD' are O; $R^7$ is —OR and $R^{7'}$ is —OR', wherein R and R' are the same $C_1$-$C_6$ alkyl; $R^{12}$ is optionally substituted phenyl, and $A_Q$ is optionally substituted phenylene.

222. The Drug Linker compound of any one of embodiments 197 to 221, wherein R" is $C_3$-$C_5$ alkylene; $R^7$ and $R^{7'}$ are —$OCH_3$; subscript a is 0, so that A is absent, or subscript a is 1, so that A is present, wherein A is an amino acid residue, —NH—$R^{PEG1}$—O—$(CH_2CH_2O)_{n'}$—$R^{PEG3}$—C(=O)—, or other amine-containing acid moiety when HE is —C(=O), or A is $C_1$-$C_6$ alkylene-C(=O) or —$R^{PEG1}$—O—$(CH_2CH_2O)_{n'}$—$R^{PEG3}$—C(=O) when HE is absent; and $R^{PEG1}$ and $R^{PEG3}$ are independently selected $C_1$-$C_4$ alkylene.

223. The Drug Linker compound of embodiment 219, wherein the compound has the structure of:

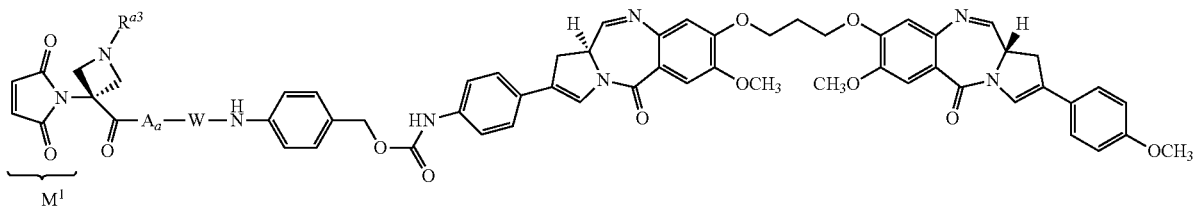

wherein A, when present, is an α-amino acid or a β-amino acid residue; and $R^{a3}$ is —H, wherein the basic nitrogen atom bonded to $R^3$ is optionally protonated.

224. The Drug Linker compound of embodiment 219 wherein the compound has the structure of:

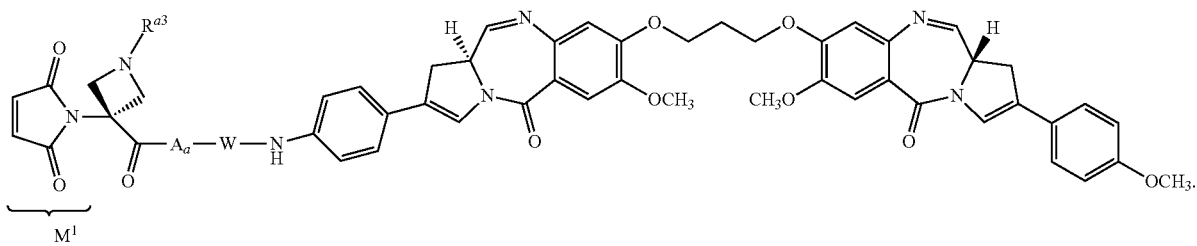

225. The Drug Linker compound of any one of embodiments 130 to 224, wherein if D, or D as D⁺, is that of a biologically active compound or derivative thereof, wherein that compound or its derivative is hydrophobic or has a S log P<0, then A or a subunit thereof is -L$^P$(PEG), wherein L$^P$ is a single unit or has 1, 2, 3 or 4 subunits.

226. The Drug Linker compound of claim 225 wherein -L$^P$- or a subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the substituted sulfur is in reduced or oxidized form.

227. The Drug Linker compound of embodiment 225 wherein -L$^P$- or a subunit thereof is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

228. The Drug Linker compound of embodiment 225 wherein L$_P$ or a subunit thereof is selected from the group consisting of lysine, glutamic acid, aspartic acid, cysteine, penicillamine, serine or threonine in its D- or L-stereochemical configuration.

229. The Drug Linker compound of embodiment 225, wherein -L$^P$- or a subunit thereof has the structure of Formula L$^P$-1 or L$^P$-2:

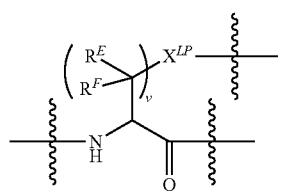

(Formula L$^P$-1)

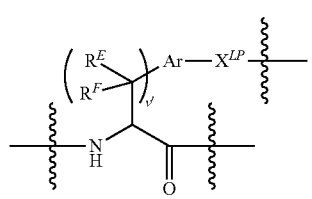

(Formula L$^P$-2)

wherein subscript v is an integer ranging from 1 to 4; subscript v' is an integer ranging from 0 to 4; X$^{LP}$ is provided by a natural or un-natural amino acid side chain or is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)—, or heterocyclo; wherein each R$^{LP}$ is independently selected from the group consisting of hydrogen and optionally substituted C$_1$-C$_6$ alkyl or two of R$^{LP}$ together along with their intervening atoms define a C$_5$-C$_6$ heterocyclo and any remaining R$^{LP}$ are as previously defined; Ar is a C$_6$-C$_{10}$ arylene or a C$_5$-C$_{10}$ heteroarylene, optionally substituted; each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene or optionally substituted C$_5$-C$_{10}$ heteroarylene, or R$^E$ and R$^F$ together with the carbon atom to which both are attached defines an optionally substituted spiro C$_3$-C$_6$ carbocyclo, or R$^E$ and R$^F$ from adjacent carbon atoms together with these atoms and any intervening carbon atoms defines an optionally substituted C$_5$-C$_6$ carbocyclo with any remaining R$^E$ and R$^F$ as previously defined; wherein one of the wavy lines indicate the point of covalent attachment of a PEG Unit and the other wavy lines indicates covalent attachment of Formula L$^P$-1 or Formula L$^P$-2 within the structure representing the Drug Linker compound.

230. The Drug Linker compound of embodiment 225 wherein -L$^P$(PEG)- or a PEG-containing subunit thereof has the structure of Formula L$^P$-3 or Formula L$^P$-4:

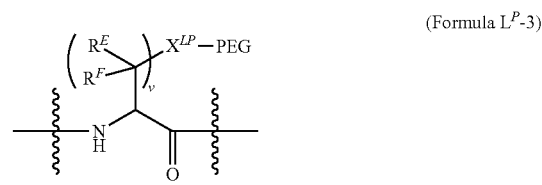

(Formula L$^P$-3)

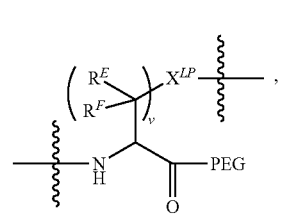

(Formula L$^P$-4)

231. The Drug Linker compound of embodiment 229 or 230 wherein the side chain of —C(R$^E$)(R$^F$)—X$^{LP}$ is provided by a natural or un-natural amino acid side chain.

232. The Drug Linker compound of embodiment 229 or 230 wherein R$^E$ and R$^F$ are independently selected from the group consisting of —H and —C$_1$-C$_4$ alkyl.

232. The Drug Linker compound of any one of embodiments 229 to 232 wherein X$^{LP}$ is selected from the group consisting of —O—, —NH, —S— and —C(=O)—.

233. The Drug Linker compound of embodiment 229 wherein the compound has the structure of:

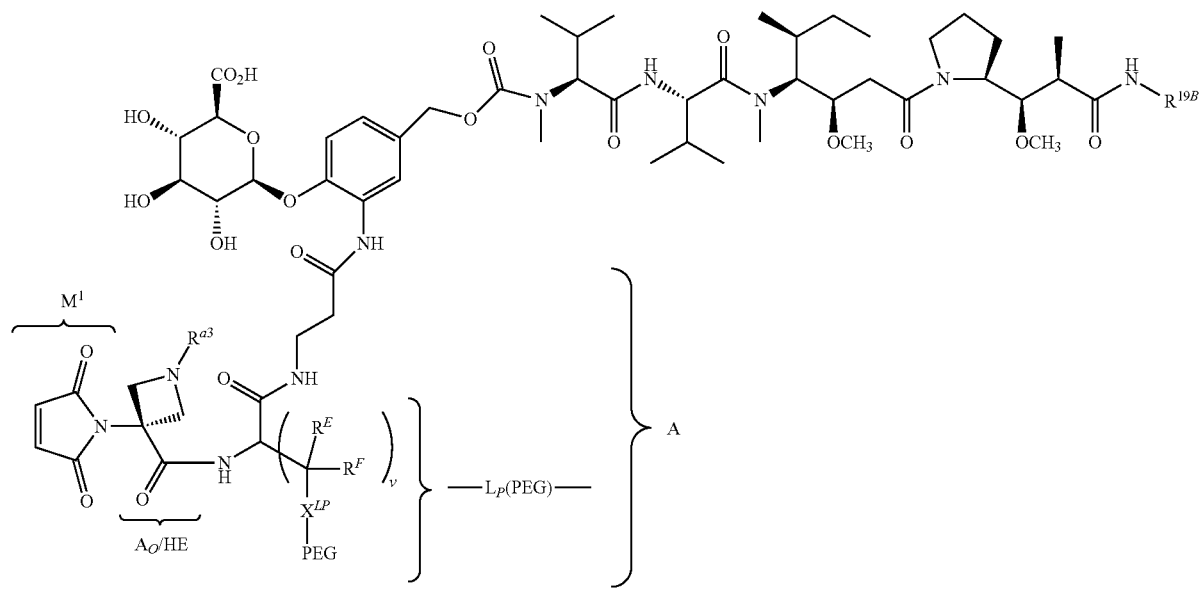

wherein $R^3$ is —H, optionally substituted $C_1$-$C_6$ alkyl or optionally substituted —$C_1$-$C_4$ alkylene-($C_6$-$C_{10}$ aryl), wherein the basic nitrogen bonded to $R^3$ is optionally protonated; and $R^{19B}$ is —CH(CH$_3$)—CH(OH)-Ph, —CH(CO$_2$H)—CH(OH)—CH$_3$, or —CH(CO$_2$H)—CH$_2$Ph.

234. The Drug Linker compound of embodiment 229 wherein the compound has the structure of:

wherein $R^{2A}$ is —C(=O)CH$_3$, —CH$_2$CH$_3$, —CH$_2$CH=CH$_2$ or —CH$_2$C(=CH$_2$)CH$_3$; $R^{a3}$ is —H, optionally substituted $C_1$-$C_6$ alkyl or optionally substituted —$C_1$-$C_4$ alkylene-($C_6$-$C_{10}$ aryl), wherein the basic nitrogen atom bonded to $R^3$ is optionally protonated; subscript u is 0 or 1; and $R^{7B}$ is —OH when subscript u is 1 or is absent when subscript u is 0.

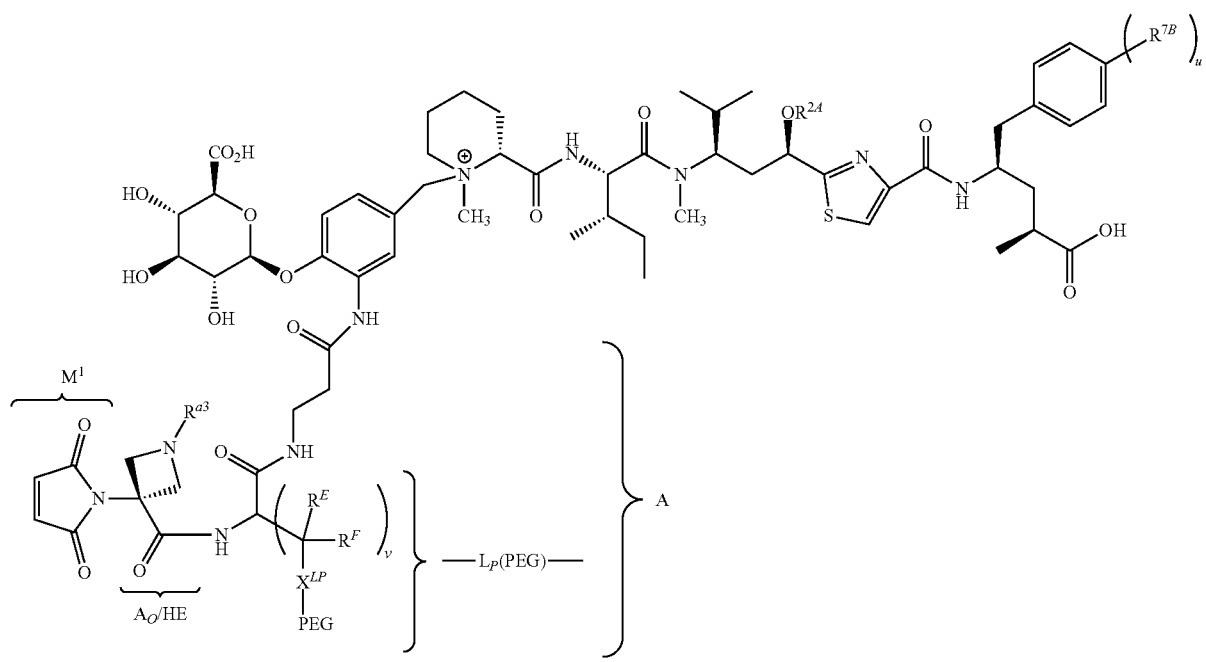

235. The Drug Linker compound of any one of embodiments 229-234 wherein PEG has the structure selected from the group consisting of:

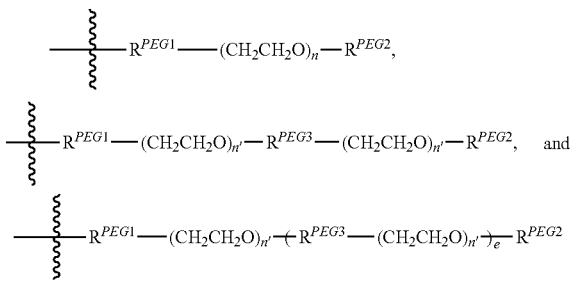

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

236. The Drug Linker compound of any one of embodiments 229 to 234 wherein —$X^{LP}$—PEG has the structure of:

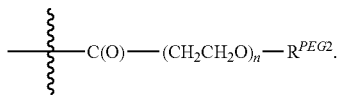

237. The Drug Linker compound of embodiment 235 or 236 wherein subscript n is 12 and $R^{PEG2}$ is hydrogen or —CH$_3$.

238. The Drug Linker compound of any one of embodiments 134 to 151 wherein —Y'-D has the structure of:

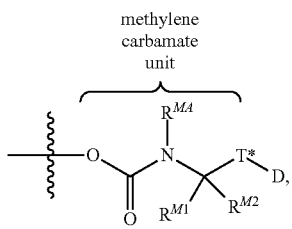

wherein Y' is a methylene carbamate unit; the wavy line indicates the point of covalent attachment of the methylene carbamate unit to the remainder of the Ligand Drug Conjugate composition structure; D is a Drug Unit having an optionally substituted functional group incorporated into the methylene carbamate unit; T* is a heteroatom of said Drug Unit functional group; $R^M$, $R^{M1}$ and $R^{M2}$ independently are hydrogen, optionally substituted $C_1$-$C_6$ alkyl, optionally substituted $C_6$-$C_{14}$ aryl, or optionally substituted C-linked $C_3$-$C_8$ heteroaryl, or $R^M$ and $R^{M1}$ together with the nitrogen and carbon atoms to which they are attached define an azetidine, pyrrolidine, piperidine or homopiperidine heterocyclo, and $R^{M2}$ is hydrogen; wherein activation of the Glucuronide Unit or Peptide Cleavable Unit of the Drug Linker compound or of a Ligand Drug Conjugate compound prepared from the Drug Linker compound releases D as a biologically active compound or derivative thereof having a functional group comprised of -T*—H.

239. The Drug Linker compound of claim 223=8 wherein the methylene carbamate unit covalently attached to D has the structure of:

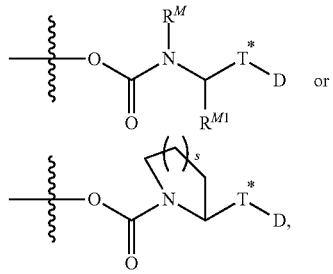

wherein subscript s is 0, 1 or 2.

240. The Drug Linker compound of claim 239 wherein the methylene carbamate unit covalently attached to D has the structure of:

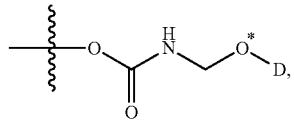

wherein activation of the Glucuronide Unit or Peptide Cleavable Unit of the Drug Linker compound of a Ligand Drug Conjugate compound prepared from the Drug Linker compound releases D as a biologically active compound or derivative thereof having a hydroxyl functional group whose oxygen heteroatom corresponds to O*.

241. The Drug Linker compound of any one of embodiments 130-224 wherein the first optional Stretcher Unit (A) or a subunit thereof has the structure of formula (3) or formula (4):

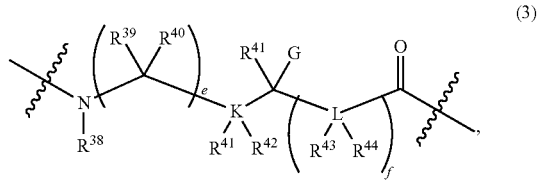

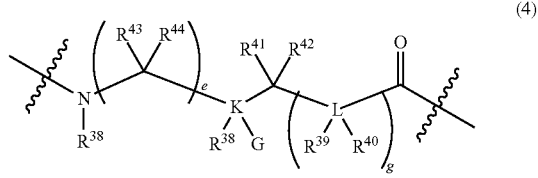

wherein the wavy lines indicated covalent attachment within the composition structure; wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12;

wherein G is hydrogen, optionally substituted $C_1$-$C_6$ alkyl, —OH, —OR$^{PR}$, —CO$_2$H, CO$_2$R$^{PR}$, wherein R$^{PR}$ is a suitable protecting, or G is —N(R$^{PR}$)(R$^{PR}$), wherein R$^{PR}$ are independently a protecting group or R$^{PR}$ together form a suitable protecting group, or G is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted $C_1$-$C_6$ alkyl;

wherein R$^{38}$ is hydrogen or optionally substituted $C_1$-$C_6$ alkyl; R$^{39}$-R are independently selected from the group consisting of hydrogen, optionally substituted $C_1$-$C_6$ alkyl, optionally substituted $C_6$-$C_{24}$ aryl, and optionally substituted $C_5$-$C_{24}$ heteroaryl, or R$^{39}$, R$^{40}$ together with the carbon to which both are attached, or R$^{41}$, R$^{42}$ together with K to which both are attached when K is a carbon atom define a $C_3$-$C_6$ carbocyclo, and R$^{41}$—R$^{44}$ are as defined herein, or R$^{43}$, R$^{44}$ together with L to which both are attached when L is a carbon atom define a $C_3$-$C_6$ cycloalkyl, and R$^{39}$-R$^{42}$ are as defined herein, or R$^{40}$ and R$^{41}$, or R$^{40}$ and R$^{43}$, or R$^{41}$ and R$^{43}$ to together with the carbon atom or heteroatom to which they are attached and the atoms intervening between those carbon atoms and/or heteroatoms define a $C_5$-$C_6$ carbocyclo or a $C_5$-$C_6$ heterocyclo, and R$^{39}$, R$^{44}$ and the remainder of remainder of R$^{40}$-R$^{43}$ are as defined herein, provided that when K is O or S, R$^{41}$ and R$^{42}$ are absent, and when K is N, one of R$^{41}$, R$^{42}$ is absent, and when L is O or S, R$^{43}$ and R$^{44}$ are absent, and when L is N, one of R$^{43}$, R$^{44}$ is absent, or A has a structure of an alpha-amino, beta-amino or another amine-containing acid residue.

242. The Drug Linker compound of embodiment 241, wherein formula (3) or formula (4) has the structure of formula (3a) or formula (4a):

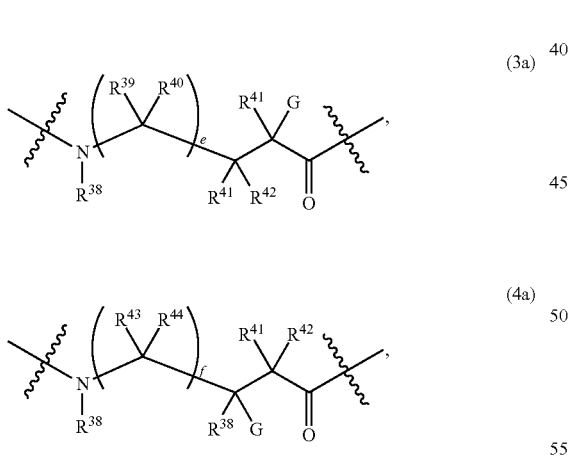

wherein subscript e and f are independently 0 or 1.

243. A method of preparing a Ligand Drug Conjugate composition comprising the step of contacting a Drug Linker compound of any one of claims 130 to 242 with a targeting agent having a reactive thiol functional group under conditions suitable for effecting Michael addition of the thiol to the indicated maleimide (M$^1$) moiety of the Drug Linker compound for incorporation of the targeting agent as a Ligand Unit in a Ligand Drug Conjugate compound of the composition.

244. A compound having the structure of:

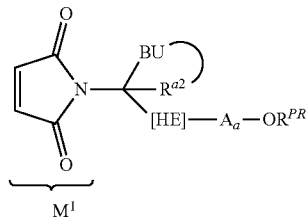

or a salt thereof, wherein HE is —C(=O)—; R$^{PR}$ is H or a suitable carboxylic acid protecting group; BU is a Basic Unit and R$^2$ is an optionally substituted $C_1$-$C_{12}$ alkyl group that together with the carbon atom to which both are attached, as represented by the curved line, define an optionally substituted $C_3$-$C_{20}$ heterocyclo having a skeletal secondary or tertiary basic nitrogen atom or a $C_3$-$C_{20}$ carbocyclo having exocyclic substitution by a basic nitrogen atom of a primary, secondary or tertiary amine functional group or an optionally substituted basic $C_1$-$C_{12}$ aminoalkyl, wherein the basic nitrogen atom of the amine or aminoalkyl is attributable to BU, and is optionally protonated or protected by a suitable nitrogen-protecting group; subscript a is 0 or 1; A is absent when subscript a is 0, or when subscript a is 1 A has the structure of formula (3) or formula (4):

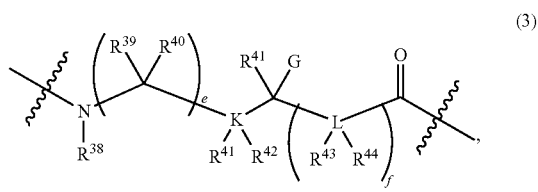

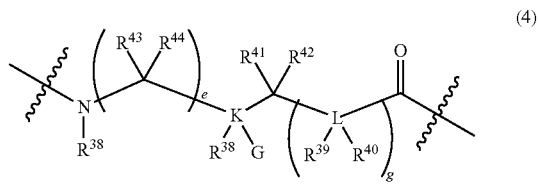

wherein the wavy lines indicate covalent attachment within the compound structure; wherein K and L independently are C, N, O or S, provided that when K or L is O or S, R$^{41}$ and R$^{42}$ to K or R$^{43}$ and R$^{44}$ to L are absent, and when K or L are N, one of R$^{41}$, R$^{42}$ to K or one of R$^{42}$, R$^{43}$ to L are absent, and provided that no two adjacent L are independently selected as N, O, or S; wherein subscripts e and f are independently selected integers that range from 0 to 12, and subscript g is an integer ranging from 1 to 12;

wherein G is hydrogen, optionally substituted $C_1$-$C_6$ alkyl, —OH, —OR$^{PR}$, —CO$_2$H, CO$_2$R$^{PR}$, wherein R$^{PR}$ is a suitable protecting, or G is —N(R$^{PR}$)(R$^{PR}$), wherein R$^{PR}$ are independently a protecting group or R$^{PR}$ together form a suitable protecting group, or G is —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted $C_1$-$C_6$ alkyl;

wherein R$^{38}$ is hydrogen or optionally substituted $C_1$-$C_6$ alkyl; R$^{39}$-R$^{44}$ are independently selected from the group consisting of hydrogen, optionally substituted $C_1$-$C_6$ alkyl, optionally substituted aryl, and optionally substituted heteroaryl, or R$^{39}$, R$^{40}$ together with the carbon atom to which both are attached, or $R^{41}$, $R^{42}$ together with K to which both are attached when K is a carbon atom define a $C_3$-$C_6$ carbocyclo, and $R^{41}$-$R^{44}$ are as defined herein, or $R^{43}$, $R^{44}$ together with L to which both are attached when L is a carbon atom define a $C_3$-$C_6$ cycloalkyl, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of remainder of $R^{40}$-$R^{43}$ are as defined herein, provided that when K is O or S, $R^{41}$ and $R^{42}$ are absent, and when K is N, one of $R^{41}$, $R^{42}$ is absent, and when L is O or S, $R^{43}$ and $R^{44}$ are absent, and when L is N, one of $R^{43}$, $R^{44}$ is absent, or A is an alpha-amino, beta-amino or another amine-containing acid residue.

245. The compound of embodiment 244 wherein formula (3) or formula (4) has the structure of formula (3a) or formula (4a):

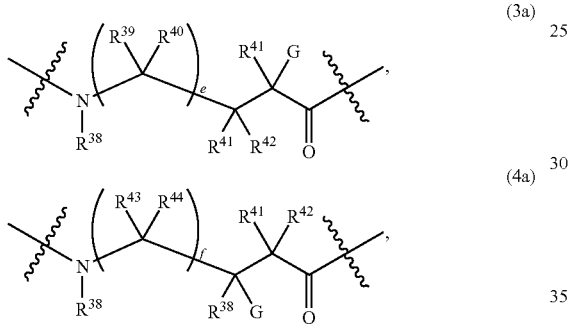

wherein subscript e and f are independently 0 or 1.

246. The compound of embodiment 244 wherein BU and $R^{a2}$ together with the carbon atom to which both are attached, define an optionally substituted $C_4$-$C_6$ heterocyclo having a skeletal secondary or tertiary basic nitrogen atom, wherein the basic nitrogen atom is attributable to BU and is optionally protonated or protected by a suitable nitrogen-protecting group.

247. The compound of embodiment 246, wherein the compound has the structure of:

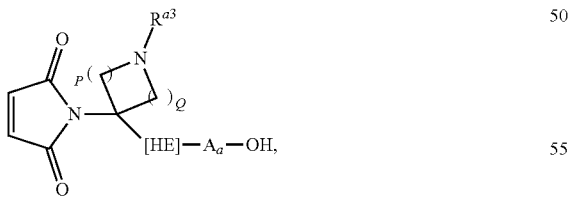

or a salt thereof, wherein subscript P is 1 or 2; subscript Q ranges from 1 to 6; and $R^{a3}$ is —H, optionally substituted $C_1$-$C_6$ alkyl, optionally substituted —$C_1$-$C_4$ alkylene-($C_6$-$C_{10}$ aryl) or —$R^{PEG1}$—O—($CH_2CH_2O$)$_{n'}$—$R^{PEG2}$, wherein $R^{PEG1}$ is $C_1$-$C_4$ alkylene; $R^{PEG2}$ is —H or $C_1$-$C_4$ alkylene; and subscript n' ranges from 1 to 36; and wherein the basic nitrogen bonded to $R^{a3}$ is optionally protonated, or $R^{a3}$ is an acid-labile nitrogen protecting group.

248. The compound of embodiment 247, wherein subscript P is 1 and subscript Q is 1, 2 or 3 or subscript P is 2 and Q is 1 or 2.

249. The compound of embodiment 248, wherein subscript P is 1, subscript Q is 1.

250. The compound of embodiment 248, wherein subscript P is 2, subscript Q is 2.

251. The compound of embodiment 244, wherein BU and $R^{a2}$ together with the carbon atom to which both are attached define a $C_5$-$C_6$ carbocyclo having exocyclic substitution by a basic nitrogen atom of a primary, secondary or tertiary amine functional group or by an aminomethyl group, optionally substituted, wherein the basic nitrogen atom of the amine or aminomethyl is attributable to BU and is optionally protonated or protected by a suitable nitrogen-protecting group.

252. The compound of embodiment 251, wherein the compound has the structure of:

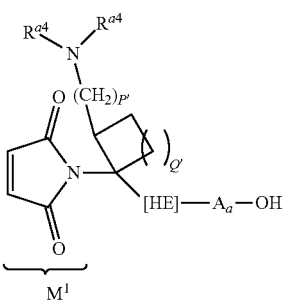

or a salt thereof, wherein subscript P' is 0 or 1; subscript Q' is 0, or Q' ranges from 1 to 6; each $R^{a4}$ is independently selected from the group consisting of hydrogen and optionally substituted $C_1$-$C_6$ alkyl, or both $R^{a4}$ together with the basic nitrogen atom to which they are attached define a basic nitrogen-containing $C_3$-$C_8$ heterocyclyl, optionally substituted, wherein in either instance the basic nitrogen is optionally protonated, or one $R^{a4}$ is hydrogen or an optionally substituted $C_1$-$C_6$ alkyl and the other $R^{a4}$ is a suitable nitrogen-protecting group, or both $R^{a4}$ together form a suitable nitrogen-protecting group.

253. The compound of embodiment 247, wherein the compound has the structure of:

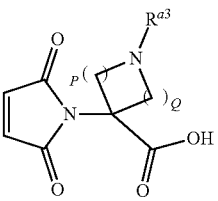

or a salt thereof, wherein subscript P is 1 or 2 and subscript Q is 1 or 2; and $R^{a3}$ is H, $C_1$-$C_4$ alkyl, —$CH_2Ph$, —$CH_2CH_2Ph$ or —$R^{PEG1}$—O—($CH_2CH_2O$)$_{n'}$—$R^{PEG2}$, wherein $R^{PEG1}$ is —$CH_2$— or —$CH_2CH_2$—; $R^{PEG2}$ is —H, —$CH_3$ or —$CH_2CH_3$; subscript n' ranges from 1 to 36; and wherein phenyl is optionally substituted and the basic nitrogen bonded to $R^{a3}$ is optionally protonated, or $R^{a3}$ is —C(=O)-t-Bu (BOC).

254. The compound of embodiment 253 wherein the compound has the structure of:

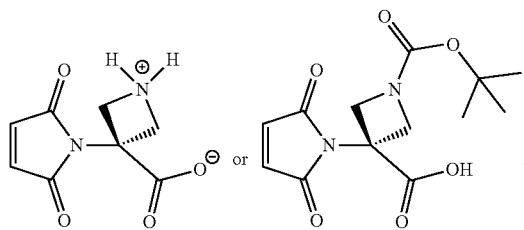

255. The compound of embodiment 253, wherein the compound has the structure of:

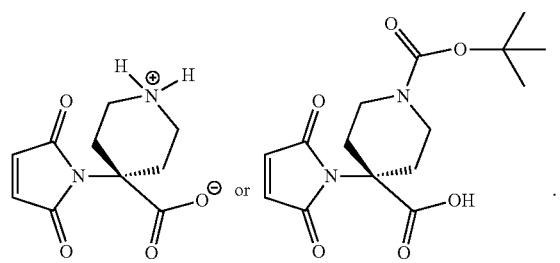

EXAMPLES

General Information.

All commercially available anhydrous solvents were used without further purification. Analytical thin layer chromatography was performed on silica gel 60 F254 aluminum sheets (EMD Chemicals, Gibbstown, NJ). Radial chromatography was performed on Chromatotron apparatus (Harris Research, Palo Alto, CA). Column chromatography was performed on a Biotage Isolera One™ flash purification system (Charlotte, NC). Analytical HPLC was performed on a Varian ProStar™ 210 solvent delivery system configured with a Varian ProStar 330 PDA detector. Samples were eluted over a C12 Phenomenex Synergi™ 2.0×150 mm, 4 m, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass mass spectrometer interfaced to an HP Agilent 1100 HPLC instrument equipped with a C12 Phenomenex Synergi 2.0×150 mm, 4 m, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2™ ToF mass spectrometer interfaced to a Waters 2695 Separations Module with a Waters 2996 Photodiode Array Detector; the column, mobile phases, gradient, and flow rate were same as for LC-MS system 1. UPLC-MS system 1 consisted of a Waters SQ mass detector interfaced to an Acquity Ultra Performance™ liquid chromatograph equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min). UPLC-MS system 2 consisted of a Waters Xevo G2 ToF mass spectrometer interfaced to a Waters Acquity H-Class Ultra Performance™ liquid chromatograph equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.7 mL/min). Preparative HPLC was carried out on a Varian ProStar™ 210 solvent delivery system configured with a Varian ProStar 330 PDA detector. Products were purified over a C12 Phenomenex Synergi 10.0×250 mm, 4 m, 80 Å reverse phase column eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was 4.6 mL/min with monitoring at 254 nm. Monitoring of Conjugate hydrolysis in the conversion of Formula 1 to Formula 2 was by UPLC-MS using a Waters Xevo G2-S QTOF interfaced to a Waters H Class UPLC equipped with an Agilent Technologies PLRP-S 300 Å, 2.1×50×3 μm reversed-phase column was used. Coupling constants (J) are reported in hertz. Analysis of the Cathepsin B digestion mixtures was performed on a Waters Acquity UPLC-SQ MS system equipped with an Acquity UPLC BEH C18 1.7 μm, 2.1×50 mm reverse-phase column. The eluent consisted of a linear gradient of acetonitrile from 3% to 97% in 0.1% aqueous formic acid over 2 min, followed by isocratic 97% acetonitrile for 1 min at flow rate 0.5 mL/min. NMR spectral data were collected on a Varian Mercury™ 400 MHz spectrometer.

Example 1: (Z)-1-(tert-butoxycarbonyl)-3-(3-carboxyacrylamido)-azetidine-3-carboxylic acid

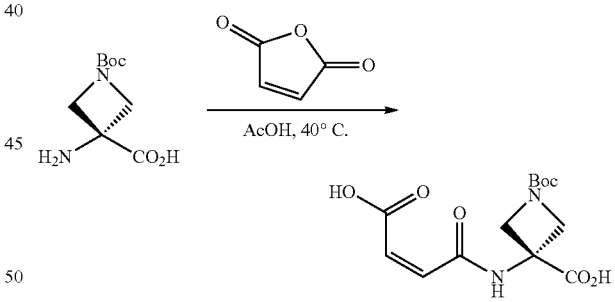

A 20 mL vial equipped with stir bar was charged with azetidine amino acid (0.89 g, 4.1 mmol), maleic anhydride (0.40 g, 4.1 mmol) and AcOH (8 mL). The mixture was stirred at 40° C. for 10 min then stirred at RT for 3 h. The solvent was removed in vacuo and the residue was taken up in DMSO/0.1% TFA in $H_2O$ (1:1, 2.0 mL). The reaction was purified by preparative HPLC and the product fractions were lyophilized to afford 0.84 g (65% yield) of the title compound.

Analytical UPLC-MS: $t_R$=0.84 min, m/z (ES+) calculated 315.11 (M+H)$^+$, found 315.13. $^1$H NMR (400 MHz, DMF-$d_7$): δ 10.2 (s, 1H), 6.78 (d, J=12.4 Hz, 1H), 6.54 (d, J=12.4 Hz, 1H), 4.94 (br m, 2H), 4.29 (br m, 2H), 1.59 (s, 9H). $^{13}$C NMR (100 MHz, DMF-$d_7$): δ 171.7, 166.3, 165.7, 133.3, 131.5, 79.5, 53.7, 27.8

Example 2: 1-(tert-butoxycarbonyl)-3-(2,5-dioxo-2,5-dihydro-1H-pyrrol-1-yl)azetidine-3-carboxylic acid (Boc-mAze)

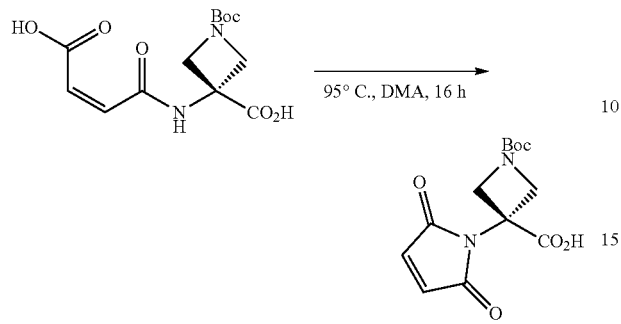

A 100 mL flask was charged with azetidine diacid (460 mg, 1.46 mmol), DMA (20 mL), and 4 Å molecular sieves (1.4 g). The reaction was stirred for 16 h at 95° C. The reaction was cooled to RT and filtered over Celite. The solvent was removed in vacuo. The residue was dissolved in DMSO (4 mL) and water (1 mL) and purified by preparative HPLC. The product fractions were collected and lyophilized to afford 120 mg (28% yield) of the title compound.

Analytical UPLC-MS: $t_R$=1.04 min, m/z (ES+) calculated 319.09 (M+Na)$^+$, found 319.10. $^1$H NMR (400 MHz, DMF-$d_7$): δ 7.14 (s, 2H), 4.57 (br m, 2H), 4.39 (br m, 2H), 1.44 (s, 9H). $^{13}$C NMR (100 MHz, DMF-$d_7$): δ 172.6, 172.0, 156.8, 136.4, 80.4, 54.3, 28.7

Example 3: (Z)-1-(tert-butoxycarbonyl)-4-(3-carboxyacrylamido)-piperidine-4-carboxylic acid

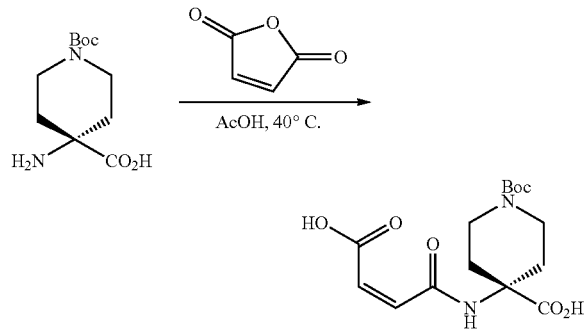

A 50 mL flask was charged with amino acid (1.0 g, 4.1 mmol), maleic anhydride (401 mg, 4.1 mmol), and AcOH (15 mL). The mixture was heated at 40° C. for 15 minutes then the reaction was stirred at RT for 2 h. The solvent was removed in vacuo and the residue was dissolved in 10 mL DCM. Hexane was added portion-wise (1 mL portions, 13 mL total) until the product began to crash out. The flask was placed in a -20° C. freezer overnight and filtered. The precipitate was dried in a vacuum desiccator to afford 800 mg (57% yield) of the title compound.

Analytical UPLC-MS: $t_R$=0.96 min, m/z (ES+) calculated 365.13 (M+Na)$^+$, found 365.19.

Example 4: 1-(tert-butoxycarbonyl)-4-(2,5-dioxo-2,5-dihydro-1H-pyrrol-1-yl)piperidine-4-carboxylic acid (Boc-mPip)

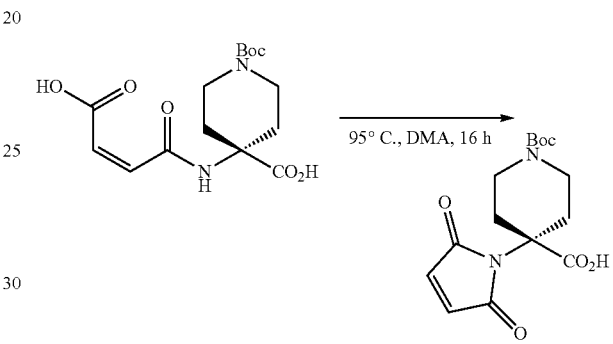

A 20 mL vial was charged with piperidine diacid (200 mg, 0.58 mmol), DMA (5 mL), and 4 Å molecular sieves (580 mg). The reaction was heated to 95° C. and stirred for 16 h. The reaction was cooled to RT and filtered over Celite. The solvent was removed in vacuo. The residue was dissolved in DMSO (2 mL) and water (0.5 mL) and purified by preparative HPLC. The product fractions were collected and lyophilized to afford 32 mg (17% yield) of the title compound.

Analytical UPLC-MS: $t_R$=1.16 min, m/z (ES+) calculated 347.12 (M+Na)$^+$, found 347.18.

Example 5: mPip-Val-Cit-PABC-MMAE

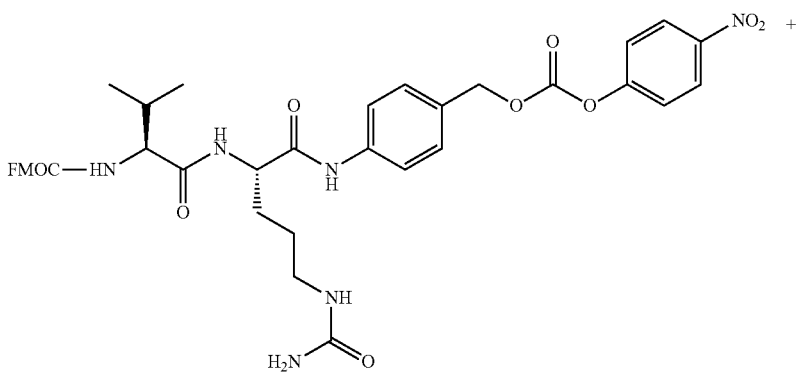

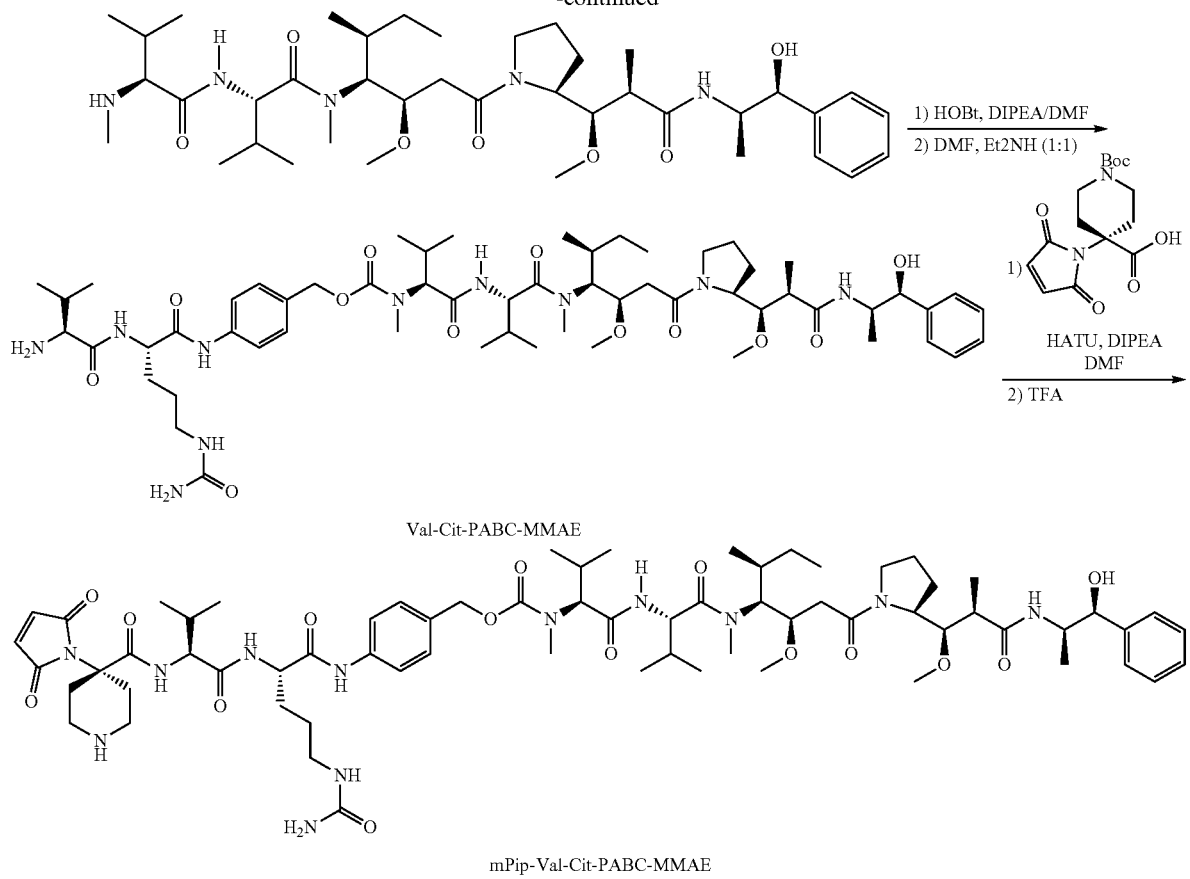

Val-Cit-PABC-MMAE mPip-Val-Cit-PABC-MMAE

Step 1: A vial was charged with the BOC protected form of the $L_{SS}$ component 4-(2,5-dioxo-2,5-dihydro-1H-pyrrol-1-yl)piperidine-4-carboxylic acid (4.0 mg, 0.012 mmol), which is abbreviated as Boc-mPip, HATU (4.7 mg, 0.012 mmol), DIPEA (6.4 μL, 0.037 mmol), and DCM (0.5 mL). The reaction was stirred for 15 min and Val-Cit-PABC-MMAE was added to the reaction. After 3 h, DMSO was added to the reaction and the product was purified by preparative HPLC and lyophilized to afford 8.1 mg (45% yield) of the BOC protected Drug Linker compound. The preparation of BOC protected intermediate 4-((S)-2-((S)-2-amino-3-methylbutanamido)-5-ureidopentanamido)benzyl (4-nitrophenyl) carbonate and its condensation with val-cit-PABC-MMAE is as previously described by WO2013173337 and is specifically incorporated by reference herein.

Step 2: A vial containing BOC-protected Drug Linker compound (8.1 mg, 0.006 mmol) was charged with TFA (1.5 mL, 20% in DCM) at 0° C. The reaction was allowed to warm to RT and stirred for 3 h. The reaction was diluted with DMSO and put under vacuum for 15 min to remove DCM. The product was purified by preparative HPLC and lyophilized to afford 3.0 mg (40% yield) of the title Drug Linker compound.

Analytical UPLC-MS: $t_R$=1.30 min, m/z (ES+) calculated 1329.78 (M+H)⁺, found 1329.92.

Example 6: mAze-Val-Cit-PABC-MMAE

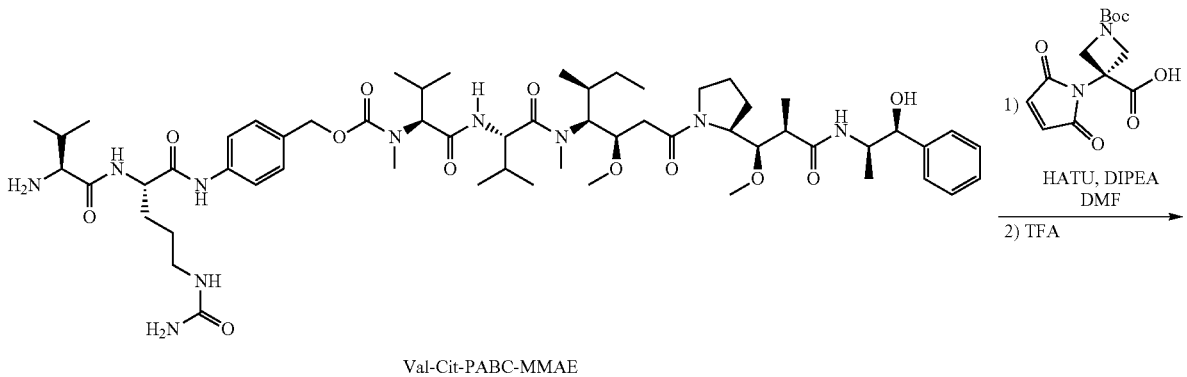

Val-Cit-PABC-MMAE

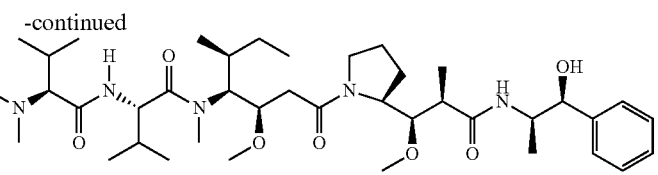
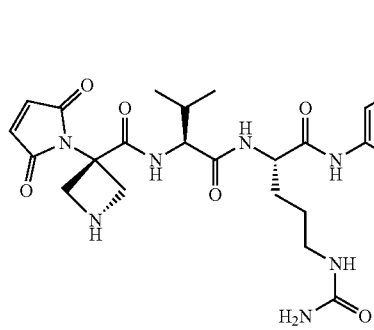

mAze-Val-Cit-PABC-MMAE

Peptide coupling of the intermediate val-cit-PABC-MMAE prepared as previously described (WO2013173337) with the BOC-protected form of the $L_{SS}$ component 3-(2,5-dioxo-2,5-dihydro-1H-pyrrol-1-yl)azetidine-3-carboxylic acid and subsequent BOC deprotection to provide the Drug Linker compound mAze-Val-Cit-PABC-MMAE was conducted in the same manner as for mPip-Val-Cit-PABC-MMAE of Example 5.

Analytical UPLC-MS: $t_R$=1.29 min, m/z (ES+) calculated 1301.75 (M+H)$^+$, found 1301.87.

Example 7: mAze-Lys-(PEG$_{12}$)-GluC-MMAE

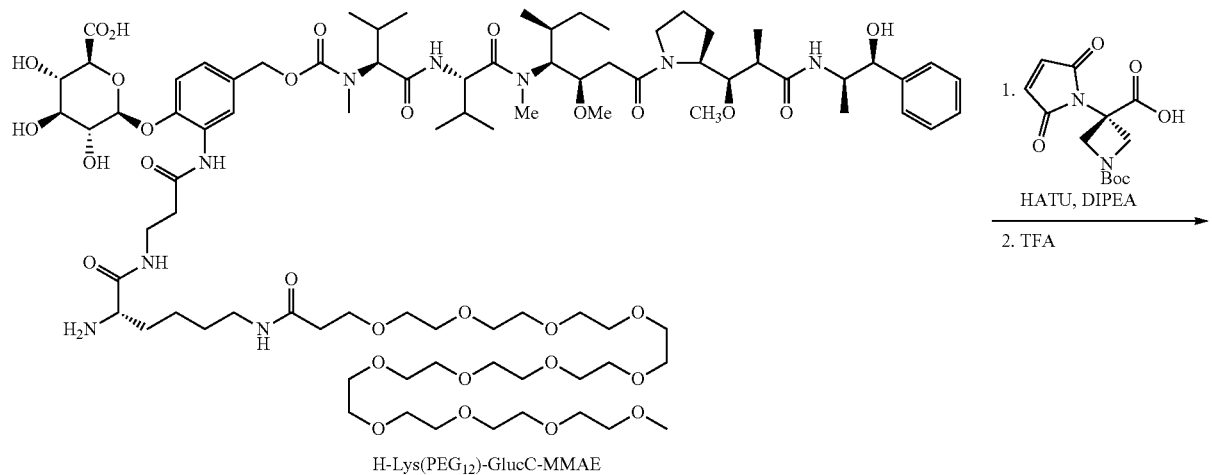

H-Lys(PEG$_{12}$)-GlucC-MMAE

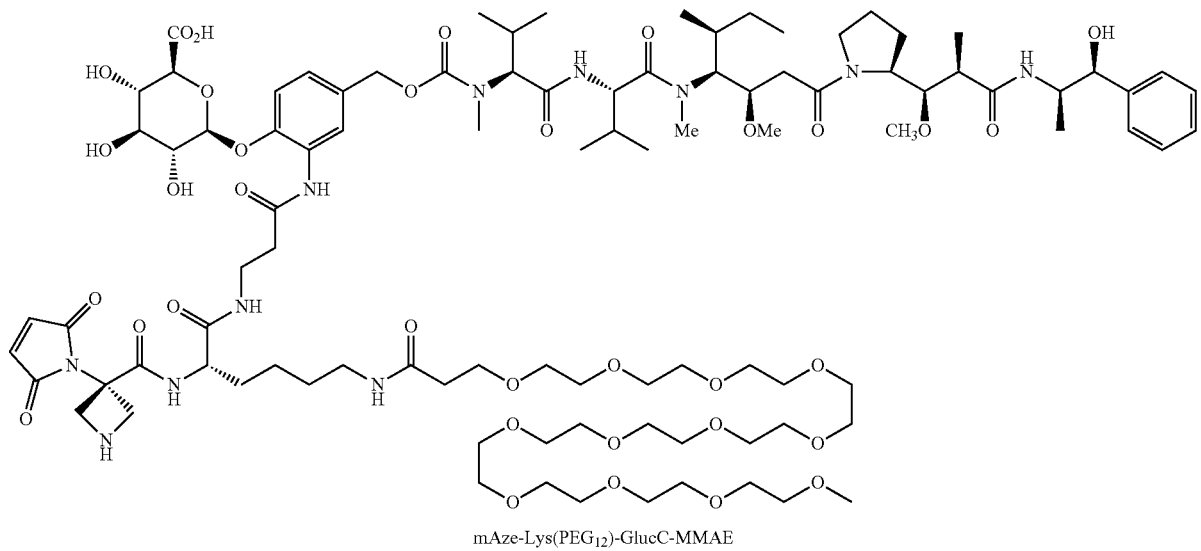

mAze-Lys(PEG$_{12}$)-GlucC-MMAE

253

Peptide coupling of the intermediate H-Lys(PEG$_{12}$)-GlucC MMAE with the BOC-protected form of the L$_{SS}$ component 3-(2,5-dioxo-2,5-dihydro-1H-pyrrol-1-yl)azetidine-3-carboxylic acid and subsequent BOC deprotection to provide mAze-Lys(PEG$_{12}$)-GluC-MMAE was conducted in the same manner as for mPip-Val-Cit-PABC-MMAE of Example 5. The preparation of the Drug Linker compound intermediate H-Lys(PEG$_{12}$)-GluC-MMAE is previously described by WO2015057699 and is specifically incorporated by reference herein Analytical UPLC-MS: t$_R$=1.22 min, m/z (ES+) calculated 1015.53 (M+Na+H)$^{2+}$, found 1015.76.

Example 8: Ph-nBu-mAze

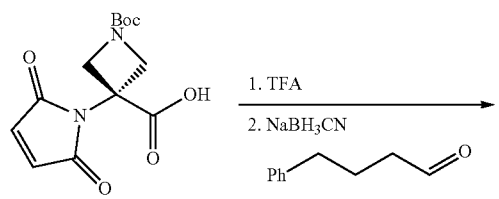

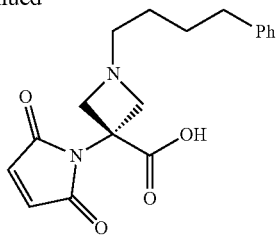

A vial containing BOC-protected maleimide (25 mg, 0.084 mmol) was charged with TFA (1 mL, 20% in DCM). The reaction was stirred at RT for 2 h, and the solvent was removed in vacuo.

Deprotected maleimide (5 mg, 0.025 mmol) was transferred to a vial and suspended a solution of 1% AcOH in DMF (300 μL). 4-Phenylbutanal (5 mg, 0.034 mmol) and NaBH$_3$CN (33 μL, 0.034 mmol, 1.0 M in THF) were added and the reaction was stirred at RT for 1 h. Reaction was purified on HPLC and lyophilized to afford 4 mg (48% yield) of the title compound.

Analytical UPLC-MS: t$_R$=0.89 min, m/z (ES+) calculated 329.15 (M+H)$^+$, found 329.21.

Example 9: Ph-nBu-mAze-Val-Cit-PABC-MMA

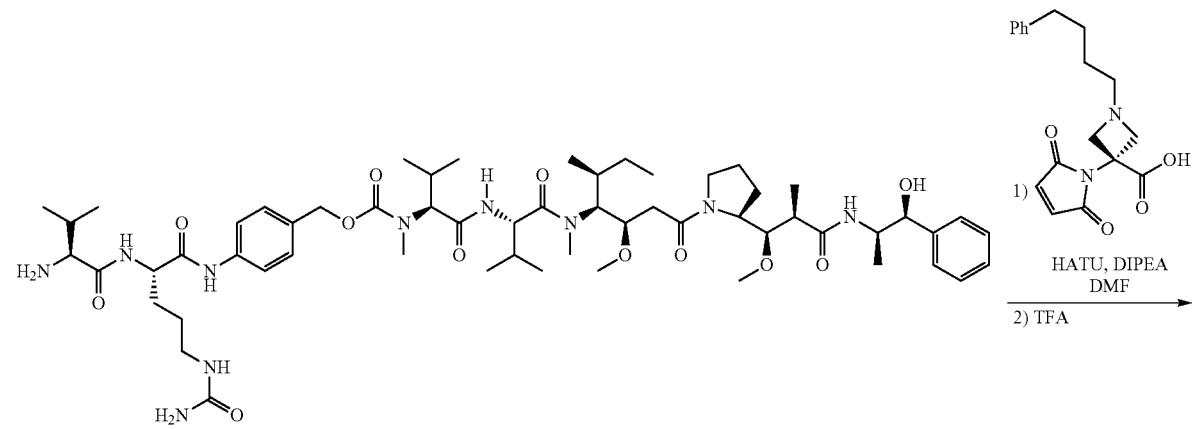

Val-Cit-PABC-MMAE

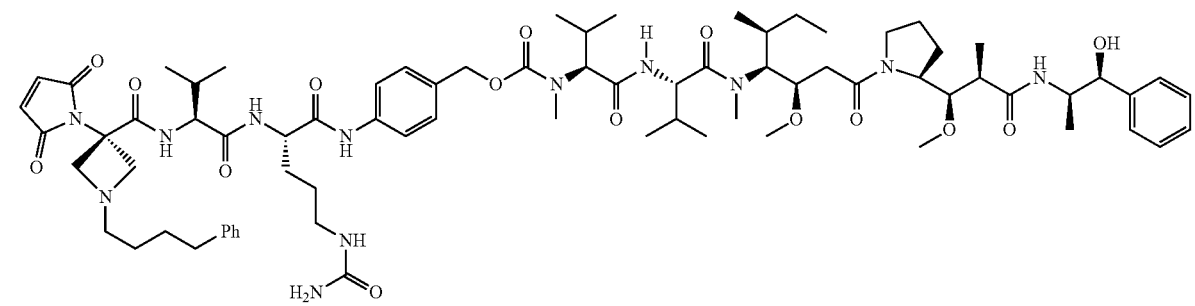

Ph-nBu-mAze-Val-Cit-PABC-MMAE

A vial was charged with the $L_{SS}$ component 3-(2,5-dioxo-2,5-dihydro-1H-pyrrol-1-yl)-1-(4-phenylbutyl)azetidine-3-carboxylic acid (2.0 mg, 0.006 mmol), which is abbreviated as Ph-nBu-mAze, DIPEA, HATU (2.1 mg, 0.005 mmol), DIPEA (3.0 μL, 0.017 mmol), and DCM (0.5 mL). The reaction was stirred for 15 min and Val-Cit-PABC-MMAE (6.4 mg, 0.006 mmol) was added and the reaction was stirred at RT for 3 h. DMSO (0.5 mL) and 0.1% TFA in $H_2O$ (0.5 mL) were added to the solution. The product was purified by preparative HPLC and lyophilization afforded 1.3 mg (17% yield) of the title Drug Linker compound.

Analytical UPLC-MS: $t_R$=1.45 min, m/z (ES+) calculated 1433.84 (M+H)$^+$, found 1433.99.

Example 10: $PEG_{12}$-mAze

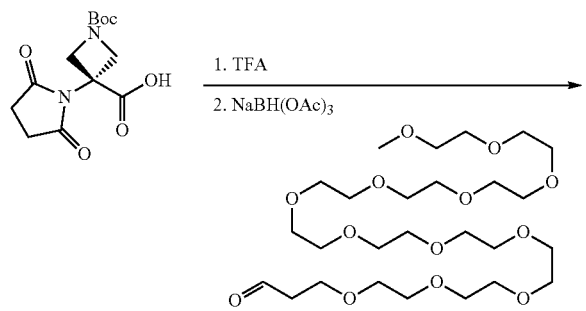

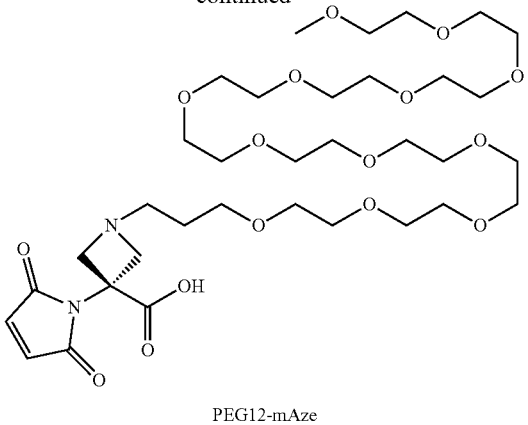

PEG12-mAze

The $L_{SS}$ component 3-(2,5-dioxo-2,5-dihydro-1H-pyrrol-1-yl)-1-(2,5,8,11,14,17,20,23,26,29,32,35-dodecaoxaoctatriacontan-38-yl)azetidine-3-carboxylic acid, abbreviated as $PEG_{12}$-mAze, was prepared in the same manner as Ph-nBu-mAze of Example 8.

Analytical UPLC-MS: $t_R$=0.76 min, m/z (ES+) calculated 753.40 (M+H)$^+$, found 753.58.

Example 11: $PEG_{12}$-mAze-Val-Cit-PABC-MMAE

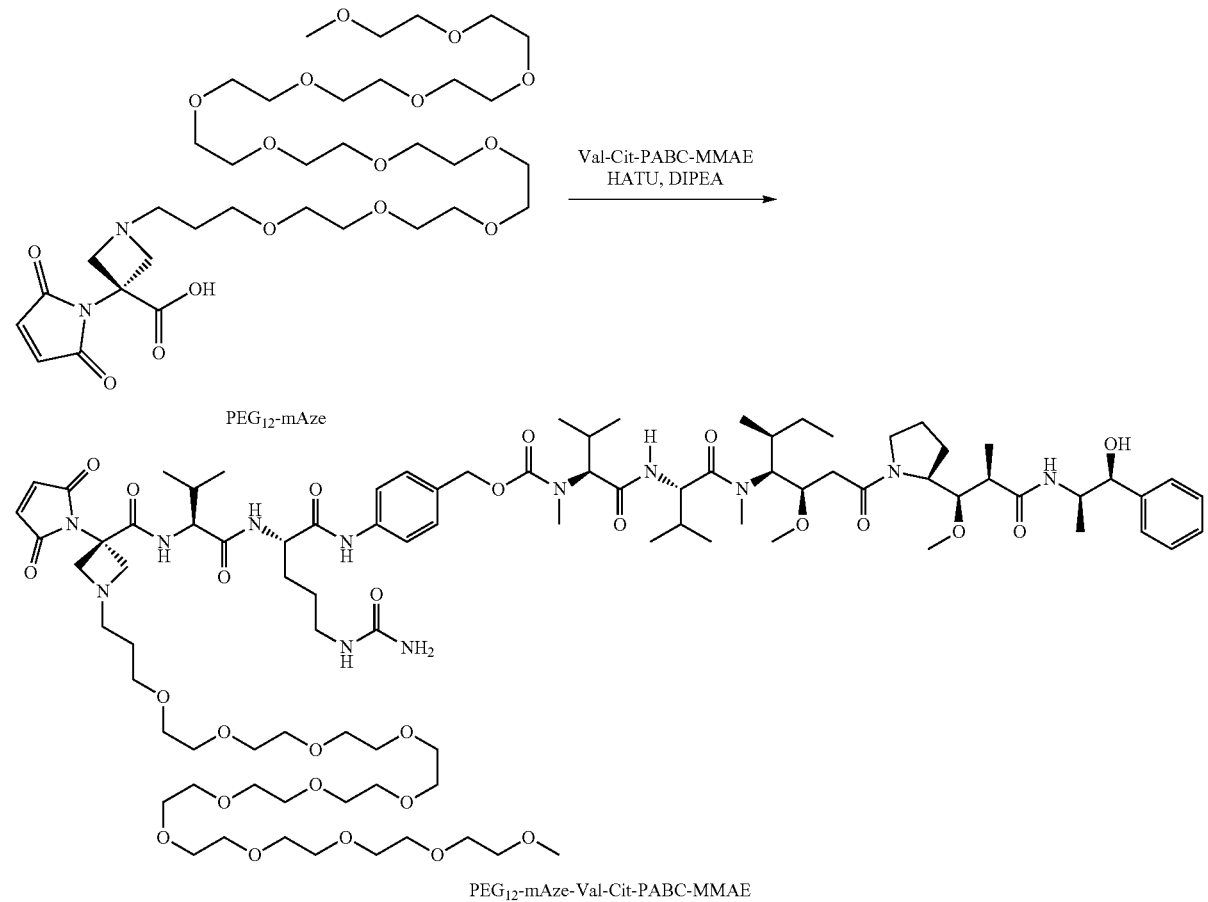

$PEG_{12}$-mAze-Val-Cit-PABC-MMAE

Peptide coupling of the $L_{SS}$ component $PEG_{12}$-mAze with val-cit-PABC-MMAE to provide the title Drug Linker compound $PEG_{12}$-mAze-val-cit-PABC-MMAE was prepared in the same manner as Ph-nBu-mAze-val-cit-PABC-MMAE of Example 9.

Analytical UPLC-MS: $t_R$=1.38 min, m/z (ES+) calculated 1858.10 (M+H)+, found 1858.54.

Example 12: mAze-GlucC-MMAE

Peptide coupling of the BOC-protected form of $L_{SS}$ component mAze with the linker intermediate GlucC-MMAE and subsequent BOC deprotection provides the title Drug Linker compound mAze-GlucC-MMAE was conducted in the same manner as for mPip-val-cit-PABC-MMAE of Example 5. Preparation of the linker intermediate GlucC-MMAE was as previously described by WO2007011968 and is specifically incorporated by reference herein.

Analytical UPLC-MS: $t_R$=1.15 min, m/z (ES+) calculated 1308.66 (M+H)+, found 1308.91.

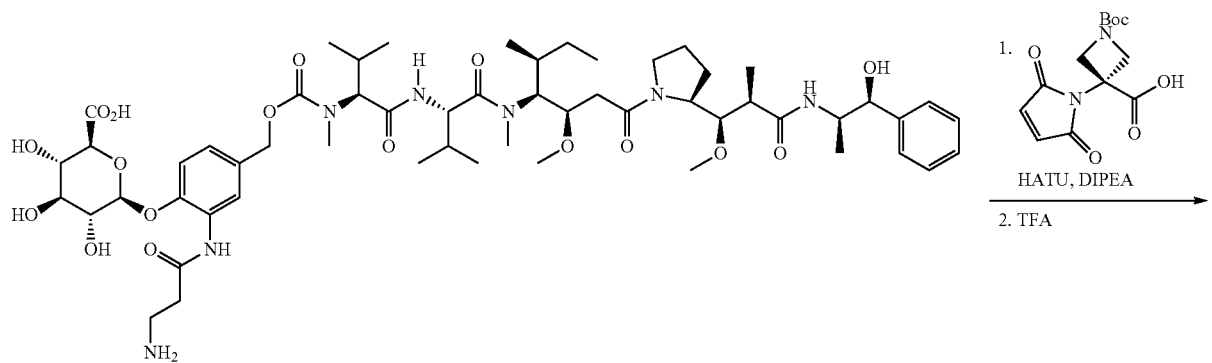

GlucC-MMAE

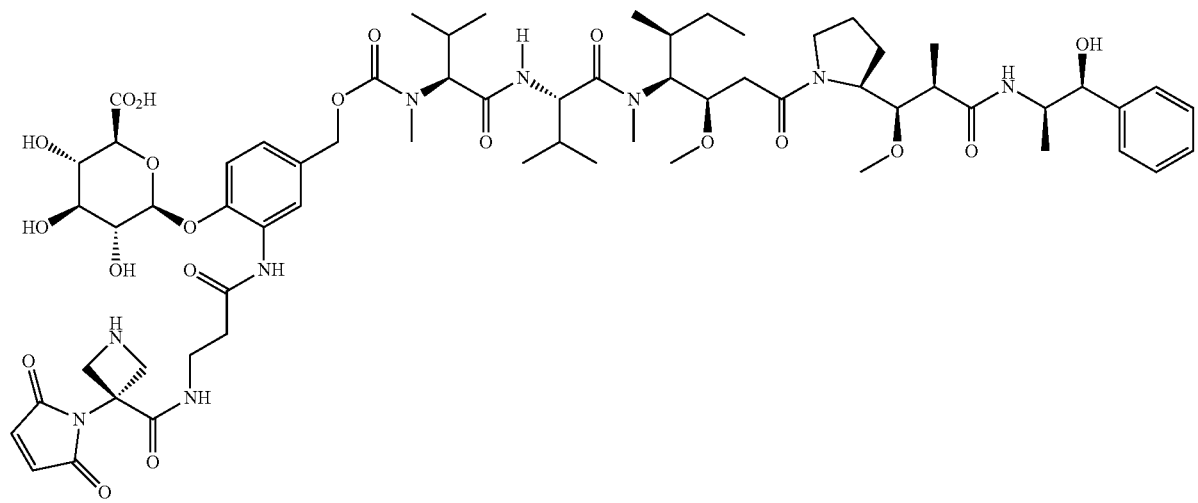

mAze-GlucC-MMAE

Example 13: N-Me-mAze-GlucC-MMAE

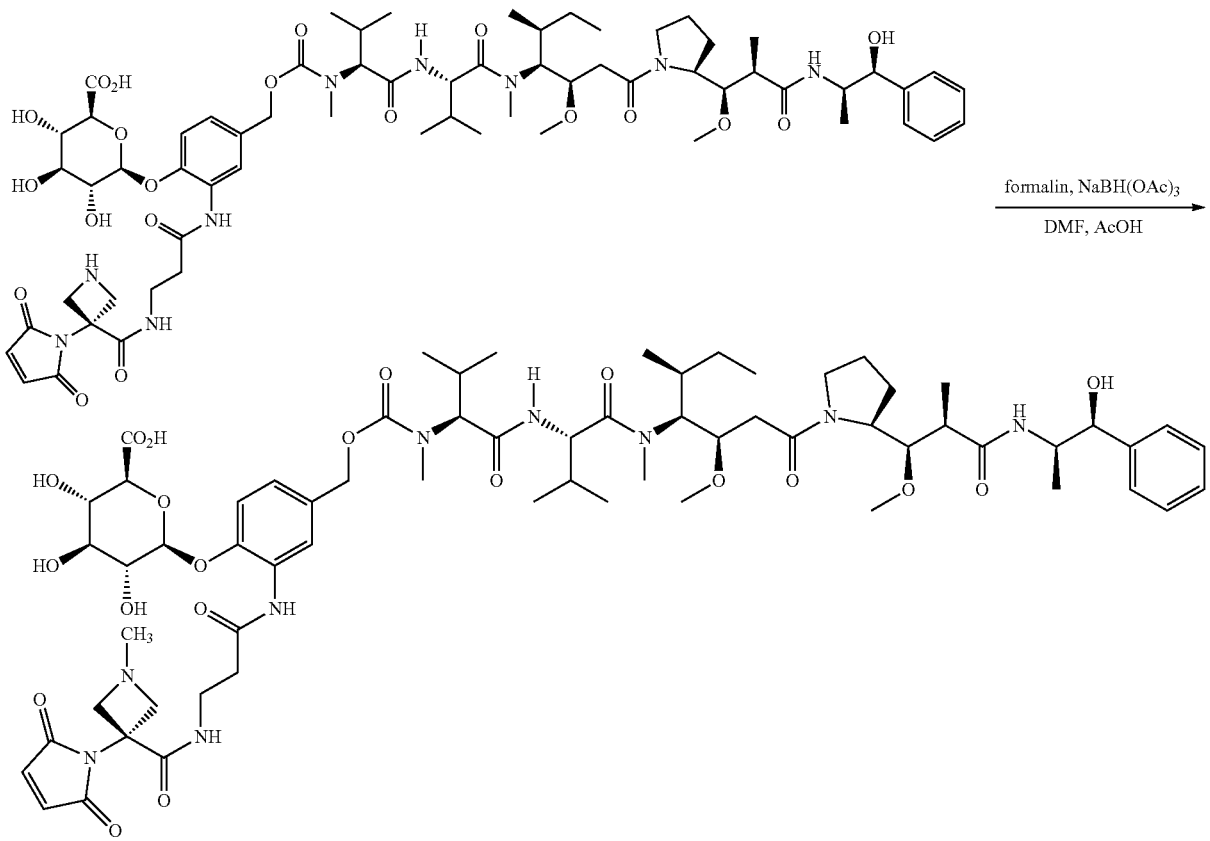

A vial was charged with mAze-GlucC-MMAE (4 mg, 0.003 mmol), AcOH (0.2 µL, 0.003 mmol), formalin (0.3 µL, 0.03 mmol) and DMF (0.3 mL). The reaction was stirred for 10 min then NaBH(OAc)$_3$ (0.6 mg, 0.003 mmol) was added. The reaction was stirred for 2 h and additional formalin (0.9 µL, 0.09 mmol) and NaBH(OAc)$_3$ (1.8 mg, 0.009) were added. The resulting reaction mixture was stirred for 16 h then purified by preparative HPLC to provide the title drug linker compound.

Analytical UPLC-MS: $t_R$=1.15 min, m/z (ES+) calculated 1322.68 (M+H)$^+$, found 1322.95.

Example 14: N-Et-mAze-GlucC-MMAE

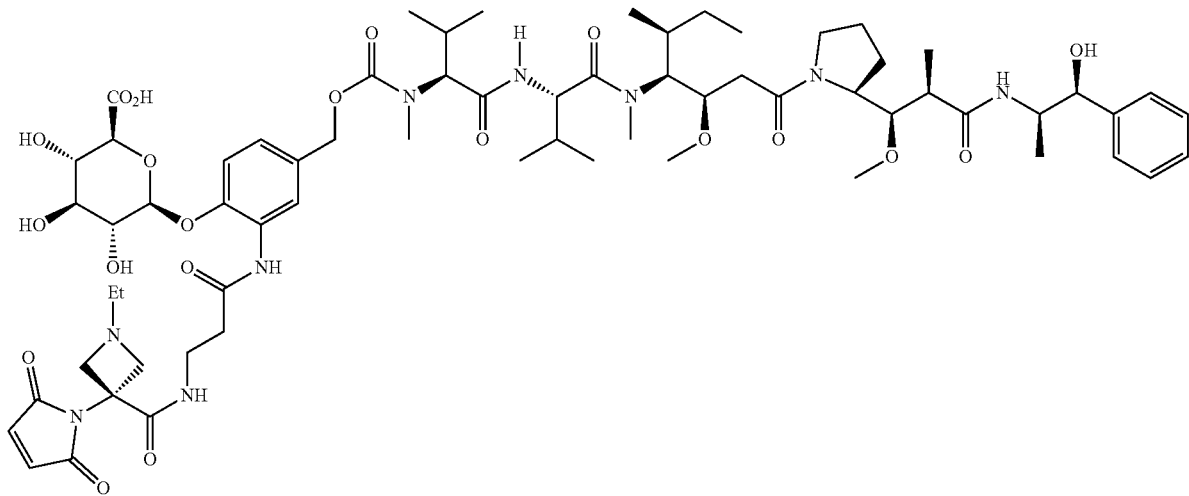

N-Et-mAze-GlucC-MMAE

The title Drug Linker compound was prepared in the same manner as N-Me-mAze-Gluc-MMAE of Example 13.

Analytical UPLC-MS: $t_R$=1.16 min, m/z (ES+) calculated 1336.98 (M+H)+, found 1336.69.

Example 15: N—(CH$_2$CH$_2$OCH$_3$)-mAze-GlucC-MMAE

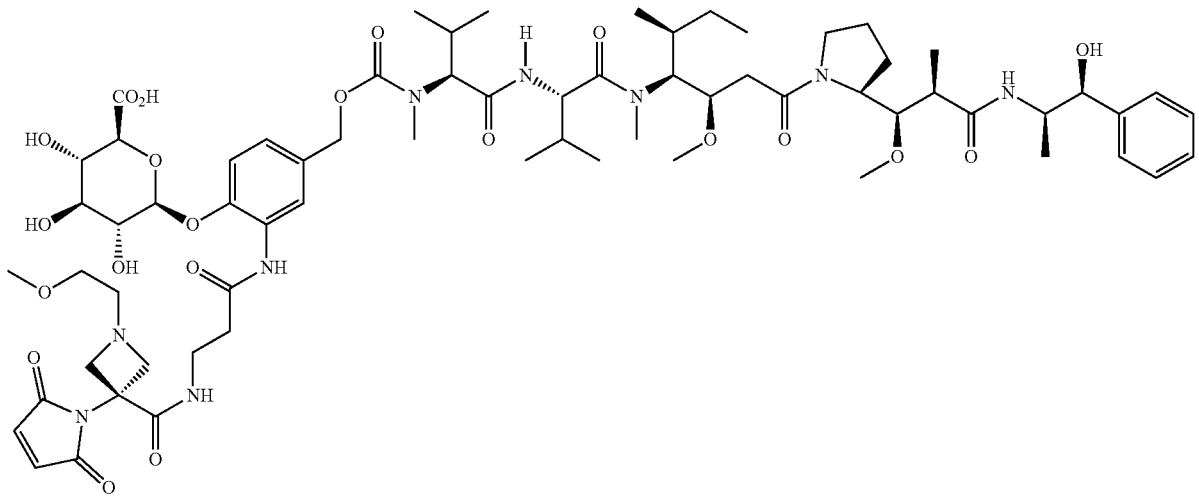

N-(CH$_2$CH$_2$OCH$_3$)-mAze-GlucC-MMAE

The title Drug Linker compound was prepared in the same manner as N-Me-mAze-GlucC-MMAE of Example 13.

Analytical UPLC-MS: $t_R$=1.20 min, m/z (ES+) calculated 1366.70 (M+H)$^+$, found 1366.99.

Example 16: PEG$_{12}$-mAze-GlucC-MMAE

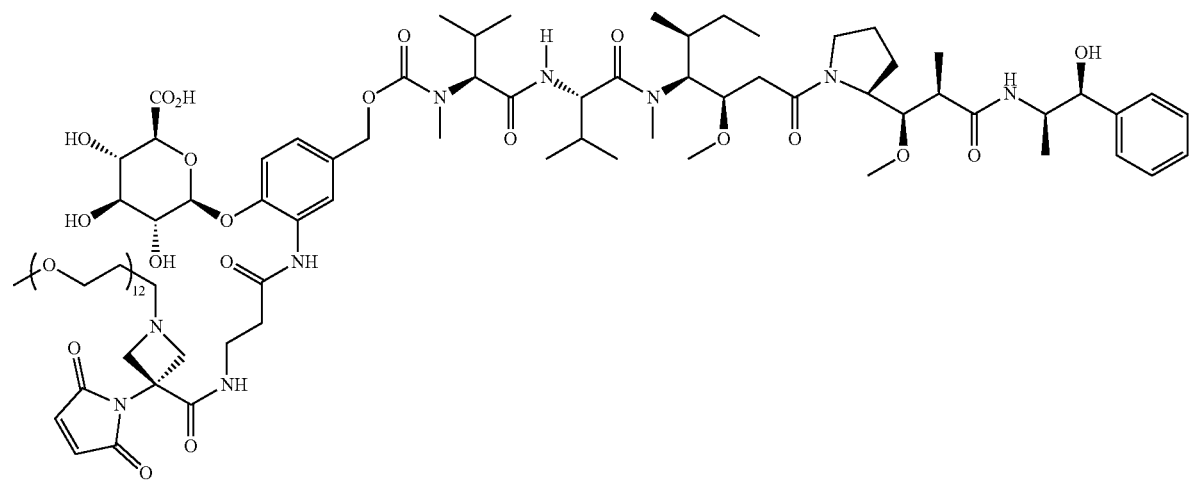

PEG$_{12}$-mAze-GlucC-MMAE

The title Drug Linker compound was prepared in the same manner as N-Me-mAze-GlucC-MMAE of Example 13.

Analytical UPLC-MS: $t_R$=1.22 min, m/z (ES+) calculated 1866.01 (M+H)$^+$, found 1866.37.

Example 17: mAze-Val-Ala-PABC-MMAE

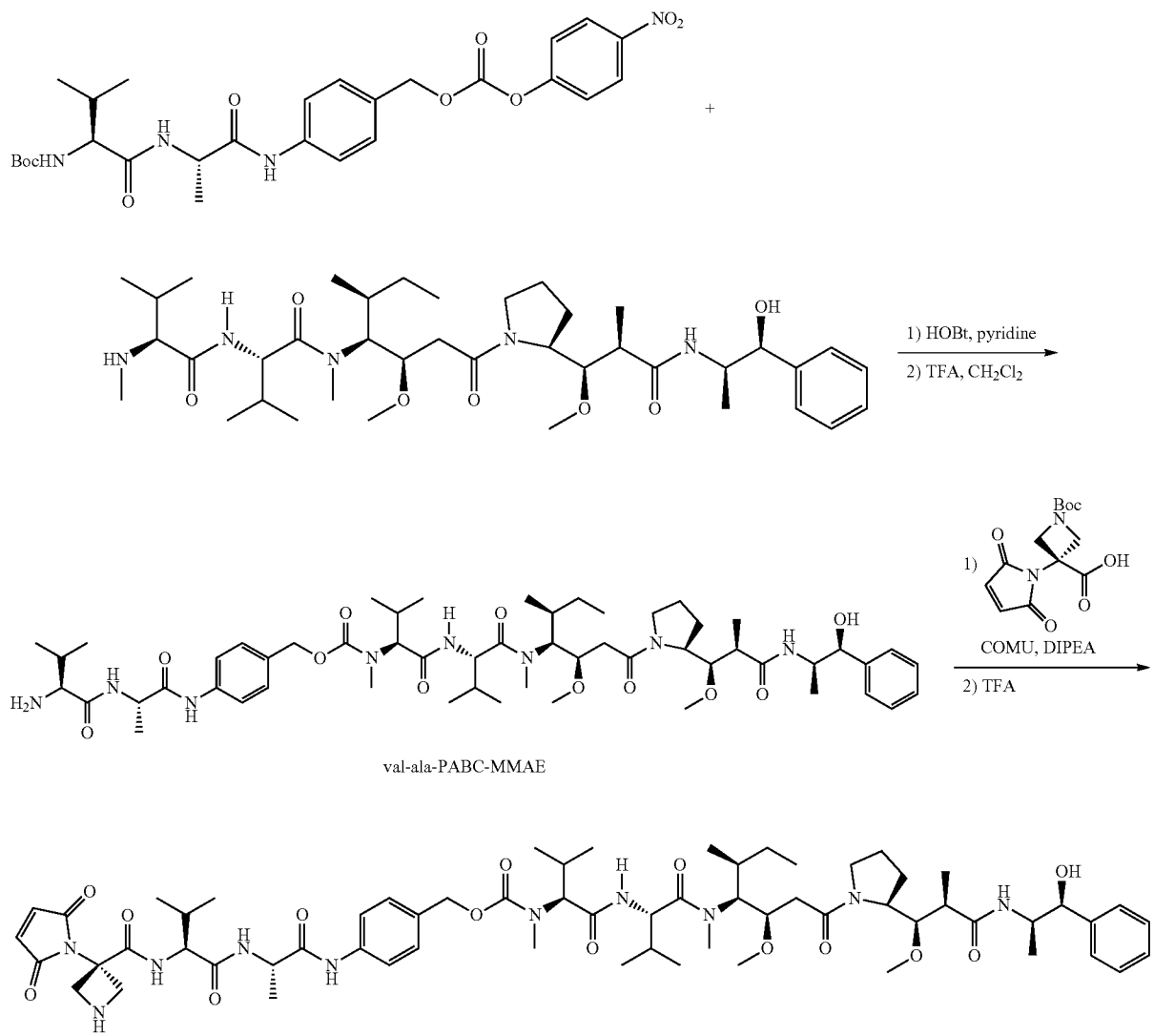

val-ala-PABC-MMAE

Peptide coupling of the intermediate val-ala-PABC-MMAE with the BOC protected form of the $L_{SS}$ component 3-(2,5-dioxo-2,5-dihydro-1H-pyrrol-1-yl)azetidine-3-carboxylic acid and subsequent BOC deprotection to provide the title Drug Linker compound was conducted in the same manner as described for the preparation mAze-val-cit-PABC-MMAE of Example 6.

Analytical UPLC-MS: $t_R$=1.41 min, m/z (ES+) calculated 1215.70 (M+H)$^+$, found 1215.96.

Example 19: mAze-Glu-Dap-AT

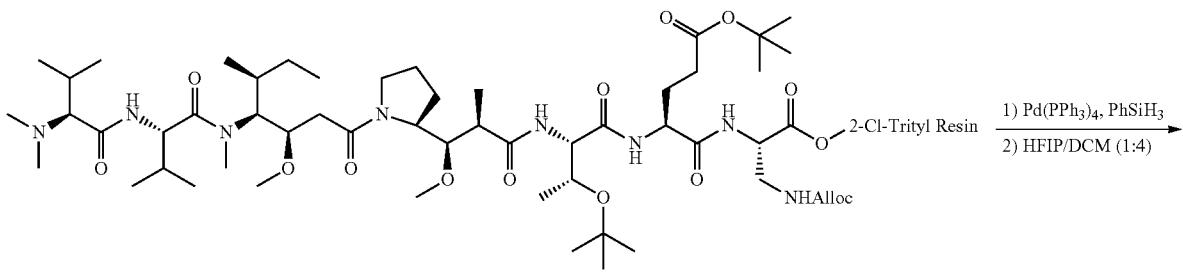

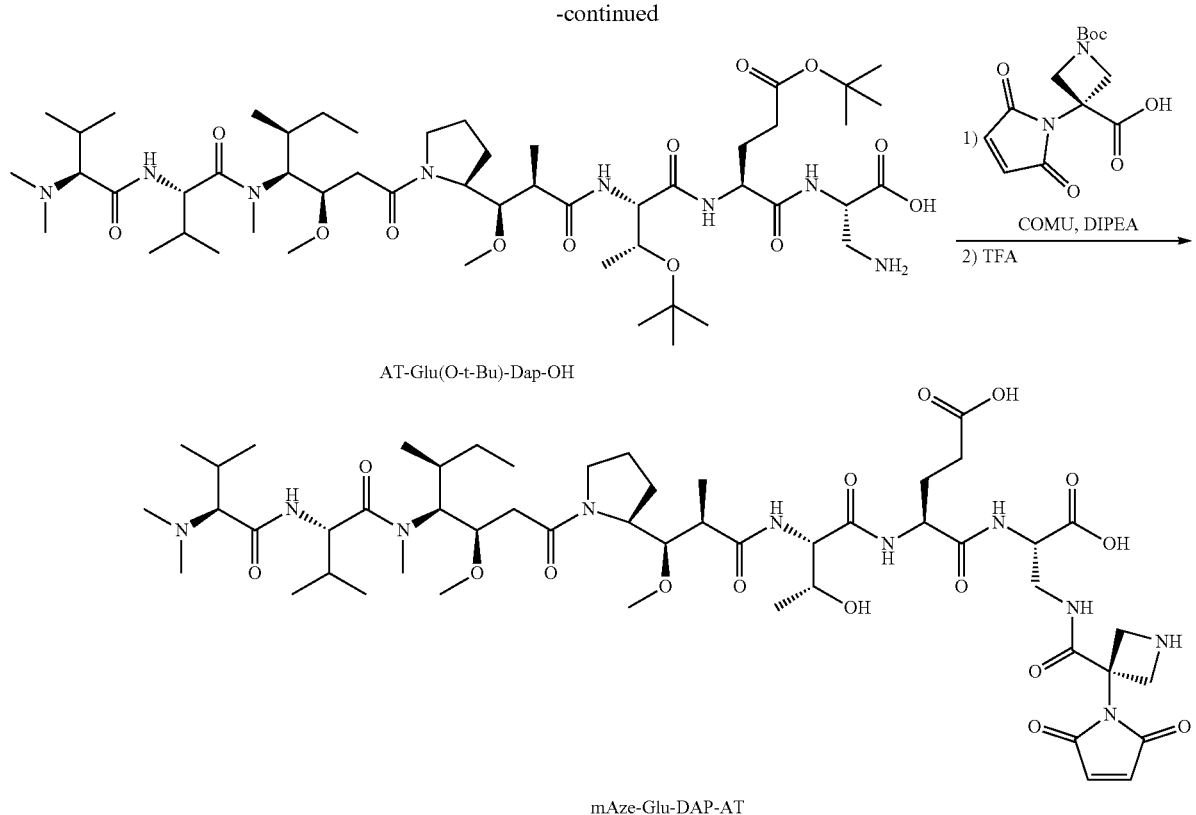

AT-Glu(O-t-Bu)-Dap-OH mAze-Glu-DAP-AT

Peptide coupling of the BOC protected form of the L$_{SS}$ component 3-(2,5-dioxo-2,5-dihydro-1H-pyrrol-1-yl)azetidine-3-carboxylic acid with the drug linker intermediate AT-Glu(O-t-Bu)-Dap-OH and subsequent BOC deprotection to provide the title Drug Linker compound was conducted in the same manner as for the preparation of mAze-val-cit-PABC-MMAE of Example 6. Preparation of the Drug Linker compound intermediate AT-Glu(O-t-Bu)-Dap-OH by coupling of auristatin T to the suitably protected resin dipeptide (S)-4-amino-5-(((S)-2-amino-1-carboxyethyl)amino)-5-oxopentanoic acid is as previously described.

Analytical UPLC-MS: $t_R$=0.86 min, m/z (ES+) calculated 547.31 (M+2H)$^{2+}$, found 547.46.

Example 20: (Z)-1-(tert-butoxycarbonyl)-3-(3-carboxyacrylamido)-piperidine-3-carboxylic acid

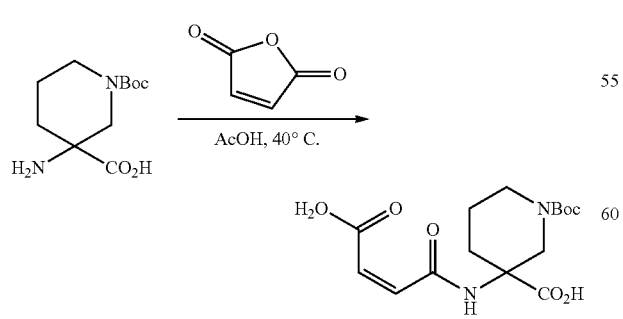

A 50 mL flask was charged with amino acid (500 mg, 2.0 mmol), maleic anhydride (201 mg, 2.0 mmol), and AcOH (15 mL). The mixture was heated at 40° C. for 15 minutes then the reaction was stirred at RT for 2 h. The solvent was removed in vacuo and the residue was dissolved in 10 mL DCM. Hexane was added portion-wise (1 mL portions, 13 mL total) until the product began to crash out. The flask was placed in a -20° C. freezer overnight and filtered. The precipitate was dried in a vacuum desiccator to afford 430 mg (61% yield) of the title compound.

Analytical UPLC-MS: $t_R$=0.91 min, m/z (ES+) calculated 343.15 (M+H)$^+$, found 343.17.

Example 21: 1-(tert-butoxycarbonyl)-3-(2,5-dioxo-2,5-dihydro-1H-pyrrol-1-yl)piperidine-3-carboxylic acid (Boc-mPipA)

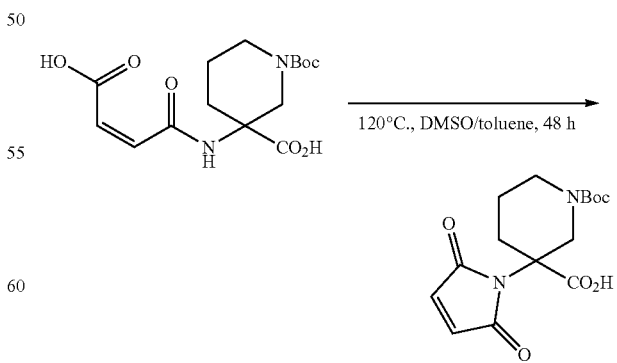

A 20 mL vial was charged with the piperidine diacid (430 mg, 1.25 mmol), DMSO (5 mL), toluene (50 mL) and 4 Å molecular sieves (1.25 g). The reaction was heated to 120°

C. and stirred for 48 h. The reaction was cooled to RT and filtered over Celite. The solvent was removed in vacuo. The residue was dissolved in DMSO (2 mL) and water (0.5 mL) and purified by preparative HPLC. The product fractions were collected and lyophilized to afford 23 mg (6% yield) of the title compound.

Analytical UPLC-MS: $t_R$=1.16 min, m/z (ES+) calculated 347.12 (M+Na)$^+$, found 347.14.

Example 22: mPipA-Val-Cit-PAB-MMAE

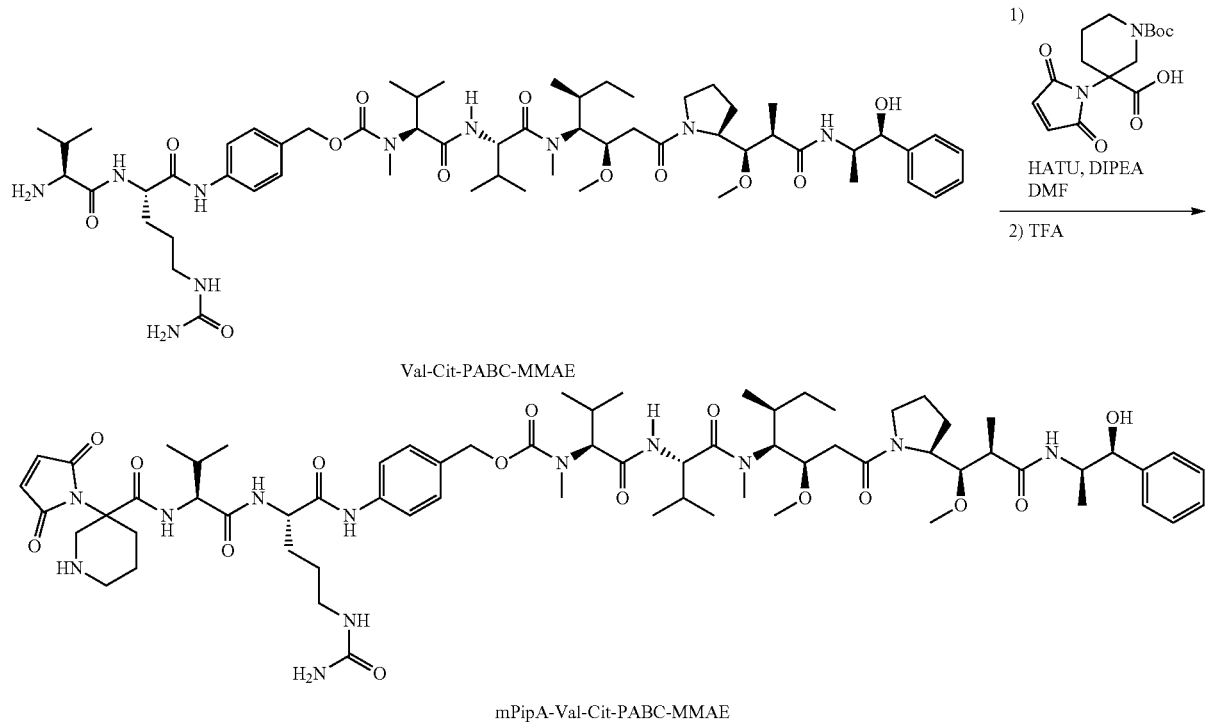

Val-Cit-PABC-MMAE mPipA-Val-Cit-PABC-MMAE

A vial was charged with the BOC protected form of the $L_{SS}$ component (3.0 mg, 0.009 mmol) 3-(2,5-dioxo-2,5-dihydro-1H-pyrrol-1-yl)piperidine-3-carboxylic acid, which is abbreviated as Boc-mPipA, HATU (3.5 mg, 0.009 mmol), DIPEA (6.4 µL, 0.037 mmol), and DCM (0.5 mL). The reaction was stirred for 15 min and val-cit-PABC-MMAE (10.3, 0.009 mmol) was added to the reaction. After 3 h, TFA (1.5 mL, 20% in DCM) was added at 0° C. The reaction was allowed to warm to RT and stirred for 3 h. The reaction was diluted with DMSO and put under vacuum for 15 min to remove DCM. The product was purified by preparative HPLC and lyophilized to afford 2.3 mg (17% yield) of the title compound.

Analytical UPLC-MS: $t_R$=1.73 min, m/z (ES+) calculated 1329.78 (M+H)$^+$, found 1329.12.

Example 23: Alternative Self-Stabilizing Linkers Incorporating a Cyclic Basic Units Other intermediates for preparing Drug Linker compounds that incorporate a cyclic Basic Unit resulting from formal cyclization is to the basic nitrogen of an acyclic Basic Unit are those having the formula of

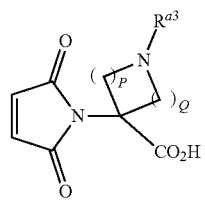

wherein subscript P is 1 and subscript Q is 3, 4, 5 or 6 and $R^{a3}$ is —C(=O)O-t-Bu (BOC) are prepared according to the following reaction scheme:

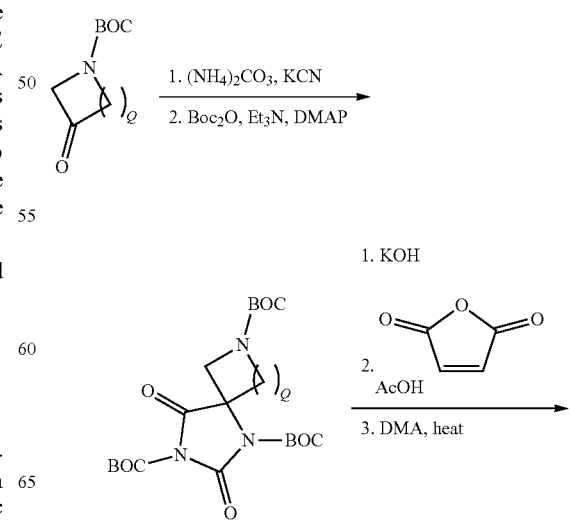

Still other intermediates for preparing Drug Linker compounds that incorporate a cyclic Basic Unit resulting from formal cyclization is to the alkyl moiety that bears the basic amine nitrogen of an acyclic Basic Unit are those having the formula of:

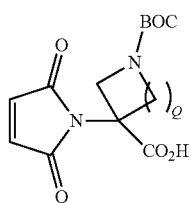

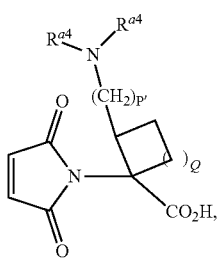

wherein subscript P' is 0 and subscript Q' is 0, or is an integer ranging from 1 to 6, one $R^{a4}$ is hydrogen and the other is —C(=O)O-t-Bu (BOC), are prepared according to the following reaction scheme:

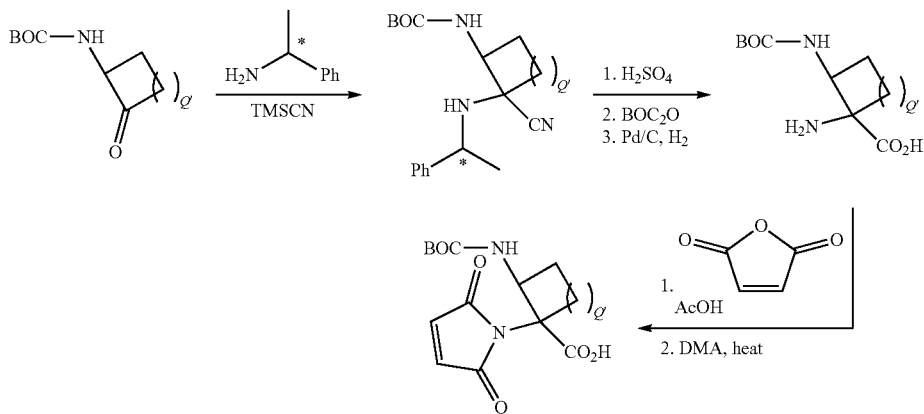

In the above reaction scheme the indicated carbon (*) may be in the R or S configuration for diastereomeric selective formation of the BOC-protected intermediate if desired.

Example 24. Hydrolysis Kinetics for Conversion of Antibody Drug Conjugates of Formula 1 to Those of Formula 2

The intensities of the non-hydrolyzed and hydrolyzed peaks in the mass spectra of a self-stabilizing conjugate composition of Formula 1 during its conversion to a self-stabilized conjugate composition of Formula 2, was monitored to determine the hydrolysis kinetics of $M^2$ in the $L_{SS}$ primary linker of Formula 1 to $M^3$ of the $L_S$ primary linker of Formula 2. That was done by plotting the percent of the total population of the composition that has hydrolyzed at each time point versus time The data were then fit to the exponential equation $$H = H_{max} \times (1 - e^{(-Kt)})$$

where H is the observed percent hydrolysis at time t, $H_{max}$ is the asymptotic maximal % hydrolysis, and K is the hydrolysis rate constant. The half-life for the hydrolysis reaction is defined as $$t_{1/2} = \ln(2)/K$$

When this procedure is performed for drug linker moieties that are conjugated through the light chain of a reduced $IgG_1$ antibody, the analysis is quite straightforward as there is only one conjugation site per light chain and the reaction is a simple progression from the un-hydrolyzed $M^2$ moiety of $L_{SS}$ to the hydrolyzed $M^3$ moiety of $L_S$ which is accompanied by a mass change of +18 Daltons. Performing that analysis on the heavy chain is more involved by the fact that there are a total of three conjugation sites per heavy chain, resulting in a series of peaks of +18, +36, and +54 Daltons as each of the drug linker moieties conjugated to these sites undergoes hydrolysis. The analysis of the heavy chain is further complicated by the presence of multiple glycoforms. However, despite those complexities it has previously been found that the observed kinetic profiles for the light and heavy chains are very similar (WO2013173337). Thus, data to characterize hydrolysis rates for conversion of self-stabilizing to self-stabilized primary linkers in an Antibody Drug Conjugate only requires evaluation hydrolysis of its light chain drug linker moieties.

For that evaluation a series of Antibody Drug Conjugates with DAR of 8 were prepared from Drug Linker compounds varying in identity of the self-stabilizing linker ($L_{SS}$) component by contacting the corresponding Drug Linker compounds as their TFA salts, which are obtained subsequent to their purification by RP-HPLC, with fully disulfide reduced human $IgG_1$ antibody (cAC10). Reduction of cAC10 was carried out on a 10 mL MabSelect™ SuRe LX column in line with an ÄKTA Start™ system. The column was equilibrated with 5 column volumes (CV) of PBS pH 7.4+5 mM ethylenediamine-tetraacetic acid (EDTA) at a 5 mL/min flow rate. Antibody was loaded onto the column at 3 mL/min for 15 minutes. After binding, the column was washed with 5 CV of PBS pH 7.4+5 mM EDTA at 5 mL/min. The antibody was reduced with 10 mM tris(2-carboxyethyl) phosphine (TCEP), 5 mM EDTA, 100 mM potassium phosphate pH 7.4 for 30 min at 1 mL/min. The column was washed with 5 CV of PBS pH 7.4 at 5 mL/min. Reduced antibody was eluted with 50 mM glycine pH 3.0 at 3 mL/min. Eluent was collected and neutralized with 800 mM potassium phosphate, 500 mM NaCl, 50 mM EDTA pH 7.4 10% (v/v), for a final concentration of 80 mM potassium phosphate, 50 mM NaCl, and 5 mM EDTA. Reduced antibody was concentrated by ultrafiltration (centrifugation at 4,000×g through a Millipore 30 kDa MWCO filter) and stored at −80° C. Reduction was monitored by analytical reversed-phase chromatography to ensure there were 8 free thiols/Ab. The analytical reverse-phase chromatography was carried out on a Waters H Class UPLC equipped with an Agilent Technologies PLRP-S 300 Å, 2.1×50×3 m reversed-phase column eluted with 0.05% trifluoroacetic acid in water (line A) and 0.01% trifluoroacetic acid in acetonitrile (line B).

Working aliquots of fully reduced cAC10 antibody were prepared by diluting the antibody into PBS+50 mM potassium phosphate pH 7.4 for a final concentration of 1.06 mg/mL. The diluted stock was divided into 200 µL aliquots in reaction vials and stored at −80° C. to be used for each hydrolysis experiment. A single aliquot was thawed at room temperature for each hydrolysis time course experiment. DMSO and 30% excess drug-linker as the TFA salt were added to the reaction vial containing the thawed antibody aliquot for a final 10% (v/v) DMSO concentration and pH of 7.4. The temperature of the reaction vial was controlled and held at 22° C. for the duration of the study. The conjugation reaction vial was agitated and 5 µL of its mixed solution was immediately injected and analyzed by reversed-phase chromatography by elution with a 72% to 52% gradient over 3.5 minutes using 0.05% trifluoroacetic acid in water (line A) and 0.01% trifluoroacetic acid in acetonitrile (line B) in line with a mass spectrometer. There was a 2 minute delay between initiation of conjugation reaction by addition of the Drug Linker compound and the first injection, which was considered time zero for the analysis. The UPLC-MS ran 30 replicate 5 µL injections from the same reaction vial with subsequent injections made 6.2 minutes apart. The mass spectroscopy data were deconvoluted with the MaxEnt algorithm of Unifi™ software. The peak intensity values attributed to the antibody light-chain having non-hydrolyzed and hydrolyzed drug linker moieties were used to determine the extent of the hydrolysis reaction at each time point. Those values were plotted against time and fitted with a single exponential equation using Prism 6.0™ (GraphPad Software, San Diego, CA) to determine reaction rate constants, which were then converted to reaction half-times by the standard transformation of t1/2=ln(2)/k.

Table 1 provides hydrolysis half-live ($t_{1/2}$) values for conversion of Conjugates of Formula 1 to those of Formula 2, wherein the Conjugates have a MMAE Drug Unit with a uniform drug loading of 8 (i.e., subscript p is 8), a val-cit Peptide Cleavable Unit and a self-stabilizing Linker Unit containing either an acyclic Basic Unit (Conjugate A) or a cyclic Basic Unit in which the basic nitrogen of that acyclic Basic Unit has been formally cyclized to $R^{a2}$ of Formula 1, wherein that variable group is methyl or ethyl, so as to define a $C_4$-heterocyclo (Conjugate B) or a $C_6$-heterocyclo (Conjugate C), respectively. Those formal cyclizations to Conjugates B and C result in both having a cyclic Basic Unit with a basic secondary amine so that variable group $R^{a3}$ of Formula 1, which is bonded to the basic nitrogen atom, is hydrogen. To determine the effect of additional substitution of that nitrogen atom, which results in a cyclic Basic Unit having a tertiary basic amine, $R^{a3}$ in Conjugate B is changed from hydrogen to —CH2-(CH2)3-Ph and —CH$_2$—(CH$_2$)$_2$—O—(CH$_2$O—)$_{11}$—CH$_3$ to provide Conjugate D and Conjugate E, respectively. Table 1 also provides hydrolysis half-live values for conversion of Conjugates of Formula 1 to Formula 2, wherein the Conjugates have a MMAE Drug Unit in parallel orientation to a PEG Unit, a Glucuronide Unit and a self-stabilizing Linker Unit that contain either an acyclic Basic Unit (Conjugate F) or a cyclic Basic Unit in the form of a $C_4$-heterocyclo moiety in which the skeletal basic nitrogen is that of a secondary amine (Conjugate G) in comparison to a similar Conjugate having no PEG Unit (Conjugate H) and to another Conjugate additionally having methyl as the $R^{a3}$ variable group of Formula 1 (Conjugate I) so that the skeletal basic nitrogen is that of a tertiary amine. Table 1 further provides the $t_{1/2}$ value for conversion of a Conjugate of Formula 1 to that of Formula 2, wherein the Conjugate is identical to that of Conjugate G except the PEG Unit has been relocated to its cyclic Basic Unit thus providing a cyclic Basic Unit in the form of a $C_4$-heterocyclo moiety in which the skeletal basic nitrogen is that of a tertiary amine (Conjugate L) due to substitution by the PEG Unit. Also for comparative purposes, Table 1 provides $t_{1/2}$ values for Conjugates similar to that of Conjugate L in which the PEG Unit attached to the basic nitrogen of the cyclic Basic Unit has been truncated (Conjugate K) or removed (Conjugate J) so that in both instances the skeletal basic nitrogen of the cyclic Basic Unit remains that of a tertiary amine (i.e., $R^{a3}$ is —CH$_2$CH$_2$OCH$_3$ or —CH$_2$CH$_3$).

The $t_{1/2}$ values of Table 1 were determined at pH 7.4 (22° C.) for hydrolysis of L$_{SS}$ succinimide (M$^2$) moieties of Formula 1 to L$_S$ succinic acid amide (M$^3$) moieties of Formula 2 for Conjugates A-L. If $t_{1/2}$ for M$^2$ to M$^3$ hydrolysis is low for the conversion of a Conjugate of Formula 1 to that of Formula 2 to an extent that hydrolysis does not effectively compete with retro-Michael addition, which would result in premature loss of drug linker moiety from the Conjugate, the cyclic BU-assisted hydrolysis rate can be increased by increasing the pH and/or temperature of the hydrolysis medium. The effect of pH on $t_{1/2}$ is exemplified for Conjugate I for which $t_{1/2}$ decreased from 3.27 hr. at pH 7.4 to 2.20 h at pH 8.0.

TABLE 1

Half-Life values for conversion of Conjugates of Formula 1 to those of Formula 2 at pH 7.4 (22° C.)

| Conjugate | $t_{1/2}$ (hr.) |
| --- | --- |
| A | 0.50 |
| B | 1.15 |
| C | 4.48 |
| D | 77.6 |
| E | 12.5 |
| F | 0.42 |
| G | 0.68 |
| H | 1.78 |
| I | 3.27 |
| J | 3.25 |
| K | 26.7 |
| L | 9.62 |

Example 25. Cytotoxicity of Antibody Drug Conjugates

Cytotoxicities of Conjugates A-D of Example 24 toward CD30$^+$ cancer cells, which are targeted by their cAC10 antibody Ligand Unit, were evaluated in accordance with the generalized in vitro assay procedures of Example 28.

The cytotoxicity results are provided by Table 2. As a positive control a cAC10 Antibody Drug Conjugate was tested against the same panel of CD30+ cancer cells. That ADC (Conjugate M) has the same —W—$Y_y$-D moiety in its secondary linker as does Conjugates A-D, but has no Basic Unit as a component of its required Stretcher Unit $A_R$. It should be noted that during the incubation time course in the in vitro assay (96 h) no detectable loss of the auristatin Drug Unit due to premature release of MMAE drug linker is expected for Conjugates A-D based upon the results from the stability assay of Example 27, whereas the cytotoxicity of Conjugate M may be confounded due to up to 50% premature loss of MMAE from that conjugate during the time course of the study.

TABLE 2

$IC_{50}$ values for cAC10 (anti-CD30) ADCs on a panel of CD30 positive cell lines, [ng/mL of Ab]

| ADC | DAR | L-428 Hodgkin's Lymphoma | L-540cy Hodgkin's Lymphoma | L-82 Anaplastic large cell lymphoma |
|---|---|---|---|---|
| B | 8.0 | >1000 (52) | 2.6 (12)[1] | 1.3 (9) |
| C | 7.4 | >1000 (74) | 2.0 (9) | 1.5 (9) |
| D | 7.8 | >1000 (73) | 5.3 (9) | 1.9 (10) |
| A | 7.7 | >1000 (73) | 3.1 (10) | 1.4 (10) |
| E | 7.7 | 3.8 (33) | 1.4 (5) | 1.4 (10) |
| F | 8.0 | 3.3 (39) | 0.9 (4) | 1.5 (10) |
| M | 8.0 | >1000 (92) | 3.3 (8) | 6.3 (10) |

[1]Parenthetic values represent percent viable cells remaining on day 7

Conjugates A-D have identical —W—$Y_y$-D (val-cit-PABC-MMAE) moieties in their secondary linkers, wherein D is an auristatin Drug Unit, W is val-cit and Y is a PAB-based self-immolative Spacer Unit attached to a self-immolative carbamate functional group bonded to D, but have different Basic Units in their primary linkers. Thus, Conjugates B-D contain different heterocyclo cyclic Basic Units and Conjugate A contains an acyclic Basic Unit. The data of Table 2 demonstrates that conjugates with a Peptide Cleavable Unit and having a cyclic Basic Unit substantially retain the cytotoxicity of a conjugate identical in structure except for the presence of an acyclic Basic Unit.

Conjugate F and G have identical secondary linkers of formula A-W—$Y_y$-D, wherein D is the same auristatin Drug Unit as in Conjugates A-D, A is an -$L^P$(PEG)-moiety, and W is a Glucuronide Unit, which has a PAB-based self-immolative Spacer Unit also attached to a self-immolative carbamate functional group to which D is bound. Conjugate F is comparable to Conjugate G by having the same secondary linker but having an acyclic Basic Unit in the primary linker. Thus, the data of Table 2 also demonstrates that conjugates with a Glucuronide Unit in the secondary linker and having a cyclic Basic Unit in the primary linker substantially retain the cytotoxicity of a conjugate identical in structure except for the primary linker having an acyclic Basic Unit.

The structures of the Drug Linker compounds used in the preparation of Conjugates A-M of Tables 1 and 2 are as follows:

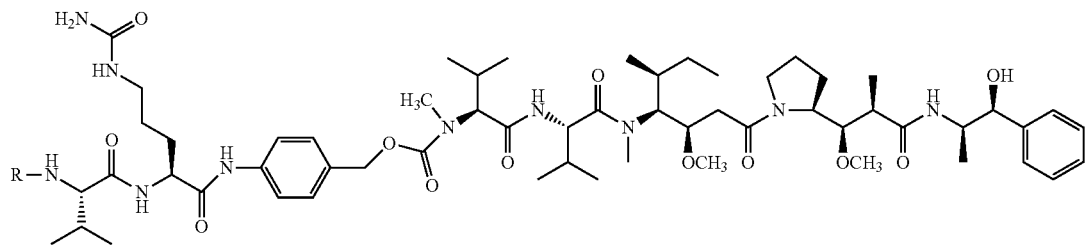

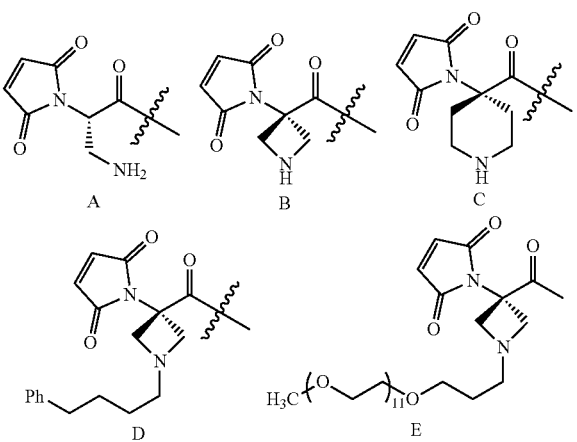

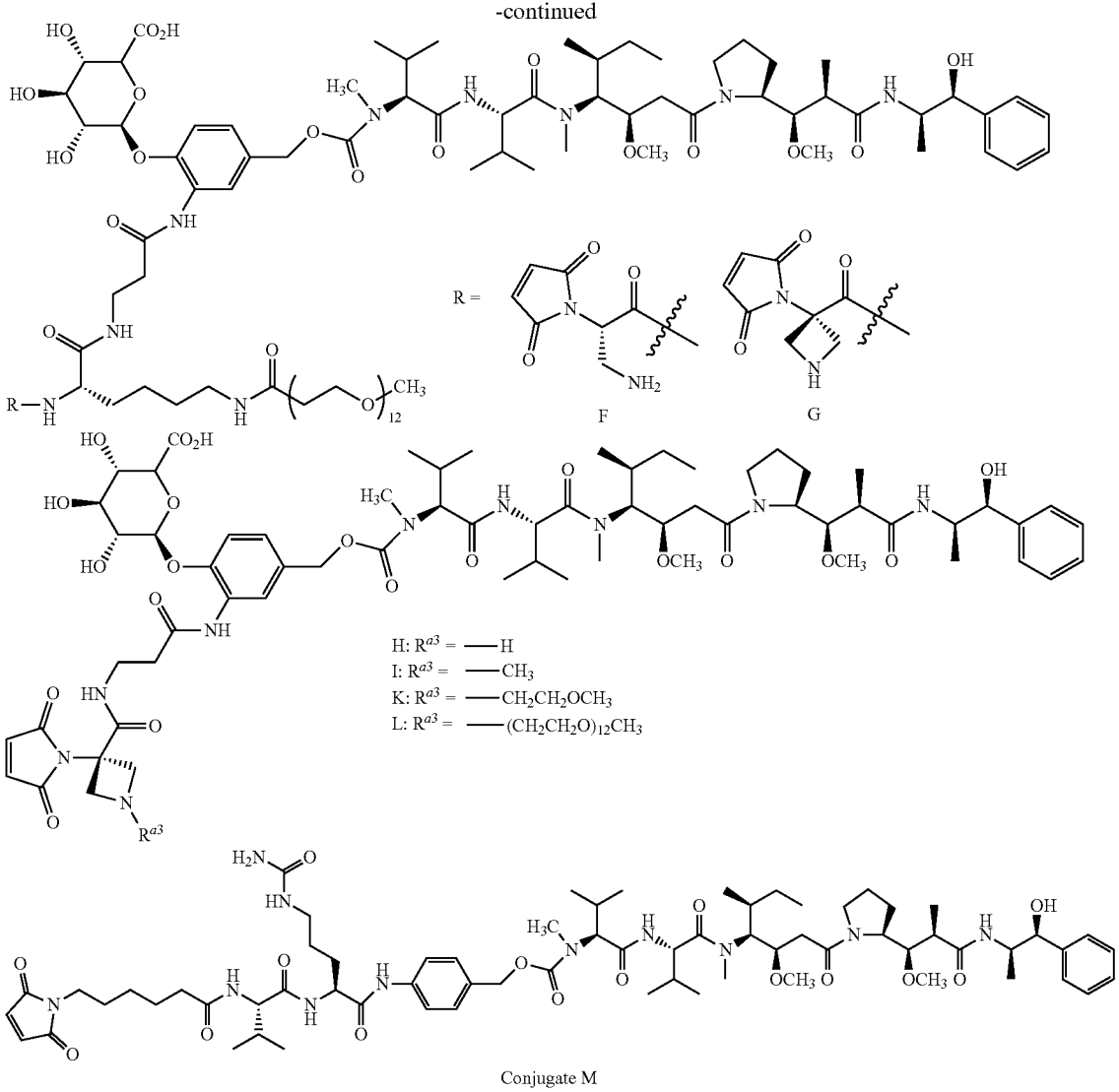

Conjugate M

Example 26. Drug Unit Release Kinetics and their Effects on Antibody Drug Conjugate Cytotoxicity Drug Linkers compounds having auristatin T as the Drug Unit were dissolved in 10% DMSO in PBS and quickly quenched with 120 mol % of N-acetyl-cysteine using to form the corresponding NAC conjugates. Solution was then incubated for 1 h at room temperature to allow for hydrolysis of succinimide ring. Concentrations of the NAC conjugates were then adjusted to 5 mM.

Enzymatic digestion assay was performed following the generic Sigma-Aldrich "Enzymatic Assay of Cathepsin B" protocol using fresh solutions of 8 mM L-Cysteine HCl in 352 mM potassium phosphate, 48 mM sodium phosphate, 4 mM EDTA, pH 6.0 at 40° C. Human Cathepsin B (Calbiochem, 0.47 mg/mL protein concentration, specific activity 324.00 U/mg P) was activated for 30 min. at 37° C. in a solution of enzyme (2 μL), 8 mM L-Cysteine (15 μL), Brij (18 μL), water (5 VL). NAC conjugates (10 μL of 5 mM solution) were prepared form Drug Linker compounds containing an acyclic Basic Unit that have structures of Formula I in which the curved line is not present.

The Conjugates corresponding in structure to that of Formula 1 in which the curved line is not present, subscript p is 1 and L is a cysteine residue was converted to the corresponding Conjugates of Formula 2 by controlled hydrolysis. The Drug Linker compounds used in preparation of the NAC conjugates differ only by the stereochemical configuration at the carbon to which the acyclic Basic Unit is attached with each Drug Linker compound containing about 2.5% of the opposite stereochemistry. Each NAC conjugate was enzymatically digested by its addition to the enzyme activation mixture and incubation at 37° C. overnight for release of the auristatin Drug Unit. Analyses of the resultant digestion mixtures were performed on a Waters Acquity UPLC-SQ MS system equipped with an Acquity UPLC BEH C18 1.7 μm, 2.1×50 mm reverse-phase column. The column was eluted with a linear gradient of acetonitrile from 3% to 97% in 0.1% aqueous formic acid over 2 min, followed by isocratic 97% acetonitrile for 1 min at flow rate 0.5 mL/min. Identity of the released drug (auristatin T) was confirmed by comparing retention time of the appearing peak and the mass of corresponding molecular ion to the reference-standard of the drug.

Panel A of FIG. 1 shows the HPLC analysis of the enzymatic digestion of the NAC conjugate prepared from the Drug Linker compound predominately having the S configuration (NAC-S) at the carbon bearing the acyclic Basic Unit. Panel B shows the analysis of the NAC conjugate prepared from the Drug Linker compound predominately having the R configuration (NAC-R) at that same carbon. The HPLC analyses show appreciable release of auristatin T (AT) from NAC-S after enzymatic digestion by Cathepsin B, but no detectable release of the auristatin drug from NAC-R. The structure of the Drug Linker compound used in the preparation of NAC-S is shown below:

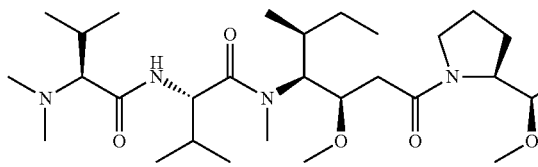
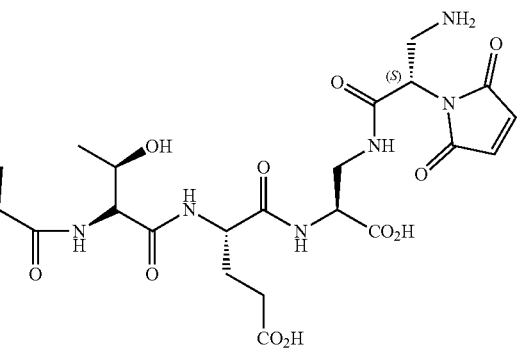

The results of the study unexpectedly show that the stereochemical configuration of an acyclic Basic Unit within a $L_S$-containing drug linker moiety of a Ligand Drug Conjugate can influence the efficiency of Drug Unit release.

Antibody Drug Conjugates were prepared from reduced hBU12 antibody, which was prepared in analogous manner to that of Example 24, and the same Drug Linker compounds used in the preparation of NAC-S and NAC-R. The cytotoxicity of the Conjugates towards CD19+ cancer cells, which are the targeted by the Conjugate's antibody Ligand Unit, were evaluated by in vitro assays, the general procedure for which is described below. The results are summarized by Table 3 and show that reduced efficiency of Drug Unit release from model NAC conjugates translates to reduced cytoxicity of the corresponding ADCs.

TABLE 3

IC$_{50}$ values for hBU12 (anti-CD19) ADCs on the panel of CD19 positive cell lines, [ng/mL of Ab]

| ADC (drug-linker isomer) | DAR | Ramos NHL (Burkitt's) | DoHH2 NHL (Follicular) |
|---|---|---|---|
| hBU12-AT (S-isomer) | 8.0 | 1.6 | 5.6 |
| hBU12-AT (R-isomer) | 8.0 | 8 | 484 |

Even in those instances in which the stereochemical integrity of the carbon bearing the acyclic Basic Unit has no discernable effect on Drug Unit release or otherwise has no adverse consequence on the cytotoxicity of a Ligand Drug Conjugate, loss of that integrity possess significant problems in manufacturing of the Conjugate. Variability in the structural composition of any medicant, including that of Ligand Drug Conjugate typically possess unacceptable for a subject to be administered that medicant. An Ligand Drug Conjugate stabilized by the action of a cyclic Basic Unit has that variability removed since the carbon atom of the corresponding Conjugate stabilized by an acyclic Basic to which that Basic Unit is attached no longer has a bound hydrogen atom that would allow for racemization.

Example 27. Stability of Antibody Drug Conjugates to Drug Linker Loss

Figure 2:
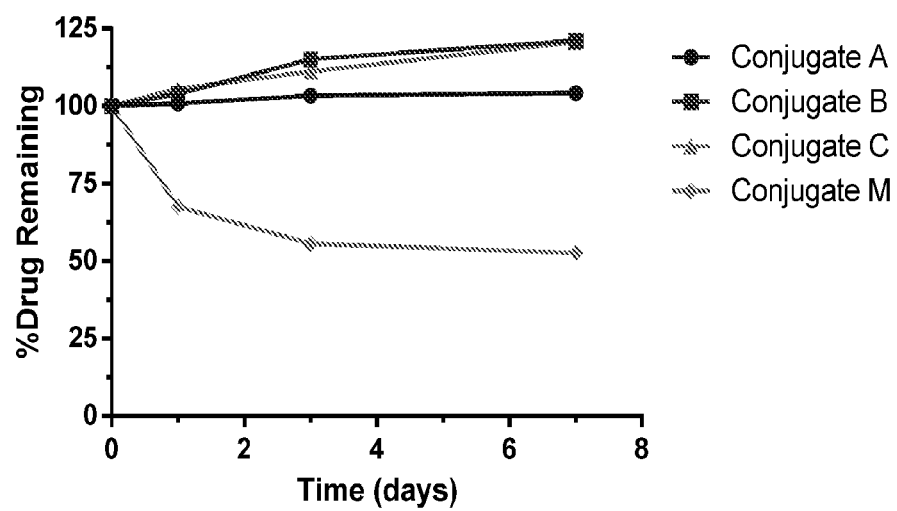
FIG. 2. Ex vivo plasma stability of cAC10 Antibody Drug Conjugates having a MMAE Drug Unit (8-load) linked via protease-cleavable val-cit dipeptide having a self-stabilizing Linker Units comprised of a secondary Basic Unit cyclized as a secondary amine within a 4-membered (Conjugate B) or 6-membered (Conjugate C) heterocyclo in comparison to a cAC10 Antibody Drug Conjugate having the parent, acyclic Basic Unit (Conjugate A) or a related Antibody Drug Conjugate having no self-stabilizing Ligand Unit (Conjugate M).

Stability in rat plasma ex vivo of Conjugates A-D were evaluated in the following manner. Each ADC was spiked into rat plasma and incubated at 37° C. for 7 days. At seven time points during this incubation, aliquots were removed and frozen at −80° C. until completion of the time course. The ADCs were then isolated from each sample and MMAE released proteolytically from the isolated ADCs using Cathepsin B as described previously by Sanderson R. J. et al. "In vivo drug-linker stability of an anti-CD30 dipeptide-linked auristatin immunoconjugate" Clin. Cancer Res. (2005) 11: 843-852, the procedure for which is specifically incorporated by reference herein. The released MMAE was then quantified by LC-MS/MS and normalized to the initial value for each. The time course for premature release of MMAE is depicted by FIG. 2, which shows the percentage of retained (and hence premature loss of) auristatin Drug Unit as a function of time. Conjugates B, C and D contain cyclic Basic Units and Conjugate A contains an acyclic Basic Unit. In all of those conjugates no premature loss of Drug Unit occurred during the 7 day time course of the study. In contrast, the positive control conjugate (Conjugate M), which is similar in structure to Conjugate A-D but contains no Basic Unit, loses up to 50% of its Drug Unit. Those results show that an cyclic Basic Unit substantially retains the stability benefit of an acyclic Basic Unit.

Example 28: In Vitro Assays

Cells cultured in log-phase growth were seeded for 24 h in 96-well plates containing 150 μL RPMI 1640 supplemented with 20% FBS. Serial dilutions of antibody-drug conjugates in cell culture media were prepared at 4× working concentrations; 50 μL of each dilution was added to the 96-well plates. Following addition of ADC, cells were incubated with test articles for 4 d at 37° C. After 96 h, growth inhibition was assessed by CellTiter-Glo® (Promega, Madison, WI) and luminescence was measured on a plate reader. The IC$_{50}$ value, determined in triplicate, is defined herein as the concentration that results in a 50% reduction in cell growth relative to untreated controls.

Example 29: In Vivo Xenograft Models

All experiments were conducted in concordance with the Animal Care and Use Committee in a facility fully accredited by the Association for Assessment and Accreditation of Laboratory Animal Care. Efficacy experiments were conducted in L540cy Hodgkin's lymphoma and Karpas:KarpasBVR anaplastic large cell lymphoma xenograft models. Tumor cells, as a cell suspension, were implanted subcutaneous in immune-compromised SCID mice. Upon tumor engraftment, mice were randomized to study groups when the average tumor volume reached about 100 mm³. The ADC or controls were dosed once via intraperitoneal injection. Tumor volume as a function of time was determined using the formula (L×W²)/2. Animals were euthanized when tumor volumes reached 1000 mm³. Mice showing durable regressions were terminated around day 100 post implant.

Example 30: ADC Pharmacokinetic (PK) Experiments

Pharmacokinetic (PK) experiments were performed using radiolabeled antibody or ADC. PK test articles were radiolabeled using the following procedure. To a solution of antibody or ADC in PBS supplemented with an additional 50 mM potassium phosphate (pH 8.0) and 50 mM sodium chloride was added 55 µCi N10 succinimidyl propionate, [propionate-2,3-3H]-(Moravek Biochemicals, Cat. No.: MT 919, 80 Ci/mmol, 1 mCi/mL, 9:1 hexane:ethyl acetate solution) per mg of antibody or ADC. The resulting mixture was vortexed and left at room temperature for 2 hours. The mixture was centrifuged at 4,000×g for 5 minutes and the lower aqueous layer was removed and split into Amicon Ultra-15 Centrifugal Filter Units (Millipore, Cat. No.: UFC903024, 30 kDa MWCO). Unconjugated radioactivity was removed by 4 rounds of dilution and centrifugation at 4,000×g. The resulting products were filtered through sterile 0.22 m Ultrafree-MC Centrifugal Filter Units (Millipore, Cat. No.: UFC30GV0S) and the final antibody or ADC concentration was measured spectrophotometrically. The specific activity (µCi/mg) of each product was determined by liquid scintillation counting.

The pharmacokinetic properties of the unconjugated antibody or ADC were examined in several rodent models. In each experiment, 1-3 mg of radiolabeled antibody or ADC per kg of animal weight were injected via the tail vein. Each test article was dosed once in replicate animals. Blood was drawn into K₂EDTA tubes via the saphenous vein or by cardiac puncture for terminal bleeds at various time points. Plasma was isolated by centrifugation for 10 minutes at 10,000×g. A 10-20 µL of sample of plasma from each time point was added to 4 mL Ecoscint-A liquid scintillation cocktail (National Diagnostics) and the total radioactivity was measured by liquid scintillation 5 counting. The resulting disintegrations per minute values were converted to µCi and the specific activity of the radiolabeled test articles was used to calculate the concentration of antibody or ADC remaining in the plasma at each time point.

What is claimed is:

1. A Ligand Drug Conjugate (LDC) compound, wherein the compound is represented by the structure of Formula 1 or Formula 2:

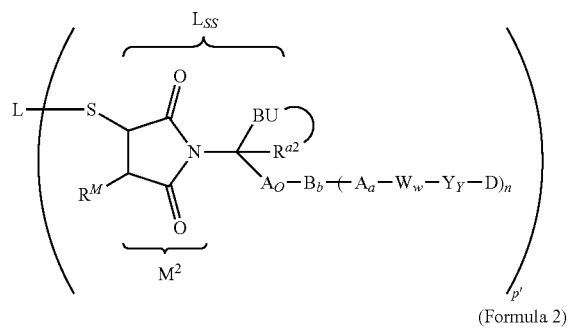

(Formula 1)

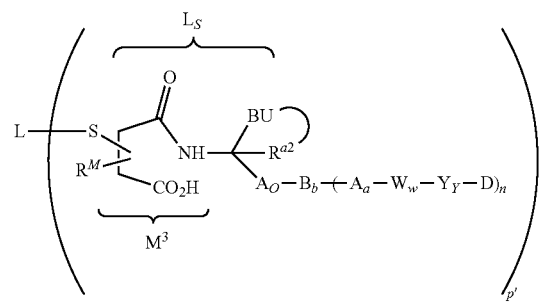

(Formula 2)

or a pharmaceutically acceptable salt thereof, wherein
L is a Ligand Unit, wherein the Ligand Unit is an antibody or an antigen binding fragment thereof;
S is a sulfur atom of the Ligand Unit, which in Formula 2 is bonded to the carbon atom α or β to the carboxylic acid functional group of the indicated succinic acid amide ($M^3$) moiety;
$R^M$ is hydrogen or an optionally substituted $C_1$-$C_6$ alkyl, which in Formula 2 is bonded to the saturated carbon atom adjacent to the carbon substituted by L-S—;
subscript w is 0 or 1;
subscript n is 1, 2, 3 or 4;
subscript a is 0 or 1;
subscript b is 0 or 1,
provided that subscript b is 1 when subscript n is 2, 3 or 4 and subscript b is 0 when subscript n is 1;
A is a first optional Stretcher Unit comprising an α-amino acid, a β-amino acid or other amine-containing acid residue;
$A_O$ is —C(=O)—;
B is an optional Branching Unit comprising a natural or un-natural amino acid or other amine-containing acid residue having a functionalized side chain; and
wherein each of A, $A_O$ and B is an independently selected single unit or is optionally comprised or consists of two, three or four independently selected subunits;
Y is optionally present as an optionally substituted heteroatom, an optionally substituted functional group or a Spacer Unit, independently selected when subscript y is 2 so that $Y_y$ is —Y—Y'—, wherein Y and Y' are, respectively, a first and second optionally substituted heteroatom, optionally substituted functional group or Spacer Unit;
subscript w is 0 or 1, wherein W is absent when subscript w is 0, or when subscript w is 1 then
W is a Peptide Cleavable Unit, or
W is a Glucuronide Unit of formula —Y(W')—, wherein W' represents a carbohydrate moiety with glycosidic bonding to Y through a optionally substituted heteroatom;

provided that Y bonded to W' is a self-immolative Spacer Unit;

subscript y is 0, 1 or 2, provided that subscript y is 1 or 2, when W is a Glucuronide Unit, in which instance subscript y is inclusive of the self-immolative Spacer Unit bonded to W', except that subscript y is 1 and Y of the Glucuronide Unit is bonded to D when D is a quaternized Drug Unit ($D^+$) that is a tubulysin or auristatin, and provided that subscript y is 1 and Y is a self-immolative Spacer Unit bonded to D and W when W is a Peptide Cleavable Unit and D is a quaternized Drug Unit ($D^+$) that is a tubulysin or auristatin;

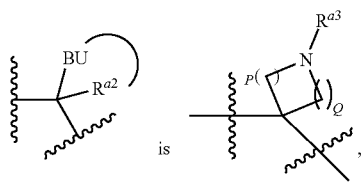

is subscript P is 1 and subscript Q is 1, 2 or 3, or subscript P is 2 and Q is 1 or 2;

and wherein $R^{a3}$ is —H, $C_1$-$C_6$ alkyl, —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36;

wherein the basic nitrogen bonded to $R^{a3}$ is optionally protonated;

D is a Drug Unit that is a tubulysin or auristatin, or

D is a quaternized Drug Unit that is a tubulysin or auristatin represented as $D^+$ so that $D^+$ replaces D in Formula 1 and Formula 2 provided that subscript w is 1;

wherein if subscript w is 1, activation of the Glucuronide Unit by a glycosidase or activation of the Peptide Cleavable Unit by a protease within a Ligand Drug Conjugate compound initiates release of the Drug Unit or quaternized Drug Unit as a tubulysin or auristatin from that Ligand Drug Conjugate compound, or if subscript w is 0, a tubulysin or auristatin is released from a Ligand Drug Conjugate compound on enzymatic or non-enzymatic cleavage of a bond within a drug linker moiety of the Conjugate compound that attaches $Y_y$-D to the indicated $L_{SS}$ or $L_S$ structure of that drug linker moiety; and wherein subscript p' is an integer ranging from 1 to 24.

2. The Ligand Drug Conjugate compound of claim 1, wherein the compound is represented by the structure of:

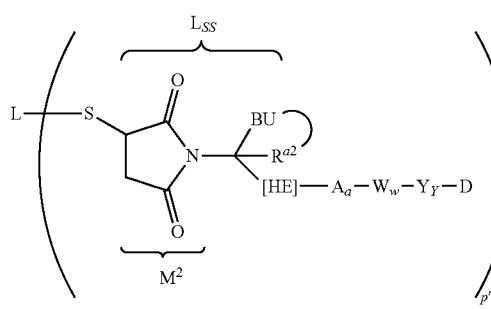

or

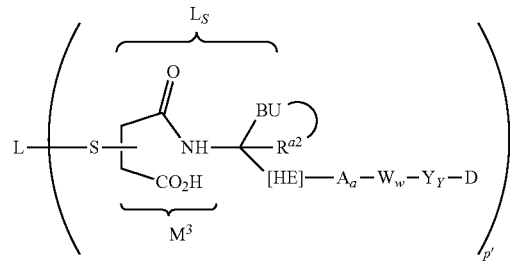

or pharmaceutically acceptable salt(s) thereof, wherein [HE] as $A_O$ is an optional Hydrolysis Enhancing Unit that is —C(=O)—;

subscript w is 1;

W is Peptide Cleavable Unit, or

W is a Glucuronide Unit of formula —Y(W')— having the structure of:

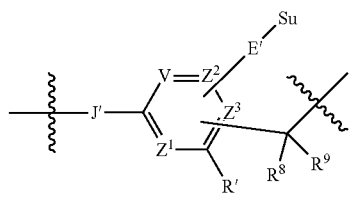

wherein Su is a carbohydrate moiety and -E'- represents an optionally substituted heteroatom of a glycosidic bond cleavable by a glycosidase so that Su-E' is W' and the remainder of the Glucuronide Unit structure is a self-immolative Spacer Unit bonded to W';

J' is a heteroatom, optionally substituted;

V, $Z^1$, $Z^2$ and $Z^3$ are independently =N— or =C($R^{24}$)—, wherein each $R^{24}$ is independently selected from the group consisting of hydrogen and $C_1$-$C_{12}$ alkyl, $C_2$-$C_{12}$ alkenyl and $C_2$-$C_{12}$ alkynyl, optionally substituted, and halogen, an electron withdrawing group, an electron donating group, -E'-Su, and —C($R^8$)($R^9$)—, provided that one and only one —C($R^8$)($R^9$)— moiety and one and only one —E'-Su moiety is present, wherein one of V, $Z^1$, $Z^2$ and $Z^3$ is =C($R^{24}$)— in which $R^{24}$ is —C($R^8$)($R^9$)— and another of V, $Z^1$, $Z^2$ and $Z^3$ is =C($R^{24}$)— in which $R^{24}$ is —E'-Su, provided the —C($R^8$)($R^9$)— and —E'-Su moieties are ortho or para to each other;

$R^8$ and $R^9$ independently are hydrogen, or $C_1$-$C_{12}$ alkyl, $C_2$-$C_{12}$ alkenyl or $C_2$-$C_{12}$ alkynyl, optionally substituted, or $C_6$-$C_{20}$ aryl or $C_5$-$C_{20}$ heteroaryl, optionally substituted, or $R^8$ and $R^9$ together with the carbon atom to which both are attached define an optionally substituted $C_5$-$C_{20}$ carbocyclo; and R' is hydrogen or —$NO_2$, or other electron withdrawing group or —$OC_1$—$C_6$ alkyl, or other electron donating group; and wherein glycosidase cleavage of the glycosidic bond within a Ligand Drug Conjugate compound initiates release of the Drug Unit or quaternized Drug Unit as a tubulysin or auristatin from that Ligand Drug Conjugate compound;

wherein the wavy line adjacent to J' indicates the point of covalent attachment of the Glucuronide Unit to A when subscript a is 1 or to the indicated $L_{SS}$ or $L_S$ primary linker when subscript a is 0; and the wavy line adjacent to the —C($R^8$)($R^9$)— moiety indicates the point of covalent attachment of the Glucuronide Unit to Y' when subscript y is 2, or to D/$D^+$ when subscript y is 1.

3. The Ligand Drug Conjugate compound of claim 2 wherein W is a Glucuronide Unit in which —W—$Y_y$-D and —W-$D^+$ have structures of:

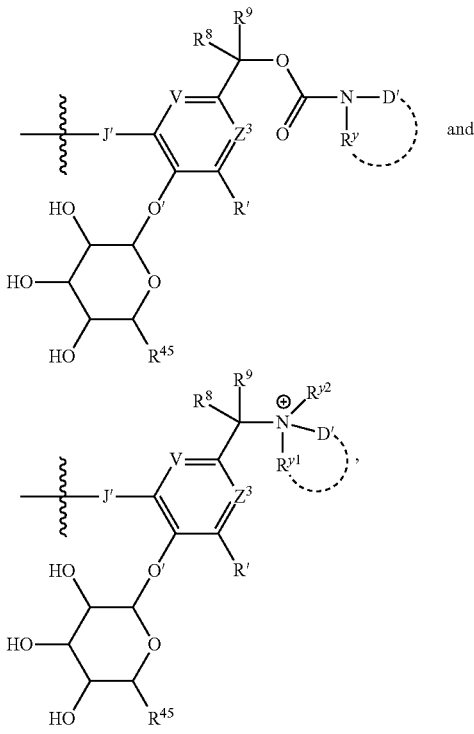

respectively, or a pharmaceutically acceptable salt thereof, or in pharmaceutically acceptable salt form, or W is a Peptide Cleavable Unit and —$Y_y$-D— and —$Y_y$-$D^+$ have structures of:

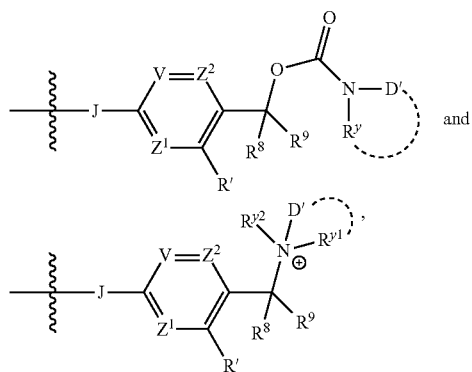

respectively, or pharmaceutically acceptable salts thereof, or in pharmaceutically acceptable salt forms,
wherein
J or J' is an independently selected heteroatom, optionally substituted;
the dotted curve line indicates optional cyclization of $R^y$ or $R^{y1}$ to D';
$R^{45}$ is —CH2OH or —$CO_2H$;
N($R^Y$)D' and —$N^+$($R^{y1}$)($R^{y2}$)D' moieties, with or without cyclization, represent D and $D^+$, respectively, wherein D' is the remainder of D or $D^+$;
wherein $R^y$ is hydrogen or optionally substituted $C_1$-$C_6$ alkyl in absence of cyclization to D' or $R^y$ is optionally substituted $C_1$-$C_6$ alkylene when cyclized to D';
$R^{y1}$ is optionally substituted $C_1$-$C_6$ alkyl, in absence of its cyclization within $D^+$, or $R^{y1}$ is optionally substituted $C_1$-$C_6$ alkylene when cyclized within $D^+$;
$R^{y2}$ is hydrogen or optionally substituted $C_1$-$C_6$ alkyl; and
wherein —O'— as E' represents the oxygen heteroatom of an O-glycosidic bond cleavable by a glycosidase, wherein cleavage of that bond or the bond between W and J, as indicated by the wavy line adjacent to J, within a Ligand Drug Conjugate compound initiates release of D as a primary or secondary amine-containing tubulysin or auristatin or initiates release of $D^+$ as a tertiary amine-containing tubulysin or auristatin from that Ligand Drug Conjugate compound.

4. The Ligand Drug Conjugate compound of claim 2, wherein the compound is represented by the structure of:

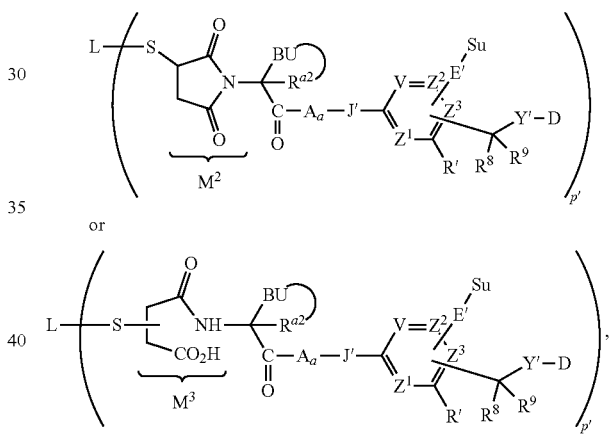

or pharmaceutically acceptable salt(s) thereof, wherein
Su is a carbohydrate moiety;
E' is a heteroatom, optionally substituted, of a glycosidic bond cleavable by a glycosidase;
J' represents a heteroatom, optionally substituted;
Y' is absent or Y' is —O—, —S—, —NH— or —O—C(=O)—, provided that Y' is absent when D is a quaternized Drug Unit ($D^+$) that is a tubulysin or auristatin;
V, $Z^1$, $Z^2$ and $Z^3$ independently are =N— or =C($R^{24}$)—, wherein each $R^{24}$ is independently selected from the group consisting of hydrogen and $C_1$-$C_8$ alkyl, $C_2$-$C_8$ alkenyl and $C_2$-$C_8$ alkynyl, optionally substituted, halogen, an electron withdrawing group, an electron donating group, —O'-Su, —C($R^8$)($R^9$)—Y'-D and —C($R^8$)($R^9$)-$D^+$,
provided that one and only one of —C($R^8$)($R^9$)—Y'-D and —C($R^8$)($R^9$)-$D^+$ moieties and one and only one —O'-Su moiety is present;
wherein one of V, $Z^1$, $Z^2$ and $Z^3$ is =C($R^{24}$)—, in which $R^{24}$ is —C($R^8$)($R^9$)—Y'-D or —C($R^8$)($R^9$)-$D^+$ and another of V, $Z^1$, $Z^2$ and $Z^3$ is =C($R^{24}$)—, in which $R^{24}$ is —O'-Su, provided the —O'-Su and —C(R$^8$)(R$^9$)—Y'-D or —C(R$^8$)(R$^9$)-D$^+$ moieties are ortho or para to each other;

R$^8$ and R$^9$ independently are hydrogen, C$_1$-C$_8$ alkyl, C$_2$-C$_8$ alkenyl and C$_2$-C$_8$ alkynyl, optionally substituted, or C$_5$-C$_{10}$ aryl or C$_5$-C$_{10}$ heteroaryl, optionally substituted or R$^8$ and R$^9$ together with the carbon atom to which both are attached define an optionally substituted C$_5$-C$_6$ carbocyclo; and wherein glycosidase cleavage of the glycosidic bond within a Ligand Drug Conjugate compound initiates release of D/D$^+$ as a biologically active compound or derivative thereof tubulysin or auristatin from that Ligand Drug Conjugate compound, or wherein the compound is represented by the structure of:

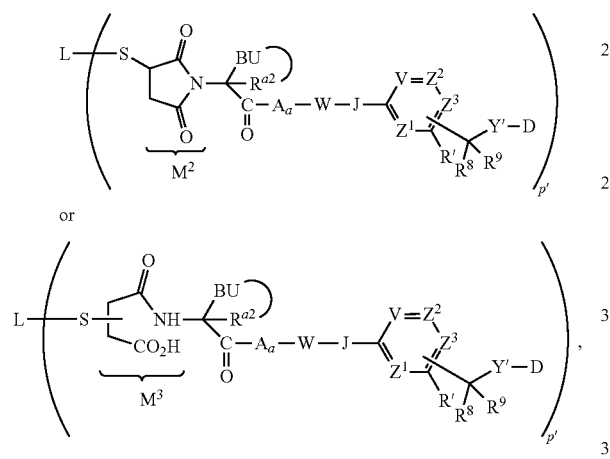

or pharmaceutically acceptable salt(s) thereof, wherein

J is a heteroatom, optionally substituted;

Y' is absent or Y' is —O—, —S—, —NH— or -O—C(=O)—, provided that —Y'— is absent when D is a quaternized Drug Unit (D$^+$) that is a tubulysin or auristatin;

W is a Peptide Cleavable Unit;

V, Z$^1$, Z$^2$ and Z$^3$ are independently =N— or =C(R$^{24}$)—, wherein each R$^{24}$ is independently selected from the group consisting of hydrogen and C$_1$-C$_8$ alkyl, C$_2$-C$_8$ alkenyl and C$_2$-C$_8$ alkynyl, optionally substituted, halogen, an electron withdrawing group, an electron donating group, —C(R$^8$)(R$^9$)—Y'-D and —C(R$^8$)(R$^9$)-D$^+$, provided that one and only one of —C(R$^8$)(R$^9$)—Y'-D and —C(R$^8$)(R$^9$)-D$^+$ moieties is present, wherein one of V, Z$^1$, Z$^2$ and Z$^3$ is =C(R$^{24}$)—, in which R$^{24}$ is —C(R$^8$)(R$^9$)—Y'-D or —C(R$^8$)(R$^9$)-D$^+$, provided the —C(R$^8$)(R$^9$)—Y'-D or —C(R$^8$)(R$^9$)-D$^+$ moiety is ortho or para to J;

R$^8$ and R$^9$ independently are hydrogen, C$_1$-C$_8$ alkyl, C$_2$-C$_8$ alkenyl and C$_2$-C$_8$ alkynyl, optionally substituted, or C$_5$-C$_{10}$ aryl or C$_5$-C$_{10}$ heteroaryl, optionally substituted, or R$^8$ and R$^9$ together with the carbon atom to which both are attached define an optionally substituted C$_5$-C$_6$ carbocyclo;

wherein protease action on W results in cleavage of the W-J bond within a Ligand Drug Conjugate so as to initiate release of D/D$^+$ as a tubulysin or auristatin from that Ligand Drug Conjugate compound.

5. The Ligand Drug Conjugate compound of claim 4, wherein the compound is represented by the structure of:

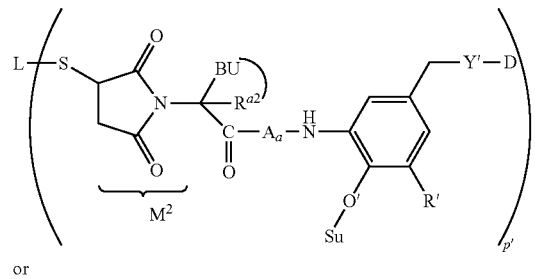

or

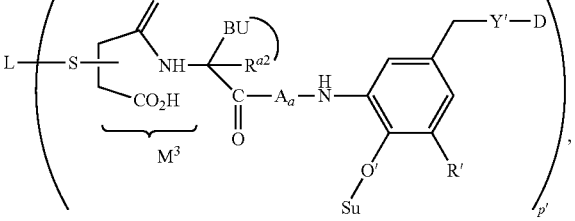

or pharmaceutically acceptable salt(s) thereof, wherein

R' is hydrogen or —NO$_2$; and

O'— represents the oxygen atom of an O-glycosidic bond cleavable by a glycosidase, or wherein the compound is represented by the structure of:

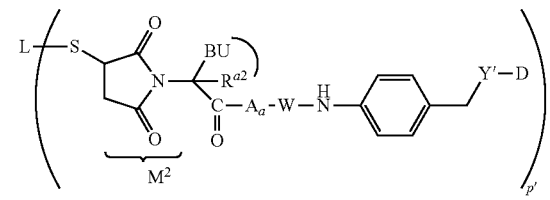

or

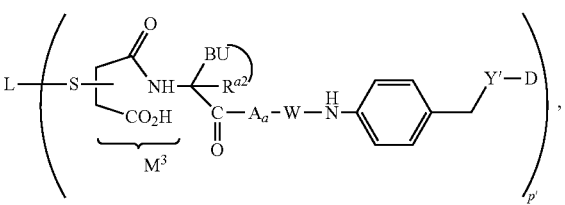

or pharmaceutically acceptable salt(s) thereof.

6. The Ligand Drug Conjugate compound of claim 5, wherein the compound is represented by the structure of:

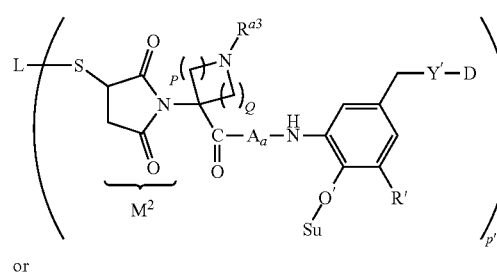

or

-continued

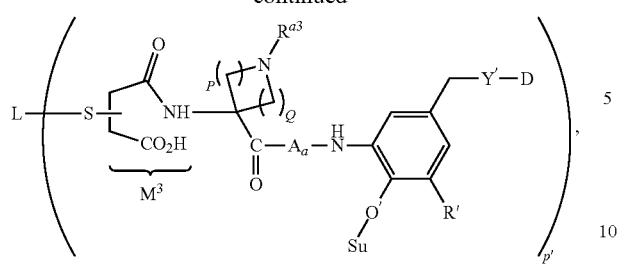

or pharmaceutically acceptable salt(s) thereof,
or
wherein the compound is represented by the structure of:

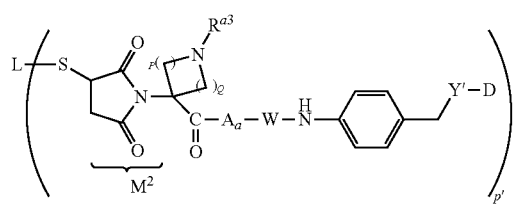

or

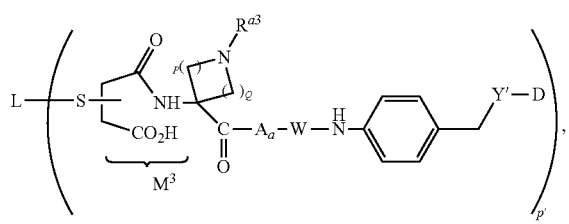

or pharmaceutically acceptable salt(s) thereof.

7. The Ligand Drug Conjugate compound of claim 6, wherein subscript P is 1, and subscript Q is 1.

8. The Ligand Drug Conjugate compound of claim 5, wherein —O'-Su has the structure of:

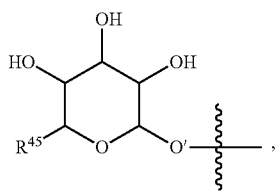

wherein the wavy line represents covalent bonding of O' to the remainder of the structure representing the Ligand Drug Conjugate compound: and $R^{45}$ is —$CH_2OH$ or —$CO_2H$, or a pharmaceutically acceptable salt thereof, or wherein W is a Peptide Cleavable Unit comprised of a dipeptide wherein the C-terminus of the dipeptide is covalently bonded to J wherein the dipeptide provides for a recognition site for a regulatory or lysosomal protease for cleavage by said protease of the W-J bond within a Ligand Drug Conjugate so as to initiate release of D or $D^+$ as a tubulysin or auristatin from that Ligand Drug Conjugate compound, wherein the dipeptide of W has the structure of:

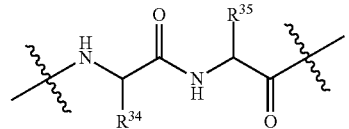

wherein $R^{34}$ is benzyl, methyl, isopropyl, isobutyl, sec-butyl, —CH(OH)CH3 or has the structure of

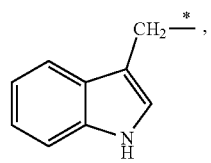

wherein the asterisk indicates the point of covalent attachment to the dipeptide backbone; and $R^{35}$ is methyl or —$(CH_2)_3NH(C=O)NH_2$, or $R^{35}$ is —$(CH_2)_4$—$NH_2$, —$(CH_2)_3NH(C=NH)NH_2$, or —$(CH_2)_2CO_2H$, or a pharmaceutically acceptable salt thereof; and wherein the wavy lines indicate the points of covalent attachment of the dipeptide into the structure representing the Ligand Drug Conjugate compound.

9. The Ligand Drug Conjugate compound of claim 8 wherein the dipeptide of W is selected from the group consisting of -Phe-Lys-, -Val-Ala-, -Val-Lys-, -Ala-Lys-, -Val-Cit-, -Phe-Cit-, -Leu-Cit-, -Ile-Cit-, -Phe-Arg-, -Trp-Cit- and pharmaceutically acceptable salts thereof, wherein Cit is citrulline.

10. The Ligand Drug Conjugate compound of claim 4 wherein D is a quaternized Drug Unit ($D^+$) that is a tubulysin or auristatin, Y' is absent and subscript y is 1 wherein Y bonded to $D^+$ is a self-immolative Spacer Unit.

11. The Ligand Drug Conjugate compound of claim 10, wherein the compound is represented by the structure of:

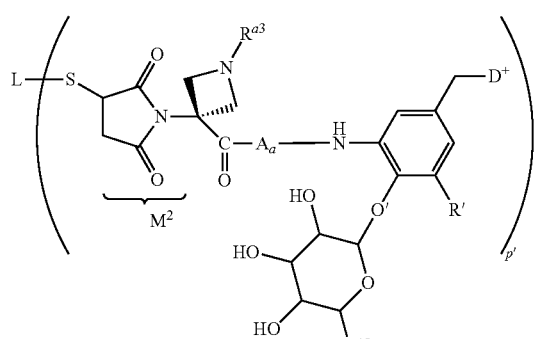

or

-continued

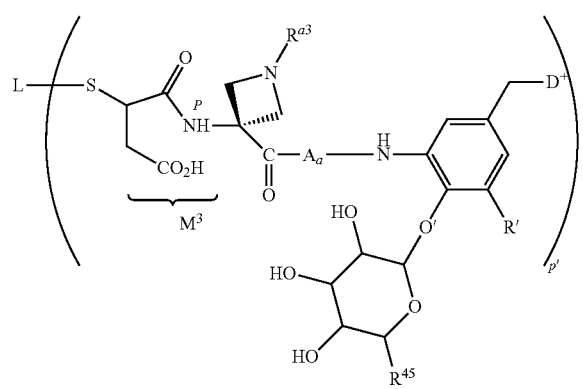

in pharmaceutically acceptable salt form(s), wherein

R' is hydrogen or —NO$_2$; and

R$^{45}$ is —CH$_2$OH or —CO$_2$H, or the compound is represented by the structure of:

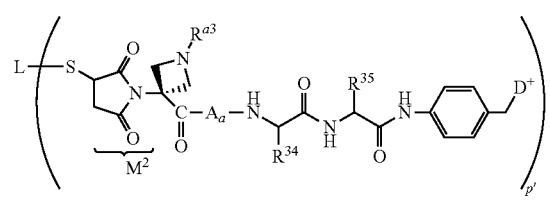

or

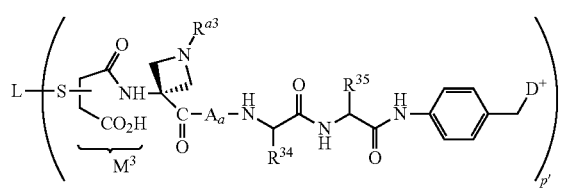

in pharmaceutically acceptable salt form(s), wherein in either compound,

R$^{a3}$ is —H, optionally substituted C$_1$-C$_6$ alkyl, optionally substituted —C$_1$-C$_4$ alkylene-(C$_6$-C$_{10}$ aryl) or —R$^{PEG1}$—O—(CH$_2$CH$_2$O)$_{n'}$—R$^{PEG2}$;

R$^{PEG1}$ is C$_1$-C$_4$ alkylene;

R$^{PEG2}$ is —H or C$_1$-C$_4$ alkyl;

subscript n' ranges from 1 to 36; and wherein the basic nitrogen atom bonded to R$^{a3}$ is optionally protonated.

12. The Ligand Drug Conjugate compound of claim 1 wherein -D$^+$ is a quaternized tubulysin Drug Unit having the structure of:

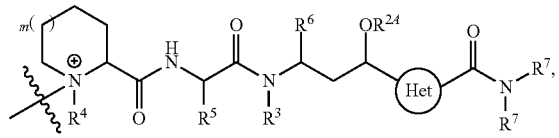

in pharmaceutically acceptable salt form, wherein subscript m is 0 or 1;

R$^{2A}$ is hydrogen or optionally substituted C$_1$-C$_{12}$ alkyl, or R$^{2A}$ along with the oxygen atom to which it is attached defines an O-linked substituent other than —OH;

the circled moiety represents a 5-membered nitrogen-containing heteroarylene, wherein the indicated required substituents to that heteroarylene are in a 1,3-relationship with each other with optional substitution at the remaining positions;

R$^3$ is hydrogen or optionally substituted C$_1$-C$_{12}$ alkyl;

R$^4$, R$^5$ and R$^6$ are optionally substituted C$_1$-C$_{12}$ alkyl, independently selected;

one R$^7$ is hydrogen or optionally substituted C$_1$-C$_{12}$ alkyl and the other R$^7$ is optionally substituted (C$_6$-C$_{20}$ aryl)-C$_1$-C$_{12}$ alkyl- or (C$_5$-C$_{20}$ heteroaryl)-C$_1$-C$_{12}$ alkyl-;

wherein the wavy line indicates the point of covalent attachment of D$^+$ to the remainder of the compound structure.

13. The Ligand Drug Conjugate compound of claim 12 wherein the quaternized tubulysin Drug Unit —D$^+$ has the structure of:

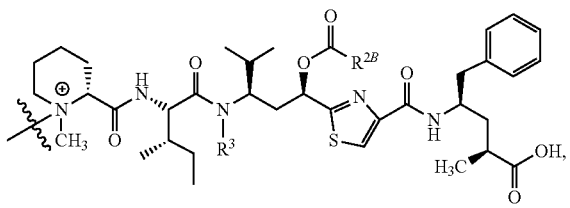

in pharmaceutically acceptable salt form, wherein

R$^3$ is —CH$_3$ or —CH$_2$CH$_2$CH$_3$;

R$^{2B}$ is —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$, or wherein the quaternized tubulysin Drug Unit —D$^+$ has the structure of:

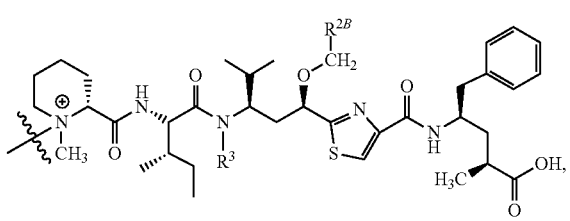

in pharmaceutically acceptable salt form, wherein

R$^{2B}$ is —H, methyl, ethyl, vinyl or —C(═CH$_2$)CH$_3$.

14. The Ligand Drug Conjugate compound of claim 12 wherein the compound is represented by the structure of:

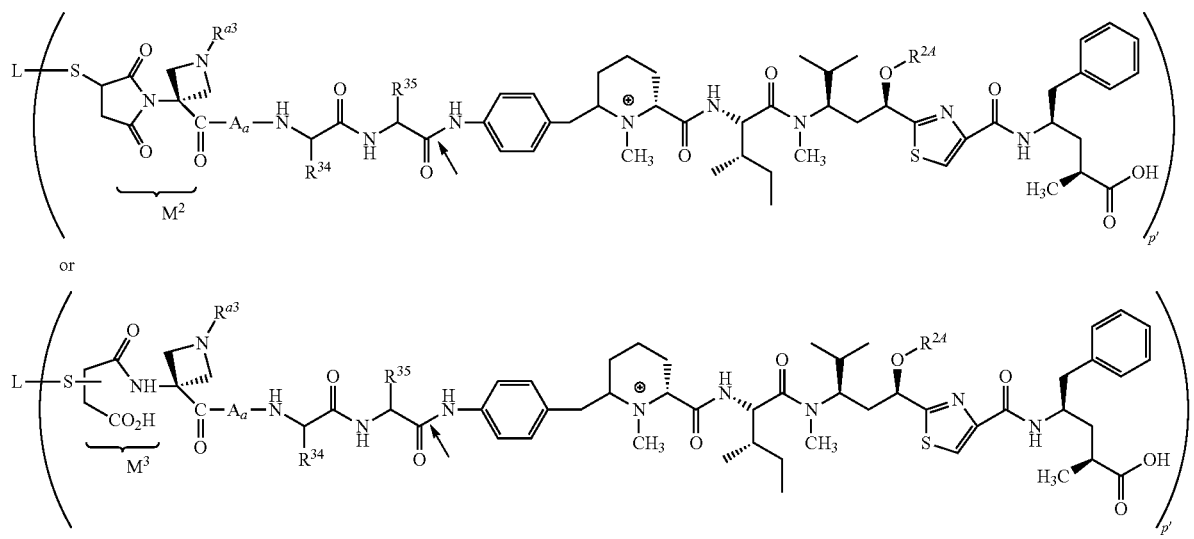

in pharmaceutically acceptable salt form(s), wherein subscript a is 1, so that A is present, wherein A is an alpha-amino, beta-amino or another amine-containing acid residue;
$R^{a3}$ is —H or $C_1$-$C_4$ alkyl;
$R^{2A}$ is C(=O)CH$_3$, —CH$_2$CH$_3$, —CH$_2$CH=CH$_2$ or —CH$_2$C(=CH$_2$)CH$_3$;

$R^{34}$ is isopropyl;
$R^{35}$ is methyl or —(CH$_2$)$_3$NH(C=O)NH$_2$; and
wherein the basic nitrogen atom bonded to $R^{a3}$ is optionally protonated, or wherein the compound is represented by the structure of:

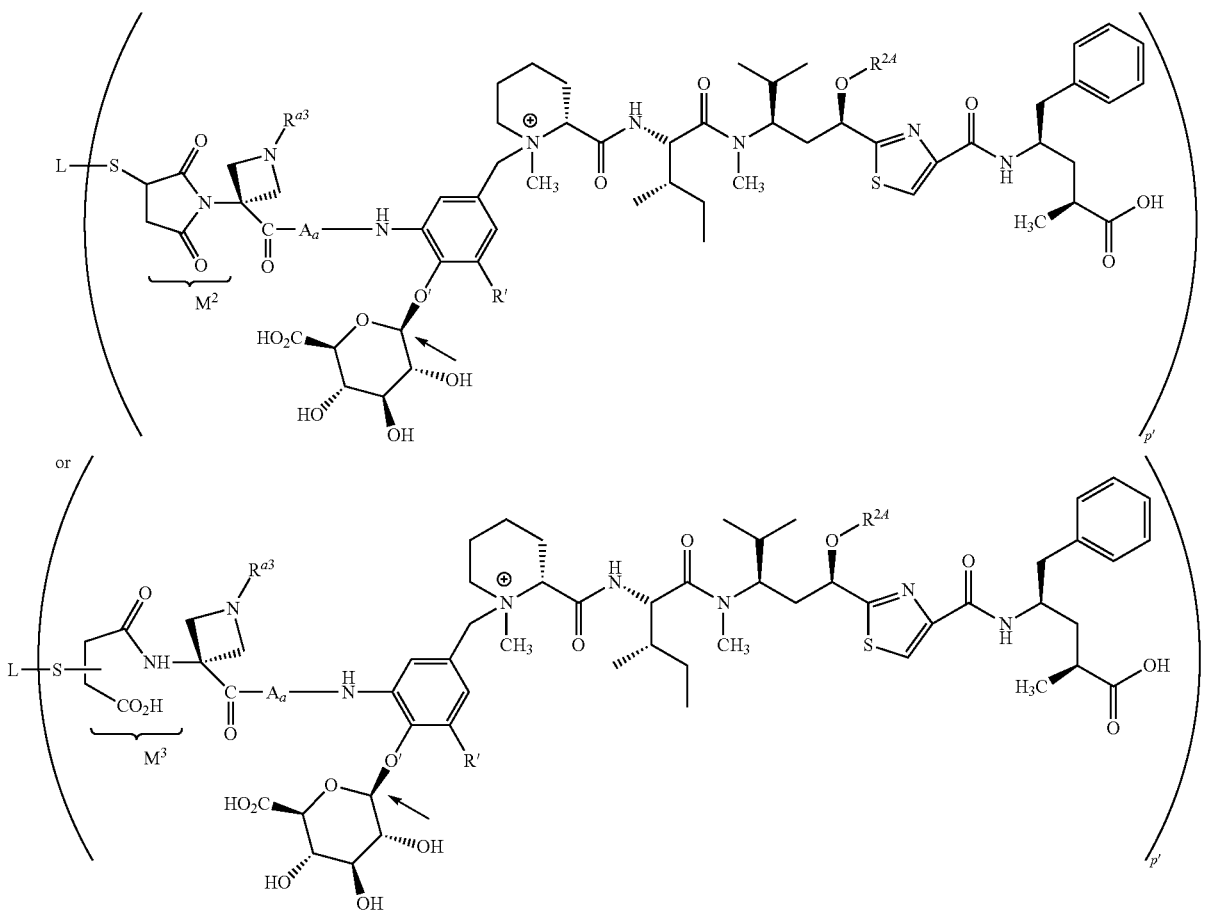

in pharmaceutically acceptable salt form(s), wherein
subscript a is 1, so that A is present, wherein A is an alpha-amino, beta-amino or another amine-containing acid residue;
$R^{a3}$ is —H or $C_1$-$C_4$ alkyl;
$R^{2A}$ is —C(=O)CH$_3$, —CH$_2$CH$_3$, —CH$_2$CH=CH$_2$ or —CH$_2$C(=CH$_2$)CH$_3$; and
wherein the basic nitrogen atom bonded to $R^{a3}$ is optionally protonated.

15. The Ligand Drug Conjugate compound of claim 6 wherein the compound is represented by the structure of:

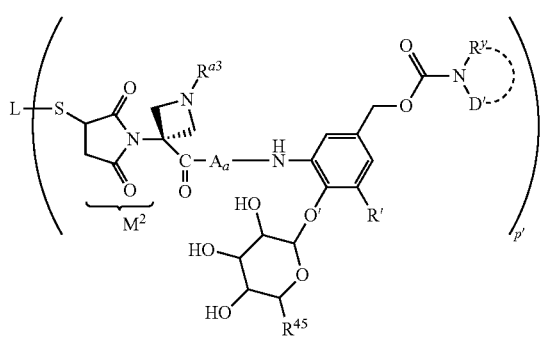

or

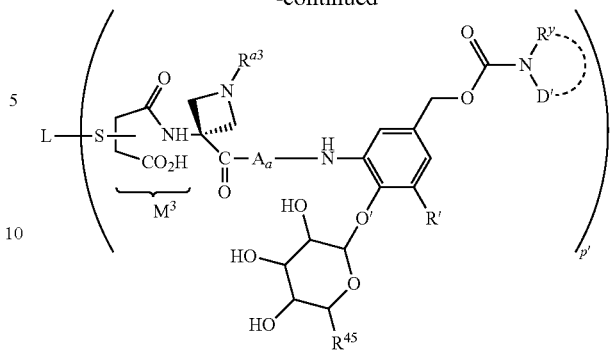

or pharmaceutically acceptable salt(s) thereof, wherein
subscript a is 1, so that A is present, wherein A is an alpha-amino, beta-amino or another amine-containing acid residue;
$R^{a3}$ is —H, $C_1$-$C_6$ alkyl, —$C_1$-$C_4$ alkylene-($C_6$-$C_{10}$ aryl), or $R^{PEG1}$—O—(CH$_2$CH$_2$O)$_{n'}$—$R^{PEG2}$ wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated;
R' is hydrogen or —NO$_2$;
$R^{45}$ is —CH$_2$OH or —CO$_2$H;
—N(R$^y$)D' represents D, wherein D' is the remainder of D, and wherein the dotted line indicates optional cyclization of R$^y$ to D', wherein R$^y$ is hydrogen or optionally substituted $C_1$-$C_6$ alkyl in absence of cyclization to D' or R$^y$ is optionally substituted $C_1$-$C_6$ alkylene when cyclized to D';
wherein —O'— represents the oxygen heteroatom of an O-glycosidic bond cleavable by a glycosidase, wherein said cleavage within a Ligand Drug Conjugate initiates release of D as a primary or secondary amine-containing tubulysin or auristatin from that Ligand Drug Conjugate compound, or
wherein the compound is represented by:

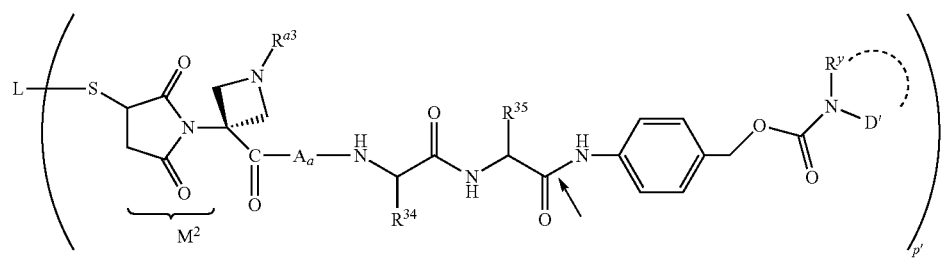

or

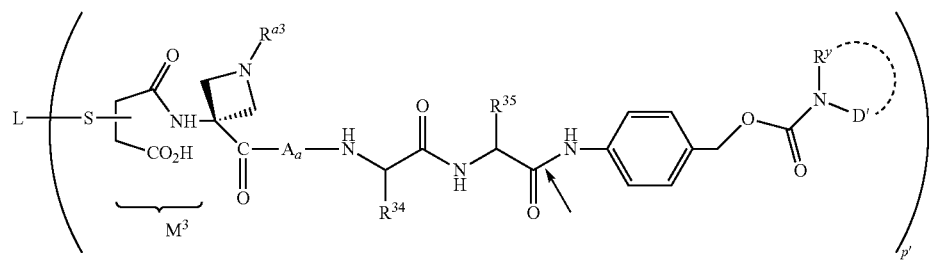

or pharmaceutically acceptable salt(s) thereof, wherein
subscript a is 1, so that A is present, wherein A is an alpha-amino, beta-amino or another amine-containing acid residue;

$R^{a3}$ is —H, $C_1$-$C_6$ alkyl, —$C_1$-$C_4$ alkylene-($C_6$-$C_{10}$ aryl), or —$R^{PEG1}$—O—$(CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen atom bonded to $R^{a3}$ is optionally protonated;

$R^{34}$ is methyl or isopropyl;

$R^{35}$ is methyl, —$(CH_2)_4$—$NH_2$, —$(CH_2)_3NH(C=O)NH_2$, —$(CH_2)_3NH(C=NH)NH_2$, or, —$(CH_2)_2CO_2H$;

—N($R^y$)D' represents -D having covalent attachment to the remainder of the compound structure, wherein D' is the remainder of D, and wherein the dotted line indicates optional cyclization of $R^y$ to D', wherein $R^y$ is hydrogen or optionally substituted $C_1$-$C_6$ alkyl in absence of cyclization to D', or $R^y$ is optionally substituted $C_1$-$C_6$ alkylene when cyclized to D'; and wherein protease cleavage of the indicated bond within a Ligand Drug Conjugate initiates release of D as a primary or secondary amine-containing tubulysin or auristatin from that Ligand Drug Conjugate compound.

16. The Ligand Drug Conjugate compound of claim 15, wherein the auristatin that is released is an auristatin drug compound having the structure of:

$R^{14}$ is hydrogen or methyl, or $R^{13}$ and $R^{14}$ taken together with the carbon to which they are attached comprise a $C_3$-$C_8$ carbocyclo;

$R^{15}$ is hydrogen or $C_1$-$C_8$ alkyl;

$R^{16}$ is hydrogen, $C_1$-$C_8$ alkyl, $C_3$-$C_8$ carbocyclyl, $C_6$-$C^{24}$ aryl, —$C_6$-$C_{24}$—$X^1$-aryl, —$X^1$—($C_3$-$C_8$ carbocyclyl), $C_3$-$C_8$ heterocyclyl and —$X^1$—($C_3$-$C_8$ heterocyclyl);

$R^{17}$ independently are hydrogen, —OH, $C_1$-$C_8$ alkyl, $C_3$-$C_8$ carbocyclyl and O—($C_1$-$C_8$ alkyl);

$R^{18}$ is hydrogen or optionally substituted $C_1$-$C_8$ alkyl;

$R^{19}$ is —$C(R^{19A})_2$—$C(R^{19A})_2$—$C_6$-$C_{24}$ aryl, —$C(R^{19A})_2$—$C(R^{19A})_2$—($C_3$-$C_8$ heterocyclyl) or —$C(R^{19A})_2$—$C(R^{19A})_2$—($C_3$-$C_8$ carbocyclyl), wherein $C_6$-$C_{24}$ aryl and $C_3$-$C_8$ heterocyclyl are optionally substituted;

$R^{19A}$ independently are hydrogen, optionally substituted $C_1$-$C_8$ alkyl, —OH or optionally substituted —O—$C_1$-$C_8$ alkyl;

$R^{20}$ is hydrogen or $C_1$-$C_{20}$ alkyl, $C_6$-$C_{24}$ aryl or $C_3$-$C_8$ heterocyclyl, optionally substituted, or —$(R^{47}O)_m$—$R^{48}$, or —$(R^{47}O)_m$—$CH(R^{49})_2$;

$R^{21}$ is $C_1$-$C_8$ alkylene-($C_6$-$C_{24}$ aryl) or —$C_1$-$C_8$ alkylene-($C_5$-$C_{24}$ heteroaryl), optionally substituted, or $C_1$-$C_8$ hydroxylalkyl, or optionally substituted $C_3$-$C_8$ heterocyclyl;

Z is O, S, NH, or $NR^{46}$;

$R^{46}$ is optionally substituted $C_1$-$C_8$ alkyl;

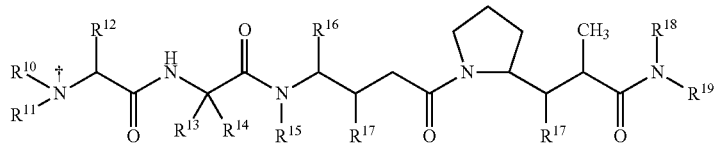

$D_E$

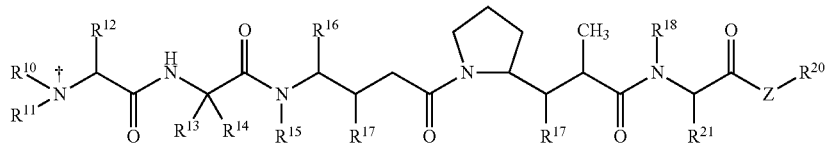

$D_F$ or a pharmaceutically acceptable salt thereof or in a pharmaceutically acceptable salt form, wherein the dagger indicates the site of covalent attachment of the nitrogen atom of the auristatin compound's secondary amine that provides a carbamate functional group, wherein —OC(=O)— of that functional group is Y', on incorporation of the auristatin drug compound as -D into a Ligand Drug Conjugate compound in which subscript y is 2;

one of $R^{10}$ and $R^{11}$ is hydrogen and the other is $C_1$-$C_8$ alkyl, $R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl);

$R^{13}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl and —$X^1$—($C_3$-$C_8$ heterocyclyl);

subscript m is an integer ranging from 1-1000;

$R^{47}$ is $C_2$-$C_8$ alkyl;

$R^{48}$ is hydrogen or $C_1$-$C_8$ alkyl;

$R^{49}$ independently are —COOH, —$(CH_2)_n$—$N(R^{50})_2$, —$(CH_2)_n$—$SO_3H$, or —$(CH_2)_n$—$SO_3$—$C_1$-$C_8$ alkyl;

$R^{50}$ independently are $C_1$-$C_8$ alkyl, or —$(CH2)_n$—COOH;

subscript n is an integer ranging from 0 to 6; and $X^1$ is $C_1$-$C_{10}$ alkylene, or wherein the released auristatin drug compound incorporated into —D with covalent attachment through a carbamate functional group is monomethylauristatin E (MMAE) or monomethylauristatin F (MMAF).

17. The Ligand Drug Conjugate compound of claim 16 wherein the compound is represented by the structure of:

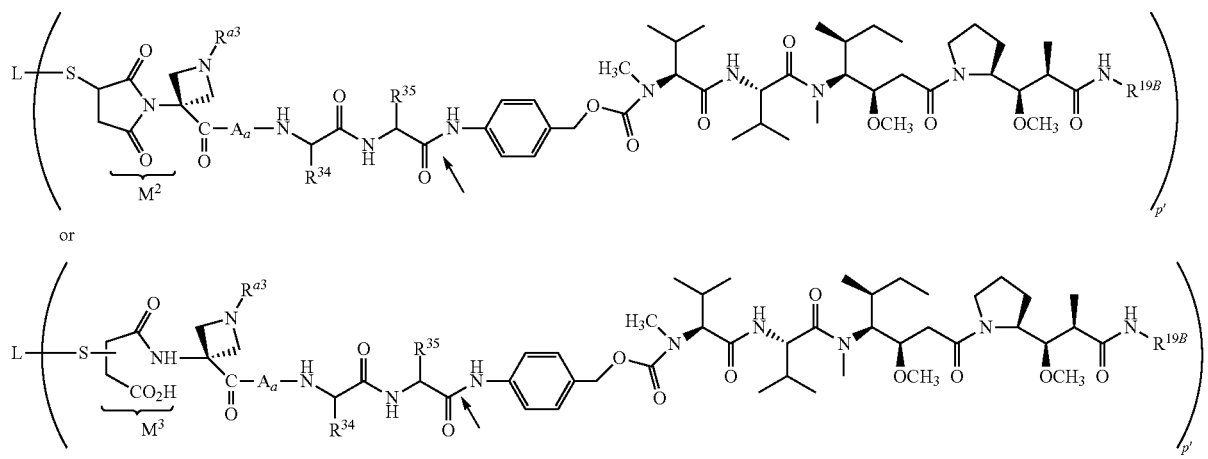

or pharmaceutically acceptable salt(s) thereof, wherein subscript a is 1 so that A is present, wherein A is an alpha-amino, beta-amino or another amine-containing acid residue;

$R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—$(CH_2CH_2O)_{n'}$—$R^{PEG2}$;

$R^{PEG1}$ is $C_4$ alkylene;
$R^{PEG2}$ is —H or $C_1$-$C_4$ alkyl;
subscript n' ranges from 1 to 36; and
wherein the basic nitrogen atom bonded to $R^{a3}$ is optionally protonated;

$R^{19B}$ is —CH($CH_3$)—CH(OH)-Ph, —CH($CO_2H$)—CH(OH)—$CH_3$, or —CH($CO_2H$)—$CH_2$Ph;

$R^{34}$ is isopropyl; and $R^{35}$ is methyl or —$(CH_2)_3$NH(C=O)$NH_2$, or wherein the compound is represented by the structure of:

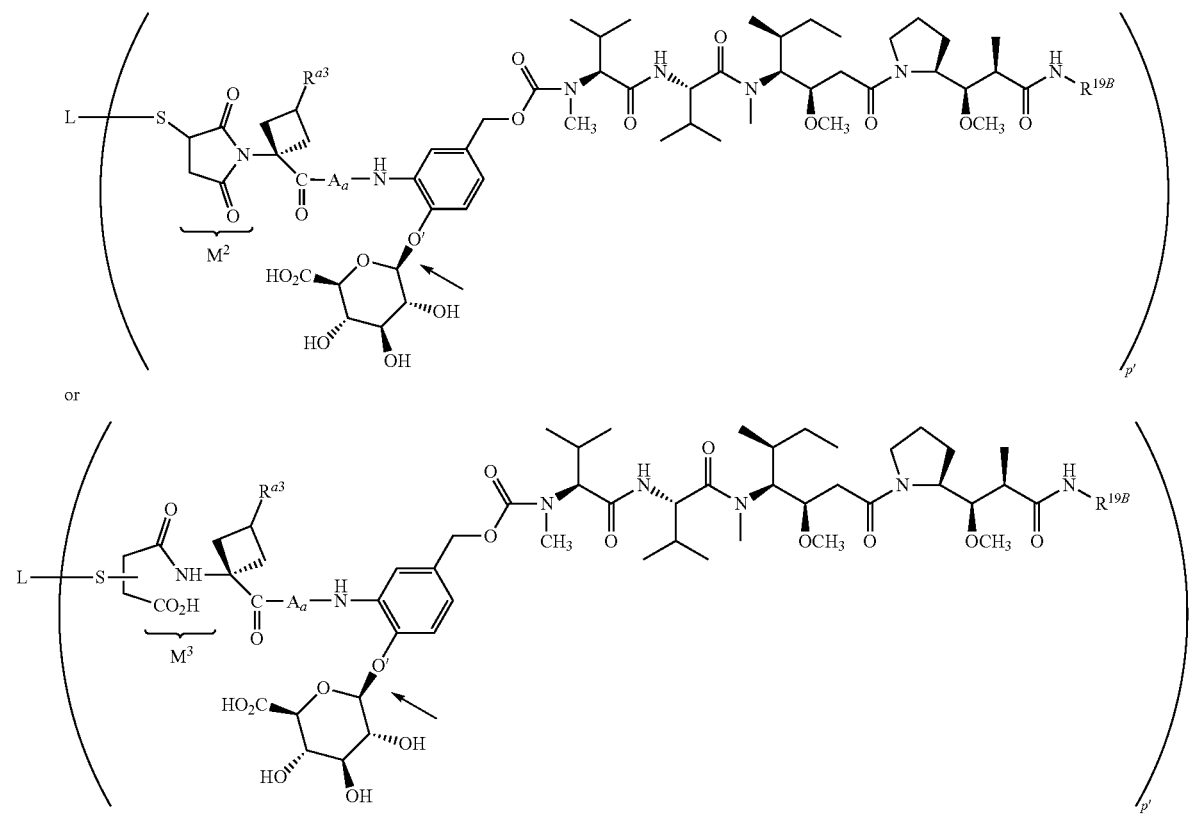

or pharmaceutically acceptable salt(s) thereof, wherein subscript a is 1, so that A is present, wherein A is an alpha-amino, beta-amino or another amine-containing acid residue;

$R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—$(CH_2CH_2O)_{n'}$—$R^{PEG2}$;

$R^{PEG1}$ is $C_4$ alkylene;

$R^{PEG2}$ is —H or $C_1$-$C_4$ alkyl;

subscript n' ranges from 1 to 36; and wherein the basic nitrogen bonded to $R^{a3}$ is optionally protonated; and $R^{19B}$ is —CH($CH_3$)—CH(OH)-Ph, —CH($CO_2H$)—CH(OH)—$CH_3$, or —CH($CO_2H$)—$CH_2$Ph.

18. The Ligand Drug Conjugate compound of claim 1 wherein the compound is represented by the structure of Formula 1a or Formula 2a:

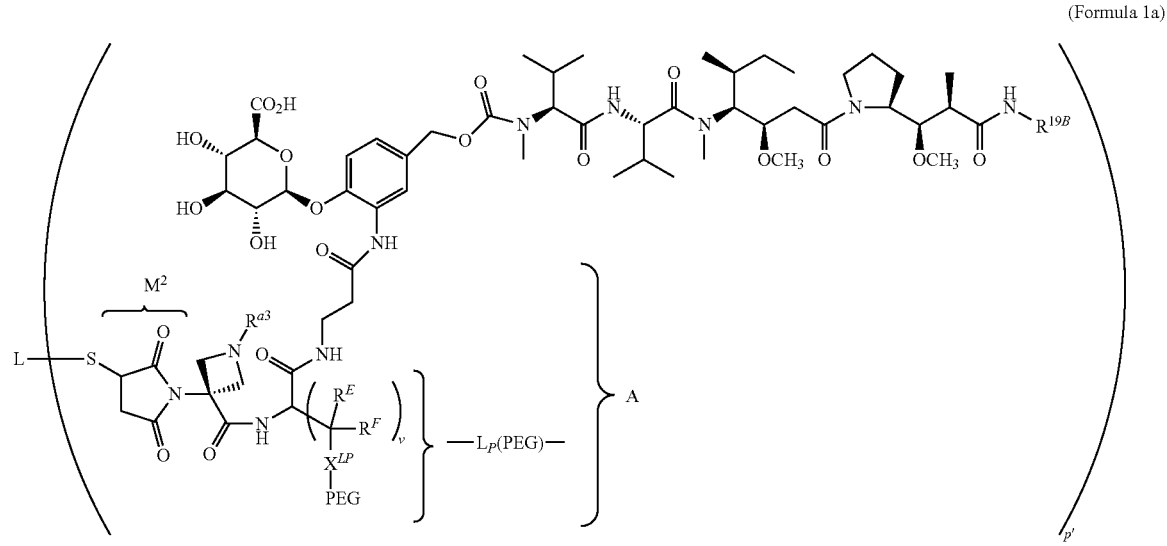

(Formula 1a)

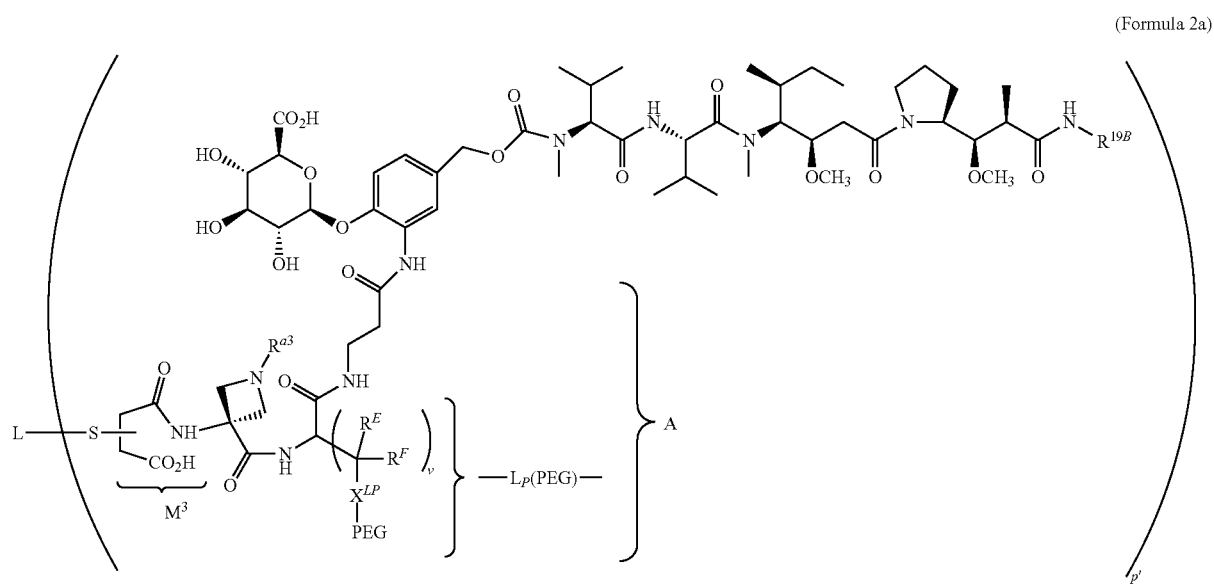

(Formula 2a)

or pharmaceutically acceptable salt(s) thereof, wherein R$^{19B}$ is —CH(CH$_3$)—CH(OH)-Ph, —CH(CO$_2$H)—CH(OH)—CH$_3$, or —CH(CO$_2$H)—CH$_2$Ph;

or
wherein the compound is represented by the structure of Formula 1b or Formula 2b:

(Formula 1b)

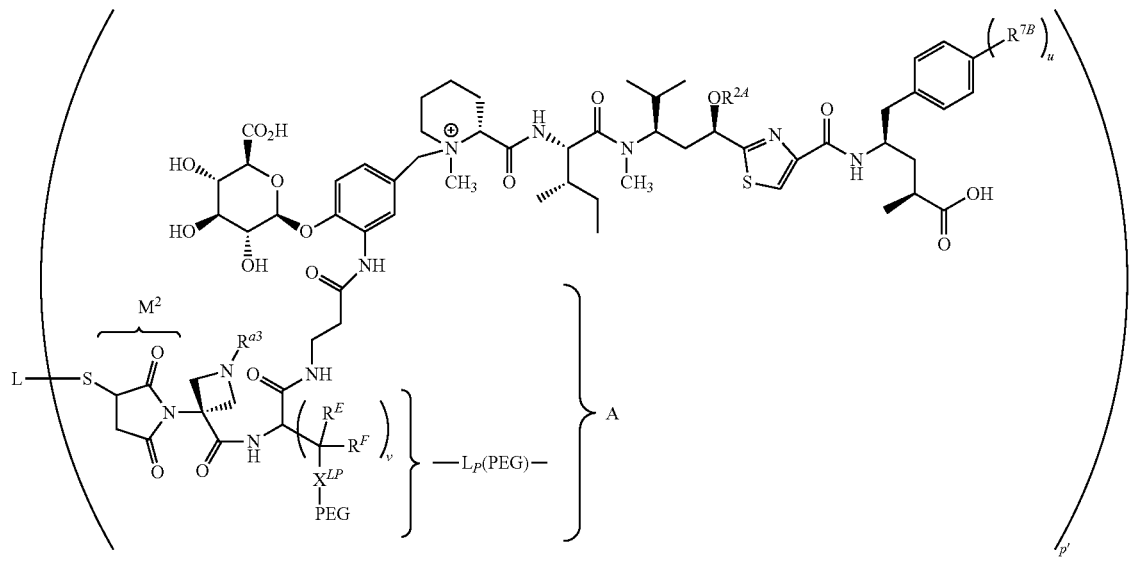

or (Formula 2b)

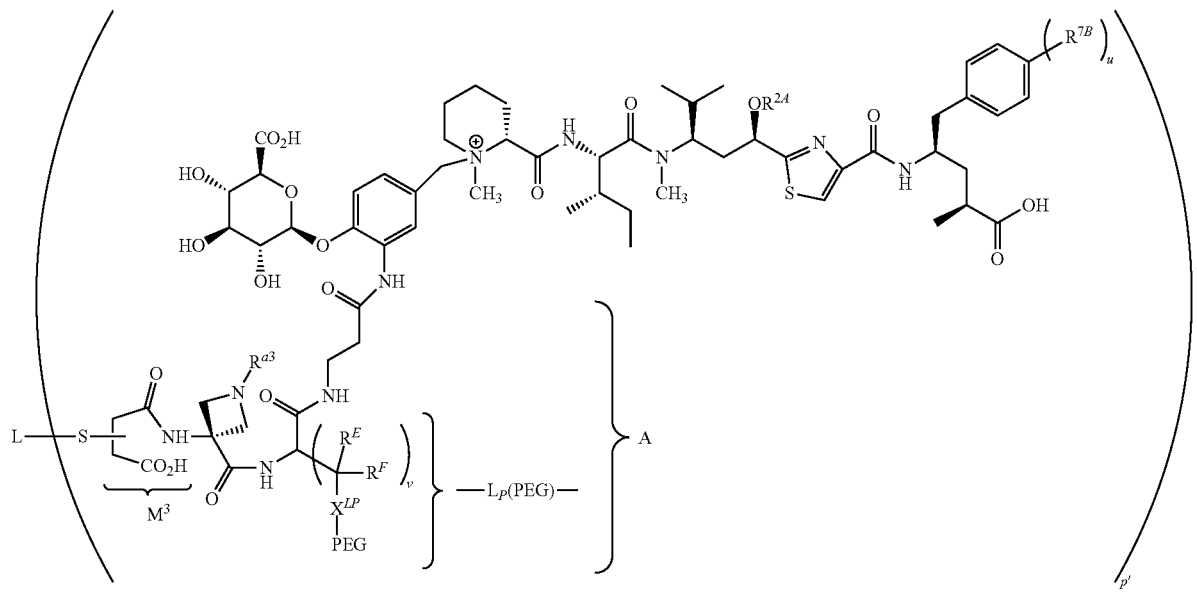

or pharmaceutically acceptable salt(s) thereof, wherein
R$^{2A}$ is C(=O)CH$_3$, —CH$_2$CH$_3$, —CH$_2$CH=CH$_2$ or —CH$_2$C(=CH$_2$)CH$_3$;
subscript u is 0 or 1; and
R$^{7B}$ is —OH when subscript u is 1 or is absent when subscript u is 0
wherein in Formula 1a, Formula 2a, Formula 1b and Formula 2b,
S is a sulfur atom of the Ligand Unit, wherein that sulfur atom in Formula 2a is bonded the carbon α or β to the carboxylic acid functional group of the indicated succinic acid amide (M$^3$) moiety, R$^{a3}$ is —H, optionally substituted C$_1$-C$_6$ alkyl or optionally substituted —C$_1$-C$_4$ alkylene-(C$_6$-C$_{10}$ aryl), wherein the basic nitrogen atom bonded to R$^{a3}$ is optionally protonated;
L$_P$ is a Parallel Connector Unit;
PEG is a PEG Unit;
subscript v is an integer ranging from 1 to 4;
each R$^E$ and R$^F$ is independently selected from the group consisting of —H, optionally substituted C$_1$-C$_6$ alkyl, optionally substituted C$_2$-C$_6$ alkylene, optionally substituted C$_6$-C$_{10}$ arylene or optionally substituted C$_5$-C$_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined, $X^{LP}$ is provided by a natural or un-natural amino acid side chain or is selected from the group consisting of –O-, —$NR^{LP}$—, —S—, —S(=O)—, —S(=O)$_2$—, —C(=O)—, —C(=O)N($R^{LP}$)—, —N($R^{LP}$)C(=O)N($R^{LP}$)—, and —N($R^{LP}$)C(=N$R^{LP}$)N($R^{LP}$)—, or $C_3$-$C_8$ heterocyclo;

wherein each $R^{LP}$ is independently selected from the group consisting of hydrogen and optionally substituted $C_1$-$C_6$ alkyl, or two of $R^{LP}$ together along with the carbons atoms to which they are attached and their intervening atoms define a $C_5$-$C_6$ heterocyclo and any remaining $R^{LP}$ are as previously defined.

19. The Ligand Drug Conjugate compound of claim 18 wherein —$X^{LP}$-PEG has the structure of:

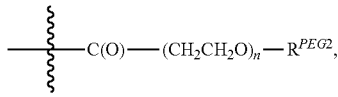

wherein $R^{PEG2}$ is a PEG Capping Unit; and
subscript n ranges from 2 to 72, or
wherein subscript n is 12 and $R^{PEG2}$ is hydrogen or —$CH_3$.

20. The Ligand Drug Conjugate compound of claim 1, wherein the first optional Stretcher Unit (A), or a subunit thereof, is present and has the structure of formula (3a) or formula (4a):

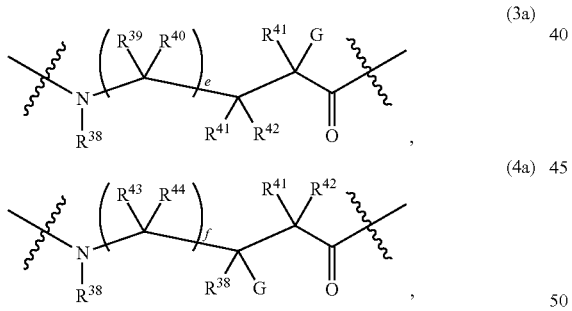

or a pharmaceutically acceptable salt thereof, wherein subscript e and f are independently 0 or 1,
G is hydrogen, optionally substituted $C_1$-$C_6$ alkyl, —OH, —$OR^{PR}$, —$CO_2H$, $CO_2R^{PR}$, wherein $R^{PR}$ is a suitable protecting, or G is —N($R^{PR}$)($R^{PR}$), wherein $R^{PR}$ are independently a protecting group or $R^{PR}$ together form a suitable protecting group, or G is —N($R^{45}$)($R^{46}$), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl;

$R^{39}$, $R^{40}$, $R^{41}$, $R^{42}$, $R^{43}$, $R^{44}$ are independently selected from the group consisting of hydrogen, optionally substituted $C_1$-$C_6$ alkyl, optionally substituted aryl, and optionally substituted heteroaryl, or $R^{39}$, $R^{40}$ together with the carbon to which both are attached, and $R^{41}$ to $R^{44}$ are as defined herein, or $R^{41}$, $R^{42}$ together with the carbon atom to which both are attached define a $C_3$-$C_6$ carbocyclo, and $R^{39}$, $R^{43}$ and $R^{44}$ are as defined herein, or $R^{43}$, $R^{44}$ together with the carbon atom to which both are attached define a $C_3$-$C_6$ cycloalkyl, and $R^{39}$ to $R^{42}$ are as defined herein, or $R^{40}$ and $R^{41}$, or $R^{40}$ and $R^{43}$, or $R^{41}$ and $R^{43}$ to together with the carbon atoms to which they are attached and the atoms intervening between those carbon atoms define a $C_5$-$C_6$ carbocyclo, and $R^{39}$, $R^{44}$ and the remainder of $R^{40}$-$R^{43}$ are as defined herein, or A or a subunit thereof is an alpha-amino or beta-amino acid residue.

21. The Ligand Drug Conjugate compound of claim 1 wherein the Ligand Unit is an antibody Ligand Unit, thereby defining an antibody drug conjugate (ADC),
wherein the moiety targeted by the antibody Ligand Unit is an accessible cell-surface antigen of abnormal cells, wherein the targeted antigen is capable of cellular internalization of bound ADC and is present in greater copy number on the abnormal cells in comparison to normal cells distant from the site of the abnormal cells, or wherein the targeted moiety of the antibody Ligand Unit is an accessible cell-surface antigen of a vascular epithelial cell in the vicinity of abnormal cells, wherein said antigen is capable of cellular internalization of bound ADC and is present in greater copy number on said cells in comparison to normal epithelial cells distant from the site of the abnormal cells.

22. The Ligand Drug Conjugate compound of claim 21 wherein subscript p' is 2, 4, or 8; and
the sulfur atom of the antibody Ligand Unit bonded to the succinic acid ($M^2$) moiety or succinic acid amide ($M^3$) moiety is that of a cysteine residue of the antibody or antigen-binding fragment thereof.

23. A pharmaceutical composition comprising the Ligand Drug Conjugate compound of claim 1 and one, two, three or more excipients, wherein the pharmaceutical composition is in the form of a liquid or a lyophilized solid.

* * * * *